United States Patent
Roščic et al.

(10) Patent No.: US 10,961,238 B2
(45) Date of Patent: Mar. 30, 2021

(54) MODULATORS OF HEDGEHOG (HH) SIGNALING PATHWAY

(71) Applicant: E-THERAPEUTICS PLC, Oxfordshire (GB)

(72) Inventors: Maja Roščic, Zagreb (HR); Filip Kolundžic, Zagreb (HR); Dinko Žiher, Zagreb (HR); Tanja Poljak, Zagreb (HR); Srinivasamurthy Vadlamudi, Oxfordshire (GB); Colin Stubberfield, Oxfordshire (GB)

(73) Assignee: E-THERAPEUTICS PLC, Oxfordshire (GB)

( * ) Notice: Subject to any disclaimer, the term of this patent is extended or adjusted under 35 U.S.C. 154(b) by 0 days.

(21) Appl. No.: 16/344,586

(22) PCT Filed: Oct. 25, 2017

(86) PCT No.: PCT/GB2017/053215
§ 371 (c)(1),
(2) Date: Apr. 24, 2019

(87) PCT Pub. No.: WO2018/078360
PCT Pub. Date: May 3, 2018

(65) Prior Publication Data
US 2020/0055847 A1   Feb. 20, 2020

(30) Foreign Application Priority Data

Oct. 26, 2016 (GB) .................................... 1618097
Jul. 27, 2017 (GB) .................................... 1712077

(51) Int. Cl.
| | | |
|---|---|---|
| C07D 471/04 | (2006.01) | |
| C07D 401/14 | (2006.01) | |
| C07D 487/04 | (2006.01) | |
| C07D 401/12 | (2006.01) | |
| C07D 495/04 | (2006.01) | |
| C07D 405/14 | (2006.01) | |
| C07D 413/14 | (2006.01) | |
| C07D 417/14 | (2006.01) | |
| C07D 491/048 | (2006.01) | |

(52) U.S. Cl.
CPC ......... *C07D 471/04* (2013.01); *C07D 401/12* (2013.01); *C07D 401/14* (2013.01); *C07D 405/14* (2013.01); *C07D 413/14* (2013.01); *C07D 417/14* (2013.01); *C07D 487/04* (2013.01); *C07D 491/048* (2013.01); *C07D 495/04* (2013.01)

(58) Field of Classification Search
CPC .. C07D 471/04; C07D 401/14; C07D 487/04; C07D 401/12; C07D 495/04; C07D 405/14; C07D 413/14; C07D 417/14; C07D 491/048

USPC ....................................................... 546/193
See application file for complete search history.

(56) References Cited

U.S. PATENT DOCUMENTS

| | | |
|---|---|---|
| 2009/0054410 A1 | 2/2009 | Griffioen et al. |
| 2013/0143860 A1 | 6/2013 | Yoshihara et al. |

FOREIGN PATENT DOCUMENTS

| | | | |
|---|---|---|---|
| DE | | 3610588 A1 | 10/1986 |
| WO | | 9312086 * | 6/1993 |
| WO | WO 2014/027053 A1 | | 2/2014 |
| WO | WO 2015/001348 A1 | | 1/2015 |
| WO | WO 2015/082499 A2 | | 6/2015 |
| WO | WO 2016/020324 A1 | | 2/2016 |
| WO | WO 2016/071293 A2 | | 5/2016 |
| WO | WO 2017/040757 A1 | | 3/2017 |

OTHER PUBLICATIONS

Alcedo J, et al., "The *Drosophila* smoothened Gene Encodes a Seven-Pass Membrane Protein, a Putative Receptor for the Hedgehog Signal," Cell, vol. 86, 1996, pp. 221-232.
Berman DM, et al., "Medulloblastoma Growth Inhibition by Hedgehog Pathway Blockade." Science, vol. 297, 2002, pp. 1559-1561.
Bielesz B, et al., "Epithelial Notch Signaling Regulates Interstitial Fibrosis Development in the Kidneys of Mice and Humans," The Journal of Clinical Investigation, vol. 120, No. 11, 2010, pp. 4040-4054.
Bitgood MJ, et al., "Sertoli Cell Signaling by Desert Hedgehog Regulates The Male Germline," Curr Biol 6, 1996, pp. 298-304.
Boor P, et al., "Renal Fibrosis: Novel Insights Into Mechanisms and Therapeutic Targets," Nature Reviews Nephrology, vol. 6, 2010, pp. 643-656.
Chen JK, et al., "Inhibition of Hedgehog signaling by direct binding of cyclopamine to Smoothened." Genes & Development; 16, 2002, pp. 2743-2748.
Chen Y, et al., "Sonic Hedgehog Dependent Phosphorylation by CK1α and GRK2 Is Required for Ciliary Accumulation and Activation of Smoothened," PLoS Biol; vol. 9, Issue 6, 2011, pp. 1-16.
Chiang C, et al., "Cyclopia and Defective Axial Patterning in Mice Lacking Sonic Hedgehog Gene Function," Nature, vol. 383, 1996, pp. 407-413.

(Continued)

*Primary Examiner* — Niloofar Rahmani
(74) *Attorney, Agent, or Firm* — K&L Gates LLP

(57) ABSTRACT

There are described compounds of formula (I): and there use as a medicament in the treatment of conditions involving abnormal activation and/or malfunction of the of the hedgehog pathway, such as cancer, fibrosis and chronic graft-versus-host disease (cGVHD).

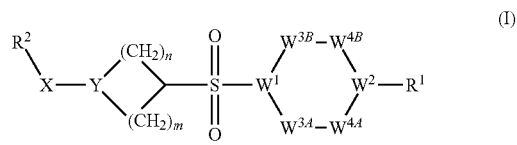

18 Claims, 1 Drawing Sheet

(56) References Cited

OTHER PUBLICATIONS

Coon V, et al., "Molecular Therapy Targeting Sonic Hedgehog and Hepatocyte Growth Factor Signaling in a Mouse Model of Medulloblastoma." Mol Cancer Thor. 9(9); 2010, pp. 2627-2636.
Dierks C, et al., "Expansion of Bcr-Abl-Positive Leukemic Stem Cells Is Dependent on Hedgehog Pathway Activation," Cancer Cell 14, 2008, pp. 238-249.
Echelard Y, et al., "Sonic Hedgehog, A Member Of A Family of Putative Signaling Molecules, Is implicated In The Regulation Of CNS Polarity," Cell 75, 1993, pp. 1417-1430.
Epstein EH, "Basal Cell Carcinomas: Attack Of The Hedgehog," Nat Rev Cancer 8(10), 2008, pp. 743-754.
Fabian SL, et al., "Hedgehog-Gli Pathway Activation during Kidney Fibrosis," The American Journal of Pathology, vol. 180(4), 2012, pp. 1441-1453.
Grande MT, et al, "Deletion of H-Ras Decreases Renal Fibrosis And Myofibroblast Activation Following Ureteral Obstruction in Mice," Kidney International, 2010, 77, pp. 509-518.
He W, et al., "WNT/β-Catenin Signaling Promotes Renal Interstitial Fibrosis," J. Am. Soc. Nephrol, vol. 20, 2009, pp. 765-776.
Hui C, et al., "Gli Proteins in Development and Disease," Annu Rev Cell Dev Biol 27, 2011, pp. 513-537.
Incardona P, et al., "Receptor-Mediated Endocytosis of Soluble and Membrane-Tethered Sonic Hedgehog by Patched-1." Proc Natl Acad Sci, vol. 97. No. 22, 2000, pp. 12044-12049.
Ingham PW, et al., "Hedgehog Signaling in Animal Development: Paradigms and Principles," Genes Dev 15, 2001, pp. 3059-3087.
Jung H, et al., "Aberrant Hedgehog Ligands induce Progressive Pancreatic Fibrosis by Paracrine Activation of Myofibroblasts and Ductular Cells in Transgenic Zebrafish," PLoS ONE, vol. 6, issue 12, 2011, pp. 1-15.
Kimonis VE, et al., "Clinical Manifestations in 105 Persons with Nevoid Basal Cell Carcinoma Syndrome,"—PubMed—NCBI. Am J Med Genet 69(3), 1997, pp. 299-308.
Kool M, et al., "Integrated Genomics Identifies Five Medulloblastoma Subtypes with Distinct Genetic Profiles, Pathway Signatures and Clinicopathological Features," 2008; PLoS One 3(8) 1-14 (DOI: 10.1371/journat.pone.0003088).
Kubo M, et al., "Hedgehog Signaling Pathway is a New Therapeutic Target for Patients with Breast Cancer," Cancer Res. 2004, 64 pp. 6071-6074.
Lai K. et al., "Sonic Hedgehog Regulates Adult Neural Progenitor Proliferation in Vitro and in Vivo," Nat Neurosci 6, 2002, pp. 21-27.
Levy V, et al., "Distinct Stem Cell Populations Regenerate the Follicle and Interfollicular Epidermis," Dev Cell 9, 2005, pp. 855-861.
List A, et al., "Opportunities for Trisenox® (arsenic trioxide) in the Treatment of Myelodysplastic Syndromes," Leukemia 17, 2003, pp. 1499-1507.
Liu Y., "Renal Fibrosis: New Insights Into The Pathogenesis And Therapeutics," Kidney International, vol. 69, 2006, pp. 213-217.
Metcalfe C, et al., "Hedgehog Fights Back: Mechanisms of Acquired Resistance against Smoothened Antagonists." Cancer Res. 2011, 71(15):5057-5061.
Mimeault M, et al., "Cytotoxic Effects Induced By Docetaxel, Gefitinib And Cyclopamine on Side Population and Non-Side Population Cell Fractions from Human Invasive Prostate Cancer Cells," Mol Cancer Thor 9(3), 2010, pp. 617-630.
Mohler J, et al., "Molecular Organization And Embryonic Expression of the Hedgehog Gene Involved in Cell-Cell Communication in Segmental Patterning of *Drosophila*," Development, 115, 1992, pp. 957-971.
Murone M, et al., "Sonic Hedgehog Signaling by the Patched-Smoothened Receptor Complex," Curr Biol 9, 1999, pp. 76-84.
Niu L. et al., "Leptin stimulates alpha1 (I) collagen expression in human hapetic stellate cells via the phosphatidylinositol 3-kinase/Akt singalling pathway," Liver Int. 27(9) 1265-72 (2007)—abstract only.

Nusslein-Volhard C, et al., "Mutations Affecting Segment Number and Polarity in *Drosophila*," Abstract: PubMed—NCBI. Nature 287, 1980, pp. 795-801.
Omenetti A, et al., "Hedgehog mediated mesenchymal-epithelial interactions modulate hepatic response to bile duct ligation," Laboratory investigation 87:499-514 (2007).
Pak E, et al., "Hedgehog Signal Transduction: Key Players, Oncogenic Drivers, and Cancer Therapy." Dev Cell 38(4), 2016, pp. 333-344.
Pan S, et al., "Discovery of NVP-LDE225, a Potent and Selective Smoothened Antagonist," ACS Med Chem Lett, 1, 2010, pp. 130-134.
Pathi S, et al., "Comparative biological responses to human Sonic, Indian, and Desert hedgehog." Mech Dev 106, 2001, pp. 107-117.
Perler FB, "Protein Splicing of Inteins and Hedgehog Autoproteolysis: Structure, Function, and Evolution." Cell vol. 92, 1998, pp. 1-4.
Petrova E. et al., "inhibitors of Hedgehog Acyltransferase Block Sonic Hedgehog Signaling." Nat Chem Bial 9(4), 2013, pp. 247-249.
Pricl, S., et al. "Smoothened (SMO) Receptor Mutations Dictate Resistance to Vismodegib in Basal Cell Carcinoma," Molecular Oncology 2015, vol. 9; pp. 389-397.
Rimkus TK, et al., "Targeting the Sonic Hedgehog Signaling Pathway: Review of Smoothened and GLI inhibitors." Cancers (Basel) 8; 22; 2016, DOI: 10.3390/cancers8020022, pp. 1-23.
Robarge KD, et al., "GDC-0449—A potent inhibitor of the Hedgehog Pathway," Bioorganic & Medicinal Chemistry Letters 2009, 19, pp. 5576-5581.
Ruiz i Altaba A, "Gli Proteins Encode Context-Dependent Positive and Negative Functions: Implications for Development and Disease," Development, 126 (1999), pp. 3205-3216.
Sanchez P. et al. "Inhibition of Prostate Cancer Proliferation by Interference with Sonic Hedgehog-GLI1 Signaling." Proc Natl Aced Sci USA, 101(34), (2004) pp. 12561-12566.
Sekulic A, et al., "Efficacy and Safety of Vismodegib in Advanced Basal-Cell Carcinoma," N Engl J Med, 366, 2012, pp. 2171-2179.
Sharpe HJ, et al., "Genomic Analysis of Smoothened Inhibitor Resistance in Basal Cell Carcinoma," Cancer Cell 27(3), 2015, pp. 327-341.
St-Jacques B, et al., "Indian Hedgehog Signaling Regulates Proliferation and Differentiation of Chondrocytes and is Essential for Bone Formation," Genes Dev 13, 1999, pp. 2072-2086.
Stone DM, et al., "The Tumour-Suppressor Gene Patched Encodes a Candidate Receptor for Sonic Hedgehog," Nature, vol. 384, 1996, pp. 129-133.
Taipale J, et al., "Patched Acts Catalytically to Suppress the Activity of Smoothened," Nature, vol. 418, 2002, pp. 892-897.
Thayer SP, et al., "Hedgehog is an Early and Late Mediator of Pancreatic Cancer Tumorigenesis," Nature, vol. 425 (2003) pp. 851-856.
Tojo M, et al., "Expression of a Sonic Hedgehog Signal Transducer, Hedgehog-Interacting Protein, by Human Basal Cell Carcinoma," Br J Dermatol 2002, vol. 146, pp. 69-73.
Varnat F, et al., "Human Colon Cancer Epithelial Cells Harbour Active Hedgehog-GLI Signalling that is Essential for Tumour Growth, Recurrence, Metastasis and Stem Cell Survival and Expansion," EMBO Molecular Medicine (2009) vol. 1, pp. 338-351.
Watkins DN, et al., "Hedgehog Signalling Within Airway Epithelial Progenitors and in Small-Cell Lung Cancer," Nature, vol. 422 (2003) pp. 313-317.
Yauch RL, et al., "A paracrine Requirement for Hedgehog Signalling in Cancer," Nature, vol. 455 (2008) pp. 406-410.
Zerr P, et al., "Inhibition of Hedgehog Signalling for the Treatment of Murine Sclerodermatous Chronic Graft-Versus-Host Disease," Blood, vol. 120. No. 14 (2012) pp. 2909-2917.
Zhao C, et al., "Hedgehog Signalling is Essential for Maintenance of Cancer Stem Cells in Myeloid Leukaemia," Nature, vol. 450 (2009) pp. 776-779.
Zhao Y, et al., "Hedgehog Regulates Smoothened Activity by inducing a Conformational Switch," Nature, vol. 450 (2007) pp. 252-258.
Zeisberg M. et al., "Mechanisms of Tubulointerstitial Fibrosis," J. Am. Soc. Nephrol. 21, 2010, pp. 1819-1834.

(56) References Cited

OTHER PUBLICATIONS

Niu, L, et al., "Leptin stimulates alpha1(I) collagen expression in human hepatic stellate cells via the phosphatidylinositol 3-kinase/Akt signalling pathway" Liver Int 27(9)1265-1272 (2007) (full cite).

* cited by examiner

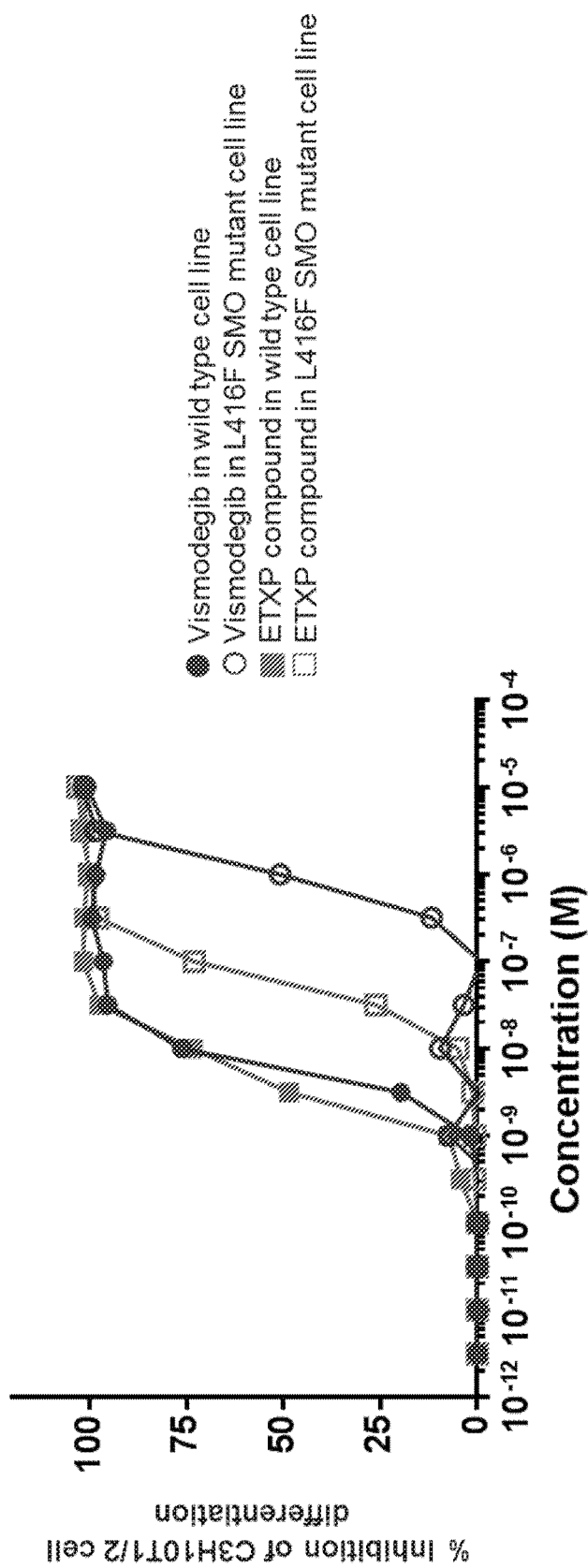
Percent inhibition of C3H10T1/2 cell differentiation of vismodegib compared to compound of the invention (compound number 174), in wild type versus SMO L416F mutant cell line.

MODULATORS OF HEDGEHOG (HH)
SIGNALING PATHWAY

CROSS REFERENCE TO RELATED
APPLICATIONS

This application is a national phase under 35 U.S.C. § 371 of International Patent Application No. PCT/GB2017/053215 filed on Oct. 25, 2017, which claims priority to and benefit of United Kingdom Patent Application Nos. 1618097.8 filed on Oct. 26, 2016 and 1712077.5 filed on Jul. 27, 2017, and the entirety of these applications are incorporated by reference herein.

FIELD OF THE INVENTION

The present invention relates to compounds that are modulators of the hedgehog (Hh) signalling pathway, and their use in the treatment of diseases and/or conditions associated with the abnormal activation and/or malfunction of this pathway.

In particular, compounds of the invention are modulators of the Hh signalling pathway. The present invention also relates to methods for the preparation of the compounds of the invention, to intermediates for their preparation, to pharmaceutical compositions comprising a compound of the invention, to the use of a compound of the invention as therapeutic agents, and to methods for the treatment of diseases and/or conditions associated with the abnormal activation and/or malfunction of Hh signalling pathway by administering a compound of the invention.

BACKGROUND OF THE INVENTION

The evolutionarily conserved Hh signalling pathway plays an important role in tissue development and is a major regulator of cell differentiation, cell proliferation and tissue polarity (Ingham & McMahon, 2001). Disruption of this pathway underlies a variety of developmental disorders affecting multiple organ systems and improper activation of the pathway can lead to malignancy (Pak & Segal, 2016), fibrosis (Fabian et al., 2012), GVHD (Zerr et al, 2012) and amongst other indications, angiogenic disorders.

The Hh signalling pathway is named after a gene first identified in *Drosophila melanogaster*. Mutations of this gene were found to result in a continuous lawn of denticles (spiky processes) covering the anterior half of the larval cuticle, rather than the posterior half where they are usually found (Nusslein-Volhard & Wieschaus, 1980). This unusual phenotype led to the gene name hedgehog (Hh). The Hh gene product was later identified as a secreted glycoprotein ligand that triggers an intracellular signalling cascade critical for segment polarity (Mohler & Vani, 1992). Whilst flies possess one Hh gene, three are found in mammals: Sonic (SHH), Indian (IHH) and Desert (DHH) (Echelard et al., 1993). SHH is the best studied and is of fundamental importance during embryo development and post-natal homeostasis (Echelard et al., 1993; Chiang et al., 1996). There are few parts of the vertebrate body plan that are not influenced in some way by a SHH signal. The other two members of the family, IHE and DHH, have been shown to participate in bone development and spermatogenesis, respectively (Bitgood et al., 1996; St-Jacques et al., 1999). Although vertebrate Hh signalling is critical for many aspects of development, the importance of this pathway in later life appears more limited. During adulthood, the Hh pathway maintains normal tissue homeostasis and plays a regulatory role in stem cells (Lai et al., 2002; Levy et al., 2005).

All Hh proteins are initially synthesized as an inactive precursor protein with an amino-terminal signalling domain and a carboxy-terminal intein-like domain which is later removed by autocatalytic cleavage (Perler, 1998). The Hh signalling pathway is initiated when the Hh protein binds to its receptor, a 12-transmembrane domain (TMD) protein called Patched1 (PTCH1) (Stone et al., 1996). In the absence of the Hh ligand, PTCH1 blocks the downstream pathway by inhibiting the central positive mediator of Hh signalling, a 7-TMD G-protein-coupled-like receptor called Smoothened (SMO) (Alcedo et al., 1996; Murone et al., 1999). When the Hh ligand binds to PTCH1, repression of SMO is released due to internalization and degradation of both PTCH1 and Hh (Incardona et al., 2000). The mechanism by which PTCH1 inhibits SMO and how Hh releases this suppression is unknown, but it is thought that PTCH1 inhibits the transport or synthesis of SMO rather than a direct inhibitory interaction (Taipale et al., 2002). Upon release of PTCH1, SMO is able to enter the primary cilium and become phosphorylated by casein kinase 1 (CK1) and the G-protein coupled receptor kinase 2 (GPRK-2) to assume its activated conformation (Chen et al., 2011). Activated SMO results in nuclear localization and accumulation of the glioma-associated transcription factors (GLi) which are the terminal effectors of the Hh signalling cascade. In mammals there are 3 GLi transcription factors (GLi1, GLi2 and GLi3) (Ruiz i Altaba, 1999). Gli1 and Gli2 function as transcriptional activators of Hh signalling, whereas Gli3 functions primarily as a repressor. Ultimately, it is the balance of the collective activator and repressor functions of the Gli transcription factors that determines the status of the Hh transcriptional program.

Uncontrolled activation of the Hh signalling pathway has been implicated in a wide range of tumours with an estimated 25% of human cancer deaths resulting from cancers with hyperactivated Hh signalling (Berman et al., 2002; Tojo et al., 2002; Thayer et al., 2003; Watkins et al., 2003; Kubo et al., 2004; Sanchez et al., 2004; Dierks et al., 2008). Aberrant activation of the SHH pathway has been shown in a variety of human cancers, including, basal cell carcinoma, malignant gliomas, medulloblastoma, leukaemias, and cancers of the breast, lung, pancreas, and prostate. Tumorigenesis, tumour progression and therapeutic response have all been shown to be impacted by the SHH signalling pathway.

An explanation for this is that Hh pathway has been shown to regulate cell proliferation in adults by activation of genes involved in cell cycle progression such as cyclin D which is involved in G1-S transition. Also, SHH blocks cell-cycle arrest mediated by p21, an inhibitor of cyclin dependent kinases. Hh signalling is further implicated in cancer by inducing components in the EGFR pathway (EGF, Her2) involved in proliferation as well as components in the PDGF (PDGFα) and VEGF pathways involved in angiogenesis. Nuclear accumulation of GLi activates target genes that promote several oncogenic properties to tumour cells, including, genes involved in proliferation (cyclin D1, MYC), resistance to apoptosis (BCL-2), angiogenesis (ANG1/2), epithelial to mesenchymal transition (SNAIL) and stem cell self-renewal (NANOG, SOX2) (Hui & Angers, 2011). Improper activation of the Hh pathway can occur due to somatic mutations in upstream pathway elements such as SMO and PTCH1 (Epstein, 2008; Kool et al., 2008) or due to enhanced SHH ligand signalling (Varnat et al., 2009). Improper activation of the Hh pathway has been studied in detail in two tumour types in particular—basal cell carcinoma and medulloblastoma. Both of these cancers are prevalent in patients with basal cell nevus syndrome, an autosomal dominant disorder that presents itself with craniofacial and skeletal abnormalities. The cause of this syndrome has been found to be due to a loss of function mutation in the PTCH1 gene resulting in dysregulated Hh signalling (Kimonis et al., 1997). The SHH pathway has also been implicated in the regulation and maintenance of cancer stem cells. In chronic myeloid leukaemia and breast cancer, studies have shown that SHH signalling is essential for the maintenance of cancer stem cells and inhibition of the SHH pathway resulted in decreased stem cell propagation and renewal (Zhao et al., 2009). Furthermore, studies in epithelial cancers have found that tumours cells actually secrete the SHH ligand in a paracrine fashion to stimulate the production of growth factors to promote tumour progression and survival (Yauch et al., 2008).

Development of therapeutics targeting the Hh signalling pathway has primarily focused on targeting the SMO and GLi1 proteins. SMO inhibition prevents the downstream activation of the GLi transcription factors leading to suppression of the genes associated with cancer progression. SMO inhibition was first observed during binding studies with the natural steroidal alkaloid cyclopamine. Cyclopamine binds to the heptahelical TMD of SMO and prevents the conformational change that is required to activate SMO (Chen et al., 2002; Zhao et al., 2007). Whilst treatment with cyclopamine was shown to effectively reduce tumour growth in vivo, its efficacy was undermined by many potent side effects (Mimeault et al., 2010).

Vismodegib was developed as a second generation cyclopamine derivative. It also binds to SMO and was the first in class drug approved for treating cancer by targeting of the hedgehog pathway (Robarge et al., 2009). Vismodegib is currently used in the clinic to treat basal cell carcinoma (BCC) (Sekulic et al., 2012). Sonidegib (LDE225, erismodegib) was the second SMO antagonist approved for the treatment of BCC and its mechanism of action has been determined as cell cycle arrest and apoptosis (Pan et al., 2010). There are also several other SMO antagonists currently in clinical trials including saridegib (Phase I), BMS-833923 (Phase I & II), glasdegib (Phase II) and taladegib (Phase I & II) (Rimkus et al., 2016). However, a major setback to the targeting of SMO in the Hh signalling cascade has been the observation of spontaneous mutations that develop as a response to SMO inhibitors (Sharpe et al., 2015). For example, despite initial tumour regression, after 3 months treatment with vismodegib, resistance was observed with the appearance of novel SMO mutations (Metcalfe & de Sauvage, 2011).

The GLi transcription factors have also been singled out as potential therapeutic targets due to their role as the terminal effectors of the hedgehog pathway. However, the list of GLi antagonists (GANTS) is not as extensive as that of SMO antagonists and the only FDA-approved inhibitor of GLi is arsenic trioxide (ATO) which has been approved for the treatment of promyelocytic leukaemia (List et al., 2003). ATO binds directly to GLi1 and GLi2 preventing their nuclear accumulation in response to the Hh signal. This is currently in several clinical trials for a wide range of other cancer types (phase I to IV) (Rimkus et al., 2016). GANTs, were discovered at the National Cancer Institute in a GLi-luciferase reporter assay screen in HEK293 cells. GANT-58 and GANT-61 were both discovered to inhibit GLI-mediated gene activation, though GANT-61 showed more specificity towards GLI proteins and more effectively reduced GLI1 and GLI2 DNA-binding ability. GANT-61 has shown potent inhibition of GLI1 and GLI2 in many cancer cell lines, including rhabdomyosarcoma, osteosarcoma, neuroblastoma, and ovarian cancer (Rimkus et al, 2016). In a human prostate cancer xenograft model in mice, GANT-61 reduced tumour growth and proliferation and strongly reduced expression of PTCH1 mRNA (Rimkus et al, 2016). No clinical trials are currently ongoing using GANT-61 to treat any type of cancer.

Efforts have also been made to develop inhibitors directly targeting SHh as it is the most potent of the three Hh ligands (Pathi et al., 2001). These include a monoclonal antibody 5E1 (Coon et al., 2010) and an inhibitor of the enzyme SHH at which is critical to the synthesis of SHE (Petrova et al., 2013). Both are currently in pre-clinical development (Rimkus et al., 2016).

Due to the prevalence of Hh signalling pathway dysregulation in multiple cancers and the resistance problems associated with current therapeutics, there is a need for potent inhibitors of the Hh signalling pathway, especially those targeting components other than SMO.

Abnormal activation has also been shown to result in excessive extracellular matrix deposition, resulting in fibrosis.

In fibrosis, tissue parenchyma cell necrosis is caused by sustained inflammatory stimulation and is a pathologic process with enhanced production and excessive deposition of extracellular matrix (ECM). Fibrosis is a repairing process and also induces sclerosis and tissue hypofunction when the injury is persistent or the repair process is not sufficient. Tissue fibrosis is the common final outcome of a wide variety of chronic diseases, regardless of the initial causes (Liu, 2006; Boor et al., 2010; Zeisberg and Neilson, 2010). It is known that some signalling pathways have an important role in the occurrence and development of tissue fibrosis, such as Wnt/β-catenin (He et al., 2009), Notch (Bielesz et al., 2010), Ras-Raf-Mek (Grande et al., 2010), and the PI3K/Akt (phosphoinositide 3-kinase/protein kinase B) pathway (Niu et al., 2007). Recently, evidence has suggested that the Hh signalling pathway may be involved in fibrogenesis in multiple tissues (Omenetti et al., 2007; Jung et al., 2011; Fabian et al., 2012). Systemic sclerosis (SSc) is characterized by aberrant activation of fibroblasts with increased release of extracellular matrix components. The hedgehog pathway is activated in patients with SSc. Hedgehog signaling stimulates the release of collagen and myofibroblast differentiation in vitro and is sufficient to induce fibrosis in vivo. These findings identify the hedgehog cascade as a profibrotic pathway in SSc. More specifically, Gli-2 is activated by Hh signaling and induces the transcription of hedgehog target genes. The expression of Gli-2 is significantly increased in the skin fibroblasts of SSc patients compared to healthy controls.

Hh signalling has also been found to be activated in human and murine chronic graft-versus-host disease (cGVHD) with increased expression of SHE and accumulation of the transcription factors GLi-1 and GLi-2. cGVHD is a prognosis limiting complication of allogeneic stem cell transplantation. Treatment with a small-molecule antagonist of SMO, abrogated the activation of Hh signalling and protected against experimental cGVHD (Zerr et al, 2012).

The hedgehog pathway is therefore implicated in numerous conditions where there is unmet clinical need and current hedgehog inhibitors are limited by resistance due to mutations. The compounds of the present invention have been identified as hedgehog modulators useful as a medicament in the treatment of diseases and/or conditions associated with the abnormal activation and/or malfunction of the hedgehog signalling pathway.

SUMMARY OF THE INVENTION

The present invention is based on the identification that a compound of the invention may be useful as a medicament in the treatment of diseases and/or conditions associated with the abnormal activation and/or malfunction of the hedgehog (Hh) signalling pathway. In a particular aspect, a compound of the invention is a modulator of Hh signalling pathway. More particularly, a compound of the invention is useful in the treatment of conditions associated with the abnormal activation of the hedgehog pathway.

The present invention also relates to methods for the preparation of the compounds of the invention, to intermediates for their preparation, to pharmaceutical compositions comprising a compound of the invention, to the use of a compound of the invention as therapeutic agents, and to methods for the treatment of diseases and/or conditions associated with the abnormal activation and/or malfunction of Hh signalling pathway by administering a compound of the invention.

In a one aspect the invention relates to a compound of Formula (I):

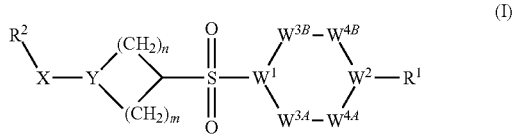

or a pharmaceutically acceptable salt, or a solvate, or a solvate of the salt thereof, for use as a medicament, wherein: integers n and m are selected from:
  (i) 1, 2 and 3, provided that sum of n and m is 2, 3 or 4; or
  (ii) 0 and 1, provided that the sum of n and m is 1;
Y is CH, N or NH, provided that Y is NH only when the sum of n and m is 1;
$W^1$ is N;
$W^2$ is CH, C or N, provided when $W^2$ is C one of $W^{4A}$ and $W^{4B}$ is —CH— and is connected to $W^2$ by a double bond and the other is —$CH_2$—
$W^{3A}$ and $W^{3B}$ are —$CH_2$— or —CH($R^3$)—, wherein $R^3$ is methyl;
$W^{4A}$ and $W^{4B}$ are —$CH_2$— or —CH—, provided that when one of $W^{4A}$ and $W^{4B}$ is —CH— the other is —$CH_2$—;
$R^1$ is selected from:
  (i) a fused 9-10 membered bicyclic heteroaryl optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —C(=O)O$C_{1-6}$alkyl, —O(C=O)$C_{1-6}$alkyl, —C(=O)O—$C_{0-4}$alkyl-cycloalkyl, $C_{0-6}$alkyl-phenyl (wherein phenyl may be optionally substituted by $C_{1-4}$alkyl), —C(=O)NH$C_{1-6}$alkyl, —NHC(=O)$C_{1-6}$alkyl, —$SO_2$—$C_{1-6}$alkyl, —$SO_2$—N($C_{1-6}$ alkyl)$_2$, —$SO_2$-phenyl, and 5-6-membered heteroaryl wherein phenyl and heteroaryl independently from each other may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;
  (ii) 5-6 membered heteroaryl optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —C(=O)O$C_{1-6}$alkyl, —O(C=O)$C_{1-6}$alkyl, —C(=O)O—$C_{0-4}$alkyl-cycloalkyl, $C_{0-6}$alkyl-phenyl (wherein phenyl may be optionally substituted by $C_{1-4}$alkyl), —C(=O)NH$C_{1-6}$alkyl, —NHC(=O)$C_{1-6}$alkyl, —$SO_2$—$C_{1-6}$alkyl, —$SO_2$—N($C_{1-6}$ alkyl)$_2$, —$SO_2$-phenyl, and 5-6-membered heteroaryl wherein phenyl and heteroaryl independently from each other may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;
  (iii) 6-10 membered aryl optionally substituted by one or more groups independently selected from halogen, CN, OH, $NO_2$, $C_{1-6}$alkyl, $C_{2-6}$alkenyl, $C_{2-6}$alkynyl, —$OC_{1-6}$alkyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl;
  (iv) a fused 8-10 membered partially unsaturated bicyclic heterocyclyl optionally substituted by one or more groups independently selected from halogen, CN, OH, $NO_2$, $C_{1-6}$alkyl, $C_{2-6}$alkenyl, $C_{2-6}$alkynyl, —$OC_{1-6}$alkyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl; and
  (v) a 5-6 membered monocyclic heterocycloalkyl optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;
X is absent or a bivalent group selected from:
  (a) —($CH_2$)$x^1$-, wherein $x^1$ is 1, 2 or 3;
  (b) —($CH_2$)$x^2$-C($CH_3$)$_2$—($CH_2$)$x^3$-, wherein $x^2$ is 1 or 2 and $x^3$ is 1;
  (c) —C(=O)—($CH_2$)$x^4$-, wherein $x^4$ is zero, 1 or 2;
  (d) —C(=O)O—($CH_2$)$x^5$-, wherein $x^5$ is zero, 1, 2 or 3;
  (e) —C(=O)$NR^x$—($CH_2$)$x^6$-, wherein
    (e.i) $x^6$ is zero, 1 or 2 and $R^x$ is H or $C_{1-4}$alkyl, or
    (e.ii) $x^6$ is zero and $R^x$ together with $R^2$ and with nitrogen to which $R^x$ and $R^2$ are attached form a heterocycloalkyl ring which may have one additional heteroatom selected from O or N, and said heterocycloalkyl may be optionally substituted by one or more $C_{1-4}$alkyl groups;

(f) —C(=S)NR^y—, wherein R^y is H or $C_{1-4}$alkyl; and
(g) —SO_2—;
R^2 is selected from:
(i) $C_{1-10}$alkyl optionally substituted by one or more groups independently selected from OH, —OC_{1-4}alkyl, —NHC_{1-4}alkyl, and —N(C_{1-4}alkyl)_2;
(ii) —NHC_{1-4}alkyl, —N(C_{1-4}alkyl)_2;
(iii) 3-10 membered cycloalkyl optionally substituted by one or more groups independently selected from OH, halogen, CN, NH_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, —$C_{1-6}$alkyl-OH, —C(=O)C_{1-6}alkyl, —C(=O)OC_{1-6}alkyl, —C(=O)OH, —C(=O)NH_2, —C_{0-6}alkyl-NH—C_{1-6}alkyl and —C_{0-6}alkyl-N(C_{1-6}alkyl)_2;
(iv) 5-6 membered heterocycloalkyl optionally substituted by one or more groups independently selected from OH, halogen, CN, NH_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, —C_{1-6}alkyl-OH, —C(=O)C_{1-6}alkyl, —C(=O)OC_{1-6}alkyl, —C(=O)OH, and —C(=O)NH_2;
(v) phenyl optionally substituted by one or more groups independently selected from halogen, CN, OH, NO_2, $C_{1-6}$alkyl, $C_{2-6}$alkenyl, $C_{2-6}$alkynyl, —OC_{1-6}alkyl, O-phenyl, haloC_{1-6}alkyl, haloC_{1-6}alkyloxy, —C_{1-6}alkyl-OH, NH_2, N—(C_{1-6}-alkyl)amino, N,N-di(C_{1-6}alkyl)amino, —C(=O)C_{1-6}alkyl, —C(=O)OH, —O(C=O)C_{1-6}alkyl, —C(=O)OC_{1-6}alkyl, —C(=O)NHC_{1-6}alkyl and —NHC(=O)C_{1-6}alkyl;
(vi) 5-6 membered heteroaryl optionally substituted by one or more groups independently selected from halogen, CN, OH, NO_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, C_{1-6}alkyl-OH, NH_2, N—(C_{1-6}-alkyl)amino, N,N-di(C_{1-6}alkyl)amino, —C(=O)C_{1-6}alkyl, —OC(=O)C_{1-6} alkyl, —C(=O)OH, —C(=O)OC_{1-6}alkyl, —C(=O)NHC_{1-6}alkyl, —NHC(=O)C_{1-6}alkyl, and 3-6-membered cycloalkyl wherein said cycloalkyl may optionally be substituted by one or more groups independently selected from halogen, CN, OH, NO_2, $C_{1-6}$alkyl, $C_{2-6}$alkenyl, $C_{2-6}$alkynyl, haloC_{1-6}alkyloxy, NH_2, N—(C_{1-6}-alkyl)amino, N,N-di(C_{1-6}alkyl)amino, —C(=O)C_{1-6}alkyl, —OC(=O)C_{1-6}alkyl, —C(=O)OH, —C(=O)OC_{1-6}alkyl, —C(=O)NHC_{1-6}alkyl and —NHC(=O)C_{1-6}alky; and
(vii) H and X is absent.
In one aspect the invention relates to a compound of the invention according to Formula (I):

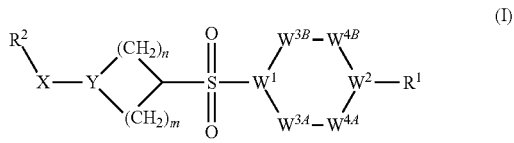

(I)

or a salt, or a solvate, or a solvate of the salt thereof,
wherein,
integers n and m are selected from:
(i) 1, 2 and 3, provided that sum of n and m is 2, 3 or 4; or
(ii) 0 and 1, provided that the sum of n and m is 1;
Y is CH, N or NH, provided that Y is NH only when the sum of n and m is 1;
W^1 is N;
W^2 is CH, C or N, provided when W^2 is C one of W^{4A} and W^{4B} is —CH— and is connected to W^2 by a double bond and the other is —CH_2—
W^{3A} and W^{3B} are —CH_2— or —CH(R^3)—, wherein R^3 is methyl;
W^{4A} and W^{4B} are —CH_2— or —CH—, provided that when one of W^{4A} and W^{4B} is —CH— the other is —CH_2—;
R^1 is selected from:
(i) a fused 9-10 membered bicyclic heteroaryl optionally substituted by one or more groups independently selected from halogen, CN, OH, NO_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, —C_{1-6}alkyl-OH, NH_2, N—(C_{1-6}-alkyl)amino, N,N-di(C_{1-6}alkyl)amino, —C(=O)C_{1-6}alkyl, —C(=O)OH, —C(=O)OC_{1-6}alkyl, —O(C=O)C_{1-6}alkyl, —C(=O)O—C_{0-4}alkyl-cycloalkyl, C_{0-6}alkyl-phenyl (wherein phenyl may be optionally substituted by C_{1-4}alkyl), —C(=O)NHC_{1-6}alkyl, —NHC(=O)C_{1-6}alkyl, —SO_2—C_{1-6}alkyl, —SO_2—N(C_{1-6} alkyl)_2, —SO_2-phenyl, and 5-6-membered heteroaryl wherein phenyl and heteroaryl independently from each other may be optionally substituted by one or more groups independently selected from halogen, CN, OH, NO_2, $C_{1-6}$alkyl, $C_{2-6}$alkenyl, $C_{2-6}$alkynyl, haloC_{1-6} alkyl, —OC_{1-6}alkyl, haloC_{1-6}alkyloxy, C_{1-6}alkyl-OH, NH_2, N—(C_{1-6}-alkyl)amino, N,N-di(C_{1-6}alkyl)amino, —C(=O)C_{1-6}alkyl, —OC(=O)C_{1-6} alkyl, —C(=O)OH, —C(=O)OC_{1-6}alkyl, —C(=O)NHC_{1-6}alkyl and —NHC(=O)C_{1-6}alkyl, provided that when W^1 is N, W^{3A}, W^{3B}, W^{4A}, and W^{4B} are —CH_2—, n and m are 1 or 2, sum of n and m is 3, X is —(CH_2)x^1, x^1 is 1, and R^2 is unsubstituted phenyl, then R^1 cannot represent benzothiazole-2-yl;
(ii) 5-6 membered heteroaryl optionally substituted by one or more groups independently selected from halogen, CN, OH, NO_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, —C_{1-6}alkyl-OH, NH_2, N—(C_{1-6}-alkyl)amino, N,N-di(C_{1-6}alkyl)amino, —C(=O)C_{1-6}alkyl, —C(=O)OH, —C(=O)OC_{1-6}alkyl, —O(C=O)C_{1-6}alkyl, —C(=O)O—C_{1-4}alkyl-cycloalkyl, C_{0-6}alkyl-phenyl (wherein phenyl may be optionally substituted by C_{1-4}alkyl), —C(=O)NHC_{1-6}alkyl, —NHC(=O)C_{1-6}alkyl, —SO_2—C_{1-6}alkyl, —SO_2—N(C_{1-6} alkyl)_2, —SO_2-phenyl, and 5-6-membered heteroaryl wherein phenyl and heteroaryl independently from each other may be optionally substituted by one or more groups independently selected from halogen, CN, OH, NO_2, $C_{1-6}$alkyl, $C_{2-6}$alkenyl, $C_{2-6}$alkynyl, haloC_{1-6}alkyl, —OC_{1-6}alkyl, haloC_{1-6}alkyloxy, C_{1-6}alkyl-OH, NH_2, N—(C_{1-6}-alkyl)amino, N,N-di(C_{1-6}alkyl)amino, —C(=O)C_{1-6}alkyl, —OC(=O)C_{1-6}alkyl, —C(=O)OH, —C(=O)OC_{1-6}alkyl, —C(=O)NHC_{1-6}alkyl and —NHC(=O)C_{1-6}alkyl;
(iii) 6-10 membered aryl optionally substituted by one or more groups independently selected from halogen, CN, OH, NO_2, $C_{1-6}$alkyl, $C_{2-6}$alkenyl, $C_{2-6}$alkynyl, —OC_{1-6}alkyl, haloC_{1-6}alkyl, haloC_{1-6}alkyloxy, —C_{1-6}alkyl-OH, NH_2, N—(C_{1-6}-alkyl)amino, N,N-di(C_{1-6}alkyl)amino, —C(=O)C_{1-6}alkyl, —C(=O)OH, —O(C=O)C_{1-6}alkyl, —C(=O)OC_{1-6}alkyl, —C(=O)NHC_{1-6}alkyl and —NHC(=O)C_{1-6}alkyl;
(iv) a fused 8-10 membered partially unsaturated bicyclic heterocyclyl optionally substituted by one or more groups independently selected from halogen, CN, OH, NO_2, $C_{1-6}$alkyl, $C_{2-6}$alkenyl, $C_{2-6}$alkynyl, —OC_{1-6}alkyl, haloC_{1-6}alkyl, haloC_{1-6}alkyloxy, —C_{1-6}alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl; and (v) a 5-6 membered monocyclic heterocycloalkyl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

X is absent or a bivalent group selected from:
(a) —(CH$_2$)x$^1$-, wherein x$^1$ is 1, 2 or 3;
(b) —(CH$_2$)x$^2$-C(CH$_3$)$_2$—(CH$_2$)x$^3$-, wherein x$^2$ is 1 or 2 and x$^3$ is 1;
(c) —C(=O)—(CH$_2$)x$^4$-, wherein x$^4$ is zero, 1 or 2;
(d) —C(=O)O—(CH$_2$)x$^5$-, wherein x$^5$ is zero, 1, 2 or 3;
(e) —C(=O)NR$^x$—(CH$_2$)x$^6$-, wherein
 (e.i) x$^6$ is zero, 1 or 2 and R$^x$ is H or C$_{1-4}$alkyl, or
 (e.ii) x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl may be optionally substituted by one or more C$_{1-4}$alkyl groups;
(f) —C(=S)NR$^y$—, wherein R$^y$ is H or C$_{1-4}$alkyl; and
(g) —SO$_2$—;

R$^2$ is selected from:
(i) C$_{1-10}$alkyl optionally substituted by one or more groups independently selected from OH, —OC$_{1-4}$alkyl, —NHC$_{1-4}$alkyl, and —N(C$_{1-4}$alkyl)$_2$;
(ii) —NHC$_{1-4}$alkyl, —N(C$_{1-4}$alkyl)$_2$;
(iii) 3-10 membered cycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$;
(iv) 5-6 membered heterocycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, and —C(=O)NH$_2$;
(v) 6-membered aryl (phenyl) optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl, provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$alkyl, and pyridyl optionally substituted by halogen;
(vi) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl, —NHC(=O)C$_{1-6}$alkyl, and 3-6-membered cycloalkyl wherein said cycloalkyl may optionally be substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alky; and (vii) H and X is absent, provided that when W$^1$ is N, W$^2$ is CH, W$^{3A}$, W$^{3B}$, W$^{4A}$, and W$^{4B}$ are —CH$_2$—, sum of n and m is 3 or 4, then R$^1$ cannot represent piperidinyl, and when W$^1$ and W$^2$ are N, W$^{3A}$, W$^{3B}$, W$^{4A}$, and W$^{4B}$ are —CH$_2$—, sum of n and m is 3 or 4, then R$^1$ cannot represent phenyl optionally substituted by CH$_3$ or halogen, pyridinyl, pyrimidinyl or thiazolyl;

provided that when X is —(C=O)(CH$_2$)x$^4$, x$^4$ is zero, R$^2$ is unsubstituted cyclopentyl or phenyl optionally substituted by halogen, W$^1$ is N, W$^2$ is CH or N, W$^{3A}$ and W$^{3B}$ are —CH$_2$— or —CH(R$^3$)—, R$^3$ is CH$_3$, W$^{4A}$, and W$^{4B}$ are —CH$_2$—, then R$^1$ is a fused 9-10 membered bicyclic heteroaryl or a fused 8-10 membered partially unsaturated bicyclic heterocyclyl; or a pharmaceutically acceptable salt or a solvate thereof.

The present invention also relates to pharmaceutical compositions comprising a compound of the invention.

In a further aspect, the present invention provides a pharmaceutical composition comprising a compound of the invention and a pharmaceutical carrier, excipient or diluent.

According to the invention there is further provided a pharmaceutical composition comprising a compound of the invention for use in the treatment of conditions involving abnormal activation and/or malfunction of the of the hedgehog pathway whereby the condition involving abnormal activation of the hedgehog pathway is one or more of cancer, fibrosis and chronic graft-versus-host disease (cGVHD).

According to this aspect of the invention there is further provided a pharmaceutical composition comprising a compound of the invention for use in the treatment of conditions involving abnormal activation and/or malfunction of the of the hedgehog pathway whereby the condition involving abnormal activation of the hedgehog pathway is cancer, as herein defined.

According to a further aspect of the invention there is provided a pharmaceutical composition comprising a compound of the invention for use in the treatment of conditions involving abnormal activation of the hedgehog pathway whereby the condition involving abnormal activation of the hedgehog pathway is fibrosis, as herein defined.

According to a further aspect of the invention there is provided a pharmaceutical composition comprising a compound of the invention for use in the treatment of conditions involving abnormal activation of the hedgehog pathway whereby the condition involving abnormal activation of the hedgehog pathway is Chronic graft-versus-host disease (cGVHD), as herein defined.

In a particular aspect, the pharmaceutical composition may additionally comprise a second therapeutically active ingredient suitable for use in combination with compounds of the invention.

Moreover, the compounds of the invention, useful in the pharmaceutical compositions and treatment methods disclosed herein, are pharmaceutically acceptable as prepared and used.

In another aspect, the invention relates to a compound of the invention for use in therapy.

In a further aspect, the invention relates to a compound of Formula I for use in the manufacture of a medicament for the treatment of diseases and/or conditions associated with the abnormal activation and/or malfunction of the hedgehog (Hh) signalling pathway.

In another aspect, the invention relates to the use of a compound of the invention in the manufacture of a medicament for the treatment of diseases and/or conditions associated with the abnormal activation and/or malfunction of the hedgehog (Hh) signalling pathway.

According to this aspect of the invention the disease or condition associated with the abnormal activation or malfunction of the Hh signalling pathway is one or more of cancer, fibrosis and chronic graft-versus-host disease (cGVHD).

According to this aspect of the invention there is further provided a compound of Formula I for use in the treatment of conditions involving abnormal activation and/or malfunction of the of the hedgehog pathway whereby the condition involving abnormal activation of the hedgehog pathway is cancer, as herein defined.

According to a further aspect of the invention there is provided a compound of Formula I for use in the treatment of conditions involving abnormal activation of the hedgehog pathway whereby the condition involving abnormal activation of the hedgehog pathway is fibrosis, as herein defined.

According to a further aspect of the invention there is provided a compound of Formula I for use in the treatment of conditions involving abnormal activation of the hedgehog pathway whereby the condition involving abnormal activation of the hedgehog pathway is Chronic graft-versus-host disease (cGVHD), as herein defined.

In a further aspect, the invention relates to methods of the treatment of diseases and/or conditions associated with the abnormal activation and/or malfunction of the hedgehog (Hh) signalling pathway by administering of an effective amount of a compound of the invention or one or more pharmaceutical compositions of the invention.

In another aspect of the invention, this invention provides methods of treatment of a subject, in particular humans, susceptible to or afflicted with diseases and/or conditions associated with the abnormal activation and/or malfunction of the hedgehog (Hh) signalling pathway selected from among those listed herein, and particularly proliferative diseases, which methods comprise the administration of an effective amount of a compound of the invention or one or more pharmaceutical compositions of the invention.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

DETAILED DESCRIPTION OF THE INVENTION

Definitions

It will be understood that the present invention covers all combinations of aspects, suitable, convenient and preferred groups described herein.

When describing the invention, which may include processes, compounds, pharmaceutical compositions containing such compounds and methods of using such compounds and compositions, the following terms, if present, have the following meanings unless otherwise indicated. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

When ranges are referred to herein, for example but without limitation, $C_{0-6}$alkyl, the citation of a range should be considered a representation of each member of said range. By way of example $C_0$alkyl means that alkyl group is absent. Thus, for example, selected member $C_0$alkyl-aryl of a range $C_{0-6}$alkyl-aryl means that aryl group is directly attached without an alkyl spacer.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxylacetyl, and the like.

The term "alkyl" as used herein as a group or a part of a group refers to a straight or branched aliphatic hydrocarbon having the specified number of carbon atoms. Particular alkyl groups have 1 to 18 carbon atoms; more particular alkyl groups have 1 to 6 carbon atoms, and even more particular alkyl groups have 1 to 4 carbon atoms. Suitably alkyl groups have 1 or 2 carbon atoms. Branched means that one or more alkyl groups such as methyl, ethyl or propyl is attached to a linear alkyl chain. Exemplary branched chain groups include isopropyl, iso-butyl, t-butyl and isoamyl. Examples of alkyl groups as used herein include methyl, ethyl, n-propyl, isopropyl, n-butyl, tert-butyl, sec-butyl, n-pentyl, n-hexyl, 1,2-dimethylbutyl, octyl, decyl, undecyl, dodecyl tridecyl, tetradecyl, pentadecyl, hexadecyl, heptadecyl and octadecyl.

The term "alkyloxy" or "alkoxy", as used herein, refers to a straight or branched chain alkyl group, as previously defined, attached to the parent molecular moiety through an oxygen atom containing the specified number of carbon atoms. Particular alkoxy groups have between 1 and 6 carbon atoms. More particular alkoxy groups have between 1 and 4 carbon atoms. For example, $C_{1-4}$alkoxy means a straight or branched alkoxy containing at least 1, and at most 4, carbon atoms. Examples of "alkoxy" as used herein include, but are not limited to, methoxy, ethoxy, n-propoxy, isopropoxy, n-butoxy, tert-butoxy, sec-butoxy, n-pentoxy, n-hexoxy, and 1,2-dimethylbutoxy.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Particular "alkenyl" groups have 2 to 4 carbon atoms and containing at least one double bond. Examples of "alkenyl" as used herein include ethenyl, 2-propenyl, 3-butenyl, 2-butenyl, 2-pentenyl, 3-pentenyl, 3-methyl-2-butenyl, 3-methyl but-2-enyl, 3-hexenyl and 1,1-dimethylbut-2-enyl.

The term "alkynyl" as used herein as a group or a part of a group refers to a straight or branched hydrocarbon chain containing the specified number of carbon atoms and containing at least one triple bond. For example, the term "$C_{2-6}$alkynyl" means a straight or branched alkynyl containing at least 2, and at most 6, carbon atoms and containing at least one triple bond. Examples of "alkynyl" as used herein include, but are not limited to, propynyl, 1-butynyl, 2-butynyl, 1-pentynyl and 3-methyl-1-butynyl.

The term "alkylene" as used herein as a group or a part of a group refers to a branched or straight chained alkyl group containing from 1 to 6 carbon atoms, having single bonds for attachment to other groups at two different carbon atoms. Examples of such alkylene groups include methylene, ethylene, n-propylene, isopropylene, n-butylene, isobutylene, pentylene, and hexylene. Particular alkylene groups have between 1 and 4 carbon atoms. More particular it is methylene (—$CH_2$—) or ethylene (—$CH_2$—$CH_2$—).

The term "amino" refers to the radical —$NH_2$.

The term "amino protecting group" refers to a substituent on a functional amino group which prevent undesired reactions and degradations during synthetic procedures are carried out on other functional groups on the compound, and which may be selectively removed after certain synthetic step. Examples of 'amino protecting group' include: acyl type protecting groups (e.g. formyl, trifluoroacetyl and acetyl), aromatic urethane type protecting groups (e.g. benzyloxycarbonyl (Cbz) and substituted Cbz and 9-fluorenyl-methoxycarbonyl (Fmoc)), aliphatic urethane protecting groups (e.g. methoxycarbonyl, ethoxycarbonyl, t-butyloxycarbonyl (Boc), isopropyloxycarbonyl and cyclohexyloxycarbonyl) and alkyl type protecting groups (e.g. benzyl, trityl, chlorotrityl).

The term "aryl" refers to a monovalent aromatic hydrocarbon group derived by the removal of one hydrogen atom from a single carbon atom of a parent aromatic ring system. In particular aryl refers to a mono-, bicyclic or tricyclic carbocyclic ring system having at least one aromatic ring that includes the number of ring members specified. Specifically, the term includes groups that have from 6 to 10 ring members. Where the aryl group is a monocyclic ring system it preferentially contains 6 carbon atoms and is phenyl. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, tetrahydronaphthalene and trinaphthalene. Particularly aryl groups include phenyl, naphthyl, indenyl, and tetrahydronaphthyl. More particular aryl group is phenyl.

The term "carboxy" refers to the radical —C(O)OH.

The term "carbamoyl" or "amido" refers to the radical —C(O)$NH_2$.

The term "comprise", and variations such as "comprises" and "comprising", throughout the specification and the claims which follow, unless the context requires otherwise, will be understood to imply the inclusion of a stated integer or step or group of integers but not to the exclusion of any other integer or step or group of integers or steps.

The term "compound(s) of the invention" or "compound(s) according to the invention", and equivalent expressions refers to compounds of Formula (I) (whether in solvated or unsolvated form), as herein described, including any subset or embodiment of compounds of Formula (I), or their pharmaceutically acceptable salts (whether in solvated or unsolvated form). Suitably, said expression includes the pharmaceutically acceptable salts, and solvates (e.g. hydrates) thereof. The compound(s) of the invention may possess one or more asymmetric centres; such compounds can therefore be produced as individual (R)- or (S)-stereoisomers or as mixtures thereof. Where stereochemistry is not defined in the relevant Formula (e), then the term compound(s) of the invention includes enantiomers and diastereoisomers of these compounds.

The term "cyano" to the radical —CN.

The term "cycloalkyl" as used herein, refers to a monocyclic or polycyclic saturated hydrocarbon ring containing the stated number of carbon atoms, for example, 3 to 10 carbon atoms. Particular "cycloalkyl" groups are monocyclic or four connected cyclohexane ring like in case of adamantane. Examples of "cycloalkyl" groups include cyclopropyl, cyclobutyl, cyclopentyl, cyclohexyl, cycloheptyl, bicyclo[2.2.1]heptyl, cyclooctyl, cyclononyl, cyclodecycl, and adamantly. Particular cycloalkyl groups include cyclopropyl, cyclobutyl, cyclopentyl, cyclohexyl and adamantyl.

The term "cycloalkenyl" as used herein, refers to a monocyclic hydrocarbon ring containing the stated number of carbon atoms, for example, 3 to 7 carbon atoms, and at least one double bond. Examples of "cycloalkenyl" groups include cyclopropenyl, cyclobutenyl, cyclopentenyl, cyclohexenyl and cycloheptenyl. Particular cycloalkenyl groups include cyclopentenyl and cyclohexenyl. More particular cycloalkenyl group is cyclohexenyl.

The term "halogen" or "halo" or "Hal" refers to fluoro (F), chloro (Cl), bromo (Br) and iodo (I). Particular halo groups are either fluoro or chloro. More particular halo group is chloro.

The term "hetero" when used to describe a compound or a group present on a compound means that one or more carbon atoms in the compound or group have been replaced by a nitrogen, oxygen, or sulfur heteroatom. For example, having from 1 to 4 heteroatoms, particularly from 1 to 3 heteroatoms, and more typically 1 or 2 heteroatoms, for example a single heteroatom.

The term "heteroaryl or heteroaromatic" as used herein refers to a 5-6 membered monocyclic aromatic ring or a fused 9-10 membered bicyclic aromatic ring containing up to four heteroatoms independently selected from nitrogen, sulphur and oxygen and the number of ring members specified. Monocyclic heteroaryl ring may contain up to three heteroatoms. Typically, monocyclic heteroaryl will contain up to 3 heteroatoms, usually up to 2, for example a single heteroatom. The bicyclic heteroaryl may contain up to four heteroatoms. Typically, bicyclic heteroaryl will contain up to 4 heteroatoms, more typically up to 3 heteroatoms, more usually up to 2, for example a single heteroatom. In one embodiment, the heteroaryl ring contains at least one or two nitrogen atoms. The nitrogen atoms in the heteroaryl rings can be basic, as in the case of an imidazole or pyridine, or essentially non-basic as in the case of a pyrrole nitrogen. In general, the number of basic nitrogen atoms present in the heteroaryl group, including any amino group substituents of the ring, will be less than five. Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, thiadiazolyl and tetrazolyl groups. Examples of six membered monocyclic heteroaryl groups include but are not limited to pyridinyl, pyrazinyl, pyridazinyl, pyrimidinyl, triazinyl and tetrazinyl. Particular monocyclic heteroaryl groups are those derived from imidazole, pyrazole and pyridine.

Examples of fused heteroaryl rings include pyrrolopyridine, pyrrolopyrimidine, pyrazolopyridine, thienopyridine, furopyridine, azaindole, diazaindole, imidazopyridine, benzothiazole, quinoline, isoquinoline, quinazoline, quinoxaline, pteridine, cinnoline, phthalazine, naphthyridine, indole, isoindole, indazole, purine, benzofurane, isobenzofurane, benzoimidazole, benzoxazole, benzoisoxazole, benzoisothiazole, benzoxadiazole, benzothiadiazole, and the like. Particular fused heteroaryl groups are derived from pyrrolopyridine, pyrrolopyrimidine, pyrazolopyridine, thienopyridine, furopyridine, indole, azaindole, diazaindole, imidazopyridine, benzothiazole, quinoline, in particular pyrrolopyridine.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen) and preferably 1 to 4 heteroatoms.

The term "heterocyclic" as used herein, refers to a stable non-aromatic 3-, 4-, 5-, 6- or 7-membered monocyclic ring or a 7-, 8-, 9-, 10-, 11- or 12-membered bicyclic ring or a 10-, 11-, 12-, 13-, 14- or 15-membered tricyclic ring; each of which may be saturated or partially unsaturated containing at least one, e.g. 1 to 3, heteroatoms selected from oxygen, nitrogen or sulphur, where in a 8-12 membered bicyclic heterocycle one ring may be aromatic but the other one has to be fully saturated and one ring may be carbocyclic and need to include one heterocyclic ring. Monocyclic heterocycle ring may contain up to three heteroatoms. Typically, monocyclic heterocycle will contain up to 3 heteroatoms, usually up to 2, for example a single heteroatom. The bicyclic heterocycle may contain up to four heteroatoms. Typically, bicyclic heterocycle will contain up to 4 heteroatoms, more typically up to 3 heteroatoms, more usually up to 2, for example a single heteroatom. In one embodiment, the heterocycle ring contains at least one or two heteroatoms. The nitrogen and sulfur heteroatoms may optionally be oxidized, and the nitrogen heteroatom may optionally be quaternized. Examples of monocyclic rings include azetidine, pyrrolidine, pyrazolidine, oxazolidine, piperidine, piperazine, pyrane, morpholine, thiomorpholine, thiazolidine, oxirane, oxetane, dioxolane, dioxane, oxathiolane, oxathiane, dithiane, dihydrofurane, tetrahydrofurane, dihydropyrane, tetrahydropyrane, tetrahydropyridine, tetrahydropyrimidine, tetrahydrothiophene, tetrahydrothiopyrane and the like. Particular monocyclic heterocyclic groups include pyrrolidinyl, piperidinyl, piperazinyl, tetrahydropyranyl, morpholinyl and azetidinyl. Examples of bicyclic rings include 6,8-dihydro-5H-imidazo[1,2-a]pyrazine, 6,7-dihydro-5H-pyrrolo[1,2-a]imidazole, 5,6,7,8-tetrahydro-imidazo[1,2-a]pyridine, 2,3-dihydro-furo[3,2-b]pyridine, indoline, isoindoline, benzodioxole, tetrahydroisoquinoline and the like.

As used herein, the term "heterocycloalkyl" refers to a stable non-aromatic ring structure, mono-cyclic or polycyclic, containing one or more heteroatoms, particularly one or two heteroatoms independently selected from N, O and S and the number of ring atoms specified. The heterocycloalkyl ring structure may have from 3 to 7 ring members. A fused heterocyclic ring system may include carbocyclic rings and need only include one heterocyclic ring. Examples of heterocyclic rings include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone (2-pyrrolidone or 3-pyrrolidone), tetrahydrofuran, tetrahydrothiophene, dioxane, tetrahydropyran (e.g. 4-tetrahydro pyranyl), imidazolidinone, pyrazolidine, piperazine, and N-alkyl piperazines such as N-methyl piperazine and the like. Further examples include thiomorpholine and its S-oxide and S,S-dioxide (particularly thiomorpholine). Still further examples include azetidine, piperidone, piperazone, and N-alkyl piperidines such as N-methyl piperidine. Particular "heterocycloalkyl" groups are monocyclic. Particular heterocycloalkyl groups include pyrrolidinyl, piperidinyl, piperazinyl, tetrahydropyranyl, morpholinyl and azetidinyl.

As used herein, the term "heterocycloalkenyl" refers to a stable non-aromatic ring structure, mono-cyclic or polycyclic, containing one or more heteroatoms, particularly one or two heteroatoms independently selected from N, O and S, and the number of ring atoms specified, and further containing at least one carbon-carbon double bonds or carbon-heteroatom double bonds in the ring as long as the ring is not rendered aromatic by their presence. The heterocycloalkenyl structure may have from 3 to 7 ring members. A fused heterocycloalkenyl ring system may include carbocyclic rings and need only include one heterocycloalkenyl ring. Examples of heterocyclic rings include pyran (2H-pyran or 4H-pyran), dihydrothiophene, dihydropyran, dihydrofuran (2,3-dihydrofuran or 2,5-dihydrofuran), dihydrothiopyran, dihydrothiazole, imidazoline (2-imidazoline, 3-imidazoline, and 4-imidazoline), oxazoline, thiazoline, 2-pyrazoline, tetrahydropyridine, and the like. Still further examples include N-alkyl tetrahydropyridine such as N-methyl tetrahydropyridine.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

The term "hydroxy" or "hydroxyl" refers to the radical —OH.

The term "hydroxy protecting group" refers to a substituent on an functional hydroxyl group which prevent undesired reactions and degradations during synthetic procedures, and which may be selectively removed after certain synthetic step. Examples of 'hydroxy protecting group' include: ester and ether hydroxyl protecting group. Examples of ester hydroxyl protecting group include: formyl, —OC(O)C$_{1-4}$alkyl such as acetyl (Ac or —C(O)CH$_3$), methoxyacetyl, chloroacetyl, dichloroacetyl, trichloroacety, trifluoroacetyl, triphenylmethoxyacetyl, phenoxyacetyl, benzoylformyl, benzoyl (Bz or —C(O)C$_6$H$_5$), benzyloxycarbonyl (Cbz or —C(O)—O—CH$_2$C$_6$H$_5$), methoxycarbonyl, tert-butoxycarbonyl, isopropoxycarbonyl, diphenylmethoxycarbonyl or 2-(trimethylsilyl)ethoxycarbonyl and the like. Examples of ether hydroxyl protecting group include: alkyl silyl groups such as trimethylsilyl (TMS), tert-butyldimethylsilyl, triethylsilyl, triisopropylsilyl and the like. Examples of suitable "hydroxy protecting group" include; —OC(O)C$_{1-4}$ alkyl such as acetyl (Ac or —C(O)CH$_3$), benzoyl (Bz), benzyloxycarbonyl (Cbz) and trimethylsilyl (TMS). Suitably, "hydroxy protecting group" is: triethylsilyl or acetyl (Ac or —C(O)CH$_3$). Conveniently, "hydroxy protecting group" is: Ac or Cbz.

The term "sulfonamide" refers to the —NR—SO$_2$—R wherein each R is independently H, alkyl, carbocycle, heterocycle, carbocycloalkyl or heterocycloalkyl), a carbocycle or a heterocycle. Particular sulfonamide groups are alkylsulfonamide (e.g. —NH—SO$_2$-alkyl), for example methylsulfonamide; arylsulfonamdie (i.e. —NH—SO$_2$-aryl) for example phenylsulfonamide; aralkylsulfonamide, for example benzylsulfonamide.

The term "sulfonyl" means a —SO$_2$—R group wherein R is alkyl, carbocycle, heterocycle, carbocycloalkyl or heterocycloalkyl. Particular sulfonyl groups are alkylsulfonyl (i.e. —SO$_2$— alkyl), for example methylsulfonyl; arylsulfonyl, for example phenylsulfonyl; aralkylsulfonyl, for example benzylsulfonyl.

The term "nitro" refers to the radical —NO$_2$.

The term "cyano" refers to the radical —CN.

The term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties. Only in case of fused 8-9 membered heterocycle one of the ring moieties may be aromatic but in that case the other ring of such fused 8-9-membered heterocycle has to be saturated.

The term "intermediates(s) of the invention" or "intermediate(s) according to the invention", and equivalent expressions refers to compounds of formulae (II), (III), (IV) and (V) (whether in solvated or unsolvated form), as herein described, including any subset or embodiment of compounds of formulae (II), (III), (IV) and (V), or their salts (whether in solvated or unsolvated form). Suitably, said expression includes the salts, and solvates (e.g. hydrates) thereof. The intermediate(s) of the invention may possess one or more asymmetric centres; such intermediate(s) can therefore be produced as individual (R)- or (S)-stereoisomers or as mixtures thereof. Where stereochemistry is not defined in the relevant Formula (e), then the term intermediate(s) of the invention includes enantiomers and diastereoisomers of these compounds.

The term "inert solvent" or "solvent inert to the reaction", as used herein, refers to a solvent that cannot react with the dissolved compounds including non-polar solvent such as hexane, toluene, diethyl ether, diisopropylether, chloroform, ethyl acetate, THF, dichloromethane; polar aprotic solvents such as acetonitrile, acetone, N,N-dimethylformamide, N,N-dimethylacetamide, dimethyl sulfoxide, pyridine, and polar protic solvents such as lower alcohol, acetic acid, formic acid and water.

The term "lower alcohol", as used herein, refers to a $C_{1-4}$alcohol, such as for example, methanol, ethanol, propanol, isopropanol, butanol, t-butanol, and the like.

The term "substituted" refers to a group in which one or more hydrogen atoms are each independently replaced with the same or different substituent(s).

As used herein, the term "substituted with one or more" refers to one to four substituents. In one embodiment it refers to one to three substituents. In further embodiment it refers to one or two substituents. In a yet further embodiment it refers to one substituent.

The term "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government or the corresponding agency in countries other than the United States or listed in the U.S. Pharmacopoeia or other generally recognized pharmacopoeia for use in mammals, and more particularly in humans. "Pharmaceutically acceptable salt" refers to a salt of a compound that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminium ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

The term "pharmaceutically acceptable ester" refers to esters which hydrolyse in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

"Pharmaceutically acceptable vehicle" refers to a diluent, adjuvant, excipient or carrier with which a compound of the invention is administered.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

The term "prodrug" or "pharmaceutically acceptable prodrug" as used herein refers to compounds, including derivatives of the compounds of the invention, which have metabolically cleavable groups and are converted within the body e.g. by solvolysis or under physiological conditions into the compounds of the invention which are pharmaceutically active in vivo. Pharmaceutically acceptable prodrugs are described in: Bundgard, H. Design of Prodrugs, pp. 7-9, 21-24, Elsevier, Amsterdam 1985, T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130. Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl) oxy)alkylesters. Particularly useful are the $C_1$-$C_8$ alkyl, $C_2$-$C_8$ alkenyl, aryl and arylalkyl esters of the compounds of the invention.

The term "solvate" refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The term "isotopic variant" refers to a compound that contains unnatural proportions of isotopes at one or more of the atoms that constitute such compound For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

The term "isomer(s)" refers to compounds that have the same molecular formula but differ in the nature or sequence of bonding of their atoms or the arrangement of their atoms in space. Isomers that differ in the arrangement of their atoms in space are termed "stereoisomers".

"Diastereomers" are stereoisomers that are not mirror images of one another and those that are non-superimposable mirror images of each other are termed 'enantiomers'. When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, which are likewise formed by treatment with acid or base. Tautomeric forms may be relevant to the attainment of the optimal chemical reactivity and biological activity of a compound of interest.

The term "subject" refers to an animal, in particular a mammal and more particular to a human or a domestic animal serving as a model for a disease (for example guinea pigs, mice, rats, gerbils, fish, birds, cats, rabbits, dogs, horses, cows, monkeys, chimpanzees or like). Specifically, the subject is a human. The terms "patient" and "subject" are used interchangeably herein.

"Effective amount" means the amount of a compound that, when administered to a subject for the prophylaxis or treatment of a disease and/or condition, is sufficient to effect such prophylaxis or such treatment for the disease and/or condition. The "effective amount" can vary depending on the compound, the disease and/or condition and its severity, and the age, weight, etc., of the subject.

"Preventing" or "prevention" refers to a reduction in risk of acquiring or developing a disease and/or condition (i.e., causing at least one of the clinical symptoms of the disease and/or condition not to develop in a subject that may be exposed to a disease and/or condition-causing agent, or predisposed to the disease and/or condition in advance of disease and/or condition onset).

The term "prophylaxis" is related to "prevention", and refers to a measure or procedure the purpose of which is to prevent, rather than to treat or cure a disease.

"Treating" or "treatment" of any disease and/or condition refers, in one embodiment, to ameliorating the disease and/or condition (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease and/or condition, either physically, (e.g., stabilization of a discernible symptom), physiologically, (e.g., stabilization of a physical parameter), or both. In a further embodiment, "treating" or "treatment" relates to slowing the progression of the disease and/or condition.

"Maintenance therapy" refers to a preventive therapy that follows successful initial treatment of the acute phase of the illness where regular (usually smaller) doses of the drug are delivered to the patient to prevent recurrence and worsening of the disease.

Modulators of the Hh signalling pathway include modulators of a pathway which is a target of the Hh signalling pathway; and includes Hh signalling pathway inhibitors, in which the inhibition may be complete or partial.

As used herein the term Hedgehog (Hh) includes three Hedgehog homologues, Desert (DHH) (Protein accession O43323), Indian (IHH) (Protein accession Q14623), and Sonic (SHH) (Protein accession Q15465).

The term Hh modulators as used herein may be SMO inhibitors, GLI inhibitors, SHH inhibitors, or inhibitors of any other proteins within the Hh signalling cascade.

The term Hh modulators as used herein may differentially regulate the activity of SMO, GLI, SHH, or any other proteins within the Hh signalling cascade.

The term Hh modulators as used herein may differentially regulate the activity of GLI, SHH, or any other proteins within the Hh signalling cascade without inhibition of SMO.

The term Hh modulators as used herein may differentially regulate the expression of SMO, GLI, SHH, or any other proteins within the Hh signalling cascade.

The term Hh modulators as used herein may differentially regulate the expression of GLI, SHH, or any other proteins within the Hh signalling cascade without inhibition of SMO.

As used herein the term "diseases and/or conditions associated with the abnormal activation and/or malfunction of Hh signalling pathway" refers to group of diseases and conditions including proliferative diseases, such as cancers; fibrosis and GVHD, etc. as herein defined.

The term 'abnormal activation' used herein refers to aberrant activation, reduced inhibition, increased expression, increased signalling or inappropriate activation.

The term "amidation" used herein refers to a chemical process of formal union of carboxylic acids and amines and formation of amide functionality. It is necessary to first activate the carboxylic acid, in a process that usually takes place by converting the OH of the acid into a good leaving group prior to treatment with the amine in the presence of a base. Suitable methods for activation of carboxylic groups are, but not limited to, formation of acyl halides, acyl azides, mixed anhydrides, activated esters and the like. Acyl halides may be prepared in non-protic solvents treating the carboxylic acid with halide sources like, but not limited to, thionyl chloride, oxalyl chloride, phosphorus pentachloride, triphosgene, cyanuric fluoride, cyanuric chloride, BoP-Cl, PyBroP and the like. Mixed anhydrides may be prepared in non-protic solvents with reagents like, but not limited to, pivalyl chloride, EEDQ and the like. Suitable coupling reagents used in the process of amidation via active esters are, but not limited to, carbodiimides like DCC, DIC, EDAC, uronium salts like HATU, TATU, HBTU, TBTU, TDBTU, phosphonium salts like PyBoP, BoP, DEPBT. These coupling reagents can be used as stand-alone activators or in the presence of additives like, but not limited to, HOAt, HOBt and the like. Other suitable amidation coupling reagents that operate on different mechanism of carboxylic group activation are, but not limited to, DPPA, T3P®, CDI, Mukaiyama reagent and the like. Activation can also be performed by using solid supported versions of the abovementioned coupling reagents like, but not limited to, PS-CDI, PS-EDC, PS-BoP and the like. Suitable bases used in amidation process are, but not limited to, sodium hydrocarbonate, potassium hydrocarbonate, sodium carbonate, potassium carbonate, TEA, DIPEA, DBU, DBN, DABCO and the like. A more thorough discussion of amidation can be found in Valeur, E., et al. Chem. Soc. Rev. (2009), 38, 606.

The term "esterification" used herein refers to a chemical process of formal union of carboxylic acids and alcohols and formation of ester functionality. Suitable methods for synthesis of esters are Fisher, Mitsunobu, Steglich conditions, transesterification, acylation with appropriate acyl halides, decarboxylative esterification, oxidative esterification and redox esterification. Acyl halides may be prepared in non-protic solvents treating the carboxylic acid with halide sources like, but not limited to, thionyl chloride, oxalyl chloride, phosphorus pentachloride, triphosgene, fluoride, cyanuric chloride and the like. Suitable coupling reagents used in the process of esterification are, but not limited to, p-nitrophenylchloroformate, thiopyridyl chloroformate, 2,2'-(4-t-Bu-N-alkylimidazolyl)disulfide, Mukaiyama salts, 2,4,6-trichlorobenzoyl chloride, DEAD/PPh3, TFFH, DCC, TBTU, TATU, COMU and the like. Suitable bases used in esterification process are, but not limited to, sodium hydrocarbonate, potassium hydrocarbonate, sodium carbonate, potassium carbonate, TEA, DIPEA, DBU, DBN, DABCO and the like.

The term "reductive amination" used herein refers to chemical process of conversion of a carbonyl group and an amine to higher substituted amine via an intermediate imine. The carbonyl group is most commonly a ketone or an aldehyde. The imine intermediate is reduced to the amine by various reducing agents including, but not limited to, sodium borohydride, sodium triacetoxyborohydride, sodium cyanoborohydride, zinc and hydrochloric acid, hydrogen and transition metal catalyst, formic acid and its organic or inorganic salts, iron pentacarbonyl. Generally alcoholic solvents are used. Preferred conditions are sodium cyanoborohydride in methanolic media in the presence of acetic acid.

The present invention is based on the identification that a compound of the invention may be useful as a medicament in the treatment of diseases and/or conditions associated with the abnormal activation and/or malfunction of the hedgehog (Hh) signalling pathway. In a particular aspect, a compound of the invention is an inhibitor of Hh signalling pathway. More particularly, a compound of the invention is useful in the treatment of proliferative diseases. The present invention also relates to methods for the preparation of the compounds of the invention, to intermediates for their preparation, to pharmaceutical compositions comprising a compound of the invention, to the use of a compound of the invention as therapeutic agents, and to methods for the treatment of diseases and/or conditions associated with the abnormal activation and/or malfunction of Hh signalling pathway by administering a compound of the invention.

Accordingly, in another aspect the present invention relates to a compound of Formula (I):

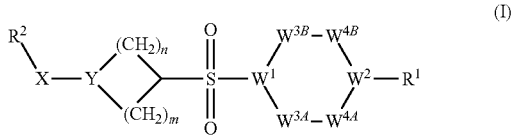

(I)

or a pharmaceutically acceptable salt, or a solvate, or a solvate of the salt thereof for use as a medicament, wherein:
integers n and m are selected from:
(i) 1, 2 and 3, provided that sum of n and m is 2, 3 or 4; or
(ii) 0 and 1, provided that the sum of n and m is 1;
Y is CH, N or NH, provided that Y is NH only when the sum of n and m is 1;
$W^1$ is N;
$W^2$ is CH, C or N, provided when $W^2$ is C one of $W^{4A}$ and $W^{4B}$ is —CH— and is connected to $W^2$ by a double bond and the other is —CH$_2$—
$W^{3A}$ and $W^{3B}$ are —CH$_2$— or —CH($R^3$)—, wherein $R^3$ is methyl;
$W^{4A}$ and $W^{4B}$ are —CH$_2$— or —CH—, provided that when one of $W^{4A}$ and $W^{4B}$ is —CH— the other is —CH$_2$—;
$R^1$ is selected from:
(i) a fused 9-10 membered bicyclic heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(═O)OC$_{1-6}$alkyl, —O(C═O)C$_{1-6}$alkyl, —C(═O)O—C$_{0-4}$alkyl-cycloalkyl, C$_{0-6}$alkyl-phenyl (wherein phenyl may be optionally substituted by C$_{1-4}$alkyl), —C(═O)NHC$_{1-6}$alkyl, —NHC(═O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$ alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$ alkyl, —C(═O)OH, —C(═O)OC$_{1-6}$alkyl, —C(═O)NHC$_{1-6}$alkyl and —NHC(═O)C$_{1-6}$alkyl;
(ii) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(═O)OC$_{1-6}$alkyl, —O(C═O)C$_{1-6}$alkyl, —C(═O)O—C$_{1-4}$alkyl-cycloalkyl, C$_{0-6}$alkyl-phenyl (wherein phenyl may be optionally substituted by C$_{1-4}$alkyl), —C(═O)NHC$_{1-6}$alkyl, —NHC(═O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$ alkyl, —C(═O)NHC$_{1-6}$alkyl and —NHC(═O)C$_{1-6}$ alkyl;
(iii) 6-10 membered aryl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$ alkyl, haloC$_{1-6}$alkyl, haloC$_{1-6}$alkyloxy, —C$_{1-6}$ alkyl-OH, NH$_2$, N—(C$_{1-6}$-alkyl)amino, N,N-di(C$_{1-6}$ alkyl)amino, —C(═O)C$_{1-6}$alkyl, —C(═O)OH, —O(C═O)C$_{1-6}$alkyl, —C(═O)OC$_{1-6}$alkyl, —C(═O) NHC$_{1-6}$ alkyl and —NHC(═O)C$_{1-6}$alkyl;
(iv) a fused 8-10 membered partially unsaturated bicyclic heterocyclyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —O(C═O)C$_{1-6}$alkyl, —C(═O)OC$_{1-6}$alkyl, —C(═O)NHC$_{1-6}$alkyl and —NHC(═O)C$_{1-6}$alkyl; and
(v) a 5-6 membered monocyclic heterocycloalkyl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl) amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$ alkyl, —C(═O)NHC$_{1-6}$alkyl and —NHC(═O)C$_{1-6}$ alkyl;
X is absent or a bivalent group selected from:
(a) —(CH$_2$)x$^1$-, wherein x$^1$ is 1, 2 or 3;
(b) —(CH$_2$)x$^2$-C(CH$_3$)$_2$—(CH$_2$)x$^3$-, wherein x$^2$ is 1 or 2 and x$^3$ is 1;
(c) —C(═O)—(CH$_2$)x$^4$-, wherein x$^4$ is zero, 1 or 2;
(d) —C(═O)O—(CH$_2$)x$^5$-, wherein x$^5$ is zero, 1, 2 or 3;
(e) —C(═O)NR$^x$—(CH$_2$)x$^6$-, wherein
(e.i) x$^6$ is zero, 1 or 2 and R$^x$ is H or C$_{1-4}$alkyl, or
(e.ii) x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl may be optionally substituted by one or more C$_{1-4}$alkyl groups;
(f) —C(═S)NR$^y$—, wherein R$^y$ is H or C$_{1-4}$alkyl; and
(g) —SO$_2$—;
R$^2$ is selected from:
(i) C$_{1-10}$alkyl optionally substituted by one or more groups independently selected from OH, —OC$_{1-4}$alkyl, —NHC$_{1-4}$alkyl, and —N(C$_{1-4}$alkyl)$_2$;
(ii) —NHC$_{1-4}$alkyl, —N(C$_{1-4}$alkyl)$_2$;
(iii) 3-10 membered cycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$ alkyl-OH, —C(═O)C$_{1-6}$alkyl, —C(═O)OC$_{1-6}$alkyl, —C(═O)OH, —C(═O)NH$_2$, —C$_{0-6}$alkyl-NH—C$_{1-6}$ alkyl and —C$_{0-6}$alkyl-N(C$_{1-6}$alkyl)$_2$;
(iv) 5-6 membered heterocycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(═O)C$_{1-6}$alkyl, —C(═O)OC$_{1-6}$alkyl, —C(═O)OH, and —C(═O) NH$_2$;
(v) phenyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —O(C═O)C$_{1-6}$alkyl, —C(═O)OC$_{1-6}$alkyl, —C(═O)NHC$_{1-6}$alkyl and —NHC(═O)C$_{1-6}$alkyl;

(vi) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$ alkyl, —C(═O)OH, —C(═O)OC$_{1-6}$alkyl, —C(═O)NHC$_{1-6}$alkyl, —NHC(═O)C$_{1-6}$alkyl, and 3-6-membered cycloalkyl wherein said cycloalkyl may optionally be substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$alkyl, —C(═O)NHC$_{1-6}$alkyl and —NHC(═O)C$_{1-6}$alky; and (vii) H and X is absent.

In one aspect the invention relates to a compound of the invention according to Formula (I):

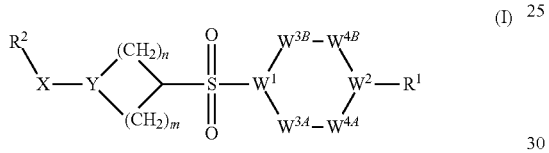

or a salt, or a solvate, or a solvate of the salt thereof, wherein; integers n and m are selected from:

(i) 1, 2 and 3, provided that sum of n and m is 2, 3 or 4; or (ii) 0 and 1, provided that the sum of n and m is 1;

Y is CH, N or NH, provided that Y is NH only when the sum of n and m is 1;

W$^1$ is N;

W$^2$ is CH, C or N, provided when W$^2$ is C one of W$^{4A}$ and W$^{4B}$ is —CH— and is connected to W$^2$ by a double bond and the other is —CH$_2$—

W$^{3A}$ and W$^{3B}$ are —CH$_2$— or —CH(R$^3$)—, wherein R$^3$ is methyl;

W$^{4A}$ and W$^{4B}$ are —CH$_2$— or —CH—, provided that when one of W$^{4A}$ and W$^{4B}$ is —CH— the other is —CH$_2$—;

R$^1$ is selected from:

(i) a fused 9-10 membered bicyclic heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(═O)OC$_{1-6}$alkyl, —O(C═O)C$_{1-6}$ alkyl, —C(═O)O—C$_{0-4}$alkyl-cycloalkyl, C$_{0-6}$alkyl-phenyl (wherein phenyl may be optionally substituted by C$_{1-4}$alkyl), —C(═O)NHC$_{1-6}$alkyl, —NHC(═O)C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$alkyl, —C(═O)NHC$_{1-6}$alkyl and —NHC(═O)C$_{1-6}$alkyl, provided that when W$^1$ is N, W$^{3A}$, W$^{3B}$, W$^{4A}$, and W$^{4B}$ are —CH$_2$—, n and m are 1 or 2, sum of n and m is 3, X is —(CH$_2$)x$^1$, x$^1$ is 1, and R$^2$ is unsubstituted phenyl, then R$^1$ cannot represent benzothiazole-2-yl;

(ii) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(═O)OC$_{1-6}$alkyl, —O(C═O)C$_{1-6}$alkyl, —C(═O)O—C$_{1-4}$alkyl-cycloalkyl, C$_{0-6}$alkyl-phenyl (wherein phenyl may be optionally substituted by C$_{1-4}$alkyl), —C(═O)NHC$_{1-6}$ alkyl, —NHC(═O)C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_1$-6alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$alkyl, —C(═O)NHC$_{1-6}$alkyl and —NHC(═O)C$_{1-6}$alkyl;

(iii) 6-10 membered aryl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$ alkyl, haloC$_{1-6}$alkyl, haloC$_{1-6}$alkyloxy, —C$_{1-6}$ alkyl-OH, NH$_2$, N—(C$_{1-6}$-alkyl)amino, N,N-di(C$_{1-6}$ alkyl)amino, —C(═O)C$_{1-6}$alkyl, —C(═O)OH, —O(C═O)C$_{1-6}$alkyl, —C(═O)OC$_{1-6}$alkyl, —C(═O) NHC$_{1-6}$ alkyl and —NHC(═O)C$_{1-6}$alkyl;

(iv) a fused 8-10 membered partially unsaturated bicyclic heterocyclyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —O(C═O)C$_{1-6}$alkyl, —C(═O)OC$_{1-6}$alkyl, —C(═O)NHC$_{1-6}$alkyl and —NHC(═O)C$_{1-6}$alkyl; and (v) a 5-6 membered monocyclic heterocycloalkyl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl) amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$ alkyl, —C(═O)NHC$_{1-6}$alkyl and —NHC(═O)C$_{1-6}$ alkyl;

X is absent or a bivalent group selected from:

(a) —(CH$_2$)x$^1$-, wherein x$^1$ is 1, 2 or 3;

(b) —(CH$_2$)x$^2$-C(CH$_3$)$_2$—(CH$_2$)x$^3$-, wherein x$^2$ is 1 or 2 and x$^3$ is 1;

(c) —C(═O)—(CH$_2$)x$^4$-, wherein x$^4$ is zero, 1 or 2;

(d) —C(═O)O—(CH$_2$)x$^5$-, wherein x$^5$ is zero, 1, 2 or 3;

(e) —C(═O)NR$^x$—(CH$_2$)x$^6$-, wherein (e.i) x$^6$ is zero, 1 or 2 and R$^x$ is H or C$_{1-4}$alkyl, or (e.ii) x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl may be optionally substituted by one or more C$_{1-4}$alkyl groups;

(f) —C(═S)NR$^y$—, wherein R$^y$ is H or C$_{1-4}$alkyl; and (g) —SO$_2$—;

$R^2$ is selected from:
(i) $C_{1-10}$alkyl optionally substituted by one or more groups independently selected from OH, —$OC_{1-4}$alkyl, —$NHC_{1-4}$alkyl, and —$N(C_{1-4}alkyl)_2$;
(ii) —$NHC_{1-4}$alkyl, —$N(C_{1-4}alkyl)_2$;
(iii) 3-10 membered cycloalkyl optionally substituted by one or more groups independently selected from OH, halogen, CN, $NH_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, —C(=O)$C_{1-6}$alkyl, —C(=O)$OC_{1-6}$alkyl, —C(=O)OH, —C(=O)$NH_2$, —$C_{0-6}$alkyl-NH—$C_{1-6}$alkyl and —$C_{0-6}$alkyl-N($C_{1-6}$alkyl)$_2$;
(iv) 5-6 membered heterocycloalkyl optionally substituted by one or more groups independently selected from OH, halogen, CN, $NH_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, —C(=O)$C_{1-6}$ alkyl, —C(=O)$OC_{1-6}$alkyl, —C(=O)OH, and —C(=O)$NH_2$;
(v) 6-membered aryl (phenyl) optionally substituted by one or more groups independently selected from halogen, CN, OH, $NO_2$, $C_{1-6}$alkyl, $C_{2-6}$alkenyl, $C_{2-6}$alkynyl, —$OC_{1-6}$alkyl, O-phenyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)$OC_{1-6}$alkyl, —C(=O)NH$C_{1-6}$alkyl and —NHC(=O)$C_{1-6}$alkyl, provided when X is bivalent group —C(=O)O—$(CH_2)x^5$-, $x^5$ is 1, and $R^2$ is unsubstituted phenyl, $W^1$ is N, $W^2$ is CH or N, $W^{3A}$, $W^{3B}$, $W^{4A}$, and $W^{4B}$ are —$CH_2$—, sum of n and m is 4, then $R^1$ is other that phenyl optionally substituted by $C_{1-6}$ alkyl or —$OC_{1-6}$ alkyl, pyridyl optionally substituted by halogen;
(vi) 5-6 membered heteroaryl optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$ alkyl, —C(=O)OH, —C(=O)$OC_{1-6}$alkyl, —C(=O)NH$C_{1-6}$alkyl, —NHC(=O)$C_{1-6}$alkyl, and 3-6-membered cycloalkyl wherein said cycloalkyl may optionally be substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)$OC_{1-6}$alkyl, —C(=O)NH$C_{1-6}$alkyl and —NHC(=O)$C_{1-6}$alkyl; and
(vii) H and X is absent, provided that when $W^1$ is N, $W^2$ is CH, $W^{3A}$, $W^{3B}$, $W^{4A}$, and $W^{4B}$ are —$CH_2$—, sum of n and m is 3 or 4, then $R^1$ cannot represent piperidinyl, and when $W^1$ and $W^2$ are N, $W^{3A}$, $W^{3B}$, $W^{4A}$, and $W^{4B}$ are —$CH_2$—, sum of n and m is 3 or 4, then $R^1$ cannot represent phenyl optionally substituted by $CH_3$ or halogen, pyridinyl, pyrimidinyl or thiazolyl;
provided that when X is —(C=O)$(CH_2)x^4$, $x^4$ is zero, $R^2$ is unsubstituted cyclopentyl or phenyl optionally substituted by halogen, $W^1$ is N, $W^2$ is CH or N, $W^{3A}$ and $W^{3B}$ are —$CH_2$— or —CH($R^3$)—, $R^3$ is $CH_3$, $W^{4A}$, and $W^{4B}$ are —$CH_2$—, then $R^1$ is a fused 9-10 membered bicyclic heteroaryl or a fused 8-10 membered partially unsaturated bicyclic heterocyclyl; or a pharmaceutically acceptable salt or a solvate thereof.

In one embodiment, the invention relates to a compound of Formula (I), wherein Formula (I) is selected from subset of formulae (I-1), (I-2), (I-3), (I-4), (I-5), (I-6) and (I-7), wherein $R^1$, $R^2$, $R^3$, X, $W^1$, $W^2$, $W^{3A}$, $W^{3B}$, $W^{4A}$, $W^{4B}$, $R^x$, n and m are as defined above or as defined in any embodiment herein and below. In another embodiment, Formula (I) is selected from subset of formulae (I-1), (I-3), (I-4), (I-5), (I-6) and (I-7). In a particular embodiment, Formula (I) is selected from subset of formulae (I-1), (I-3), (I-4) and (I-7). In another particular embodiment, Formula (I) is selected from subset of formulae (I-1), (I-5) and (I-6).

In one embodiment, the invention relates to a compound of Formula (I), wherein Y is N and the sum of n and m is 2, 3 or 4. Preferably when Y is N the sum of n and m is 2.

In one embodiment, the invention relates to a compound of Formula (I), wherein Y is CH and the sum of n and m is 2, 3 or 4. Preferably when Y is CH the sum of n and m is 2.

In another embodiment, the invention relates to a compound of Formula (I), integers n and m are selected from 1, 2 and 3, provided that sum of n and m is 2 when Y is CH or is 2, 3 or 4 when Y is N.

In one embodiment, the invention relates to a compound of Formula (I), wherein Y is NH and the sum of n and m is 1.

In another embodiment, the invention relates to a compound of Formula (I), wherein integer n is 0 and integer m is 1, when Y is NH In one embodiment, the invention relates to a compound of Formula (I), wherein $W^1$ is N and $W^2$ is CH or C.

In another embodiment, the invention relates to a compound of Formula (I), wherein $W^1$ and $W^2$ are N.

In one embodiment, the invention relates to a compound of Formula (I), wherein $W^{3A}$ and $W^{3B}$ are —$CH_2$—.

In another embodiment, the invention relates to a compound of Formula (I), wherein $W^{3A}$ is —$CH_2$— and $W^{3B}$ is —CH($R^3$)— or $W^{3A}$ is —CH($R^3$)— and $W^{3B}$ is —$CH_2$—.

In one embodiment, the invention relates to a compound of Formula (I), wherein $R^3$ is methyl.

In one embodiment, the invention relates to a compound of Formula (I), wherein $W^{4A}$ and $W^{4B}$ are —$CH_2$—.

In another embodiment, the invention relates to a compound of Formula (I), wherein $W^{4A}$ is —$CH_2$— and $W^{4B}$ is —CH— and $W^{4B}$ is connected to $W^2$ by a double bond or $W^{4A}$ is —CH— and $W^{4A}$ is connected to $W^2$ by a double bond and $W^{4B}$ is —$CH_2$—.

In one embodiment, the invention relates to a compound of Formula (I), wherein one of $W^{3A}$ and $W^{3B}$ is —$CH_2$— and the other is —CH($R^3$)—, one of $W^{4A}$ and $W^{4B}$ is —$CH_2$— and the other is CH, and $W^2$ is C.

In another embodiment $W^{3A}$, $W^{3B}$, $W^{4A}$ and $W^{4B}$ are —$CH_2$— and $W^2$ is N.

In one embodiment, the invention relates to a compound of Formula (I), wherein ring

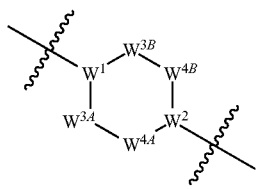

is selected from

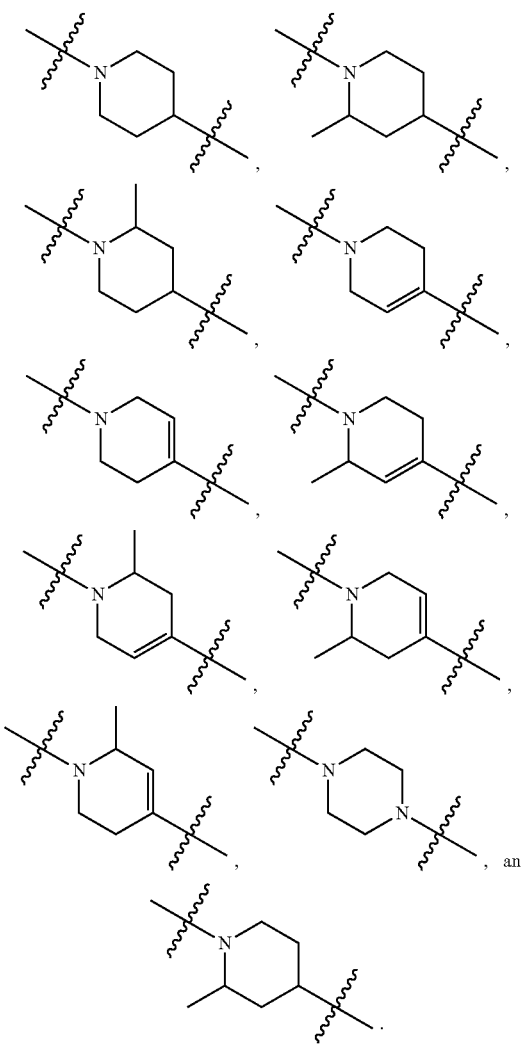

In another embodiment, the invention relates to a compound of Formula (I), wherein ring

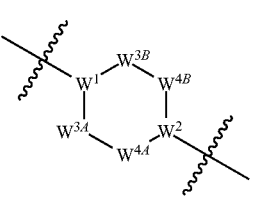

is selected from

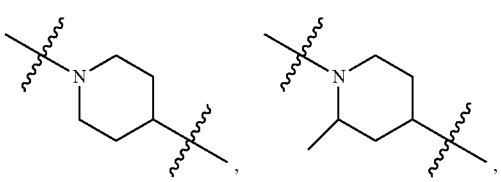

-continued

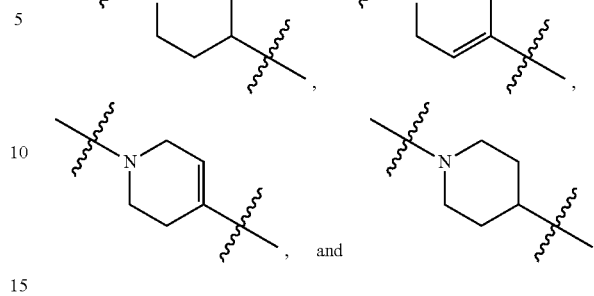

In a particular embodiment, the invention relates to a compound of Formula (I), wherein ring

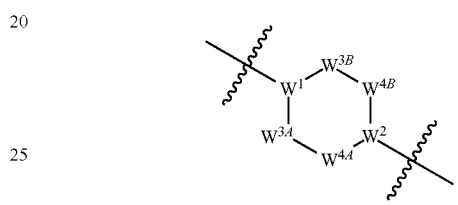

is selected from

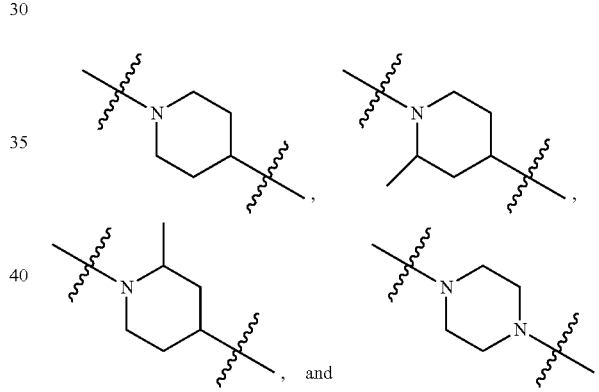

In another particular embodiment, the invention relates to a compound of Formula (I), wherein ring

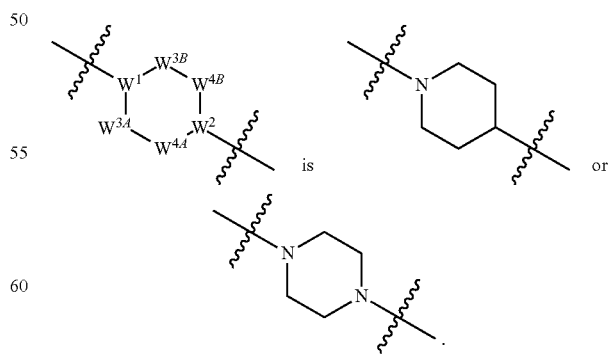

In one embodiment, the invention relates to a compound of Formula (I), wherein sum of n and m is 2, and integers n and m are both 1.

In one embodiment, the invention relates to a compound of Formula (I), wherein sum of n and m is 3, one of integers n and m is 1 and the other is 2. In a particular embodiment, integer n is 1, integer m is 2, and sum of n and m is 3.

In one embodiment, the invention relates to a compound of Formula (I), wherein sum of n and m is 4, integer n is 1 or 2, and integer m is 2 or 3. In a particular embodiment, integers n and m are both 2. In another particular embodiment, n is 1 and m is 3.

In one embodiment, the invention relates to a compound of Formula (I), wherein ring

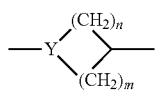

represents

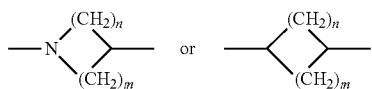

in which n and m are each 1, 2 and 3, provided that sum of n and m is 2, 3 or 4.

When the compound of Formula (I) contains the ring:

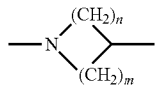

the ring is selected from

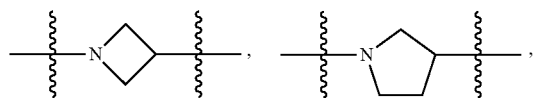

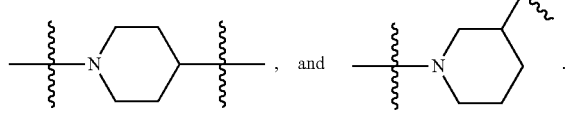

In a particular embodiment, ring

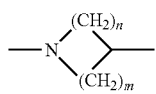

is

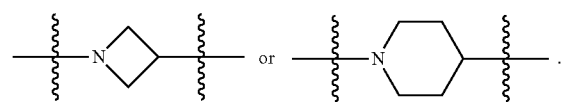

In another particular embodiment ring

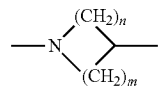

is

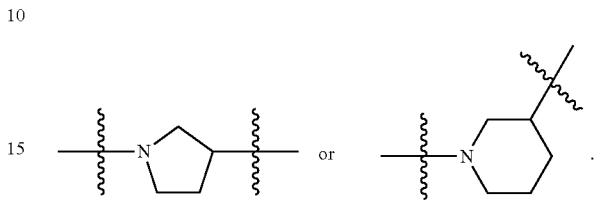

In one embodiment, the invention relates to a compound of Formula (I), wherein the sum of n and m is 1.

In one embodiment, the invention relates to a compound of Formula (I), wherein subunit

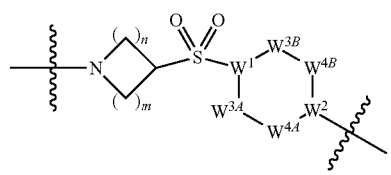

is selected from

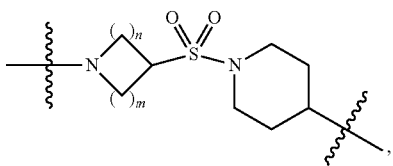

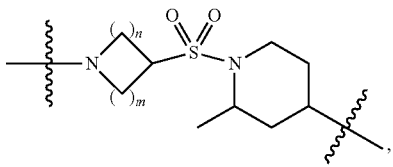

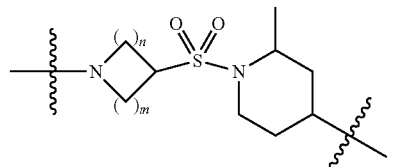

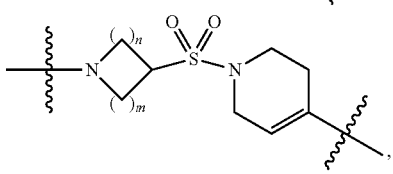

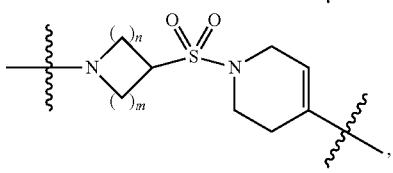

-continued
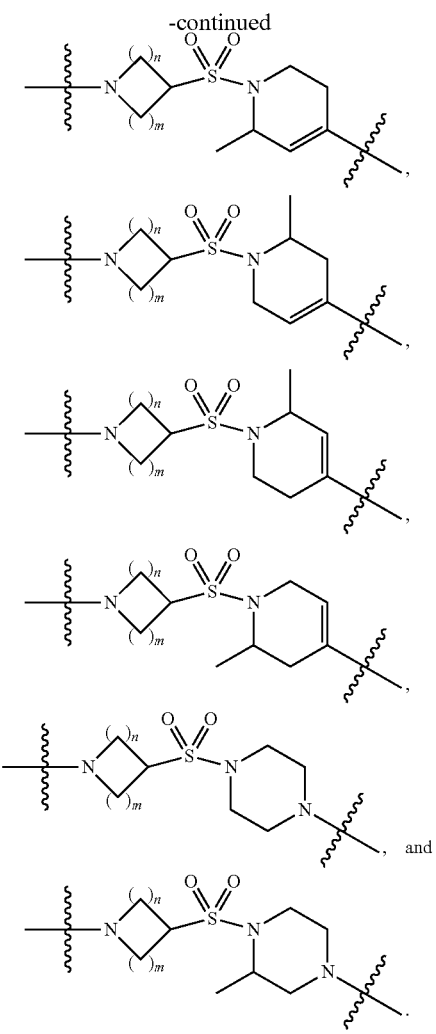
In a particular embodiment, subunit
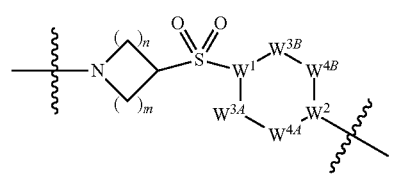
is selected from
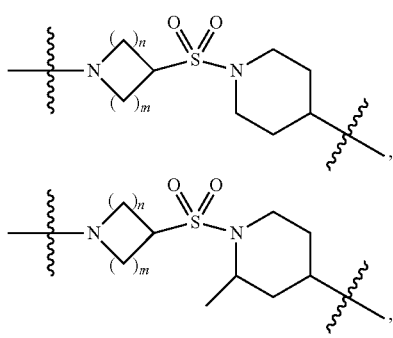
-continued
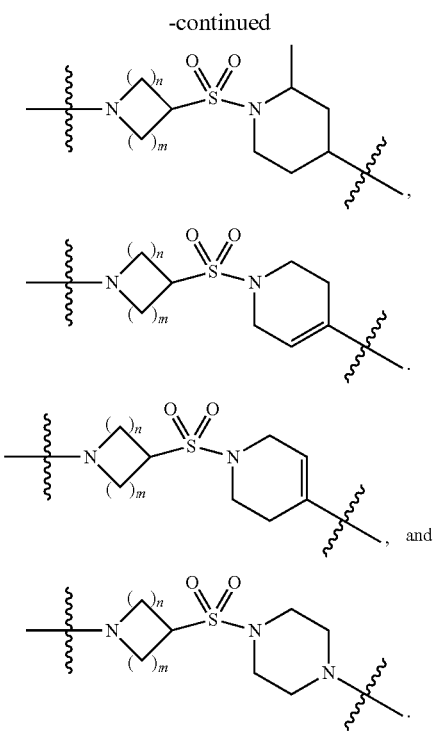
In another particular embodiment, subunit
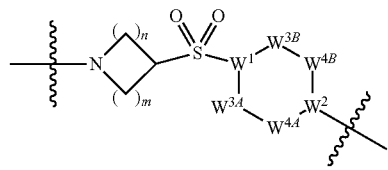
is selected from
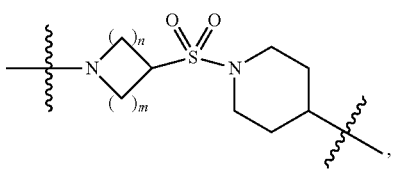
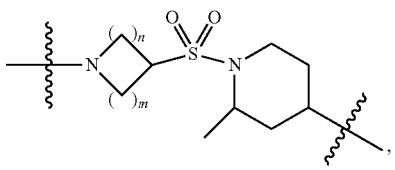
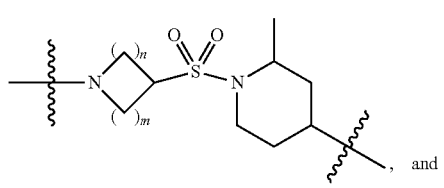

-continued
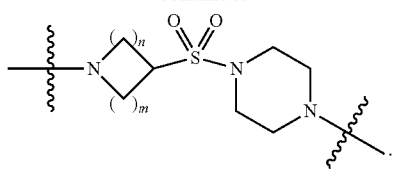
In one embodiment, the invention relates to a compound of Formula (I), wherein subunit
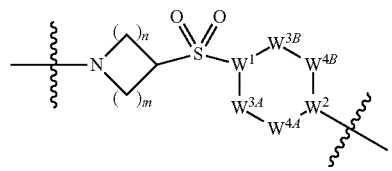
is selected from
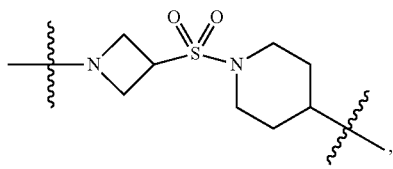
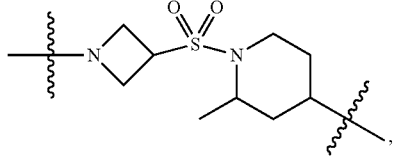 [SMILES: *N1CCN(S(=O)(=O)C2CN(*)C2)C(C)C1]
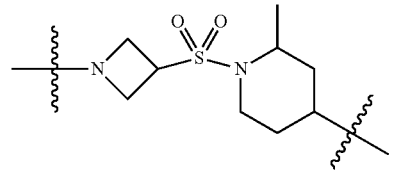
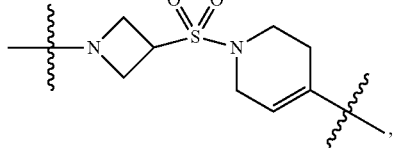
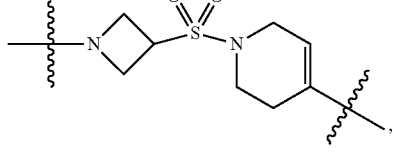
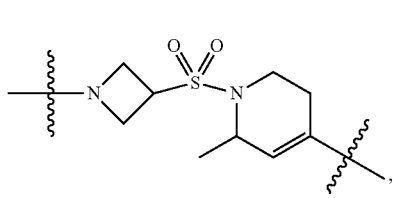
-continued
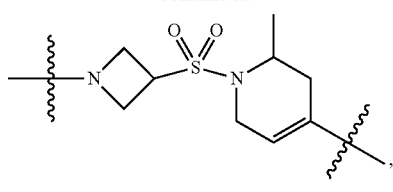
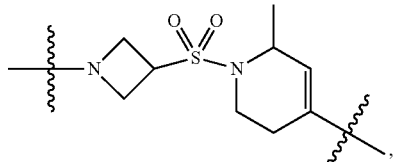
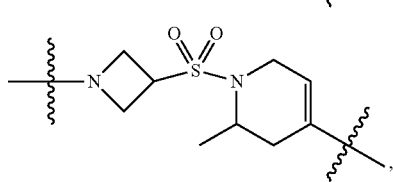
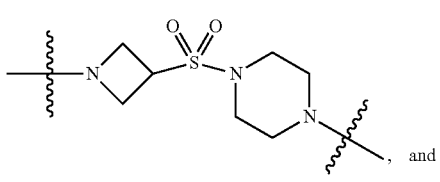
, and
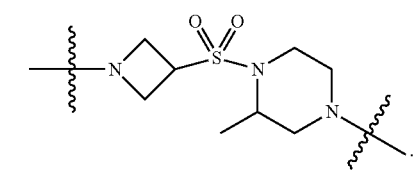
.
In one embodiment, the invention relates to a compound of Formula (I), wherein subunit
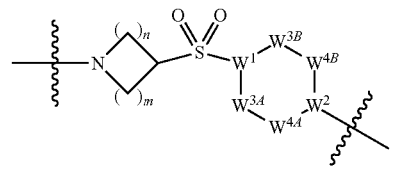
is selected from
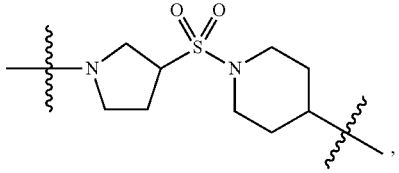
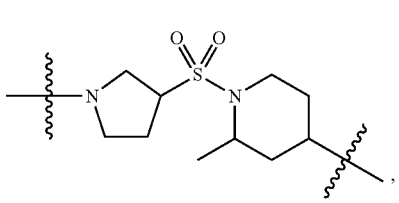

-continued
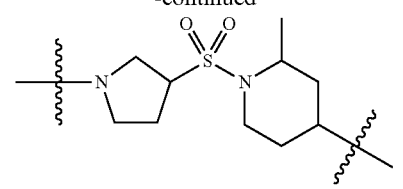,
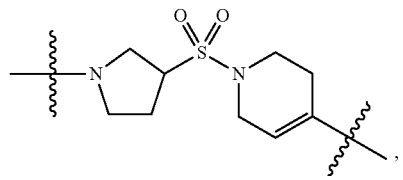,
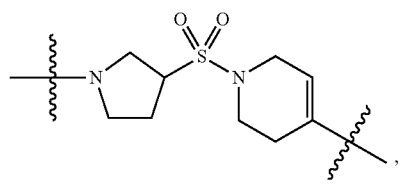,
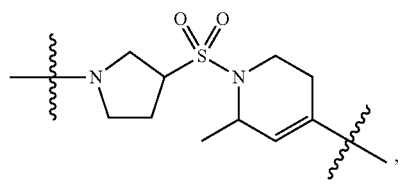,
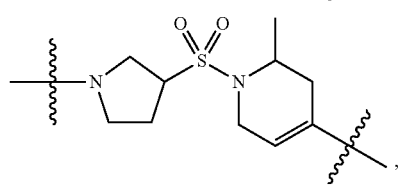,
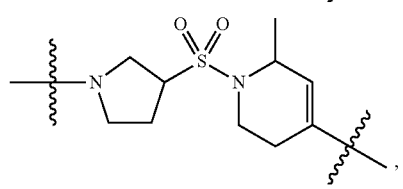,
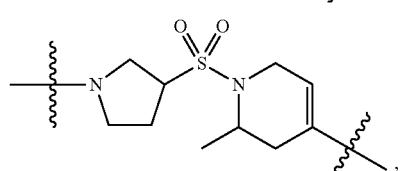,
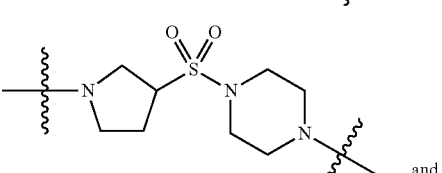, and
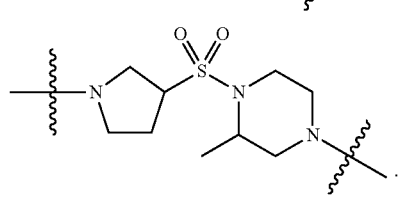.
In a particular aspect of the invention the compound of Formula (I) is provided wherein subunit
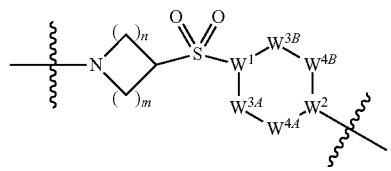
is:
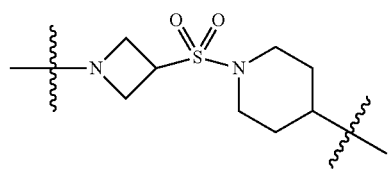 [SMILES: *C1CCN(S(=O)(=O)C2CN(*)C2)CC1]
In one embodiment, the invention relates to a compound of Formula (I), wherein subunit
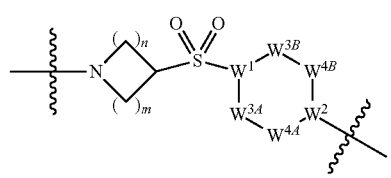
is selected from
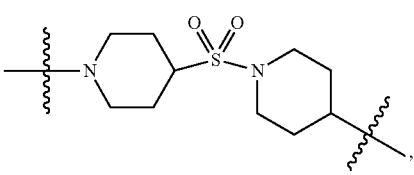,
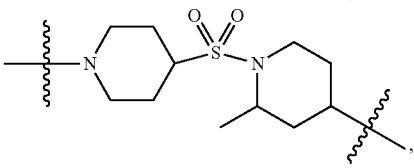,
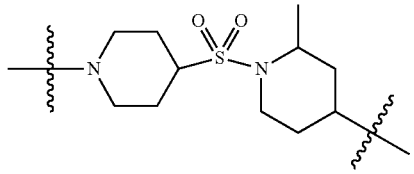,
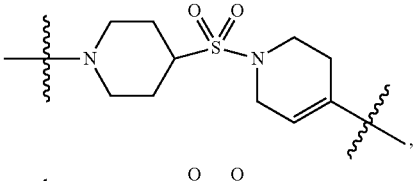,
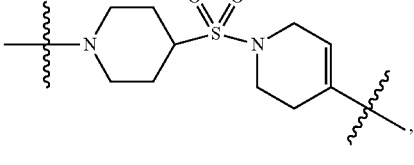,

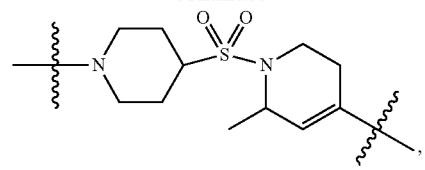
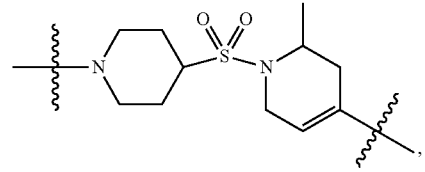
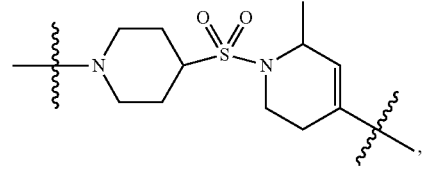
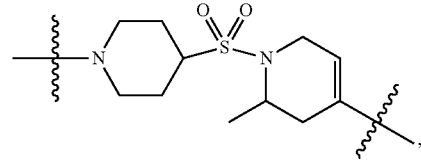
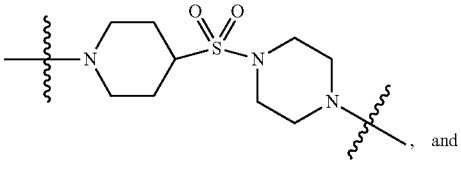
, and
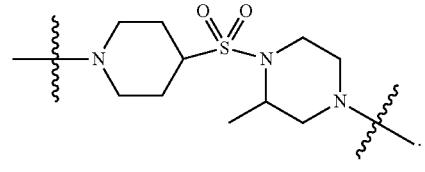 [SMILES: *N1CCC(S(=O)(=O)N2CCN(*)CC2C)CC1]
.
In a particular aspect of the invention the compound of Formula (I) is provided wherein subunit
is:
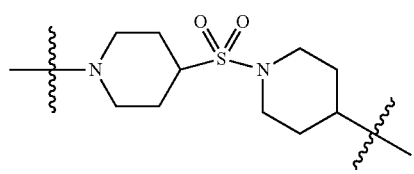 [SMILES: *C1CCN(S(=O)(=O)C2CCN(*)CC2)CC1]
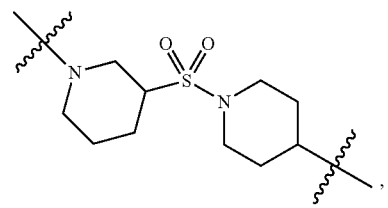
is selected from
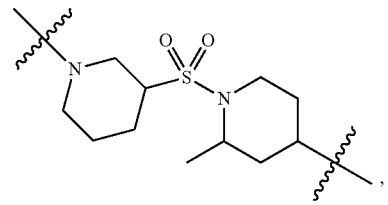
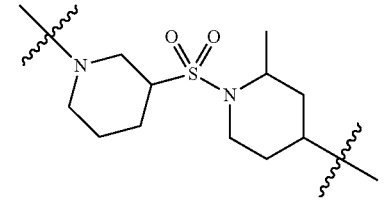
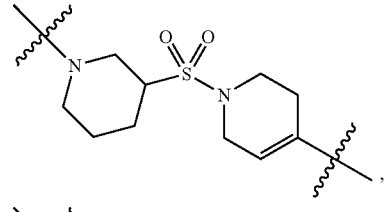
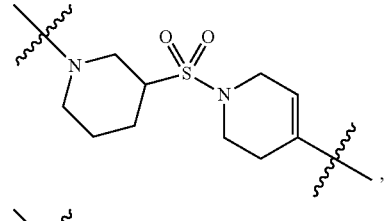
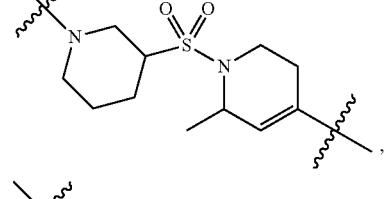
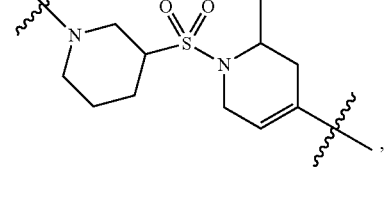
,
In one embodiment, the invention relates to a compound of Formula (I), wherein subunit -continued

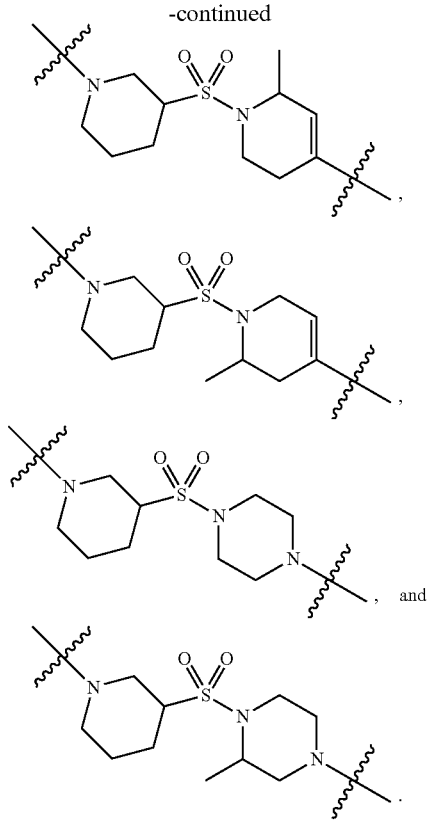

In one embodiment when the compound of Formula (I) contains the ring:

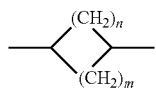

the ring is:

In one embodiment, the invention relates to a compound of Formula (I), wherein subunit

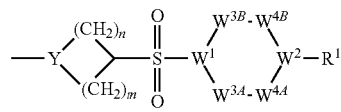

is

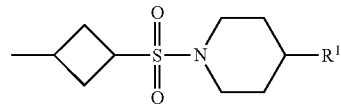

In a particular aspect of the invention the compound of Formula (I) is provided wherein subunit

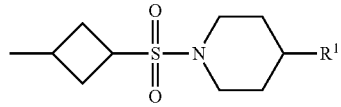

is selected from:

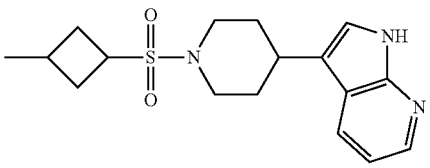

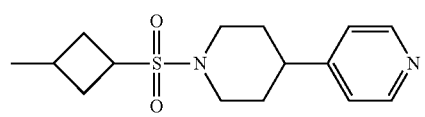

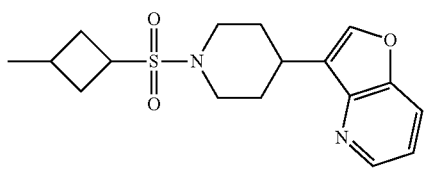

In a particular aspect of the invention the compound of Formula (I) is provided wherein

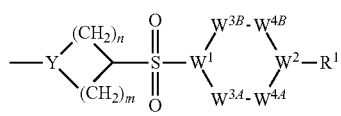

is

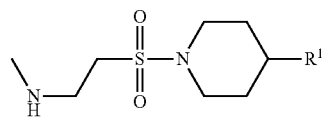

In one embodiment, the invention relates to a compound of Formula (I), which comprises a compound of formula (Ia):

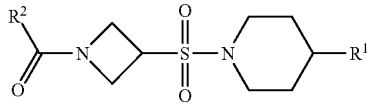

(Ia)

in which R¹ is selected from the group consisting of:

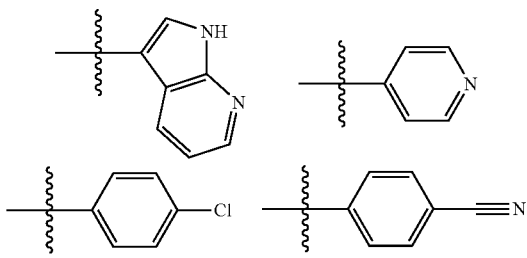

and R² is selected from the group consisting of:

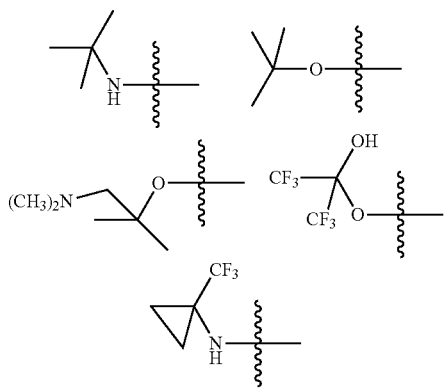

or a pharmaceutically acceptable salt or a solvate thereof.

In one embodiment, the invention relates to a compound of Formula (I), wherein R¹ is selected from: (i) a fused 9-10 membered bicyclic heteroaryl, (ii) 5-6 membered heteroaryl, (iii) 6-10 membered aryl, (iv) a fused 8-10 membered partially unsaturated bicyclic heterocyclyl, and (v) a 5-6 membered monocyclic heterocycloalkyl each of (i), (ii), (iii), (iv), and (v) as defined above or as defined in any embodiment herein and below for use as a medicament. In another embodiment, R¹ is selected from: (i) a fused 9-10 membered bicyclic heteroaryl, (ii) 5-6 membered heteroaryl, (iii) 6-10 membered aryl, and (iv) a fused 8-10 membered partially unsaturated bicyclic heterocyclyl for use as a medicament. In a particular embodiment, R¹ is selected from: a fused 9-10 membered bicyclic heteroaryl, 5-6 membered heteroaryl, and a fused 8-10 membered partially unsaturated bicyclic heterocyclyl for use as a medicament. In another particular embodiment, R¹ is a fused 9-10 membered bicyclic heteroaryl or a fused 8-10 membered partially unsaturated bicyclic heterocyclyl for use as a medicament. In further particular embodiment, R¹ is a fused 9-10 membered bicyclic heteroaryl or 5-6 membered heteroaryl for use as a medicament. In more particular embodiment, R¹ is a fused 9-10 membered bicyclic heteroaryl for use as a medicament.

In one embodiment, the invention relates to a compound of Formula (I), wherein R¹ is selected from: (i) a fused 9-10 membered bicyclic heteroaryl, (ii) 5-6 membered heteroaryl, (iii) 6-10 membered aryl, (iv) a fused 8-10 membered partially unsaturated bicyclic heterocyclyl, and (v) a 5-6 membered monocyclic heterocycloalkyl each of (i), (ii), (iii), (iv), and (v) as defined above or as defined in any embodiment herein and below. In another embodiment, R¹ is selected from: (i) a fused 9-10 membered bicyclic heteroaryl, (ii) 5-6 membered heteroaryl, (iii) 6-10 membered aryl, and (iv) a fused 8-10 membered partially unsaturated bicyclic heterocyclyl. In a particular embodiment, R¹ is selected from: a fused 9-10 membered bicyclic heteroaryl, 5-6 membered heteroaryl, and a fused 8-10 membered partially unsaturated bicyclic heterocyclyl. In another particular embodiment, R¹ is a fused 9-10 membered bicyclic heteroaryl or a fused 8-10 membered partially unsaturated bicyclic heterocyclyl. In further particular embodiment, R¹ is a fused 9-10 membered bicyclic heteroaryl or 5-6 membered heteroaryl. In more particular embodiment, R¹ is a fused 9-10 membered bicyclic heteroaryl.

In one embodiment, the invention relates to a compound of Formula (I), wherein when R¹ is a fused 9-10 membered bicyclic heteroaryl said fused 9-10 membered bicyclic heteroaryl is optionally substituted by one or more groups independently selected from halogen, CN, OH, NO₂, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, NH₂, N—($C_{1-6}$-alkyl)amino, N,N-di($C_{1-6}$alkyl)amino, —C(=O)$C_{1-6}$alkyl, —C(=O)OH, —C(=O)O$C_{1-6}$alkyl, —O(C=O)$C_{1-6}$alkyl, —C(=O)O—$C_{0-4}$alkyl-cycloalkyl, $C_{0-6}$alkyl-phenyl (wherein phenyl may be optionally substituted by $C_{1-4}$alkyl), —C(=O)NH$C_{1-6}$alkyl, —NHC(=O)$C_{1-6}$alkyl, —SO₂—$C_{1-6}$alkyl, —SO₂—N($C_{1-6}$ alkyl)₂, —SO₂-phenyl, and 5-6-membered heteroaryl wherein phenyl and heteroaryl independently from each other may be optionally substituted by one or more groups independently selected from halogen, CN, OH, NO₂, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, NH₂, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl. In another embodiment, R¹ is a fused 9-10 membered bicyclic heteroaryl optionally substituted by one or more groups independently selected from halogen, $C_{1-6}$alkyl, halo$C_{1-6}$alkyl, —O$C_{1-6}$alkyl, —C(=O)O$C_{1-6}$alkyl, —C(=O)O—$C_{0-4}$alkyl-cycloalkyl, —SO₂—$C_{1-6}$alkyl, —SO₂—N($C_{1-6}$ alkyl)₂, —SO₂-phenyl, and 5-6-membered heteroaryl wherein phenyl and heteroaryl independently from each other may be optionally substituted by one or more $C_{1-6}$alkyl groups. In another embodiment, R¹ is a fused 9-10 membered bicyclic heteroaryl optionally substituted by one or more groups independently selected from F, methyl, CF₃, —OCH₃, —C(=O)OCH₃, —C(=O)O—$C_{0-4}$alkyl-cycloalkyl (suitably —C(=O)O—(CH₂)₀₋₁-cycloalkyl, wherein cycloalkyl is cyclobutyl or cyclohexyl), —SO₂CH₃, —SO₂N(CH₃)₂, —SO₂-phenyl, and 5-membered heteroaryl (suitably pyrazolyl) wherein phenyl and heteroaryl independently from each other may be optionally substituted by one or more $C_{1-6}$alkyl groups (suitably by methyl). In a particular embodiment, R¹ is a fused 9-10 membered bicyclic heteroaryl selected from azaindolyl, pyrrolopyridinyl (suitably 1H-pyrrolo[2,3-b]pyridinyl, 1H-pyrrolo[2,3-b]pyridinyl), furopyridinyl (suitably 4-furo[3,2-b]pyridin, 4-furo[2,3-b]pyridinyl), thienopyridinyl (suitably 4-thieno[3,2-b]pyridinyl, 4-thieno[2,3-b]pyridinyl), pyrollopyrazinyl (suitably 5H-pyrrolo[2,3-b]pyrazinyl), pyrrolopyrimidinyl (suitably 7H-pyrrolo[2,3-d]pyrimidinyl), pyrazolopyrazinyl (suitably 4-pyrazolo[1,5-a]pyrazinyl), pyrrolopyrimidinyl (suitably 7H-pyrrolo[2,3-d]pyrimidinyl), pyrazolopyridinyl (suitably 1H-pyrazolo[3,4-b]pyridinyl), imidazopyridinyl (suitably 4-imidazo[1,2-a]pyridinyl), quinolinyl, indolyl, bezothiazolyl, benzoisothiazolyl, furopyridinyl (suitably furo[3,2-b]pyridinyl), thienopyridinyl (suitably thieno[3,2-b]pyridinyl), which may be optionally substituted by one or more groups as defied above. In another particular embodiment R¹ is a fused 9-10 membered bicyclic heteroaryl selected from azaindolyl, pyrrolopyridinyl (suitably 1H-pyrrolo[2,3-b]pyridinyl, 1H-pyrrolo[2,3-b]pyridinyl), furopyridinyl (suitably 4-furo[3,2-b]pyridin, 4-furo[2,3-b]pyridinyl), thienopyridinyl (suitably 4-thieno[3,2-b]pyridinyl, 4-thieno[2,3-b]pyridinyl), pyrollopyrazinyl (suitably 5H-pyrrolo[2,3-b]pyrazinyl), pyrrolopyrimidinyl (suitably 7H-pyrrolo[2,3-d]pyrimidinyl), pyrazolopyrazinyl (suitably 4-pyrazolo[1,5-a]pyrazinyl), pyrrolopyrimidinyl (suitably 7H-pyrrolo[2,3-d]pyrimidinyl), pyrazolopyridinyl (suitably 1H-pyrazolo[3,4-b]pyridinyl), imidazopyridinyl (suitably 4-imidazo[1,2-a]pyridinyl), quinolinyl, indolyl, bezothiazolyl, benzoisothiazolyl, furopyridinyl (suitably furo[3,2-b]pyridinyl), thienopyridinyl (suitably thieno[3,2-b]pyridinyl), which may be unsubstituted or optionally substituted by one group independently selected from F, methyl, $CF_3$, —$OCH_3$, —C(=O)$OCH_3$, —C(=O)O—$C_{0-4}$alkyl-cycloalkyl (suitably —C(=O)O—$(CH_2)_{0-1}$-cycloalkyl, wherein cycloalkyl is cyclobutyl or cyclohexyl), —$SO_2CH_3$, —$SO_2N(CH_3)_2$, —$SO_2$-phenyl, and 5-membered heteroaryl (suitably pyrazolyl) wherein phenyl and heteroaryl independently from each other may be optionally substituted by one or more $C_{1-6}$alkyl groups (suitably by methyl). In more particular embodiment, $R^1$ is azaindolyl, pyrrolopyridinyl (suitably 1H-pyrrolo[2,3-b]pyridinyl or 1H-pyrrolo[2,3-b]pyridinyl), furopyridinyl (suitably 4-furo[3,2-b]pyridin-3-yl) or thienopyridinyl (suitably 4-thieno[3,2-b]pyridinyl), optionally substituted as defined above. In another more particular embodiment, $R^1$ is azaindolyl or pyrrolopyridinyl (suitably 1H-pyrrolo[2,3-b]pyridinyl or 1H-pyrrolo[2,3-b]pyridinyl), which may be unsubstituted or optionally substituted by one group as defined above.

In one embodiment, the invention relates to a compound of Formula (I), wherein when $R^1$ is a fused 9-10 membered bicyclic heteroaryl said fused 9-10 membered bicyclic heteroaryl is optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —C(=O)$OC_{1-6}$alkyl, —O(C=O)$C_{1-6}$alkyl, —C(=O)O—$C_{0-4}$alkyl-cycloalkyl, $C_{0-6}$alkyl-phenyl (wherein phenyl may be optionally substituted by $C_{1-4}$alkyl), —C(=O)$NHC_{1-6}$alkyl, —$NHC(=O)C_{1-6}$alkyl, —$SO_2$—$C_{1-6}$alkyl, —$SO_2$—N($C_{1-6}$ alkyl)$_2$, —$SO_2$-phenyl, and 5-6-membered heteroaryl wherein phenyl and heteroaryl independently from each other may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)$OC_{1-6}$alkyl, —C(=O)$NHC_{1-6}$alkyl and —$NHC(=O)C_{1-6}$alkyl; provided that when $W^1$ is N, $W^{3A}$, $W^{3B}$, $W^{4A}$, and $W^{4B}$ are —$CH_2$—, n and m are 1 or 2, sum of n and m is 3, X is —$(CH_2)x^1$, $x^1$ is 1, and $R^2$ is unsubstituted phenyl, then $R^1$ cannot represent benzothiazole-2-yl. In another embodiment, $R^1$ is a fused 9-10 membered bicyclic heteroaryl optionally substituted by one or more groups independently selected from halogen, $C_{1-6}$alkyl, halo$C_{1-6}$alkyl, —$OC_{1-6}$alkyl, —C(=O)$OC_{1-6}$alkyl, —C(=O)O—$C_{0-4}$alkyl-cycloalkyl, —$SO_2$—$C_{1-6}$alkyl, —$SO_2$—N($C_{1-6}$ alkyl)$_2$, —$SO_2$-phenyl, and 5-6-membered heteroaryl wherein phenyl and heteroaryl independently from each other may be optionally substituted by one or more $C_{1-6}$alkyl groups; provided that when $W^1$ is N, $W^{3A}$, $W^{3B}$, $W^{4A}$, and $W^{4B}$ are —$CH_2$—, n and m are 1 or 2, sum of n and m is 3, X is —$(CH_2)x^1$, $x^1$ is 1, and $R^2$ is unsubstituted phenyl, then $R^1$ cannot represent benzothiazole-2-yl. In another embodiment, $R^1$ is a fused 9-10 membered bicyclic heteroaryl optionally substituted by one or more groups independently selected from F, methyl, $CF_3$, —$OCH_3$, —C(=O)$OCH_3$, —C(=O)O—$C_{0-4}$alkyl-cycloalkyl (suitably —C(=O)O—$(CH_2)_{0-1}$-cycloalkyl, wherein cycloalkyl is cyclobutyl or cyclohexyl), —$SO_2CH_3$, —$SO_2N(CH_3)_2$, —$SO_2$-phenyl, and 5-membered heteroaryl (suitably pyrazolyl) wherein phenyl and heteroaryl independently from each other may be optionally substituted by one or more $C_{1-6}$alkyl groups (suitably by methyl); provided that when $W^1$ is N, $W^{3A}$, $W^{3B}$, $W^{4A}$, and $W^{4B}$ are —$CH_2$—, n and m are 1 or 2, sum of n and m is 3, X is —$(CH_2)x^1$, $x^1$ is 1, and $R^2$ is unsubstituted phenyl, then $R^1$ cannot represent benzothiazole-2-yl. In a particular embodiment, $R^1$ is a fused 9-10 membered bicyclic heteroaryl selected from azaindolyl, pyrrolopyridinyl (suitably 1H-pyrrolo[2,3-b]pyridinyl, 1H-pyrrolo[2,3-b]pyridinyl), furopyridinyl (suitably 4-furo[3,2-b]pyridin, 4-furo[2,3-b]pyridinyl), thienopyridinyl (suitably 4-thieno[3,2-b]pyridinyl, 4-thieno[2,3-b]pyridinyl), pyrollopyrazinyl (suitably 5H-pyrrolo[2,3-b]pyrazinyl), pyrrolopyrimidinyl (suitably 7H-pyrrolo[2,3-d]pyrimidinyl), pyrazolopyrazinyl (suitably 4-pyrazolo[1,5-a]pyrazinyl), pyrrolopyrimidinyl (suitably 7H-pyrrolo[2,3-d]pyrimidinyl), pyrazolopyridinyl (suitably 1H-pyrazolo[3,4-b]pyridinyl), imidazopyridinyl (suitably 4-imidazo[1,2-a]pyridinyl), quinolinyl, indolyl, bezothiazolyl, benzoisothiazolyl, furopyridinyl (suitably furo[3,2-b]pyridinyl), thienopyridinyl (suitably thieno[3,2-b]pyridinyl), which may be optionally substituted by one or more groups as defied above provided that when $W^1$ is N, $W^{3A}$, $W^{3B}$, $W^{4A}$, and $W^{4B}$ are —$CH_2$—, n and m are 1 or 2, sum of n and m is 3, X is —$(CH_2)x^1$, $x^1$ is 1, and $R^2$ is unsubstituted phenyl, then $R^1$ cannot represent benzothiazole-2-yl. In another particular embodiment $R^1$ is a fused 9-10 membered bicyclic heteroaryl selected from azaindolyl, pyrrolopyridinyl (suitably 1H-pyrrolo[2,3-b]pyridinyl, 1H-pyrrolo[2,3-b]pyridinyl), furopyridinyl (suitably 4-furo[3,2-b]pyridin, 4-furo[2,3-b]pyridinyl), thienopyridinyl (suitably 4-thieno[3,2-b]pyridinyl, 4-thieno[2,3-b]pyridinyl), pyrollopyrazinyl (suitably 5H-pyrrolo[2,3-b]pyrazinyl), pyrrolopyrimidinyl (suitably 7H-pyrrolo[2,3-d]pyrimidinyl), pyrazolopyrazinyl (suitably 4-pyrazolo[1,5-a]pyrazinyl), pyrrolopyrimidinyl (suitably 7H-pyrrolo[2,3-d]pyrimidinyl), pyrazolopyridinyl (suitably 1H-pyrazolo[3,4-b]pyridinyl), imidazopyridinyl (suitably 4-imidazo[1,2-a]pyridinyl), quinolinyl, indolyl, bezothiazolyl, benzoisothiazolyl, furopyridinyl (suitably furo[3,2-b]pyridinyl), thienopyridinyl (suitably thieno[3,2-b]pyridinyl), which may be unsubstituted or optionally substituted by one group independently selected from F, methyl, $CF_3$, —$OCH_3$, —C(=O)$OCH_3$, —C(=O)O—$C_{0-4}$alkyl-cycloalkyl (suitably —C(=O)O—$(CH_2)_{0-1}$-cycloalkyl, wherein cycloalkyl is cyclobutyl or cyclohexyl), —$SO_2CH_3$, —$SO_2N(CH_3)_2$), —$SO_2$-phenyl, and 5-membered heteroaryl (suitably pyrazolyl) wherein phenyl and heteroaryl independently from each other may be optionally substituted by one or more $C_{1-6}$alkyl groups (suitably by methyl); provided that when $W^1$ is N, $W^{3A}$, $W^{3B}$, $W^{4A}$, and $W^{4B}$ are —$CH_2$—, n and m are 1 or 2, sum of n and m is 3, X is —$(CH_2)x^1$, $x^1$ is 1, and $R^2$ is unsubstituted phenyl, then $R^1$ cannot represent benzothiazole-2-yl. In a more particular embodiment, $R^1$ is azaindolyl, pyrrolopyridinyl (suitably 1H-pyrrolo[2,3-b]pyridinyl or 1H-pyrrolo[2,3-b]pyridinyl), furopyridinyl (suitably 4-furo[3,2-b]pyridin-3-yl) or thienopyridinyl (suitably 4-thieno[3,2-b]pyridinyl), optionally substituted as defined above. In another more particular embodiment, $R^1$ is azaindolyl or pyrrolopyridinyl (suitably 1H-pyrrolo[2,3-b]pyridinyl or 1H-pyrrolo[2,3-b]pyridinyl), which may be unsubstituted or optionally substituted by one group as defined above.

In one embodiment, the invention relates to a compound of Formula (I), wherein when $R^1$ is a 5-6 membered heteroaryl said 5-6 membered heteroaryl is optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —C(=O)O$C_{1-6}$alkyl, —O(C=O)$C_{1-6}$alkyl, —C(=O)O—$C_{0-4}$alkyl-cycloalkyl, $C_{0-6}$alkyl-phenyl (wherein phenyl may be optionally substituted by $C_{1-4}$alkyl), —C(=O)NH$C_{1-6}$alkyl, —NHC(=O)$C_{1-6}$alkyl, —$SO_2$—$C_{1-6}$alkyl, —$SO_2$—N($C_{1-6}$alkyl)$_2$, —$SO_2$-phenyl, and 5-6-membered heteroaryl wherein phenyl and heteroaryl independently from each other may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl. In another embodiment, $R^1$ is a 5-6 membered heteroaryl optionally substituted by one or more groups independently selected from $C_{1-6}$alkyl, —O$C_{1-6}$alkyl, CN and $C_{0-6}$alkyl-phenyl wherein phenyl is unsubstituted. In a particular embodiment, $R^1$ is 5-membered heteroaryl (suitably imidazolyl) optionally substituted as defined above. In another particular embodiment, $R^1$ is 6-membered heteroaryl (suitably pyridinyl or pyridazinyl) optionally substituted as defined above. In more particular embodiment $R^1$ is imidazolyl optionally substituted by one $C_{1-6}$alkyl (suitably methyl) or by one —$CH_2$-phenyl, wherein phenyl is unsubstituted. In another more particular embodiment, $R^1$ is pyridinyl or pyridazinyl optionally substituted by one or two substituents independently selected from methyl, $OCH_3$, CN or —$CH_2$-phenyl, wherein phenyl is unsubstituted. In further more particular embodiment, $R^1$ is unsubstituted pyridinyl or pyridazinyl.

In one embodiment, the invention relates to a compound of Formula (I), wherein when $R^1$ is 6-10 membered aryl said 6-10 membered aryl is optionally substituted by one or more groups independently selected from halogen, CN, OH, $NO_2$, $C_{1-6}$alkyl, $C_{2-6}$alkenyl, $C_{2-6}$alkynyl, —O$C_{1-6}$alkyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl. In another embodiment, $R^1$ is phenyl optionally substituted by one or more groups independently selected from halogen, CN, OH, $NO_2$, $C_{1-6}$alkyl, $C_{2-6}$alkenyl, $C_{2-6}$alkynyl, —O$C_{1-6}$alkyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl. In a particular embodiment $R^1$ is phenyl optionally substituted by one or more groups independently selected from $C_{1-6}$alkyl, —O$C_{1-6}$alkyl, N,N-di($C_{1-6}$alkyl)amino and CN. In a more particular embodiment $R^1$ is phenyl optionally substituted by one or two groups independently selected from $C_{1-6}$alkyl (suitably methyl), —O$C_{1-6}$ alkyl (suitably $OCH_3$), N,N-di($C_{1-6}$alkyl)amino (suitably —N($CH_3$)$_2$) and CN.

In one embodiment, the invention relates to a compound of Formula (I), wherein when $R^1$ is a fused 8-10 membered partially unsaturated bicyclic heterocyclyl said fused 8-10 membered partially unsaturated bicyclic heterocyclyl is optionally substituted by one or more groups independently selected from halogen, CN, OH, $NO_2$, $C_{1-6}$alkyl, $C_{2-6}$alkenyl, $C_{2-6}$alkynyl, —O$C_{1-6}$alkyl, halo$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl. In another embodiment, $R^1$ is a fused 8-10 membered partially unsaturated bicyclic heterocyclyl which may be unsubstituted or optionally substituted by one or two groups independently selected from halogen (suitably F), $C_{1-6}$alkyl (suitably methyl), halo$C_{1-6}$alkyl (suitably $CF_3$) and —C(=O)O$C_{1-6}$ alkyl (suitably —C(=O)OCH($CH_3$)$_3$ or —C(=O)O$CH_3$). In a particular embodiment $R^1$ is selected from dihydroimidazopyrazinyl (suitably 6,8-dihydro-5H-imidazo[1,2-a]pyrazinyl), dihydropyrroloimidazolyl (suitably 6,7-dihydro-5H-pyrrolo[1,2-a]imidazolyl), dihydrofuropyridinyl (suitably 2,3-dihydrofuro[2,3-b]pyridine) and tertahydroimidazopyridinyl (suitably 5,6,7,8-tetrahydroimidazo[1,2-a]pyridinyl), which may be unsubstituted or optionally substituted by one group independently selected from halogen (suitably F), $C_{1-6}$alkyl (suitably methyl), halo$C_{1-6}$alkyl (suitably $CF_3$) and —C(=O)O$C_{1-6}$alkyl (suitably —C(=O)OCH($CH_3$)$_3$ or —C(=O)O$CH_3$).

In one embodiment, the invention relates to a compound of Formula (I), wherein when $R^1$ is a 5-6 membered monocyclic heterocycloalkyl said 5-6 membered monocyclic heterocycloalkyl is optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —O$C$(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl. In another embodiment $R^1$ is a 5-6 membered monocyclic heterocycloalkyl which is unsubstituted. In a particular embodiment $R^1$ is a 6 membered monocyclic heterocycloalkyl which is unsubstituted. In a more particular embodiment $R^1$ is tetrahydropyranyl.

In one embodiment, the invention relates to a compound of Formula (I-2) which is subset of Formula (I), wherein X is absent and $R^2$ is hydrogen for use as a medicament.

In one embodiment, the invention relates to a compound of Formula (I-2) which is subset of Formula (I), wherein X is absent and $R^2$ is hydrogen for use as intermediate for preparation of compound of formula (I) wherein $R^2$ is other than hydrogen. In another embodiment, the invention relates to the compound of Formula (I-2), which is subset of Formula (I), wherein X is absent and $R^2$ is hydrogen for use as intermediate for preparation of compound of formula (I), wherein $R^2$ is selected from (i), (ii), (iii), (iv), (v) and (vi) as defined for $R^2$ above or as defined for $R^2$ in any embodiments herein and below.

In one embodiment, the invention relates to a compound of Formula (I-2) which is subset of Formula (I), wherein X is absent and $R^2$ is H, provided that when $W^1$ is N, $W^2$ is CH, $W^{3A}$, $W^{3B}$, $W^{4A}$, and $W^{4B}$ are —$CH_2$—, sum of n and m is 3 or 4, then $R^1$ cannot represent piperidinyl, and when $W^1$ and $W^2$ are N, $W^{3A}$, $W^{3B}$, $W^{4A}$, and $W^{4B}$ are —$CH_2$—, sum of n and m is 3 or 4, then $R^1$ cannot represent phenyl optionally substituted by $CH_3$ or halogen, pyridinyl, pyrimidinyl or thiazolyl.

In one embodiment, the invention relates to a compound of Formula (I-2) which is subset of Formula (I), wherein X is absent and $R^2$ is H, provided that when $W^1$ is N, $W^2$ is CH, $W^{3A}$, $W^{3B}$, $W^{4A}$, and $W^{4B}$ are —CH$_2$—, sum of n and m is 3 or 4, then $R^1$ cannot represent piperidinyl, and when $W^1$ and $W^2$ are N, $W^{3A}$, $W^{3B}$, $W^{4A}$, and $W^{4B}$ are —CH$_2$—, sum of n and m is 3 or 4, then $R^1$ cannot represent phenyl optionally substituted by CH$_3$ or halogen, pyridinyl, pyrimidinyl or thiazolyl for use as a medicament.

In one embodiment, the invention relates to a compound of Formula (I-2) which is subset of Formula (I), wherein X is absent and $R^2$ is H, provided that when $W^1$ is N, $W^2$ is CH, $W^{3A}$, $W^{3B}$, $W^{4A}$, and $W^{4B}$ are —CH$_2$—, sum of n and m is 3 or 4, then $R^1$ cannot represent piperidinyl, and when $W^1$ and $W^2$ are N, $W^{3A}$, $W^{3B}$, $W^{4A}$, and $W^{4B}$ are —CH$_2$—, sum of n and m is 3 or 4, then $R^1$ cannot represent phenyl optionally substituted by CH$_3$ or halogen, pyridinyl, pyrimidinyl or thiazolyl for use as intermediate for preparation of compound of formula (I) wherein $R^2$ is other than H. In another embodiment, the invention relates to a compound of Formula (I-2) which is subset of Formula (I), wherein X is absent and $R^2$ is H, provided that when $W^1$ is N, $W^2$ is CH, $W^{3A}$, $W^{3B}$, $W^{4A}$, and $W^{4B}$ are —CH$_2$—, sum of n and m is 3 or 4, then $R^1$ cannot represent piperidinyl, and when $W^1$ and $W^2$ are N, $W^{3A}$, $W^{3B}$, $W^{4A}$, and $W^{4B}$ are —CH$_2$—, sum of n and m is 3 or 4, then $R^1$ cannot represent phenyl optionally substituted by CH$_3$ or halogen, pyridinyl, pyrimidinyl or thiazolyl for use as intermediate for preparation of compound of formula (I) wherein $R^2$ is selected from (i), (ii), (iii), (iv), (v) and (vi) as defined for $R^2$ above or as defined for $R^2$ in any embodiments herein and below.

In one embodiment, the invention relates to a compound of Formula (I-6) which is subset of Formula (I), wherein X is absent, $R^2$ is selected from (i), (ii), (iii), (iv), (v) and (vi) as defined for $R^2$ above or as defined for $R^2$ in any embodiments herein and below. In another embodiment, X is absent and $R^2$ is selected from $C_{1-10}$alkyl, 3-10 membered cycloalkyl, 6-membered aryl (phenyl) and 5-6 membered heteroaryl each of which may be optionally substituted as defined above or as defined in any of the embodiments herein and below. In a particular embodiment, X is absent and $R^2$ is $C_{1-10}$alkyl or 5-6 membered heteroaryl, each of which may be optionally substituted as defined above or as defined in any of the embodiments herein and below. In another particular embodiment, X is absent and $R^2$ is 3-10 membered cycloalkyl or 6-membered aryl (phenyl), each of which may be optionally substituted as defined above or as defined in any of the embodiments herein and below.

In one embodiment, the invention relates to a compound of Formula (I-6) which is subset of Formula (I), wherein X is absent $R^2$ is selected from (i), (ii), (iii), (iv), (v) and (vi) as defined for $R^2$ above or as defined for $R^2$ in any of the embodiments herein and below for use as a medicament. In another embodiment, X is absent and $R^2$ is selected from $C_{1-10}$alkyl, 3-10 membered cycloalkyl, 6-membered aryl (phenyl) and 5-6 membered heteroaryl each of which may be optionally substituted as defined in any of the embodiments herein for use as a medicament. In a particular embodiment, X is absent and $R^2$ is $C_{1-10}$alkyl or 5-6 membered heteroaryl, each of which may be optionally substituted as defined above or as defined in any of the embodiments herein and below for use as a medicament. In another particular embodiment, X is absent and $R^2$ is 3-10 membered cycloalkyl or 6-membered aryl (phenyl), each of which may be optionally substituted as defined above or as defined in any of the embodiments herein and below for use as a medicament.

In one embodiment, the invention relates to a compound of Formula (I-6) which is subset of Formula (I), wherein X is absent and when $R^2$ is $C_{1-10}$alkyl said $C_{1-10}$alkyl is optionally substituted by one or more groups independently selected from OH, —OC$_{1-4}$alkyl, —NHC$_{1-4}$alkyl, and —N(C$_{1-4}$alkyl)$_2$. In another embodiment, X is absent and $R^2$ is $C_{1-10}$alkyl optionally substituted by one or more —N(C$_{1-4}$alkyl)$_2$ groups. In a particular embodiment, X is absent and $R^2$ is $C_{1-7}$alkyl optionally substituted by one or two —N(C$_{1-4}$ alkyl)$_2$ groups (suitably by one or two N(CH$_3$)$_2$ or N(CH$_2$CH$_3$)$_2$ groups). In more particular embodiment, X is absent and $R^2$ is $C_{3-7}$alkyl (suitably branched $C_{3-7}$alkyl such as isopropyl, 2,2-dimetlypropyl, 2,4-dimethylpentanyl or a like) wherein alkyl is unsubstituted. In another more particular embodiment, X is absent and $R^2$ is $C_{3-7}$alkyl optionally substituted by one or two N(CH$_3$)$_2$ or N(CH$_2$CH$_3$)$_2$ groups.

In one embodiment, the invention relates to a compound of Formula (I-6) which is subset of Formula (I), wherein X is absent and when $R^2$ is 3-10 membered cycloalkyl said 3-10 membered cycloalkyl is optionally substituted by one or more groups independently selected from OH, halogen, CN, NH$_2$, $C_{1-6}$alkyl, $C_{2-6}$alkenyl, $C_{2-6}$alkynyl, haloC$_{1-6}$alkyloxy, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$. In another embodiment, X is absent and $R^2$ is 3-6 membered unsubstituted cycloalkyl. In a particular embodiment, 3-6 membered cycloalkyl is cyclopentyl.

In one embodiment, the invention relates to a compound of Formula (I-6) which is subset of Formula (I), wherein X is absent and when $R^2$ is 6-membered aryl (phenyl) said 6-membered aryl (phenyl) is optionally substituted by one or more groups independently selected from halogen, CN, OH, NO$_2$, $C_{1-6}$alkyl, $C_{2-6}$alkenyl, $C_{2-6}$alkynyl, —OC$_{1-6}$alkyl, 0-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl. In another embodiment, X is absent and $R^2$ is 6-membered aryl (phenyl) wherein aryl is unsubstituted. In a particular embodiment, X is absent and $R^2$ is phenyl.

In one embodiment, the invention relates to a compound of Formula (I-6) which is subset of Formula (I), wherein X is absent and when $R^2$ is 5-6 membered heteroaryl said 5-6 membered heteroaryl is optionally substituted by one or more groups independently selected from halogen, CN, OH, NO$_2$, $C_{1-6}$alkyl, $C_{2-6}$alkenyl, $C_{2-6}$alkynyl, haloC$_{1-6}$alkyl, —OC$_{1-6}$alkyl, haloC$_{1-6}$alkyloxy, $C_{1-6}$alkyl-OH, NH$_2$, N—(C$_{1-6}$-alkyl)amino, N,N-di(C$_{1-6}$alkyl)amino, —C(=O) C$_{1-6}$alkyl, —OC(=O)C$_{1-6}$alkyl, —C(=O)OH, —C(=O) OC$_{1-6}$alkyl, —C(=O)NHC$_{1-6}$alkyl, —NHC(=O)C$_{1-6}$alkyl, and 3-6-membered cycloalkyl wherein said cycloalkyl may optionally be substituted by one or more groups independently selected from halogen, CN, OH, NO$_2$, $C_{1-6}$alkyl, $C_{2-6}$alkenyl, $C_{2-6}$alkynyl, haloC$_{1-6}$alkyl, —OC$_{1-6}$alkyl, haloC$_{1-6}$alkyloxy, $C_{1-6}$alkyl-OH, NH$_2$, N—(C$_{1-6}$-alkyl) amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl. In another embodiment, X is absent and $R^2$ is 5-6 membered heteroaryl optionally substituted by one or more groups independently selected from halogen (suitably F), CN, $C_{1-6}$alkyl (suitably methyl), haloC$_{1-6}$alkyl (suitably CF$_3$), —OC$_{1-6}$alkyl (suitably OCH$_3$ or OCH$_2$CH$_3$, preferably OCH$_2$CH$_3$), $C_{1-6}$alkyl-OH (suitably CH$_2$OH or CH$_2$CH$_2$OH, preferably CH$_2$CH$_2$OH) and —C(=O)OC$_{1-6}$alkyl (suitably —C(=O)OCH$_3$) and 3-6-membered cycloalkyl (suitably unsubstituted cycloalkyl). In a particular embodiment, X is absent and $R^2$ is 6-membered heteroaryl (suitably pyridinyl or pyrimidinyl, preferably pyridinyl, more preferably pyridyn-2-yl or pyridyn-4-yl, even more preferably pyridyn-2-yl) optionally substituted by one or more groups independently selected from halogen (suitably F), CN, $C_{1-6}$alkyl (suitably methyl), halo$C_{1-6}$alkyl (suitably $CF_3$), —$OC_{1-6}$alkyl (suitably $OCH_3$ or $OCH_2CH_3$, preferably $OCH_2CH_3$), $C_{1-6}$alkyl-OH (suitably $CH_2OH$ or $CH_2CH_2OH$, preferably $CH_2CH_2OH$) and 3-6-membered cycloalkyl (suitably unsubstituted cyclopropyl). In another particular embodiment, X is absent and $R^2$ is 5-membered heteroaryl (suitably oxazolyl or thiazolyl) optionally substituted by one —C(=O)O$C_{1-6}$alkyl group (suitably by one —C(=O)OCH$_3$). In a more particular embodiment, X is absent and $R^2$ is 6-membered heteroaryl (suitably pyridinyl or pyrimidinyl, preferably pyridinyl, more preferably pyridyn-2-yl or pyridyn-4-yl, even more preferably pyridyn-2-yl) optionally substituted by one or two groups independently selected from halogen (suitably F), CN, $C_{1-6}$alkyl (suitably methyl), halo$C_{1-6}$alkyl (suitably $CF_3$), —$OC_{1-6}$alkyl (suitably $OCH_3$ or $OCH_2CH_3$, preferably $OCH_2CH_3$), $C_{1-6}$alkyl-OH (suitably $CH_2OH$ or $CH_2CH_2OH$, preferably $CH_2CH_2OH$) and 3-6-membered cycloalkyl (suitably unsubstituted cycloalkyl, preferably cyclopropyl).

In one embodiment, the invention relates to a compound of Formula (I-6) which is subset of Formula (I), wherein X is —$(CH_2)x^1$-, integer $x^1$ is 1, 2 or 3 and $R^2$ is selected from (i), (ii), (iii), (iv), (v) and (vi) as defined for $R^2$ above or as defined for $R^2$ in any of the embodiments herein and below. In another embodiment, X is —$(CH_2)x^1$-, integer $x^1$ is 1, 2 or 3 and $R^2$ is selected from $C_{1-10}$alkyl, 3-10 membered cycloalkyl, 5-6 membered heterocycloalkyl and 5-6 membered heteroaryl each of which may be optionally substituted as defined above or in any of the embodiments herein and below. In a particular embodiment, X is —$(CH_2)x^1$-, integer $x^1$ is 1, 2 or 3 and $R^2$ is 5-6 membered heteroaryl optionally substituted as defined above or in any of the embodiments herein and below. In another particular embodiment, X is —$(CH_2)x^1$-, integer $x^1$ is 1 or 2 and $R^2$ is 5-6 membered heteroaryl optionally substituted as defined in any of the embodiments herein.

In one embodiment, the integer $x^1$ is 1, 2 or 3. In another embodiment, integer $x^1$ is 1 or 2. In a particular embodiment, integer $x^1$ is 1. In another particular embodiment, integer $x^1$ is 2.

In one embodiment, the invention relates to a compound of Formula (I-6) which is subset of Formula (I), wherein X is —$(CH_2)x^1$-, integer $x^1$ is 1, 2 or 3 and when $R^2$ is $C_{1-10}$alkyl said $C_{1-10}$alkyl is optionally substituted by one or more groups independently selected from OH, —$OC_{1-4}$alkyl, —$NHC_{1-4}$alkyl, and —N($C_{1-4}$alkyl)$_2$. In another embodiment, X is —$(CH_2)x^1$-, integer $x^1$ is 1, 2 or 3 and $R^2$ is $C_{1-10}$alkyl (suitably tert-butyl) which is unsubstituted. In one embodiment, the invention relates to a compound of Formula (I-6) which is subset of Formula (I), wherein X is —$(CH_2)x^1$-, integer $x^1$ is 1, 2 or 3 and when $R^2$ is 3-10 membered cycloalkyl said 3-10 membered cycloalkyl is optionally substituted by one or more groups independently selected from OH, halogen, CN, $NH_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, —C(=O)$C_{1-6}$alkyl, —C(=O)O$C_{1-6}$alkyl, —C(=O)OH, —C(=O)NH$_2$, —$C_{0-6}$alkyl-NH—$C_{1-6}$alkyl and —$C_{0-6}$alkyl-N($C_{1-6}$alkyl)$_2$. In another embodiment, X is —$(CH_2)x^1$-, integer $x^1$ is 1 or 2, and $R^2$ is 3-6 membered cycloalkyl (suitably cyclopentyl) optionally substituted by one or more $C_{1-6}$alkyl (suitably methyl, ethyl or propyl) or —$C_{0-6}$alkyl-N($C_{1-6}$alkyl)$_2$ (suitably —$CH_2N(CH_3)_2$ or —$CH_2N(CH_2CH_3)_2$) groups. In a particular embodiment, 3-6 membered cycloalkyl is cyclopentyl optionally substituted by one group as defined herein.

In one embodiment, the invention relates to a compound of Formula (I-6) which is subset of Formula (I), wherein X is —$(CH_2)x^1$-, integer $x^1$ is 1, 2 or 3 and when $R^2$ is 5-6 membered heterocycloalkyl said 5-6 membered heterocycloalkyl is optionally substituted by one or more groups independently selected from OH, halogen, CN, $NH_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, —$C_{1-6}$alkyl-OH, —C(=O)$C_{1-6}$alkyl, —C(=O)O$C_{1-6}$alkyl, —C(=O)OH, and —C(=O)NH$_2$. In another embodiment, X is —$(CH_2)x^1$-, integer $x^1$ is 1 or 2, and $R^2$ is 5-6 membered heterocycloalkyl optionally substituted by one or more $C_{1-6}$alkyl (suitably methyl, ethyl or propyl) or —$C_{0-6}$alkyl-N($C_{1-6}$alkyl)$_2$ (suitably —$CH_2N(CH_3)_2$ or —$CH_2N(CH_2CH_3)_2$) groups. In a particular embodiment, 5-6 membered heterocycloalkyl is oxetanyl optionally substituted by one group as defined herein.

In one embodiment, the invention relates to a compound of Formula (I-6) which is subset of Formula (I), wherein X is —$(CH_2)x^1$-, integer $x^1$ is 1, 2 or 3 and when $R^2$ is 5-6 membered heteroaryl said 5-6 membered heteroaryl is optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —$OC(=O)C_{1-6}$alkyl, —C(=O)OH, —C(=O)O$C_{1-6}$alkyl, —C(=O)NH$C_{1-6}$alkyl, —NHC(=O)$C_{1-6}$alkyl, and 3-6-membered cycloalkyl wherein said cycloalkyl may optionally be substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —$OC_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —$OC(=O)C_{1-6}$alkyl, —C(=O)OH, —C(=O)O$C_{1-6}$alkyl, —C(=O)NH$C_{1-6}$alkyl and —NHC(=O)$C_{1-6}$alky. In another embodiment, X is —$(CH_2)x^1$—, integer $x^1$ is 1, 2 or 3 and $R^2$ is 5-6 membered heteroaryl selected from oxazolyl, isoxazolyl, thiophenyl, thiazolyl, pyrrolyl, furanyl and pyridinyl which is unsubstituted or optionally substituted by one or more $C_{1-6}$alkyl (suitably by one or two methyl).

In one embodiment, the invention relates to a compound of Formula (I-6) which is subset of Formula (I), wherein X is —$(CH_2)x^2$-$C(CH_3)_2$—$(CH_2)x^3$-, integer $x^2$ is 1 or 2, integer $x^3$ is 1, and $R^2$ is selected from (i), (ii), (iii), (iv), (v) and (vi) as defined for $R^2$ above or as defined for $R^2$ in any of the embodiments herein and below. In another embodiment, X is —$(CH_2)x^2$-$C(CH_3)_2$—$(CH_2)x^3$-, integer $x^2$ is 1 or 2, integer $x^3$ is 1, and $R^2$ is selected from —NH$C_{1-4}$alkyl, —N($C_{1-4}$alkyl)$_2$, and 5-6 membered heterocycloalkyl each of which may be optionally substituted as defined above or as defined in any of the embodiments herein and below. In a particular embodiment, X is —$(CH_2)x^2$-$C(CH_3)_2$—$(CH_2)x^3$-, integer $x^2$ is 1 or 2, integer $x^3$ is 1, and $R^2$ is —N($C_{1-4}$alkyl)$_2$ (suitably N($CH_3)_2$ or N($CH_2CH_3)_2$, preferably it is N($CH_2CH_3)_2$) or 5-6 membered heterocycloalkyl (suitably morpholinyl). In another particular embodiment, X is —$(CH_2)x^2$-$C(CH_3)_2$—$(CH_2)x^3$-, integer $x^2$ is 1, integer $x^3$ is 1, and $R^2$ is —N($C_{1-4}$alkyl)$_2$ (suitably N($CH_3)_2$ or N($CH_2CH_3)_2$, preferably it is N($CH_2CH_3)_2$) or 5-6 membered heterocycloalkyl (suitably morpholinyl), and $R^2$ is unsubstituted.

In one embodiment, the invention relates to a compound of Formula (I-5) which is subset of Formula (I), wherein X is —C(=O)—$(CH_2)x^4$-, integer $x^4$ is zero, 1 or 2, and $R^2$ is selected from (i), (ii), (iii), (iv), (v) and (vi) as defined for $R^2$ above or as defined for $R^2$ in any of the embodiments herein and below for use as a medicament. In another embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below for use as a medicament. In a particular embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below, provided that when X is —(C=O)(CH$_2$)x$^4$, x$^4$ is zero, $R^2$ is unsubstituted cyclopentyl or phenyl optionally substituted by halogen, $W^1$ is N, $W^2$ is CH or N, $W^{3,4}$ and $W^{3B}$ are —CH$_2$— or —CH(R$^3$)—, $R^3$ is CH$_3$, $W^{4,4}$, and $W^{4B}$ are —CH$_2$—, then $R^1$ is a fused 9-10 membered bicyclic heteroaryl or a fused 8-10 membered partially unsaturated bicyclic heterocyclyl for use as a medicament.

In one embodiment, the invention relates to a compound of Formula (I-5) which is subset of Formula (I), wherein X is —C(=O)—(CH$_2$)x$^4$-, integer x$^4$ is zero, 1 or 2, and $R^2$ is selected from (i), (ii), (iii), (iv), (v) and (vi) as defined for $R^2$ above or as defined for $R^2$ in any of the embodiments herein and below. In another embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below. In a particular embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or in any of the embodiments herein and below, provided that when X is (C=O)(CH$_2$)x$^4$, x$^4$ is zero, $R^2$ is unsubstituted cyclopentyl or phenyl optionally substituted by halogen, $W^1$ is N, $W^2$ is CH or N, $W^{3,4}$ and $W^{3B}$ are —CH$_2$— or —CH(R$^3$)—, $R^3$ is CH$_3$, $W^{4,4}$, and $W^{4B}$ are —CH$_2$—, then $R^1$ is a fused 9-10 membered bicyclic heteroaryl or a fused 8-10 membered partially unsaturated bicyclic heterocyclyl. In another particular embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 5-6 membered heterocycloalkyl and 5-6 membered heteroaryl. In further particular embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 5-6 membered heterocycloalkyl, 5-6 membered heteroaryl each of which may be optionally substituted as defined in any of the embodiments herein and above; substituted 3-10 membered cycloalkyl, and substituted 6-membered aryl (phenyl) as defined herein and above. In a more particular embodiment, X is —C(=O)—(CH$_2$)x$^4$-, integer x$^4$ is zero, 1 or 2, and $R^2$ is selected from $C_{1-10}$alkyl, NHC$_{1-4}$alkyl, —N(C$_{1-4}$alkyl)$_2$; 5-6 membered heterocycloalkyl, and 5-6 membered heteroaryl each of which may be optionally substituted as defined in any of the embodiments herein and above.

In one embodiment, X is —C(=O)—(CH$_2$)x$^4$-, integer x$^4$ is zero, 1 or 2, and when $R^2$ is $C_{1-10}$alkyl, said $C_{1-10}$alkyl is optionally substituted by one or more groups independently selected from OH, —OC$_{1-4}$alkyl, —NHC$_{1-4}$alkyl, and —N(C$_{1-4}$alkyl)$_2$. In another embodiment, X is —C(=O)—(CH$_2$)x$^4$-, integer x$^4$ is zero, 1 or 2, and $R^2$ is $C_{1-4}$alkyl (suitably methyl, ethyl, propyl, isopropyl, 2-methyl-propyl, butyl, tert-butyl) which is unsubstituted or optionally substituted by one or more groups independently selected from OH, —OC$_{1-4}$alkyl, —NHC$_{1-4}$alkyl, and —N(C$_{1-4}$alkyl)$_2$. In a particular embodiment, X is —C(=O)—(CH$_2$)x$^4$-, integer x$^4$ is zero, 1 or 2, $R^2$ is $C_{1-4}$alkyl (suitably isopropyl 2-methyl-propyl, butyl, or tert-butyl) and $R^2$ is unsubstituted. In a more particular embodiment, integer x$^4$ is zero.

In one embodiment, X is —C(=O)—(CH$_2$)x$^4$-, integer x$^4$ is zero, 1 or 2, and when $R^2$ is NHC$_{1-4}$alkyl or —N(C$_{1-4}$alkyl)$_2$ said $C_{1-4}$alkyl is methyl, ethyl, propyl, isopropyl, butyl or tert-butyl. In a particular embodiment, X is —C(=O)—(CH$_2$)x$^4$-, integer x$^4$ is zero and $R^2$ is —N(C$_{1-4}$alkyl)$_2$ wherein $C_{1-4}$alkyl is methyl or ethyl. In another particular embodiment, X is —C(=O)—(CH$_2$)x$^4$-, integer x$^4$ is zero, 1 or 2, and $R^2$ is NHC$_{1-4}$alkyl wherein $C_{1-4}$alkyl is isopropyl or tert-butyl. In more particular embodiment, X is —C(=O)—(CH$_2$)x$^4$-, integer x$^4$ is zero and $R^2$ is NHC$_{1-4}$alkyl wherein $C_{1-4}$alkyl (suitably it is tert-butyl).

In one embodiment, X is —C(=O)—(CH$_2$)x$^4$-, integer x$^4$ is zero, 1 or 2, and when $R^2$ is 3-10 membered cycloalkyl said 3-10 membered cycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$. In another embodiment, X is —C(=O)—(CH$_2$)x$^4$-, integer x$^4$ is zero, 1 or 2, and $R^2$ is 3-6 membered unsubstituted cycloalkyl (suitably cyclopropyl, cyclobutyl, cyclopentyl or cyclohexyl). In a particular embodiment, X is —C(=O)—(CH$_2$)x$^4$-, integer x$^4$ is zero, $R^2$ is 3-10 membered cycloalkyl is 3-6 membered unsubstituted cycloalkyl (suitably cyclopropyl, cyclobutyl, or cyclohexyl).

In one embodiment, X is —C(=O)—(CH$_2$)x$^4$-, integer x$^4$ is zero, 1 or 2, and when $R^2$ is 3-10 membered cycloalkyl said 3-10 membered cycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$; provided that when X is —(C=O)(CH$_2$) x$^4$, x$^4$ is zero, $R^2$ is unsubstituted cyclopentyl, $W^1$ is N, $W^2$ is CH or N, $W^{3,4}$ and $W^{3B}$ are —CH$_2$— or —CH(R$^3$)—, $R^3$ is CH$_3$, $W^{4,4}$, and $W^{4B}$ are —CH$_2$—, then $R^1$ is a fused 9-10 membered bicyclic heteroaryl or a fused 8-10 membered partially unsaturated bicyclic heterocyclyl. In another embodiment, X is —C(=O)—(CH$_2$)x$^4$-, integer x$^4$ is zero, 1 or 2, and $R^2$ is 3-6 membered unsubstituted cycloalkyl (suitably cyclopropyl, cyclobutyl, cyclopentyl or cyclohexyl). In a particular embodiment, X is —C(=O)—(CH$_2$)x$^4$-, integer x$^4$ is zero, $R^2$ is 3-10 membered cycloalkyl is 3-6 membered unsubstituted cycloalkyl (suitably cyclopropyl, cyclobutyl, or cyclohexyl). In one embodiment, X is —C(=O)—(CH$_2$)x$^4$-, integer x$^4$ is zero, 1 or 2, and when $R^2$ is 5-6 membered heterocycloalkyl said 5-6 membered heterocycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, and —C(=O)NH$_2$. In another embodiment, X is —C(=O)—(CH$_2$)x$^4$-, integer x$^4$ is zero, 1 or 2, and $R^2$ is 5-6 membered heterocycloalkyl optionally substituted by one or more $C_{1-6}$alkyl (suitably by one or more methyl groups). In a particular embodiment, X is —C(=O)—(CH$_2$)x$^4$-, integer x$^4$ is zero, R$^2$ is 5-6 membered heterocycloalkyl (suitably morpholinyl, piperidinyl, or pyrrolidinyl) which is unsubstituted or substituted by one or more $C_{1-6}$alkyl (suitably by one or more methyl groups).

In one embodiment, X is —C(=O)—(CH$_2$)x$^4$-, integer x$^4$ is zero, 1 or 2, and when R$^2$ is 6-membered aryl (phenyl) said 6-membered aryl (phenyl) is optionally substituted by one or more groups independently selected from halogen, CN, OH, NO$_2$, $C_{1-6}$alkyl, $C_{2-6}$alkenyl, $C_{2-6}$alkynyl, —O$C_{1-6}$alkyl, O-phenyl, halo$C_{1-6}$alkyl, halo$C_{1-6}$alkyloxy, —$C_{1-6}$alkyl-OH, NH$_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl. In another embodiment, X is —C(=O)—(CH$_2$)x$^4$-, integer x$^4$ is zero, 1 or 2, and R$^2$ is phenyl optionally substituted by $C_{1-6}$alkyl (suitably by tert-butyl). In a particular embodiment, X is —C(=O)—(CH$_2$)x$^4$-, integer x$^4$ is zero, and R$^2$ is phenyl optionally substituted by $C_{1-6}$alkyl (suitably by tert-butyl).

In one embodiment, X is —C(=O)—(CH$_2$)x$^4$-, integer x$^4$ is zero, 1 or 2, and when R$^2$ is 6-membered aryl (phenyl) said 6-membered aryl (phenyl) is optionally substituted by one or more groups independently selected from halogen, CN, OH, NO$_2$, $C_{1-6}$alkyl, $C_{2-6}$alkenyl, $C_{2-6}$alkynyl, —O$C_{1-6}$alkyl, O-phenyl, halo$C_{1-6}$alkyl, halo$C_{1-6}$alkyloxy, —$C_{1-6}$alkyl-OH, NH$_2$, N—($C_{1-6}$-alkyl)amino, N,N-di($C_{1-6}$alkyl)amino, —C(=O)$C_{1-6}$alkyl, —C(=O)OH, —O(C=O)$C_{1-6}$alkyl, —C(=O)O$C_{1-6}$alkyl, —C(=O)NH$C_{1-6}$alkyl and —NHC(=O)$C_{1-6}$alkyl; provided that when X is —(C=O)(CH$_2$)x$^4$, x$^4$ is zero, R$^2$ is phenyl optionally substituted by halogen, W$^1$ is N, W$^2$ is CH or N, W$^{3A}$ and W$^{3B}$ are —CH$_2$— or —CH(R$^3$)—, R$^3$ is CH$_3$, W$^{4A}$, and W$^{4B}$ are —CH$_2$—, then R$^1$ is a fused 9-10 membered bicyclic heteroaryl or a fused 8-10 membered partially unsaturated bicyclic heterocyclyl. In another embodiment, X is —C(=O)—(CH$_2$)x$^4$-, integer x$^4$ is zero, 1 or 2, and R$^2$ is phenyl optionally substituted by $C_{1-6}$alkyl (suitably by tert-butyl). In a particular embodiment, X is —C(=O)—(CH$_2$)x$^4$-, integer x$^4$ is zero, and R$^2$ is phenyl optionally substituted by $C_{1-6}$alkyl (suitably by tert-butyl).

In one embodiment, X is —C(=O)—(CH$_2$)x$^4$-, integer x$^4$ is zero, 1 or 2, and when R$^2$ is 5-6 membered heteroaryl said 5-6 membered heteroaryl is optionally substituted by one or more groups independently selected from halogen, CN, OH, NO$_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, NH$_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl, —NHC(=O)$C_{1-6}$alkyl, and 3-6-membered cycloalkyl wherein said cycloalkyl may optionally be substituted by one or more groups independently selected from halogen, CN, OH, NO$_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, NH$_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alky. In another embodiment, X is —C(=O)—(CH$_2$)x$^4$-, integer x$^4$ is zero, 1 or 2, and R$^2$ is 5-6 membered heteroaryl optionally substituted by one or more $C_{1-6}$alkyl groups (suitably by one or two methyl groups). In a particular embodiment, X is —C(=O)—(CH$_2$)x$^4$-, integer x$^4$ is zero or 1, and R$^2$ is 5-6 membered heteroaryl (suitably oxazolyl, isoxazolyl, thiophenyl, imidazolyl, pyridinyl; preferably it is oxazolyl or isoxazolyl) which is unsubstituted or substituted by one or two methyl groups.

In one embodiment, integer x$^4$ is zero or 1. In another embodiment, integer x$^4$ is 1 or 2. In a further embodiment, integer x$^4$ is zero.

In one embodiment, the invention relates to a compound of Formula (I-4) which is subset of Formula (I), wherein X is —C(=O)O—(CH$_2$)x$^5$-, integer x$^5$ is zero, 1, 2 or 3, and R$^2$ is selected from (i), (ii), (iii), (iv), (v) and (vi) as defined for R$^2$ above or as defined for R$^2$ in any of the embodiments herein and below for use as a medicament. In another embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below for use as a medicament. In a particular embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined in any of the embodiments herein and above; provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other that phenyl optionally substituted by $C_{1-6}$ alkyl or —O$C_{1-6}$ alkyl, pyridyl optionally substituted by halogen for use as a medicament.

In one embodiment, the invention relates to a compound of Formula (I-4) which is subset of Formula (I), wherein X is —C(=O)O—(CH$_2$)x$^5$-, integer x$^5$ is zero, 1, 2 or 3, and R$^2$ is selected from (i), (ii), (iii), (iv), (v) and (vi) as defined for R$^2$ above or as defined for R$^2$ in any of the embodiments herein and below. In another embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below. In a particular embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, 6-membered aryl (phenyl) and 5-6 membered heteroaryl each of which may be optionally substituted as defined above or as defined in any of the embodiments herein and below; provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other that phenyl optionally substituted by $C_{1-6}$ alkyl or —O$C_{1-6}$ alkyl, pyridyl optionally substituted by halogen. In another particular embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, 5-6 membered heteroaryl each of which may be optionally substituted as defined above or as defined in any of the embodiments herein and below, and substituted 6-membered aryl (phenyl) as defined above or as defined in any of the embodiments herein and below. In a more particular embodiment, X is —C(=O)O—(CH$_2$)x$^5$-, integer x$^5$ is zero, 1, 2 or 3, and R$^2$ is selected from $C_{1-10}$alkyl, NH$C_{1-4}$alkyl, —N($C_{1-4}$alkyl)$_2$; 3-10 membered cycloalkyl, 5-6 membered heterocycloalkyl, and 5-6 membered heteroaryl each of which may be optionally substituted as defined above or as defined in any of the embodiments herein and below.

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is C$_{1-10}$alkyl said C$_{1-10}$alkyl is optionally substituted by one or more groups independently selected from OH, —OC$_{1-4}$alkyl, —NHC$_{1-4}$alkyl, and —N(C$_{1-4}$alkyl)$_2$. In another embodiment, X is —C(=O)O—(CH$_2$)x$^5$-, integer x$^5$ is zero, 1, 2 or 3, and R$^2$ is C$_{1-10}$alkyl optionally substituted by one or more OC$_{1-4}$alkyl (suitably by one OCH$_3$ group) or —N(C$_{1-4}$alkyl)$_2$ groups (suitably by one N(CH$_3$)$_2$ or NCH$_2$(CH$_3$)$_2$). In a particular embodiment, X is —C(=O)O—(CH$_2$)x$^5$-, integer x$^5$ is zero, 1 or 2, and R$^2$ is C$_{1-4}$alkyl (suitably methyl, ethyl, propyl, isopropyl, tert-butyl, 2-methyl-propan-2-yl) optionally substituted by one or more OC$_{1-4}$alkyl (suitably by one OCH$_3$ group) or —N(C$_{1-4}$alkyl)$_2$ group (suitably by one N(CH$_3$)$_2$ or NCH$_2$(CH$_3$)$_2$). In another particular embodiment, X is —C(=O)O—(CH$_2$)x$^5$-, integer x$^5$ is zero or 1, and R$^2$ is C$_{1-4}$alkyl (suitably methyl, ethyl, propyl, isopropyl, tert-butyl, 2-methyl-propan-2-yl) optionally substituted by one OC$_{1-4}$alkyl (suitably by one OCH$_3$ group) or —N(C$_{1-4}$alkyl)$_2$ group (suitably by one N(CH$_3$)$_2$ or NCH$_2$(CH$_3$)$_2$). In a more particular embodiment, X is —C(=O)O—(CH$_2$)x$^5$-, integer x$^5$ is zero or 1, and R$^2$ is unsubstituted tert-butyl.

In one embodiment, the invention relates to a compound of Formula (I-1) which is subset of Formula (I), wherein X is —C(=O)O—(CH$_2$)x$^5$-, integer x$^5$ is zero and R$^2$ is unsubstituted tert-butyl for use as a medicament.

In one embodiment, the invention relates to a compound of Formula (I-1) which is subset of Formula (I), wherein X is —C(=O)O—(CH$_2$)x$^5$-, integer x$^5$ is zero and R$^2$ is unsubstituted tert-butyl.

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is —NHC$_{1-4}$alkyl or —N(C$_{1-4}$alkyl)$_2$ said C$_{1-4}$alkyl is methyl, ethyl, propyl, isopropyl, butyl or tert-butyl. In another embodiment, X is —C(=O)O—(CH$_2$)x$^5$-, integer x$^5$ is zero, 1 or 2, and R$^2$ is —N(C$_{1-4}$alkyl)$_2$. In another embodiment, X is —C(=O)O—(CH$_2$)x$^5$-, integer x$^5$ is zero, 1 or 2, and R$^2$ is N(CH$_3$)$_2$ or NCH$_2$(CH$_3$)$_2$.

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is 3-10 membered cycloalkyl said 3-10 membered cycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$. In another embodiment, X is —C(=O)O—(CH$_2$)x$^5$-, integer x$^5$ is zero, 1, 2 or 3, and R$^2$ is 3-10 membered cycloalkyl optionally substituted by one or more groups independently selected from C$_{1-6}$alkyl (suitably by one or two independently selected from methyl, ethyl, propyl and isopropyl; more suitably by one methyl and one isopropyl) and —OC$_{1-6}$alkyl (suitably by one OCH$_3$). In a particular embodiment, X is —C(=O)O—(CH$_2$)x$^5$-, integer x$^5$ is zero or 1, and R$^2$ is 3-10 membered cycloalkyl (suitably cyclopropyl, cyclobutyl, cyclohexyl or adamantyl) optionally substituted by one or two groups selected from C$_{1-6}$alkyl (suitably by one or two independently selected from methyl, ethyl, propyl or isopropyl; more suitably by one methyl and one isopropyl) and —OC$_{1-6}$alkyl (suitably by one OCH$_3$).

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is 5-6 membered heterocycloalkyl said 5-6 membered heterocycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, and —C(=O)NH$_2$. In another embodiment, X is —C(=O)O—(CH$_2$)x$^5$-, integer x$^5$ is zero, 1, 2 or 3, and R$^2$ is 5-6 membered heterocycloalkyl optionally substituted by one or more groups independently selected from C$_{1-6}$alkyl (suitably methyl) and —C(=O)OC$_{1-6}$alkyl (suitably —C(=O)OC(CH$_3$)$_3$). In a particular embodiment, X is —C(=O)O—(CH$_2$)x$^5$-, integer x$^5$ is zero, 1, 2 or 3, and R$^2$ is 5-6 membered heterocycloalkyl (suitably oxetanyl, tetrahydrofuranyl, piperidinyl, morpholinyl, tetrahydropyranyl or dioxanyl; more suitably tetrahydrofuranyl or piperidinyl) optionally substituted by one or two groups independently selected from C$_{1-6}$alkyl (suitably by one methyl) and —C(=O)OC$_{1-6}$alkyl (suitably by one —C(=O)OC(CH$_3$)$_3$).

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is 6-membered aryl (phenyl) said 6-membered aryl (phenyl) is optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl. In another embodiment, X is —C(=O)O—(CH$_2$)x$^5$-, integer x$^5$ is zero, 1, 2 or 3, and R$^2$ is phenyl optionally substituted by one or two groups independently selected from halogen (suitably F), OH, NO$_2$, C$_{1-6}$alkyl (suitably methyl), —OC$_{1-6}$alkyl (suitably OCH$_3$), O-phenyl, haloC$_{1-6}$alkyl (suitably CF$_3$). In a particular embodiment, integer x$^5$ is zero or 1, and R$^2$ is phenyl optionally substituted by one or two groups independently selected from halogen (suitably F), OH, NO$_2$, C$_{1-6}$alkyl (suitably methyl), —OC$_{1-6}$alkyl (suitably OCH$_3$), O-phenyl, haloC$_{1-6}$alkyl (suitably CF$_3$).

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is 6-membered aryl (phenyl) said 6-membered aryl (phenyl) is optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl, provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$ alkyl, pyridyl optionally substituted by halogen. In another embodiment, X is —C(=O)O—(CH$_2$)x$^5$-, integer x$^5$ is zero, 1, 2 or 3, and R$^2$ is phenyl optionally substituted by one or two groups independently selected from halogen (suitably F), OH, NO$_2$, C$_{1-6}$alkyl (suitably methyl), —OC$_{1-6}$alkyl (suitably OCH$_3$), O-phenyl, haloC$_{1-6}$alkyl (suitably CF$_3$); provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$ alkyl, pyridyl optionally substituted by halogen. In a particular embodiment, integer x$^5$ is zero or 1, and R$^2$ is phenyl optionally substituted by one or two groups independently selected from halogen (suitably F), OH, NO$_2$, C$_{1-6}$alkyl (suitably methyl), —OC$_{1-6}$alkyl (suitably OCH$_3$), O-phenyl, haloC$_{1-6}$alkyl (suitably CF$_3$); provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$ alkyl, pyridyl optionally substituted by halogen.

In one embodiment, the invention relates to a compound of Formula (I-4) which is subset of Formula (I), wherein X is —C(=O)O—(CH$_2$)x$^5$-, integer x$^5$ is zero, 1, 2 or 3, and when R$^2$ is 5-6 membered heteroaryl said 5-6 membered heteroaryl is optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl, —NHC(=O)C$_{1-6}$alkyl, and 3-6-membered cycloalkyl wherein said cycloalkyl may optionally be substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alky. In another embodiment, X is —C(=O)O—(CH$_2$)x$^5$-, integer x$^5$ is zero, 1, 2 or 3, and R$^2$ is 5-6 membered heteroaryl optionally substituted by one or two C$_{1-6}$alkyl (suitably by methyl) groups. In a particular embodiment, X is —C(=O)O—(CH$_2$)x$^5$-, integer x$^5$ is zero or 1, and R$^2$ is 5-6 membered heteroaryl (suitably furanyl, oxazolyl, isoxazolyl or pyridinyl) optionally substituted by one or two C$_{1-6}$alkyl (suitably by methyl) groups. In a more particular embodiment, X is —C(=O)O—(CH$_2$)x$^5$-, integer x$^5$ is zero or 1, and R$^2$ is oxazolyl or isoxazolyl substituted by two methyl groups.

In one embodiment, integer x$^5$ is zero, 1, 2 or 3. In another embodiment, integer x$^5$ is zero 1 or 2. In a particular embodiment, integer x$^5$ is zero or 1. In another particular embodiment, integer x$^5$ is 2 or 3. In more particular embodiment, integer x$^5$ is zero.

In one embodiment, the invention relates to a compound of Formula (I-3) which is subset of Formula (I), wherein X is —C(=O)NR$^x$—(CH$_2$)x$^6$-, integer x$^6$ is zero, 1 or 2, R$^x$ is H or C$_{1-4}$alkyl, and R$^2$ is selected from (i), (ii), (iii), (iv), (v) and (vi) as defined for R$^2$ above or as defined for R$^2$ in any of the embodiments herein and below for use as a medicament. In another embodiment, X is —C(=O)NR$^x$—(CH$_2$)x$^6$-, integer x$^6$ is zero, 1 or 2, R$^x$ is H or C$_{1-4}$alkyl, and R$^2$ is selected from C$_{1-10}$alkyl, 3-10 membered cycloalkyl, 6-membered aryl (phenyl) and 5-6 membered heteroaryl each of which may be optionally substituted as defined above or as defined in any of the embodiments herein and below for use as a medicament.

In one embodiment, the invention relates to a compound of Formula (I-3) which is subset of Formula (I), wherein X is —C(=O)NR$^x$—(CH$_2$)x$^6$-, integer x$^6$ is zero, 1 or 2, R$^x$ is H or C$_{1-4}$alkyl, and R$^2$ is selected from (i), (ii), (iii), (iv), (v) and (vi) as defined for R$^2$ above or as defined for R$^2$ in any of the embodiments herein and below. In another embodiment, X is —C(=O)NR$^x$—(CH$_2$)x$^6$-, integer x$^6$ is zero, 1 or 2, R$^x$ is H or C$_{1-4}$alkyl, and R$^2$ is selected from C$_{1-10}$alkyl, 3-10 membered cycloalkyl, 6-membered aryl (phenyl) and 5-6 membered heteroaryl each of which may be optionally substituted as defined above or as defined in any of the embodiments herein and below.

In one embodiment, the invention relates to a compound of Formula (I-3) which is subset of Formula (I), wherein X is —C(=O)NR$^x$—(CH$_2$)x$^6$-, integer x$^6$ is zero, 1 or 2, R$^x$ is H or C$_{1-4}$alkyl, and when R$^2$ is C$_{1-10}$alkyl said C$_{1-10}$alkyl is optionally substituted by one or more groups independently selected from OH, —OC$_{1-4}$alkyl, —NHC$_{1-4}$alkyl, and —N(C$_{1-4}$alkyl)$_2$. In another embodiment, X is —C(=O)NR$^x$—(CH$_2$)x$^6$-, integer x$^6$ is zero, 1 or 2, R$^x$ is H or C$_{1-4}$alkyl (suitably R$^x$ is H or methyl, ethyl, propyl, isopropyl, butyl or tert-butyl), and R$^2$ is C$_{1-8}$alkyl which is unsubstituted or substituted by one OH group. In a particular embodiment, X is —C(=O)NR$^x$—(CH$_2$)x$^6$-, integer x$^6$ is zero or 1, R$^x$ is H, and R$^2$ is C$_1$alkyl (suitably methyl, ethyl, propyl, isopropyl, butyl, tert-butyl, 3-methyl-butan-2-yl or 2,4,4-trimethylpentan-2-yl), which is unsubstituted or substituted by one OH group. In another particular embodiment, X is —C(=O)NR$^x$—(CH$_2$)x$^6$-, integer x$^6$ is zero or 1, R$^x$ is C$_{1-4}$alkyl (suitably methyl, ethyl, propyl, isopropyl, butyl or tert-butyl), and R$^2$ is C$_{1-4}$alkyl (suitably methyl, ethyl, propyl, isopropyl, butyl or tert-butyl). Suitably R$^2$ is unsubstituted alkyl.

In one embodiment, the invention relates to a compound of Formula (I-3) which is subset of Formula (I), wherein X is —C(=O)NR$^x$—(CH$_2$)x$^6$-, integer x$^6$ is zero, 1 or 2, R$^x$ is H or C$_{1-4}$alkyl, and when R$^2$ is 3-10 membered cycloalkyl said 3-10 membered cycloalkyl is optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$. In another embodiment, X is —C(=O)NR$^x$—(CH$_2$)x$^6$-, integer x$^6$ is zero, 1 or 2, R$^x$ is H or C$_{1-4}$alkyl, and R$^2$ is 3-10 membered cycloalkyl optionally substituted by one haloC$_{1-6}$alkyl (suitably by one CF$_3$ group). In a particular embodiment, X is —C(=O)NR$^x$—(CH$_2$)x$^6$-, integer x$^6$ is zero or 1, R$^x$ is H or C$_{1-4}$alkyl, and R$^2$ is 3-10 membered cycloalkyl (suitably cyclopropyl, cyclobutyl or adamantyl) optionally substituted by one haloC$_{1-6}$alkyl (suitably by one CF$_3$ group). In another particular embodiment, X is —C(=O)NR$^x$—(CH$_2$)x$^6$-, integer x$^6$ is zero or 1 (suitably x$^6$ is zero), R$^x$ is H, and R$^2$ is 3-10 membered cycloalkyl (suitably cyclopropyl, cyclobutyl or adamantyl) optionally substituted by one haloC$_{1-6}$alkyl (suitably by one CF$_3$ group).

In one embodiment, the invention relates to a compound of Formula (I-3) which is subset of Formula (I), wherein X is —C(=O)NR$^x$—(CH$_2$)x$^6$-, integer x$^6$ is zero, 1 or 2, R$^x$ is H or C$_{1-4}$alkyl, and when R$^2$ is 6-membered aryl (phenyl) said 6-membered aryl (phenyl) is optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl, provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$ alkyl, pyridyl optionally substituted by halogen. In another embodiment, X is —C(═O)NR$^x$—(CH$_2$)x$^6$-, integer x$^6$ is zero, 1 or 2, R$^x$ is H or C$_{1-4}$alkyl, and R$^2$ is unsubstituted phenyl. In a particular embodiment, X is —C(═O)NR$^x$—(CH$_2$)x$^6$-, integer x$^6$ is zero or 1 (suitably x$^6$ is zero), R$^x$ is H, and R$^2$ is unsubstituted phenyl.

In one embodiment, the invention relates to a compound of Formula (I-3) which is subset of Formula (I), wherein X is —C(═O)NR$^x$—(CH$_2$)x$^6$-, integer x$^6$ is zero, 1 or 2, R$^x$ is H or C$_{1-4}$alkyl, and when R$^2$ is 5-6 membered heteroaryl said 5-6 membered heteroaryl is optionally substituted by one or more groups independently selected from halogen, CN, OH, NO$_2$, C$_{1-6}$alkyl, C$_{2-6}$alkenyl, C$_{2-6}$alkynyl, haloC$_{1-6}$ alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$alkyl, —C(═O)NHC$_{1-6}$alkyl, —NHC(═O)C$_{1-6}$alkyl, and 3-6-membered cycloalkyl wherein said cycloalkyl may optionally be substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$ alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$alkyl, —C(═O)OH, —C(═O)OC$_{1-6}$alkyl, —C(═O)NHC$_{1-6}$alkyl and —NHC(═O)C$_{1-6}$alky. In another embodiment, X is —C(═O)NR$^x$—(CH$_2$)x$^6$-, integer x$^6$ is zero, 1 or 2, R$^x$ is H or C$_{1-4}$alkyl (suitably R$^x$ is H or methyl), and R$^2$ is 5-6 membered (suitably oxazolyl, isoxazolyl, thiazolyl, pyrazolyl, thiophenyl, furanyl or pyridinyl) heteroaryl optionally substituted by one or more C$_{1-6}$alkyl (suitably by one, two or three methyl groups).

In one embodiment, the invention relates to a compound of Formula (I-3) which is subset of Formula (I), wherein X is —C(═O)NR$^x$—(CH$_2$)x$^6$-, integer x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl ring may be optionally substituted by one or more C$_{1-4}$alkyl groups for use as a medicament. In another embodiment, X is —C(═O)NR$^x$—(CH$_2$)x$^6$-, integer x$^6$ is zero and R$^x$ together with R$^2$ and with nitrogen to which R$^x$ and R$^2$ are attached form a heterocycloalkyl ring which may have one additional heteroatom selected from O or N (suitably they form a pyrrolidinyl, morpholinyl or piperidinyl ring), and said heterocycloalkyl ring may be optionally substituted by one, two, three or four C$_{1-4}$alkyl groups (suitably by methyl) for use as a medicament.

In one embodiment, the invention relates to a compound of Formula (I-3) which is subset of Formula (I), wherein X is —C(═O)NR$^x$—(CH$_2$)x$^6$-, integer x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl ring may be optionally substituted by one or more C$_{1-4}$alkyl groups. In another embodiment, X is —C(═O)NR$^x$—(CH$_2$)x$^6$-, integer x$^6$ is zero and R$^x$ together with R$^2$ and with nitrogen to which R$^x$ and R$^2$ are attached form a heterocycloalkyl ring which may have one additional heteroatom selected from O or N (suitably they form a pyrrolidinyl, morpholinyl or piperidinyl ring), and said heterocycloalkyl ring may be optionally substituted by one, two, three or four C$_{1-4}$alkyl groups (suitably by methyl).

In one embodiment, the invention relates to a compound of Formula (I-3) which is subset of Formula (I), wherein X is —C(═S)NR$^y$—, R$^y$ is H or C$_{1-4}$alkyl, and R$^2$ is selected from (i), (ii), (iii), (iv), (v) and (vi) as defined for R$^2$ above or as defined for R$^2$ in any of the embodiments herein and below for use as a medicament.

In one embodiment, the invention relates to a compound of Formula (I-3) which is subset of Formula (I), wherein X is —C(═S)NR$^y$—, R$^y$ is H or C$_{1-4}$alkyl, and R$^2$ is selected from (i), (ii), (iii), (iv), (v) and (vi) as defined for R$^2$ above or as defined for R$^2$ in any of the embodiments herein and below. In another embodiment, X is —C(═S)NR$^y$—, wherein R$^y$ is H or C$_{1-4}$alkyl, and R$^2$ is C$_{1-10}$alkyl optionally substituted by one or more groups independently selected from OH, —OC$_{1-4}$alkyl, —NHC$_{1-4}$alkyl, and —N(C$_{1-4}$alkyl)$_2$. In a particular embodiment, X is —C(═S)NR$^y$—, wherein R$^y$ is H, and R$^2$ is C$_{1-4}$alkyl (suitably methyl, ethyl, propyl, isopropyl, butyl, tert-butyl) which is unsubstituted. In more particular embodiment, X is —C(═S)NR$^y$—, wherein R$^y$ is H, and R$^2$ is isopropyl or tert-butyl which is unsubstituted.

In one embodiment, the invention relates to a compound of Formula (I-7) which is subset of Formula (I), wherein X is —SO$_2$— and R$^2$ is selected from (i), (ii), (iii), (iv), (v) and (vi) as defined for R$^2$ above or as defined for R$^2$ in any of the embodiments herein and below. In another embodiment, X is —SO$_2$— and R$^2$ is selected from C$_{1-10}$alkyl, —N(C$_{1-4}$alkyl)$_2$ and 5-6 membered heterocycloalkyl each of which may be optionally substituted as defined above or as defined in any of the embodiments herein and below. In a particular embodiment, X is —SO$_2$— and R$^2$ is C$_{1-4}$alkyl (suitably methyl, ethyl, propyl, butyl; preferably it is methyl) or —N(C$_{1-4}$alkyl)$_2$ (suitably N-dimethyl, N-diethyl, N-dipropyl or N-dibutyl; preferably it is N-dimethyl) and R$^2$ is unsubstituted. In another particular embodiment, X is —SO$_2$— and R$^2$ is. 5-6 membered heterocycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(═O)C$_{1-6}$alkyl, —C(═O)OC$_{1-6}$alkyl, —C(═O)OH, and —C(═O)NH$_2$. In more particular embodiment, X is —SO$_2$— and R$^2$ is. 5-6 membered heterocycloalkyl (suitably piperazinyl) optionally substituted by one or two groups —C(═O)OC$_{1-6}$alkyl (suitably —C(═O)OC$_{1-4}$alkyl, preferably —C(═O)O-tertbutyl).

In one embodiment, the compound of the invention is selected amongst the compounds 1 to 411.

Specific compounds of formula I according to this aspect of the invention which may be mentioned include those selected from the group consisting of:

tert-butyl 3-[4-(5-fluoro-1H-pyrrolo[2,3-b]pyridin-3-yl)piperidin-1-yl]sulfonylazetidine-1-carboxylate; [1]

tert-butyl 3-[4-(5-methyl-1H-pyrrolo[2,3-b]pyridin-3-yl)piperidin-1-yl]sulfonylazetidine-1-carboxylate; [2]

tert-butyl 3-[4-(3-benzylimidazol-4-yl)piperidin-1-yl]sulfonylazetidine-1-carboxylate; [3]

tert-butyl 3-[1-[1-[(2-methylpropan-2-yl)oxycarbonyl]azetidin-3-yl]sulfonylpiperidin-4-yl]-6,8-dihydro-5H-imidazo[1,2-a]pyrazine-7-carboxylate; [4]

tert-butyl 3-[4-(6,7-dihydro-5H-pyrrolo[1,2-a]imidazol-3-yl)piperidin-1-yl]sulfonylazetidine-1-carboxylate; [5]

tert-butyl 3-[4-(4-methoxyphenyl)piperidin-1-yl]sulfonylazetidine-1-carboxylate; [6]

tert-butyl 4-[4-(1H-pyrrolo[2,3-b]pyridin-4-yl)piperidin-1-yl]sulfonylpiperidine-1-carboxylate; [7]

tert-butyl 4-[4-[1-(4-methylphenyl)sulfonylpyrrolo[2,3-b]pyridin-4-yl]piperidin-1-yl]sulfonylpiperidine-1-carboxylate; [8]

tert-butyl 4-[4-(2,4-dimethylphenyl)piperidin-1-yl]sulfonylpiperidine-1-carboxylate; [9]

tert-butyl 4-[4-(7H-pyrrolo[2,3-d]pyrimidin-4-yl)piperidin-1-yl]sulfonylpiperidine-1-carboxylate; [10]
tert-butyl 4-(4-quinolin-4-ylpiperidin-1-yl)sulfonylpiperidine-1-carboxylate; [11]
tert-butyl 4-[4-[7-(4-methylphenyl)sulfonylpyrrolo[2,3-d]pyrimidin-4-yl]piperidin-1-yl]sulfonylpiperidine-1-carboxylate; [12]
tert-butyl 4-[4-(4-methoxyphenyl)piperidin-1-yl]sulfonylpiperidine-1-carboxylate; [13]
tert-butyl 4-(4-phenylpiperidin-1-yl)sulfonylpiperidine-1-carboxylate; [14]
methyl 3-[1-[1-[(2-methylpropan-2-yl)oxycarbonyl]azetidin-3-yl]sulfonylpiperidin-4-yl]-1H-pyrrolo[2,3-b]pyridine-5-carboxylate; [15]
methyl 3-[1-[1-[(2-methylpropan-2-yl)oxycarbonyl]piperidin-4-yl]sulfonylpiperidin-4-yl]-1H-pyrrolo[2,3-b]pyridine-5-carboxylate; [16]
tert-butyl 3-(4-thieno[3,2-b]pyridin-3-ylpiperidin-1-yl)sulfonylazetidine-1-carboxylate; [17]
tert-butyl 4-(4-thieno[3,2-b]pyridin-3-ylpiperidin-1-yl)sulfonylpiperidine-1-carboxylate; [18]
tert-butyl 4-[4-(1H-pyrrolo[2,3-b]pyridin-3-yl)piperidin-1-yl]sulfonylpiperidine-1-carboxylate; [19]
tert-butyl 4-[4-(oxan-4-yl)piperidin-1-yl]sulfonylpiperidine-1-carboxylate; [20]
N-phenyl-4-(4-pyridin-4-ylpiperidin-1-yl)sulfonylpiperidine-1-carboxamide; [21]
tert-butyl 3-(4-pyridin-4-ylpiperidin-1-yl)sulfonylazetidine-1-carboxylate; [22]
tert-butyl 4-(4-pyridin-4-ylpiperidin-1-yl)sulfonylpiperidine-1-carboxylate; [23]
3-(4-pyridin-4-ylpiperidin-1-yl)sulfonyl-N-[1-hydroxy-3-methylbutan-2-yl]azetidine-1-carboxamide; [24]
N-(3,5-dimethyl-1,2-oxazol-4-yl)-3-(4-pyridazin-3-ylpiperidin-1-yl)sulfonylazetidine-1-carboxamide; [25]
3-[4-(1H-pyrrolo[2,3-b]pyridin-3-yl)piperidin-1-yl]sulfonyl-N-[1-hydroxy-3-methylbutan-2-yl]azetidine-1-carboxamide; [26]
(2-methoxyphenyl) 3-(4-pyridin-4-ylpiperidin-1-yl)sulfonylazetidine-1-carboxylate; [27]
(4-methoxycyclohexyl) 3-(4-pyridin-4-ylpiperidin-1-yl)sulfonylazetidine-1-carboxylate; [28]
oxan-4-yl 3-(4-pyridin-4-ylpiperidin-1-yl)sulfonylazetidine-1-carboxylate; [29]
(oxolan-2-yl)methyl 3-(4-pyridin-4-ylpiperidin-1-yl)sulfonylazetidine-1-carboxylate; [30]N-tert-butyl-N-methyl-3-(4-pyridin-4-ylpiperidin-1-yl)sulfonylazetidine-1-carboxamide; [31]
[3-(4-pyridin-4-ylpiperidin-1-yl)sulfonylazetidin-1-yl]-(3,3,5,5-tetramethylmorpholin-4-yl)methanone; [32]
3-(4-pyridin-4-ylpiperidin-1-yl)sulfonyl-N-(2,4,4-trimethylpentan-2-yl)azetidine-1-carboxamide; [33]
[3-(4-furo[2,3-b]pyridin-5-ylpiperidin-1-yl)sulfonylazetidin-1-yl]-(3,3,5,5-tetramethylmorpholin-4-yl)methanone; [34]
[(2R,6S)-2,6-dimethylmorpholin-4-yl]-[3-(4-furo[2,3-b]pyridin-5-ylpiperidin-1-yl) sulfonylazetidin-1-yl]methanone; [35]
3-[4-(2,3-dihydrofuro[2,3-b]pyridin-5-yl)piperidin-1-yl]sulfonyl-N-(3,5-dimethyl-1,2-oxazol-4-yl)azetidine-1-carboxamide; [36]
N-(3,5-dimethyl-1,2-oxazol-4-yl)-3-(4-furo[2,3-b]pyridin-5-ylpiperidin-1-yl) sulfonylazetidine-1-carboxamide; [37]
cyclohexyl 3-(4-furo[2,3-b]pyridin-5-ylpiperidin-1-yl)sulfonylazetidine-1-carboxylate; [38]
N-(3,5-dimethyl-1,2-oxazol-4-yl)-3-[4-(H-pyrrolo[3,2-b]pyridin-3-yl)piperidin-1-yl]sulfonylazetidine-1-carboxamide; [39]
cyclohexyl 3-[1-(1-cyclohexyloxycarbonylazetidin-3-yl)sulfonylpiperidin-4-yl] pyrrolo [3,2-b]pyridine-1-carboxylate; [40]
cyclohexyl 3-[4-(1H-pyrrolo[3,2-b]pyridin-3-yl)piperidin-1-yl]sulfonylazetidine-1-carboxylate; [41]
N-(3,5-dimethyl-1,2-oxazol-4-yl)-3-[4-(5-methylpyrrolo[2,3-b]pyrazin-7-yl)piperidin-1-yl]sulfonylazetidine-1-carboxamide; [42]
N-(3,5-dimethyl-1,2-oxazol-4-yl)-3-[4-(5H-pyrrolo[2,3-b]pyrazin-7-yl)piperidin-1-yl]sulfonylazetidine-1-carboxamide; [43]
cyclohexyl 3-[4-(5H-pyrrolo[2,3-b]pyrazin-7-yl)piperidin-1-yl]sulfonylazetidine-1-carboxylate; [44]
tert-butyl 3-[(2R)-2-methyl-4-(1H-pyrrolo[2,3-b]pyridin-3-yl)piperidin-1-yl]sulfonylazetidine-1-carboxylate; [45]
tert-butyl 3-[2-methyl-4-(1H-pyrrolo[2,3-b]pyridin-3-yl)piperidin-1-yl]sulfonylazetidine-1-carboxylate; [46]
tert-butyl 3-[4-(5-methoxypyridin-2-yl)piperidin-1-yl]sulfonylazetidine-1-carboxylate; [47]
tert-butyl 3-[4-(6-methoxypyridin-3-yl)piperidin-1-yl]sulfonylazetidine-1-carboxylate; [48]
tert-butyl 3-[4-(1H-pyrrolo[3,2-b]pyridin-3-yl)piperidin-1-yl]sulfonylazetidine-1-carboxylate; [49]
[1-(dimethylamino)-2-methylpropan-2-yl] 3-[4-(1H-pyrrolo[2,3-b]pyridin-3-yl)piperidin-1-yl]sulfonylazetidine-1-carboxylate; [50]
(1-methylpiperidin-4-yl)methyl 3-[4-(1H-pyrrolo[2,3-b]pyridin-3-yl)piperidin-1-yl]sulfonylazetidine-1-carboxylate; [51]
2-(diethylamino)ethyl 3-[4-(1H-pyrrolo[2,3-b]pyridin-3-yl)piperidin-1-yl]sulfonylazetidine-1-carboxylate; [52]
3-(4-methylpiperazin-1-yl)propyl 3-[4-(1H-pyrrolo[2,3-b]pyridin-3-yl)piperidin-1-yl]sulfonylazetidine-1-carboxylate; [53]
2-morpholin-4-ylethyl 3-[4-(1H-pyrrolo[2,3-b]pyridin-3-yl)piperidin-1-yl]sulfonylazetidine-1-carboxylate; [54]
N-[(3,5-dimethyl-1,2-oxazol-4-yl)methyl]-3-[4-(1H-pyrrolo[2,3-b]pyridin-3-yl)piperidin-1-yl]sulfonylazetidine-1-carboxamide; [55]
3,5-dimethyl-4-[2-[3-[4-(1H-pyrrolo[2,3-b]pyridin-3-yl)piperidin-1-yl]sulfonylazetidin-1-yl]ethyl]-1,2-oxazole; [56]
3-[4-(1H-pyrrolo[2,3-b]pyridin-3-yl)piperidin-1-yl]sulfonyl-N-[1-(trifluoromethyl) cyclopropyl]azetidine-1-carboxamide; [57]
3-piperidin-1-ylpropyl 3-[4-(1H-pyrrolo[2,3-b]pyridin-3-yl)piperidin-1-yl]sulfonylazetidine-1-carboxylate; [58]
2-piperidin-1-ylethyl 3-[4-(1H-pyrrolo[2,3-b]pyridin-3-yl)piperidin-1-yl]sulfonylazetidine-1-carboxylate; [59]
2-(oxan-4-yl)ethyl 3-[4-(1H-pyrrolo[2,3-b]pyridin-3-yl)piperidin-1-yl]sulfonylazetidine-1-carboxylate; [60]
3,5-dimethyl-4-[[3-[4-(1H-pyrrolo[2,3-b]pyridin-3-yl)piperidin-1-yl]sulfonylazetidin-1-yl]methyl]-1,2-oxazole; [61]
(3,5-dimethyl-1,2-oxazol-4-yl)methyl 3-[4-(1H-pyrrolo[2,3-b]pyridin-3-yl)piperidin-1-yl]sulfonylazetidine-1-carboxylate; [62]
2-(3,5-dimethyl-1,2-oxazol-4-yl)-1-[3-[4-(1H-pyrrolo[2,3-b]pyridin-3-yl)piperidin-1-yl]sulfonylazetidin-1-yl]ethanone; [63]
[3-[4-(1H-pyrrolo[2,3-b]pyridin-3-yl)piperidin-1-yl]sulfonylazetidin-1-yl]-(2,2,6,6-tetramethylpiperidin-1-yl)methanone; [64]

2-methoxyethyl 3-[4-(1H-pyrrolo[2,3-b]pyridin-3-yl)piperidin-1-yl]sulfonylazetidine-1-carboxylate; [65]
2,2-dimethylpropyl 3-[4-(1H-pyrrolo[2,3-b]pyridin-3-yl)piperidin-1-yl]sulfonylazetidine-1-carboxylate; [66]
(oxolan-2-yl)methyl 3-[4-(1H-pyrrolo[2,3-b]pyridin-3-yl)piperidin-1-yl]sulfonylazetidine-1-carboxylate; [67]
3-[1-[1-(thiophen-2-ylmethyl)azetidin-3-yl]sulfonylpiperidin-4-yl]-1H-pyrrolo[2,3-b]pyridine; [68]
3-[1-[1-(1H-pyrrol-2-ylmethyl)azetidin-3-yl]sulfonylpiperidin-4-yl]-1H-pyrrolo[2,3-b]pyridine; [69]
3-[1-[1-(furan-2-ylmethyl)azetidin-3-yl]sulfonylpiperidin-4-yl]-1H-pyrrolo[2,3-b]pyridine; [70]
3-[1-(1-pyridin-4-ylazetidin-3-yl)sulfonylpiperidin-4-yl]-1H-pyrrolo[2,3-b]pyridine; [71]
pyridin-4-yl-[3-[4-(1H-pyrrolo[2,3-b]pyridin-3-yl)piperidin-1-yl]sulfonylazetidin-1-yl]methanone; [72]
2,2-dimethyl-1-[3-[4-(1H-pyrrolo[2,3-b]pyridin-3-yl)piperidin-1-yl]sulfonylazetidin-1-yl]propan-1-one; [73]
(4-tert-butylphenyl)-[3-[4-(1H-pyrrolo[2,3-b]pyridin-3-yl)piperidin-1-yl]sulfonylazetidin-1-yl]methanone; [74]
cyclohexyl 3-[4-(1H-pyrrolo[2,3-b]pyridin-3-yl)piperidin-1-yl]sulfonylazetidine-1-carboxylate; [75]
benzyl 3-[4-(1H-pyrrolo[2,3-b]pyridin-3-yl)piperidin-1-yl]sulfonylazetidine-1-carboxylate; [76]
(4-fluorophenyl) 3-[4-(1H-pyrrolo[2,3-b]pyridin-3-yl)piperidin-1-yl]sulfonylazetidine-1-carboxylate; [77]
N-(1,3-oxazol-4-ylmethyl)-3-[4-(1H-pyrrolo[2,3-b]pyridin-3-yl)piperidin-1-yl]sulfonylazetidine-1-carboxamide; [78]
imidazol-1-yl-[3-[4-(1 H-pyrrolo[2,3-b]pyridin-3-yl)piperidin-1-yl]sulfonylazetidin-1-yl]methanone; [79]
3-[4-(1H-pyrrolo[2,3-b]pyridin-3-yl)piperidin-1-yl]sulfonyl-N-(1,3-thiazol-5-ylmethyl)azetidine-1-carboxamide; [80]
N-[(1-methylpyrazol-3-yl)methyl]-3-[4-(1H-pyrrolo[2,3-b]pyridin-3-yl)piperidin-1-yl]sulfonylazetidine-1-carboxamide; [81]
N,N-diethyl-3-[4-(1H-pyrrolo[2,3-b]pyridin-3-yl)piperidin-1-yl]sulfonylazetidine-1-carboxamide; [82]
furan-2-ylmethyl 3-[4-(1H-pyrrolo[2,3-b]pyridin-3-yl)piperidin-1-yl]sulfonylazetidine-1-carboxylate; [83]
3-[4-(1H-pyrrolo[2,3-b]pyridin-3-yl)piperidin-1-yl]sulfonyl-N-(2-thiophen-2-ylethyl)azetidine-1-carboxamide; [84]
3-[4-(1H-pyrrolo[2,3-b]pyridin-3-yl)piperidin-1-yl]sulfonyl-N-(thiophen-2-ylmethyl)azetidine-1-carboxamide; [85]
piperidin-1-yl-[3-[4-(1 H-pyrrolo[2,3-b]pyridin-3-yl)piperidin-1-yl]sulfonylazetidin-1-yl]methanone; [86]
pyrrolidin-1-yl-[3-[4-(1 H-pyrrolo[2,3-b]pyridin-3-yl)piperidin-1-yl]sulfonylazetidin-1-yl]methanone; [87]
morpholin-4-yl-[3-[4-(1H-pyrrolo[2,3-b]pyridin-3-yl)piperidin-1-yl]sulfonylazetidin-1-yl]methanone; [88]
3-[1-(1-propan-2-ylazetidin-3-yl)sulfonylpiperidin-4-yl]-1H-pyrrolo[2,3-b]pyridine; [89]N,N-dimethyl-3-[4-(1H-pyrrolo[2,3-b]pyridin-3-yl)piperidin-1-yl]sulfonylazetidine-1-sulfonamide; [90]
3-[1-(1-methylsulfonylazetidin-3-yl)sulfonylpiperidin-4-yl]-1H-pyrrolo[2,3-b]pyridine; [91]
tert-butyl 3-[4-[1-(dimethylsulfamoyl)pyrrolo[2,3-b]pyridin-3-yl]piperidin-1-yl]sulfonylazetidine-1-carboxylate; [92]
tert-butyl 3-[4-(1-methylsulfonylpyrrolo[2,3-b]pyridin-3-yl)piperidin-1-yl]sulfonylazetidine-1-carboxylate; [93]
tert-butyl 3-[4-(1-methylpyrrolo[2,3-b]pyridin-3-yl)piperidin-1-yl]sulfonylazetidine-1-carboxylate; [94]
3-[4-(1H-pyrrolo[2,3-b]pyridin-3-yl)piperidin-1-yl]sulfonyl-N-[(1,3,5-trimethylpyrazol-4-yl)methyl]azetidine-1-carboxamide; [95]
N-pyridin-3-yl-3-[4-(1H-pyrrolo[2,3-b]pyridin-3-yl)piperidin-1-yl]sulfonylazetidine-1-carboxamide; [96]
propan-2-yl 3-[4-(1H-pyrrolo[2,3-b]pyridin-3-yl)piperidin-1-yl]sulfonylazetidine-1-carboxylate; [97]
N-propan-2-yl-3-[4-(1H-pyrrolo[2,3-b]pyridin-3-yl)piperidin-1-yl]sulfonylazetidine-1-carboxamide; [98]
N-(furan-2-ylmethyl)-3-[4-(1H-pyrrolo[2,3-b]pyridin-3-yl)piperidin-1-yl]sulfonylazetidine-1-carboxamide; [99]
tert-butyl 3-(4-imidazo[1,2-a]pyridin-3-ylpiperidin-1-yl)sulfonylazetidine-1-carboxylate
tert-butyl 3-[4-(5,6,7,8-tetrahydroimidazo[1,2-a]pyridin-3-yl)piperidin-1-yl]sulfonylazetidine-1-carboxylate; [101]
tert-butyl 3-[4-(3-methylimidazol-4-yl)piperidin-1-yl]sulfonylazetidine-1-carboxylate;
ethyl 4-(4-pyridin-4-ylpiperidin-1-yl)sulfonylpiperidine-1-carboxylate; [103]
N-cyclobutyl-4-(4-pyridin-4-ylpiperidin-1-yl)sulfonylpiperidine-1-carboxamide; [104]
propan-2-yl 4-(4-pyridin-4-ylpiperidin-1-yl)sulfonylpiperidine-1-carboxylate; [105]
methyl 4-(4-pyridin-4-ylpiperidin-1-yl)sulfonylpiperidine-1-carboxylate; [106]
N-tert-butyl-4-[4-(1H-pyrrolo[2,3-b]pyridin-3-yl)piperidin-1-yl]sulfonylpiperidine-1-carboxamide; [107]
N-tert-butyl-3-[4-(1H-pyrrolo[2,3-b]pyridin-3-yl)piperidin-1-yl]sulfonylazetidine-1-carboxamide; [108]
3-[1-(azetidin-3-ylsulfonyl)piperidin-4-yl]-1H-pyrrolo[2,3-b]pyridine; [109]
tert-butyl 3-[4-(1H-pyrrolo[2,3-b]pyridin-3-yl)piperidin-1-yl]sulfonylazetidine-1-carboxylate; [110]
N-tert-butyl-4-(4-pyridin-4-ylpiperidin-1-yl)sulfonylpiperidine-1-carboxamide; [111]
tert-butyl 4-[4-[4-(dimethylamino)phenyl]piperidin-1-yl]sulfonylpiperidine-1-carboxylate;
4-[1-(1-phenylpiperidin-4-yl)sulfonylpiperidin-4-yl]pyridine; [113]
phenyl 4-(4-pyridin-4-ylpiperidin-1-yl)sulfonylpiperidine-1-carboxylate; [114]
tert-butyl 4-[4-(5-methoxy-1H-pyrrolo[2,3-b]pyridin-3-yl)piperidin-1-yl]sulfonylpiperidine-1-carboxylate; [115]
tert-butyl 4-[4-[5-(trifluoromethyl)-1H-pyrrolo[2,3-b]pyridin-3-yl]piperidin-1-yl]sulfonylpiperidine-1-carboxylate; [116]
tert-butyl 4-[4-[5-(1-methylpyrazol-4-yl)-1H-pyrrolo[2,3-b]pyridin-3-yl]piperidin-1-yl]sulfonylpiperidine-1-carboxylate; [117]
3-[1-(1-pyridin-2-ylazetidin-3-yl)sulfonylpiperidin-4-yl]-1H-pyrrolo[2,3-b]pyridine; [118]
N-methyl-N-propan-2-yl-3-[4-(1H-pyrrolo[2,3-b]pyridin-3-yl)piperidin-1-yl]sulfonylazetidine-1-carboxamide; [119]
N-(3,5-dimethyl-1,2-oxazol-4-yl)-3-[4-(1H-pyrrolo[2,3-b]pyridin-3-yl)piperidin-1-yl]sulfonylazetidine-1-carboxamide; [120]
tert-butyl 3-[4-[5-(trifluoromethyl)-1H-pyrrolo[2,3-b]pyridin-3-yl]piperidin-1-yl]sulfonylazetidine-1-carboxylate; [121]
tert-butyl 3-[4-[5-(1-methylpyrazol-4-yl)-1H-pyrrolo[2,3-b]pyridin-3-yl]piperidin-1-yl]sulfonylazetidine-1-carboxylate; [122]
tert-butyl 3-[4-(5-methoxy-1H-pyrrolo[2,3-b]pyridin-3-yl)piperidin-1-yl]sulfonylazetidine-1-carboxylate; [123]
tert-butyl 3-(4-furo[2,3-b]pyridin-5-ylpiperidin-1-yl)sulfonylazetidine-1-carboxylate; [124]

tert-butyl 3-[4-(1H-indol-3-yl)piperidin-1-yl]sulfonylazetidine-1-carboxylate; [125]
methyl 3-(4-furo[3,2-b]pyridin-3-ylpiperidin-1-yl)sulfonylazetidine-1-carboxylate; [126]
tert-butyl 3-[4-(2,3-dihydrofuro[3,2-b]pyridin-3-yl)piperidin-1-yl]sulfonylazetidine-1-carboxylate; [127]
tert-butyl 3-[4-(5H-pyrrolo[2,3-b]pyrazin-7-yl)piperidin-1-yl]sulfonylazetidine-1-carboxylate; [128]
tert-butyl 3-[4-[5-(4-methylphenyl)sulfonylpyrrolo[2,3-b]pyrazin-7-yl]piperidin-1-yl]sulfonylazetidine-1-carboxylate; [129]
tert-butyl 3-(4-pyrazolo[1,5-a]pyrazin-3-ylpiperidin-1-yl)sulfonylazetidine-1-carboxylate; [130]
tert-butyl 3-(4-furo[3,2-b]pyridin-3-ylpiperidin-1-yl)sulfonylazetidine-1-carboxylate; [131]
tert-butyl 4-(4-furo[3,2-b]pyridin-3-ylpiperidin-1-yl)sulfonylpiperidine-1-carboxylate; [132]
tert-butyl 4-[4-(1H-indol-3-yl)piperidin-1-yl]sulfonylpiperidine-1-carboxylate; [133]
3-[1-[1-[2-(3,5-dimethyl-1,2-oxazol-4-yl)ethyl]azetidin-3-yl]sulfonylpiperidin-4-yl]furo[3,2-b]pyridine; [134]
N-(3,5-dimethyl-1,2-oxazol-4-yl)-3-(4-furo[3,2-b]pyridin-3-ylpiperidin-1-yl) sulfonylazetidine-1-carboxamide; [135]
oxan-4-yl 3-(4-furo[3,2-b]pyridin-3-ylpiperidin-1-yl)sulfonylazetidine-1-carboxylate; [136]
[3-(4-furo[3,2-b]pyridin-3-ylpiperidin-1-yl)sulfonylazetidin-1-yl]-morpholin-4-ylmethanone; [137]
2-(3,5-dimethyl-1,2-oxazol-4-yl)-1-[3-(4-furo[3,2-b]pyridin-3-ylpiperidin-1-yl) sulfonylazetidin-1-yl]ethanone; [138]
3-(4-furo[3,2-b]pyridin-3-ylpiperidin-1-yl)sulfonyl-N-[1-(trifluoromethyl)cyclopropyl]azetidine-1-carboxamide; [139]
2,2-dimethyipropyl 3-(4-furo[3,2-b]pyridin-3-ylpiperidin-1-yl)sulfonylazetidine-1-carboxylate; [140]
cyclohexyl 3-(4-furo[3,2-b]pyridin-3-ylpiperidin-1-yl)sulfonylazetidine-1-carboxylate; [141]
methyl 2-[3-[4-(1H-pyrrolo[2,3-b]pyridin-3-yl)piperidin-1-yl]sulfonylazetidin-1-yl]-1,3-oxazole-5-carboxylate; [142]
3-[1-[1-(2,2-dimethylpropyl)azetidin-3-yl]sulfonylpiperidin-4-yl]-1H-pyrrolo[2,3-b]pyridine; [143]
[1-(dimethylamino)-2-methylpropan-2-yl] 3-(4-pyridin-4-ylpiperidin-1-yl) sulfonylazetidine-1-carboxylate; [144]
N,N-diethyl-2,2-dimethyl-3-[3-[4-(1H-pyrrolo[2,3-b]pyridin-3-yl)piperidin-1-yl]sulfonylazetidin-1-yl]propan-1-amine; [145]
4-[2,2-dimethyl-3-[3-[4-(1H-pyrrolo[2,3-b]pyridin-3-yl)piperidin-1-yl]sulfonylazetidin-1-yl]propyl]morpholine; [146]
[1-(dimethylamino)-2-methylpropan-2-yl] 3-[4-(1H-pyrrolo[2,3-b]pyridin-3-yl)piperidin-1-yl]sulfonylpyrrolidine-1-carboxylate; [147]
3-[1-[1-(2,4-dimethylpentan-3-yl)azetidin-3-yl]sulfonylpiperidin-4-yl]-1H-pyrrolo[2,3-b]pyridine; [148]
N-(1-hydroxy-3-methylbutan-2-yl)-3-[4-(1H-pyrrolo[2,3-b]pyridin-3-yl)piperidin-1-yl]sulfonylpyrrolidine-1-carboxamide; [149]
tert-butyl 3-[4-(1H-pyrrolo[2,3-b]pyridin-3-yl)piperidin-1-yl]sulfonylpyrrolidine-1-carboxylate; [150]
methyl 3-[4-(1H-pyrrolo[2,3-b]pyridin-3-yl)piperidin-1-yl]sulfonylazetidine-1-carboxylate; [151]
(1-methoxy-2-methylpropan-2-yl) 3-[4-(1H-pyrrolo[2,3-b]pyridin-3-yl)piperidin-1-yl]sulfonylazetidine-1-carboxylate; [152]
[(2S)-butan-2-yl] 3-[4-(1H-pyrrolo[2,3-b]pyridin-3-yl)piperidin-1-yl]sulfonylazetidine-1-carboxylate; [153]
cyclobutylmethyl 3-[1-[1-(cyclobutylmethoxycarbonyl)azetidin-3-yl]sulfonylpiperidin-4-yl]pyrrolo[2,3-b]pyridine-1-carboxylate; [154]
3-[1-(1-pyrimidin-2-ylazetidin-3-yl)sulfonylpiperidin-4-yl]-1H-pyrrolo[2,3-b]pyridine; [155]
N-tert-butyl-N-ethyl-3-[4-(1H-pyrrolo[2,3-b]pyridin-3-yl)piperidin-1-yl]sulfonylazetidine-1-carboxamide; [156]
3-[1-[1-(pyridin-3-ylmethyl)azetidin-3-yl]sulfonylpiperidin-4-yl]-1H-pyrrolo[2,3-b]pyridine; [157]
3-[1-(1-cyclopentylazetidin-3-yl)sulfonylpiperidin-4-yl]-1H-pyrrolo[2,3-b]pyridine; [158]
3-[1-[1-[(3-methyloxetan-3-yl)methyl]azetidin-3-yl]sulfonylpiperidin-4-yl]-1H-pyrrolo[2,3-b]pyridine; [159]
(3,5-dimethyl-1,2-oxazol-4-yl) 3-[4-(1H-pyrrolo[2,3-b]pyridin-3-yl)piperidin-1-yl]sulfonylazetidine-1-carboxylate; [160]
1-adamantyl 3-[4-(1H-pyrrolo[2,3-b]pyridin-3-yl)piperidin-1-yl]sulfonylazetidine-1-carboxylate; [161]
[(2R)-oxolan-2-yl]methyl 3-[4-(1H-pyrrolo[2,3-b]pyridin-3-yl)piperidin-1-yl]sulfonylazetidine-1-carboxylate; [162]
[(2S)-oxolan-2-yl]methyl 3-[4-(1H-pyrrolo[2,3-b]pyridin-3-yl)piperidin-1-yl]sulfonylazetidine-1-carboxylate; [163]
[(2R,6R)-2,6-dimethylmorpholin-4-yl]-[3-[4-(1H-pyrrolo[2,3-b]pyridin-3-yl)piperidin-1-yl]sulfonylazetidin-1-yl]methanone; [164]
[(3S,5S)-3,5-dimethylmorpholin-4-yl]-[3-[4-(1H-pyrrolo[2,3-b]pyridin-3-yl)piperidin-1-yl]sulfonylazetidin-1-yl]methanone; [165]
[(1S,2R,5S)-5-methyl-2-propan-2-ylcyclohexyl] 3-[4-(1H-pyrrolo[2,3-b]pyridin-3-yl) piperidin-1-yl]sulfonylazetidine-1-carboxylate; [166]
N,N-dimethyl-3-[4-(1H-pyrrolo[2,3-b]pyridin-3-yl)piperidin-1-yl]sulfonylazetidine-1-carboxamide; [167]
cyclohexylmethyl 3-[4-(1H-pyrrolo[2,3-b]pyridin-3-yl)piperidin-1-yl]sulfonylazetidine-1-carboxylate; [168]
[3-[4-(1H-pyrrolo[2,3-b]pyridin-3-yl)piperidin-1-yl]sulfonylazetidin-1-yl]-(3,3,5,5-tetramethylmorpholin-4-yl)methanone; [169]
[(2R,6S)-2,6-dimethylmorpholin-4-yl]-[3-[4-(1H-pyrrolo[2,3-b]pyridin-3-yl)piperidin-1-yl]sulfonylazetidin-1-yl]methanone; [170]
N-(1-adamantyl)-3-[4-(1H-pyrrolo[2,3-b]pyridin-3-yl)piperidin-1-yl]sulfonylazetidine-1-carboxamide; [171]
tert-butyl 4-[3-[4-(1H-pyrrolo[2,3-b]pyridin-3-yl)piperidin-1-yl]sulfonylazetidin-1-yl]sulfonylpiperazine-1-carboxylate; [172]
N,N-di(propan-2-yl)-3-[4-(1H-pyrrolo[2,3-b]pyridin-3-yl)piperidin-1-yl]sulfonylazetidine-1-carboxamide; [173]
N-tert-butyl-3-[4-(1H-pyrrolo[2,3-b]pyridin-3-yl)piperidin-1-yl]sulfonylazetidine-1-carbothioamide; [174]
3-[4-(1H-pyrrolo[2,3-b]pyridin-3-yl)piperidin-1-yl]sulfonyl-N-(2,4,4-trimethylpentan-2-yl) azetidine-1-carboxamide; [175]
N-tert-butyl-N-methyl-3-[4-(1H-pyrrolo[2,3-b]pyridin-3-yl)piperidin-1-yl]sulfonylazetidine-1-carboxamide; [176]
tert-butyl 3-(4-thieno[2,3-b]pyridin-3-ylpiperidin-1-yl) sulfonylazetidine-1-carboxylate; [177]
N-(furan-2-ylmethyl)-N-methyl-3-[4-(1H-pyrrolo[2,3-b]pyridin-3-yl)piperidin-1-yl]sulfonylazetidine-1-carboxamide; [178]
N-propan-2-yl-3-[4-(1H-pyrrolo[2,3-b]pyridin-3-yl)piperidin-1-yl]sulfonylazetidine-1-carbothioamide; [179]
(4-methoxycyclohexyl) 3-[4-(1H-pyrrolo[2,3-b]pyridin-3-yl)piperidin-1-yl]sulfonylazetidine-1-carboxylate; [180]

3-[1-[1-(3-cyclopropylpyridin-2-yl)azetidin-3-yl]sulfonylpiperidin-4-yl]-1H-pyrrolo[2,3-b]pyridine; [181]

[2-[3-[4-(1H-pyrrolo[2,3-b]pyridin-3-yl)piperidin-1-yl]sulfonylazetidin-1-yl]pyridin-3-yl]methanol; [182]

(2-hydroxyphenyl) 3-[4-(1H-pyrrolo[2,3-b]pyridin-3-yl)piperidin-1-yl]sulfonylazetidine-1-carboxylate; [183]

3-[1-[1-[3,6-bis(trifluoromethyl)pyridin-2-yl]azetidin-3-yl]sulfonylpiperidin-4-yl]-1H-pyrrolo[2,3-b]pyridine; [184]

3-[1-[1-[6-methoxy-3-(trifluoromethyl)pyridin-2-yl]azetidin-3-yl]sulfonylpiperidin-4-yl]-1H-pyrrolo[2,3-b]pyridine; [185]

3-[1-[1-[3-(trifluoromethyl)pyridin-2-yl]azetidin-3-yl]sulfonylpiperidin-4-yl]-1H-pyrrolo[2,3-b]pyridine; [186]

4-methyl-2-[3-[4-(1H-pyrrolo[2,3-b]pyridin-3-yl)piperidin-1-yl]sulfonylazetidin-1-yl]pyridine-3-carbonitrile; [187]

3-[1-[1-[6-methyl-3-(trifluoromethyl)pyridin-2-yl]azetidin-3-yl]sulfonylpiperidin-4-yl]-1H-pyrrolo[2,3-b]pyridine; [188]

cyclohexyl-[3-[4-(1H-pyrrolo[2,3-b]pyridin-3-yl)piperidin-1-yl]sulfonylazetidin-1-yl]methanone; [189]

cyclopentyl-[3-[4-(1H-pyrrolo[2,3-b]pyridin-3-yl)piperidin-1-yl]sulfonylazetidin-1-yl]methanone; [190]

cyclopropyl-[3-[4-(1H-pyrrolo[2,3-b]pyridin-3-yl)piperidin-1-yl]sulfonylazetidin-1-yl]methanone; [191]

pyridin-2-yl-[3-[4-(1H-pyrrolo[2,3-b]pyridin-3-yl)piperidin-1-yl]sulfonylazetidin-1-yl]methanone; [192]

[3-[4-(1H-pyrrolo[2,3-b]pyridin-3-yl)piperidin-1-yl]sulfonylazetidin-1-yl]-thiophen-2-ylmethanone; [193]

2-methyl-1-[3-[4-(1H-pyrrolo[2,3-b]pyridin-3-yl)piperidin-1-yl]sulfonylazetidin-1-yl]propan-1-one; [194]

3-methyl-1-[3-[4-(1H-pyrrolo[2,3-b]pyridin-3-yl)piperidin-1-yl]sulfonylazetidin-1-yl]butan-1-one; [195]

[(3R)-oxolan-3-yl] 3-[4-(1H-pyrrolo[2,3-b]pyridin-3-yl)piperidin-1-yl]sulfonylazetidine-1-carboxylate; [196]

[(3S)-oxolan-3-yl] 3-[4-(1H-pyrrolo[2,3-b]pyridin-3-yl)piperidin-1-yl]sulfonylazetidine-1-carboxylate; [197]

cyclobutyl 3-[4-(1H-pyrrolo[2,3-b]pyridin-3-yl)piperidin-1-yl]sulfonylazetidine-1-carboxylate; [198]

(3-methyloxetan-3-yl)methyl 3-[4-(1H-pyrrolo[2,3-b]pyridin-3-yl)piperidin-1-yl]sulfonylazetidine-1-carboxylate; [199]

[(2R)-butan-2-yl] 3-[4-(1H-pyrrolo[2,3-b]pyridin-3-yl)piperidin-1-yl]sulfonylazetidine-1-carboxylate; [200]

cyclobutylmethyl 3-[4-(1H-pyrrolo[2,3-b]pyridin-3-yl)piperidin-1-yl]sulfonylazetidine-1-carboxylate; [201]

(3,5-dimethyl-1,2-oxazol-4-yl)methyl 3-(4-pyridin-4-ylpiperidin-1-yl)sulfonylazetidine-1-carboxylate; [202]

N-[(3,5-dimethyl-1,2-oxazol-4-yl)methyl]-3-(4-pyridin-4-ylpiperidin-1-yl) sulfonylazetidine-1-carboxamide; [203]

cyclopropylmethyl 3-[4-(1H-pyrrolo[2,3-b]pyridin-3-yl)piperidin-1-yl]sulfonylazetidine-1-carboxylate; [204]

2-(3,5-dimethyl-1,2-oxazol-4-yl)-1-[3-(4-pyridin-4-ylpiperidin-1-yl)sulfonylazetidin-1-yl]ethanone; [205]

N-ethyl-N-propan-2-yl-3-[4-(1H-pyrrolo[2,3-b]pyridin-3-yl)piperidin-1-yl]sulfonylazetidine-1-carboxamide; [206]

(3-phenoxyphenyl)methyl 3-[4-(1H-pyrrolo[2,3-b]pyridin-3-yl)piperidin-1-yl]sulfonylazetidine-1-carboxylate; [207]

(3,5-dimethylphenyl) 3-[4-(1H-pyrrolo[2,3-b]pyridin-3-yl)piperidin-1-yl]sulfonylazetidine-1-carboxylate; [208]

(3-fluoro-4-methoxyphenyl)methyl 3-[4-(1H-pyrrolo[2,3-b]pyridin-3-yl)piperidin-1-yl]sulfonylazetidine-1-carboxylate; [209]

piperidin-4-yl 3-[4-(1H-pyrrolo[2,3-b]pyridin-3-yl)piperidin-1-yl]sulfonylazetidine-1-carboxylate; [210]

tert-butyl 4-[3-[4-(1H-pyrrolo[2,3-b]pyridin-3-yl)piperidin-1-yl]sulfonylazetidine-1-carbonyl]oxypiperidine-1-carboxylate; [211]

pyridin-3-yl 3-[4-(1H-pyrrolo[2,3-b]pyridin-3-yl)piperidin-1-yl]sulfonylazetidine-1-carboxylate; [212]

(3-nitrophenyl)methyl 3-[4-(1H-pyrrolo[2,3-b]pyridin-3-yl)piperidin-1-yl]sulfonylazetidine-1-carboxylate; [213]

(4-methoxyphenyl)methyl 3-[4-(1H-pyrrolo[2,3-b]pyridin-3-yl)piperidin-1-yl]sulfonylazetidine-1-carboxylate; [214]

(3-methoxyphenyl) 3-[4-(1H-pyrrolo[2,3-b]pyridin-3-yl)piperidin-1-yl]sulfonylazetidine-1-carboxylate; [215]

[2-(trifluoromethyl)phenyl]methyl 3-[4-(1H-pyrrolo[2,3-b]pyridin-3-yl)piperidin-1-yl]sulfonylazetidine-1-carboxylate; [216]

(2-methoxyphenyl) 3-[4-(1H-pyrrolo[2,3-b]pyridin-3-yl)piperidin-1-yl]sulfonylazetidine-1-carboxylate; [217]

oxan-4-yl 3-[4-(1H-pyrrolo[2,3-b]pyridin-3-yl)piperidin-1-yl]sulfonylazetidine-1-carboxylate; [218]

(4-methoxyphenyl) 3-[4-(1H-pyrrolo[2,3-b]pyridin-3-yl)piperidin-1-yl]sulfonylazetidine-1-carboxylate; [219]

1,3-dioxan-5-yl 3-[4-(1H-pyrrolo[2,3-b]pyridin-3-yl)piperidin-1-yl]sulfonylazetidine-1-carboxylate; [220]

tert-butyl 3-[4-(4-fluoro-1H-pyrrolo[2,3-b]pyridin-3-yl)piperidin-1-yl]sulfonylazetidine-1-carboxylate; [221]

oxetan-3-yl 3-[4-(1H-pyrrolo[2,3-b]pyridin-3-yl)piperidin-1-yl]sulfonylazetidine-1-carboxylate; [222]

tert-butyl 3-[4-(4-methyl-1H-pyrrolo[2,3-b]pyridin-3-yl)piperidin-1-yl]sulfonylazetidine-1-carboxylate; [223]

tert-butyl 3-[4-(2-methyl-1H-pyrrolo[2,3-b]pyridin-3-yl)piperidin-1-yl]sulfonylazetidine-1-carboxylate; [224]

tert-butyl 3-[4-(1,2-benzothiazol-3-yl)piperazin-1-yl]sulfonylazetidine-1-carboxylate; [225]

tert-butyl 3-[4-(1H-pyrrolo[2,3-b]pyridin-3-yl)piperazin-1-yl]sulfonylazetidine-1-carboxylate; [226]

tert-butyl 4-[4-(4-methoxyphenyl)piperazin-1-yl]sulfonylpiperidine-1-carboxylate; [227]

tert-butyl 3-[[4-(1H-pyrrolo[2,3-b]pyridin-3-yl)-3,6-dihydro-2H-pyridin-1-yl]sulfonyl]azetidine-1-carboxylate; [228]

tert-butyl 4-[[4-(1H-pyrazolo[3,4-b]pyridin-3-yl)-3,6-dihydro-2H-pyridin-1-yl]sulfonyl]piperidine-1-carboxylate; [229]

tert-butyl 4-[(4-thieno[3,2-b]pyridin-3-yl-3,6-dihydro-2H-pyridin-1-yl)sulfonyl]piperidine-1-carboxylate; [230]

tert-butyl 3-[(4-furo[3,2-b]pyridin-3-yl-3,6-dihydro-2H-pyridin-1-yl)sulfonyl]azetidine-1-carboxylate; [231]

tert-butyl 4-[(4-furo[3,2-b]pyridin-3-yl-3,6-dihydro-2H-pyridin-1-yl)sulfonyl]piperidine-1-carboxylate; [232]

tert-butyl 4-[[4-(7H-pyrrolo[2,3-d]pyrimidin-5-yl)-3,6-dihydro-2H-pyridin-1-yl]sulfonyl]piperidine-1-carboxylate; [233]

tert-butyl 3-[(4-furo[2,3-b]pyridin-5-yl-3,6-dihydro-2H-pyridin-1-yl)sulfonyl]azetidine-1-carboxylate; [234]

tert-butyl 4-[[4-[7-(4-methylphenyl)sulfonylpyrrolo[2,3-d]pyrimidin-5-yl]-3,6-dihydro-2H-pyridin-1-yl]sulfonyl]piperidine-1-carboxylate; [235]

tert-butyl 4-[[4-(1H-pyrrolo[2,3-b]pyridin-4-yl)-3,6-dihydro-2H-pyridin-1-yl]sulfonyl]piperidine-1-carboxylate; [236]

tert-butyl 4-[[4-[1-(4-methylphenyl)sulfonylpyrrolo[2,3-b]pyridin-4-yl]-3,6-dihydro-2H-pyridin-1-yl]sulfonyl]piperidine-1-carboxylate; [237]

tert-butyl 4-[[4-(7H-pyrrolo[2,3-d]pyrimidin-4-yl)-3,6-dihydro-2H-pyridin-1-yl]sulfonyl]piperidine-1-carboxylate; [238]

tert-butyl 4-[[4-[7-(4-methylphenyl)sulfonylpyrrolo[2,3-d]pyrimidin-4-yl]-3,6-dihydro-2H-pyridin-1-yl]sulfonyl]piperidine-1-carboxylate; [239]
tert-butyl 3-[4-(4-cyano-2-methylphenyl)piperazin-1-yl]sulfonylazetidine-1-carboxylate; [240]
methyl 2-[3-[4-(1H-pyrrolo[2,3-b]pyridin-3-yl)piperidin-1-yl]sulfonylazetidin-1-yl]-1,3-thiazole-4-carboxylate; [241]
2-[3-[4-(1H-pyrrolo[2,3-b]pyridin-3-yl)piperidin-1-yl]sulfonylazetidin-1-yl]pyridine-4-carbonitrile; [242]
3-[1-[1-(6-ethoxypyridin-2-yl)azetidin-3-yl]sulfonylpiperidin-4-yl]-1H-pyrrolo[2,3-b]pyridine; [243]
3-[1-(1-pyridin-2-ylpyrrolidin-3-yl)sulfonylpiperidin-4-yl]-1H-pyrrolo[2,3-b]pyridine; [244]
methyl 2-[3-[4-(1H-pyrrolo[2,3-b]pyridin-3-yl)piperidin-1-yl]sulfonylazetidin-1-yl]-1,3-thiazole-5-carboxylate; [245]
methyl 2-[3-[4-(1H-pyrrolo[2,3-b]pyridin-3-yl)piperidin-1-yl]sulfonylazetidin-1-yl]-1,3-oxazole-4-carboxylate; [246]
N,N-dimethyl-1-[1-[[3-[4-(1H-pyrrolo[2,3-b]pyridin-3-yl)piperidin-1-yl]sulfonylazetidin-1-yl]methyl]cyclopentyl]methanamine; [247]
tert-butyl 3-[4-(1H-pyrrolo[2,3-b]pyridin-3-yl)piperidin-1-yl]sulfonylpiperidine-1-carboxylate; [248]
3-[1-(pyrrolidin-3-yl)sulfonylpiperidin-4-yl]-1H-pyrrolo[2,3-b]pyridine; [249]
N-[(2S)-1-hydroxy-3-methylbutan-2-yl]-3-[4-(1H-pyrrolo[2,3-b]pyridin-3-yl)piperidin-1-yl]sulfonylazetidine-1-carboxamide; [250]
N-[(2R)-1-hydroxy-3-methylbutan-2-yl]-3-[4-(1H-pyrrolo[2,3-b]pyridin-3-yl)piperidin-1-yl]sulfonylazetidine-1-carboxamide; [251]
4-methoxy-2-[3-[4-(1H-pyrrolo[2,3-b]pyridin-3-yl)piperidin-1-yl]sulfonylazetidin-1-yl]pyridine-3-carbonitrile; [252]
3-[1-[1-(3-fluoropyridin-2-yl)azetidin-3-yl]sulfonylpiperidin-4-yl]-1H-pyrrolo[2,3-b]pyridine; [253]
3-[1-[1-(3-methylpyridin-2-yl)azetidin-3-yl]sulfonylpiperidin-4-yl]-1H-pyrrolo[2,3-b]pyridine; [254]
2-[2-[3-[4-(1H-pyrrolo[2,3-b]pyridin-3-yl)piperidin-1-yl]sulfonylazetidin-1-yl]pyridin-3-yl]propan-2-ol; [255]
(4,4-dimethyl-1,3-oxazolidin-3-yl)-[3-[4-(1H-pyrrolo[2,3-b]pyridin-3-yl)piperidin-1-yl]sulfonylazetidin-1-yl]methanone; [256]
3-[1-[1-(4-methylpyridin-2-yl)azetidin-3-yl]sulfonylpiperidin-4-yl]-1H-pyrrolo[2,3-b]pyridine; [257]
2-[3-(4-pyridin-4-ylpiperidin-1-yl)sulfonylazetidin-1-yl]pyridine-4-carbonitrile; [258]
[2-[3-(4-pyridin-4-ylpiperidin-1-yl)sulfonylazetidin-1-yl]pyridin-3-yl]methanol; [259]
ethyl 2-[3-(4-pyridin-4-ylpiperidin-1-yl)sulfonylazetidin-1-yl]-1,3-oxazole-4-carboxylate; [260]
2-[3-(4-pyridin-4-ylpiperidin-1-yl)sulfonylazetidin-1-yl]-1,3-oxazole-4-carboxamide; [261]
N-(3,5-dimethyl-1,2-oxazol-4-yl)-3-(4-pyridin-4-ylpiperidin-1-yl)sulfonylazetidine-1-carboxamide; [262]
[(2R)-butan-2-yl] 3-(4-pyridin-4-ylpiperidin-1-yl)sulfonylazetidine-1-carboxylate; [263]
cyclohexyl 3-(4-pyridin-4-ylpiperidin-1-yl)sulfonylazetidine-1-carboxylate; [264]
3-(4-pyridin-4-ylpiperidin-1-yl)sulfonyl-N-[1-(trifluoromethyl)cyclopropyl]azetidine-1-carboxamide; [265]
cyclohexylmethyl 3-(4-pyridin-4-ylpiperidin-1-yl)sulfonylazetidine-1-carboxylate; [266]
3-[1-(azetidin-3-ylsulfonyl)piperidin-4-yl]-1-(5-methylpyridin-2-yl)pyrrolo[2,3-b]pyridine; [267]
2-[3-(4-pyridin-4-ylpiperidin-1-yl)sulfonylazetidin-1-yl]pyridine; [268]
tert-butyl 3-(4-pyridin-4-ylpiperidin-1-yl)sulfonylpyrrolidine-1-carboxylate; [269]
3-[1-(1-pyridin-3-ylazetidin-3-yl)sulfonylpiperidin-4-yl]-1H-pyrrolo[2,3-b]pyridine; [270]
N-tert-butyl-N-methyl-3-(4-pyridin-4-ylpiperidin-1-yl)sulfonylpyrrolidine-1-carboxamide; [271]
N-tert-butyl-N-methyl-3-[4-(1H-pyrrolo[2,3-b]pyridin-3-yl)piperidin-1-yl]sulfonylpyrrolidine-1-carboxamide; [272]
methyl cis-3-[4-(1H-pyrrolo[2,3-b]pyridin-3-yl)piperidin-1-yl]sulfonylcyclobutane-1-carboxylate; [273]
methyl trans-3-[4-(1H-pyrrolo[2,3-b]pyridin-3-yl)piperidin-1-yl]sulfonylcyclobutane-1-carboxylate; [274]
N-(3-methoxyphenyl)-3-[4-(1H-pyrrolo[2,3-b]pyridin-3-yl)piperidin-1-yl]sulfonyl azetidine-1-carboxamide; [275]
N-(4-methylphenyl)-3-[4-(1H-pyrrolo[2,3-b]pyridin-3-yl)piperidin-1-yl]sulfonylazetidine-1-carboxamide; [276]
N-(5-fluoro-2-methylphenyl)-3-[4-(1H-pyrrolo[2,3-b]pyridin-3-yl)piperidin-1-yl]sulfonyl azetidine-1-carboxamide; [277]
N-tert-butyl-N-methyl-3-[4-(1H-pyrrolo[2,3-b]pyridin-3-yl)piperidin-1-yl]sulfonyl cyclobutane-1-carboxamide; [278]
N-(3-methoxyphenyl)-N-methyl-3-[4-(1H-pyrrolo[2,3-b]pyridin-3-yl)piperidin-1-yl]sulfonylazetidine-1-carboxamide; [279]
(4-fluorophenyl) 3-(4-pyridin-4-ylpiperidin-1-yl)sulfonylazetidine-1-carboxylate; [280]
N-(3-methoxyphenyl)-3-(4-pyridin-4-ylpiperidin-1-yl)sulfonylazetidine-1-carboxamide; [281]
N-(4-methylphenyl)-3-(4-pyridin-4-ylpiperidin-1-yl)sulfonylazetidine-1-carboxamide; [282]
tert-butyl 3-[4-(1,3-benzothiazol-2-yl)piperidin-1-yl]sulfonylazetidine-1-carboxylate; [283]
N-[(3,5-dimethyl-1,2-oxazol-4-yl)methyl]-3-[4-(1H-pyrrolo[2,3-b]pyridin-3-yl)piperidin-1-yl]sulfonylcyclobutane-1-carboxamide; [284]
N-(3,5-dimethyl-1,2-oxazol-4-yl)-3-[4-(1H-pyrrolo[2,3-b]pyridin-3-yl)piperidin-1-yl]sulfonylcyclobutane-1-carboxamide; [285]
N-(5-fluoro-2-methylphenyl)-3-(4-pyridin-4-ylpiperidin-1-yl)sulfonylazetidine-1-carboxamide; [286]
3-(1-cyclobutylsulfonylpiperidin-4-yl)-1H-pyrrolo[2,3-b]pyridine; [287]
cis-N-tert-butyl-N-methyl-3-[4-(1H-pyrrolo[2,3-b]pyridin-3-yl)piperidin-1-yl]sulfonyl cyclobutane-1-carboxamide; [289]
trans-N-tert-butyl-N-methyl-3-[4-(1H-pyrrolo[2,3-b]pyridin-3-yl)piperidin-1-yl]sulfonyl cyclobutane-1-carboxamide; [290]
cyclohexyl N-[2-(4-pyridin-4-ylpiperidin-1-yl)sulfonylethyl]carbamate; [291]
cyclohexyl N-[2-[4-(1H-pyrrolo[2,3-b]pyridin-3-yl)piperidin-1-yl]sulfonylethyl]carbamate; [292]
3-[4-(1,3-benzothiazol-2-yl)piperidin-1-yl]sulfonyl-N-[1-(trifluoromethyl)cyclopropyl]azetidine-1-carboxamide; [293]
3-[4-(1,3-benzothiazol-2-yl)piperidin-1-yl]sulfonyl-N-(3,5-dimethyl-1,2-oxazol-4-yl) azetidine-1-carboxamide; [294]
cis-N-(3,5-dimethyl-1,2-oxazol-4-yl)-3-(4-pyridin-4-ylpiperidin-1-yl)sulfonylcyclobutane-1-carboxamide; [295]
cis-morpholin-4-yl-[3-[4-(1H-pyrrolo[2,3-b]pyridin-3-yl)piperidin-1-yl]sulfonylcyclobutyl] methanone; [296]

cis-3-[4-(1H-pyrrolo[2,3-b]pyridin-3-yl)piperidin-1-yl] sulfonyl-N-[1-(trifluoromethyl) cyclopropyl]cyclobutane-1-carboxamide; [297]

trans-3-[4-(1H-pyrrolo[2,3-b]pyridin-3-yl)piperidin-1-yl] sulfonyl-N-[1-(trifluoromethyl) cyclopropyl]cyclobutane-1-carboxamide; [298]

tert-butyl 3-[4-(1H-benzimidazol-2-yl)piperidin-1-yl]sulfonylazetidine-1-carboxylate; [299]

3-[4-(1H-benzimidazol-2-yl)piperidin-1-yl]sulfonyl-N-[1-(trifluoromethyl)cyclopropyl]azetidine-1-carboxamide; [300]

tert-butyl 3-(4-phenylpiperidin-1-yl)sulfonylazetidine-1-carboxylate; [301]

tert-butyl 3-[4-(4-chloro-2-methylphenyl)piperidin-1-yl] sulfonylazetidine-1-carboxylate; [302]

tert-butyl 3-[4-(4-cyanophenyl)piperidin-1-yl]sulfonylazetidine-1-carboxylate; [303]

tert-butyl 3-[4-(4-chlorophenyl)piperidin-1-yl]sulfonylazetidine-1-carboxylate; [304]

3-[4-(1,3-benzoxazol-2-yl)piperidin-1-yl]sulfonyl-N-[1-(trifluoromethyl)cyclopropyl]azetidine-1-carboxamide; [305]

2-[di(propan-2-yl)amino]-1-[3-(4-phenylpiperidin-1-yl) sulfonylazetidin-1-yl]ethanone; [306]

2-(dimethylamino)-1-[3-(4-phenylpiperidin-1-yl)sulfonylazetidin-1-yl]propan-1-one; [307]

trans-morpholin-4-yl-[3-[4-(1H-pyrrolo[2,3-b]pyridin-3-yl) piperidin-1-yl]sulfonyl cyclobutyl] methanone; [308]

cis-N-(3,5-dimethyl-1,2-oxazol-4-yl)-3-[4-(1H-pyrrolo[2,3-b]pyridin-3-yl)piperidin-1-yl]sulfonylcyclobutane-1-carboxamide; [309]

trans-N-(3,5-dimethyl-1,2-oxazol-4-yl)-3-[4-(1H-pyrrolo[2,3-b]pyridin-3-yl)piperidin-1-yl]sulfonylcyclobutane-1-carboxamide; [310]

4-phenyl-2-[3-[4-(1H-pyrrolo[2,3-b]pyridin-3-yl)piperidin-1-yl]sulfonylazetidin-1-yl]-1,3-thiazole; [311]

2-[3-[4-(1H-pyrrolo[2,3-b]pyridin-3-yl)piperidin-1-yl] sulfonylazetidin-1-yl]-1,3-benzothiazole; [312]

3-[1-[1-[[1-(trifluoromethyl)cyclopropyl]methyl]azetidin-3-yl]sulfonylpiperidin-4-yl]-1H-pyrrolo[2,3-b]pyridine; [313]

3,3-dimethyl-1-[3-[4-(1H-pyrrolo[2,3-b]pyridin-3-yl)piperidin-1-yl]sulfonylazetidin-1-yl]butan-2-one; [314]

[(2S)-1-methylpyrrolidin-2-yl]-[3-(4-phenylpiperidin-1-yl) sulfonylazetidin-1-yl]methanone; [315]

(3,5-dimethyl-1,2-oxazol-4-yl)-[3-(4-phenylpiperidin-1-yl) sulfonylazetidin-1-yl]methanone; [316]

1-[3-[4-(4-chloro-2-methylphenyl)piperidin-1-yl]sulfonylazetidin-1-yl]-2-[di(propan-2-yl)amino]ethanone; [317]

[3-[4-(4-chloro-2-methylphenyl)piperidin-1-yl]sulfonylazetidin-1-yl]-[(2S)-1-methyl pyrrolidin-2-yl]methanone; [318]

N-tert-butyl-3-[4-(4-chlorophenyl)piperidin-1-yl]sulfonylazetidine-1-carboxamide; [319]

oxan-4-yl 3-[4-(4-chlorophenyl)piperidin-1-yl]sulfonylazetidine-1-carboxylate; [320]

3-[4-(4-chlorophenyl)piperidin-1-yl]sulfonyl-N-[(2R)-1-hydroxy-3-methylbutan-2-yl]azetidine-1-carboxamide; [321]

3-[4-(4-chlorophenyl)piperidin-1-yl]sulfonyl-N-(3,5-dimethyl-1,2-oxazol-4-yl)azetidine-1-carboxamide; [322]

3,3,3-trifluoro-2,2-dimethyl-1-[3-[4-(1H-pyrrolo[2,3-b] pyridin-3-yl)piperidin-1-yl]sulfonyl azetidin-1-yl]propan-1-one; [323]

4-[1-[1-[2-[di(propan-2-yl)amino]acetyl]azetidin-3-yl] sulfonylpiperidin-4-yl]benzonitrile; [324]

2-(dimethylamino)-1-[3-[4-(1H-pyrrolo[2,3-b]pyridin-3-yl) piperidin-1-yl]sulfonylazetidin-1-yl]ethanone; [325]

2-[di(propan-2-yl)amino]-1-[3-[4-(1H-pyrrolo[2,3-b]pyridin-3-yl)piperidin-1-yl]sulfonyl azetidin-1-yl]ethanone; [326]

tert-butyl 3-[4-(4-fluorophenyl)piperidin-1-yl]sulfonylazetidine-1-carboxylate; [327]

3-(4-furo[3,2-b]pyridin-3-ylpiperidin-1-yl)sulfonyl-N-[(2R)-1,1,1-trifluoropropan-2-yl]azetidine-1-carboxamide; [328]

2-(dimethylamino)-1-[3-(4-furo[3,2-b]pyridin-3-ylpiperidin-1-yl)sulfonylazetidin-1-yl]ethanone; [329]

2-[di(propan-2-yl)amino]-1-[3-(4-furo[3,2-b]pyridin-3-ylpiperidin-1-yl)sulfonylazetidin-1-yl]ethanone; [330]

3-[4-(4-cyanophenyl)piperidin-1-yl]sulfonyl-N-[1-(trifluoromethyl)cyclopropyl]azetidine-1-carboxamide; [331]

3-[4-(1H-pyrrolo[2,3-b]pyridin-3-yl)piperidin-1-yl]sulfonyl-N-[(2R)-1,1,1-trifluoropropan-2-yl]azetidine-1-carboxamide; [332]

4,4,4-trifluoro-3-hydroxy-1-[3-[4-(1H-pyrrolo[2,3-b]pyridin-3-yl)piperidin-1-yl]sulfonyl azetidin-1-yl]-3-(trifluoromethyl)butan-1-one; [333]

4,4,4-trifluoro-1-[3-(4-furo[3,2-b]pyridin-3-ylpiperidin-1-yl)sulfonylazetidin-1-yl]-3-hydroxy-3-(trifluoromethyl) butan-1-one; [334]

N-(4-cyanophenyl)-3-[4-(1H-pyrrolo[2,3-b]pyridin-3-yl)piperidin-1-yl]sulfonylazetidine-1-carboxamide; [335]

tert-butyl N-[3-[4-(1H-pyrrolo[2,3-b]pyridin-3-yl)piperidin-1-yl]sulfonylcyclobutyl]carbamate; [336]

2-[3-(4-pyridin-4-ylpiperidin-1-yl)sulfonylazetidin-1-yl]-1, 3-benzothiazole; [337]

2-[3-[4-(1H-pyrrolo[2,3-b]pyridin-3-yl)piperidin-1-yl] sulfonylazetidin-1-yl]-1,3-benzoxazole; [338]

tert-butyl 3-[4-(1H-pyrrolo[2,3-c]pyridin-3-yl)piperidin-1-yl]sulfonylazetidine-1-carboxylate; [339]

N-cyclopropyl-3-[4-(4-fluorophenyl)piperidin-1-yl]sulfonyl-N-methylazetidine-1-carboxamide; [340]

3-[4-(4-chlorophenyl)piperidin-1-yl]sulfonyl-N-[1-(trifluoromethyl)cyclopropyl]azetidine-1-carboxamide; [341]

2-(3,5-dimethyl-1,2-oxazol-4-yl)-1-[3-[4-(4-fluorophenyl) piperidin-1-yl]sulfonylazetidin-1-yl]ethanone; [342]

2-[di(propan-2-yl)amino]-1-[3-[4-(4-fluorophenyl)piperidin-1-yl]sulfonylazetidin-1-yl]ethanone; [343]

3-[4-(4-fluorophenyl)piperidin-1-yl]sulfonyl-N-[1-hydroxy-3-methylbutan-2-yl] azetidine-1-carboxamide; [344]

trans-3-(4-furo[3,2-b]pyridin-3-ylpiperidin-1-yl)sulfonyl-N-[1-(trifluoromethyl) cyclopropyl]cyclobutane-1-carboxamide; [345]

trans-N-tert-butyl-3-(4-furo[3,2-b]pyridin-3-ylpiperidin-1-yl)sulfonylcyclobutane-1-carboxamide; [346]

tert-butyl 3-[4-(6-methyl-1H-pyrrolo[2,3-b]pyridin-3-yl)piperidin-1-yl]sulfonylazetidine-1-carboxylate; [347]

3-[4-(4-cyanophenyl)piperidin-1-yl]sulfonyl-N-[1-hydroxy-3-methylbutan-2-yl]azetidine-1-carboxamide; [348]

4-[1-[1-[2-(3,5-dimethyl-1,2-oxazol-4-yl)acetyl]azetidin-3-yl]sulfonylpiperidin-4-yl]benzonitrile; [349]

3-[4-(4-cyanophenyl)piperidin-1-yl]sulfonyl-N-cyclopropyl-N-methylazetidine-1-carboxamide; [350]

4-[1-[1-[4,4,4-trifluoro-3-hydroxy-3-(trifluoromethyl)butanoyl]azetidin-3-yl]sulfonyl piperidin-4-yl]benzonitrile; [351]

N-tert-butyl-3-[4-(4-cyanophenyl)piperidin-1-yl]sulfonylazetidine-1-carboxamide; [352]

1-[1-[[2-(difluoromethoxy)phenyl]methyl]azetidin-3-yl] sulfonyl-4-phenylpiperidine; [353]

tert-butyl 3-[4-(2,4-dimethylphenyl)piperidin-1-yl]sulfonylazetidine-1-carboxylate; [354]
3-[4-(1H-pyrrolo[2,3-c]pyridin-3-yl)piperidin-1-yl]sulfonyl-N-[1-(trifluoromethyl) cyclopropyl]azetidine-1-carboxamide; [355]
3-[1-(1-pyridin-2-ylazetidin-3-yl)sulfonylpiperidin-4-yl]-1H-pyrrolo[3,2-b]pyridine; [356]
trans-tert-butyl N-[3-[4-(1H-pyrrolo[2,3-b]pyridin-3-yl)piperidin-1-yl]sulfonylcyclobutyl]carbamate; [357]
cis-tert-butyl N-[3-[4-(1H-pyrrolo[2,3-b]pyridin-3-yl)piperidin-1-yl]sulfonylcyclobutyl]carbamate; [358]
N-(2,4-dichlorophenyl)-3-(4-furo[3,2-b]pyridin-3-ylpiperidin-1-yl)sulfonylazetidine-1-carboxamide; [359]
N-(3-fluoro-2-methylphenyl)-3-(4-furo[3,2-b]pyridin-3-ylpiperidin-1-yl)sulfonylazetidine-1-carboxamide; [360]
cis-3-(4-furo[3,2-b]pyridin-3-ylpiperidin-1-yl)sulfonyl-N-[1-(trifluoromethyl)cyclopropyl]cyclobutane-1-carboxamide; [361]
cis-N-tert-butyl-3-(4-furo[3,2-b]pyridin-3-ylpiperidin-1-yl)sulfonylcyclobutane-1-carboxamide; [362]
N-(3-fluoro-2-methylphenyl)-3-[4-(1H-pyrrolo[2,3-b]pyridin-3-yl)piperidin-1-yl]sulfonyl azetidine-1-carboxamide; [363]
N-(2-methylphenyl)-3-[4-(1H-pyrrolo[2,3-b]pyridin-3-yl)piperidin-1-yl]sulfonylazetidine-1-carboxamide; [364]
N-(5-fluoro-2-methylphenyl)-3-(4-furo[3,2-b]pyridin-3-ylpiperidin-1-yl)sulfonylazetidine-1-carboxamide; [365]
3-[4-(4-cyanophenyl)piperidin-1-yl]sulfonyl-N-(5-fluoro-2-methylphenyl)azetidine-1-carboxamide; [366]
N-(5-fluoro-2-methylphenyl)-3-[4-(4-fluorophenyl)piperidin-1-yl]sulfonylazetidine-1-carboxamide; [367]
N-(5-fluoro-2-methylphenyl)-3-[4-(6-methyl-1H-pyrrolo[2,3-b]pyridin-3-yl)piperidin-1-yl]sulfonylazetidine-1-carboxamide; [368]
3-(4-furo[3,2-b]pyridin-3-ylpiperidin-1-yl)sulfonyl-N-(2-methylphenyl)azetidine-1-carboxamide; [369]
N-tert-butyl-3-(4-furo[3,2-b]pyridin-3-ylpiperidin-1-yl)sulfonylazetidine-1-carboxamide; [370]
[(2R)-butan-2-yl] 3-(4-furo[3,2-b]pyridin-3-ylpiperidin-1-yl)sulfonylazetidine-1-carboxylate; [371]
(4,4-dimethyl-1,3-oxazolidin-3-yl)-[3-(4-furo[3,2-b]pyridin-3-ylpiperidin-1-yl)sulfonyl azetidin-1-yl]methanone; [372]
3-(4-furo[3,2-b]pyridin-3-ylpiperidin-1-yl)sulfonyl-N-[(2S)-1-hydroxy-3-methylbutan-2-yl]azetidine-1-carboxamide; [373]
[(2R,6S)-2,6-dimethylmorpholin-4-yl]-[3-(4-furo[3,2-b]pyridin-3-ylpiperidin-1-yl)sulfonyl azetidin-1-yl]methanone; [374]
1-[3-[4-(4-fluorophenyl)piperidin-1-yl]sulfonylazetidin-1-yl]-3,3-dimethylbutan-2-one; [375]
1-[3-[4-furo[3,2-b]pyridin-3-ylpiperidin-1-yl)sulfonylazetidin-1-yl]-3,3-dimethylbutan-2-one; [376]
1-[3-(4-furo[3,2-b]pyridin-3-ylpiperidin-1-yl)sulfonylazetidin-1-yl]-2-(oxan-4-yl)ethanone; [377]
4-[1-[1-(3,3-dimethyl-2-oxobutyl)azetidin-3-yl]sulfonylpiperidin-4-yl]benzonitrile; [378]
4,4,4-trifluoro-3-hydroxy-1-[3-[4-(1H-pyrrolo[3,2-b]pyridin-3-yl)piperidin-1-yl]sulfonyl azetidin-1-yl]-3-(trifluoromethyl)butan-1-one; [379]
oxan-4-yl 3-[4-(6-methyl-1H-pyrrolo[2,3-b]pyridin-3-yl)piperidin-1-yl]sulfonylazetidine-1-carboxylate; [380]
[(2R,6S)-2,6-dimethylmorpholin-4-yl]-[3-[4-(6-methyl-1H-pyrrolo[2,3-b]pyridin-3-yl) piperidin-1-yl]sulfonylazetidin-1-yl]methanone; [381]
N-(2,6-dimethylphenyl)-3-(4-furo[3,2-b]pyridin-3-ylpiperidin-1-yl)sulfonylazetidine-1-carboxamide; [382]
N-(3-fluorophenyl)-3-(4-furo[3,2-b]pyridin-3-ylpiperidin-1-yl)sulfonylazetidine-1-carboxamide; [383]
N-(2-chloro-5-fluorophenyl)-3-(4-furo[3,2-b]pyridin-3-ylpiperidin-1-yl)sulfonylazetidine-1-carboxamide; [384]
N-(2-chloro-5-fluorophenyl)-3-[4-(1H-pyrrolo[2,3-b]pyridin-3-yl)piperidin-1-yl]sulfonyl azetidine-1-carboxamide; [385]
1-[3-[4-(4-chlorophenyl)piperidin-1-yl]sulfonylazetidin-1-yl]-2-(3,5-dimethyl-1,2-oxazol-4-yl) ethanone; [386]
N-(2-fluoro-6-methylphenyl)-3-[4-(1H-pyrrolo[2,3-b]pyridin-3-yl)piperidin-1-yl]sulfonyl azetidine-1-carboxamide; [387]
(2S)-3,3,3-trifluoro-2-hydroxy-2-methyl-1-[3-[4-(1H-pyrrolo[2,3-b]pyridin-3-yl)piperidin-1-yl]sulfonylazetidin-1-yl]propan-1-one; [388]
N-(3-fluorophenyl)-3-[4-(1H-pyrrolo[2,3-b]pyridin-3-yl)piperidin-1-yl]sulfonylazetidine-1-carboxamide; [389]
N-(2,6-difluorophenyl)-3-[4-(1H-pyrrolo[2,3-b]pyridin-3-yl)piperidin-1-yl]sulfonyl azetidine-1-carboxamide; [390]
N-(2,6-dimethylphenyl)-3-[4-(1H-pyrrolo[2,3-b]pyridin-3-yl)piperidin-1-yl]sulfonyl azetidine-1-carboxamide; [391]
N-(4-fluoro-2-methylphenyl)-3-(4-furo[3,2-b]pyridin-3-ylpiperidin-1-yl)sulfonylazetidine-1-carboxamide; [392]
[3-[4-(4-chlorophenyl)piperidin-1-yl]sulfonylazetidin-1-yl]-[(2R,6S)-2,6-dimethyl morpholin-4-yl]methanone; [393]
N-(4-fluoro-2-methylphenyl)-3-[4-(1H-pyrrolo[2,3-b]pyridin-3-yl)piperidin-1-yl]sulfonylazetidine-1-carboxamide; [394]
(2S)-3,3,3-trifluoro-1-[3-(4-furo[3,2-b]pyridin-3-ylpiperidin-1-yl)sulfonylazetidin-1-yl]-2-hydroxy-2-methylpropan-1-one; [395]
1-[3-[4-(4-chlorophenyl)piperidin-1-yl]sulfonylazetidin-1-yl]-3,3-dimethylbutan-2-one; [396]
3-hydroxy-3-methyl-1-[3-[4-(1H-pyrrolo[2,3-b]pyridin-3-yl)piperidin-1-yl]sulfonyl azetidin-1-yl]butan-1-one; [397]
1-[3-(4-furo[3,2-b]pyridin-3-ylpiperidin-1-yl)sulfonylazetidin-1-yl]-3-hydroxy-3-methylbutan-1-one; [398]
N-(4-fluoro-2-methylphenyl)-3-(4-furo[3,2-b]pyridin-3-ylpiperidin-1-yl)sulfonyl-N-methylazetidine-1-carboxamide; [399]
3-[4-(4-chlorophenyl)piperidin-1-yl]sulfonyl-N-(5-fluoro-2-methylphenyl)azetidine-1-carboxamide; [400]
4,4,4-trifluoro-3-hydroxy-1-[3-(4-pyridin-4-ylpiperidin-1-yl)sulfonylazetidin-1-yl]-3-(trifluoromethyl)butan-1-one; [401]
[3-[4-(4-chlorophenyl)piperidin-1-yl]sulfonylazetidin-1-yl]-morpholin-4-ylmethanone; [402]
N-(2,6-difluorophenyl)-3-(4-furo[3,2-b]pyridin-3-ylpiperidin-1-yl)sulfonylazetidine-1-carboxamide; [403]
3,3,3-trifluoro-1-[3-(4-furo[3,2-b]pyridin-3-ylpiperidin-1-yl)sulfonylazetidin-1-yl]-2,2-dimethylpropan-1-one; [404]
4,4,4-trifluoro-3-hydroxy-3-methyl-1-[3-[4-(1H-pyrrolo[2,3-b]pyridin-3-yl) piperidin-1-yl]sulfonylazetidin-1-yl]butan-1-one; [405]
4,4,4-trifluoro-1-[3-(4-furo[3,2-b]pyridin-3-ylpiperidin-1-yl)sulfonylazetidin-1-yl]-3-hydroxy-3-methylbutan-1-one; [406]
[3-(4-furo[3,2-b]pyridin-3-ylpiperidin-1-yl)sulfonylazetidin-1-yl]-[(2S)-1-methylpyrrolidin-2-yl]methanone; [407]
1-[3-(4-furo[3,2-b]pyridin-3-ylpiperidin-1-yl)sulfonylazetidin-1-yl]-3-methylbutan-1-one; [408]

tert-butyl 3-[4-(2-methylphenyl)piperidin-1-yl]sulfonylazetidine-1-carboxylate; [409]
tert-butyl 3-(4-quinolin-4-ylpiperidin-1-yl)sulfonylazetidine-1-carboxylate; [410] and
[3-[4-(4-chlorophenyl)piperidin-1-yl]sulfonylazetidin-1-yl]-(4,4-dimethyl-1,3-oxazolidin-3-yl)methanone; [411]
or a pharmaceutically acceptable salt or a solvate thereof.

In one aspect of the invention, specific compounds of formula I which may be mentioned include those selected from the group consisting of:
namely, compounds 57, 135, 138, 152, 156, 160, 166, 171, 175, 176, 213, 216, 217, 374, 380 and 381; or a pharmaceutically acceptable salt or a solvate thereof.

In another aspect of the invention, specific compounds of formula I which may be mentioned include those selected from the group consisting of:
namely, compounds 8, 17, 18, 19, 26, 27, 33, 34, 39, 41, 43, 44, 45, 49, 50, 54, 55, 56, 59, 60, 62, 63, 64, 66, 67, 75, 76, 77, 84, 85, 96, 107, 108, 110, 118, 119, 120, 124, 125, 128, 131, 136, 139, 140, 141, 147, 149, 150, 153, 154, 161, 162, 163, 164, 168, 169, 170, 172, 174, 177, 178, 179, 180, 181, 182, 189, 190, 193, 195, 197, 198, 199, 200, 201, 204, 205, 206, 207, 209, 211, 212, 214, 215, 218, 219, 220, 223, 242, 243, 250, 251, 253, 254, 255, 256, 257, 272, 277, 278, 285, 289, 293, 297, 309, 311, 312, 314, 319, 321, 322, 323, 324, 326, 328, 329, 330, 331, 332, 333, 334, 335, 336, 338, 341, 342, 347, 349, 357, 358, 359, 360, 361, 362, 363, 364, 365, 370, 371, 372, 373, 376, 377, 379, 382, 383, 384, 385, 386, 387, 388, 389, 390, 391, 392, 393 and 394;
or a pharmaceutically acceptable salt or a solvate thereof.

In another aspect of the invention, specific compounds of formula I which may be mentioned include those selected from the group consisting of:
namely, compounds 1, 3, 6, 7, 11, 12, 13, 14, 16, 22, 23, 24, 28, 31, 32, 35, 38, 48, 51, 52, 58, 65, 69, 70, 73, 78, 80, 81, 82, 86, 87, 88, 90, 91, 94, 95, 97, 98, 99, 100, 109, 111, 112, 115, 116, 122, 123, 126, 127, 132, 133, 134, 137, 142, 143, 144, 151, 155, 165, 173, 183, 184, 185, 186, 187, 188, 191, 192, 194, 196, 202, 208, 210, 221, 222, 228, 230, 231, 232, 234, 235, 237, 239, 241, 244, 245, 246, 248, 252, 262, 263, 264, 265, 266, 269, 270, 271, 273, 274, 275, 276, 283, 284, 290, 292, 294, 296, 298, 301, 302, 303, 304, 306, 308, 310, 313, 317, 320, 327, 337, 343, 344, 345, 348, 351, 352, 366, 369, 375, 378, 395, 396, 397, 398, 399, 400, 401 and 402;
or a pharmaceutically acceptable salt or a solvate thereof.

In another aspect of the invention, specific compounds of formula I which may be mentioned include those selected from the group consisting of:
namely, compounds 2, 4, 5, 9, 10, 15, 20, 21, 29, 30, 36, 37, 40, 42, 46, 47, 53, 61, 71, 72, 74, 79, 83, 89, 92, 93, 101, 102, 103, 104, 105, 106, 113, 114, 117, 121, 129, 130, 145, 146, 148, 157, 158, 159, 167, 203, 224, 225, 226, 227, 229, 233, 236, 238, 240, 247, 258, 259, 260, 261, 267, 268, 279, 280, 281, 282, 286, 287, 291, 295, 299, 300, 305, 307, 315, 316, 318, 325, 339, 340, 346, 350, 353, 354, 355, 356, 367 and 368;
or a pharmaceutically acceptable salt or a solvate thereof.

In another aspect of the invention, specific compounds of formula I which may be mentioned include those selected from the group consisting of:
namely, compounds 28, 81, 90, 94, 113, 128, 151, 162, 168, 174, 176, 179, 183, 185, 224, 225 and 231;
or a pharmaceutically acceptable salt or a solvate thereof.

In another aspect of the invention, specific compounds of formula I which may be mentioned include those selected from the group consisting of:
namely, compounds 16, 34, 67, 97, 107, 112, 115, 116, 122, 124, 131, 143, 154, 162, 223, 228, 239, 255, 256, 265, 274, 284, 285, 292, 294, 296, 298, 308, 313, 314, 319, 328, 333, 334, 347, 388, 395, 396, 397, 401 and 410;
or a pharmaceutically acceptable salt or a solvate thereof.

In another aspect of the invention, specific compounds of formula I which may be mentioned include those selected from the group consisting of:
namely, compounds 94, 144, 319, 331, 333 and 334;
or a pharmaceutically acceptable salt or a solvate thereof.

In one embodiment the compound and intermediate of the invention is not an isotopic variant.

In one aspect a compound and intermediate of the invention according to any one of the embodiments herein described is a free base.

In one aspect a compound and intermediate of the invention according to any one of the embodiments herein described is a salt.

In one aspect a compound of the invention according to any one of the embodiments herein described is a pharmaceutically acceptable salt.

In one aspect a compound and intermediate of the invention according to any one of the embodiments herein described is a solvate of the compound.

In one aspect a compound of the invention according to any one of the embodiments herein described is a solvate of a salt of a compound, in particular a solvate of a pharmaceutically acceptable salt.

Similarly, reference to intermediates of the invention, whether or not they themselves are claimed, is meant to embrace their salts, and solvates, where the context so permits.

With regard to stereoisomers, the compounds and intermediates of the invention have more than one asymmetric carbon atom. In the general formula(e) as drawn, the solid wedge shaped bond indicates that the bond is above the plane of the paper. The broken bond indicates that the bond is below the plane of the paper.

It will be appreciated that the substituents on the compounds and intermediates of the invention may also have one or more asymmetric carbon atoms. Thus, the compounds and intermediates of the invention may occur as individual enantiomers or diastereomers. All such isomeric forms are included within the present invention, including mixtures thereof.

Where a compound and intermediate of the invention contains an alkenyl group, cis (Z) and trans (E) isomerism may also occur. The present invention includes the individual stereoisomers of the compound and, where appropriate, the individual tautomeric forms thereof, together with mixtures thereof.

Separation of diastereoisomers or cis and trans isomers may be achieved by conventional techniques, e.g. by fractional crystallisation, chromatography or HPLC. A stereoisomeric mixture of the agent may also be prepared from a corresponding optically pure intermediate or by resolution, such as by HPLC, of the corresponding mixture using a suitable chiral support or by fractional crystallisation of the diastereoisomeric salts formed by reaction of the corresponding mixture with a suitable optically active acid or base, as appropriate.

Unless otherwise stated, in formulae disclosed herein a bond drawn without any attached group means a methyl group.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

While specified groups for each embodiment have generally been listed above separately, a compound and intermediate of the invention may be one for which one or more variables (R groups and/or integers) is selected from one or more embodiments according to any of the Formula (e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds of the invention according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H. Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, substituted aryl, and arylalkyl esters of the compounds of the invention.

A person of skill in the art will appreciate that when administered in vivo compounds of the invention may be metabolised and that some of these biological metabolites may be active. In one aspect, the present invention therefore provides for biologically active metabolites of compounds of the invention.

Pharmaceutical Compositions

While it is possible that, for use in the methods of the invention, a compound of the invention may be administered as the bulk substance, it is preferable to present the active ingredient in a pharmaceutical formulation as a pharmaceutical composition. Thus, when employed as a pharmaceutical, a compound of the invention is typically administered in the form of a pharmaceutical composition. Such compositions can be prepared in a manner well known in the pharmaceutical art and comprise at least one active compound. Generally, a compound of this invention is administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, and intranasal. Depending on the intended route of delivery, a compound of this invention is preferably formulated as either injectable or oral compositions or as salves, as lotions or as patches all for transdermal administration.

The compounds of the invention can be administered for immediate-, delayed-, modified-, sustained-, pulsed- or controlled-release applications.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

In one aspect, oral compositions are slow, delayed or positioned release (e.g., enteric especially colonic release) tablets or capsules. This release profile can be achieved for example, by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of methacrylic acid and its esters, and combinations thereof. Plasticizers such as, but not limited to polyethylene glycol, dibutylphthalate, triacetin and castor oil may be used. A pigment may also be used to colour the film. Suppositories are be prepared by using carriers like cocoa butter, suppository bases such as Suppocire C, and Suppocire NA50 (supplied by Gattefossé Deutschland GmbH, D-Weil am Rhein, Germany) and other Suppocire type excipients obtained by interesterification of hydrogenated palm oil and palm kernel oil ($C_8$-$C_{18}$ triglycerides), esterification of glycerol and specific fatty acids, or polyglycosylated glycerides, and Witepsol® (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated castor oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and methacrylic acid esters. These latter materials may also be applied to tablets by compression coating. Pharmaceutical compositions can be prepared by mixing a therapeutically effective amount of the active substance with a pharmaceutically acceptable carrier that can have different forms, depending on the way of administration. Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions (e.g., starch, sugar, kaolin, binders disintegrating agents) preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Pharmaceutical compositions containing compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilisers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminium silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesiumaluminium silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable flavourings for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the compound of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and flavourings.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., a hydrofluoroalkane such as 1,1,1,2-tetrafluoroethane (HFA 134AT) or 1,1,1,2,3,3,3-heptafluoropropane (HFA 227EA), or a mixture thereof. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10% w/w, more preferably 0.01-1% w/w of the active compound.

A therapeutically effective amount of the compound of the present invention can be determined by methods known in the art. The therapeutically effective quantities may vary and will depend on the severity of the disease, the age and the general physiological condition of the subject, the potency of the compound, the route of administration and the pharmaceutical formulation used. The therapeutic doses will generally be from about 10 to 2000 mg/day and suitably from about 30 to 1500 mg/day. Other ranges may be used, including, for example, 50-500 mg/day, 50-300 mg/day, 100-200 mg/day. Thus, the therapeutic dose may be about 10 mg/day, about 10 mg/day, about 50 mg/day, about 100 mg/day, about 150 mg/day, about 200 mg/day, about 250 mg/day, about 300 mg/day, about 350 mg/day, about 400 mg/day, about 450 mg/day, about 500 mg/day, about 550 mg/day, about 600 mg/day, about 650 mg/day, about 700 mg/day, about 750 mg/day, about 800 mg/day, about 850 mg/day, about 900 mg/day, about 950 mg/day, about 1,000 mg/day, about 1,050 mg/day, about 1,100 mg/day, about 1,150 mg/day, about 1,200 mg/day, about 1,250 mg/day, about 1,300 mg/day, about 1,350 mg/day, about 1,400 mg/day, about 1,450 mg/day, about 1,500 mg/day, about 1,550 mg/day, about 1,600 mg/day, about 1,650 mg/day, about 1,700 mg/day, about 1,750 mg/day, about 1,800 mg/day, about 1,850 mg/day, about 1,900 mg/day, about 1,950 mg/day or about 2,000. The daily dose as employed for acute human treatment will range from 0.01 to 40 mg/kg body weight, suitably 2 to 20 mg/kg body weight, or suitably 5 to 10 mg/kg body weight, which may be administered in one to four daily doses, for example, depending on the route of administration and the condition of the subject. When the composition comprises dosage units, each unit may contain 10 mg to 2 g of active ingredient, suitably 200 mg to 1 g of active ingredient.

Administration may be once a day, twice a day, or more often, and may be decreased during a maintenance phase of treatment of the disease, e.g. once every second or third day instead of every day or twice a day. The dose and the administration frequency will depend on the clinical signs with the reduction or absence of at least one or more, preferably more than one, clinical signs of the acute phase known to the person skilled in the art. In one aspect of the present invention, administration is once daily oral dosing.

The present invention is related to a pharmaceutical composition comprising from about 10 to 2000 mg of a compound of Formula (I), or a pharmaceutically acceptable salt thereof, and at least one pharmaceutically acceptable excipient, e.g. from about 0.1 to 2 g of one or more pharmaceutically acceptable excipients.

Methods of Treatment

It has been identified that compounds of the invention modulate the Hh signalling pathway and are useful for the treatment of diseases and/or conditions associated with abnormal activation and/or malfunction of the Hh signalling pathway. Such diseases and conditions include proliferative diseases, such as cancers; fibrosis and GVHD, etc. as herein defined.

In one embodiment, the present invention provides novel compounds of the invention, or pharmaceutical compositions comprising a compound of the invention, for use as a medicament. In a particular embodiment, the present invention provides novel compounds of the invention or pharmaceutical compositions comprising a compound of the invention, for use in the treatment of conditions involving abnormal activation of the hedgehog pathway.

In one embodiment of the invention we provide a method of treatment of a disease or condition associated with abnormal activation and/or malfunction of the of the hedgehog pathway which comprises the administration of a therapeutically effective amount of a compound of Formula I to a patient suffering from such a disease or condition:

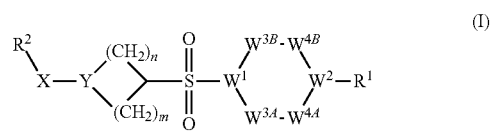

(I)

wherein:

integers n and m are selected from:
(i) 1, 2 and 3, provided that sum of n and m is 2, 3 or 4; or
(ii) 0 and 1, provided that the sum of n and m is 1;

Y is CH, N or NH, provided that Y is NH only when the sum of n and m is 1;

$W^1$ is N;

$W^2$ is CH, C or N, provided when $W^2$ is C one of $W^{4A}$ and $W^{4B}$ is —CH— and is connected to $W^2$ by a double bond and the other is —CH$_2$—

$W^{3A}$ and $W^{3B}$ are —CH$_2$— or —CH(R$^3$)—, wherein R$^3$ is methyl;

$W^{4A}$ and $W^{4B}$ are —CH$_2$— or —CH—, provided that when one of $W^{4A}$ and $W^{4B}$ is —CH— the other is —CH$_2$—;

integers n and m are selected from 1, 2 and 3, provided that sum of n and m is 2, 3 or 4;

$R^1$ is selected from:
(i) a fused 9-10 membered bicyclic heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —C(=O)OC$_{1-6}$alkyl, —O(C=O)C$_{1-6}$alkyl, —C(=O)O—C$_{0-4}$alkyl-cycloalkyl, C$_{0-6}$alkyl-phenyl (wherein phenyl may be optionally substituted by C$_{1-4}$alkyl), —C(=O)NHC$_{1-6}$alkyl, —NHC(=O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;
(ii) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —C(=O)OC$_{1-6}$alkyl, —O(C=O)C$_{1-6}$alkyl, —C(=O)O—C$_{1-4}$alkyl-cycloalkyl, C$_{0-6}$alkyl-phenyl (wherein phenyl may be optionally substituted by C$_{1-4}$alkyl), —C(=O)NHC$_{1-6}$alkyl, —NHC(=O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;
(iii) 6-10 membered aryl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$ alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$ alkyl and —NHC(=O)C$_{1-6}$alkyl;
(iv) a fused 8-10 membered partially unsaturated bicyclic heterocyclyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl; and
(v) a 5-6 membered monocyclic heterocycloalkyl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$ alkyl, —C(=O)NHC$_{1-6}$alkyl and —NHC(=O)C$_{1-6}$ alkyl;

X is absent or a bivalent group selected from:
(a) —(CH$_2$)x$^1$-, wherein x$^1$ is 1, 2 or 3;
(b) —(CH$_2$)x$^2$-C(CH$_3$)$_2$—(CH$_2$)x$^3$-, wherein x$^2$ is 1 or 2 and x$^3$ is 1;
(c) —C(=O)—(CH$_2$)x$^4$-, wherein x$^4$ is zero, 1 or 2;
(d) —C(=O)O—(CH$_2$)x$^5$-, wherein x$^5$ is zero, 1, 2 or 3;
(e) —C(=O)NR$^x$—(CH$_2$)x$^6$-, wherein
(e.i) x$^6$ is zero, 1 or 2 and R$^x$ is H or C$_{1-4}$alkyl, or
(e.ii) x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl may be optionally substituted by one or more C$_{1-4}$alkyl groups;
(f) —C(=S)NR$^y$—, wherein R$^y$ is H or C$_{1-4}$alkyl; and
(g) —SO$_2$—;

$R^2$ is selected from:
(i) C$_{1-10}$alkyl optionally substituted by one or more groups independently selected from OH, —OC$_{1-4}$alkyl, —NHC$_{1-4}$alkyl, and —N(C$_{1-4}$alkyl)$_2$;
(ii) —NHC$_{1-4}$alkyl, —N(C$_{1-4}$alkyl)$_2$;
(iii) 3-10 membered cycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$;
(iv) 5-6 membered heterocycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, and —C(=O)NH$_2$;
(v) phenyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl;
(vi) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$ alkyl, —C(=O)OH, —C(=O)O$C_{1-6}$alkyl, —C(=O)NH$C_{1-6}$alkyl, —NHC(=O)$C_{1-6}$alkyl, and 3-6-membered cycloalkyl wherein said cycloalkyl may optionally be substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, $NH_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alky; and (vii) H and X is absent;

or a pharmaceutically acceptable salt or a solvate thereof.

The embodiments of the compounds of the invention and the compounds for use as a medicament described herein shall be construed as also being applicable to the method of treatment described herein.

In one embodiment of the invention the disease or condition associated with the abnormal activation or malfunction of the Hh signalling pathway is one or more of cancer, fibrosis and chronic graft-versus-host disease (cGVHD).

According to a further aspect of the invention we provide a method treatment of conditions involving abnormal activation and/or malfunction of the of the hedgehog pathway whereby the condition involving abnormal activation of the hedgehog pathway is cancer.

According to a further aspect of the invention there is provided a method of treatment of cancer, by modulating the Hh signalling pathway, which comprises the administration of a therapeutically effective amount of a novel compound of the invention.

According to a yet further aspect of the invention we provide a method of treating cancer as hereinbefore described wherein the cancer is selected from one or more of basal cell carcinoma, neuroectodermal tumours such as medullablastoma, meningioma, hemangioma, glioblastoma, pancreatic adenocarcinoma, squamous lung carcinoma, small-cell lung carcinoma, non-small cell lung carcinoma, chondrosarcoma, breast carcinoma, rhabdomyosarcoma, oesophageal cancer, stomach cancer, biliary tract cancer, renal carcinoma, thyroid carcinoma, primary cancer, breast cancer, colon cancer, prostate cancer, non-small cell lung cancer, glioblastoma, lymphoma, melanoma, mesothelioma, liver cancer, intrahepatic bile duct cancer, oesophageal cancer, pancreatic cancer, stomach cancer, laryngeal cancer, brain cancer, ovarian cancer, testicular cancer, cervical cancer, oral cancer, pharyngeal cancer, renal cancer, thyroid cancer, uterine cancer, urinary bladder cancer, hepatocellular carcinoma, thyroid carcinoma, osteosarcoma, small cell lung cancer, leukaemia, myeloma, gastric carcinoma and metastatic cancers.

In one preferred embodiment of the invention there is provided a method of treating cancer as hereinbefore described wherein the cancer is selected from one or more of basal cell carcinoma, neuroectodermal tumours such as medullablastoma, meningioma, hemangioma, glioblastoma, pancreatic adenocarcinoma, squamous lung carcinoma, small-cell lung carcinoma, non-small cell lung carcinoma, chondrosarcoma, breast carcinoma, rhabdomyosarcoma, oesophageal cancer, stomach cancer, biliary tract cancer, renal carcinoma and thyroid carcinoma.

In a further preferred embodiment of the invention there is provided a method of treating cancer as hereinbefore described wherein the cancer is selected from one or more of basal cell carcinoma, metastatic colorectal cancer, small-cell lung cancer, advanced stomach cancer, pancreatic cancer, medulloblastoma and chondrosarcoma.

According to a further aspect of the invention we provide a method treatment of conditions involving abnormal activation of the hedgehog pathway whereby the condition involving abnormal activation of the hedgehog pathway is fibrosis.

Whereby fibrosis is cell necrosis caused by sustained inflammatory stimulation.

Whereby fibrosis is selected from one or more of pulmonary fibrosis, cystic fibrosis, cirrhosis, atrial fibrosis, endomyocardial fibrosis, myocardial infarction scaring, glial scar, arthrofibrosis, Crohn's disease, Dupuytren's contracture, keloid, mediastinal fibrosis, myelofibrosis, Peyronie's disease, nephrogenic systemic fibrosis, progressive massive fibrosis, retroperitoneal fibrosis, scleroderma/systemic sclerosis and adhesive capsulitis.

Whereby fibrosis is selected from one or more of liver, kidney, bile duct, pancreas, cardiac, systemic sclerosis/scleroderma and myelofibrosis.

Whereby liver fibrosis is selected from one or more of cirrhosis, chronic liver diseases, obesity-related liver disease or chronic viral hepatitis.

Whereby pulmonary fibrosis, includes, but is not limited to, idiopathic or usual interstitial pneumonia, autoimmune lung diseases, chronic obstructive pulmonary disease (COPD), inflammatory pulmonary fibrosis, fibrosis secondary to asthma; adult respiratory distress syndrome; pulmonary sarcosis; fibrosis secondary to lung cancer, fibrosis secondary to graft-versus-host reaction; fibrosis secondary to viral diseases, including influenza virus, or Severe Acute Respiratory Syndrome (SARS).

According to a further aspect of the invention we provide a method treatment of conditions involving abnormal activation of the hedgehog pathway whereby the condition involving abnormal activation of the hedgehog pathway is chronic graft-versus-host disease (cGVHD).

According to this aspect of the invention GVHD is as a result of transplantation.

A compound of the invention can be administered as the sole active agent or it can be administered in combination with a second therapeutic agent, including other compounds that demonstrate the same or a similar therapeutic activity and that are determined to safe and efficacious for such combined administration. In a specific embodiment, co-administration of two (or more) agents allows for significantly lower doses of each to be used, thereby reducing the side effects seen.

Thus, according to this aspect of the invention there is provided a compound of Formula I, or a pharmaceutically acceptable salt thereof, as herein described, in combination with a second therapeutically active ingredient.

In one embodiment, a compound of the invention or a pharmaceutical composition comprising the compound of the invention is administered as a medicament. In a specific embodiment, said pharmaceutical composition additionally comprises a further active ingredient. Thus, according to this aspect of the invention there is further provided a pharmaceutical composition comprising a compound of Formula I, or a pharmaceutically acceptable salt thereof, in combination with a second therapeutically active ingredient, optionally in association with a pharmaceutically acceptable adjuvant, diluent or carrier.

In one embodiment, a compound of the invention is co-administered with another therapeutic agent for the treatment of conditions and/or diseases involving abnormal activation of the hedgehog pathway.

According to a further aspect of the invention the second therapeutic agent may act as a hedgehog modulator.

According to this aspect of the invention the second therapeutic agent may act as a hedgehog modulator via downstream effectors including, but not limited to, SMO, GLI, SHH or tGLI1 (truncated, gain-of-function isoform of the GLI1 transcription factor).

Examples of SMO inhibitors include cyclopamine, vismodegib, erismodegib, saridegib, CUR61414, BMS-833923/XL139, glasdegib, PF-5274857, TAK-441, taladegib MRT-92 and jervine.

Examples of GLI inhibitors include Arsenic Trioxide (ATO) and GANTs (GLI antagonists) as described herein.

Examples of SHH inhibitors include RU-SKI 43 and SHH Monoclonal Antibodies.

Examples of tGLI1 target gene inhibitors include, CD24, VEGF-A, VEGFR2, HPA1 and TEM7.

Cancer

When the condition involving abnormal activation of the hedgehog pathway is cancer particular agents include, but are not limited to: other anticancer treatments such a chemotherapeutic agent, an immunotherapeutic agent, a gene therapy agent, and a radiotherapeutic agent.

According to a this aspect of the invention the second therapy is selected from the group consisting of one or more of a chemotherapeutic agent; an alkylating agent, such as carmustine or temozolamide; a mitotic inhibitor, such as taxanes, (e.g. paclitaxol or docetaxol) or vinca alkaloids (e.g. vinblastine, vincristine, vindestine or vinorelbine); platinum derived compounds (e.g. carboplatin, cisplatin, nedaplatin, oxaliplatin, triplatin tetranitrate or satraplatin); dihydrofolate reductase inhibitors (e.g. aminopterin, methotrexate, pemetrexed or pralatrexate); a DNA polymerase inhibitor (e.g. cytarabine); a ribonucleotide reductase inhibitor (e.g. gemcitabine); a thymidylate synthase inhibitors (e.g. fluorouracil, capecitabine, tegafur, carmofur or floxuridine); aspirin; a non-steroidal anti-inflammatory agent (e.g. ibuprofen); a steroidal anti-inflammatory agent (e.g. a corticosteroid, such as, prednisolone or cortisol); a non-drug oncology therapeutic agent; radiotherapy; tumour embolisation; surgery; and ultrasound.

More preferably the second therapeutic agent may comprise: alemtuzumab, ipilimumab, nivolumab, ofatumumab, rituximab, actinomycin, azacitidine, azathioprin, carboplatin, capecitabin, cisplatin, cyclophosphamide, cytarabine, daunorubicin, docetaxel, doxifluridine, doxorubicin, epirubicin, etoposide, fluorouracil, gemcitabine, hydroxyurea, idarubicin, imatinib, imiquimod, irinotecan, mechlorethamine, mercaptopurin, methotrexate, mitoxantrone, oxaliplatin, paclitaxel, pemetrexed, sorafenib, temozolomide, teniposide, tioguanine, topotecan, valrubicin, vinblastine, vincristine, vindesine, vinorelbine or vismodegib.

In one aspect of the invention the additional therapeutic agent may be an immunotherapeutic agent.

The immunotherapeutic agent may consist of one or more of CAR-T cells, vectors, vaccines, armed antibodies; an agent capable of enhancing use of the immune system to treat cancer; an agent of the monoclonal antibody class capable of enhancing use of the immune system to treat cancer; an agent of the interferon class capable of enhancing use of the immune system to treat cancer.

In one aspect of the invention the immunotherapeutic agent consists of one or more of CAR-T cells, vectors, vaccines, and armed antibodies.

In another aspect of the invention the immunotherapeutic agent consists of any agent capable of enhancing use of the immune system to treat cancer.

In another aspect of the invention the immunotherapeutic agent consists of any agent of the monoclonal antibody class capable of enhancing use of the immune system to treat cancer.

In another aspect of the invention the immunotherapeutic agent consists of any agent of the interferon class capable of enhancing use of the immune system to treat cancer.

In another aspect of the invention the immunotherapeutic agent consists of any agent of the interleukin class capable of enhancing use of the immune system to treat cancer.

Such an immunotherapeutic agent may be checkpoint inhibitor as herein described, e.g. an agent which targets immune checkpoints, wherein immune checkpoints are those pathways within the system for maintaining self-tolerance and modulating the duration and amplitude of physiological immune responses.

According to this aspect of the invention the checkpoint inhibitor may be an agent which targets, i.e. inhibits, one or more of CTLA4, PD1, PDL1, PDL2, CD80, CD86, CD28, B7RP1, ICOS, B7-H3, B7-H4, HVEM, BTLA, MHC-Class 1, MHC-Class 2, KIR, TCR, LAG3, CD137L, CD137, OX40L, OX40, CD70, CD27, CD40, CD40L, GALS, TIM3, A2aR, CD52, CD20, CD274 and CD279.

In a preferred aspect of the invention checkpoint inhibitor is one or more of a CTLA4, PD1 or PDL1 inhibitor.

Examples of CTLA4 inhibitor, include, but shall not be limited to one or more of ipilimumab, nivolumab, rituximab, pembrolizumab, ofatumumab, BMS-936559, MedI-4736, MPDL-3280A, MSB0010718C, pidilizumab and MK-3475. A particular CTLA4 inhibitor which may be mentioned is ipilimumab.

Examples of PD1 inhibitor, include, but shall not be limited to one or more of nivolumab, pidilizumab and MK-3475.

Examples of PDL1 inhibitor, include, but shall not be limited to, one or more of BMS-936559, MedI-4736, MPDL-3280A and MSB0010718C.

Fibrosis

When the condition involving abnormal activation of the hedgehog pathway is fibrosis particular agents include, but are not limited to: Inhibitors of SMO, ALK kinase, Notch, Wnt, Jak kinase or Bcl2.

According to this aspect of the invention examples include, pirfenidone, nintedanib, gamma secretase inhibitors, RO4929097, MRK-003, MK-0752 and PF03084014.

According to this aspect of the invention, particular examples include bevacizumab (Avastin), itraconazole, carboxyamidotriazole, TNP-470, CM101, IFN-α, IL-12, platelet factor-4, suramin, SU5416, thrombospondin, VEGFR antagonists, angiostatic steroids with heparin, Cartilage-Derived Angiogenesis Inhibitory Factor, matrix metalloproteinase inhibitors, angiostatin, endostatin, 2-methoxyestradiol, tecogalan tetrathiomolybdate, thalidomide, thrombospondin, prolactin, αVβ3.inhibitors, linomide, tasquinimod, ranibizumab, sorafenib (Nexavar®), sunitinib (Sutent®), pazopanib (Votrient®) and everolimus (Afinitor®).

The compounds of the invention may be administered prior to, during or post-surgery, whereby surgery may be palliative or curative.

Co-administration includes any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Synthetic Procedures
General

Compounds of Formula (I), and salts and solvates thereof; and intermediates of formulae (II), (III), (IV) and (V) may be prepared by the general methods outlined herein or any method known in the art, said methods constituting a further aspect of the invention. In the following description, the groups $R^1$, $R^2$, $R^3$, $W^1$, $W^2$, $W^{3A}$, $W^{3B}$, $W^{4A}$, $W^{4B}$, n and m have the meaning defined herein for the compounds of Formula (I) as herein described, unless otherwise stated.

A compound of the invention, as well as intermediate compounds of the invention, can be prepared from readily available starting materials using the following general methods and procedures. It will be appreciated that where typical or preferred process conditions (i.e. reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Third Edition, Wiley, New York, 1999, and references cited therein.

The following methods are presented with details as to the preparation of a compound of the invention as well as intermediate of the invention as defined hereinabove and the comparative examples.

Compounds of the invention, as well as intermediates of the invention, may be prepared from known or commercially available starting materials and reagents by one skilled in the art of organic synthesis, using methods known to the person skilled in the art or by methods described herein.

All reagents were of commercial grade and were used as received without further purification, unless otherwise stated. Commercially available anhydrous solvents were used for reactions conducted under inert atmosphere. Reagent grade solvents were used in all other cases, unless otherwise specified.

A compound of the invention as well as intermediate of the invention can be separated from a reaction mixture and further purified by a method such as column chromatography, high pressure liquid chromatography, or recrystallization. Column chromatography is performed on silica gel 60 (70-200 μm). Flash chromatography is carried out using prepacked columns with 15 or 50 μm particle size silica gel. Preparative thin layer chromatography is carried out using pre-coated silica gel 2000 micron UV254 nm plates (thickness 2.0 mm).

Thin layer chromatography is performed using pre-coated silica gel 60E-254 plates (thickness 0.25 mm).

NMR spectra are recorded on Bruker DPX 300 MHz equipped with a 5 mm BBI probe, Bruker AV400 MHz equipped with a 5 mm PABBO probe, Bruker DRX 500 MHz equipped with a 5 mm PABBI probe and Bruker Avance III 600 spectrometer equipped with a 5 mm RT BBI probe. The samples are recorded at 25° C. using DMSO-$d_6$ or CDCl$_3$ as a solvent, unless otherwise stated. Chemical shifts (δ) for $^1$H NMR spectra are reported in parts per million (ppm) relative to tetramethylsilane (δ 0.00) as internal reference.

Electrospray MS spectra are obtained on Waters Acquity UPLC with Waters Acquity PDA detector and SQD mass spectrometer. Columns used: UPLC BEH C18 1.7 μm, 2.1×5 mm VanGuard Pre-column with Acquity UPLC BEH C18 1.7 μm, 2.1×50 mm Column or Acquity UPLC CSH C18 1.7 μm, 2.1×50 mm Column. All the methods are using MeCN/H$_2$O gradients. MeCN and H$_2$O contains either 0.1% Formic Acid or 10 mM NH$_4$HCO$_3$.

For preparative purification HPLC Waters Mass Directed Autopurification System is used. The system is composed of Waters Sample Manager 2767, Waters System Fluid Organizer, Waters Binary Gradient Module 2545, Waters 515 HPLC Pump, Waters Photodiode Array Detector 2998 and Waters Micromass ZQ MS detector. Software used: FractionLynx and MassLynx v4.1. General HPLC method parameters: gradient mobile phase of 0.1% formic acid in H$_2$O and MeCN or 10 mM NH$_4$HCO$_3$ pH=10 and MeCN. Column XBridge 30×150 mm, 5 μm. PDA detector settings: wavelength: 210-400 nm, resolution: 1.2 nm, sampling rate: 1.0 points/sec, filter response: 1.

Microwave heating is performed with a Biotage Initiator.

Pharmaceutically acceptable acid addition salts, which also represent an object of the present invention, may be obtained by reaction of a compound of Formula (I) with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzenesulfonic acid, methane sulfonic acid, laurylsulfonic acid, stearic acid, palmitic acid, succinic acid, ethylsuccinic acid, lactobionic acid, oxalic acid, salicylic acid and similar acid, in a solvent inert to the reaction. Addition salts are isolated by evaporating the solvent or, alternatively, by filtration after a spontaneous precipitation or a precipitation by the addition of a non-polar co-solvent.

The present invention will now be described by way of example only with reference to the accompanying FIGURE in which:

FIG. 1 is a graph of the percent inhibition of C3H10T1/2 cell differentiation of vismodegib compared to compound of the invention (compound number 174), in wild type versus SMO L416F mutant cell line.

The following abbreviations listed in Table 1 are used in the Examples and other parts of the description.

TABLE 1

List of abbreviations used in experimental section:

| Abbreviation | Definition |
| --- | --- |
| μL | Microliter |
| aq. | Aqueous |
| BINAP | 2,2'-Bis(diphenylphosphino)-1,1'-binaphthyl |
| BnMe$_3$NCl | Benzyltrimethylammonium chloride |
| Boc | tert-Butyloxycarbonyl |
| BOP | (Benzotriazol-1-yloxy)tris(dimethylamino)phosphonium hexafluorophosphate |
| BPin | Boronic acid pinacol ester |
| br. s. | broad singlet |
| nBu$_4$NCl | Tetrabutylammonium chloride |
| CDI | 1,1'-Carbonyldiimidazole |
| Cpd | Compound |
| Cpd# | Compound number |
| d | doublet |
| DCM | Dichloromethane |
| DIPEA or | N,N-diisopropylethylamine |

TABLE 1-continued

List of abbreviations used in experimental section:

| Abbreviation | Definition |
|---|---|
| DiPEA | |
| 4-DMAP | 4-(Dimethylamino)pyridine |
| DMF | N,N-Dimethylformamide |
| DMSO | Dimethylsulfoxide |
| DSC | N,N'-Disuccinimidyl carbonate |
| EDCxHCl | N-(3-Dimethylaminopropyl)-N'-ethylcarbodiimide hydrochloride |
| equiv. | Equivalents |
| EtOAc | Ethyl acetate |
| EtOH | Ethanol |
| g | gram |
| h | hour(s) |
| Hal | Halogen |
| HATU | 1-[Bis(dimethylamino)methylene]-1H-1,2,3-triazolo[4,5-b]pyridinium 3-oxid hexafluorophosphate |
| HOBt | Hydroxybenzotriazole |
| HPLC | High-performance liquid chromatography |
| Int | Intermediate |
| iPrOH | Isopropyl alcohol |
| KOtBu | Potassium tert-butoxide |
| LiHMDS | Lithium bis(trimethylsilyl)amide |
| LCMS | Liquid Chromatography-Mass Spectrometry |
| m | multiplet |
| MeCN | Acetonitrile |
| MeOH | Methanol |
| mg | milligram |
| min | minute |
| mL | millilitre |
| mmol | millimoles |
| MTBE | Methyl tert-butyl ether |
| Mtd | Method |
| MW | Molecular weight |
| NBS | N-bromosuccinimide |
| NCS | N-chlorosuccinimide |
| NMR | Nuclear Magnetic Resonance |
| Pd/C | Palladium on Carbon 10% |
| Pd(PPh$_3$)$_4$ | Tetrakis(triphenylphosphine)palladium(0) |
| Pd(dppf)Cl$_2$ | [1,1'-Bis(diphenylphosphino)ferrocene]-dichloropalladium(II) |
| Pd-PEPPSI-IPr | [1,3-Bis(2,6-Diisopropylphenyl)imidazol-2-ylidene](3-chloropyridyl)palladium(II) dichloride |
| RT | Room temperature |
| RuPhos | 2-Dicyclohexylphosphino-2',6'-diisopropoxybiphenyl |
| RuPhos Pd G1, MTBE adduct; | Chloro-(2-Dicyclohexylphosphino-2',6'-diisopropoxy-1,1'-biphenyl)[2-(2-aminoethyl)phenyl]palladium(II)-methyl-t-butyl ether adduct |
| RuPhos pre-catalyst | |
| tBu | tert-Butyl |
| s | singlet |
| SCX | Strong Cation Exchange |
| t | triplet |
| TEA | Triethylamine |
| TFA | Trifluoroacetic acid |
| THF | Tetrahydrofuran |
| TLC | Thin-layer chromatography |
| TsCl | 4-Toluenesulfonyl chloride |
| UPLC | Ultra-performance liquid chromatography |

The compounds and processes of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where reactions are described as having been carried out in a similar manner to earlier, more completely described reactions, the general reaction conditions used were essentially the same. Work up conditions used were of the types standard in the art, but may have been adapted from one reaction to another. In the procedures that follow, reference to the product of a Description or Example by number is typically provided. This is provided merely for assistance to the skilled chemist to identify the starting material used. The starting material may not necessarily have been prepared from the batch referred to. A compound of the invention as well as intermediate of the invention can be produced according to the following procedures.

SYNTHETIC PREPARATION OF THE COMPOUND OF THE INVENTION

Intermediates

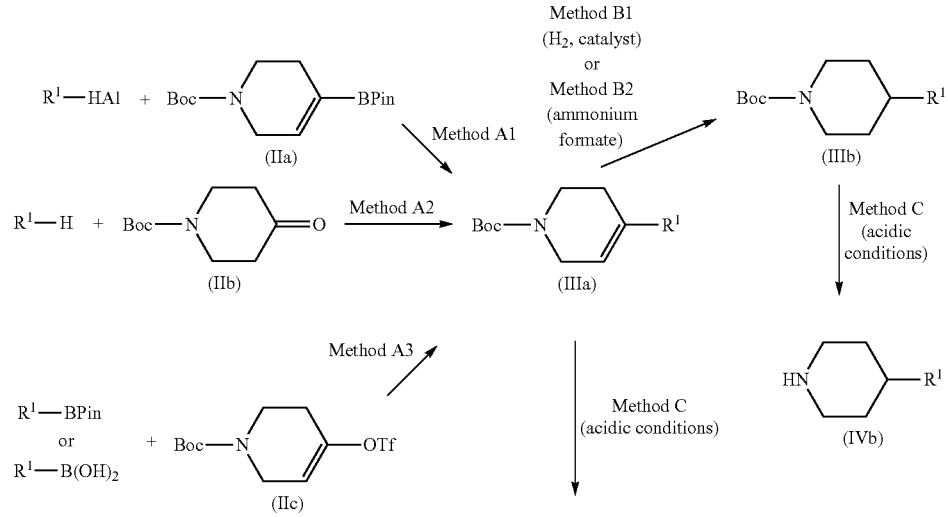

Scheme 1A

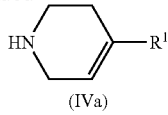

(IVa)

Scheme 1B

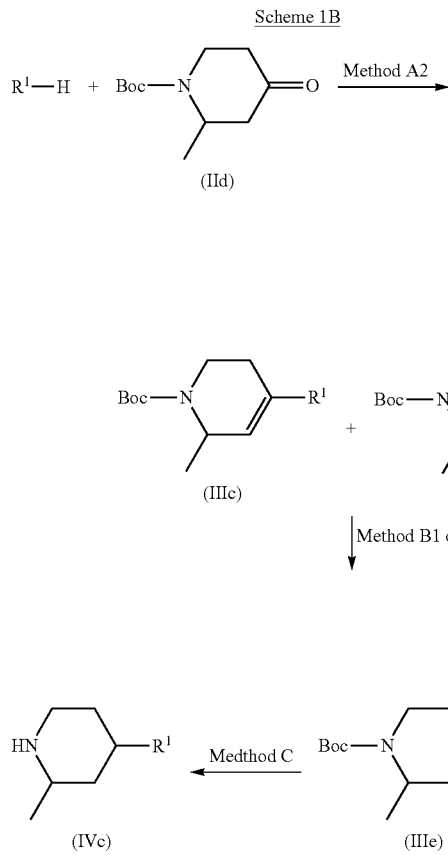

Method A1: General Procedure for Preparation of Piperidine Intermediates of Formula (IIIa) by Suzuki Coupling The reaction is typically performed by combining the appropriate aryl or heteroaryl halide of formula $R^1$-Hal (1 equiv.) and N-Boc-1,2,5,6-tetrahydropyridine-4-boronic acid pinacol ester of formula (IIa) (1-1.2 equiv.) in the presence of a palladium catalyst (0.05-0.2 equiv.) such as $Pd(PPh_3)_4$, $Pd(dppf)Cl_2 \times CH_2Cl_2$ or any other suitable catalyst and a base (1-5 equiv.) such as sodium carbonate or potassium carbonate, in suitable solvent or mixture of solvents (typically mixture of dioxane and water) under inert atmosphere. The resulting mixture is stirred at temperature of typically 120° C. for 2-18 h by using conventional heating or for 15-40 min at 120° C. by using microwave irradiation. The expected Intermediate of formula (IIIa) may be isolated and, if desired, further purified by methods known to one skilled in the art.

Example A1.1

Illustrative synthesis of Methyl 3-(1-tert-butoxycarbonyl-3,6-dihydro-2H-pyridin-4-yl)-1-(p-tolylsulfonyl)pyrrolo[2,3-b]pyridine-5-carboxylate

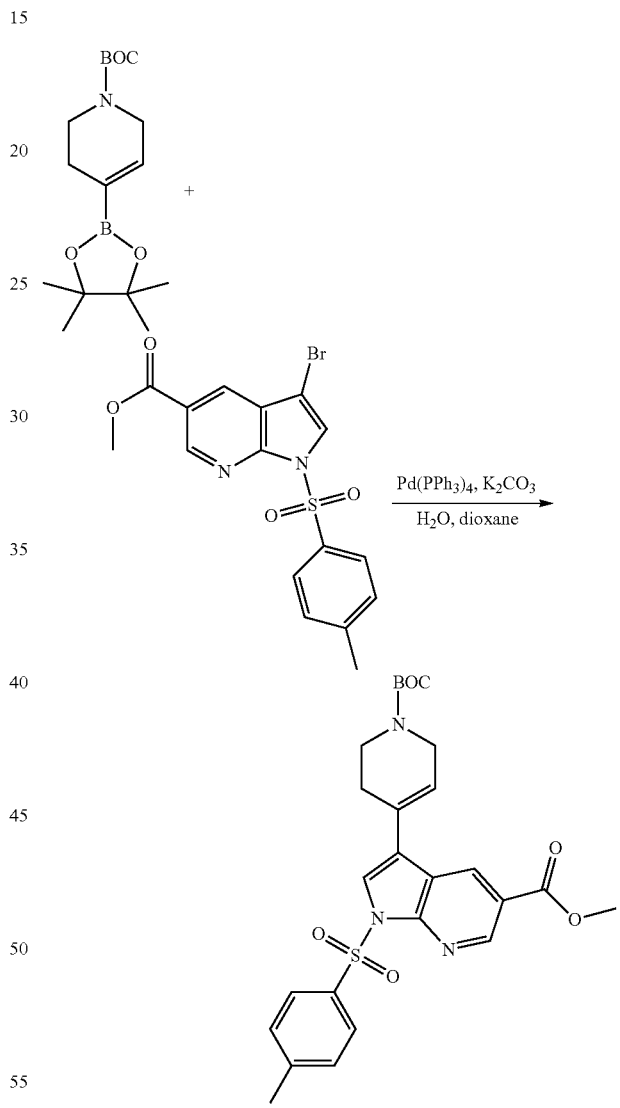

To the solution of tert-butyl 4-(4,4,5,5-tetramethyl-1,3,2-dioxaborolan-2-yl)-3,6-dihydro-2H-pyridine-1-carboxylate (298.3 mg, 1.2 equiv.), methyl 3-bromo-1-(p-tolylsulfonyl)pyrrolo[2,3-b]pyridine-5-carboxylate (329.0 mg, 1 equiv.), and potassium carbonate (111.1 mg, 1 equiv.) in degassed dioxane/water 2:1 (10.0 mL), $Pd(PPh_3)_4$ (92.9 mg, 0.1 equiv.) was added and the solution was further degassed by bubbling argon for 5 minutes. Microwave flask was sealed and heated at 120° C. in a sand bath for two hours. Solution was cooled to RT, transferred to a separatory funnel containing distilled water, and extracted with EtOAc (3×100 mL) The combined organic extracts were dried over Na₂SO₄, filtered, and solvent was removed in vacuo to yield the crude product, which was purified by flash chromatography on silica gel (eluting with: cyclohexane/EtOAc gradient; 0-25% of EtOAc) to afford the expected product (322.4 mg). LCMS: MW (calcd): 511.59; MS (ES⁺, m/z): 512.2 [M+H]⁺.

Example A1.2

Illustrative synthesis of tert-Butyl 4-furo[3,2-b]pyridin-3-yl-3,6-dihydro-2H-pyridine-1-carboxylate

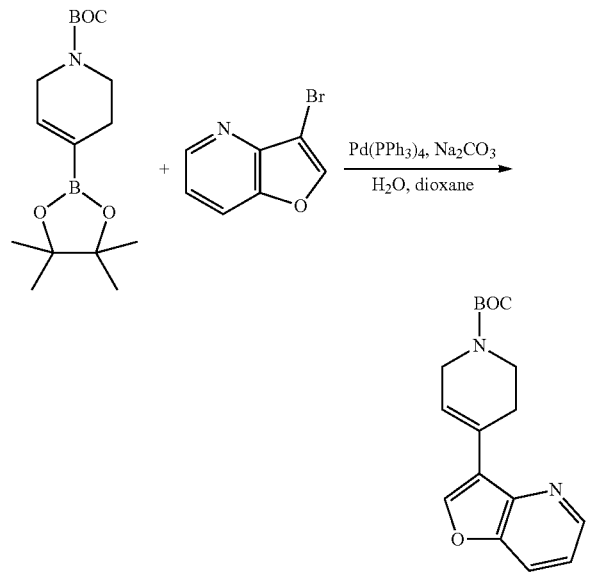

A mixture of tert-butyl 4-(4,4,5,5-tetramethyl-1,3,2-dioxaborolan-2-yl)-3,6-dihydro-2H-pyridine-1-carboxylate (371 mg, 1 equiv.), 3-bromofuro[3,2-b]pyridine (238 mg, 1 equiv.) and tetrakis(triphenylphosphine)palladium(O) (277 mg, 0.2 equiv.) in 1,4-dioxane (12 mL) and sodium carbonate, 2M aq. solution (1.8 mL, 3 equiv.) was purged with argon for 5 min. The resulting mixture was sealed in microwave vial and heated under microwave irradiation for 30 min at 120° C. The reaction mixture was poured into water and extracted with EtOAc (2×). The organic layers were combined, washed with water and brine, dried and evaporated. The obtained residue was purified by flash chromatography on silica gel (eluting with: cyclohexane/ EtOAc gradient; 0-30% of EtOAc) to afford the expected product (270 mg). LCMS: MW (calcd): 300.35; MS (ES⁺, m/z): 301.5 [M+H]⁺; 245.5 [M-tBu+H]⁺; 201.5 [M-Boc+ H]⁺.

Method A2: General Procedure for Preparation of Piperidine Intermediates of Formulae (IIIa), (IIIc) and (IIId) by Condensation The reaction is typically performed by adding the appropriate heteroaryl of formula R¹—H (0.5-1.2 equiv.) and KOH or KOtBu (2-4 equiv.) to a solution of the appropriate Boc-4-piperidone derivative of formula (IIb) or (IId) (1 equiv.) in ethanol or methanol. The resulting mixture is heated at room temperature to reflux for 4-24 h. The expected intermediate of formulae (IIIa), (IIIc) and (IIId) may be isolated and, if desired, further purified by methods known to one skilled in the art.

Example A2.1

Illustrative Synthesis of tert-Butyl 2-methyl-4-(1H-pyrrolo[2,3-b]pyridin-3-yl)-3,6-dihydro-2H-pyridine-1-carboxylate and tert-Butyl 6-methyl-4-(1H-pyrrolo[2,3-b]pyridin-3-yl)-3,6-dihydro-2H-pyridine-1-carboxylate (Two Regioisomers)

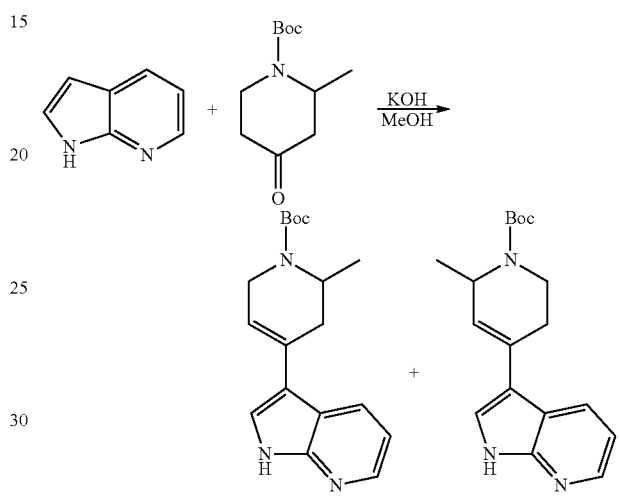

To the solution of tert-butyl 2-methyl-4-oxo-piperidine-1-carboxylate (500 mg, 1 equiv.) in MeOH (5 mL), 1H-pyrrolo[2,3-b]pyridine (332 mg, 1.2 equiv.) and KOH (394 mg, 3 equiv.) were added and the resulting mixture stirred at reflux temperature for 9 h and then overnight at room temperature. The reaction was quenched with saturated aq. ammonium chloride (25 mL) and extracted with ethyl acetate twice. The combined extracts were washed with brine, dried over Na₂SO₄ and solvent evaporated to afford the expected product as a mixture of two regioisomers (730 mg), which was used without further purification in the next reaction step. LCMS: MW (calcd): 313.39; MS (ES⁺, m/z): 314.3 [M+H]⁺.

Method A3: General Procedure for Preparation of Piperidine Intermediate of Formula (IIIa) by Suzuki Coupling The reaction is typically performed by combining appropriate pinacol boronate of formula R¹-BPin (1 equiv.) and 1-(tert-butoxycarbonyl)-1,2,3,6-tetrahydropyridin-4-yl trifluoromethanesulfonate of formula (IIc) (1 equiv.) in the presence of a palladium catalyst (0.08 equiv.) such as Pd(PPh₃)₄ and a base (1 equiv.) such as potassium carbonate in suitable solvent or mixture of solvents (suitably mixture of dioxane and water) under inert atmosphere. The resulting mixture is stirred at the temperature of 120° C. for 18 h. The expected intermediate of the formula (IIIa) may be isolated and, if desired, further purified by methods known to one skilled in the art.

Alternatively, reaction is performed by combining appropriate arylboronic acid of formula R¹—B(OH)₂ (1.2 equiv.) and 1-(tert-butoxycarbonyl)-1,2,3,6-tetrahydropyridin-4-yl trifluoromethanesulfonate of formula (IIc) (1 equiv.) in the presence of a palladium catalyst (0.01 equiv.) such as Pd-PEPPSI-IPr and a base (1.3 equiv.) such as potassium tert-butoxide in a suitable solvent (such as iPrOH) under inert atmosphere. The resulting mixture is stirred at RT for 18-48 h. The expected intermediate of the formula (IIIa) may be isolated and, if desired, further purified by methods known to one skilled in the art.

Example A3.1

Illustrative Synthesis of tert-Butyl 4-[7-(p-tolylsulfonyl)pyrrolo[2,3-d]pyrimidin-5-yl]-3,6-dihydro-2H-pyridine-1-carboxylate

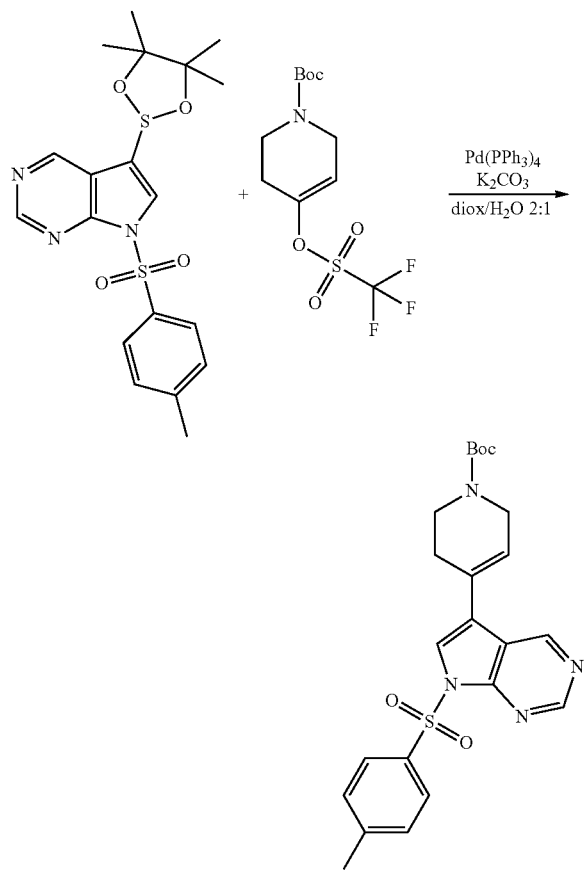

To the solution of 7-(p-tolylsulfonyl)-5-(4,4,5,5-tetramethyl-1,3,2-dioxaborolan-2-yl)pyrrolo[2,3-d]pyrimidine (127 mg, 1 equiv.), tert-butyl 4-(trifluoromethylsulfonyloxy)-3,6-dihydro-2H-pyridine-1-carboxylate (105 mg, 1 equiv.), and potassium carbonate (60 mg, 1.4 equiv.) in degassed dioxane/H$_2$O 2:1 (4.0 mL), Pd(PPh$_3$)$_4$ (31 mg, 0.08 equiv.) was added and the solution degassed by bubbling argon for 5 minutes. The resulting mixture was sealed in microwave flask and heated at 120° C. for 18 h. The reaction mixture was cooled to RT, then transferred to a separatory funnel containing distilled water, and extracted with EtOAc (4×80 mL). The combined organic extracts were dried over Na$_2$SO$_4$, filtered, and solvent was removed in vacuo giving yellow oil which was purified by preparative TLC eluting with 70% EtOAc/cyclohexane to afford the expected product (83 mg). LCMS: MW (calcd): 454.54; MS (ES$^+$, m/z): 455.6 [M+H]$^+$.

Example A3.2

Illustrative Synthesis of tert-Butyl 4-(2,4-dimethylphenyl)-3,6-dihydro-2H-pyridine-1-carboxylate

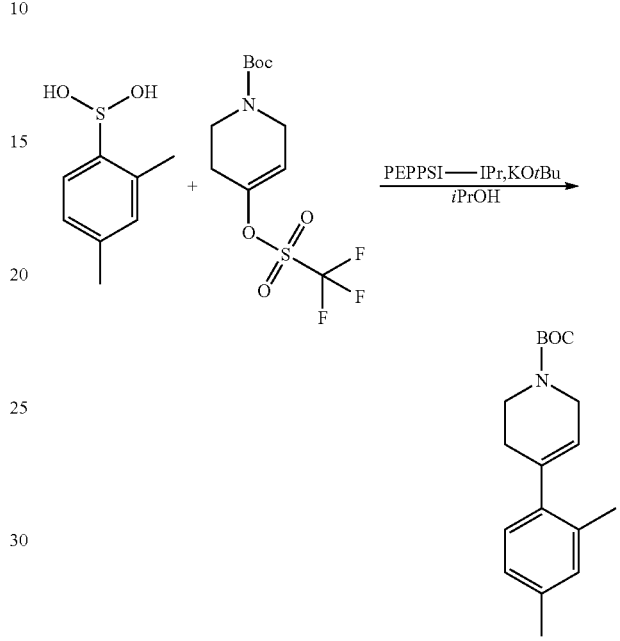

A 10-mL flask was charged with potassium tert-butoxide (219 mg, 1.3 equiv.) and PEPPSI-IPr catalyst (10 mg, 0.01 equiv.). The flask was sealed and content was purged with argon. Then, degassed isopropanol (5 mL) was added, and the content was stirred at room temperature for 10 min. (2,4-Dimethylphenyl)boronic acid (216.3 mg, 1.2 equiv.) was added as a solid, followed by tert-butyl 4-(trifluoromethylsulfonyloxy)-3,6-dihydro-2H-pyridine-1-carboxylate (500 mg, 1 equiv.). The reaction mixture was stirred for 48 h at RT, then diluted with EtOAc, transferred to a separatory funnel containing distilled water, and extracted with EtOAc (2×200 mL). The combined organic extracts were dried over anhydrous Na$_2$SO$_4$, filtered, solvent was removed in vacuo and the obtained residue was purified by flash chromatography on silica gel (eluting with: cyclohexane/EtOAc gradient; 0-5% of EtOAc) to afford the expected product (250 mg). LCMS: MW (calcd): 287.40; MS (ES$^+$, m/z): 232.2 [M-tBu+H]$^+$.

Method B1: General Procedure for Preparation of Piperidine Intermediate of Formula (IIIb) and (IIIe) by Hydrogenation of Double Bond Typically, to a MeOH or EtOH solution of the appropriate intermediate of formulae (IIIa), (IIIc) or (IIId) wherein double bond functionality is present catalyst (10 wt % Pd/C or PtO$_2$) is added and the resulting mixture hydrogenated at atmospheric pressure (balloon filled with hydrogen) or in Parr apparatus at 2-5 bar for 1-48 h. The expected intermediate of formulae (IIIb) or (IIIe) may be isolated and, if desired, further purified by methods known to one skilled in the art.

Example B1.1

Illustrative Synthesis of tert-Butyl 4-furo[3,2-b]pyridin-3-ylpiperidine-1-carboxylate

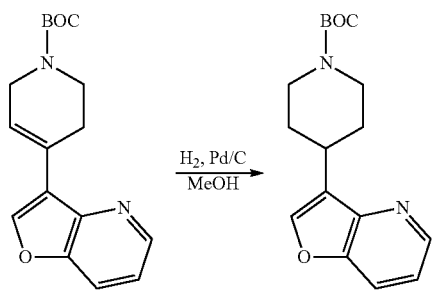 [SMILES: "MeOH" ; CC(C)(C)OC(=O)N1CC=C(c2coc3cccnc23)CC1 ; CC(C)(C)OC(=O)N1CCC(c2coc3cccnc23)CC1]

To a solution of tert-butyl 4-furo[3,2-b]pyridin-3-yl-3,6-dihydro-2H-pyridine-1-carboxylate (270 mg, 1 equiv.) in dry MeOH (15 mL), 10% wt % Pd/C (96 mg, 0.1 equiv.) was added. The resulting mixture was stirred under $H_2$ and atmospheric pressure (balloon filled with hydrogen) at RT for 5 h. The mixture was filtered through a pad of Celite, washed with MeOH and filtrate concentrated in vacuo to afford the expected product (245 mg), which was used in the next reaction step without further purification. LCMS: MW (calcd): 302.37; MS (ES$^+$, m/z): 303.54 [M+H]$^+$.

Method B2: General Procedure for Preparation of Piperidine Intermediate of Formula (IIIb) and (IIIe) by Transfer Hydrogenation with Ammonium Formate The reaction is typically performed by adding ammonium formate (5-10 equiv.) and 10 wt % Pd/C (0.08-0.5 equiv.) to a solution of the appropriate intermediate of formulae (IIIa), (IIIc) or (IIId) (1 equiv.) in EtOH or MeOH or any other suitable solvent. The resulting mixture is heated typically at 50-90° C. for 30 min to 30 h to afford the expected intermediate of formula (Mb) and (Me), which may be isolated and, if desired, further purified by methods known to one skilled in the art.

Example B2.1

Illustrative Synthesis of tert-Butyl 2-methyl-4-(1H-pyrrolo[2,3-b]pyridin-3-yl)piperidine-1-carboxylate

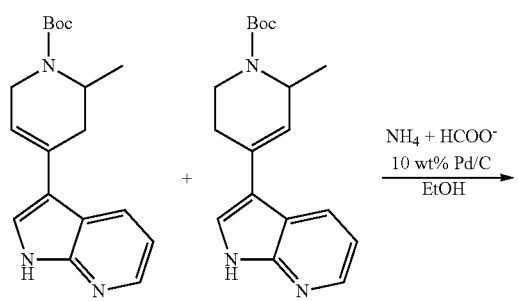

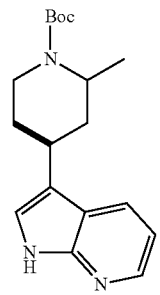

To the solution of two regioisomers, tert-butyl 2-methyl-4-(1H-pyrrolo[2,3-b]pyridin-3-yl)-3,6-dihydro-2H-pyridine-1-carboxylate and tert-butyl 6-methyl-4-(1H-pyrrolo[2,3-b]pyridin-3-yl)-3,6-dihydro-2H-pyridine-1-carboxylate (730 mg, 1 equiv.) in EtOH (15 mL) ammonium formate (734 mg, 5 equiv.) and 10% Pd/C (195 mg) were added. The mixture was sealed in the reaction tube and stirred at 90° C. for 90 min. The mixture was then filtered over the pad of Celite, the pad was washed thoroughly with MeOH and the filtrate was evaporated to dryness to afford the expected product (780 mg), which was used in the next step without further purification. LCMS: MW (calcd): 315.41; MS (ES$^+$, m/z): 316.3 [M+H]$^+$.

Method C: General Procedure for N-Boc Deprotection

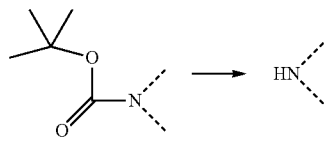

Method Ci: Preparation of Intermediate of Formula (IV) by Boc Deprotection

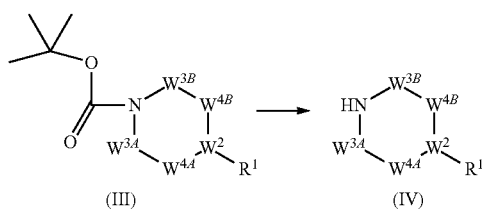

Typically, to a solution of the appropriate intermediate of formula (III), in suitable solvent or mixture of solvents (suitably in DCM), TFA (2-200 equiv.) is added and the reaction mixture stirred at room temperature for 1 to 24 h to give the corresponding intermediate (IV). The expected product may be isolated and, if desired further purified by methods known to one skilled in the art.

Alternatively, to a solution of the appropriate intermediate of formula (III), in suitable solvent (typically DCM), dioxane, HCl (20-200 equiv.) solution is added and the reaction mixture stirred for 1 to 24 hours at room temperature to give the corresponding intermediate of formula (IV), which is isolated typically by solvent removal and, if desired, may be further purified by methods known to one skilled in the art.

Example C1.1

Illustrative Synthesis of 3-(4-Piperidyl)furo[3,2-b]pyridine

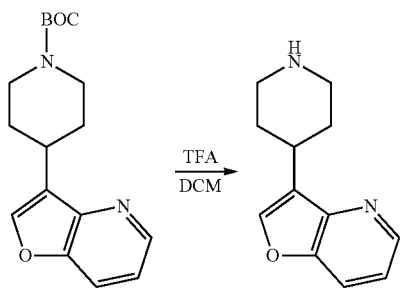 [SMILES: CC(C)(C)OC(=O)N1CCC(c2coc3cccnc23)CC1 ; c1cnc2c(C3CCNCC3)coc2c1]

To a solution of tert-butyl 4-furo[3,2-b]pyridin-3-ylpiperidine-1-carboxylate, (240 mg, 1 equiv.) in DCM (4 mL) TFA (608 μL, 10 equiv.) was added. The resulting mixture was stirred at RT for 3 h. The mixture was neutralized with saturated solution of sodium bicarbonate, then basified to pH 11-12 with 6M NaOH and extracted with DCM (3×). The organic layers were collected, dried over phase separator filter tube and evaporated to afford the expected product (140 mg), which was used in the next step without further purification. LCMS: MW (calcd): 202.25; MS (ES+, m/z): 203.45 [M+H]+.

Example C1.2

Illustrative Synthesis of 3-Piperazin-1-yl-1H-pyrrolo[2,3-b]pyridine

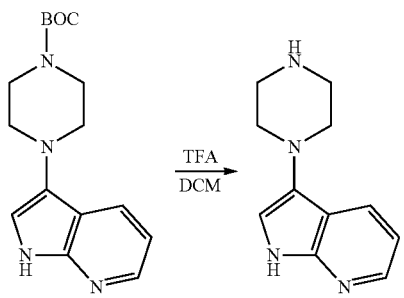 [SMILES: CC(C)(C)OC(=O)N1CCN(c2c[nH]c3ncccc23)CC1 ; c1cnc2[nH]cc(N3CCNCC3)c2c1]

To a solution of tert-butyl 4-(1H-pyrrolo[2,3-b]pyridin-3-yl)piperazine-1-carboxylate (160 mg, 1 equiv.) in DCM (4 mL) TFA (608 μL, 15 equiv.) was added. The resulting mixture was stirred at RT for 4 h. The reaction mixture was applied to a SCX column and eluted with MeOH followed by 2M ammonia in MeOH. Ammonia/MeOH fractions were combined and evaporated to afford the expected product (105 mg). LCMS: MW (calcd): 202.26; MS (ES+, m/z): 203.12 [M+H]+.

Example C1.3

Illustrative Synthesis of Methyl 3-(4-piperidyl)-1-(p-tolylsulfonyl)pyrrolo[2,3-b]pyridine-5-carboxylate Hydrochloride Salt

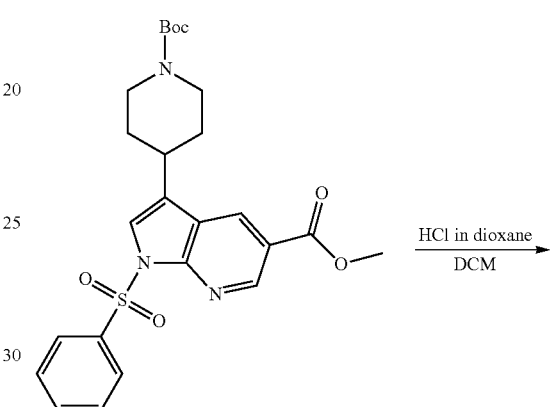

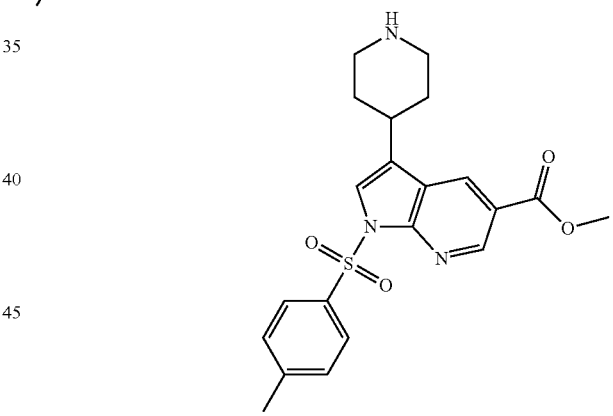

To the solution of methyl 3-(1-tert-butoxycarbonyl-4-piperidyl)-1-(p-tolylsulfonyl)pyrrolo[2,3-b]pyridine-5-carboxylate (54.0 mg, 1 equiv.) in DCM (4.0 mL), HCl 4.0 M in dioxane (2.0 mL) was added and the solution stirred at RT for 30 min. Then, solvent was removed in vacuo to afford the expected product as white powder (47.0 mg), which was used in subsequent steps without release of the free base. LCMS: MW (calcd): 413.49; MS (ES+, m/z): 414.2 [M+H]+.

Scheme 1C

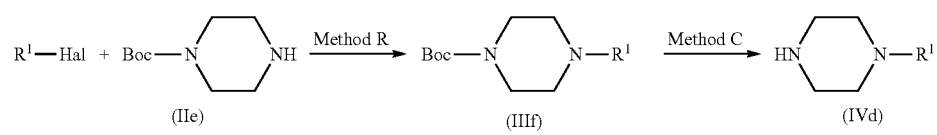

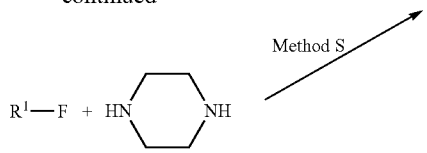

Method R: General Procedure for Preparation of Piperazine Intermediates of Formula (IIIf) by Buchwald-Hartwig Reaction The reaction is typically performed by adding under argon atmosphere LiHMDS, 1.3 M THF solution (2.5 equiv.) to a mixture of appropriate heteroaryl halide of formula $R^1$-Hal (1 equiv.), 1-Boc-piperazine of formula (IIe) (1.2-1.3 equiv.), RuPhos (0.02-0.05 equiv.) and Ruphos pre-catalyst, MTBE adduct (0.02-0.05 equiv.) in THF. The resulting mixture is purged with argon for 5 min, then sealed in vial and heated for 3 h at 70-75° C. The expected product of formula (IIIf) may be isolated and, if desired, further purified by methods known to one skilled in the art.

Example R1.1

Illustrative Synthesis of tert-Butyl 4-(1H-pyrrolo[2,3-b]pyridin-3-yl)piperazine-1-carboxylate

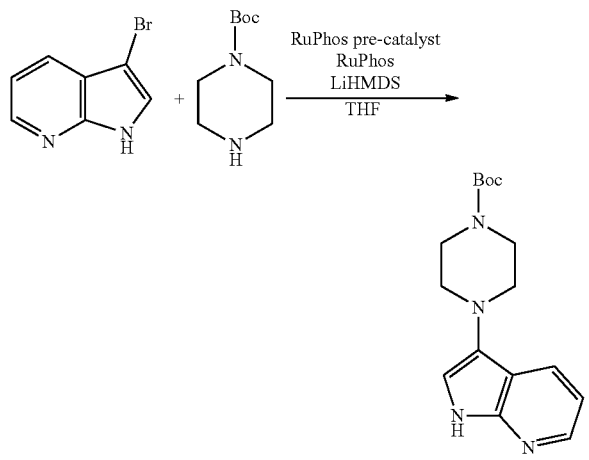

To a mixture of tert-butyl piperazine-1-carboxylate (224 mg, 1.2 equiv.), 3-bromo-1H-pyrrolo[2,3-b]pyridine (197 mg, 1 equiv.), RuPhos (9.3 mg, 0.02 equiv.) and Ruphos Pd G1, MTBE adduct (16.3 mg, 0.02 equiv.) in THF (2 mL), under argon atmosphere LiHMDS, 1.3 M THF solution (1.92 mL, 2.5 equiv.) was added. The resulting mixture was purged with argon for 5 min, then sealed in vial and heated for 3 h at 70° C. The reaction mixture was cooled to RT, quenched by the addition of 1M HCl (1.5 mL), diluted with EtOAc and poured into sodium bicarbonate sat. solution. After extracting with 3 portions of EtOAc, the combined organic layers were dried and solvent evaporated. The obtained residue was purified by flash chromatography on silica gel (eluting with cyclohexane/EtOAc gradient; 0-100% of EtOAc) to afford the expected product (165 mg). LCMS: MW (calcd): 302.37; MS (ES+, m/z): 303.21 [M+H]+.

Method S: $S_NAr$

Typically, to a solution of aryl halide (1 equiv.) in a suitable solvent such as DMSO, the piperazine (5 equiv.) is added and the resulting mixture is stirred at 140° C. for 5 h. The expected product of formula (IVd) may be isolated and, if desired, further purified by methods known to one skilled in the art.

Example S1.1

Illustrative Synthesis of 3-Methyl-4-piperazin-1-yl-benzonitrile 3-methyl-4-piperazin-1-yl-benzonitrile

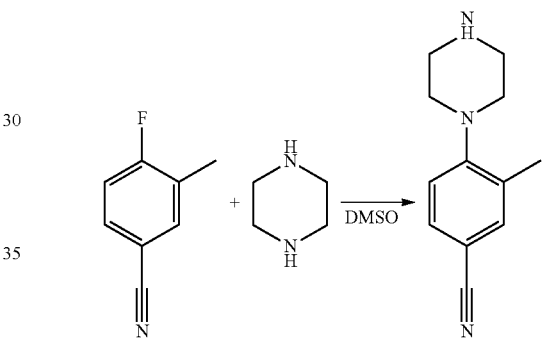

To a stirred solution of 4-fluoro-3-methylbenzonitrile (2.03 g, 1 equiv.) in dry DMSO (8 mL) piperazine (6.46 g, 5 equiv.) was added at RT, the mixture was heated to 140° C. and stirred for 5 h. The reaction mixture was poured into water (100 mL) and the reaction vessel was rinsed with water (50 mL). The resulting suspension was filtered, rinsed with water (3×20 mL) and the resulting solid was left to dry in vacuum oven at 40° C. overnight to afford the expected product (1.80 g). LCMS: MW (calcd): 201.27; MS (ES+, m/z): 202.51 [M+H]+.

Method E: General Procedure for NTs-Protection

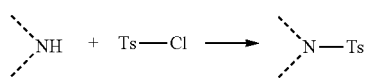

The reaction is typically performed by adding KOtBu (1 equiv.) to a mixture of appropriate NH functionality containing heteroaryl, for example to a heteroaryl halide intermediate of formula $R^1$-Hal (1 equiv.) in THF, followed by TsCl (1 equiv.) and the resulting mixture is stirred at RT for 1-5 h. The expected Ts-protected product, for example Ts protected $R^1$-Hal, may be isolated and, if desired, further purified by methods known to one skilled in the art.

Example E1.1

Illustrative Synthesis of 7-Bromo-5-(p-tolylsulfonyl)pyrrolo[2,3-b]pyrazine

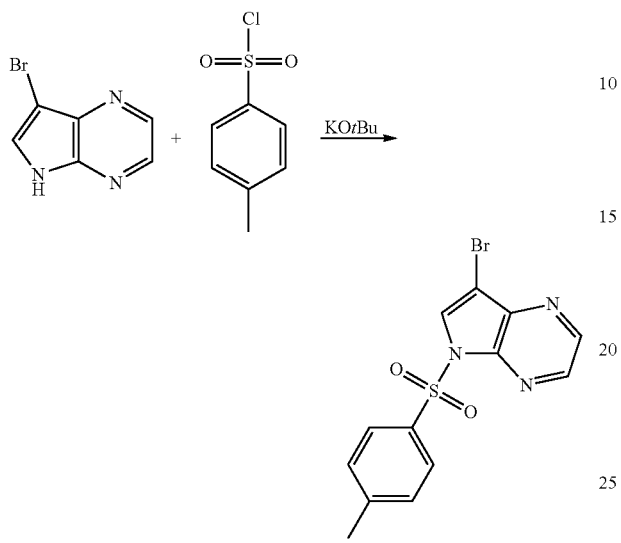

To a suspension of 7-bromo-5H-pyrrolo[2,3-b]pyrazine (396 mg, 1 equiv.) in dry THF (10 mL) under argon atmosphere KOtBu (224 mg, 1 equiv.) was added and the mixture was stirred for 5 min at RT. Then, TsCl (381 mg, 1 equiv.) was added and the resulting mixture was stirred at RT for 1 h. The reaction was quenched with water and extracted with EtOAc (3×). The organic layers were collected, washed with water and brine, dried and evaporated to dryness to afford the expected product as a solid (680 mg), which was used in the next reaction step without further purification. LCMS: MW (calcd): 352.21; MS (ES+, m/z): 351.9, 353.9 [M+H]+.

Method K: Aromatic Bromination of Heteroaryl

Typically, to a solution of the appropriate heteroaryl analogue, for example heteroaryl intermediate of formula $R^1$—H (1 equiv.) in DMF at 0° C., NBS (1 equiv.) is added under inert atmosphere, and the resulting solution is stirred at 0° C. for 20 min. The reaction mixture is allowed to reach room temperature and stirring is continued for a suitable period of time. The expected brominated heteroaryl analogue, for example brominated $R^1$ heteroaryl ring analogue, may be isolated and, if desired, further purified by methods known to one skilled in the art.

Example K1.1

Illustrative Synthesis of 3-Bromo-1H-pyrrolo[2,3-b]pyridine

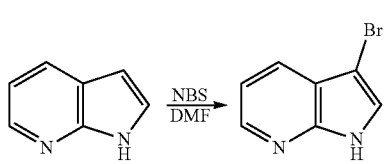

The solution of 1H-pyrrolo[2,3-b]pyridine (1.0 g, 1 equiv.) in DMF (30 mL) at 0° C. was treated portionwise with NBS (1.51 g, 1 equiv.) under argon, and the resulting solution was stirred at 0° C. for 20 min. The reaction mixture was allowed to warm to RT and stirring was continued for 10 min. Then, the reaction mixture was transferred to a separatory funnel containing distilled water, and extracted with EtOAc (2×150 mL). The combined organic extracts were dried over $Na_2SO_4$, filtered, and solvent was removed in vacuo. Crude product was recrystallized from DCM to afford the expected product (1.55 g). LCMS: MW (calcd): 197.03; MS (ES+, m/z): 197.3, 199.3 [M+H]+.

Method T: di-N-methylation of Aniline/Reductive Amination

Typically, to a solution of the appropriate aniline compound, for example aniline intermediate of formula (Mb) (1 equiv.) and the appropriate aldehyde in suitable solvent (such as THF, DCM) stirred at RT for 1 h, NaBH(OAc)$_3$ (2 equiv.) is added. The reaction mixture is stirred at RT overnight. The expected di-N-alkylated product may be isolated and, if desired further purified, by methods known to one skilled in the art.

Example T1.1

Illustrative Synthesis of tert-Butyl 4-[4-(dimethylamino)phenyl]piperidine-1-carboxylate

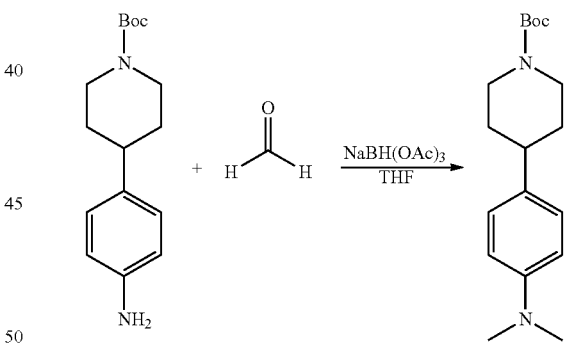

To a stirred solution of tert-butyl 4-(4-aminophenyl)piperidine-1-carboxylate (300 mg, 1 equiv.) in THF (5 mL), formaldehyde, 36.5% in water (1 mL) was added. The resulting mixture was stirred at RT for 1 h, then NaBH(OAc)$_3$ (460 mg, 2 equiv.) was added and mixture was stirred at RT overnight. The reaction mixture was diluted with EtOAc, then washed with saturated solution of sodium bicarbonate and brine. The organic layer was dried and solvent was evaporated. The obtained residue was purified by flash chromatography on silica gel (eluting with: cyclohexane/EtOAc gradient; 0-30% of EtOAc) to afford the expected product (104 mg). LCMS: MW (calcd): 304.43; MS (ES+, m/z): 305.24 [M+H]+.

Compounds

Method D: General Procedure for Preparation of Compound of Formula (I-1), (XI-1), (XII-1), (XIII-1) and (XIV-1) by Sulfonamidation

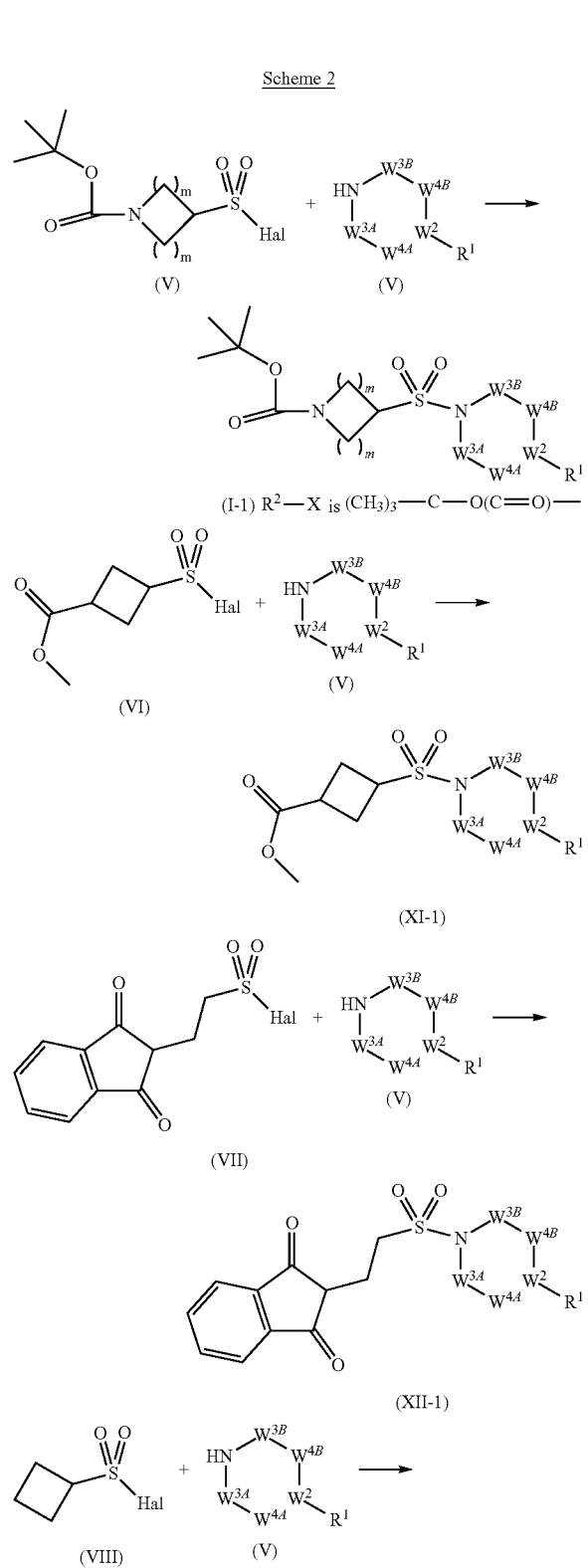

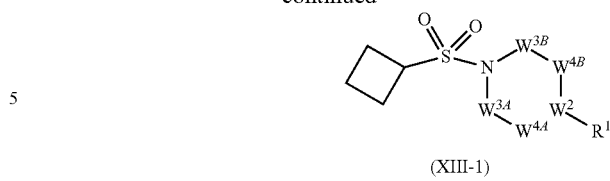

Typically, to a solution of appropriate intermediate of formula (IV) (1 equiv.) in THF (or any other suitable solvent), TEA or other suitable base (2-10 equiv.) and corresponding sulfonyl halide (suitably sulfonyl chloride) (0.9-5 equiv.) of formula (V-IX) are added. The reaction mixture is stirred at room temperature for 15 min to 24 h. The expected compound of formula (I-1), (XI-1), (XII-1), (XIII-1) or (XIV-1) may be isolated and, if desired, further purified by methods known to one skilled in the art. In addition, if desired, cis/trans isomers of compound of formula (XI-1) may be separated.

Sulfonyl halides of formula (VI), (VII), (VIII) and (IX) are commercially available; the compound of formula (X) can be prepared from commercially available starting materials using methods known to the person skilled in the art or by methods described herein.

Example D1.1

Illustrative Synthesis of tert-Butyl 3-[(4-furo[3,2-b]pyridin-3-yl-1-piperidyl)sulfonyl]azetidine-1-carboxylate (Compound 131)

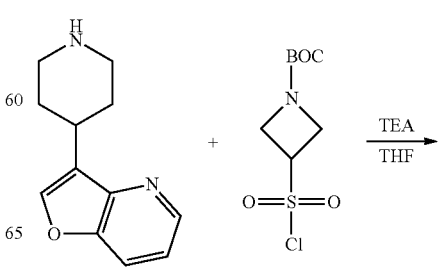

-continued

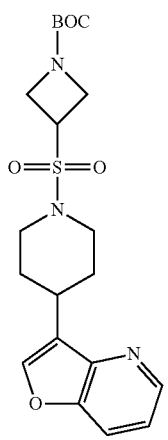

To a solution of 3-(4-piperidyl)furo[3,2-b]pyridine, (25 mg, 1 equiv.) and TEA (70 µL, 4 equiv.) in dry THF (1.5 mL) tert-butyl 3-chlorosulfonylazetidine-1-carboxylate (35 mg, 1.1 equiv.) was added and the resulting mixture was stirred at RT for 1 h. The reaction mixture was evaporated to dryness. The obtained crude was purified by flash chromatography on silica gel (eluting with cyclohexane/EtOAc gradient; 0-70% of EtOAc) to afford the expected product (35 mg). LCMS: MW (calcd): 421.51; MS (ES+, m/z): 422.72 [M+H]+; 366.62 [M-tBu+H]+; 322.61 [M-Boc+H]+.

Example D1.2

Illustrative Synthesis of tert-Butyl 3-[4-(1H-pyrrolo[2,3-b]pyridin-3-yl)piperazin-1-yl]sulfonylazetidine-1-carboxylate (Compound 226)

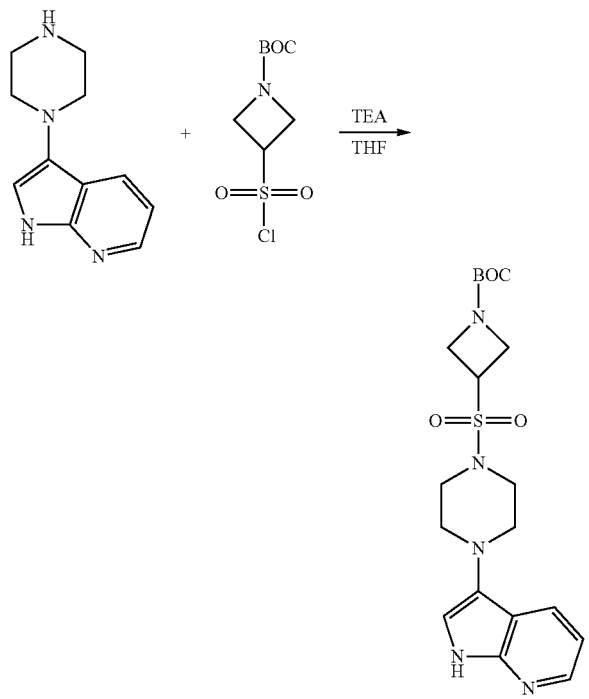

To a solution of 3-piperazin-1-yl-1H-pyrrolo[2,3-b]pyridine (20 mg, 1 equiv.) and TEA (56 µL, 4 equiv.) in dry THF (1 mL), tert-butyl 3-chlorosulfonylazetidine-1-carboxylate (28 mg, 1.1 equiv.) was added and the resulting mixture was stirred at RT for 2 h. The reaction mixture was evaporated to dryness. The obtained residue was purified by preparative LC-MS (ES+ mode, high pH method) to afford the expected product (25 mg). LCMS: MW (calcd): 421.51; MS (ES+, m/z): 422.15 [M+H]+.

Method Cf: Preparation of Compound of Formula (I-2), which is Subset of Formula (I), Wherein $R^2$ is H and X is Absent by Boc Deprotection

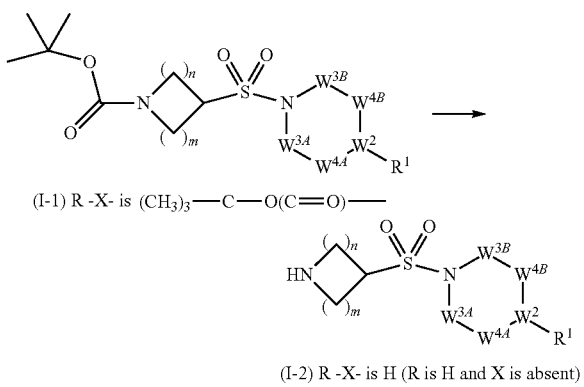

Typically, to a solution of the appropriate compound of formula (I-1) (1 equiv.), wherein $R^2X$— group is $(CH_3)_3CC(=O)O$— (Boc) in suitable solvent or mixture of solvents (suitably in DCM), TFA (2-15 equiv.) is added and the reaction mixture stirred at room temperature for 1 to 24 h to give the expected compound of formula (I-2). The expected product may be isolated and, if desired, further purified by methods known to one skilled in the art. Alternatively, to a solution of the appropriate compound of formula (I-1), wherein $R^2X$— group is $(CH_3)_3CC(=O)O$— (Boc), in suitable solvent (typically DCM), dioxane, HCl (20-200 equiv.) solution is added and the reaction mixture stirred for 1 to 24 hours at room temperature to afford the expected product (I-2), which is isolated typically by solvent removal and, if desired, may be further purified by methods known to one skilled in the art.

Method V: Ester Hydrolysis—Preparation of Compound of Formula (XI-2), which is Subset of Formula (XI), Wherein

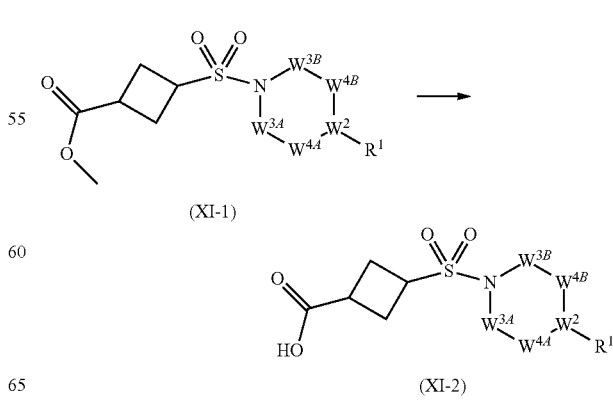

Typically, to a solution of the appropriate compound of formula (XI-1) (1 equiv.), one isomer or mixture of cis/trans isomers, in suitable solvent or mixture of solvents (suitably in THF/MeOH mixture), NaOH aq. solution (4-25 equiv.) is added. The reaction mixture is stirred at room temperature for 10 minutes to 1 h to give the expected compound(s) of formula (XI-2). The expected product(s) may be isolated and, if desired, further purified by methods known to one skilled in the art.

Example V1.1

Illustrative Synthesis of 3-[[4-(1H-pyrrolo[2,3-b]pyridin-3-yl)-1-piperidyl]sulfonyl]cyclobutanecarboxylic acid

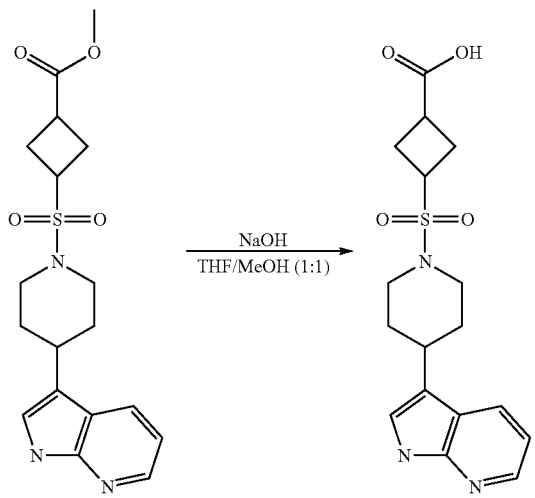 [SMILES: COC(=O)C1CC(S(=O)(=O)N2CCC(c3c[nH]c4ncccc34)CC2)C1 ; "NaOH" ; "THF/MeOH (1:1)" ; O=C(O)C1CC(S(=O)(=O)N2CCC(c3c[nH]c4ncccc34)CC2)C1]

A solution of methyl 3-[[4-(1H-pyrrolo[2,3-b]pyridin-3-yl)-1-piperidyl]sulfonyl]cyclobutanecarboxylate (mixture of cis and trans isomers) (204.3 mg, 1 equiv.) in THF/MeOH (1:1) solvent mixture (4 mL) was treated with 6 M NaOH (0.6 mL) and the resulting mixture was stirred at RT for 30 minutes. The reaction mixture was diluted with water (15 mL) and pH adjusted to 4.9 by addition of 1 M HCl. The formed white precipitate was collected by filtration and dried affording the expected product (mixture of cis and trans isomers) (180.5 mg). LCMS: MW (calcd): 363.43; MS (ES+, m/z): 364.54 [M+H]+.

Method Z: General Procedure for the Deprotection of Phthalimide—Preparation of Compound of Formula (XII-2), which is Subset of Formula (XII), Wherein

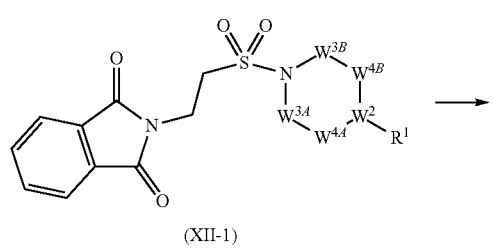

(XII-1)

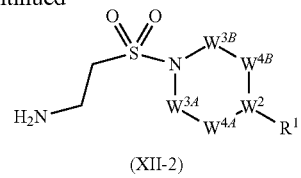

(XII-2)

Typically, to a solution of the appropriate compound of formula (XII-1) (1 equiv.) in suitable solvent such as MeOH was added hydrazine hydrate (3 equiv.). The reaction mixture is stirred at 65° C. for 4 hours to give the expected compound of formula (XII-2). The expected product may be isolated and, if desired, further purified by methods known to one skilled in the art.

Example Z1.1

Illustrative Synthesis of 2-[[4-(1H-pyrrolo[2,3-b]pyridin-3-yl)-1-piperidyl]sulfonyl]ethanamine

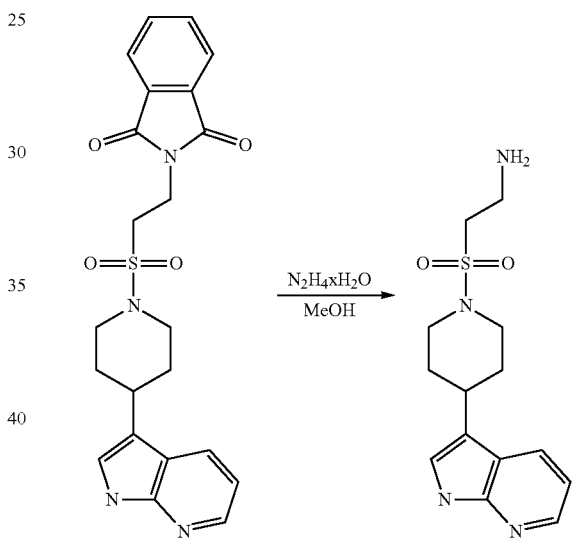

A solution of 2-[2-[[4-(1H-pyrrolo[2,3-b]pyridin-3-yl)-1-piperidyl]sulfonyl]ethyl]isoindoline-1,3-dione (37.0 mg, 1 equiv.) in MeOH (4.0 mL) was added hydrazine hydrate (15.7 μL, 3 equiv.) and the resulting mixture was stirred at 65° C. for 4 h. Solvent was removed in vacuo affording the expected product (25.9 mg). LCMS: MW (calcd): 308.4; MS (ES+, m/z): 309.5 [M+H]+.

Method F: NTs-Deprotection

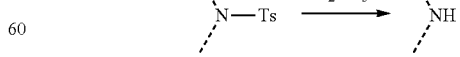

Typically, to a solution of the appropriate NTs-protected intermediate or final compound wherein nitrogen atom is Ts protected, in suitable solvent or mixture of solvents (suitably in THF/MeOH mixture) caesium carbonate (1-12 equiv.) is added and reaction mixture is stirred at room temperature to 55° C. for 1-24 h. The expected product may be isolated and, if desired, further purified by methods known to one skilled in the art.

Example F1.1

Illustrative Synthesis of tert-Butyl 3-[[4-(5H-pyrrolo[2,3-b]pyrazin-7-yl)-1-piperidyl]sulfonyl] azetidine-1-carboxylate (Compound 128)

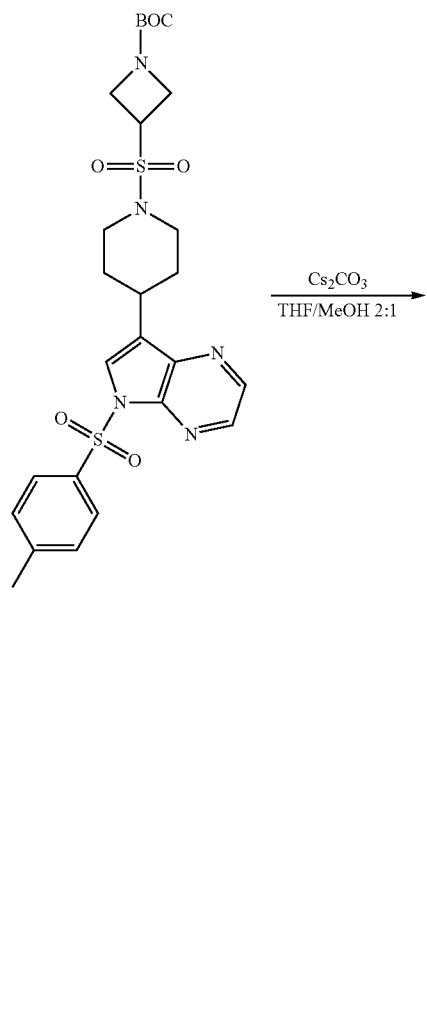

To a solution of tert-butyl 3-[[4-[5-(p-tolylsulfonyl)pyrrolo[2,3-b]pyrazin-7-yl]-1-piperidyl]sulfonyl]azetidine-1-carboxylate (57 mg, 1 equiv.) in THF/MeOH (2/1) solvent mixture (2.1 mL), caesium carbonate (98 mg, 3 equiv.) was added and the resulting mixture was stirred at RT for 1 h. The reaction mixture was evaporated to dryness. The obtained crude product was purified by flash chromatography on silica gel (eluting with DCM/MeOH gradient; 0-10% of MeOH) to afford the expected product (18 mg). LCMS: MW (calcd): 421.51; MS (ES+, m/z): 422.70 [M+H]+; 366.61 [M-tBu+H]+; 322.59 [M-Boc+H]+.

Method O: N-alkylation

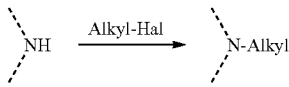

Typically, to a solution of amino derivative (1 equiv.) in THF (or any other suitable solvent) NaH, 60% dispersion in mineral oil (1.2 equiv.) is added. The resulting mixture is stirred for 30 min, then corresponding alkyl halogenide (1.1 equiv.) is added. The reaction mixture is stirred at room temperature for 2 h. The expected product may be isolated and, if desired, further purified by methods known to one skilled in the art.

Example O1.1

Illustrative Synthesis of tert-Butyl 3-[[4-(1-methylpyrrolo[2,3-b]pyridin-3-yl)-1-piperidyl]sulfonyl] azetidine-1-carboxylate (Compound 94)

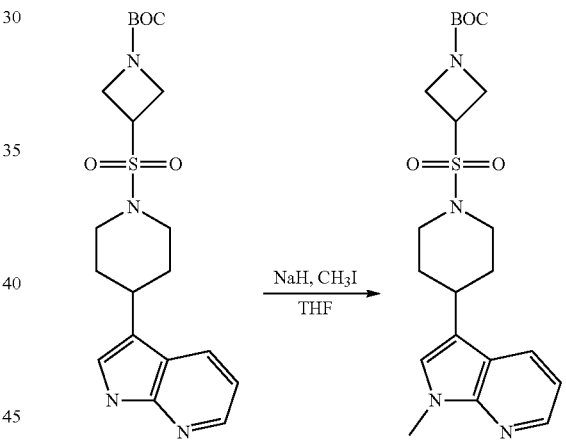

To a solution of tert-butyl 3-[[4-(1H-pyrrolo[2,3-b]pyridin-3-yl)-1-piperidyl]sulfonyl]azetidine-1-carboxylate (50 mg, 1 equiv.) in dry THF (1 mL) NaH, 60% dispersion in mineral oil (5.94 mg, 1.2 equiv.) was added. The resulting mixture was stirred for 30 min before addition of CH3I (8.15 mL, 1.1 equiv.). The reaction mixture was stirred at room temperature for 2 h. Then, NaHCO3 sat. solution (10 mL) was added, mixture was stirred for 10 minutes and extracted with EtOAc (3×20 mL). The combined organic extracts were washed with water (25 mL) and brine (25 mL), dried over Na2SO4 and evaporated to afford the crude product (49.3 mg) as yellow solid which was further purified by preparative LC-MS to afford the expected product (23 mg). LCMS: MW (calcd): 434.55; MS (ES+, m/z): 435.16 [M+H]+.

Method P: Sulfonamidation

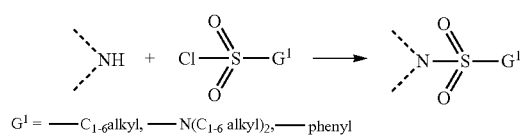

Typically, to a solution of NH functionality containing analogue (1 equiv.), for example to a compound of formula (I) analogue having $R^1$ heteroaryl group in THF (or any other suitable solvent) NaH, 60% dispersion in mineral oil (2 equiv.) is added. The resulting mixture is stirred for 30 min, then the appropriate sulfonyl chloride Cl—$SO_2$-$G^1$ (1.5 equiv.) is added and reaction mixture is stirred at room temperature for 2 h. The expected product may be isolated and, if desired, further purified by methods known to one skilled in the art.

Example P1.1

Illustrative Synthesis of tert-Butyl 3-[[4-(1-methyl-sulfonylpyrrolo[2,3-b]pyridin-3-yl)-1-piperidyl]sulfonyl]azetidine-1-carboxylate (Compound 93)

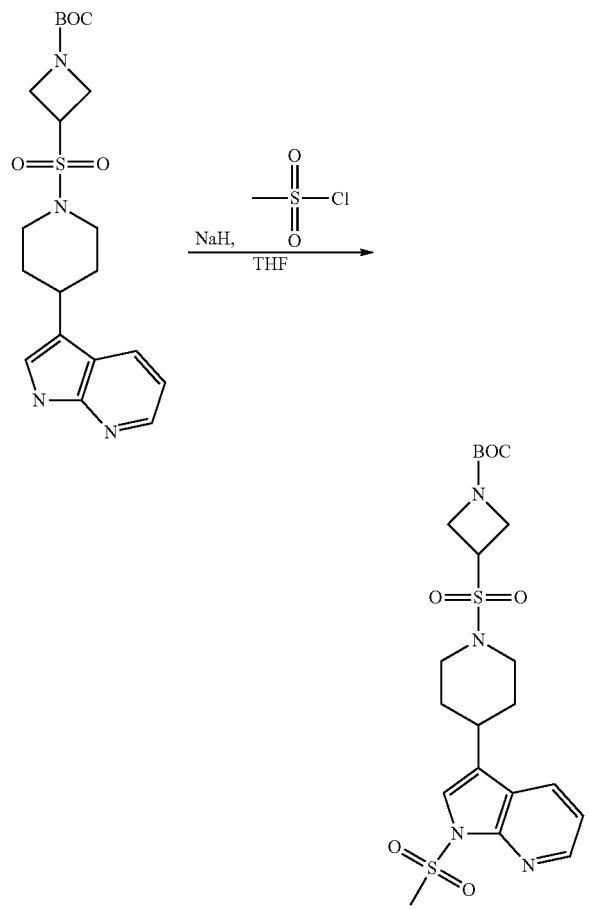

To a solution of tert-butyl 3-[[4-(1H-pyrrolo[2,3-b]pyridin-3-yl)-1-piperidyl]sulfonyl]azetidine-1-carboxylate (50 mg, 1 equiv.) in dry THF (1 mL), NaH, 60% dispersion in mineral oil (11.36 mg, 2.4 equiv.) was added. The resulting mixture was stirred for 30 min before addition of methanesulfonyl chloride (13.82 μL, 1.5 equiv.). The reaction mixture was stirred at room temperature for 2 h. Then, $NaHCO_3$ sat. solution (20 mL) was added, stirred for 10 minutes and extracted with EtOAc (3×20 mL). The combined organic extracts were washed with water (25 mL) and brine (25 mL), dried over $Na_2SO_4$ and evaporated to afford crude compound (53.6 mg) as yellow solid which was further purified by preparative LC-MS to afford the expected product (32 mg). LCMS: MW (calcd): 498.62; MS ($ES^+$, m/z): 499.20 $[M+H]^+$.

Method X: Ester Aminolysis

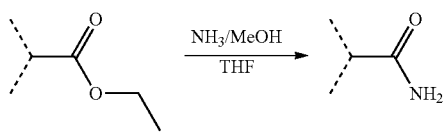

Typically, to a solution of ester derivative (1 equiv.) in THF (or any other suitable solvent) ammonia solution in methanol is added. The resulting mixture is stirred at 60° C. overnight. The expected product may be isolated and, if desired, further purified by methods known to one skilled in the art.

Example X1.1

Illustrative Synthesis of 2-[3-[[4-(4-pyridyl)-1-piperidyl]sulfonyl]azetidin-1-yl]oxazole-4-carboxamide (Compound 261)

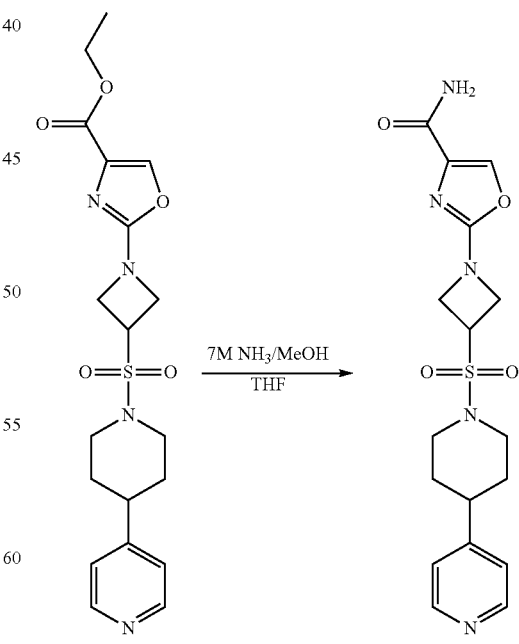

To a solution of ethyl 2-[3-[[4-(4-pyridyl-1-piperidyl]sulfonyl]azetidin-1-yl]oxazole-4-carboxylate (26 mg, 1 equiv.) in THF (2 mL) was added 7 M ammonia solution in MeOH (4 mL). The resulting mixture was stirred at 60° C. overnight. The reaction mixture was cooled to RT. Solvent was removed in vacuo. The obtained solid was washed with MeOH to yield the expected product (10.5 mg). LCMS: MW (calcd): 391.4; MS (ES+, m/z): 392.8 [M+H]+.

Method G: General Procedures for Preparation of Urea/Thio Urea Compounds of Formula (I-3), which is Subset of Formula (I) Wherein $R^2$—X— is $R^2$—N($R^x$)—C(=O)— or $R^2$—N($R^y$)—C(=S)—

Scheme 3

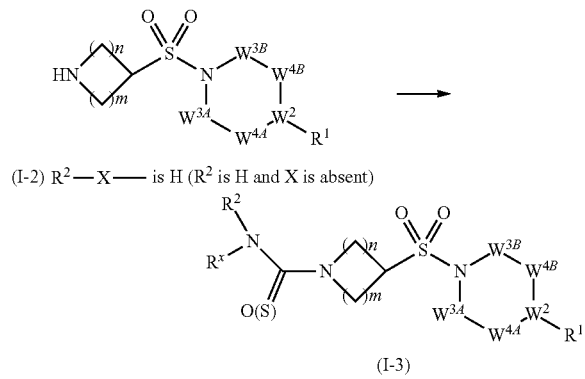

(I-2) $R^2$—X— is H ($R^2$ is H and X is absent)

(I-3)

Method G1: Carbamoyl/Thiocarbamoyl Chloride

Typically, to a solution of the appropriate compound of formula (I-2) (1 equiv.), in a suitable solvent such as DCM, THF, or DMF base (TEA) (1-3 equiv.) was added, followed by carbamoyl/thiocarbamoyl chloride (1.1 equiv.). The resulting mixture is stirred at room temperature for 1-24 h. The expected product of formula (I-3) may be isolated and, if desired, further purified by methods known to one skilled in the art.

Example G1.1

Illustrative Synthesis of N,N-Diisopropyl-3-[[4-(1H-pyrrolo[2,3-b]pyridin-3-yl)-1-piperidyl]sulfonyl]azetidine-1-carboxamide (Compound 173)

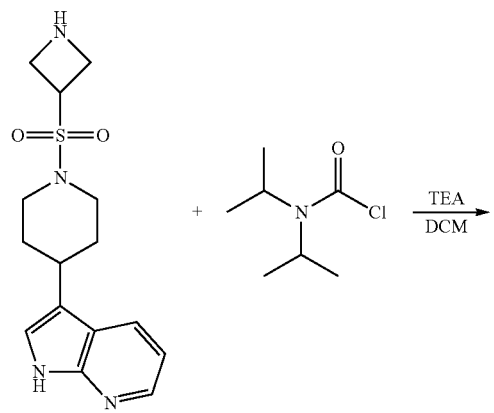

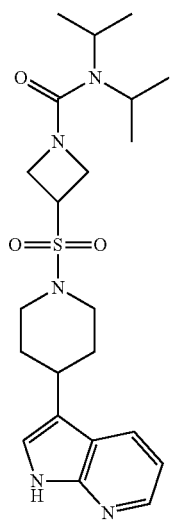

To a suspension of 3-[1-(azetidin-3-ylsulfonyl)-4-piperidyl]-1H-pyrrolo[2,3-b]pyridine (20 mg, 1 equiv.) in dry DCM (1 mL), TEA (17 μL, 2 equiv.) was added, followed by N,N-diisopropylcarbamoyl chloride (11 mg, 1.1 equiv.) and the resulting mixture was stirred at RT for 2 h. The reaction mixture was evaporated to dryness, and the obtained residue purified by preparative LC-MS (ES+ mode, high pH method) to afford the expected product (15 mg). LCMS: MW (calcd): 447.59; MS (ES+, m/z): 448.19 [M+H]+.

Method G2: Isocyanate/Isothiocyanate

The reaction is typically performed by adding 1-3 equiv. of isocyanate or isothiocyanate to a solution of the appropriate compound of formula (I-2) (1 equiv.) in a suitable solvent (such as DCM or THF) or solvent mixture (DCM/DMF mixture), with 1-3 equiv. of base such as TEA or without addition of the base. The reaction mixture is stirred at room temperature for 30 min to 24 h. The expected product of formula (I-3) may be isolated and, if desired, further purified by methods known to one skilled in the art.

Example G2.1

Illustrative Synthesis of 3-[[4-(1H-Pyrrolo[2,3-b] pyridin-3-yl)-1-piperidyl]sulfonyl]-N-[1-(trifluoromethyl)cyclopropyl]azetidine-1-carboxamide (Compound 57)

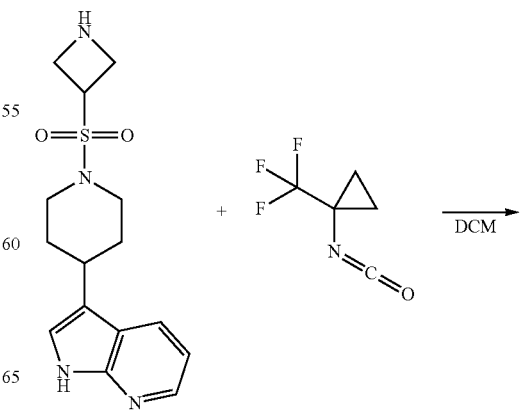

121
-continued

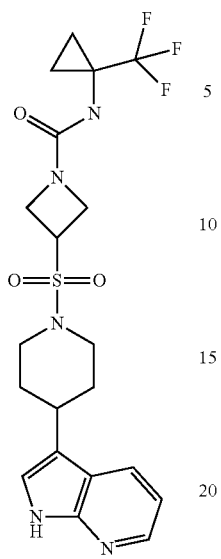

To a solution of 3-[1-(azetidin-3-ylsulfonyl)-4-piperidyl]-1H-pyrrolo[2,3-b]pyridine (32 mg, 1 equiv.) in dry DCM (1 mL), 1-isocyanato-1-(trifluoromethyl)cyclopropane (15.08 µL, 1 equiv.) was added. The reaction mixture was stirred at room temperature for 2 h. Solvent was removed in vacuo and the obtained product was purified by flash chromatography on silica gel (eluting with DCM/MeOH gradient; 0-10% MeOH). After the appropriate fractions were collected solvent was removed to afford the expected product (17.5 mg). LCMS: MW (calcd): 471.50; MS (ES$^+$, m/z): 472.66 [M+H]$^+$.

Method G3: Triphosgene

The reaction is typically performed by adding the appropriate amine (1 equiv.) and base (1-7 eq) (such as TEA or DiPEA) to a solution of triphosgene (0.18-0.5 equiv.) in a suitable solvent such as THF at 0° C. to room temperature. The resulting mixture is stirred for 20 min to 24 h at 0° C. to room temperature, then mixed with THF solution (or suspension) of the appropriate compound of formula (I-2) (0.25-1 equiv.) to which, if required, additional amount of base such as TEA or DiPEA may be added. The reaction mixture is stirred at room temperature for 1-24 h. The expected product of formula (I-3) may be isolated and, if desired, further purified by methods known to one skilled in the art.

122

Example G3.1

Illustrative Synthesis of cis-2,6-Dimethylmorpholin-4-yl]-[3-[[4-(1H-pyrrolo[2,3-b]pyridin-3-yl)-1-piperidyl]sulfonyl]azetidin-1-yl]methanone (Compound 170)

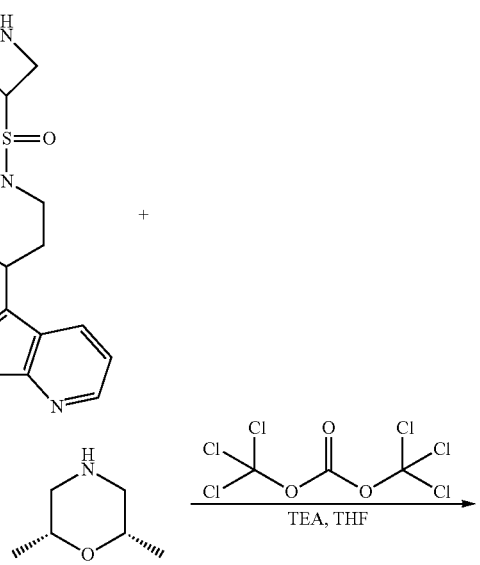

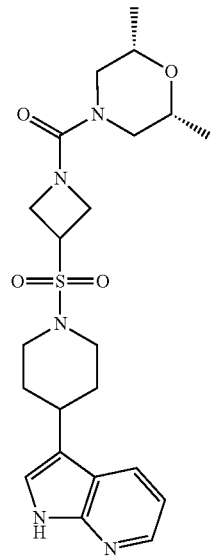

Triphosgene (22 mg, 0.37 equiv.) was dissolved in dry THF (1 mL). Then, a solution of cis-2,6-dimethylmorpholine (25 µL, 1 equiv.) and TEA (92 µL, 3.3 equiv.) in dry THF (0.5 mL) was added dropwise. The resulting slurry was stirred at RT for 30 minutes, then it was added to a suspension of 3-[1-(azetidin-3-ylsulfonyl)-4-piperidyl]-1H-pyrrolo [2,3-b]pyridine (48 mg, 0.75 equiv.) and TEA (28 µL, 1 equiv.) in dry THF (1 mL) and the mixture was stirred for 1 hour at RT. The reaction mixture was diluted with DCM, and washed with water and brine. The organic layer was dried over phase separator filter tube and concentrated under reduced pressure. The obtained residue was purified by flash chromatography on silica gel (eluting with DCM/

MeOH gradient; 0-10% of MeOH) to afford the expected product (36 mg). LCMS: MW (calcd): 461.58; MS (ES+, m/z): 462 [M+H]+.

Method G4: CDI

The reaction is typically performed by adding 1.1 equiv. of CDI to a solution of the corresponding amine (1 equiv.) in a suitable solvent such as DCM in the presence of a suitable base (typically TEA, 2 equiv.), or without presence of base. The reaction mixture is stirred at room temperature for 1-2 h, then the appropriate compound of formula (I-2) (1 equiv.) is added and resulting mixture stirred at RT for 18 h. The expected product of formula (I-3) may be isolated and, if desired, further purified by methods known to one skilled in the art.

Example G4.1

Illustrative Synthesis of N-[(1-Methylpyrazol-3-yl)methyl]-3-[[4-(1H-pyrrolo[2,3-b]pyridin-3-yl)-1-piperidyl]sulfonyl]azetidine-1-carboxamide (Compound 81)

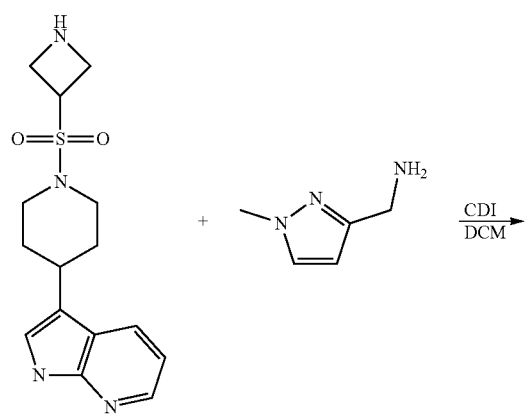

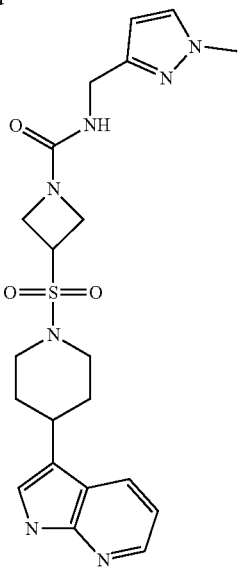

To a solution of (1-methylpyrazol-3-yl)methanamine (9.58 μL, 1 equiv.) in dry DCM (1 mL), CDI (17.83 mg, 1.1 equiv.) was added. The reaction mixture was stirred at room temperature for 2 hours. Then, 3-[1-(azetidin-3-ylsulfonyl)-4-piperidyl]-1H-pyrrolo[2,3-b]pyridine (32 mg, 1 equiv.) was added and stirring was continued at room temperature overnight. Solvent was removed in vacuo and the obtained residue was purified by preparative LC-MS to afford the expected product (6.39 mg). LCMS: MW (calcd): 457.55; MS (ES+, m/z): 458.13 [M+H]+.

Method G5: CDI/MeI

Scheme 3B

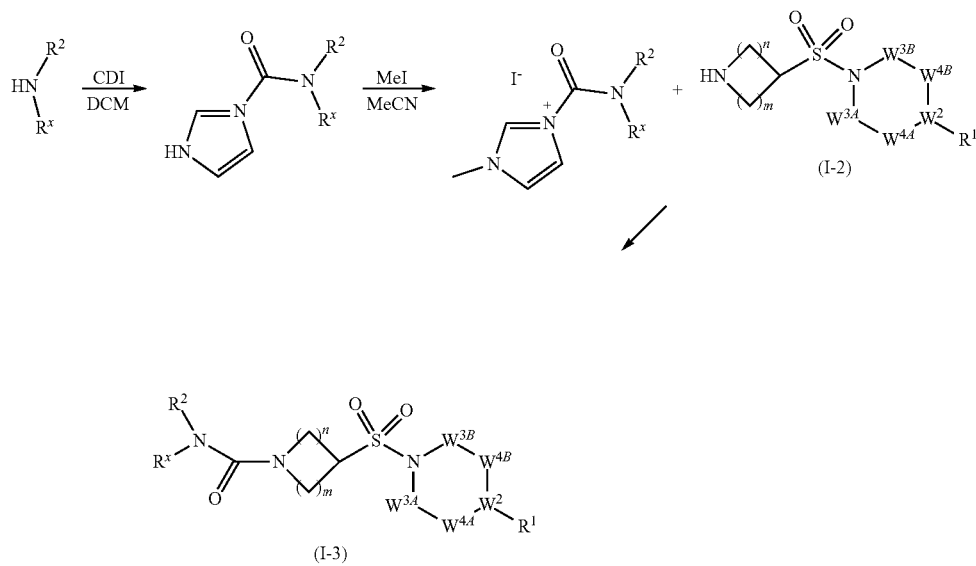

The reaction is typically performed by adding the appropriate amine (1 equiv.) to a solution of CDI (2 equiv.) in DCM (or any other suitable solvent) at 0° C. to RT under argon atmosphere. The resulting mixture is stirred at RT for 2-3 h, diluted with DCM and quenched with water. The organic layer is separated, dried over phase separator filter tube and concentrated in vacuo. The obtained residue is dissolved in dry acetonitrile, then iodomethane (5-10 equiv.) is added and the resulting mixture stirred at RT overnight. The reaction mixture is evaporated to dryness and the obtained residue added to a mixture of the appropriate compound of formula (I-2) (0.5-1 equiv.) and TEA (1-2 equiv.) in DCM (or any other suitable solvent) and stirred at RT for 30 min to 3 h. The expected product of formula (I-3) may be isolated and, if desired, further purified by methods known to one skilled in the art.

Example G5.1

Illustrative Synthesis of N-(2-Furylmethyl)-N-methyl-3-[[4-(1H-pyrrolo[2,3-b]pyridin-3-yl)-1-piperidyl]sulfonyl]azetidine-1-carboxamide (Compound 178)

Step 1: Synthesis of N-(2-furylmethyl)-N-methyl-imidazole-1-carboxamide

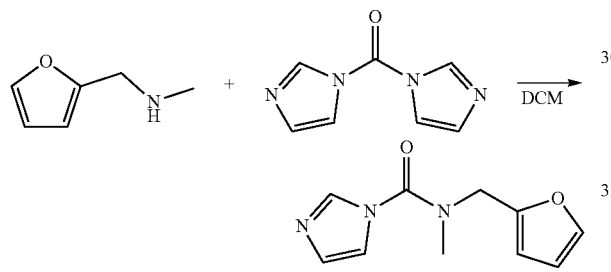

To a solution of 1,1'-carbonyldiimidazole (CDI) (487 mg, 2 equiv.) in dry DCM (5 mL), N-methylfurfurylamine (170 μL, 1 equiv.) was added in one portion and the resulting mixture was stirred at RT for 2 h. The reaction mixture was diluted with DCM and quenched with water. The organic layer was separated, dried over phase separator filter tube and concentrated in vacuo to afford the expected product (308 mg).

Step 2: Synthesis of N-(2-furylmethyl)-N,3-dimethyl-imidazol-1-ium-1-carboxamide; iodide

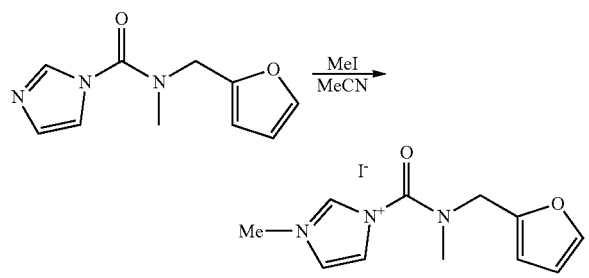

To a solution of N-(2-furylmethyl)-N-methyl-imidazole-1-carboxamide (308 mg, 1 equiv.) in dry acetonitrile (7 mL), iodomethane (561 μL, 6 equiv.) was added and the resulting mixture was stirred at RT overnight. The reaction mixture was evaporated to dryness to afford the expected product (522 mg).

Step 3: Synthesis of N-(2-Furylmethyl)-N-methyl-3-[[4-(1H-pyrrolo[2,3-b]pyridin-3-yl)-1-piperidyl]sulfonyl]azetidine-1-carboxamide (Compound 178)

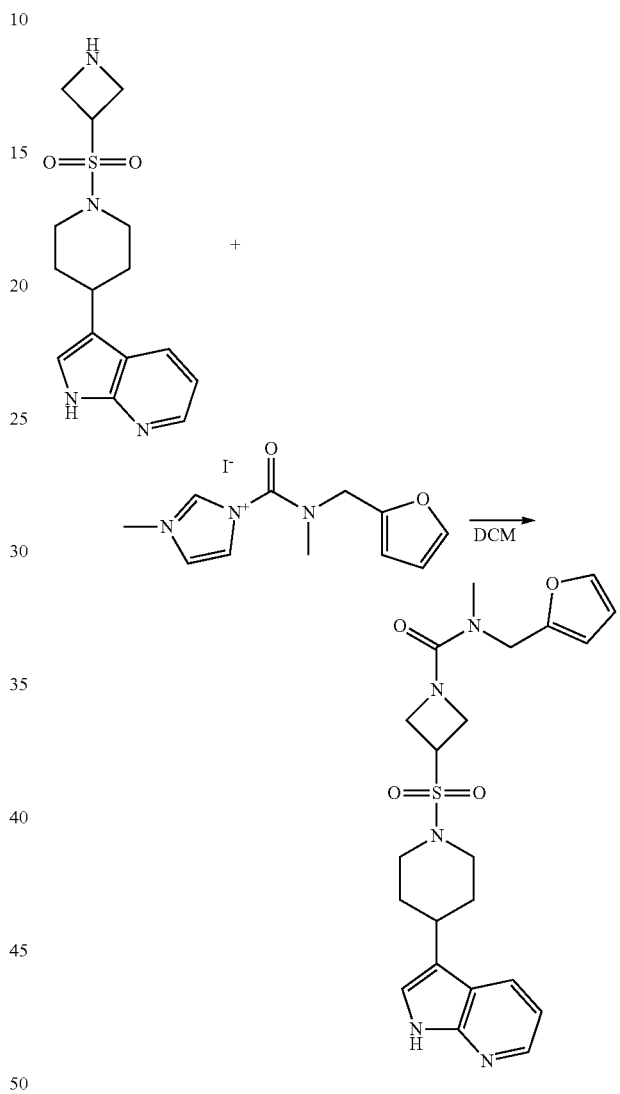

To a suspension of 3-[1-(azetidin-3-ylsulfonyl)-4-piperidyl]-1H-pyrrolo[2,3-b]pyridine (32 mg, 1 equiv.) in dry DCM (3 mL), TEA (28 μL, 2 equiv.) was added, followed by N-(2-furylmethyl)-N,3-dimethyl-imidazol-1-ium-1-carboxamide iodide (38 mg, 1.1 equiv.) and the resulting mixture was stirred at RT for 30 min. The reaction mixture was evaporated to dryness. The obtained residue was purified by preparative LC-MS (ES+ mode, high pH method) to afford the expected product (25 mg). LCMS: MW (calcd): 457.54; MS (ES+, m/z): 458.13 [M+H]+.

Method G6: DSC

The reaction is typically performed by adding a solution of N,N'-disuccinimidyl carbonate (1-2 equiv.) in DMF (or any other suitable solvent) to a solution of the appropriate compound of formula (I-2) (1 equiv.) in a suitable solvent such as DMF. To this mixture a suitable base, typically DiPEA (2-10 equiv.) is added and the reaction is stirred at RT for 5-60 min before the appropriate amine (1-3 equiv.) is added and the reaction is heated at 50-120° C. for 30 min to 24 h. The expected product of formula (I-3) may be isolated and, if desired, further purified by methods known to one skilled in the art.

Example G6.1

Illustrative Synthesis of N-[1-(Hydroxymethyl)-2-methyl-propyl]-3-[[4-(1H-pyrrolo[2,3-b]pyridin-3-yl)-1-piperidyl]sulfonyl]azetidine-1-carboxamide (Compound 26)

stirred at RT for 15 min. Then, 2-amino-3-methyl-butan-1-ol (21 µL, 1.2 equiv.) was added and the reaction was shaken at 80° C. for 1 h. Solvent was evaporated to dryness to give the crude product, which was purified by preparative LC-MS (ES+ mode, low pH method) to afford the expected racemic product (22 mg). LCMS: MW (calcd): 449.57; MS (ES+, m/z): 450.7 [M+H]+.

Method G7: Phosgene

Typically, to a solution of the appropriate amine (1 equiv.) in THF at RT is added base, typically TEA (4.0 equiv.), followed by phosgene (15 wt % solution in PhMe) (1 equiv.). Reaction mixture is stirred at RT for 5-30 min. Solution of compound of formula (I-2) (1 equiv.) in THF is added. The resulting mixture is stirred at room temperature for 30 min. The expected product of formula (I-3) may be isolated and, if desired, further purified by methods familiar to one skilled in the art.

Example G7.1

Illustrative Synthesis of [cis-2,6-dimethylmorpholin-4-yl]-[3-[4-(6-methyl-1H-pyrrolo[2,3-b]pyridin-3-yl)piperidin-1-yl]sulfonylazetidin-1-yl]methanone (Compound 381)

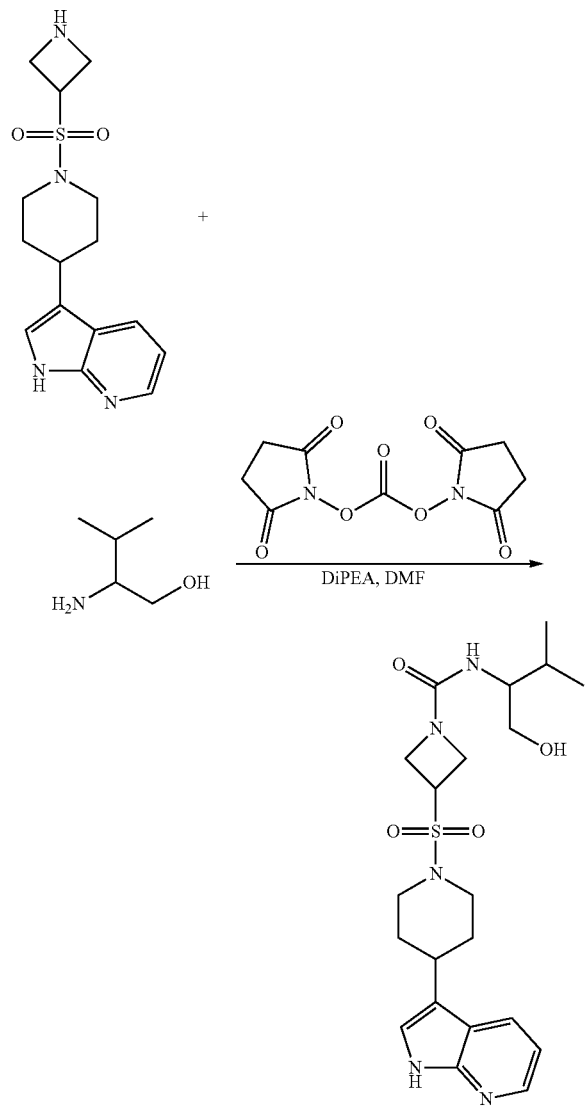

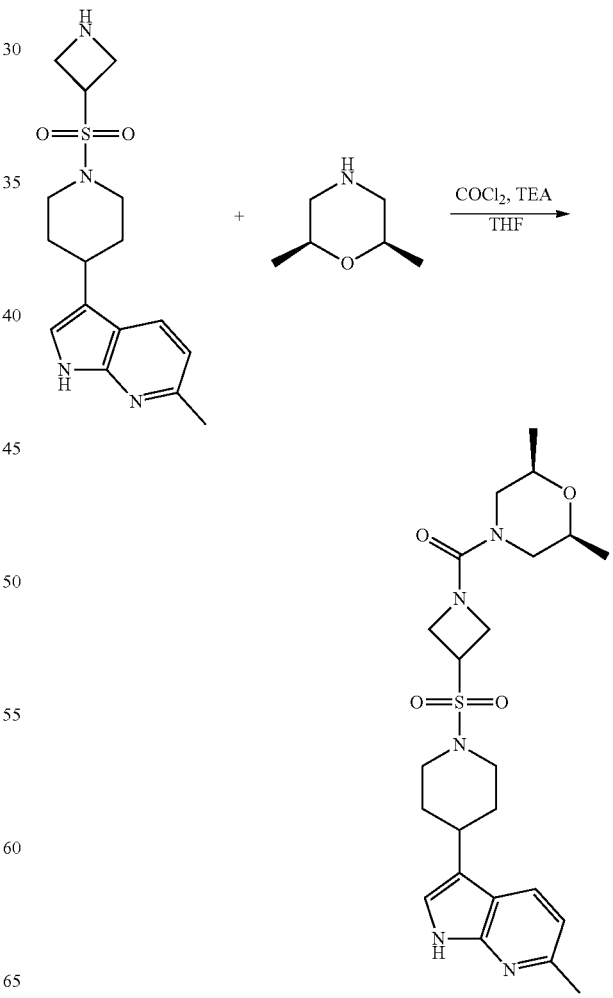

To a vial containing a solution of N,N'-disuccinimidyl carbonate (44 mg, 1.1 equiv.) in DMF (1 mL), a solution of 3-[1-(azetidin-3-ylsulfonyl)-4-piperidyl]-1H-pyrrolo[2,3-b]pyridine (compound of formula (I-2)) (50 mg, 1 equiv.) in DMF (1 mL) was added. To the resulting solution DIPEA (0.223 mL, 8.2 equiv.) was added and the reaction mixture To the solution of cis-2,6-dimethymorpholine (25.8 μL, 1 equiv.) in dry THF (3.0 mL) was added TEA (107.8 μL, 4 equiv.), followed by phosgene solution 15 wt % in toluene (137.7 μL, 1 equiv.) and the resulting solution was stirred at RT for 5 min. 3-[1-(Azetidin-3-ylsulfonyl)-4-piperidyl]-6-methyl-1H-pyrrolo[2,3-b]pyridine (86.5 mg, 1 equiv.) was added as a solution in THF (2.0 mL). After 15 min, reaction mixture was transferred to a separatory funnel containing distilled water, and was extracted with EtOAc (3×100 mL). Combined organic extracts were dried over Na$_2$SO$_4$, were filtered, and solvent was removed in vacuo to yield the crude product, which was taken up in DMSO and was purified by preparative HPLC to afford the expected product (36.3 mg). LCMS: MW (calcd): 475.6; MS (ES+, m/z): 476.0 [M+H]$^+$.

Method H: General Procedures for Preparation of Carbamate Compounds of Formula (I-4) and (XII-4), which are Subset of Formula (I) Wherein R$^2$—X— is R$^2$—O—C(=O)—

Scheme 4

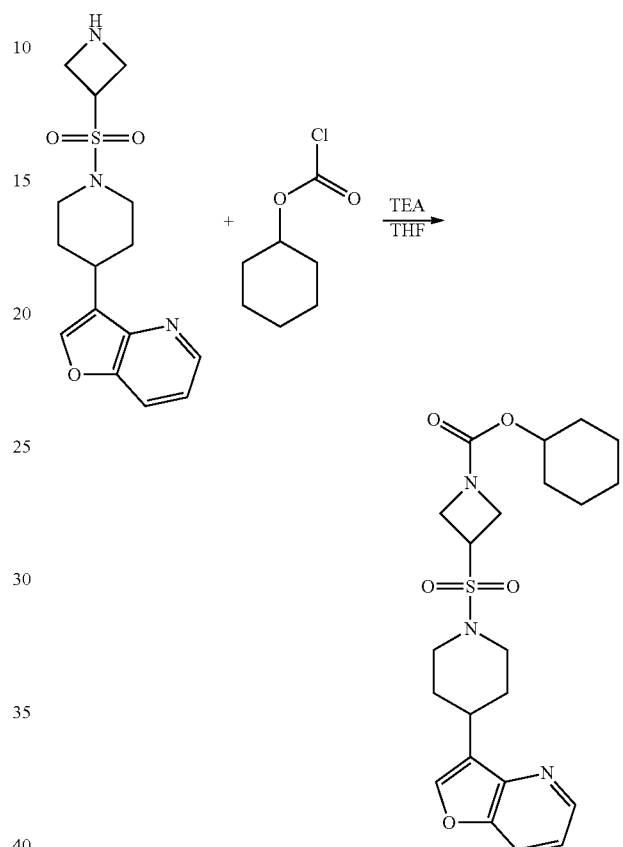

Method H1: Chloroformate

Typically, to the solution of the appropriate compound of formula (I-2) or (XII-2) (1 equiv.) in suitable solvent (such as THF, MeCN or DCM), base (1-4 equiv.) such as TEA or potassium carbonate is added, followed by addition of corresponding chloroformate (1-1.2 equiv.). The resulting mixture is stirred at room temperature for 30 min to 24 h. The expected product of formula (I-4) or (XII-4) may be isolated and, if desired, further purified by methods known to one skilled in the art.

Example H1.1

Illustrative Synthesis of Cyclohexyl 3-[(4-furo[3,2-b]pyridin-3-yl-1-piperidyl)sulfonyl]azetidine-1-carboxylate (Compound 141)

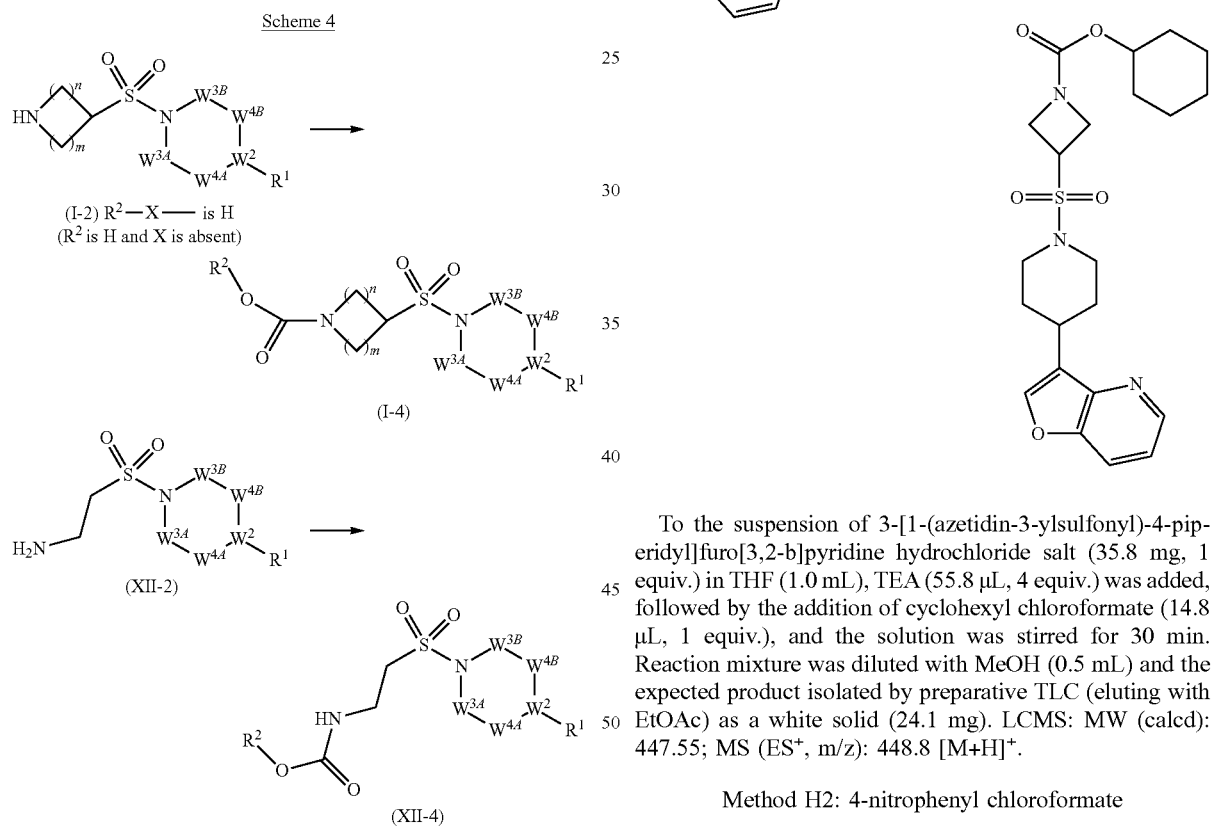

To the suspension of 3-[1-(azetidin-3-ylsulfonyl)-4-piperidyl]furo[3,2-b]pyridine hydrochloride salt (35.8 mg, 1 equiv.) in THF (1.0 mL), TEA (55.8 μL, 4 equiv.) was added, followed by the addition of cyclohexyl chloroformate (14.8 μL, 1 equiv.), and the solution was stirred for 30 min. Reaction mixture was diluted with MeOH (0.5 mL) and the expected product isolated by preparative TLC (eluting with EtOAc) as a white solid (24.1 mg). LCMS: MW (calcd): 447.55; MS (ES$^+$, m/z): 448.8 [M+H]$^+$.

Method H2: 4-nitrophenyl chloroformate

Typically, to a solution of the corresponding alcohol (1 equiv.) in a suitable solvent such as DCM at 0° C., 4-nitrophenyl chloroformate (1.1 equiv.) and DiPEA (1-2 equiv.) are added and the resulting mixture is stirred at 0° C. to RT for 1-4 h. Then, the appropriate compound of formula (I-2) (1 equiv.) and DiPEA (2-3 equiv.) are added at 0° C. and the mixture is stirred at RT overnight. The expected product of formula (I-4) may be isolated and, if desired, further purified by methods known to one skilled in the art.

Alternatively, to a solution of the appropriate compound of formula (I-2) (1 equiv.) and base such as TEA (2 equiv.) in a suitable solvent such as DCM at 0° C., 4-nitrophenyl chloroformate (1 equiv.) is added and the resulting mixture is stirred at 0° C. to RT for 1-4 h. The activated intermediate is isolated by methods known to one skilled in the art, then combined with an alcohol (3 equiv.) and base (3 equiv.) such as KOtBu in a suitable solvent such as THF and mixture is stirred at RT overnight. The expected product of formula (I-4) may be isolated and, if desired, further purified by methods known to one skilled in the art.

Example H2.1

Illustrative Synthesis of (3,5-Dimethylisoxazol-4-yl)methyl 3-[[4-(1H-pyrrolo[2,3-b]pyridin-3-yl)-1-piperidyl]sulfonyl]azetidine-1-carboxylate (Compound 62)

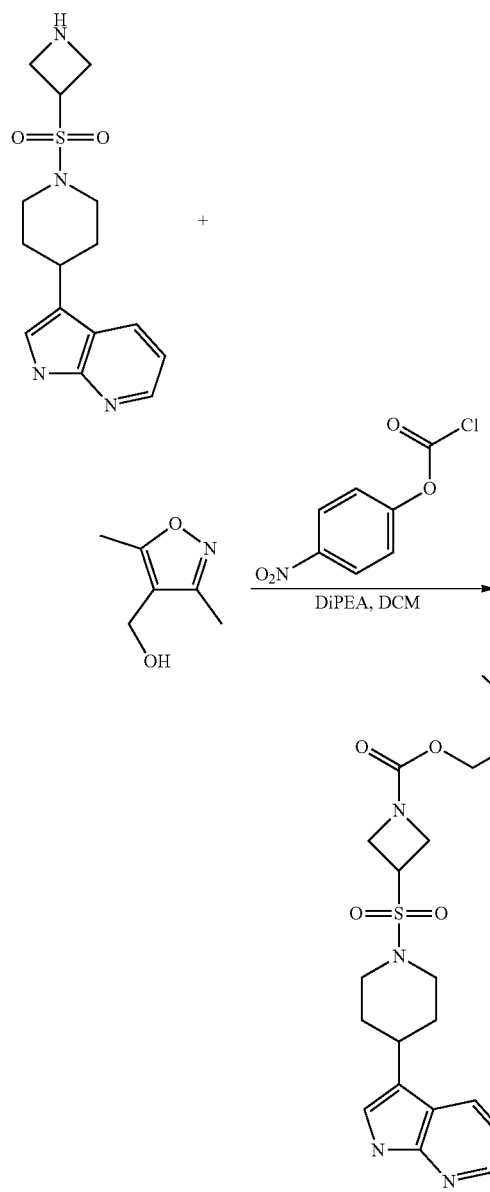

To a solution of (3,5-dimethylisoxazol-4-yl)methanol (12.71 mg, 1 equiv.) in dry DCM (600 µL) at 0° C. 4-nitrophenyl chloroformate (22.17 mg, 1.1 equiv.) and DIPEA (24.4 µL, 1.4 equiv.) were added. The reaction mixture was stirred for 1 h at 0° C. and 4 h at room temperature. The reaction mixture was cooled to 0° C. prior to the successive addition of the solution of 3-[1-(azetidin-3-ylsulfonyl)-4-piperidyl]-1H-pyrrolo[2,3-b]pyridine (32 mg, 1 equiv.) in DCM (400 µL) and DIPEA (48.77 µL, 2.8 equiv.). Reaction mixture was stirred overnight, then water was added and the aqueous layer was extracted with DCM (3×10 mL). The combined organic extracts were dried over Na$_2$SO$_4$ and evaporated. The obtained residue (69.3 mg) was purified by preparative LC-MS (ES$^+$ mode, high pH method) to afford the expected product (9.63 mg). LCMS: MW (calcd): 473.54; MS (ES$^+$, m/z): 474 [M+H]$^+$.

Method H3: Triphosgene

The reaction is typically performed by adding the appropriate alcohol (1 equiv.) and base (1-15 equiv.) (TEA, DiPEA or 2,6-lutidine) to a solution of triphosgene (0.3-0.5 equiv.) in a suitable solvent such as THF or DCM at 0° C. to RT. The resulting mixture is stirred for min to 5 h at 0° C. to RT. Then, it is combined with the solution (or suspension) of the appropriate compound of formula (I-2) (0.3-1 equiv.) in THF or DCM (with or without additional base such as TEA, DiPEA or 2,6-lutidine). The resulting mixture is stirred at RT for 1-24 h. The expected product of formula (I-4) may be isolated and, if desired, further purified by methods known to one skilled in the art.

Example H3.1

Illustrative Synthesis of 2-Tetrahydropyran-4-yl-ethyl 3-[[4-(1H-pyrrolo[2,3-b]pyridin-3-yl)-1-piperidyl]sulfonyl]azetidine-1-carboxylate (Compound 60)

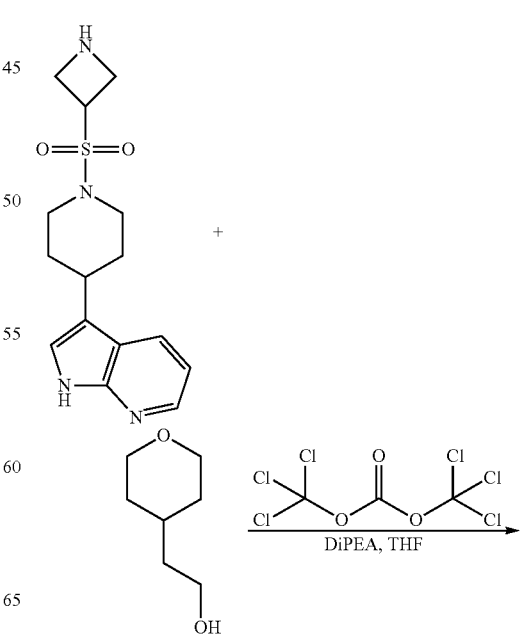

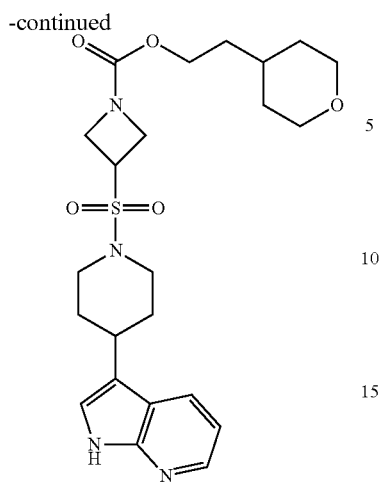

To the solution of 2-tetrahydropyran-4-ylethanol (13.26 µL, 1 equiv.) in THF (500 µL) at 0° C., DiPEA (24.4 µL, 1.4 equiv.) and triphosgene (11.9 mg, 0.4 equiv.) were added. Reaction mixture was stirred at 0° C. for 15 min, and at RT for 15 min. Then DiPEA was added (48.8 µL, 2.8 equiv.), followed by the solution of 3-[1-(azetidin-3-ylsulfonyl)-4-piperidyl]-1H-pyrrolo[2,3-b]pyridine (32 mg, 1 equiv.) in THF (1 mL). The reaction mixture was left to stir at room temperature overnight. Solvent was removed in vacuo, and the obtained residue was purified by flash chromatography on silica gel (eluting with DCM/MeOH gradient; 0-10% of MeOH). After collecting the appropriate fractions, solvent was removed in vacuo and the obtained white solid was triturated with diethyl ether to afford the expected product (19.24 mg). LCMS: MW (calcd): 476.59; MS (ES+, m/z): 477.71 [M+H]+.

Method I: General Procedures for Preparation of Amide Compounds of Formula (I-5) and (XI-5), which are Subset of Formula (I) Wherein R²—X— is R²—C(=O)—

Scheme 5

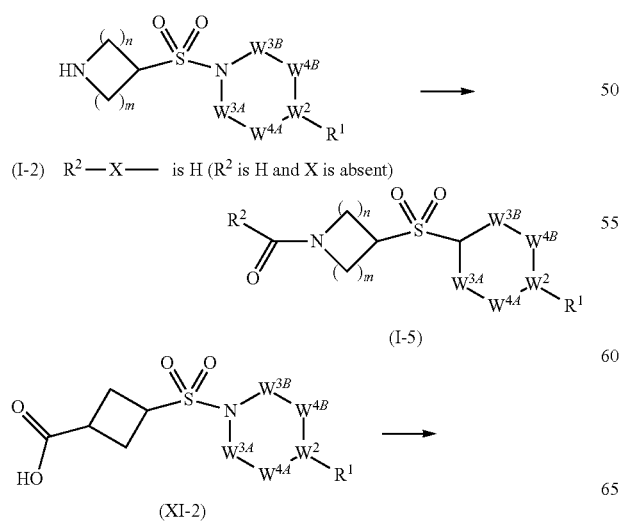

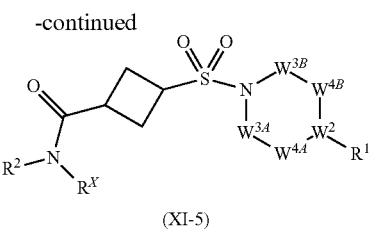

Method I1: HATU (Preparation of Compounds of Formula (I-5))

Typically, to a solution of the appropriate compound of formula (I-2) (1 equiv.) and an appropriate carboxylic acid (1.1 equiv.) in suitable solvent (such as DMF), DiPEA (2.0-3.3 equiv.) and HATU (1-1.5 equiv.) are added, and the reaction mixture is stirred at 0° C. to RT for 1 to 24 hours. The expected product of formula (I-5) may be isolated and, if desired, further purified by methods known to one skilled in the art.

Example I1.1

Illustrative Synthesis of N-2-(3,5-Dimethylisoxazol-4-yl)-acetyl 3-[(4-furo[3,2-b]pyridin-3-yl-1-piperidyl)sulfonyl]azetidine (Compound 138)

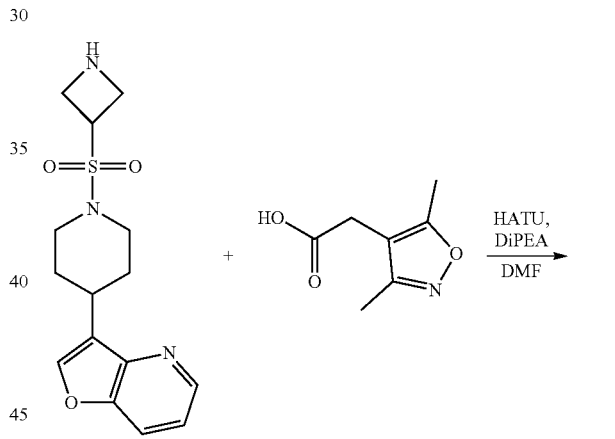

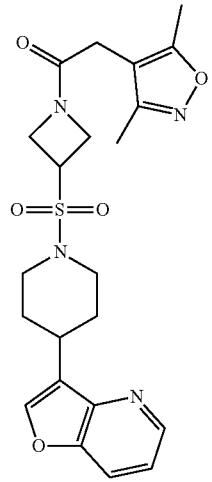

To the solution of 3-[1-(azetidin-3-ylsulfonyl)-4-piperidyl]furo[3,2-b]pyridine hydrochloride salt (35.8 mg, 1 equiv.) and 2-(3,5-dimethylisoxazol-4-yl)acetic acid (17.1 mg, 1.1 equiv.) in DMF (1.0 mL) DiPEA (57.4 µL, 3.3 equiv.) was added, followed by HATU (41.8 mg, 1.1 equiv.), and the resulting solution was stirred at RT. After one hour, reaction mixture was diluted with EtOAc (10 mL), transferred to a separatory funnel containing distilled water and extracted with EtOAc (3×100 mL). The combined organic extracts were dried over Na$_2$SO$_4$, filtered, and solvent was removed in vacuo. The crude product was purified by preparative TLC eluting with 10% MeOH/EtOAc to afford the expected product (15 mg). LCMS: MW (calcd): 458.53; MS (ES$^+$, m/z): 459.7 [M+H]$^+$.

Method I2: Amide Coupling with Acyl Chloride

The reaction is typically performed by adding TEA (2 equiv.) and the corresponding acyl chloride (1-1.2 equiv.) to a solution of the compound of formula (I-2) (1 equiv.) in DCM. The reaction mixture is stirred at RT for 1-24 h. The expected product of formula (I-5) may be isolated and, if desired, further purified by methods known to one skilled in the art.

Example I2.1

Illustrative Synthesis of Cyclohexyl-[3-[[4-(1H-pyrrolo[2,3-b]pyridin-3-yl)-1-piperidyl]sulfonyl]azetidin-1-yl]methanone (Compound 189)

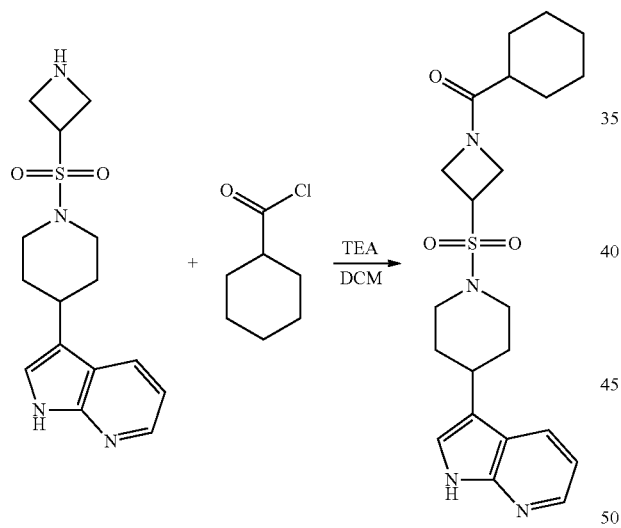

To a solution of 3-[1-(azetidin-3-ylsulfonyl)-4-piperidyl]-1H-pyrrolo[2,3-b]pyridine (32 mg, 1 equiv.) in DCM (1 mL), TEA (27.9 µL, 2 equiv.) and cyclohexanecarbonyl chloride (14.72 µL, 1.1 equiv.) were added. The reaction mixture was stirred at room temperature overnight, solvent was removed in vacuo and the residue was purified by flash chromatography on silica gel (eluting with DCM/MeOH gradient; 0-10% of MeOH). After collecting the appropriate fractions, solvent was removed in vacuo to afford the expected product (21.43 mg). LCMS: MW (calcd): 430.56; MS (ES$^+$, m/z): 431.8 [M+H]$^+$.

Method I3: EDC/4-DMAP

Typically, to a solution of the appropriate compound of formula (I-2) (1 equiv.) and the corresponding carboxylic acid (1 equiv.) in suitable solvent (such as 1,2-DCE) are added 4-DMAP (2 equiv.) and EDCxHCl (2 equiv.). The reaction mixture is stirred at RT for 2 hours. The expected product of formula (I-5) may be isolated and, if desired, further purified by methods known to one skilled in the art.

Example I3.1

Illustrative Synthesis of 4,4,4-trifluoro-3-hydroxy-1-[3-[[4-(1H-pyrrolo[2,3-b]pyridin-3-yl)-1-piperidyl]sulfonyl]azetidin-1-yl]-3-(trifluoromethyl)butan-1-one (Compound 333)

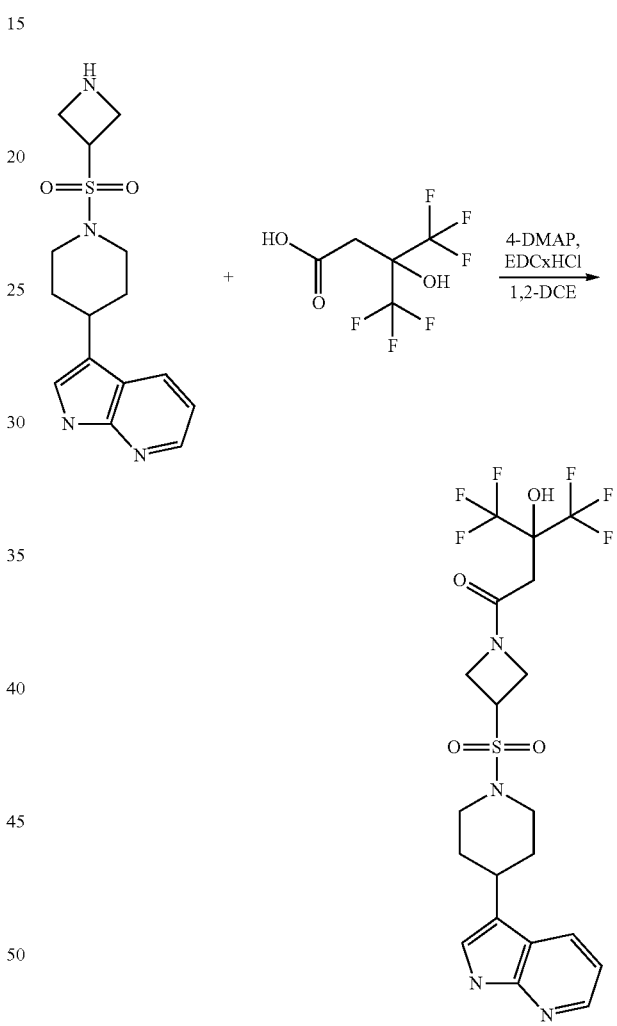

To the solution of 3-[1-(azetidin-3-ylsulfonyl)-4-piperidyl]-1H-pyrrolo[2,3-b]pyridine (30.0 mg, 1 equiv.) and 4,4,4-trifluoro-3-hydroxy-3-(trifluoromethyl)butanoic acid (21.6 mg, 1 equiv.) in dry 1,2-DCE (1.2 mL) was added 4-DMAP (23.2 mg, 2.0 equiv.) and EDCxHCl (36.4 mg, 2 equiv.) and the resulting mixture was stirred at RT. After 2 hours, reaction mixture was diluted with EtOAc (10 mL) and washed with NaHCO$_3$ sat. solution (3×10 mL) and brine (15 mL). The organic layer was dried over Na$_2$SO$_4$, filtered and solvent was removed in vacuo. The obtained residue was purified by preparative LC-MS (ES$^+$ mode, high pH method) to afford the expected product (15.1 mg). LCMS: MW (calcd): 528.47; MS (ES$^+$, m/z): 529.6 [M+H]$^+$.

Method I4: EDC/HOBt

Typically, the appropriate compound of formula (I-2) (1 equiv.), the corresponding carboxylic acid (1-1.2 equiv.), DiPEA (2.5-3 equiv.), EDC×HCl (1.3-1.5 equiv.) and HOBt (1-1.5 equiv.) are combined in suitable solvent (such as DMF) at 0° C. to RT. The reaction mixture is stirred at RT for 2 to 24 hours. The expected product of formula (I-5) may be isolated and, if desired, further purified by methods known to one skilled in the art.

Example I4.1

Illustrative Synthesis of 1-[3-[(4-furo[3,2-b]pyridin-3-yl-1-piperidyl)sulfonyl]azetidin-1-yl]-2-tetrahydropyran-4-yl-ethanone (Compound 377)

Method I5: HATU (Preparation of Compounds of Formula (XI-5))

Typically, to a solution of the appropriate compound of formula (XI-2), one isomer or mixture of cis/trans isomers, (1 equiv.) and an appropriate amine (1 equiv.) in suitable solvent (such as DMF), DiPEA (2.0-3.0 equiv.) and HATU (1-1.5 equiv.) are added, and the reaction mixture is stirred at 0° C. to RT for 1 to 24 hours. The expected product(s) of formula (XI-5) may be isolated and, if desired, further purified and isomers separated by methods known to one skilled in the art.

Example I5.1

Illustrative Synthesis of cis-N-tert-butyl-N-methyl-3-[[4-(1H-pyrrolo[2,3-b]pyridin-3-yl)-1-piperidyl]sulfonyl]cyclobutanecarboxamide (Compound 289) and trans-N-tert-butyl-N-methyl-3-[[4-(1H-pyrrolo[2,3-b]pyridin-3-yl)-1-piperidyl]sulfonyl]cyclobutanecarboxamide (Compound 290)

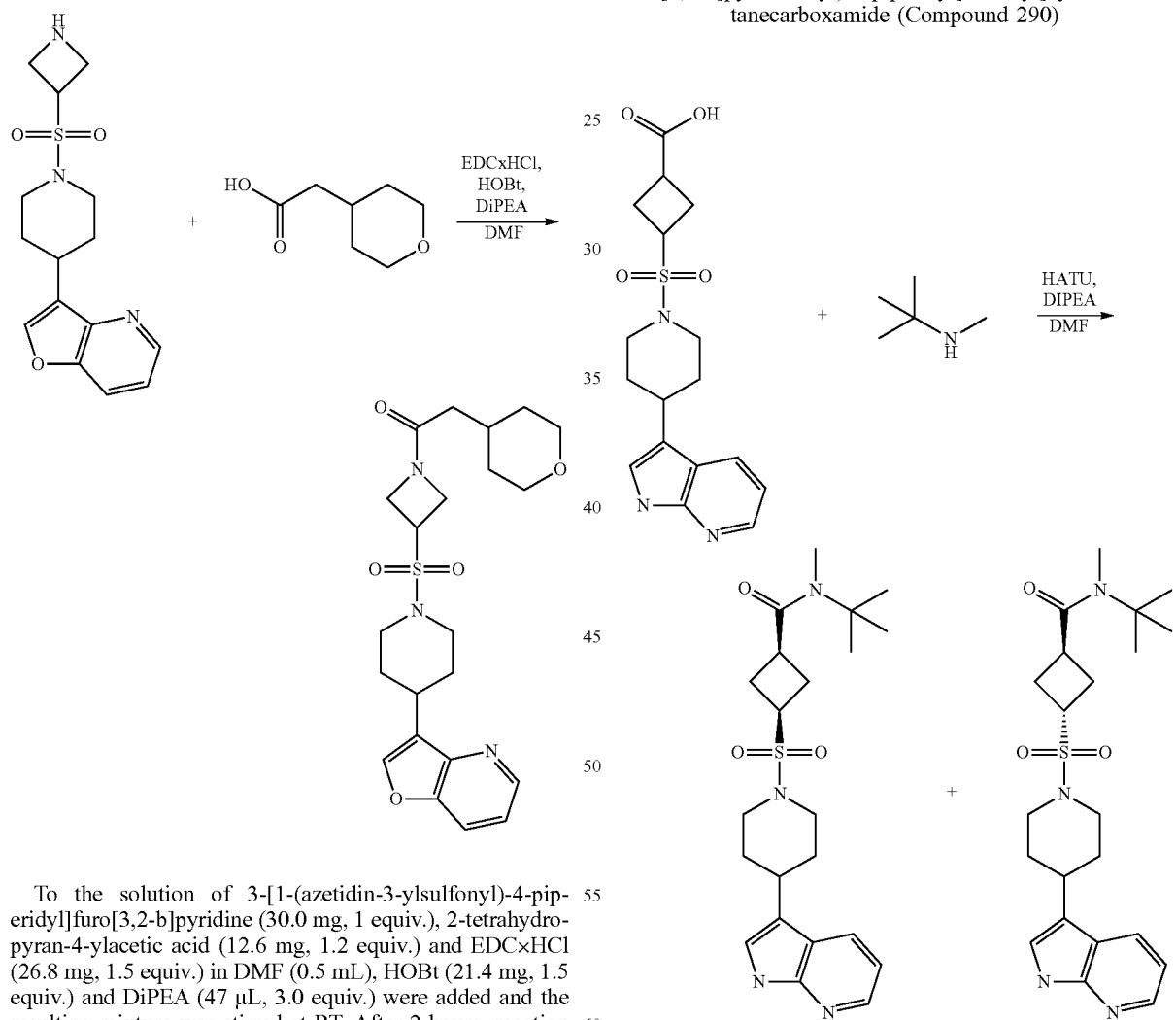

To the solution of 3-[1-(azetidin-3-ylsulfonyl)-4-piperidyl]furo[3,2-b]pyridine (30.0 mg, 1 equiv.), 2-tetrahydropyran-4-ylacetic acid (12.6 mg, 1.2 equiv.) and EDC×HCl (26.8 mg, 1.5 equiv.) in DMF (0.5 mL), HOBt (21.4 mg, 1.5 equiv.) and DiPEA (47 μL, 3.0 equiv.) were added and the resulting mixture was stirred at RT. After 2 hours, reaction mixture was diluted with EtOAc (10 mL) and washed with NaHCO₃ sat. solution (3×10 mL) and brine (15 mL). The organic layer was dried over Na₂SO₄, filtered and solvent was removed in vacuo. The obtained residue was purified by preparative LC-MS (ES⁺ mode, high pH method) to afford the expected product (17.4 mg). LCMS: MW (calcd): 447.55; MS (ES⁺, m/z): 448.2 [M+H]⁺.

To a solution of 3-[[4-(1H-pyrrolo[2,3-b]pyridin-3-yl)-1-piperidyl]sulfonyl]cyclobutanecarboxylic acid (mixture of cis/trans isomers) (54.6 mg, 1 equiv.), N-tert-butylmethylamine (18 μL, 1 equiv.) and DiPEA (63 μL, 2.2 equiv.) in DMF (1.0 mL) was added HATU (62.7 mg, 1.1 equiv.), and the resulting solution was stirred at RT. After one hour, reaction mixture was diluted with EtOAc (20 mL) and washed with NaHCO₃ sat. solution (3×15 mL) and brine (25 mL). The organic layer was dried over Na₂SO₄, filtered and solvent was removed in vacuo. The crude product (mixture of cis and trans isomers) was purified and isomers separated by preparative TLC eluting with 10% MeOH/EtOAc to afford the expected products: cis-isomer (13.38 mg) (LCMS: MW (calcd): 432.58; MS (ES⁺, m/z): 433.8 [M+H]⁺) and trans-isomer (30.44 mg) (LCMS: MW (calcd): 432.58; MS (ES⁺, m/z): 433.8 [M+H]⁺).

Method J: General Procedures for Preparation of Amine Compounds of Formula (I-6), which is Subset of Formula (I) Wherein X is Absent and R² is Other than H, or X is —(CH₂)x¹—

Scheme 6

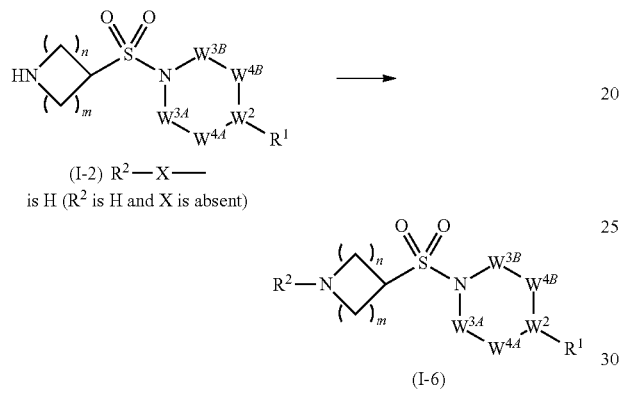

(I-2) R²—X— is H (R² is H and X is absent)

(I-6)

Method J1: N-alkylation

Typically, to a solution of compound of formula (I-2) (1 equiv.) in a suitable solvent or mixture of solvents (typically DMSO, acetonitrile, DMF or DCM), base (2-5 eq) such as DiPEA, TEA or potassium carbonate and alkyl halide (1-5 equiv.) are added. The resulting mixture is stirred at RT to 140° C. for 2-48 h by using conventional heating or for 30-40 min at 110° C. by using microwave irradiation. The expected product of formula (I-6) may be isolated and, if desired, further purified by methods known to one skilled in the art.

Example J1.1

Illustrative Synthesis of 3,5-Dimethyl-4-[2-[3-[[4-(1H-pyrrolo[2,3-b]pyridin-3-yl)-1-piperidyl]sulfonyl]azetidin-1-yl]ethyl]isoxazole (Compound 56)

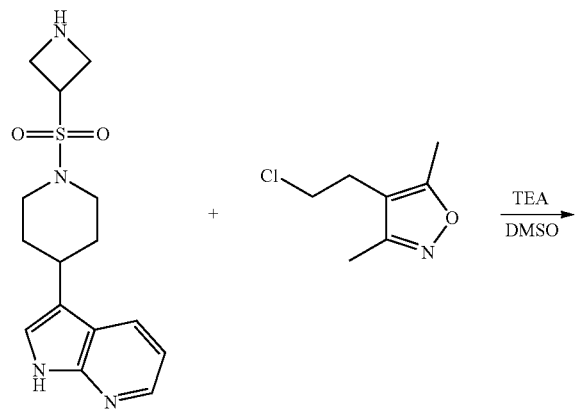

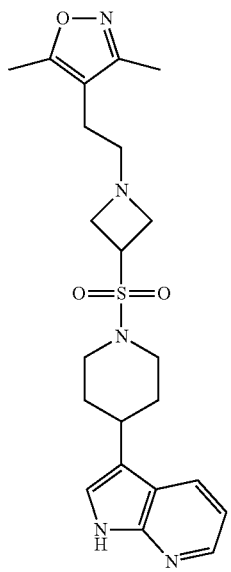

To a solution of 3-[1-(azetidin-3-ylsulfonyl)-4-piperidyl]-1H-pyrrolo[2,3-b]pyridine (32 mg, 1 equiv.) in DMSO (500 TEA (27.9 μL, 2 equiv.) and 4-(2-chloroethyl)-3,5-dimethyl-isoxazole (18 μL, 1.1 equiv.) were added. The reaction mixture was stirred at 100° C. overnight, and then purified by preparative LC-MS (ES⁺ mode, high pH method) to afford the expected product (12.39 mg). LCMS: MW (calcd): 443.56; MS (ES⁺, m/z): 444.73 [M+H]⁺.

Method J2: Reductive Amination

Typically, to a solution (or suspension) of the appropriate compound of formula (I-2) (1 equiv.) in suitable solvent (THF, DCM) or solvent mixtures (DCM/MeOH mixture), the appropriate aldehyde or ketone (1-5 equiv.) is added (in certain cases acetic acid (2 equiv.) is added). The resulting mixture is stirred at room temperature for 30 min to 3 h, then a suitable reducing agent (2-4 equiv.) (NaBH(OAc)₃, NaCNBH₃ or NaBH₄) is added. The reaction mixture is stirred at room temperature to 50° C. for 1 to 24 hours. The expected product of formula (I-6) may be isolated and, if desired further purified, by methods known to one skilled in the art.

Example J2.1

Illustrative Synthesis of 3-[1-[1-(2,2-Dimethylpropyl)azetidin-3-yl]sulfonyl-4-piperidyl]-1H-pyrrolo[2,3-b]pyridine (Compound 143)

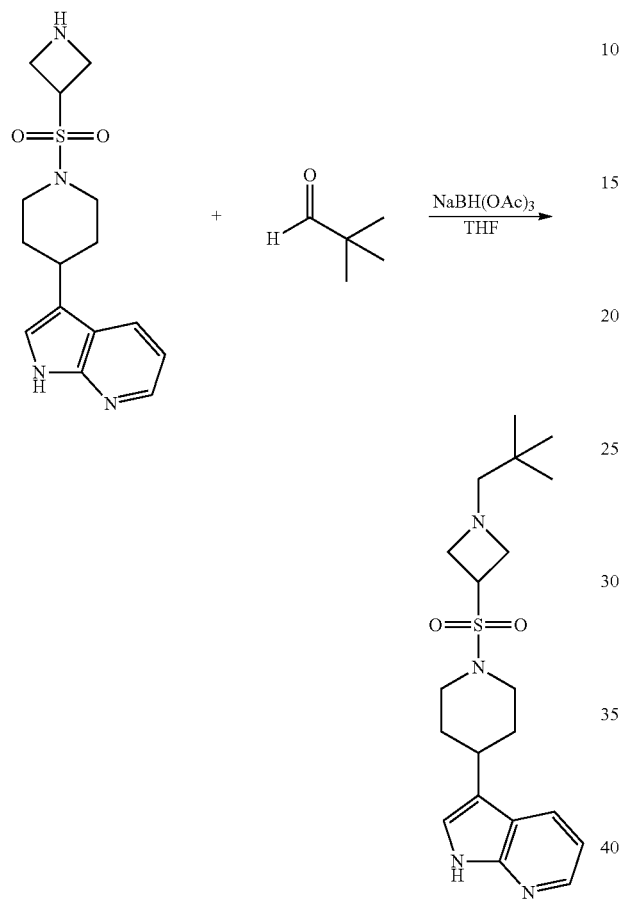

To a stirred suspension of 3-[1-(azetidin-3-ylsulfonyl)-4-piperidyl]-1H-pyrrolo[2,3-b]pyridine (32 mg, 1 equiv.) in dry THF (1 mL), 2,2-dimethylpropanal (17 µL, 1.5 equiv.) was added. The resulting mixture was stirred at RT for 1 h, then NaBH(OAc)$_3$ (42 mg, 2 equiv.) was added and the mixture was stirred at RT for 1 h. The reaction mixture was diluted with EtOAc, then washed with saturated solution of sodium bicarbonate and brine. The organic layer was dried, solvent evaporated and the obtained residue was purified by preparative LC-MS (ES$^+$ mode, high pH method) to afford the expected product (20 mg). LCMS: MW (calcd): 390.54; MS (ES$^+$, m/z): 391.86 [M+H]$^+$.

Method J3: S$_N$Ar

Typically, to a solution of the compound of formula (I-2) (1 equiv.) in a suitable solvent or mixture of solvents (typically DMSO, acetonitrile, DMF or THF), base (2-5 equiv.) such as DiPEA, TEA, potassium carbonate, or caesium carbonate, and aryl halide (0.9-3 equiv.) are added and the resulting mixture is stirred at 80-150° C. for 1-48 h. The expected product of formula (I-6) may be isolated and, if desired, further purified by methods known to one skilled in the art.

Example J3.1

Illustrative Synthesis of 3-[1-[1-(2-Pyridyl)azetidin-3-yl]sulfonyl-4-piperidyl]-1H-pyrrolo[2,3-b]pyridine (Compound 118)

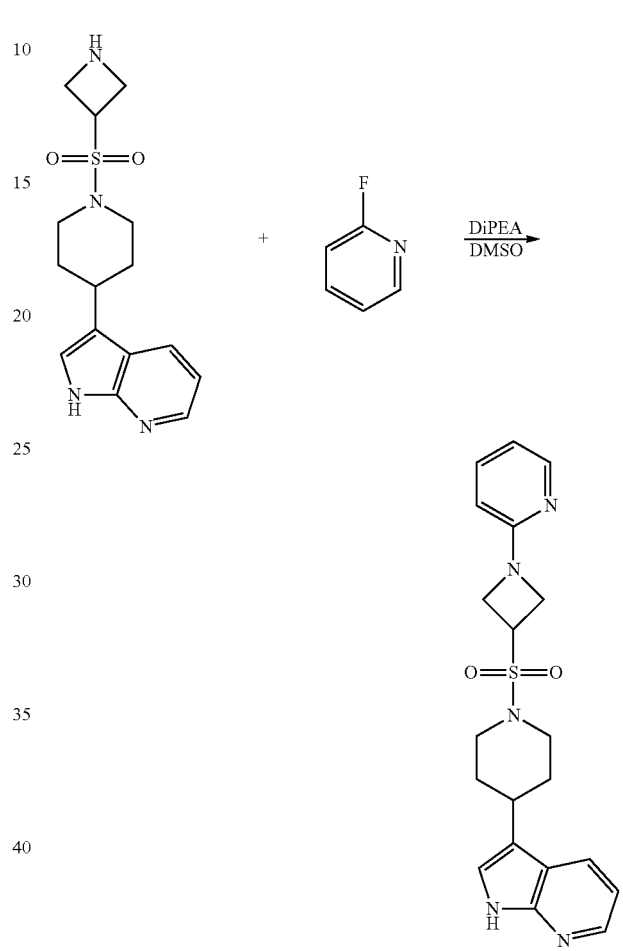

To a solution of 3-[1-(azetidin-3-ylsulfonyl)-4-piperidyl]-1H-pyrrolo[2,3-b]pyridine (32 mg, 1 equiv.) in DMSO (0.5 mL) DIPEA (52 µL, 3 equiv.) was added, followed by 2-fluoropyridine (26 µL, 3 equiv.). The resulting mixture was stirred at 100° C. overnight, diluted with acetonitrile, filtered and purified by preparative LC-MS (ES$^+$ mode, high pH method) to afford the expected product (17 mg). LCMS: MW (calcd): 397.49; MS (ES$^+$, m/z): 398 [M+H]$^+$.

Method J4: Buchwald-Hartwig Amination Reaction

Typically, to a solution of the compound of formula (I-2) (1.1 equiv.) in a suitable solvent or mixture of solvents (typically THF or toluene), aryl bromide (1 equiv.), (±)-BINAP (0.075 equiv.), TEA (0.5 equiv), and KOtBu (4 equiv) are added. The solution is degassed by bubbling Ar and Pd$_2$(dba)$_3$.CHCl$_3$ (0.025 equiv.) is added. The resulting mixture is stirred at 80-120° C. for 18 h. The expected product of formula (I-6) may be isolated and purified by methods familiar to one skilled in the art.

Example J4.1

Illustrative Synthesis of 4-[1-[(1-Phenyl-4-piperidyl)sulfonyl]-4-piperidyl]pyridine (Compound 113)

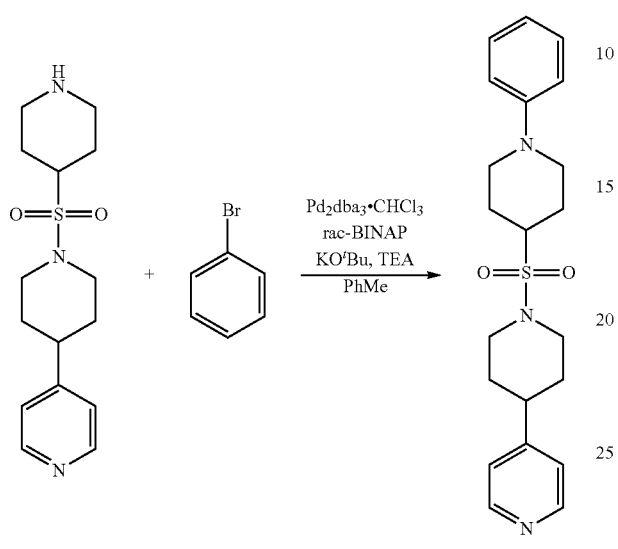

To a solution of 4-[1-(4-piperidylsulfonyl)-4-piperidyl]pyridine (50 mg, 1.1 equiv.) in toluene (3.5 mL), bromobenzene (15.36 µL, 1 equiv.), (±)-BINAP (6.82 mg, 0.075 equiv.), TEA (10.17 µL, 0.5 equiv), and KOtBu (65.52 mg, 4 equiv) were added. Reaction mixture was degassed with Ar and $Pd_2(dba)_3 \cdot CHCl_3$ (3.78 mg, 0.025 equiv.) was added. Reaction mixture was heated to 80° C., and left to stir for 18 h. Crude reaction mixture was purified by preparative TLC in DCM-MeOH 9:1. Resulting product (48.36 mg) was further purified by preparative LC-MS ($ES^+$ mode, high pH method) to yield the expected compound (21.3 mg). LCMS: MW (calcd): 385.52; MS ($ES^+$, m/z): 386.2 $[M+H]^+$.

Method Df: General Procedures for Preparation of Sulfonamide Compounds of Formula (I-7), which is Subset of Formula (I) Wherein $R^2$—X— is $R^2$—SO2-

Scheme 7

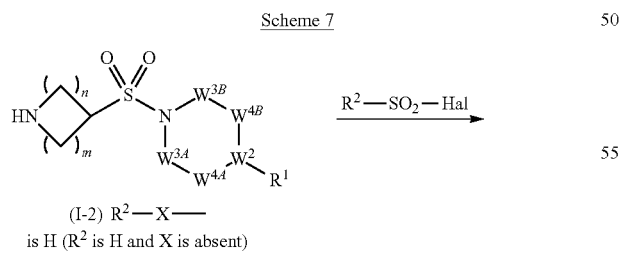

(I-2) $R^2$—X—
is H ($R^2$ is H and X is absent)

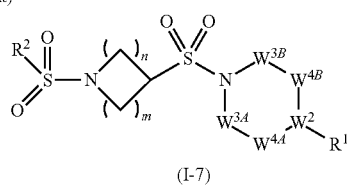

(I-7)

Typically, to a solution of appropriate compound of formula (I-2) (1 equiv.) in THF (or any other suitable solvent), TEA (2-8 equiv.), or any other suitable base and corresponding sulfonyl halide of formula $R^2$—$SO_2$—Hal (suitably sulfonyl chloride) (1-1.2 equiv.) are added. The reaction mixture is stirred at room temperature for 0.25-24 h. The expected product of formula (I-7) may be isolated and, if desired, further purified by methods known to one skilled in the art.

Example D1.1

Illustrative Synthesis of 3-[1-(1-Methylsulfonylazetidin-3-yl)sulfonyl-4-piperidyl]-1H-pyrrolo[2,3-b]pyridine (Compound 91)

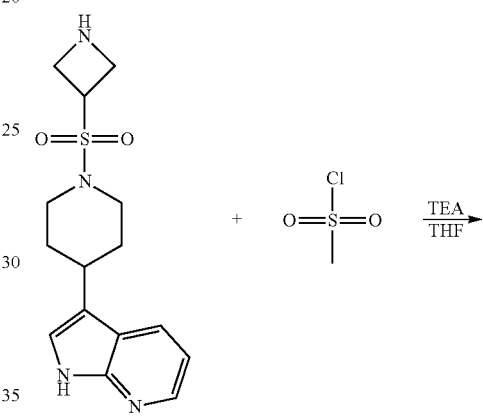

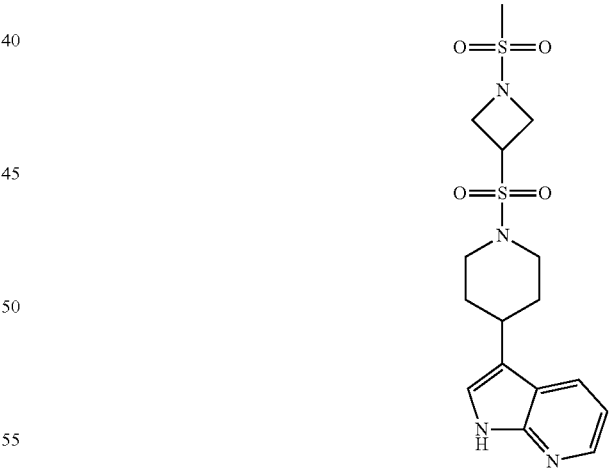

To the suspension of 3-[1-(azetidin-3-ylsulfonyl)-4-piperidyl]-1H-pyrrolo[2,3-b]pyridine (50 mg, 1 equiv.) and TEA (87 µL, 4 equiv.) in dry THF (2 mL) methanesulfonyl chloride (13.3 µL, 1.1 equiv.) was added and the resulting mixture was stirred at RT for 45 min. Solvent was evaporated to dryness, the residue was suspended in MeOH (2 mL) and the precipitate was filtered off to afford the expected product (37 mg). LCMS: MW (calcd): 398.50; MS ($ES^+$, m/z): 399.1 $[M+H]^+$.

145

Method W: Urea Methylation—General Procedure for Preparation of Compounds of Formula (I-8), which is Subset of Formula (I)

Scheme 3

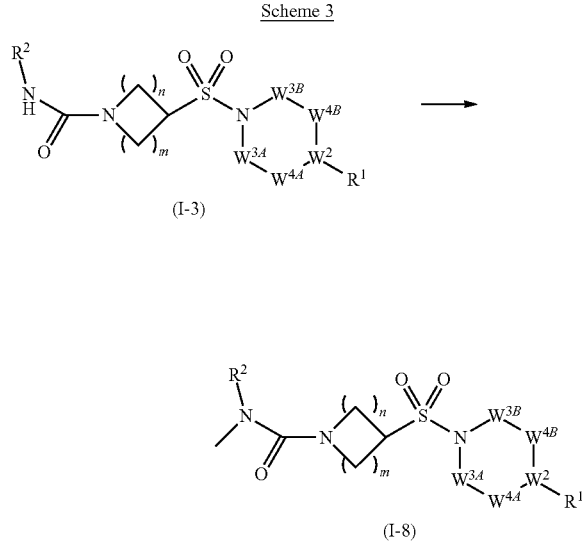

(I-3)

(I-8)

Typically, to a solution of the compound of formula (I-3) (1 equiv.) in suitable solvent such as DMF or THF at 0° C. or RT is added NaH 60% in paraffin oil (1.2-3 equiv.), followed by MeI (1.1-5 equiv.). Reaction mixture is stirred at RT for 15 min to 4 h. The expected product of formula (I-8) may be isolated and, if desired, further purified by methods familiar to one skilled in the art.

Example W1.1

Illustrative Synthesis of N-(4-fluoro-2-methyl-phenyl)-3-[(4-furo[3,2-b]pyridin-3-yl-1-piperidyl)sulfonyl]-N-methyl-azetidine-1-carboxamide (Compound 399)

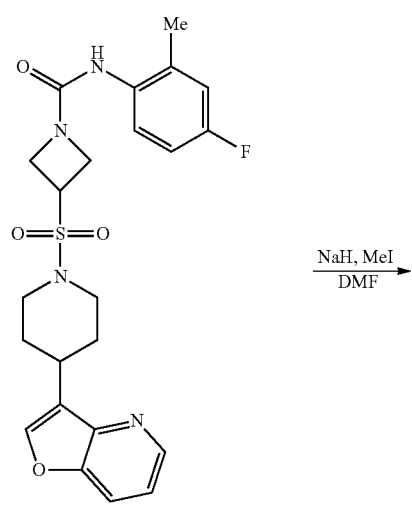

146

-continued

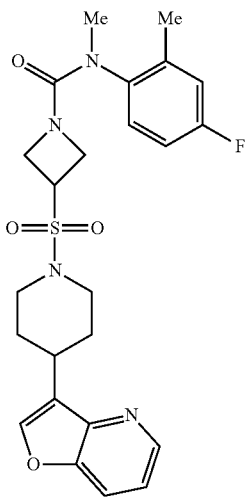

To the solution of N-(4-fluoro-2-methyl-phenyl)-3-[(4-furo[3,2-b]pyridin-3-yl-1-piperidyl)sulfonyl]azetidine-1-carboxamide (103.1 mg, 1 equiv.) in DMF (3.0 mL) at 0° C. NaH (26.2 mg, 3 equiv.) was added, followed by MeI (67.8 μL, 5 equiv.). Reaction mixture was stirred at RT for 15 min. Reaction mixture was transferred to a separatory funnel containing distilled water. Mixture was extracted with EtOAc (3×150 mL), combined organic extracts were dried over Na$_2$SO$_4$, were filtered, and solvent was removed in vacuo to yield the crude product, which was purified by preparative HPLC to afford the expected product (38.9 mg). LCMS: MW (calcd): 486.6; MS (ES+, m/z): 487.7 [M+H]$^+$.

Scheme 8

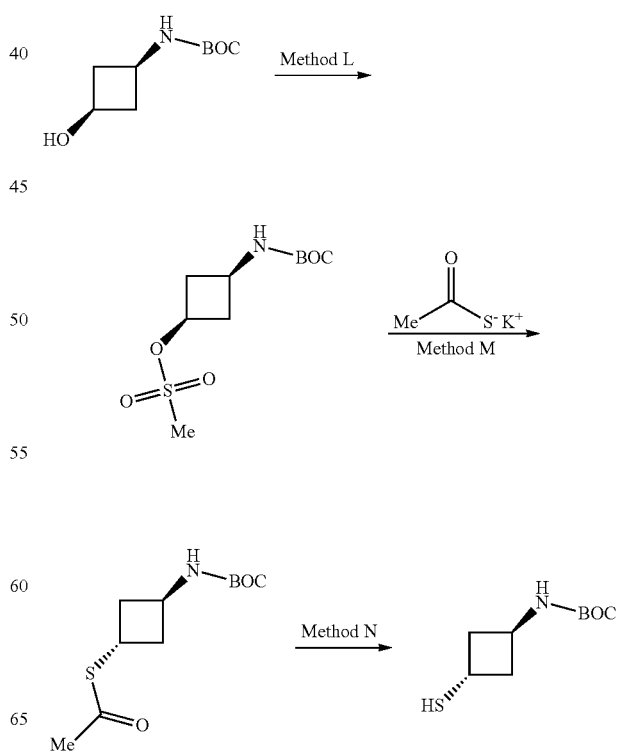

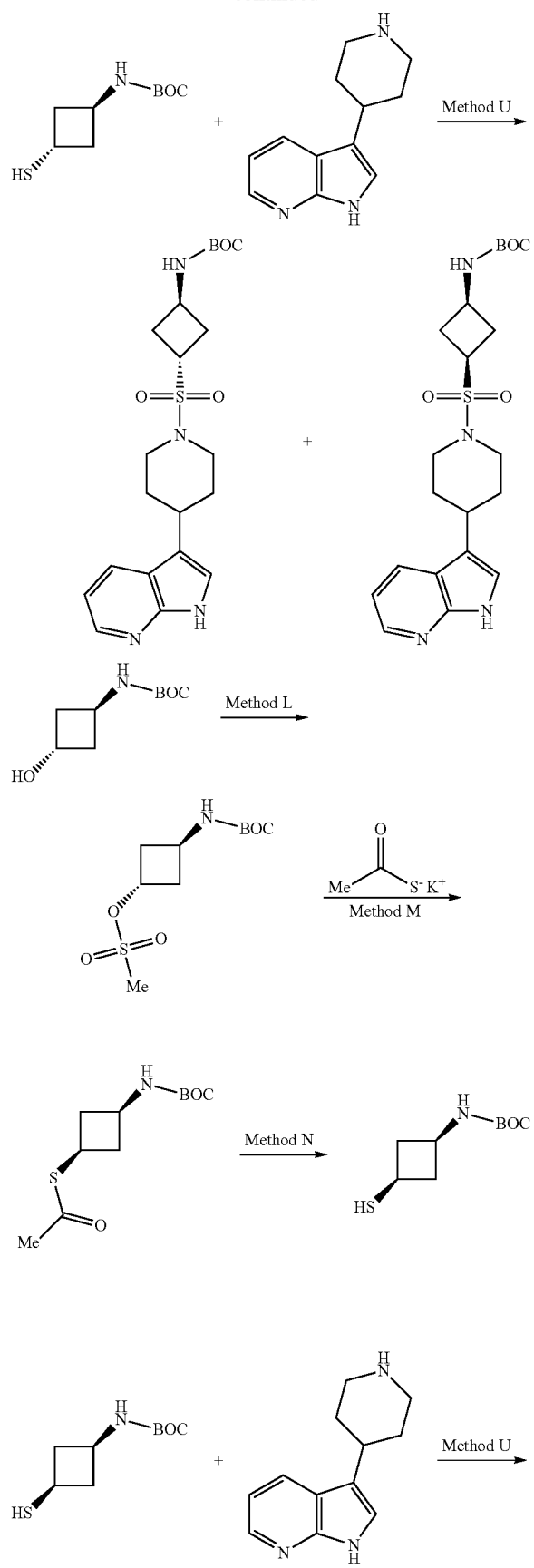

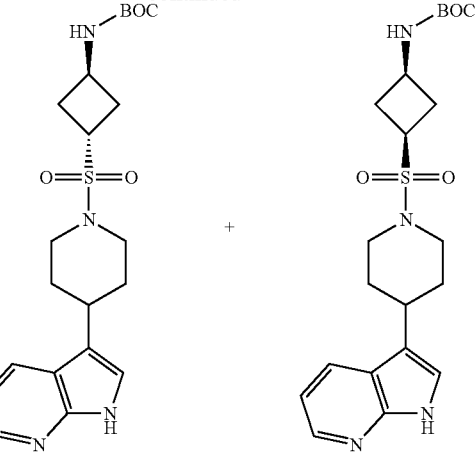

Method L: Methanesulfonyl Ester Synthesis

Solution of the alcohol (1.0 equiv.) and DiPEA (1.4 equiv.) in DCM (0.2 M) at 0° C. is treated with methanesulfonyl chloride (1.25 equiv.). Reaction mixture is stirred at RT for 1 h. The expected methanesulfonyl ester may be isolated and, if desired, further purified by methods known to one skilled in the art.

Example L1.1

Illustrative Synthesis of trans-(3-(tert-butoxycarbonylamino)cyclobutyl) methanesulfonate

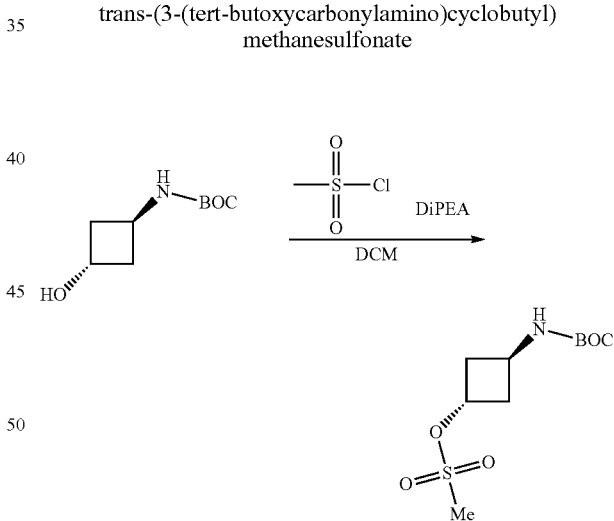

Solution of trans-tert-butyl N-(3-hydroxycyclobutyl)carbamate (500.0 mg, 1 equiv.) and DiPEA (651 μL, 1.4 equiv.) in DCM (14.0 mL) at 0° C. was treated with methanesulfonyl chloride (258.4 μL, 1.25 equiv.). Reaction mixture was stirred at RT for 1 h. Reaction was analysed by TLC (60% EtOAc/heptane) which showed complete conversion to the expected product. Reaction mixture was transferred to a separatory funnel containing distilled water, and was extracted with EtOAc (3×150 mL). Combined organic extracts were dried over $Na_2SO_4$, were filtered, and solvent was removed in vacuo to yield trans-(3-(tert-butoxycarbonylamino)cyclobutyl) methanesulfonate (694.5 mg).

Method M: Thioester Synthesis

To the degassed solution of the methanesulfonate ester (1.0 equiv.) in DMF (0.13 M) at RT is added potassium thioacetate (2.0 equiv.). Reaction mixture is degassed with Ar, and is stirred at 90° C. for 18 h. The expected thioacetate product with inversion of stereochemistry may be isolated and, if desired, further purified by methods known to one skilled in the art.

Example M1.1

Illustrative Synthesis of cis-(3-(tert-butoxycarbonylamino)cyclobutyl) thioacetate

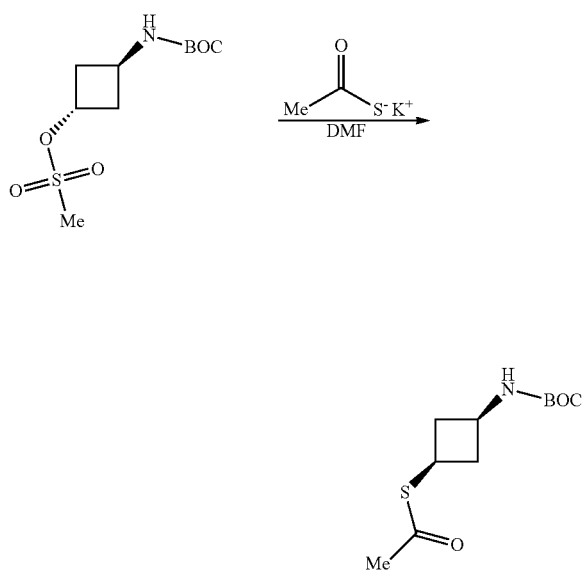

To the degassed solution of trans-(3-(tert-butoxycarbonylamino)cyclobutyl) methanesulfonate (354.5 mg, 1 equiv.) in DMF (10.0 mL) at RT was added potassium thioacetate (305.2 mg, 2 equiv.). Reaction mixture was degassed with Ar, and was stirred at 90° C. for 18 h. Reaction mixture was cooled to RT, was transferred to a separatory funnel containing distilled water, and the mixture was extracted with EtOAc (3×150 mL). Combined organic extracts were dried over Na$_2$SO$_4$, mixture was filtered, and solvent was removed in vacuo to yield the crude product (578 mg). Crude product was purified chromatographically to yield cis-(3-(tert-butoxycarbonylamino)cyclobutyl) thioacetate (248.3 mg, 75% yield, NMR consistent with pure cis isomer).

Method N: Thioester Hydrolysis

To the solution of the thioester (1.0 equiv.) in THF/MeOH 2:1 (0.03 M) at RT was added 1N NaOH (6.0 equiv.). Reaction mixture is stirred at RT for 20 min. The expected thiol product may be isolated and, if desired, further purified by methods known to one skilled in the art.

Example N1.1

Illustrative Synthesis of cis-tert-butyl-N-(3-sulfanylcyclobutyl)carbamate

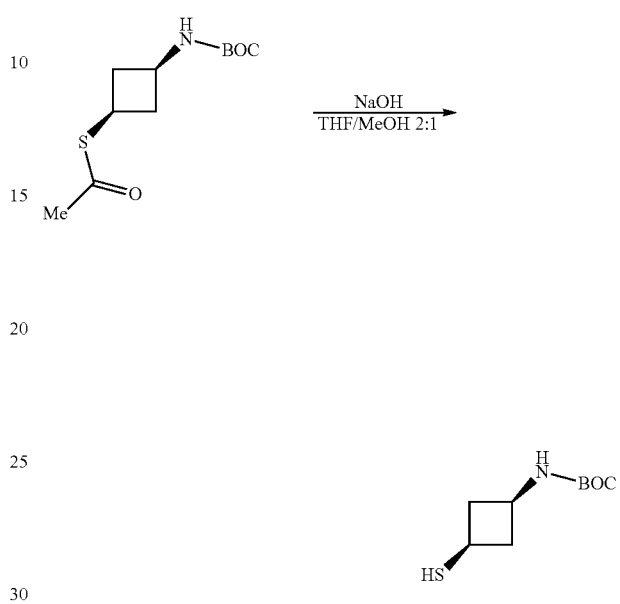

To the solution of cis-(3-(tert-butoxycarbonylamino)cyclobutyl) thioacetate (174.0 mg, 0.709 mmol) in THF/MeOH 2:1 (25.0 mL) at RT was added 1N NaOH (4.26 mL, 6 equiv.). Reaction mixture was stirred at RT for 20 min. Reaction mixture was analysed by TLC (20% EtOAc/cyclohexane) which showed complete consumption of the starting material. Reaction mixture was transferred to a separatory funnel containing distilled water and was extracted with EtOAc (2×500 mL). Combined organic extracts were dried over Na$_2$SO$_4$, and solvent was removed in vacuo to yield cis-tert-butyl-N-(3-sulfanylcyclobutyl)carbamate (152 mg, pure cis isomer by NMR analysis).

Method U: Thiol Oxidation/Sulphonamide Synthesis

To the stirred solution of the thiol (1.0 equiv.), quaternary ammonium chloride (such as BnMe$_3$NCl or nBu$_4$NCl) (4.0 equiv.), and water (2.5 equiv.) in acetonitrile (0.05 M) at 0° C. is added NCS (3.0 equiv.) and the reaction mixture is stirred at 0° C. for 45 min. Amine is added (1.1-1.4 equiv.) as a solution in acetonitrile (0.02-0.13 M). To the resulting solution is added TEA (5.5 equiv.), and the reaction mixture is stirred at RT for 20 min. The expected diastereoisomeric sulphonamide product(s) may be isolated and, if desired, further purified by methods known to one skilled in the art.

Example U1.1

Illustrative Synthesis of trans-tert-butyl-N-[3-[[4-(1H-pyrrolo[2,3-b]pyridin-3-yl)-1-piperidyl]sulfonyl]cyclobutyl]carbamate (Compound 357) and cis-tert-butyl-N-[3-[[4-(1H-pyrrolo[2,3-b]pyridin-3-yl)-1-piperidyl]sulfonyl]cyclobutyl]carbamate (Compound 358)

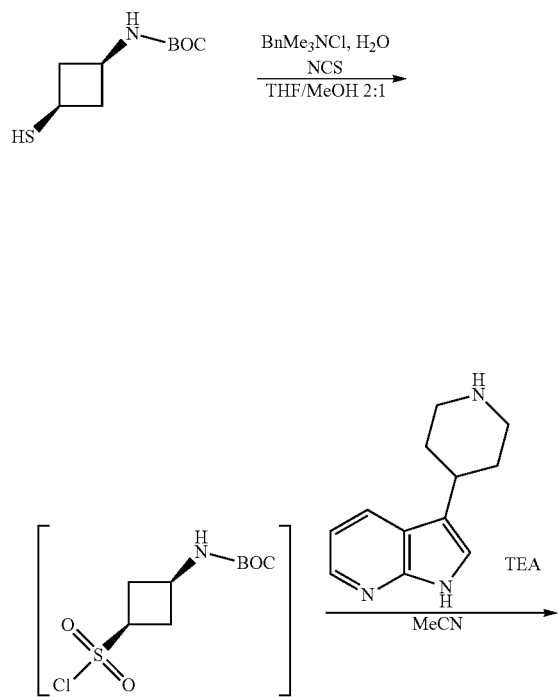

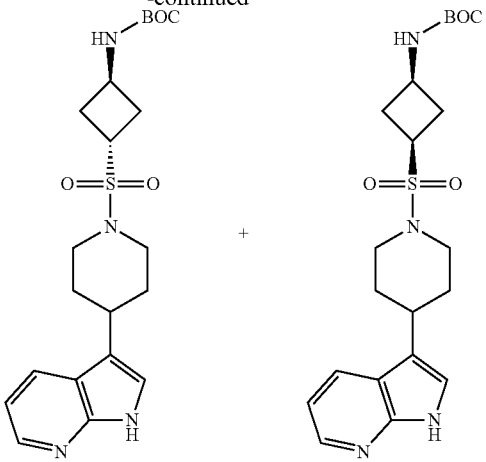

To the stirred solution of cis-tert-butyl-N-(3-sulfanylcyclobutyl)carbamate (150.0 mg, 1 equiv.), BnMe₃NCl (548.0 mg, 4 equiv.), and water (33.2 μL, 2.5 equiv.) in acetonitrile (15.0 mL) at 0° C. was added NCS (295.6 mg, 3 equiv.) and the reaction mixture was stirred at 0° C. for 45 min. 3-(4-Piperidyl)-1H-pyrrolo[2,3-b]pyridine was added (208.0 mg, 1.4 equiv.) as a solution in acetonitrile (8.0 mL). To the resulting solution was added TEA (566.6 μL, 5.5 equiv.), and the reaction mixture was stirred at RT for 20 min. Reaction mixture was transferred to a separatory funnel containing distilled water and the mixture was extracted with EtOAc (3×150 mL). Combined organic extracts were dried over Na₂SO₄, were filtered, and solvent was removed in vacuo to yield the crude product (355 mg). Crude product was purified by preparative HPLC to yield two diastereomers: trans-isomer (29.3 mg) (LCMS: MW (calcd): 434.55; MS (ES⁺, m/z): 435.15 [M+H]⁺) and cis-isomer (40.9 mg) (LCMS: MW (calcd): 434.55; MS (ES⁺, m/z): 435.17 [M+H]⁺).

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 1 | 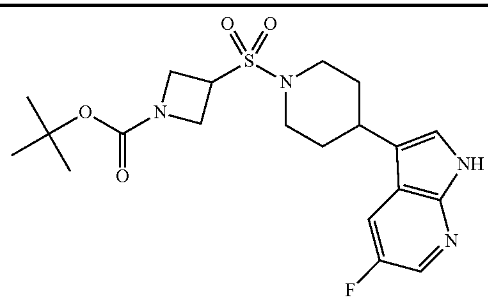 | 439.1 | ¹H NMR (400 MHz, Chloroform-d): δ = 9.03 (s, 1H), 8.19-8.15 (m, 1H), 7.57 (dd, J = 8.9, 2.6 Hz, 1H), 7.13 (d, J = 2.4 Hz, 1H), 4.27-4.21 (m, 2H), 4.17 (t, J = 8.8 Hz, 2H), 4.00-3.89 (m, 3H), 2.97 (td, J = 12.5, 2.4 Hz, 2H), 2.87 (tt, J = 12.0, 3.6 Hz, 1H), 2.08 (d, J = 13.3 Hz, 2H), 1.78 (qd, J = 12.5, 4.1 Hz, 2H), 1.43 (s, 9H) ppm. | 5-fluoro-1H-pyrrolo[2,3-b]pyridine | General method A2 using KOtBu, B1 using Pd/C, Ci using TFA, D using tert-butyl 3-chlorosulfonyl azetidine-1-carboxylate | tert-butyl 3-[4-(5-fluoro-1H-pyrrolo[2,3-b]pyridin-3-yl)piperidin-1-yl]sulfonylazetidine-1-carboxylate |
| 2 | 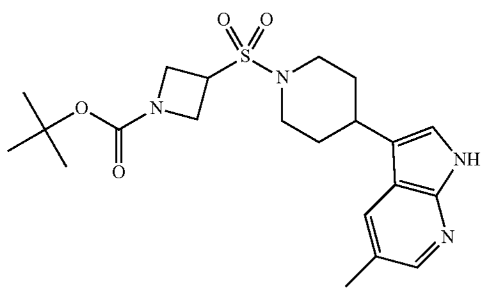 [SMILES: Cc1cnc2[nH]cc(C3CCN(S(=O)(=O)C4CN(C(=O)OC(C)(C)C)C4)CC3)c2c1] | 435.2 | ¹H NMR (600 MHz, Chloroform-d): δ = 8.83 (s, 1H), 8.14-8.11 (m, 1H), 7.70-7.67 (m, 1H), 7.01 (d, J = 2.1 Hz, 1H), 4.25 (dd, J = 9.4, 5.8 Hz, 2H), 4.17 (t, J = 8.9 Hz, 2H), 3.99-3.90 (m, 3H), 2.97 (td, J = 12.4, 2.4 Hz, 2H), 2.89 (tt, J = 11.9, 3.6 Hz, 1H), 2.42 (s, 3H), 2.09 (dd, J = 14.2, 3.4 Hz, 2H), 1.80 (qd, J = 12.4, 4.1 Hz, 2H), 1.43 (s, 9H) ppm. | 5-methyl-1H-pyrrolo[2,3-b]pyridine | General method A2 using KOtBu, B1 using Pd/C, D using TFA, D using tert-butyl 3-chlorosulfonyl azetidine-1-carboxylate | tert-butyl 3-[4-(5-methyl-1H-pyrrolo[2,3-b]pyridin-3-yl)piperidin-1-yl] sulfonylazetidine-1-carboxylate |
| 3 | 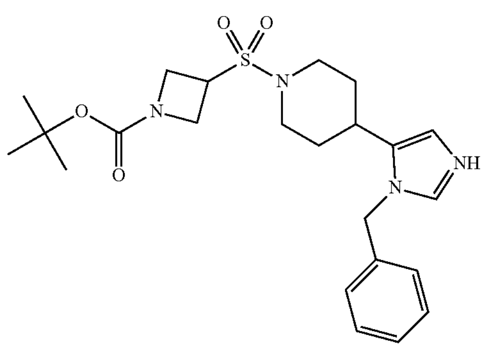 [SMILES: CC(C)(C)OC(=O)N1CC(S(=O)(=O)N2CCC(c3cncn3Cc3ccccc3)CC2)C1] | 461.2 | ¹H NMR (400 MHz, Chloroform-d): δ = 7.47 (s, 1H), 7.36-7.27 (m, 3H), 7.03-6.97 (m, 2H), 6.86 (s, 1H), 5.07 (s, 2H), 4.20-4.02 (m, 4H), 3.90-3.76 (m, 3H), 2.79-2.68 (m, 2H), 2.44 (t, J = 11.6 Hz, 1H), 1.73 (d, J = 13.0 Hz, 2H), 1.67-1.55 (m, 2H), 1.42 (s, 9H) ppm. | 1-benzyl-5-bromo-imidazole | General method A1 using K₂CO₃, B1 using Pd/C, Ci using HCl in dioxane, D using tert-butyl 3-chlorosulfonyl azetidine-1-carboxylate | tert-butyl 3-[4-(3-benzylimidazol-4-yl)piperidin-1-yl]sulfonylazetidine-1-carboxylate |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 4 | 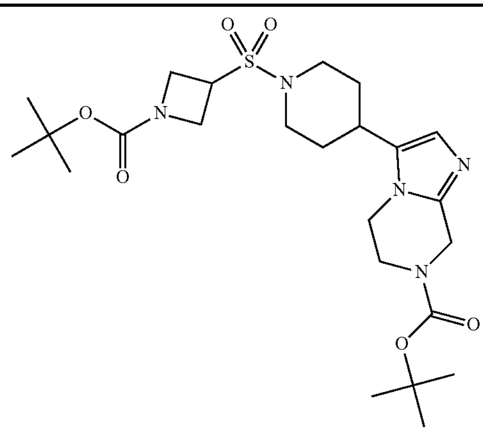 | 526.2 | ¹H NMR (400 MHz, Chloroform-d): δ = 6.74 (s, 1H), 4.65 (s, 2H), 4.25-4.10 (m, 4H), 3.95-3.87 (m, 3H), 3.83 (s, 4H), 2.92 (t, J = 12.1 Hz, 2H), 2.57 (tt, J = 11.7, 3.5 Hz, 1H), 1.96 (d, J = 13.4 Hz, 2H), 1.76-1.64 (m, 2H), 1.47 (s, 9H), 1.42 (s, 9H) ppm. | tert-butyl 3-bromo-6,8-dihydro-5H-imidazo[1,2-a]pyrazine-7-carboxylate | General method A1 using K₂CO₃, B1 using Pd/C, Ci using HCl in dioxane, D using tert-butyl 3-chlorosulfonyl azetidine-1-carboxylate | tert-butyl 3-[1-[[2-methylpropan-2-yl]oxycarbonyl] azetidin-3-yl]sulfonylpiperidin-4-yl]-6,8-dihydro-5H-imidazo[1,2-a]pyrazine-7-carboxylate |
| 5 | 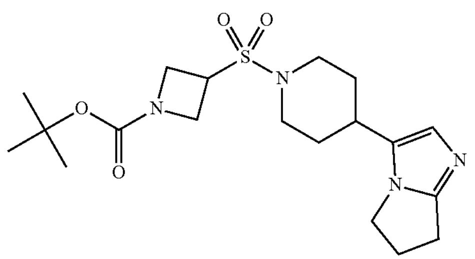 [SMILES: CC(C)(C)OC(=O)N1CC(S(=O)(=O)N2CCC(c3cnc4n3CCC4)CC2)C1] | 411.2 | ¹H NMR (300 MHz, Chloroform-d): δ = 6.88 (s, 1H), 4.25-4.12 (m, 4H), 4.04-3.97 (m, 2H), 3.97-3.88 (m, 3H), 3.11-3.03 (m, 2H), 2.99-2.89 (m, 2H), 2.70 (q, J = 7.7 Hz, 3H), 2.00 (d, J = 13.2 Hz, 2H), 1.71 (qd, J = 12.2, 8.2 Hz, 2H), 1.44 (s, 9H) ppm. | 3-bromo-6,7-dihydro-5H-pyrrolo[1,2-a]imidazole | General method A1 using K₂CO₃, B1 using Pd/C, Ci using HCl in dioxane, D using tert-butyl 3-chlorosulfonyl azetidine-1-carboxylate | tert-butyl 3-[4-(6,7-dihydro-5H-pyrrolo[1,2-a]imidazol-3-yl)piperidin-1-yl]sulfonylazetidine-1-carboxylate |
| 6 | 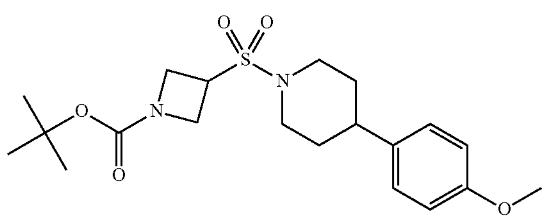 [SMILES: COc1ccc(C2CCN(S(=O)(=O)C3CN(C(=O)OC(C)(C)C)C3)CC2)cc1] | 433.1 (M + Na) | ¹H NMR (500 MHz, CHLOROFORM-d): δ = 7.11 (d, J = 8.5 Hz, 2H), 6.87 (d, J = 8.5 Hz, 2H), 4.23-4.30 (m, 2H), 4.14-4.22 (m, 2H), 3.89-4.01 (m, 3H), 3.80 (s, 3H), 2.91 (t, J = 11.7 Hz, 2H), 2.53-2.63 (m, 1H), 1.91 (d, J = 12.5 Hz, 2H), 1.66-1.79 (m, 2H), 1.46 (s, 9H) ppm. | 4-(4-methoxyphenyl)-piperidine | General method D using tert-butyl 3-chlorosulfonyl azetidine-1-carboxylate | tert-butyl 3-[4-(4-methoxyphenyl) piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 7 | 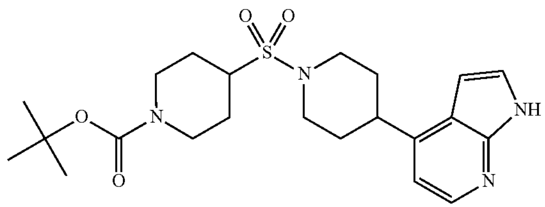 [SMILES: CC(C)(C)OC(=O)N1CCC(S(=O)(=O)N2CCC(c3ccnc4[nH]ccc34)CC2)CC1] | 449.7 | ¹H NMR (500 MHz, CHLOROFORM-d): δ = 9.26 (br. s., 1H), 8.35 (br. s., 1H), 7.33 (d, J = 3.4 Hz, 1H), 6.96 (br. s., 1H), 6.57 (d, J = 2.7 Hz, 1H), 4.16-4.42 (m, 2H), 4.02 (d, J = 12.8 Hz, 2H), 3.02-3.17 (m, 4H), 2.75 (br. s., 2H), 2.10 (d, J = 12.8 Hz, 2H), 1.90-2.06 (m, 4H), 1.70-1.82 (m, 2H), 1.47 (s, 9H) ppm. | 4-bromo-1-(p-tolylsulfonyl)-pyrrolo[2,3-b]pyridine | General method A1 using K₂CO₃, B1 using Pd/C, C1 using HCl in dioxane, D using tert-butyl 4-chlorosulfonylpiper-idine-1-carboxylate, F | tert-butyl 4-[4-(1H-pyrrolo[2,3-b]pyridin-4-yl)piperidin-1-yl]sulfonylpiper-idine-1-carboxylate |
| 8 | 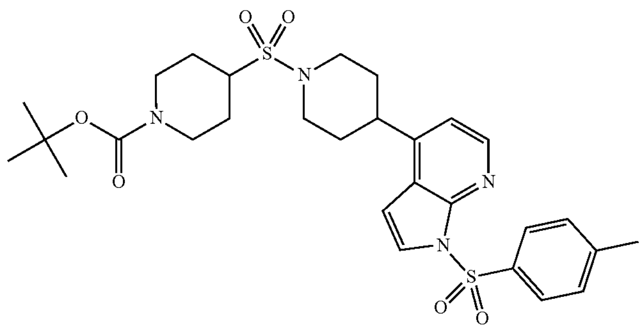 [SMILES: Cc1ccc(S(=O)(=O)n2ccc3c(C4CCN(S(=O)(=O)C5CCN(C(=O)OC(C)(C)C)CC5)CC4)ccnc32)cc1] | 603.8 | ¹H NMR (500 MHz, CHLOROFORM-d): δ = 8.37 (d, J = 4.9 Hz, 1H), 8.09 (d, J = 8.2 Hz, 2H), 7.73 (d, J = 4.0 Hz, 1H), 7.28 (d, J = 8.4 Hz, 2H), 7.00 (d, J = 4.9 Hz, 1H), 6.63 (d, J = 4.3 Hz, 1H), 4.27 (br. s., 2H), 3.98 (d, J = 13.1 Hz, 2H), 2.94-3.12 (m, 4H), 2.73 (br. s., 2H), 2.38 (s, 3H), 2.04-2.10 (m, 2H), 1.81-1.96 (m, 4H), 1.72 (qd, J = 12.5, 4.4 Hz, 2H), 1.47 (s, 9H) ppm. | 4-bromo-1-(p-tolylsulfonyl)-pyrrolo[2,3-b]pyridine | General method A1 using K₂CO₃, B1 using Pd/C, C1 using HCl in dioxane, D using tert-butyl 4-chlorosulfonylpiper-idine-1-carboxylate | tert-butyl 4-[4-[1-(4-methylphenyl)-sulfonylpyrrolo[2,3-b]pyridin-4-yl]piperidin-1-yl]sulfonylpiper-idine-1-carboxylate |
| 9 | 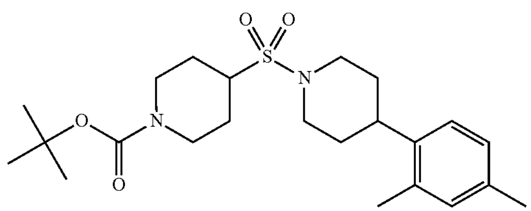 [SMILES: Cc1ccc(C2CCN(S(=O)(=O)C3CCN(C(=O)OC(C)(C)C)CC3)CC2)c(C)c1] | 437.8 | ¹H NMR (400 MHz, CHLOROFORM-d): δ = 7.03-7.07 (m, 1H), 6.94-7.01 (m, 2H), 4.25 (d, J = 12.8 Hz, 2H), 2.93-3.11 (m, 3H), 2.75-2.84 (m, 1H), 2.70 (br. s., 2H), 2.28 (s, 3H), 2.27 (s, 3H), 2.05 (d, J = 12.8 Hz, 2H), 1.64-1.84 (m, 6H), 1.45 (s, 9H) ppm. | (2,4-dimethyl-phenyl)boronic acid | General method A3, B1 using Pd/C, C1 using HCl in dioxane, D using tert-butyl 4-chlorosulfonylpiper-idine-1-carboxylate | tert-butyl 4-[4-(2,4-dimethylphenyl)piperidin-1-yl]sulfonylpiper-idine-1-carboxylate |
| 10 | 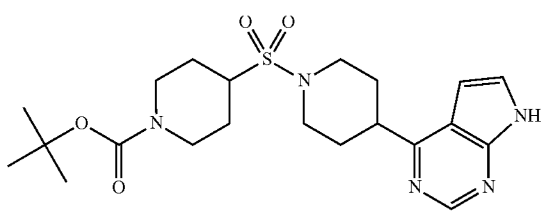 [SMILES: CC(C)(C)OC(=O)N1CCC(S(=O)(=O)N2CCC(c3ncnc4[nH]ccc34)CC2)CC1] | 450.6 | ¹H NMR (400 MHz, CHLOROFORM-d): δ = 13.68 (br. s., 1H), 9.44 (s, 1H), 7.81 (s, 1H), 7.00 (s, 1H), 4.28 (br. s., 2H), 4.06 (d, J = 11.9 Hz, 2H), 3.81-3.98 (m, 1H), 3.04-3.27 (m, 3H), 2.76 (br. s., 2H), 2.39 (br. s., 2H), 2.03-2.24 (m, 4H), 1.67-1.81 (m, 2H), 1.46 (s, 9H) ppm. | 4-chloro-7H-pyrrolo[2,3-d]pyrimidine | General method E, A1 using K₂CO₃, B1 using Pd/C, C1 using HCl in dioxane, D using tert-butyl 4-chlorosulfonylpiper-idine-1-carboxylate, F | tert-butyl 4-[4-(7H-pyrrolo[2,3-d]pyrimidin-4-yl)piperidin-1-yl]sulfonylpiper-idine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 11 | 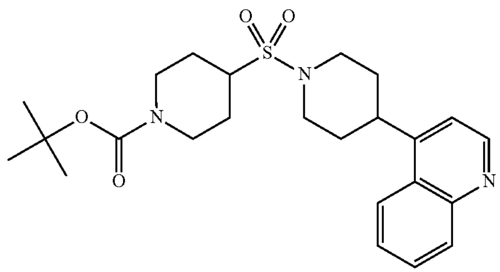 [SMILES: CC(C)(C)OC(=O)N1CCC(S(=O)(=O)N2CCC(c3ccnc4ccccc34)CC2)CC1] | 460.7 | 1H NMR (500 MHz, CHLOROFORM-d): δ = 8.95 (d, J = 5.2 Hz, 1H), 8.66 (d, J = 7.9 Hz, 1H), 8.21 (d, J = 8.5 Hz, 1H), 7.95 (t, J = 7.8 Hz, 1H), 7.81 (t, J = 7.8 Hz, 1H), 7.59 (d, J = 4.9 Hz, 1H), 4.30 (br. s., 2H), 4.05-4.12 (m, 2H), 3.65 (t, J = 12.1 Hz, 1H), 3.15-3.26 (m, 2H), 3.11 (tt, J = 11.9, 3.6 Hz, 1H), 2.75 (br. s., 2H), 2.10 (d, J = 13.1 Hz, 4H), 1.98 (qd, J = 12.4, 4.0 Hz, 2H), 1.75 (qd, J = 12.5, 4.4 Hz, 2H), 1.48 (s, 9H) ppm. | 4-(4-piperidyl)-quinoline dihydrochloride salt | General method D using tert-butyl 4-chlorosulfonylpiperidine-1-carboxylate | tert-butyl 4-(4-quinolin-4-ylpiperidin-1-yl]sulfonylpiperidine-1-carboxylate |
| 12 | 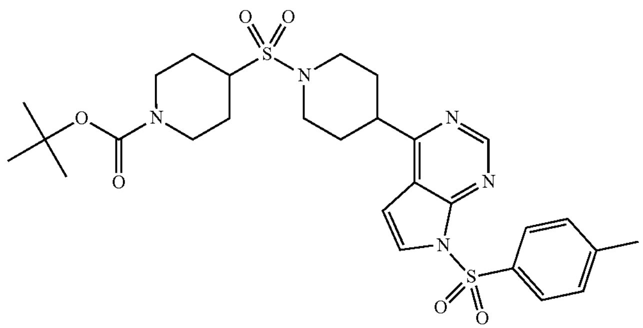 [SMILES: Cc1ccc(S(=O)(=O)n2ccc3c(C4CCN(S(=O)(=O)C5CCN(C(=O)OC(C)(C)C)CC5)CC4)ncnc32)cc1] | 604.7 | 1H NMR (500 MHz, CHLOROFORM-d): δ = 8.10-8.15 (m, 2H), 7.87-7.91 (m, 1H), 7.32-7.39 (m, 3H), 6.82-6.87 (m, 1H), 4.26 (br. s., 2H), 3.88-4.01 (m, 2H), 2.97-3.16 (m, 2H), 2.73 (br. s., 2H), 2.40-2.47 (m, 5H), 2.12-2.22 (m, 2H), 2.03-2.12 (m, 2H), 1.97-2.04 (m, 2H), 1.66-1.77 (m, 2H), 1.46 (s, 9H) ppm. | 4-chloro-7H-pyrrolo[2,3-d]pyrimidine | General method E, A1 using K2CO3, B1 using Pd/C, Ci using HCl in dioxane, D using tert-butyl 4-chlorosulfonylpiperidine-1-carboxylate | tert-butyl 4-[7-(4-methylphenyl)-sulfonylpyrrolo[2,3-d]pyrimidin-4-yl]piperidin-1-yl]sulfonylpiperidine-1-carboxylate |
| 13 | 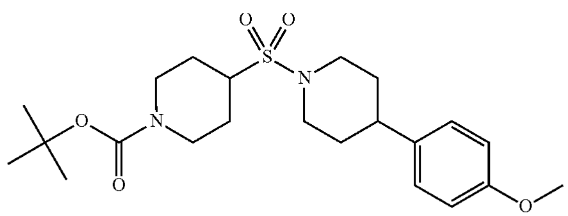 [SMILES: COc1ccc(C2CCN(S(=O)(=O)C3CCN(C(=O)OC(C)(C)C)CC3)CC2)cc1] | 439.8 | 1H NMR (400 MHz, CHLOROFORM-d): δ = 7.06-7.13 (m, 2H), 6.80-6.87 (m, 2H), 4.13-4.33 (m, 2H), 3.91 (d, J = 6.9 Hz, 2H), 3.77 (s, 3H), 2.89-3.10 (m, 3H), 2.70 (t, J = 12.4 Hz, 2H), 2.57 (tt, J = 12.0, 3.5 Hz, 1H), 2.04 (d, J = 13.0 Hz, 2H), 1.81-1.91 (m, 2H), 1.62-1.79 (m, 4H), 1.45 (s, 9H) ppm. | 4-(4-methoxyphenyl)piperidine | General method D using tert-butyl 4-chlorosulfonylpiperidine-1-carboxylate | tert-butyl 4-[4-(4-methoxyphenyl)piperidin-1-yl]sulfonylpiperidine-1-carboxylate |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 14 | 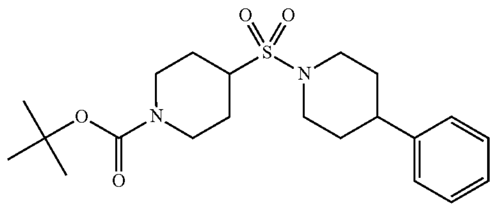 [SMILES: CC(C)(C)OC(=O)N1CCC(S(=O)(=O)N2CCC(c3ccccc3)CC2)CC1] | 409.7 | ¹H NMR (600 MHz, CHLOROFORM-d): δ = 7.28-7.31 (m, 2H), 7.16-7.23 (m, 3H), 4.24 (br. s., 2H), 3.93 (dt, J = 12.7, 2.0 Hz, 2H), 3.04 (tt, J =12.0, 3.7 Hz, 1H), 2.98 (td, J = 12.6, 2.4 Hz, 2H), 2.70 (br. s., 2H), 2.62 (tt, J = 12.2, 3.5 Hz, 1H), 2.04 (d, J = 14.1 Hz, 2H), 1.89 (dd, J = 12.7, 1.9 Hz, 2H), 1.65-1.80 (m, 4H), 1.45 (s, 9H) ppm. | 4-phenylpiperidine | General method D using tert-butyl 4-chlorosulfonylpiperidine-1-carboxylate | tert-butyl 4-(4-phenylpiperidin-1-yl)sulfonylpiperidine-1-carboxylate |
| 15 | 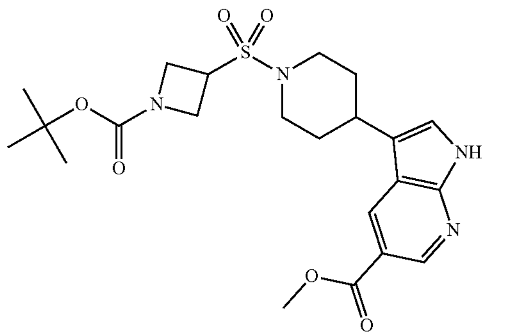 [SMILES: COC(=O)c1cnc2[nH]cc(C3CCN(S(=O)(=O)C4CN(C(=O)OC(C)(C)C)C4)CC3)c2c1] | 479.1 | ¹H NMR (500 MHz, Chloroform-d): δ = 9.99 (s, 1H), 9.02 (d, J = 2.0 Hz, 1H), 8.60 (d, J = 1.8 Hz, 1H), 7.20-7.17 (m, 1H), 4.28 (dd, J = 9.4, 5.8 Hz, 2H), 4.21 (t, J = 8.6 Hz, 2H), 4.05-3.92 (m, 6H), 3.06-2.95 (m, 3H), 2.19-2.11 (m, 2H), 1.88-1.77 (m, 2H), 1.45 (s, 9H) ppm. | methyl 3-bromo-1H-pyrrolo[2,3-b]pyridine-5-carboxylate | General method E, A1 using K₂CO₃, B1 using Pd/C, Ci using HCl in dioxane, D using tert-butyl 3-chlorosulfonyl azetidine-1-carboxylate, F | methyl 3-[1-[[(2-methylpropan-2-yl)oxycarbonyl]azetidin-3-yl]sulfonyl]-1H-pyrrolo[2,3-b]pyridine-5-carboxylate |
| 16 | 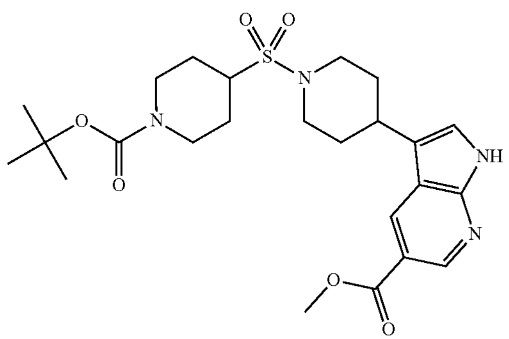 [SMILES: COC(=O)c1cnc2[nH]cc(C3CCN(S(=O)(=O)C4CCN(C(=O)OC(C)(C)C)CC4)CC3)c2c1] | 507.1 | ¹H NMR (500 MHz, Chloroform-d): δ = 9.44 (s, 1H), 9.01 (d, J = 1.9 Hz, 1H), 8.60 (d, J = 1.9 Hz, 1H), 7.18-7.15 (m, 1H), 4.37-4.19 (m, 2H), 4.02-3.95 (m, 5H), 3.14-2.97 (m, 4H), 2.81-2.66 (m, 2H), 2.17-2.04 (m, 4H), 1.88-1.69 (m, 4H), 1.48 (s, 9H) ppm. | methyl 3-bromo-1H-pyrrolo[2,3-b]pyridine-5-carboxylate | General method E, A1 using K₂CO₃, B1 using Pd/C, Ci using HCl in dioxane, D using tert-butyl 4-chlorosulfonylpiperidine-1-carboxylate, F | methyl 3-[1-[1-[(2-methylpropan-2-yl)oxycarbonyl]piperidin-4-yl]sulfonyl]piperidin-4-yl]-1H-pyrrolo[2,3-b]pyridine-5-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 17 | 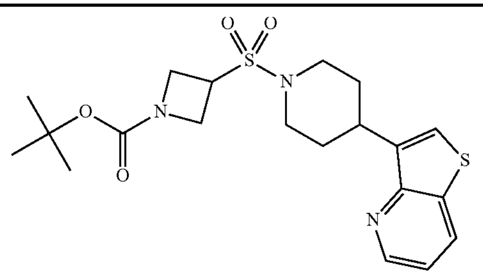 | 438.1 | ¹H NMR (600 MHz, Chloroform-d): δ = 8.67 (dd, J = 4.6, 1.5 Hz, 1H), 8.16 (dd, J = 8.2, 1.5 Hz, 1H), 7.37 (s, 1H), 7.26 (dd, J = 8.2, 4.6 Hz, 1H), 4.25 (dd, J = 9.5, 5.9 Hz, 2H), 4.17 (t, J = 8.6 Hz, 2H), 4.02-3.90 (m, 3H), 3.38 (tt, J = 10.7, 3.6 Hz, 1H), 3.03 (td, J = 12.5, 2.4 Hz, 2H), 2.20 (ddd, J = 12.6, 3.8, 2.2 Hz, 2H), 1.88-1.77 (m, 2H), 1.43 (s, 9H) ppm. | 3-bromothieno[3,2-b]pyridine | General method A1 using K₂CO₃, B1 using Pd/C, Ci using HCl in dioxane, D using tert-butyl 3-chlorosulfonyl azetidine-1-carboxylate | tert-butyl 3-(4-thieno[3,2-b]pyridin-3-yl]piperidin-1-yl]sulfonylazetidine-1-carboxylate |
| 18 | 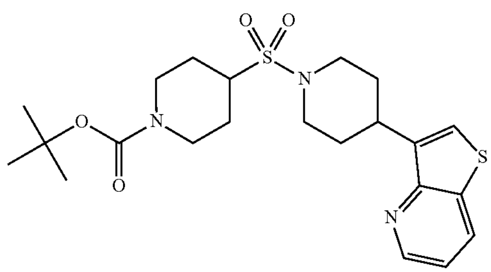 [SMILES: CC(C)(C)OC(=O)N1CCC(S(=O)(=O)N2CCC(c3csc4cccnc34)CC2)CC1] | 466.1 | ¹H NMR (600 MHz, Chloroform-d): δ = 8.67 (dd, J = 4.6, 1.5 Hz, 1H), 8.16 (dd, J = 8.2, 1.5 Hz, 1H), 7.38 (s, 1H), 7.27-7.24 (m, 1H), 4.33-4.12 (m, 2H), 3.96 (dp, J = 13.0, 2.0 Hz, 2H), 3.41 (tt, J = 12.6, 3.6 Hz, 1H), 3.12 (td, J = 12.6, 2.4 Hz, 2H), 3.05 (tt, J = 12.0, 3.7 Hz, 1H), 2.76-2.63 (m, 2H), 2.20-2.13 (m, 2H), 2.08-2.01 (m, 2H), 1.86-1.77 (m, 2H), 1.72 (qd, J = 12.6, 4.6 Hz, 2H), 1.45 (s, 9H) ppm. | 3-bromothieno[3,2-b]pyridine | General method A1 using K₂CO₃, B1 using Pd/C, Ci using HCl in dioxane, D using tert-butyl 4-chlorosulfonylpiperidine-1-carboxylate | tert-butyl 4-(4-thieno[3,2-b]pyridin-3-yl]piperidin-1-yl]sulfonylpiperidine-1-carboxylate |
| 19 | 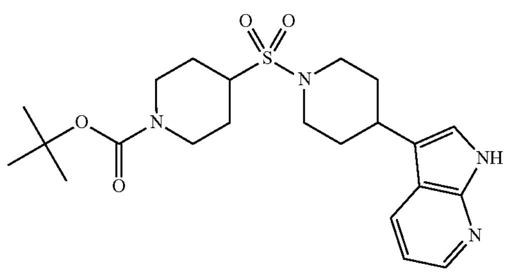 [SMILES: CC(C)(C)OC(=O)N1CCC(S(=O)(=O)N2CCC(c3c[nH]c4ncccc34)CC2)CC1] | 449.3 | ¹H NMR (600 MHz, CHLOROFORM-d): δ = 9.13 (br. s, 1H), 8.27 (d, J = 4.4 Hz, 1H), 7.93 (d, J = 7.7 Hz, 1H), 7.10-7.04 (m, 2H), 4.25 (br. s., 2H), 3.94 (d, J = 12.5 Hz, 2H), 3.06 (t, J = 12.0 Hz, 3H), 2.94 (t, J = 11.8 Hz, 1H), 2.71 (br. s., 2H), 2.03-2.13 (m, 4H), 1.82 (qd, J = 12.5, 4.1 Hz, 2H), 1.66-1.76 (m, 2H), 1.45 (s, 9H) ppm. | 3-(4-piperidyl)-1H-pyrrolo[2,3-b]pyridine | General method D using tert-butyl 4-chlorosulfonylpiperidine-1-carboxylate | tert-butyl 4-[4-(1H-pyrrolo[2,3-b]pyridin-3-yl]piperidin-1-yl]sulfonylpiperidine-1-carboxylate |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 20 | 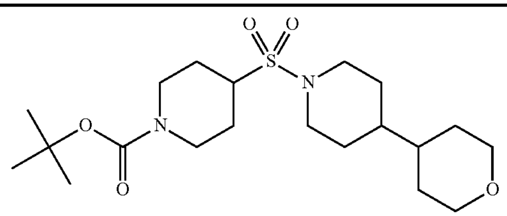 | 417.2 | ¹H NMR (500 MHz, CHLOROFORM-d): δ = 4.24 (br. s., 2H), 4.00 (d, J = 10.7 Hz, 2H), 3.85 (d, J = 12.5 Hz, 2H), 3.36 (t, J = 11.1 Hz, 2H), 2.97-3.07 (m, 1H), 2.84 (t, J = 12.1 Hz, 2H), 2.70 (br. s., 2H), 2.03 (d, J = 13.1 Hz, 2H), 1.78 (d, J = 11.9 Hz, 2H), 1.69 (qd, J = 12.4, 4.3 Hz, 2H), 1.53-1.63 (m, 2H), 1.47 (s, 9H), 1.15-1.40 (m, 6H) ppm. | 4-tetrahydropyran-4-ylpiperidine | General method D using tert-butyl 4-chlorosulfonylpiperidine-1-carboxylate | tert-butyl 4-[4-(oxan-4-yl)piperidin-1-yl]sulfonylpiperidine-1-carboxylate |
| 21 | 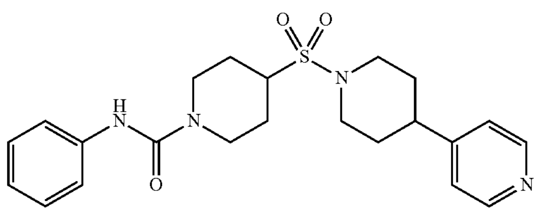 [SMILES: O=C(Nc1ccccc1)N1CCC(S(=O)(=O)N2CCC(c3ccncc3)CC2)CC1] | 429.3 | ¹H NMR (300 MHz, CHLOROFORM-d): δ = 8.51 (d, J = 5.7 Hz, 2H), 7.25-7.37 (m, 4H), 7.11 (d, J = 6.1 Hz, 2H), 6.96-7.08 (m, 1H), 6.40 (s, 1H), 4.21 (d, J = 13.8 Hz, 2H), 3.95 (d, J = 13.1 Hz, 2H), 3.12 (tt, J = 11.8, 3.9 Hz, 1H), 2.82-3.05 (m, 4H), 2.56-2.73 (m, 1H), 2.13 (d, J = 11.0 Hz, 2H), 1.85-1.97 (m, 2H), 1.71-1.85 (m, 4H) ppm. | 4-(4-piperidyl)pyridine | General method D using tert-butyl 4-chlorosulfonylpiperidine-1-carboxylate, Cf using TFA, G2 using isocyanatobenzene | N-phenyl-4-(4-pyridin-1-yl)piperidin-1-yl]sulfonylpiperidine-1-carboxamide |
| 22 | 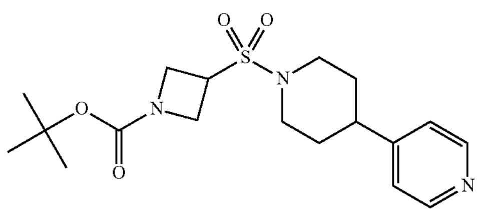 [SMILES: CC(C)(C)OC(=O)N1CC(S(=O)(=O)N2CCC(c3ccncc3)CC2)C1] | 382.2 | ¹H NMR (400 MHz, CHLOROFORM-d): δ = 8.45-8.56 (m, 2H), 7.02-7.12 (m, 2H), 4.13-4.27 (m, 4H), 3.98 (d, J = 12.6 Hz, 2H), 3.85-3.95 (m, 1H), 2.91 (td, J = 12.5, 2.4 Hz, 2H), 2.62 (tt, J = 12.2, 3.6 Hz, 1H), 1.93 (d, J = 11.5 Hz, 2H), 1.74 (qd, J = 12.7, 4.3 Hz, 2H), 1.43 (s, 9H) ppm. | 4-(4-piperidyl)pyridine | General method D using tert-butyl 3-chlorosulfonylazetidine-1-carboxylate | tert-butyl 3-(4-pyridin-4-ylpiperidin-1-yl)sulfonylazetidine-1-carboxylate |
| 23 | 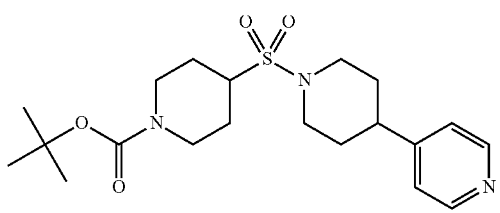 [SMILES: CC(C)(C)OC(=O)N1CCC(S(=O)(=O)N2CCC(c3ccncc3)CC2)CC1] | 410.8 | ¹H NMR (400 MHz, CHLOROFORM-d): δ = 8.51 (d, J = 5.9 Hz, 2H), 7.09-7.11 (m, 2H), 4.24 (br. s, 2H), 3.94 (d, J = 13.1 Hz, 2H), 2.93-3.07 (m, 3H), 2.59-2.75 (m, 3H), 2.04 (d, J = 12.3 Hz, 2H), 1.85-1.93 (m, 2H), 1.66-1.80 (m, 4H), 1.44 (s, 9H) ppm. | 4-(4-piperidyl)pyridine | General method D using tert-butyl 4-chlorosulfonylpiperidine-1-carboxylate | tert-butyl 4-(4-pyridin-4-ylpiperidin-1-yl)sulfonylpiperidine-1-carboxylate |

Table with Representative Compounds of Formula (I):

| Cpd # | Structure | MS (m/z ES +) | ¹H NMR Data | Starting Int/Cpd# | Sequence of Methods | Chemical Name |
|---|---|---|---|---|---|---|
| 24 | 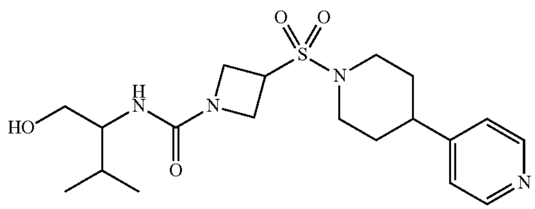 [SMILES: CC(C)C(CO)NC(=O)N1CC(S(=O)(=O)N2CCC(c3ccncc3)CC2)C1] | 411.7 | ¹H NMR (600 MHz, DMSO-d₆): δ = 8.45-8.51 (m, 2H), 7.25-7.32 (m, 2H), 6.03 (d, J = 8.44 Hz, 1H), 4.47 (t, J = 5.41 Hz, 1H), 4.32 (tt, J = 5.69, 8.44 Hz, 1H), 4.12 (t, J = 8.71 Hz, 1H), 4.08 (t, J = 8.71 Hz, 1H), 4.00 (dd, J = 5.69, 8.80 Hz, 1H), 3.94 (dd, J = 5.78, 8.89 Hz, 1H), 3.71-3.76 (m, 2H), 3.33-3.40 (m, 3H), 2.92 (dt, J = 2.11, 12.33 Hz, 2H), 2.69 (tt, J = 3.51, 12.08 Hz, 1H), 1.85 (d, J = 11.37 Hz, 2H), 1.77 (qd, J = 6.76, 13.30 Hz, 1H), 1.55-1.64 (m, 2H), 0.83 (d, J = 6.79 Hz, 3H), 0.80 (d, J = 6.79 Hz, 3H) ppm | 4-(4-piperidyl) pyridine | General method D using tert-butyl 3-chlorosulfonylazetidine-1-carboxylate, Cf using TFA, then G6 using 2-amino-3-methyl-butan-1-ol | 3-(4-pyridin-4-yl)piperidin-1-yl]sulfonyl-N-[1-hydroxy-3-methylbutan-2-yl]azetidine-1-carboxamide |
| 25 | 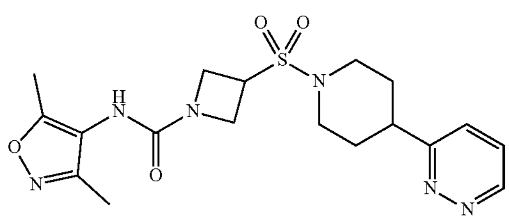 [SMILES: Cc1noc(C)c1NC(=O)N1CC(S(=O)(=O)N2CCC(c3cccnn3)CC2)C1] | 421.6 | ¹H NMR (500 MHz, DMSO-d₆): δ = 9.11 (dd, J = 2.29, 4.12 Hz, 1H), 8.03 (s, 1H), 7.60-7.68 (m, 2H), 4.36-4.44 (m, 1H), 4.26 (t, J = 8.70 Hz, 2H), 4.09 (dd, J = 5.49, 8.85 Hz, 2H), 3.80 (d, J = 12.21 Hz, 2H), 3.08 (tt, J = 3.70, 11.90 Hz, 1H), 3.02 (dt, J = 2.14, 12.20 Hz, 2H), 2.23 (s, 3H), 2.07 (s, 3H), 1.96-2.03 (m, 2H), 1.77 (dq, J = 4.12, 12.56 Hz, 2H) ppm | 3-bromopyridazine | General method A1 using Pd(dppf)Cl₂ × CH₂Cl₂, then B2, then Ci using TFA, then D using tert-butyl 3-chlorosulfonylazetidine-1-carboxylate, Cf using TFA, then G2 using 4-isocyanato-3,5-dimethylisoxazole | N-(3,5-dimethyl-1,2-oxazol-4-yl)-3-(4-pyridazin-3-yl)piperidin-1-yl]sulfonylazetidine-1-carboxamide |
| 26 | 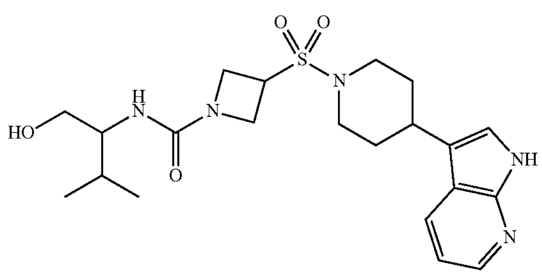 [SMILES: CC(C)C(CO)NC(=O)N1CC(S(=O)(=O)N2CCC(c3c[nH]c4ncccc34)CC2)C1] | 450.7 | ¹H NMR (500 MHz, DMSO-d₆): δ = 11.38 (br. s., 1H), 8.18 (dd, J = 1.53, 4.58 Hz, 1H), 7.98 (d, J = 7.93 Hz, 1H), 7.25 (d, J = 2.44 Hz, 1H), 7.02 (dd, J = 4.58, 7.93 Hz, 1H), 6.04 (d, J = 8.24 Hz, 1H), 4.48 (br. s., 1H), 4.30-4.37 (m, 1H), 4.14 (t, J = 8.70 Hz, 1H), 4.07-4.12 (m, 1H), 4.01-4.05 (m, 1H), 3.97 (dd, J = 5.65, 8.70 Hz, 1H), 3.73 (d, J = 11.29 Hz, 2H), 3.35-3.42 (m, 3H), 2.88-3.04 (m, 3H), 2.03 (d, J = 11.90 Hz, 2H), 1.72-1.85 (m, 1H), 1.64 (q, J = 11.80 Hz, 2H), 0.84 (d, J = 6.71 Hz, 3H), 0.81 (d, J = 6.71 Hz, 3H) ppm | 3-(4-piperidyl)-1H-pyrrolo[2,3-b]pyridine | General method D using tert-butyl 3-chlorosulfonylazetidine-1-carboxylate, then Cf using TFA, then G6 using 2-amino-3-methyl-butan-1-ol | 3-[4-(1H-pyrrolo[2,3-b]pyridin-3-yl)piperidin-1-yl]sulfonyl-N-[1-hydroxy-3-methylbutan-2-yl]azetidine-1-carboxamide |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 27 | 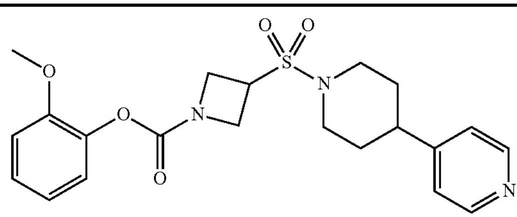 | 432.6 | ¹H NMR (600 MHz, DMSO-d₆): δ = 8.45-8.50 (m, 2H), 7.27-7.31 (m, 2H), 7.20 (ddd, J = 1.74, 7.47, 8.21 Hz, 1H), 7.10 (dd, J = 1.47, 8.25 Hz, 1H), 7.07 (dd, J = 1.65, 7.89 Hz, 1H), 6.92 (dt, J = 1.47, 7.61 Hz, 1H), 4.41-4.57 (m, 2H), 4.31 (br. s., 2H), 4.11 (br. s., 1H), 3.78 (d, J = 12.29 Hz, 2H), 3.76 (s, 3H), 2.96 (dt, J = 2.38, 12.38 Hz, 2H), 2.69 (tt, J = 3.42, 12.08 Hz, 1H), 1.87 (d, J = 11.37 Hz, 2H), 1.61 (dq, J = 4.03, 12.59 Hz, 2H) ppm | 4-(4-piperidyl) pyridine | General method D using tert-butyl 3-chlorosulfonylazetidine-1-carboxylate, Cf using TFA, then H3 using 2-methoxyphenol | (2-methoxyphenyl) 3-(4-pyridin-4-ylpiperidin-1-yl)sulfonylazetidine-1-carboxylate |
| 28 | 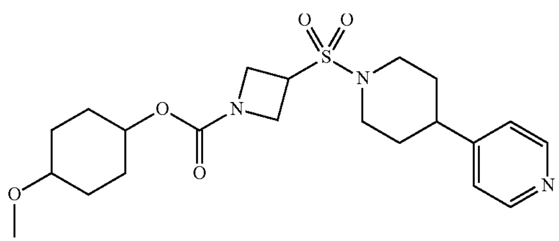 [SMILES: COC1CCC(OC(=O)N2CC(S(=O)(=O)N3CCC(c4ccncc4)CC3)C2)CC1] | 438.7 | the mixture of diastereoisomers | 4-(4-piperidyl) pyridine | General method D using tert-butyl 3-chlorosulfonylazetidine-1-carboxylate, Cf using TFA, then H3 using 4-methoxycyclohexanol | (4-methoxycyclohexyl) 3-(4-pyridin-4-ylpiperidin-1-yl)sulfonylazetidine-1-carboxylate |
| 29 | 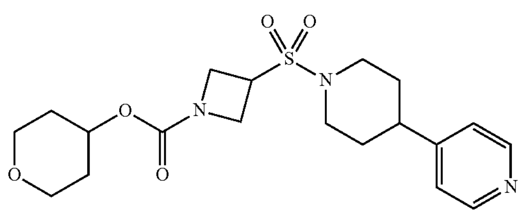 [SMILES: O=C(OC1CCOCC1)N1CC(S(=O)(=O)N2CCC(c3ccncc3)CC2)C1] | 410.6 | ¹H NMR (600 MHz, DMSO-d₆): δ = 8.42-8.53 (m, 2H), 7.22-7.33 (m, 2H), 4.71 (tt, J = 4.22, 8.71 Hz, 1H), 4.32-4.37 (m, 1H), 4.16-4.32 (m, 2H), 4.03 (br. s., 2H), 3.70-3.80 (m, 4H), 3.42 (ddd, J = 2.93, 8.99, 11.74 Hz, 2H), 2.92 (dt, J = 2.29, 12.43 Hz, 2H), 2.68 (tt, J = 3.44, 12.15 Hz, 1H), 1.79-1.88 (m, 4H), 1.59 (dq, J = 4.22, 12.59 Hz, 2H), 1.46-1.53 (m, 2H) ppm | 4-(4-piperidyl) pyridine | General method D using tert-butyl 3-chlorosulfonylazetidine-1-carboxylate, Cf using TFA, then H3 using tetrahydropyran-4-ol | oxan-4-yl 3-(4-pyridin-4-ylpiperidin-1-yl)sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 30 | 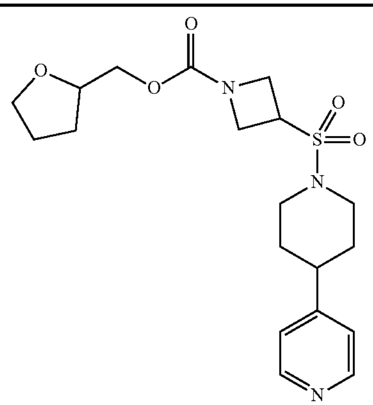 | 410.7 | ¹H NMR (500 MHz, DMSO-d₆): δ = 8.44-8.55 (m, 2H), 7.24-7.33 (m, 2H), 4.33-4.40 (m, 1H), 4.27 (br. s., 2H), 4.05 (br. s., 2H), 3.96-4.01 (m, 2H), 3.90-3.95 (m, 1H), 3.69-3.79 (m, 3H), 3.60-3.66 (m, 1H), 2.89-2.97 (m, 2H), 2.65-2.73 (m, 1H), 1.73-1.94 (m, 5H), 1.50-1.65 (m, 3H) ppm | 4-(4-piperidyl)pyridine | General method D using tert-butyl 3-chlorosulfonylazetidine-1-carboxylate, Cf using TFA, then H3 using tetrahydrofurfuryl alcohol | (oxolan-2-yl)methyl 3-(4-pyridin-4-ylpiperidin-1-yl)sulfonylazetidine-1-carboxylate |
| 31 | 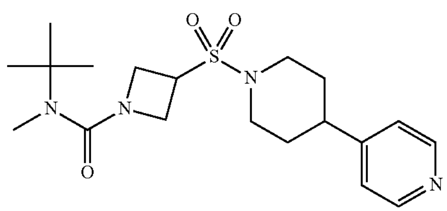 [SMILES: CN(C(=O)N1CC(S(=O)(=O)N2CCC(c3ccncc3)CC2)C1)C(C)(C)C] | 395.8 | ¹H NMR (500 MHz, DMSO-d₆): δ = 8.44-8.51 (m, 2H), 7.25-7.32 (m, 2H), 4.33 (tt, J = 5.95, 8.39 Hz, 1H), 4.08 (t, J = 8.85 Hz, 2H), 3.96 (dd, J = 5.95, 9.00 Hz, 2H), 3.74 (d, J = 12.21 Hz, 2H), 2.92 (dt, J = 1.98, 12.28 Hz, 2H), 2.66 (s, 3H), 2.68 (tt, J = 4.00, 12.50 Hz, 1H), 1.86 (d, J = 11.60 Hz, 2H), 1.61 (dq, J = 4.27, 12.51 Hz, 2H), 1.28 (s, 9H) ppm | 4-(4-piperidyl)pyridine | General method D using tert-butyl 3-chlorosulfonylazetidine-1-carboxylate, Cf using TFA, then G3 using N-tert-methyl-tert-butylamine | N-tert-butyl-N-methyl-3-(4-pyridin-4-ylpiperidin-1-yl)sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 32 | 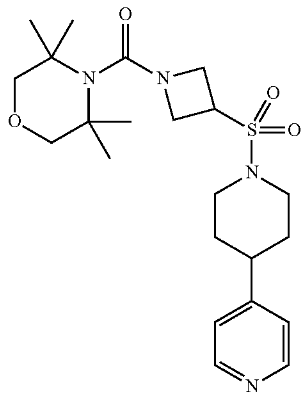 [SMILES: CC1(C)COCC(C)(C)N1C(=O)N1CC(S(=O)(=O)N2CCC(c3ccncc3)CC2)C1] | 451.6 | ¹H NMR (500 MHz, DMSO-d₆): δ = 8.44-8.52 (m, 2H), 7.25-7.32 (m, 2H), 4.22-4.32 (m, 3H), 4.05-4.14 (m, 2H), 3.73 (d, J = 12.21 Hz, 2H), 3.29 (s, 4H), 2.87-2.97 (m, 2H), 2.61-2.73 (m, 1H), 1.86 (d, J = 11.60 Hz, 2H), 1.61 (dq, J = 4.12, 12.56 Hz, 2H), 1.16 (s, 12H) ppm | 4-(4-piperidyl)pyridine | General method D using tert-butyl 3-chlorosulfonylazetidine-1-carboxylate, Cf using TFA, then G3 using 3,3,5,5-tetramethylmorpholine hydrochloride | [3-(4-pyridin-4-ylpiperidin-1-yl)sulfonylazetidin-1-yl]-(3,3,5,5-tetramethylmorpholin-4-yl)methanone |
| 33 | 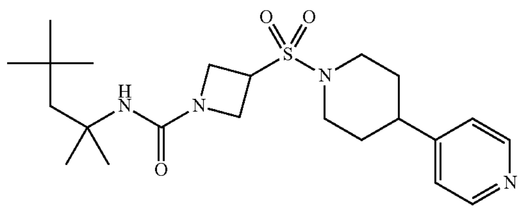 [SMILES: CC(C)(C)CC(C)(C)NC(=O)N1CC(S(=O)(=O)N2CCC(c3ccncc3)CC2)C1] | 437.6 | ¹H NMR (500 MHz, DMSO-d₆): δ = 8.44-8.53 (m, 2H), 7.25-7.32 (m, 2H), 5.75 (s, 1H), 4.29 (tt, J = 5.87, 8.32 Hz, 1H), 4.05 (t, J = 8.54 Hz, 2H), 3.95 (dd, J = 5.80, 8.85 Hz, 2H), 3.73 (d, J = 12.21 Hz, 2H), 2.87-2.95 (m, 2H), 2.69 (tt, J = 3.28, 12.13 Hz, 1H), 1.86 (d, J = 11.29 Hz, 2H), 1.67 (s, 2H), 1.60 (dq, J = 3.97, 12.61 Hz, 2H), 1.27 (s, 6H), 0.95 (s, 9H) ppm | 4-(4-piperidyl)pyridine | General method D using tert-butyl 3-chlorosulfonylazetidine-1-carboxylate, Cf using TFA, then G2 using 2-isocyanato-2,4,4-trimethyl-pentane | 3-(4-pyridin-4-ylpiperidin-1-yl)sulfonyl-N-(2,4,4-trimethylpentan-2-yl)azetidine-1-carboxamide |

| Cpd # | Structure | MS (m/z ES+) | δ NMR Data | Starting Int/Cpd# | Sequence of Methods | Chemical Name |
|---|---|---|---|---|---|---|
| 34 | 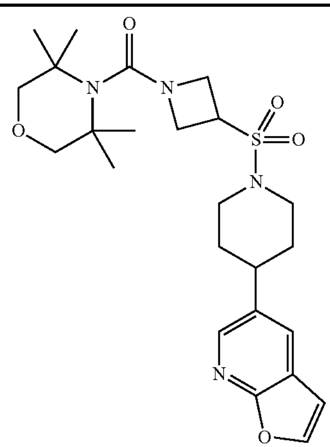 | 491.7 | ¹H NMR (500 MHz, DMSO-d₆): δ = 8.22 (d, J = 2.14 Hz, 1H), 8.08 (d, J = 2.44 Hz, 1H), 8.03 (d, J = 2.14 Hz, 1H), 6.97 (d, J = 2.44 Hz, 1H), 4.24-4.33 (m, 3H), 4.07-4.16 (m, 2H), 3.76 (d, J = 12.21 Hz, 2H), 3.30 (s, 4H), 2.89-3.00 (m, 2H), 2.78-2.88 (m, 1H), 1.89 (d, J = 11.29 Hz, 2H), 1.70 (dq, J = 3.97, 12.61 Hz, 2H), 1.12-1.20 (s, 12H) ppm | 5-bromofuro[2,3-b]pyridine | General method A1 using Pd(PPh₃)₄, then B1, using Pd/C, then Ci using TFA, then D using tert-butyl 3-chlorosulfonylazetidine-1-carboxylate, Cf using TFA, then G3 using 3,3,5,5-tetramethylmorpholine hydrochloride | [3-(4-furo[2,3-b]pyridin-5-ylpiperidin-1-yl)sulfonylazetidin-1-yl]-(3,3,5,5-tetramethylmorpholin-4-yl)methanone |
| 35 | 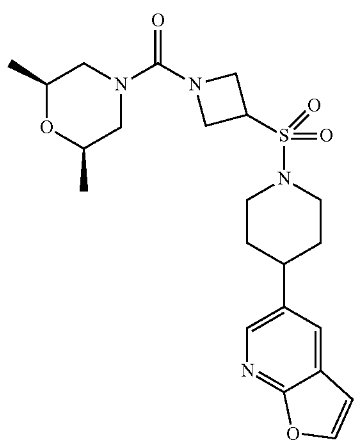 [SMILES: C[C@@H]1CN(C(=O)N2CC(S(=O)(=O)N3CCC(c4cnc5occc5c4)CC3)C2)C[C@H](C)O1] | 463.6 | ¹H NMR (500 MHz, DMSO-d₆): δ = 8.22 (d, J = 2.14 Hz, 1H), 8.08 (d, J = 2.44 Hz, 1H), 8.03 (d, J = 2.14 Hz, 1H), 6.97 (d, J = 2.44 Hz, 1H), 4.34-4.42 (m, 1H), 4.23 (t, J = 8.85 Hz, 2H), 4.10 (dd, J = 5.95, 9.00 Hz, 2H), 3.77 (d, J = 12.21 Hz, 2H), 3.56 (d, J = 13.12 Hz, 2H), 3.40-3.47 (m, 2H), 2.90-2.99 (m, 2H), 2.78-2.87 (m, 1H), 2.44 (dd, J = 10.68, 13.12 Hz, 2H), 1.89 (d, J = 12.51 Hz, 2H), 1.70 (dq, J = 4.12, 12.56 Hz, 2H), 1.06 (d, J = 6.10 Hz, 6H) ppm | 5-bromofuro[2,3-b]pyridine | General method A1 using Pd(PPh₃)₄, then B1, using Pd/C, then Ci using TFA, then D using tert-butyl 3-chlorosulfonylazetidine-1-carboxylate, Cf using TFA, then G3 using cis-2,6-dimethylmorpholine | [(2R,6S)-2,6-dimethylmorpholin-4-yl]-[3-(4-furo[2,3-b]pyridin-5-ylpiperidin-1-yl)sulfonylazetidin-1-yl]methanone |

| Cpd # | Structure | MS (m/z ES +) | δ NMR Data | Starting Int/Cpd# | Sequence of Methods | Chemical Name |
|---|---|---|---|---|---|---|
| 36 | 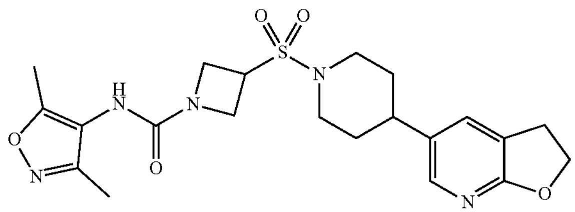 [SMILES: Cc1noc(C)c1NC(=O)N1CC(S(=O)(=O)N2CCC(c3cnc4c(c3)CCO4)CC2)C1] | 462.6 | ¹H NMR (600 MHz, DMSO-d₆): δ = 8.02 (s, 1H), 7.76 (s, 1H), 7.54 (d, J = 0.92 Hz, 1H), 4.51 (t, J = 8.62 Hz, 2H), 4.33-4.41 (m, 1H), 4.25 (t, J = 8.62 Hz, 2H), 4.06 (dd, J = 5.41, 8.71 Hz, 2H), 3.74 (d, J = 12.47 Hz, 2H), 3.17 (t, J = 8.62 Hz, 2H), 2.88-2.96 (m, 2H), 2.58-2.63 (m, 1H), 2.22 (s, 3H), 2.05 (s, 3H), 1.78 (d, J = 11.37 Hz, 2H), 1.58 (dq, J = 3.94, 12.56 Hz, 2H) ppm | 5-bromofuro [2,3-b]pyridine | General method A1 using Pd(PPh₃)₄, then B1, using Pd/C, then Ci using TFA, then D using tert-butyl 3-chlorosulfonylazetidine-1-carboxylate, Cf using TFA, then G2 using 4-isocyanato-3,5-dimethylisoxazole | 3-[4-(2,3-dihydrofuro[2,3-b]pyridin-5-yl)piperidin-1-yl]sulfonyl-N-(3,5-dimethyl-1,2-oxazol-4-yl)azetidine-1-carboxamide |
| 37 | 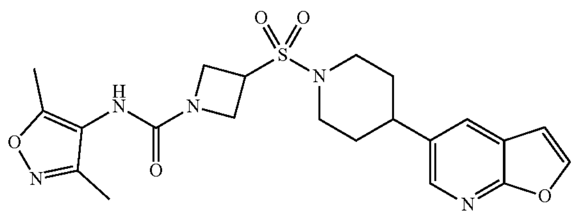 [SMILES: Cc1noc(C)c1NC(=O)N1CC(S(=O)(=O)N2CCC(c3cnc4occc4c3)CC2)C1] | 460.5 | ¹H NMR (600 MHz, DMSO-d₆): δ = 8.21 (d, J= 2.20 Hz, 1H), 8.07 (d, J = 2.57 Hz, 1H), 8.03 (s, 1H), 8.01 (d, J = 2.38 Hz, 1H), 6.94 (d, J = 2.38 Hz, 1H), 4.36-4.42 (m, 1H), 4.27 (t, J = 8.62 Hz, 2H), 4.08 (dd, J = 5.41, 9.08 Hz, 2H), 3.75-3.82 (m, 2H), 2.97 (dt, J = 2.11, 12.43 Hz, 2H), 2.85 (tt, J = 3.58, 12.10 Hz, 1H), 2.22 (s, 3H), 2.06 (s, 3H), 1.86-1.92 (m, 2H), 1.69 (dq, J = 3.94, 12.62 Hz, 2H) ppm | 5-bromofuro [2,3-b]pyridine | General method A1 using Pd(PPh₃)₄, then B1, using Pd/C, then Ci using TFA, then D using tert-butyl 3-chlorosulfonylazetidine-1-carboxylate, Cf using TFA, then G2 using 4-isocyanato-3,5-dimethylisoxazole | N-(3,5-dimethyl-1,2-oxazol-4-yl)-3-(4-furo[2,3-b]pyridin-5-ylpiperidin-1-yl)sulfonyl)azetidine-1-carboxamide |
| 38 | 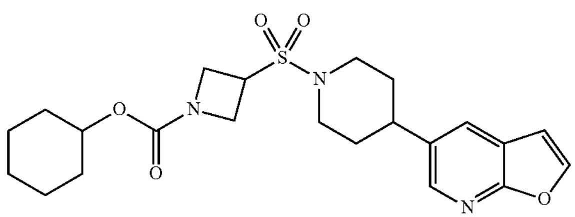 [SMILES: O=C(OC1CCCCC1)N1CC(S(=O)(=O)N2CCC(c3cnc4occc4c3)CC2)C1] | 448.7 | 1H NMR (500 MHz, DMSO-d₆): δ = 8.22 (d, J = 1.83 Hz, 1H), 8.08 (d, J = 2.44 Hz, 1H), 8.02 (d, J = 1.83 Hz, 1H), 6.97 (d, J = 2.44 Hz, 1H), 4.50-4.55 (m, 1H), 4.32-4.41 (m, 1H), 4.26 (br. s., 2H), 4.04 (br. s., 2H), 3.78 (d, J = 12.21 Hz, 2H), 2.91-3.00 (m, 2H), 2.80-2.87 (m, 1H), 1.89 (d, J = 11.29 Hz, 2H), 1.59-1.81 (m, 6H), 1.42-1.50 (m, 1H), 1.17-1.40 (m, 5H) ppm | 5-bromofuro [2,3-b]pyridine | General method A1 using Pd(PPh₃)₄, then B1, using Pd/C, then Ci using TFA, then D using tert-butyl 3-chlorosulfonylazetidine-1-carboxylate, Cf using TFA, then H1 using cyclohexyl chloroformate | cyclohexyl 3-(4-furo[2,3-b]pyridin-5-ylpiperidin-1-yl)sulfonyl)azetidine-1-carboxylate |

| Cpd # | Structure | MS (m/z ES +) | δ NMR Data | Starting Int/Cpd# | Sequence of Methods | Chemical Name |
|---|---|---|---|---|---|---|
| 39 | 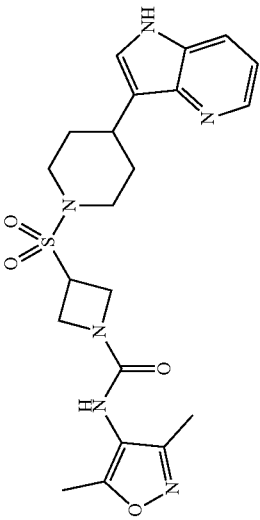 | 459.2 | ¹H NMR (500 MHz, DMSO-d₆): δ = 11.04 (d, J = 1.8 Hz, 1H), 8.28 (dd, J = 4.6, 1.2 Hz, 1H), 8.03 (s, 1H), 7.70 (dd, J = 8.1, 1.4 Hz, 1H), 7.41 (d, J = 2.7 Hz, 1H), 7.07 (dd, J = 8.2, 4.6 Hz, 1H), 4.34-4.43 (m, 1H), 4.28 (t, J = 8.7 Hz, 2H), 4.09 (dd, J = 8.9, 5.5 Hz, 2H), 3.75 (d, J = 12.5 Hz, 2H), 2.95-3.12 (m, 3H), 2.23 (s, 3H), 2.12 (d, J = 11.0 Hz, 2H), 2.06 (s, 3H), 1.76 (dq, J = 12.6, 4.1 Hz, 2H) ppm | 3-bromo-1H-pyrrolo[3,2-b]pyridine | General method E, then A1 using Pd(PPh₃)₄, followed by B2, Ci using TFA, D using tert-butyl 3-chlorosulfonylazetidine-1-carboxylate, Cf using TFA, F using Cs₂CO₃, finally G2 using 4-isocyanato-3,5-dimethylisoxazole | N-(3,5-dimethyl-1,2-oxazol-4-yl)-3-[4-(1H-pyrrolo[3,2-b]pyridin-3-yl)piperidin-1-yl]sulfonylazetidine-1-carboxamide |
| 40 | 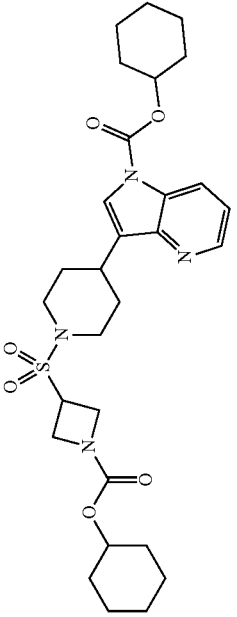 | 573.3 | ¹H NMR (500 MHz, DMSO-d₆): δ = 8.50 (dd, J = 4.6, 1.2 Hz, 1H), 8.32 (d, J = 8.2 Hz, 1H), 7.77 (s, 1H), 7.37 (dd, J = 8.2, 4.9 Hz, 1H), 4.94-5.05 (m, 1H), 4.47-4.58 (m, 1H), 4.32-4.40 (m, 1H), 4.26 (br. s., 2H), 4.03 (br. s., 2H), 3.76 (d, J = 12.2 Hz, 2H), 2.95-3.11 (m, 3H), 2.11 (d, J = 11.3 Hz, 2H), 1.98 (d, J = 5.8 Hz, 2H), 1.70-1.83 (m, 6H), 1.58-1.70 (m, 4H), 1.50-1.58 (m, 1H), 1.39-1.49 (m, 3H), 1.16-1.39 (m, 6H) ppm | 3-bromo-1H-pyrrolo[3,2-b]pyridine | General method E, then A1 using Pd(PPh₃)₄, followed by B2, Ci using TFA, D using tert-butyl 3-chlorosulfonylazetidine-1-carboxylate, Cf using TFA, F using Cs₂CO₃, finally H1 using cyclohexyl chloroformate | cyclohexyl 3-[1-(1-cyclohexyloxy carbonylazetidin-3-yl)sulfonylpiperidin-4-yl]pyrrolo[3,2-b]pyridine-1-carboxylate |
| 41 | 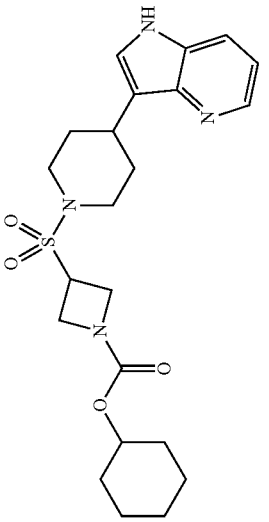 | 447.2 | ¹H NMR (500 MHz, DMSO-d₆): δ = 11.04 (br. s., 1H), 8.28 (dd, J = 4.6, 1.5 Hz, 1H), 7.41 (d, J = 2.4 Hz, 1H), 7.07 (dd, J = 8.2, 4.6 Hz, 1H), 4.48-4.56 (m, 1H), 4.32-4.38 (m, 1H), 4.26 (br. s., 2H), 4.04 (br. s., 2H), 3.67-3.79 (m, 2H), 3.02-3.10 (m, 1H), 2.94-3.02 (m, 2H), 2.11 (d, J = 11.0 Hz, 2H), 1.75 (td, J = 12.4, 3.7 Hz, 4H), 1.59-1.67 (m, 2H), 1.42-1.52 (m, 1H), 1.27-1.40 (m, 4H), 1.15-1.25 (m, 1H) ppm | 3-bromo-1H-pyrrolo[3,2-b]pyridine | General method E, then A1 using Pd(PPh₃)₄, followed by B2, Ci using TFA, D using tert-butyl 3-chlorosulfonylazetidine-1-carboxylate, Cf using TFA, F using Cs₂CO₃, finally H1 using cyclohexyl chloroformate | cyclohexyl 3-[4-(1H-pyrrolo[3,2-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 42 | 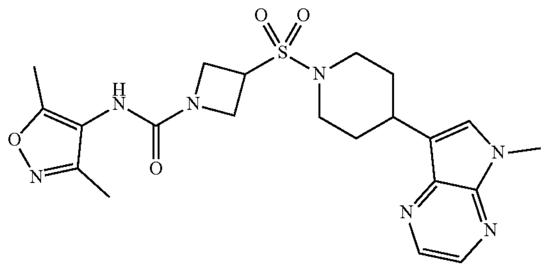 [SMILES: Cc1noc(C)c1NC(=O)N1CC(S(=O)(=O)N2CCC(c3cn(C)c4nccnc34)CC2)C1] | 474.2 | ¹H NMR (600 MHz, DMSO-d₆): δ = 8.36 (d, J = 2.6 Hz, 1H), 8.25 (d, J = 2.6 Hz, 1H), 8.02 (s, 1H), 7.70 (s, 1H), 4.33-4.41 (m, 1H), 4.26 (t, J = 8.7 Hz, 2H), 4.08 (dd, J = 9.1, 5.4 Hz, 2H), 3.78 (s, 3H), 3.74 (d, J = 12.5 Hz, 2H), 2.97-3.10 (m, 3H), 2.21 (s, 3H), 2.08-2.13 (m, 2H), 2.05 (s, 3H), 1.75 (dq, J = 12.4, 4.1 Hz, 2H) ppm | 7-bromo-5H-pyrrolo[2,3-b]pyrazine | General method E, then A1 using Pd(PPh₃)₄, followed by B1, Ci using TFA, D using tert-butyl 3-chlorosulfonylazetidine-1-carboxylate, Cf using TFA, G2 using 4-isocyanato-3,5-dimethylisoxazole, finally F using Cs₂CO₃ | N-(3,5-dimethyl-1,2-oxazol-4-yl)-3-[4-(5-methylpyrrolo[2,3-b]pyrazin-7-yl)piperidin-1-yl]sulfonylazetidine-1-carboxamide |
| 43 | 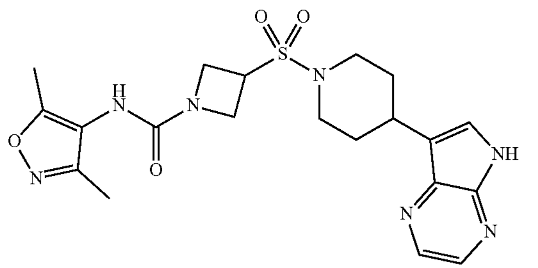 [SMILES: Cc1noc(C)c1NC(=O)N1CC(S(=O)(=O)N2CCC(c3c[nH]c4nccnc34)CC2)C1] | 460.2 | ¹H NMR (600 MHz, DMSO-d₆): δ = 11.80 (br. s., 1H), 8.34 (d, J = 2.6 Hz, 1H), 8.20 (d, J = 2.6 Hz, 1H), 8.02 (s, 1H), 7.65 (s, 1H), 4.34-4.41 (m, 1H), 4.26 (t, J = 8.7 Hz, 2H), 4.08 (dd, J = 9.1, 5.4 Hz, 2H), 3.74 (d, J = 12.3 Hz, 2H), 2.97-3.08 (m, 3H), 2.22 (s, 3H), 2.08-2.14 (m, 2H), 2.05 (s, 3H), 1.71-1.82 (m, 2H) ppm | 7-bromo-5H-pyrrolo[2,3-b]pyrazine | General method E, then A1 using Pd(PPh₃)₄, followed by B1, Ci using TFA, D using tert-butyl 3-chlorosulfonylazetidine-1-carboxylate, Cf using TFA, G2 using 4-isocyanato-3,5-dimethylisoxazole, finally F using Cs₂CO₃ | N-(3,5-dimethyl-1,2-oxazol-4-yl)-3-[4-(5H-pyrrolo[2,3-b]pyrazin-7-yl)piperidin-1-yl]sulfonylazetidine-1-carboxamide |
| 44 | 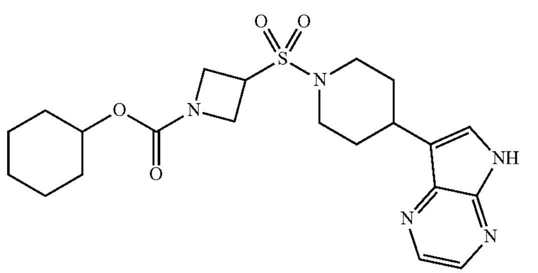 [SMILES: O=C(OC1CCCCC1)N1CC(S(=O)(=O)N2CCC(c3c[nH]c4nccnc34)CC2)C1] | 448.2 | ¹H NMR (600 MHz, DMSO-d₆): δ = 11.79 (br. s., 1H), 8.33 (d, J = 2.6 Hz, 1H), 8.20 (d, J = 2.6 Hz, 1H), 7.65 (s, 1H), 4.47-4.54 (m, 1H), 4.31-4.37 (m, 1H), 4.23 (d, J = 18.3 Hz, 2H), 4.02 (br. s., 2H), 3.72 (d, J = 12.3 Hz, 2H), 2.94-3.06 (m, 3H), 2.09 (d, J = 10.8 Hz, 2H), 1.68-1.80 (m, 4H), 1.63 (d, J = 6.1 Hz, 2H), 1.41-1.49 (m, 1H), 1.25-1.38 (m, 4H), 1.16-1.25 (m, 1H) ppm | 7-bromo-5H-pyrrolo[2,3-b]pyrazine | General method E, then A1 using Pd(PPh₃)₄, followed by B1, Ci using TFA, D using tert-butyl 3-chlorosulfonylazetidine-1-carboxylate, Cf using TFA, H1 using cyclohexyl chloroformate, finally F using Cs₂CO₃ | cyclohexyl 3-[4-(5H-pyrrolo[2,3-b]pyrazin-7-yl)piperidin-1-yl]sulfonylazetidine-1-carboxylate |

| Cpd # | Structure | MS (m/z, ES +) | δ NMR Data | Starting Int/Cpd# | Sequence of Methods | Chemical Name |
|---|---|---|---|---|---|---|
| 45 | AND Enantiomer | 435.2 | the mixture of diastereoisomers | 1H-pyrrolo[2,3-b]pyridine | General method A2 using tert-butyl (2S)-2-methyl-4-oxo-piperidine-1-carboxylate, then B2, Ci using TFA, D using tert-butyl 3-chlorosulfonylazetidine-1-carboxylate, 2 diastereoisomers isolated | tert-butyl 3-[(2R)-2-methyl-4-(1H-pyrrolo[2,3-b]pyridin-3-yl)piperidin-1-yl]sulfonylazetidine-1-carboxylate |
| 46 | 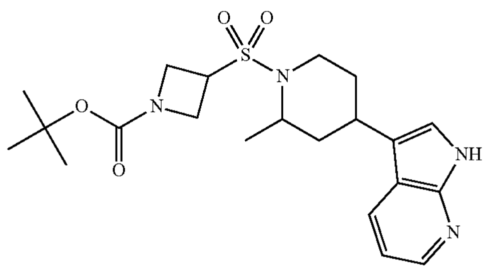 [SMILES: CC1CC(c2c[nH]c3ncccc23)CCN1S(=O)(=O)C1CN(C(=O)OC(C)(C)C)C1] | 435.1 | $^1$H NMR (500 MHz, DMSO-d$_6$): δ = 11.36 (br. s., 1H), 8.18 (d, J = 3.66 Hz, 1H), 7.98 (d, J = 7.63 Hz, 1H), 7.23 (d, J = 1.83 Hz, 1H), 7.02 (dd, J = 4.58, 7.93 Hz, 1H), 4.28-4.36 (m, 1H), 4.10-4.25 (m, 3H), 3.93 (br. s., 2H), 3.67 (d, J= 12.82 Hz, 1H), 3.28-3.31 (m, 1H), 3.18-3.27 (m, 1H), 1.98 (d, J = 12.82 Hz, 1H), 1.84-1.90 (m, 1H), 1.72-1.81 (m, 1H), 1.42-1.53 (m, 1H), 1.38 (s, 9H), 1.35 (d, J = 6.71 Hz, 3H) ppm | 1H-pyrrolo[2,3-b]pyridine | General method A2 using tert-butyl 2-methyl-4-oxo-piperidine-1-carboxylate, then B2, Ci using TFA, D using tert-butyl 3-chlorosulfonylazetidine-1-carboxylate, 1 diastereoisomer (pair of enantiomers) isolated as pure | tert-butyl 3-[2-methyl-4-(1H-pyrrolo[2,3-b]pyridin-3-yl)sulfonylazetidine-1-carboxylate |
| 47 | 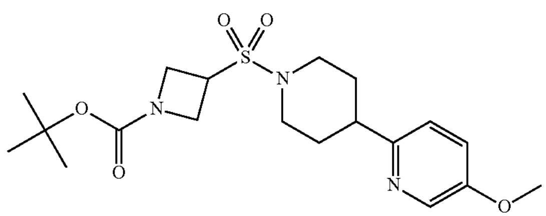 [SMILES: COc1ccc(C2CCN(S(=O)(=O)C3CN(C(=O)OC(C)(C)C)C3)CC2)nc1] | 412.2 | $^1$H NMR (500 MHz, DMSO-d$_6$): δ = 8.21 (d, J = 2.75 Hz, 1H), 7.32 (dd, J = 3.05, 8.54 Hz, 1H), 7.22 (d, J = 8.54 Hz, 1H), 4.28-4.35 (m, 1H), 4.17 (br. s., 2H), 3.92-4.01 (m, 2H), 3.80 (s, 3H), 3.72 (d, J = 12.21 Hz, 2H), 2.86-2.98 (m, 2H), 2.71-2.79 (m, 1H), 1.89 (d, J = 11.60 Hz, 2H), 1.63 (dq, J = 3.97, 12.61 Hz, 2H), 1.39 (s, 9H) ppm | 5-methoxy-2-(4-piperidyl)-pyridine | General method D using tert-butyl 3-chlorosulfonylazetidine-1-carboxylate | tert-butyl 3-[4-(5-methoxypyridin-2-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 48 | 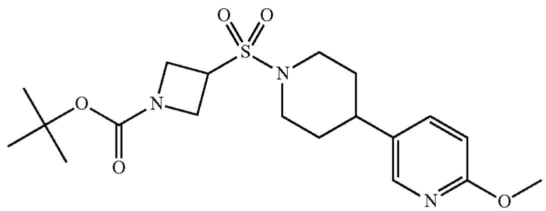 | 412.2 | ¹H NMR (500 MHz, DMSO-d₆): δ = 8.04 (d, J = 2.44 Hz, 1H), 7.62 (dd, J = 2.44, 8.54 Hz, 1H), 6.76 (d, J = 8.54 Hz, 1H), 4.27-4.35 (m, 1H), 3.97 (br. s., 2H), 3.81 (s, 3H), 3.73 (d, J = 12.21 Hz, 2H), 2.84-2.96 (m, 2H), 2.63 (tt, J = 3.40, 12.17 Hz, 1H), 1.81 (d, J = 11.29 Hz, 2H), 1.58 (dq, J = 3.97, 12.51 Hz, 2H), 1.39 (s, 9H) ppm | 2-methoxy-5-(4-piperidyl)-pyridine dihydrochloride | General method D using tert-butyl 3-chlorosulfonylaze-tidine-1-carboxylate | tert-butyl 3-[4-(6-methoxypyridin-3-yl)piperidin-1-yl]sulfonylaze-tidine-1-carboxylate |
| 49 | 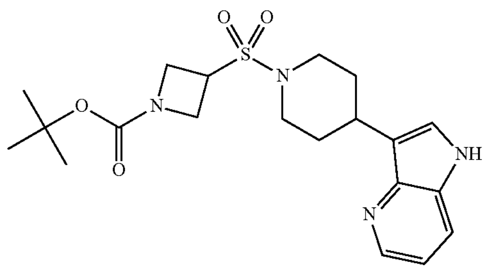 | 421.2 | ¹H NMR (500 MHz, DMSO-d₆): δ = 11.04 (br. s., 1H), 8.28 (dd, J = 1.37, 4.43 Hz, 1H), 7.70 (dd, J = 1.37, 8.09 Hz, 1H), 7.41 (d, J = 2.75 Hz, 1H), 7.07 (dd, J = 4.58, 8.24 Hz, 1H), 4.29-4.36 (m, 1H), 4.20 (br. s., 2H), 4.00 (br. s., 2H), 3.72 (d, J = 12.21 Hz, 2H), 2.94-3.09 (m, 3H), 2.11 (d, J = 10.99 Hz, 2H), 1.74 (dq, J = 3.97, 12.41 Hz, 2H), 1.39 (s, 9H) ppm | 3-bromo-1H-pyrrolo [3,2-b]pyridine | General method E, then A1 using Pd(PPh₃)₄, followed by B2, Ci using TFA, D using tert-butyl 3-chlorosulfonylaze-tidine-1-carboxylate, finally F using Cs₂CO₃ | tert-butyl 3-[4-(1H-pyrrolo[3,2-b]pyridin-3-yl)piperidin-1-yl]sulfonylaze-tidine-1-carboxylate |
| 50 | 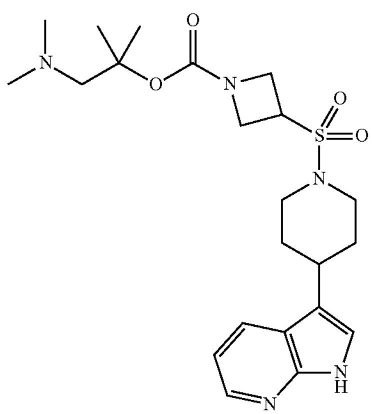 | 464.7 | ¹H NMR (300 MHz, DMSO-d₆): δ = 11.37 (br. s., 1H), 8.17 (dd, J = 1.39, 4.70 Hz, 1H), 7.96 (dd, J = 1.31, 7.93 Hz, 1H), 7.24 (d, J = 2.26 Hz, 1H), 7.01 (dd, J = 4.70, 7.84 Hz, 1H), 4.26-4.38 (m, 1H), 4.08-4.26 (m, 2H), 3.90-4.04 (m, 2H), 3.71 (d, J = 12.02 Hz, 2H), 2.84-3.04 (m, 3H), 2.44 (s, 2H), 2.18-2.24 (m, 6H), 2.01 (d, J = 12.37 Hz, 2H), 1.52-1.70 (m, 2H), 1.33-1.42 (m, 6H) ppm. | 3-(4-piperidyl)-1H-pyrrolo [2,3-b]pyridine | General method D using tert-butyl 3-chlorosulfonylaze-tidine-1-carboxylate, Cf using TFA, H3 using 1-(dimethylamino)-2-methyl-propan-2-ol | [1-(dimethylamino)-2-methylpropan-2-yl] 3-[4-(1H-pyrrolo[2,3-b]pyridin-3-yl)piperidin-1-yl]sulfonylaze-tidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 51 | 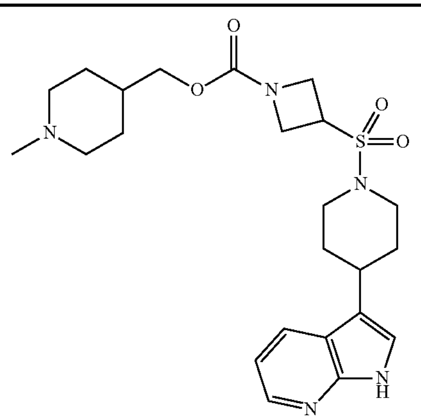 | 476.7 | ¹H NMR (300 MHz, DMSO-d₆): δ = 11.37 (s, 1H), 8.17 (dd, J = 1.39, 4.70 Hz, 1H), 7.96 (dd, J = 1.13, 7.93 Hz, 1H), 7.24 (d, J = 2.26 Hz, 1H), 7.01 (dd, J = 4.70, 7.84 Hz, 1H), 4.30-4.41 (m, 1H), 4.18-4.30 (m, 2H), 3.97-4.11 (m, 2H), 3.83 (d, J = 6.27 Hz, 2H), 3.73 (d, J = 12.19 Hz, 2H), 2.84-3.05 (m, 3H), 2.65-2.76 (m, 2H), 2.10 (s, 3H), 2.01 (d, J = 10.97 Hz, 2H), 1.76 (dt, J = 2.00, 11.54 Hz, 2H), 1.39-1.70 (m, 5H), 1.08-1.25 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H2 using (1-methyl-4-piperidyl)methanol | (1-methylpiperidin-4-yl)methyl 3-[4-(1H-pyrrolo[2,3-b]pyridin-3-yl)piperidin-1-yl]sulfonylazetidine-1-carboxylate |
| 52 | 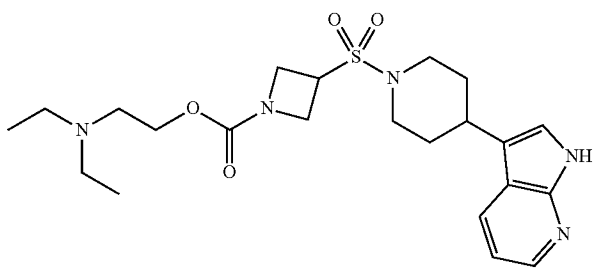 [SMILES: CCN(CC)CCOC(=O)N1CC(S(=O)(=O)N2CCC(c3c[nH]c4ncccc34)CC2)C1] | 464.7 | ¹H NMR (300 MHz, DMSO-d₆): δ = 11.37 (s, 1H), 8.17 (dd, J = 1.57, 4.70 Hz, 1H), 7.96 (dd, J = 1.31, 7.93 Hz,9 1H), 7.24 (d, J = 2.26 Hz, 1H), 7.01 (dd, J = 4.70, 7.84 Hz, 1H), 4.31-4.43 (m, 1H), 4.24 (t, J = 7.75 Hz, 2H), 3.95-4.09 (m, 4H), 3.73 (d, J = 12.19 Hz, 2H), 2.83-3.06 (m, 3H), 2.57 (t, J = 6.10 Hz, 2H), 2.40-2.46 (m, 4H), 2.02 (d, J = 11.32 Hz, 2H), 1.62 (dq, J = 4.01, 12.37 Hz, 2H), 0.92 (t, J = 7.14 Hz, 6H) ppm. | 3-(4-piperidyl)-1H-pyrrolo[2,3-b]pyridine | General method D using tert-butyl 3-chlorosulfonylazetidine-1-carboxylate, Cf using TFA, H2 using 2-(diethylamino)ethanol | 2-(diethylamino)ethyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 53 | 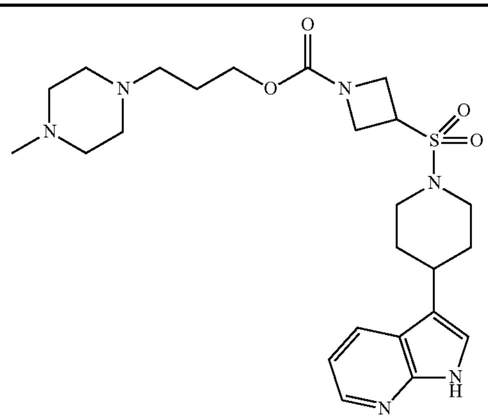 | 505.7 | ¹H NMR (300 MHz, DMSO-d₆): δ = 11.38 (br. s., 1H), 8.17 (dd, J = 4.70 Hz, 1H), 7.96 (dd, J = 1.57, 4.70 Hz, 1H), 7.24 (s, 1H), 7.01 (dd, J = 1.48, 7.93 Hz, 1H), 7.93 Hz, 1H), 4.30-4.41 (m, 1H), 4.16-4.30 (m, 2H), 3.93-4.10 (m, 4H), 3.73 (d, J = 12.02 Hz, 2H), 2.84-3.05 (m, 3H), 2.16-2.44 (m, 10H), 2.12 (s, 3H), 2.01 (d, J = 11.50 Hz, 2H), 1.52-1.75 (m, 4H) ppm. | 3-(4-piperidyl)-1H-pyrrolo[2,3-b]pyridine | General method D using tert-butyl 3-chlorosulfonylazetidine-1-carboxylate, Cf using TFA, H2 using 3-(4-methylpiperazin-1-yl)propan-1-ol | 3-(4-methylpiperazin-1-yl)propyl 3-[4-(1H-pyrrolo[2,3-b]pyridin-3-yl)piperidin-1-yl]sulfonylazetidine-1-carboxylate |
| 54 | 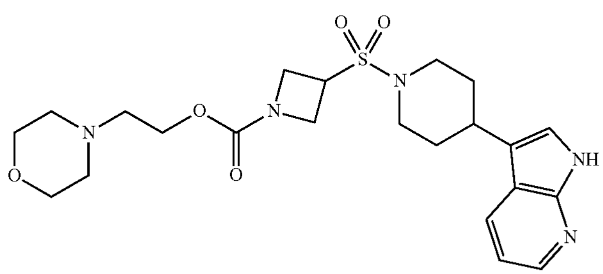 | 478.7 | ¹H NMR (300 MHz, DMSO-d₆): δ = 11.38 (s, 1H), 8.17 (dd, J = 1.57, 4.70 Hz, 1H), 7.96 (dd, J = 1.39, 7.84 Hz, 1H), 7.24 (d, J = 2.09 Hz, 1H), 7.01 (dd, J = 4.70, 7.84 Hz, 1H), 4.31-4.43 (m, 1H), 4.16-4.30 (m, 2H), 3.96-4.14 (m, 4H), 3.73 (d, J = 12.02 Hz, 2H), 3.49-3.58 (m, 4H), 2.83-3.06 (m, 3H), 2.50-2.54 (m, 2H), 2.32-2.42 (m, 4H), 2.02 (d, J = 10.80 Hz, 2H), 1.62 (dq, J = 3.83, 12.37 Hz, 2H) ppm. | 3-(4-piperidyl)-1H-pyrrolo[2,3-b]pyridine | General method D using tert-butyl 3-chlorosulfonylazetidine-1-carboxylate, Cf using TFA, H2 using 2-morpholinoethanol | 2-morpholin-4-ylethyl 3-[4-(1H-pyrrolo[2,3-b]pyridin-3-yl)piperidin-1-yl]sulfonylazetidine-1-carboxylate |

| Cpd # | Structure | MS (m/z ES+) | δ NMR Data | Starting Int/Cpd# | Sequence of Methods | Chemical Name |
|---|---|---|---|---|---|---|
| 55 | 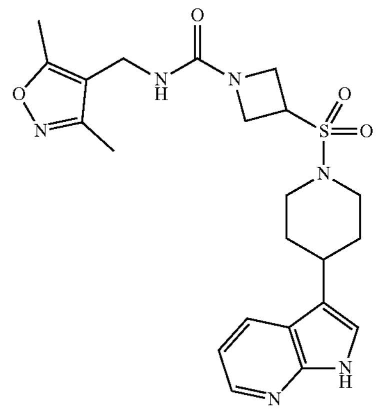 [SMILES: Cc1noc(C)c1CNC(=O)N1CC(S(=O)(=O)N2CCC(c3c[nH]c4ncccc34)CC2)C1] | 473.6 | ¹H NMR (300 MHz, DMSO-d₆): δ = 11.37 (s, 1H), 8.17 (dd, J = 1.57, 4.70 Hz, 1H), 7.97 (dd, J = 1.57, 7.84 Hz, 1H), 7.24 (s, 1H), 7.01 (dd, J = 4.70, 7.84 Hz, 1H), 6.85 (t, J = 5.49 Hz, 1H), 4.26-4.38 (m, 2H), 4.10 (t, J = 8.62 Hz, 2H), 3.89-3.99 (m, 4H), 3.71 (d, J = 12.19 Hz, 2H), 2.86-3.03 (m, 3H), 2.32 (s, 3H), 2.16 (s, 3H), 2.01 (d, J = 11.15 Hz, 2H), 1.52-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, G3 using (3,5-dimethylisoxazol-4-yl)methanamine | N-[(3,5-dimethyl-1,2-oxazol-4-yl)methyl]-3-[4-(1H-pyrrolo[2,3-b]pyridin-3-yl)piperidin-1-yl]sulfonyl]azetidine-1-carboxamide |
| 56 | 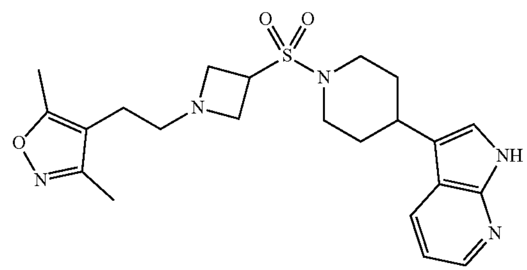 [SMILES: Cc1noc(C)c1CCN1CC(S(=O)(=O)N2CCC(c3c[nH]c4ncccc34)CC2)C1] | 444.7 | ¹H NMR (300 MHz, DMSO-d₆): δ = 11.37 (s, 1H), 8.17 (dd, J = 1.48, 4.62 Hz, 1H), 7.97 (dd, J = 1.22, 7.84 Hz, 1H), 7.24 (d, J = 2.26 Hz, 1H), 7.01 (dd, J = 4.70, 7.84 Hz, 1H), 4.12-4.26 (m, 1H), 3.67 (d, J = 12.02 Hz, 2H), 3.55 (t, J = 7.93 Hz, 2H), 3.22-3.30 (m, 4H), 2.82-2.98 (m, 3H), 2.22-2.33 (m, 5H), 2.12-2.17 (m, 3H), 2.00 (d, J = 11.67 Hz, 2H), 1.53-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J1 using 4-(2-chloroethyl)-3,5-dimethyl-isoxazole | 3,5-dimethyl-4-[2-[3-[4-(1H-pyrrolo[2,3-b]pyridin-3-yl)piperidin-1-yl]sulfonyl]azetidin-1-yl]ethyl]-1,2-oxazole |
| 57 | 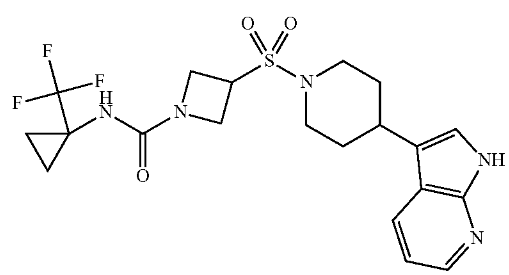 [SMILES: O=C(NC1(C(F)(F)F)CC1)N1CC(S(=O)(=O)N2CCC(c3c[nH]c4ncccc34)CC2)C1] | 472.6 | ¹H NMR (300 MHz, DMSO-d₆): δ = 11.38 (s, 1H), 8.17 (dd, J = 1.39, 4.70 Hz, 1H), 7.97 (dd, J = 1.05, 7.84 Hz, 1H), 7.42 (s, 1H), 7.24 (d, J = 2.26 Hz, 1H), 7.01 (dd, J = 4.70, 7.84 Hz, 1H), 4.25-4.39 (m, 1H), 4.12 (t, J = 8.71 Hz, 2H), 3.96 (dd, J = 5.66, 8.97 Hz, 2H), 3.71 (d, J = 12.02 Hz, 2H), 2.84-3.04 (m, 3H), 2.01 (d, J = 11.15 Hz, 2H), 1.52-1.71 (m, 2H), 1.12-1.23 (m, 2H), 0.93-1.04 (m, 2H) ppm. | 3-(4-piperidyl)-1H-pyrrolo[2,3-b]pyridine | General method D using tert-butyl 3-chlorosulfonylazetidine-1-carboxylate, Cf using TFA, G2 using 1-isocyanato-1-(trifluoromethyl)cyclopropane | 3-[4-(1H-pyrrolo[2,3-b]pyridin-3-yl)piperidin-1-yl]sulfonyl-N-[1-(trifluoromethyl)cyclopropyl]azetidine-1-carboxamide |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 58 | 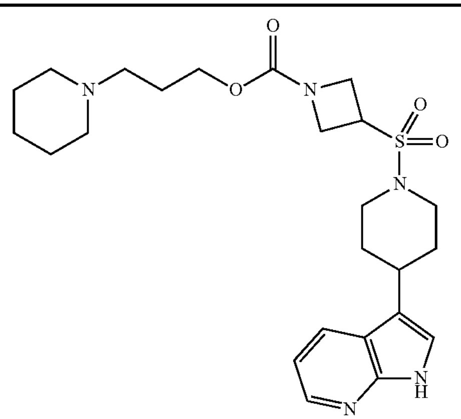 | 490.7 | 1H NMR (300 MHz, DMSO-d6): δ = 11.37 (br. s., 1H), 8.17 (dd, J = 4.62 Hz, 1H), 7.96 (dd, J = 2.44 Hz, 1H), 7.75 Hz, 1H), 7.24 (d, J = 7.84 Hz, 1H), 7.01 (dd, J = 4.70, 7.84 Hz, 1H), 4.30-4.41 (m, 1H), 4.18-4.30 (m, 2H), 3.93-4.10 (m, 4H), 3.73 (d, J = 12.37 Hz, 2H), 2.84-3.05 (m, 3H), 2.19-2.36 (m, 6H), 2.02 (d, J = 11.67 Hz, 2H), 1.53-1.76 (m, 4H), 1.41-1.51 (m, 4H), 1.28-1.40 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H3 using 3-(1-piperidyl)propan-1-ol | 3-piperidin-1-ylpropyl 3-[4-(1H-pyrrolo[2,3-b]pyridin-3-yl)piperidin-1-yl]sulfonylazetidine-1-carboxylate |
| 59 | 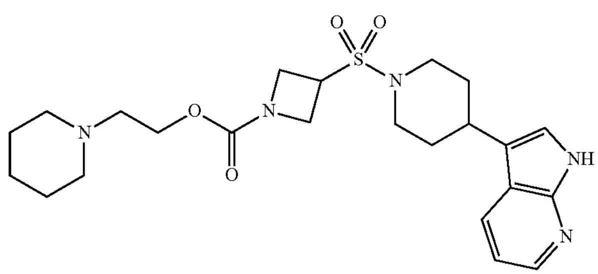 [SMILES: O=C(OCCN1CCCCC1)N1CC(S(=O)(=O)N2CCC(c3c[nH]c4ncccc34)CC2)C1] | 476.7 | 1H NMR (300 MHz, DMSO-d6): δ = 11.37 (br. s., 1H), 8.17 (dd, J = 1.39, 4.70 Hz, 1H), 7.96 (dd, J = 6.97 Hz, 1H), 7.24 (d, J = 2.09 Hz, 1H), 7.01 (dd, J = 4.62, 7.75 Hz, 1H), 4.30-4.42 (m, 1H), 4.18-4.30 (m, 2H), 3.96-4.09 (m, 4H), 3.73 (d, J = 12.54 Hz, 2H), 2.86-3.05 (m, 3H), 2.28-2.39 (m, 5H), 2.01 (d, J = 12.02 Hz, 2H), 1.52-1.71 (m, 2H), 1.40-1.50 (m, 5H), 1.27-1.39 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H3 using 2-(1-piperidyl)ethanol | 2-piperidin-1-ylethyl 3-[4-(1H-pyrrolo[2,3-b]pyridin-3-yl)piperidin-1-yl]sulfonylazetidine-1-carboxylate |
| 60 | 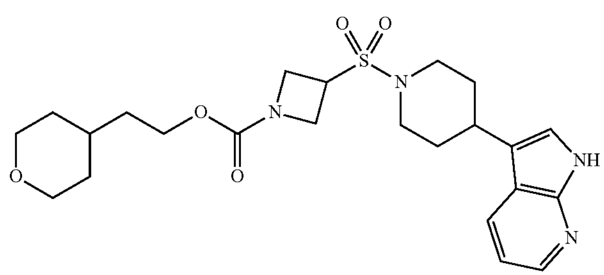 [SMILES: O=C(OCCC1CCOCC1)N1CC(S(=O)(=O)N2CCC(c3c[nH]c4ncccc34)CC2)C1] | 477.7 | 1H NMR (300 MHz, DMSO-d6): δ = 11.38 (s, 1H), 8.17 (dd, J = 1.48, 4.62 Hz,1H), 7.96 (dd, J = 1.13, 7.93 Hz, 1H), 7.24 (d, J = 2.26 Hz, 1H), 7.01 (dd, J = 4.79, 7.93 Hz, 1H), 4.30-4.41 (m, 1H), 4.18-4.30 (m, 2H), 4.03 (t, J = 6.36 Hz, 4H), 3.67-3.84 (m, 4H), 3.17-3.29 (m, 2H), 2.88-3.05 (m, 3H), 2.02 (d, J = 10.80 Hz, 2H), 1.43-1.71 (m, 7H), 1.04-1.22 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H3 using 2-tetrahydropyran-4-ylethanol | 2-(oxan-4-yl)ethyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 61 | 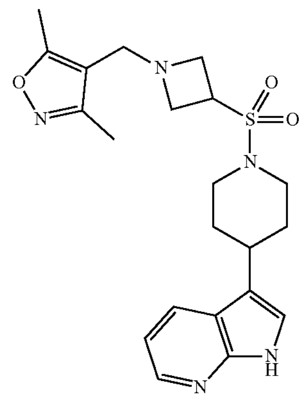 [SMILES: Cc1noc(C)c1CN1CC(S(=O)(=O)N2CCC(c3c[nH]c4ncccc34)CC2)C1] | 430.2 | ¹H NMR (300 MHz, DMSO-d₆): δ = 11.36 (s, 1H), 8.17 (dd, J = 4.70 Hz, 1H), 7.95 (dd, J = 1.22, 7.84 Hz, 1H), 7.24 (d, J = 2.26 Hz, 1H), 7.01 (dd, J = 4.70, 7.84 Hz, 1H), 4.12-4.25 (m, 1H), 3.67 (d, J = 11.84 Hz, 2H), 3.51 (t, J = 7.93 Hz, 2H), 3.36 (s, 2H), 3.21-3.30 (m, 2H), 2.81-2.99 (m, 3H), 2.35 (s, 3H), 2.17 (s, 3H), 2.00 (d, J = 10.80 Hz, 2H), 1.53-1.70 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J1 using 4-(chloromethyl)-3,5-dimethyl-isoxazole | 3,5-dimethyl-4-[[3-[4-(1H-pyrrolo[2,3-b]pyridin-3-yl)piperidin-1-yl]sulfonylazetidin-1-yl]methyl]-1,2-oxazole |
| 62 | 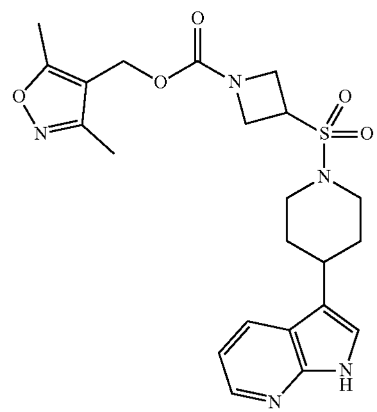 [SMILES: Cc1noc(C)c1COC(=O)N1CC(S(=O)(=O)N2CCC(c3c[nH]c4ncccc34)CC2)C1] | 474.2 | ¹H NMR (300 MHz, DMSO-d₆): δ = 11.37 (br. s., 1H), 8.17 (dd, J = 1.48, 4.62 Hz, 1H), 7.96 (dd, J = 1.39, 7.84 Hz, 1H), 7.24 (d, J = 2.26 Hz, 1H), 7.01 (dd, J = 4.70, 8.01 Hz, 1H), 4.87 (s, 2H), 4.16-4.40 (m, 3H), 3.97-4.09 (m, 2H), 3.72 (d, J = 12.19 Hz, 2H), 2.82-3.04 (m, 3H), 2.36 (s, 3H), 2.19 (s, 3H), 2.00 (d, J = 10.97 Hz, 2H), 1.51-1.70 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H2 using (3,5-dimethylisoxazol-4-yl)methanol | (3,5-dimethyl-1,2-oxazol-4-yl)methyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 63 | 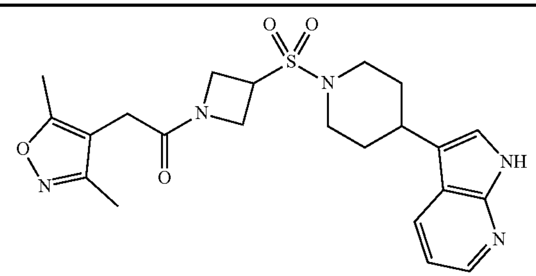 | 458.2 | ¹H NMR (300 MHz, DMSO-d₆): δ = 11.38 (s, 1H), 8.17 (dd, J = 1.22, 7.84 Hz, 1H), 7.97 (dd, J = 1.22, 7.84 Hz, 1H), 7.25 (d, J = 2.26 Hz, 1H), 7.01 (dd, J = 4.70, 7.84 Hz, 1H), 4.47-4.60 (m, 1H), 4.32-4.43 (m, 2H), 4.15-4.25 (m, 1H), 4.01 (dd, J = 4.96, 10.36 Hz, 1H), 3.75 (d, J = 12.37 Hz, 2H), 3.26 (d, J = 2.26 Hz, 2H), 2.86-3.06 (m, 3H), 2.27 (s, 3H), 2.08 (s, 3H), 1.96-2.06 (d, 2H), 1.54-1.72 (m, 2H) ppm. | 3-(4-piperidyl)-1H-pyrrolo[2,3-b]pyridine | General method D using tert-butyl 3-chlorosulfonylazetidine-1-carboxylate, Cf using TFA, I1 using 2-(3,5-dimethyl-isoxazol-4-yl)acetic acid | 2-(3,5-dimethyl-1,2-oxazol-4-yl)-1-[3-[4-(1H-pyrrolo[2,3-b]pyridin-3-yl)piperidin-1-yl]sulfonylazetidin-1-yl]ethanone |
| 64 | 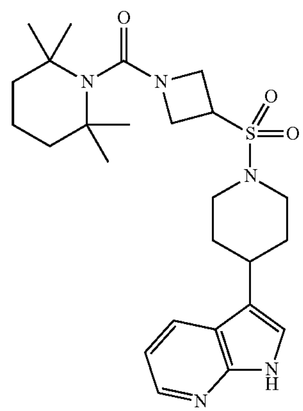 [SMILES: CC1(C)CCCC(C)(C)N1C(=O)N1CC(S(=O)(=O)N2CCC(c3c[nH]c4ncccc34)CC2)C1] | 488.1 | ¹H NMR (300 MHz, DMSO-d₆): δ = 11.37 (br. s., 1H), 8.17 (dd, J = 1.57, 4.70 Hz, 1H), 7.97 (dd, J = 2.09 Hz, 1H), 7.93 Hz, 1H), 7.25 (d, J = 1.48, 7.84 Hz, 1H), 7.01 (dd, J = 4.70, 7.84 Hz, 1H), 4.19-4.32 (m, 3H), 4.01-4.13 (m, 2H), 3.71 (d, J = 11.84 Hz, 2H), 2.84-3.05 (m, 3H), 2.02 (d, J = 10.97 Hz, 2H), 1.51-1.72 (m, 4H), 1.30-1.42 (m, 4H), 1.15 (s, 12H) ppm. | 3-(4-piperidyl)-1H-pyrrolo[2,3-b]pyridine | General method D using tert-butyl 3-chlorosulfonylazetidine-1-carboxylate, Cf using TFA, G3 using 2,2,6,6-tetramethylpiperidine | [3-[4-(1H-pyrrolo[2,3-b]pyridin-3-yl)piperidin-1-yl]sulfonylazetidin-1-yl]-(2,2,6,6-tetramethylpiperidin-1-yl)methanone |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 65 | 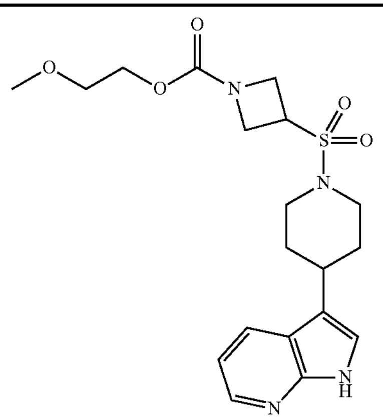 | 423.1 | ¹H NMR (300 MHz, DMSO-d₆): δ = 11.37 (br. s., 1H), 8.17 (dd, J = 4.70 Hz, 1H), 7.96 (dd, J = 1.48, 7.93 Hz, 1H), 7.25 (d, J = 1.92 Hz, 1H), 7.01 (dd, J = 4.70, 7.84 Hz, 1H), 4.17-4.43 (m, 3H), 3.95-4.15 (m, 4H), 3.73 (d, J = 12.37 Hz, 2H), 3.44-3.52 (m, 2H), 3.24 (s, 3H), 2.84-3.06 (m, 3H), 2.01 (d, J = 10.63 Hz, 2H), 1.62 (dq, J = 3.75, 12.51 Hz, 2H) ppm. | 3-(4-piperidyl)-1H-pyrrolo[2,3-b]pyridine | General method D using tert-butyl 3-chlorosulfonylaze-tidine-1-carboxylate, Cf using TFA, H1 using 2-methoxyethyl carbonochloridate | 2-methoxyethyl 3-[4-(1H-pyrrolo[2,3-b]pyridin-3-yl)piperidin-1-yl]sulfonylaze-tidine-1-carboxylate |
| 66 | 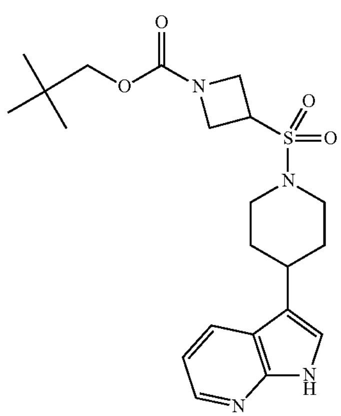 [SMILES: CC(C)(C)COC(=O)N1CC(S(=O)(=O)N2CCC(c3c[nH]c4ncccc34)CC2)C1] | 435.1 | ¹H NMR (300 MHz, DMSO-d₆): δ = 11.37 (s, 1H), 8.17 (dd, J = 1.57, 4.70 Hz, 1H), 7.96 (dd, J = 1.31, 7.93 Hz, 1H), 7.24 (d, J = 2.26 Hz, 1H), 7.01 (dd, J = 4.70, 8.01 Hz, 1H), 4.32-4.43 (m, 1H), 4.27 (br. s., 1H), 4.06 (br. s., 2H), 3.64-3.78 (m, 4H), 2.84-3.06 (m, 3H), 2.02 (d, J = 10.80 Hz, 2H), 1.62 (dq, J = 3.40, 12.40 Hz, 2H), 0.88 (s, 9H) ppm. | 3-(4-piperidyl)-1H-pyrrolo[2,3-b]pyridine | General method D using tert-butyl 3-chlorosulfonylaze-tidine-1-carboxylate, Cf using TFA, H1 using 2,2-dimethylpropyl carbonochloridate | 2,2-dimethylpropyl 3-[4-(1H-pyrrolo[2,3-b]pyridin-3-yl)piperidin-1-yl]sulfonylaze-tidine-1-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 67 | 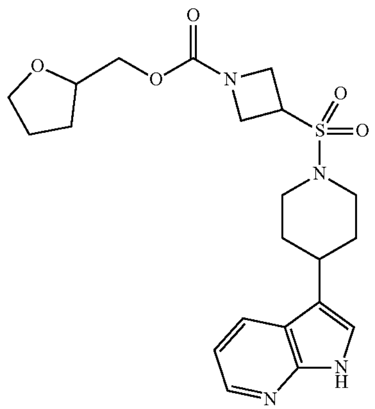 [SMILES: O=C(OCC1CCCO1)N1CC(S(=O)(=O)N2CCC(c3c[nH]c4ncccc34)CC2)C1] | 449.1 | ¹H NMR (300 MHz, DMSO-d₆): δ = 11.37 (s, 1H), 8.13-8.21 (m, 1H), 7.96 (dd, J = 1.22, 7.84 Hz, 1H), 7.21-7.27 (m, 1H), 7.01 (dd, J = 4.70, 7.84 Hz, 1H), 4.31-4.43 (m, 1H), 4.17-4.31 (m, 2H), 3.86-4.13 (m, 5H), 3.66-3.79 (m, 3H), 3.55-3.66 (m, 1H), 2.84-3.06 (m, 3H), 2.02 (d, J = 11.32 Hz, 2H), 1.72-1.94 (m, 3H), 1.46-1.70 (m, 3H) ppm. | 3-(4-piperidyl)-1H-pyrrolo[2,3-b]pyridine | General method D using tert-butyl 3-chlorosulfonylazetidine-1-carboxylate, Cf using TFA, H2 using tetrahydrofuran-2-ylmethanol | (oxolan-2-yl)methyl 3-[4-(1H-pyrrolo[2,3-b]pyridin-3-yl)piperidin-1-yl]sulfonylazetidine-1-carboxylate |
| 68 | 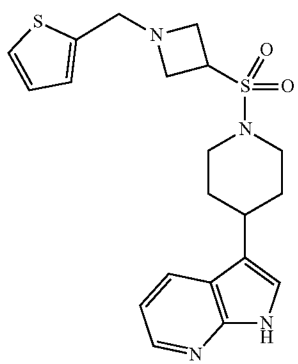 [SMILES: O=S(=O)(C1CN(Cc2cccs2)C1)N1CCC(c2c[nH]c3ncccc23)CC1] | 417.1 | ¹H NMR (300 MHz, DMSO-d₆): δ = 11.36 (br. s., 1H), 8.16 (dd, J = 1.48, 4.62 Hz, 1H), 7.96 (dd, J = 1.48, 7.93 Hz, 1H), 7.42 (dd, J = 1.39, 4.88 Hz, 1H), 7.24 (d, J = 2.26 Hz, 1H), 6.92-7.04 (m, 3H), 4.17-4.32 (m, 1H), 3.78 (s, 2H), 3.67 (d, J = 8.01 Hz, 2H), 3.59 (t, J = 8.01 Hz, 2H), 3.34-3.39 (m, 2H), 2.82-3.00 (m, 3H), 2.00 (d, J = 11.50 Hz, 2H), 1.53-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, I2 using thiophene-2-carbaldehyde | 3-[1-[1-(thiophen-2-ylmethyl)azetidin-3-yl]sulfonylpiperidin-4-yl]-1H-pyrrolo[2,3-b]pyridine |

-continued

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 69 | 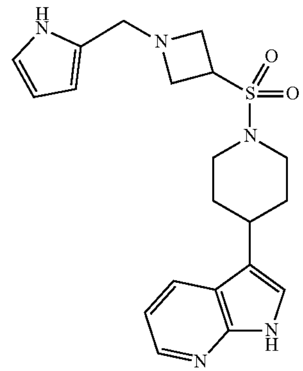 [SMILES: O=S(=O)(C1CN(Cc2ccc[nH]2)C1)N1CCC(c2c[nH]c3ncccc23)CC1] | 400.1 | ¹H NMR (300 MHz, DMSO-d₆): δ = 11.36 (br. s., 1H), 10.62-10.72 (m, 1H), 8.16 (dd, J = 1.48, 4.62 Hz, 1H), 7.95 (dd, J = 1.39, 7.84 Hz, 1H), 7.23 (d, J = 2.26 Hz, 1H), 7.00 (dd, J = 4.70, 7.84 Hz, 1H), 6.61 (dt, J = 1.65, 2.57 Hz, 1H), 5.84-5.93 (m, 2H), 4.11-4.24 (m, 1H), 3.66 (d, J = 12.02 Hz, 2H), 3.45-3.55 (m, 4H), 2.81-2.98 (m, 3H), 2.00 (d, J = 11.15 Hz, 2H), 1.52-1.70 (m, 2H) ppm. | 3-(4-piperidyl)-1H-pyrrolo[2,3-b]pyridine | General method D using tert-butyl 3-chlorosulfonylazetidine-1-carboxylate, Cf using TFA, I2 using 1H-pyrrole-2-carbaldehyde | 3-[1-[1-(1H-pyrrol-2-ylmethyl)azetidin-3-yl]sulfonylpiperidin-4-yl]-1H-pyrrolo[2,3-b]pyridine |
| 70 | 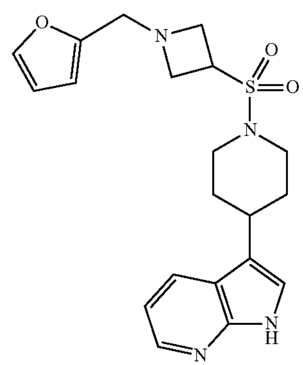 [SMILES: O=S(=O)(C1CN(Cc2ccco2)C1)N1CCC(c2c[nH]c3ncccc23)CC1] | 401.1 | ¹H NMR (300 MHz, DMSO-d₆): δ = 11.36 (br. s., 1H), 8.16 (dd, J = 1.39, 4.70 Hz, 1H), 7.96 (dd, J = 1.31, 7.93 Hz, 1H), 7.57 (dd, J = 0.87, 1.92 Hz, 1H), 7.24 (d, J = 2.26 Hz, 1H), 7.00 (dd, J = 4.70, 7.84 Hz, 1H), 6.38 (dd, J = 1.83, 3.22 Hz, 1H), 6.28 (dd, J = 0.70, 3.14 Hz, 1H), 4.20 (quin, J = 7.49 Hz, 1H), 3.67 (d, J = 12.02 Hz, 2H), 3.51-3.61 (m, 4H), 3.37 (t, J = 7.66 Hz, 2H), 2.82-2.99 (m, 3H), 2.00 (d, J = 10.97 Hz, 2H), 1.62 (dq, J = 3.75, 12.45 Hz, 2H) ppm. | 3-(4-piperidyl)-1H-pyrrolo[2,3-b]pyridine | General method D using tert-butyl 3-chlorosulfonylazetidine-1-carboxylate, Cf using TFA, I2 using furan-2-carbaldehyde | 3-[1-[1-(furan-2-ylmethyl)azetidin-3-yl]sulfonylpiperidin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 71 | 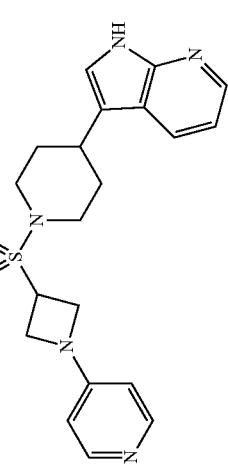 | 398.2 | ¹H NMR (300 MHz, DMSO-d₆): δ = 11.38 (br. s., 1H), 8.12-8.20 (m, 3H), 7.96 (dd, J = 1.22, 7.84 Hz, 1H), 7.23 (d, J = 2.26 Hz, 1H), 7.00 (dd, J = 4.62, 7.93 Hz, 1H), 6.41-6.48 (m, 2H), 4.49-4.61 (m, 1H), 4.27 (t, J = 8.54 Hz, 2H), 4.09 (dd, J = 5.57, 8.88 Hz, 2H), 3.77 (d, J = 12.37 Hz, 2H), 2.86-3.08 (m, 3H), 1.97-2.08 (m, 2H), 1.55-1.73 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J3 using 4-fluoropyridine, hydrochloride | 3-[1-(1-pyridin-4-ylazetidin-3-yl)sulfonylpiperidin-4-yl]-1H-pyrrolo[2,3-b]pyridine |
| 72 | 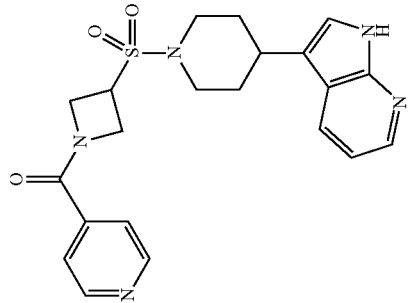 | 426.22 | ¹H NMR (300 MHz, DMSO-d₆): δ = 11.37 (s, 1H), 8.68-8.75 (m, 2H), 8.17 (dd, J = 1.48, 4.62 Hz, 1H), 7.96 (dd, J = 1.31, 7.93 Hz, 1H), 7.56-7.60 (m, 2H), 7.24 (d, J = 2.26 Hz, 1H), 7.01 (dd, J = 4.70, 7.84 Hz, 1H), 4.65-4.76 (m, 1H), 4.37-4.53 (m, 3H), 4.15-4.29 (m, 1H), 3.75 (d, J = 10.97 Hz, 2H), 2.84-3.08 (m, 3H), 2.02 (d, J = 13.76 Hz, 2H), 1.51-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, I2 using pyridine-4-carbonyl chloride, hydrochloride | pyridin-4-yl-[3-[4-(1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 73 | 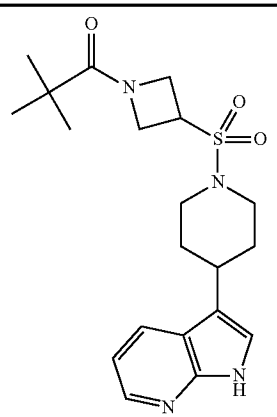 | 405.1 | ¹H NMR (300 MHz, DMSO-d₆): δ = 11.38 (br. s., 1H), 8.17 (dd, J = 1.48, 4.62 Hz, 1H), 7.97 (dd, J = 1.22, 8.01 Hz, 1H), 7.25 (d, J = 2.26 Hz, 1H), 7.01 (dd, J = 4.62, 7.93 Hz, 1H), 4.61-4.80 (m, 1H), 4.41-4.56 (m, 1H), 4.28-4.40 (m, 1H), 4.06-4.23 (m, 1H), 3.88-4.05 (m, 1H), 3.74 (d, J = 12.19 Hz, 2H), 2.84-3.06 (m, 3H), 2.02 (d, J = 11.32 Hz, 2H), 1.63 (dd, J = 3.48, 12.37 Hz, 2H), 1.10 (s, 9H) ppm. | 3-(4-piperidyl)-1H-nl pyrrolo [2,3-b]pyridine | General method D using tert-butyl 3-chlorosulfonylazetidine-1-carboxylate, Cf using TFA, I2 using 2,2-dimethyl-propanoyl chloride | 2,2-dimethyl-1-[3-[4-(1H-pyrrolo[2,3-b]pyridin-3-yl)piperidin-1-yl]sulfonylazetidin-1-yl]propan-1-one |
| 74 | 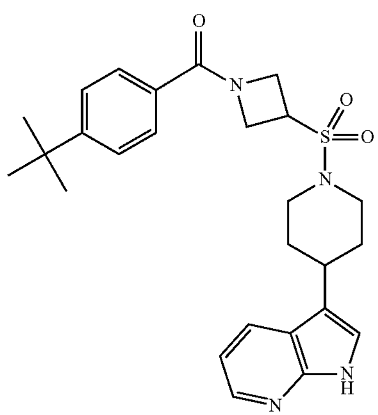 [SMILES: CC(C)(C)c1ccc(C(=O)N2CC(S(=O)(=O)N3CCC(c4c[nH]c5ncccc45)CC3)C2)cc1] | 481.1 | ¹H NMR (300 MHz, DMSO-d₆): δ = 11.37 (s, 1H), 8.17 (dd, J = 1.39, 4.70 Hz, 1H), 7.96 (dd, J = 1.13, 7.93 Hz, 1H), 7.55-7.62 (m, 2H), 7.45-7.52 (m, 2H), 7.24 (d, J = 2.44 Hz, 1H), 7.00 (dd, J = 4.62, 7.93 Hz, 1H), 4.61-4.79 (m, 1H), 4.33-4.49 (m, 3H), 4.13-4.27 (m, 1H), 3.74 (d, J = 11.67 Hz, 2H), 2.84-3.06 (m, 3H), 2.01 (d, J = 12.02 Hz, 2H), 1.53-1.71 (m, 2H), 1.29 (s, 9H) ppm. | 3-(4-piperidyl)-1H-pyrrolo [2,3-b]pyridine | General method D using tert-butyl 3-chlorosulfonylazetidine-1-carboxylate, Cf using TFA, I2 using 4-tert-butylbenzoyl chloride | (4-tert-butylphenyl)-[3-[4-(1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 75 | 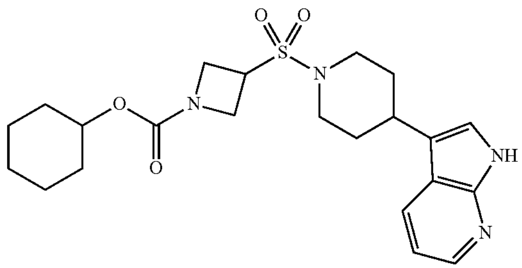 [SMILES: O=C(OC1CCCCC1)N1CC(S(=O)(=O)N2CCC(c3c[nH]c4ncccc34)CC2)C1] | 447.1 | ¹H NMR (300 MHz, DMSO-d₆): δ = 11.38 (br. s., 1H), 8.17 (dd, J = 4.70 Hz, 1H), 7.96 (dd, J = 1.48, 7.93 Hz, 1H), 7.24 (s, 1H), 7.01 (dd, J = 4.70, 7.84 Hz, 1H), 4.45-4.56 (m, 1H), 4.29-4.39 (m, 1H), 4.16-4.29 (m, 2H), 3.95-4.08 (m, 2H), 2.89-3.04 (m, 3H), 2.02 (d, J = 11.50 Hz, 2H), 1.70-1.80 (m, 2H), 1.56-1.70 (m, 4H), 1.39-1.50 (m, 1H), 1.17-1.38 (m, 5H) ppm. | 3-(4-piperidyl)-1H-pyrrolo[2,3-b]pyridine | General method D using tert-butyl 3-chlorosulfonylazetidine-1-carboxylate, Cf using TFA, H1 using cyclohexyl carbonochloridate | cyclohexyl 3-[4-(1H-pyrrolo[2,3-b]pyridin-3-yl)piperidin-1-yl]sulfonylazetidine-1-carboxylate |
| 76 | 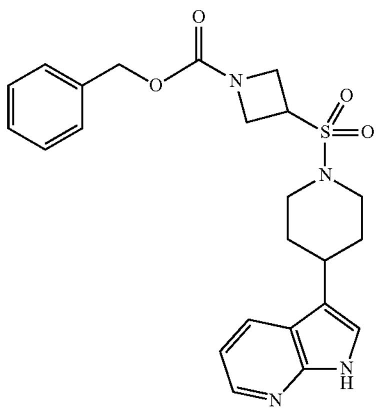 [SMILES: O=C(OCc1ccccc1)N1CC(S(=O)(=O)N2CCC(c3c[nH]c4ncccc34)CC2)C1] | 455.1 | | 3-(4-piperidyl)-1H-pyrrolo[2,3-b]pyridine | General method D using tert-butyl 3-chlorosulfonylazetidine-1-carboxylate, Cf using TFA, H1 using benzyl carbonochloridate | benzyl 3-[4-(1H-pyrrolo[2,3-b]pyridin-3-yl)piperidin-1-yl]sulfonylazetidine-1-carboxylate |
| 77 | 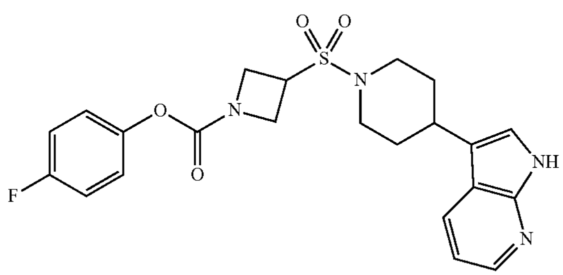 [SMILES: O=C(Oc1ccc(F)cc1)N1CC(S(=O)(=O)N2CCC(c3c[nH]c4ncccc34)CC2)C1] | 459 | ¹H NMR (300 MHz, DMSO-d₆): δ = 11.38 (br. s., 1H), 8.17 (dd, J = 1.48, 4.79 Hz, 1H), 7.97 (dd, J = 1.57, 7.84 Hz, 1H), 7.23-7.28 (m, 1H), 7.01 (dd, J = 4.62, 7.93 Hz, 1H), 4.24-4.62 (m, 4H), 4.14 (br. s., 1H), 3.78 (d, J = 12.02 Hz, 2H), 2.86-3.11 (m, 3H), 2.04 (d, J = 11.67 Hz, 2H), 1.64 (dq, J = 3.66, 12.48 Hz, 2H) ppm. | 3-(4-piperidyl)-1H-pyrrolo[2,3-b]pyridine | General method D using tert-butyl 3-chlorosulfonylazetidine-1-carboxylate, Cf using TFA, H1 using (4-fluorophenyl) carbonochloridate | (4-fluorophenyl) 3-[4-(1H-pyrrolo[2,3-b]pyridin-3-yl)piperidin-1-yl]sulfonylazetidine-1-carboxylate |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 78 | 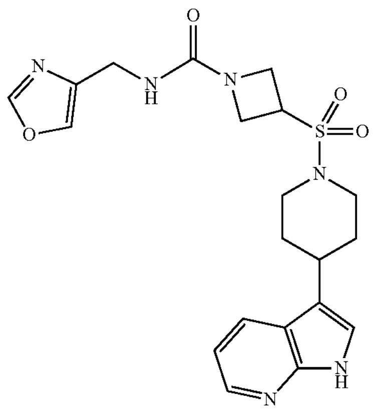 [SMILES: O=C(NCc1cocn1)N1CC(S(=O)(=O)N2CCC(c3c[nH]c4ncccc34)CC2)C1] | 445.1 | ¹H NMR (300 MHz, DMSO-d₆): δ = 11.37 (br.s., 1H), 8.29 (d, J = 0.87 Hz, 1H), 8.17 (dd, J = 1.57, 4.70 Hz, 1H), 7.96 (dd, J = 1.05 Hz, 1H), 7.86 (d, J = 1.05 Hz, 1H), 7.24 (d, J = 2.09 Hz, 1H), 6.96-7.06 (m, 2H), 4.27-4.39 (m, 1H), 4.05-4.18 (m, 4H), 3.93-4.03 (m, 2H), 3.70 (d, 2H), 3.05-2.84 (m, 3H), 2.01 (d, J = 11.15 Hz, 2H), 1.62 (dd, J = 3.31, 12.37 Hz, 2H) ppm. | 1H-pyrrolo [2,3-b]pyridine | General method A2, B1 using P₂O₂ (partial reduction), then B2, Ci using TFA, D using tert-butyl 3-chlorosulfonyl azetidine-1-carboxylate, Cf using TFA, G4 using oxazol-4-ylmethanamine | N-(1,3-oxazol-4-ylmethyl)-3-[4-(1H-pyrrolo[2,3-b]pyridin-3-yl)piperidin-1-yl]sulfonylazetidine-1-carboxamide |
| 79 | 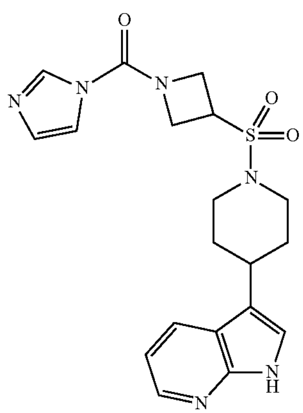 [SMILES: O=C(N1CC(S(=O)(=O)N2CCC(c3c[nH]c4ncccc34)CC2)C1)n1ccnc1] | 415.1 | ¹H NMR (300 MHz, DMSO-d₆): δ = 11.38 (br. s., 1H), 8.14-8.19 (m, 2H), 7.96 (dd, J = 1.31, 7.93 Hz, 1H), 7.58 (t, J = 1.48 Hz, 1H), 7.25 (d, J = 2.44 Hz, 1H), 7.06 (dd, J = 0.78, 1.48 Hz, 1H), 7.01 (dd, J = 4.70, 7.84 Hz, 1H), 4.85-4.25 (m, 5H), 2.85-3.09 (m, 3H), 2.02 (d, J = 11.84 Hz, 2H), 1.63 (dd, J = 3.57, 12.45 Hz, 2H) ppm. | 1H-pyrrolo [2,3-b]pyridine | General method A2, B1 using P₂O₂ (partial reduction), then B2, Ci using TFA, D using tert-butyl 3-chlorosulfonyl azetidine-1-carboxylate, Cf using TFA, G4; by-product | imidazol-1-yl-[3-[4-(1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 80 | 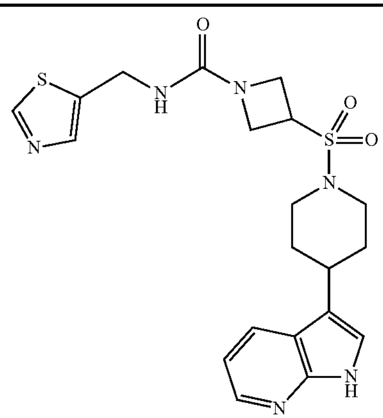 | 461 | ¹H NMR (300 MHz, DMSO-d₆): δ = 11.37 (s, 1H), 8.94 (d, J = 0.87 Hz, 1H), 8.17 (dd, J = 1.57, 4.70 Hz, 1H), 7.97 (dd, J = 1.39, 7.84 Hz, 1H), 7.73 (d, J = 0.70 Hz, 1H), 7.20-7.30 (m, 2H), 7.01 (dd, J = 4.70, 7.84 Hz, 1H), 4.40 (d, J = 5.75 Hz, 2H), 4.37-4.28 (m, 1H), 4.13 (t, J = 8.54 Hz, 2H), 3.98 (dd, J = 5.66, 8.97 Hz, 2H), 3.72 (d, J = 12.37 Hz, 2H), 2.84-3.04 (m, 3H), 2.01 (d, J = 11.50 Hz, 2H), 1.62 (dd, J = 3.66, 12.37 Hz, 2H) ppm. | 1H-pyrrolo [2,3-b]pyridine | General method A2, B1 using P₂O₂ (partial reduction), then B2, Ci using TFA, D using tert-butyl 3-chlorosulfonyl azetidine-1-carboxylate, Cf using TFA, G4 using thiazol-5-ylmethanamine | 3-[4-(1H-pyrrolo[2,3-b]pyridin-3-yl)piperidin-1-yl]sulfonyl-N-(1,3-thiazol-5-ylmethyl)azetidine-1-carboxamide |
| 81 | 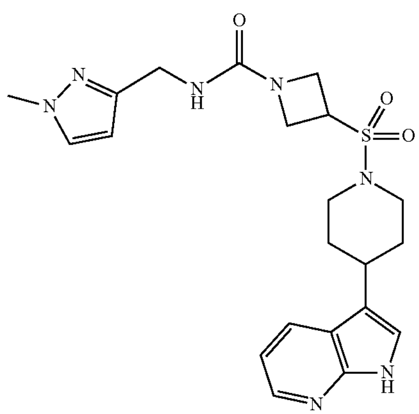 [SMILES: Cn1ccc(CNC(=O)N2CC(S(=O)(=O)N3CCC(c4c[nH]c5ncccc45)CC3)C2)n1] | 458.1 | ¹H NMR (300 MHz, DMSO-d₆): δ = 11.37 (br. s., 1H), 8.17 (dd, J = 1.48, 4.62 Hz, 1H), 7.92-8.01 (m, 1H), 7.54 (d, J = 2.09 Hz, 1H), 7.24 (d, J = 2.26 Hz, 1H), 7.01 (dd, J = 4.70, 7.84 Hz, 1H), 6.97-6.88 (m, 1H), 6.05 (d, J = 2.26 Hz, 1H), 4.26-4.39 (m, 1H), 4.05-4.16 (m, 4H), 3.92-4.02 (m, 2H), 3.75 (s, 4H), 3.70 (br. s., 1H), 2.84-3.05 (m, 3H), 2.01 (d, J = 11.15 Hz, 2H), 1.62 (dd, J = 3.14, 12.19 Hz, 2H) ppm. | 1H-pyrrolo [2,3-b]pyridine | General method A2, B1 using P₂O₂ (partial reduction), then B2, Ci using TFA, D using tert-butyl 3-chlorosulfonyl azetidine-1-carboxylate, Cf using TFA, G4 using (1-methylpyrazol-3-yl) methanamine | N-[(1-methylpyrazol-3-yl)methyl]-3-[4-(1H-pyrrolo[2,3-b]pyridin-3-yl)piperidin-1-yl]sulfonylazetidine-1-carboxamide |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 82 | 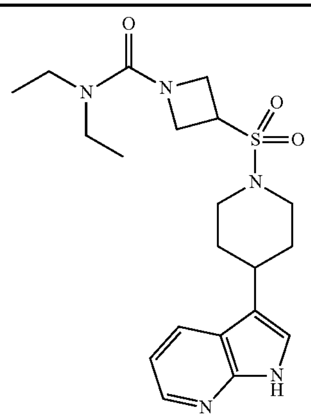 | 420.1 | ¹H NMR (300 MHz, DMSO-d₆): δ = 11.37 (s, 1H), 8.17 (dd, J = 1.48, 4.62 Hz, 1H), 7.97 (dd, J = 1.39, 7.84 Hz, 1H), 7.24 (d, J = 2.26 Hz, 1H), 7.01 (dd, J = 4.70, 7.84 Hz, 1H), 4.27-4.41 (m, 1H), 4.17 (t, J = 8.45 Hz, 2H), 3.98-4.08 (m, 2H), 3.72 (d, J = 11.84 Hz, 2H), 3.11 (q, J = 6.97 Hz, 4H), 2.83-3.03 (m, 3H), 1.96-2.08 (m, 2H), 1.63 (dd, J = 3.31, 12.37 Hz, 2H), 1.03 (t, J = 6.97 Hz, 6H) ppm. | 1H-pyrrolo[2,3-b]pyridine | General method A2, B1 using P₂O₂ (partial reduction), then B2, Ci using tert-butyl 3-chlorosulfonyl azetidine-1-carboxylate, Cf using TFA, G1 using N,N-diethylcarbamoyl chloride | N,N-diethyl-3-[4-(1H-pyrrolo[2,3-b]pyridin-3-yl)piperidin-1-yl]sulfonylazetidine-1-carboxamide |
| 83 | 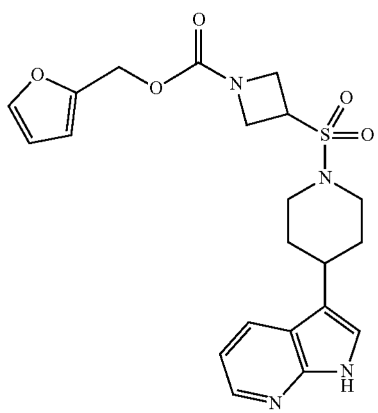 [SMILES: O=C(OCc1ccco1)N1CC(S(=O)(=O)N2CCC(c3c[nH]c4ncccc34)CC2)C1] | 445.1 | ¹H NMR (300 MHz, DMSO-d₆): δ = 11.37 (br. s., 1H), 8.17 (dd, J = 1.57, 4.70 Hz, 1H), 7.96 (dd, J = 1.48, 7.93 Hz, 1H), 7.67 (dd, J = 0.78, 1.83 Hz, 1H), 7.24 (d, J = 2.09 Hz, 1H), 7.01 (dd, J = 4.70, 7.84 Hz, 1H), 6.50 (dd, J = 0.78, 3.22 Hz, 1H), 6.44 (dd, J = 1.83, 3.22 Hz, 1H), 5.02 (s, 2H), 4.40-4.20 (m, 3H), 4.09-3.99 (m, 2H), 3.72 (d, J = 12.37 Hz, 2H), 3.03-2.82 (m, 3H), 2.00 (d, J = 11.32 Hz, 2H), 1.61 (dd, J = 3.14, 12.37 Hz, 2H) ppm. | 3-(4-piperidyl)-1H-pyrrolo[2,3-b]pyridine | General method D using tert-butyl 3-chlorosulfonyl-azetidine-1-carboxylate, Cf using TFA, H2 using 2-furylmethanol | furan-2-ylmethyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 84 | 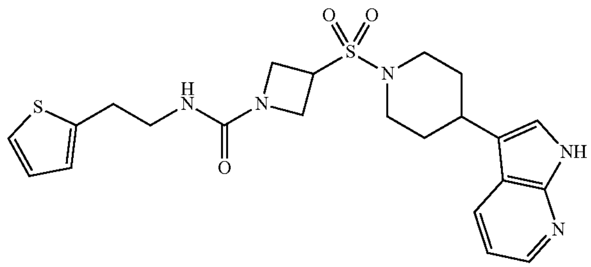 [SMILES: O=C(NCCc1cccs1)N1CC(S(=O)(=O)N2CCC(c3c[nH]c4ncccc34)CC2)C1] | 474.2 | ¹H NMR (300 MHz, DMSO-d₆): δ = 11.36 (s, 1H), 8.17 (dd, J = 1.6, 4.7 Hz, 1H), 7.97 (dd, J = 1.2, 7.8 Hz, 1H), 7.31 (dd, J = 1.2, 5.2 Hz, 1H), 7.24 (d, J = 2.4 Hz, 1H), 7.01 (dd, J = 4.7, 7.8 Hz, 1H), 6.93 (dd, J = 3.4, 5.1 Hz, 1H), 6.88-6.83 (m, 1H), 6.73 (t, J = 5.6 Hz, 1H), 4.38-4.27 (m, 1H), 4.09 (t, J = 8.5 Hz, 2H), 4.00-3.91 (m, 2H), 3.72 (d, J = 12.0 Hz, 2H), 3.25-3.15 (m, 2H), 3.04-2.85 (m, 5H), 2.06-1.96 (m, 2H), 1.71-1.54(m, 2H) ppm. | 3-(4-piperidyl)-1H-pyrrolo[2,3-b]pyridine | General method D using tert-butyl 3-chlorosulfonylazetidine-1-carboxylate, Cf using TFA, G2 using 2-(2-isocyanatoethyl) thiophene | 3-[4-(1H-pyrrolo[2,3-b]pyridin-3-yl)piperidin-1-yl]sulfonyl-N-(2-thiophen-2-ylethyl)azetidine-1-carboxamide |
| 85 | 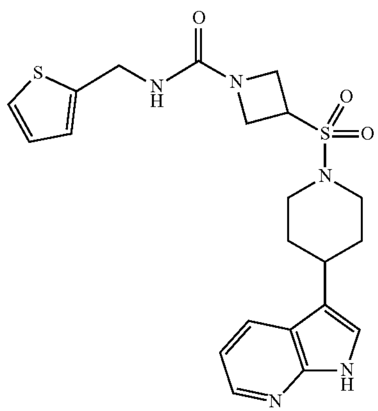 | 460.1 | ¹H NMR (300 MHz, DMSO-d₆): δ = 11.36 (s, 1H), 8.17 (dd, J = 1.5, 4.6 Hz, 1H), 7.97 (dd, J = 1.4, 7.8 Hz, 1H), 7.37-7.31 (m, 1H), 7.26-7.18 (m, 2H), 7.01 (dd, J = 4.7, 7.8 Hz, 1H), 6.95-6.89 (m, 2H), 4.38-4.30 (m, 3H), 4.12 (t, J = 8.5 Hz, 2H), 4.02-3.94 (m, 2H), 3.72 (d, J = 12.2 Hz, 2H), 3.04-2.85 (m, 3H), 2.06-1.95 (m, 2H), 1.71-1.53 (m,2H) ppm. | 3-(4-piperidyl)-1H-pyrrolo[2,3-b]pyridine | General method D using tert-butyl 3-chlorosulfonylazetidine-1-carboxylate, Cf using TFA, G4 using 2-thienylmethanamine | 3-[4-(1H-pyrrolo[2,3-b]pyridin-3-yl)piperidin-1-yl]sulfonyl-N-(thiophen-2-ylmethyl)azetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 86 | 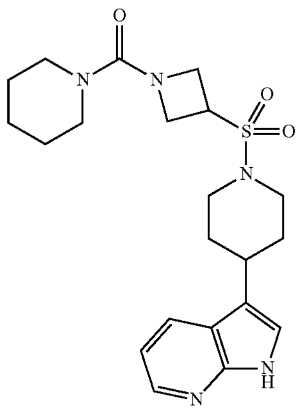 [SMILES: O=C(N1CCCCC1)N1CC(S(=O)(=O)N2CCC(c3c[nH]c4ncccc34)CC2)C1] | 432.2 | ¹H NMR (300 MHz, DMSO-d₆): δ = 11.36 (br. s., 1H), 8.17 (dd, J = 1.6, 4.7 Hz, 1H), 7.97 (dd, J = 1.2, 7.8 Hz, 1H), 7.24 (d, J = 2.4 Hz, 1H), 7.01 (dd, J = 4.7, 7.8 Hz, 1H), 4.38-4.28 (m, 1H), 4.24-4.10 (m, 2H), 4.08-3.99 (m, 2H), 3.72 (d, J = 11.7 Hz, 2H), 3.20-3.13 (m, 4H), 3.01-2.85 (m, 3H), 2.01 (d, J = 12.5 Hz, 2H), 1.71-1.58 (m, 2H),1.57-1.47 (m, 2H), 1.46-1.35 (m, 4H) ppm. | 3-(4-piperidyl)-1H-pyrrolo[2,3-b]pyridine | General method D using tert-butyl 3-chlorosulfonylazetidine-1-carboxylate, Cf using TFA, G1 using piperidine-1-carbonyl chloride | piperidin-1-yl-[3-[4-(1H-pyrrolo[2,3-b]pyridin-3-yl)piperidin-1-yl]sulfonylazetidin-1-yl]methanone |
| 87 | 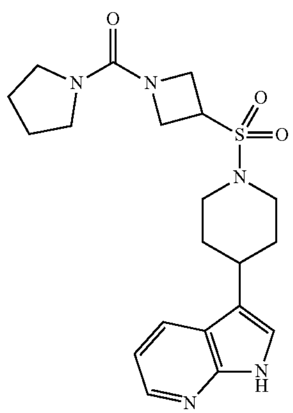 | 418.2 | ¹H NMR (300 MHz, DMSO-d₆): δ = 11.36 (br. s., 1H), 8.17 (dd, J = 1.5, 4.6 Hz, 1H), 7.97 (dd, J = 1.1, 7.9 Hz, 1H), 7.24 (d, J = 2.3 Hz, 1H), 7.01 (dd, J = 4.7, 7.8 Hz, 1H), 4.40-4.28 (m, 1H), 4.21-4.12 (m, 2H), 4.10-4.01 (m, 2H), 3.72 (d, J = 12.5 Hz, 2H), 3.24-3.15 (m,4H), 3.02-2.84 (m, 3H), 2.06-1.95 (m, 2H), 1.79-1.71 (m, 4H), 1.70-1.54 (m, 2H) ppm. | 3-(4-piperidyl)-1H-pyrrolo[2,3-b]pyridine | General method D using tert-butyl 3-chlorosulfonylazetidine-1-carboxylate, Cf using TFA, G1 using pyrrolidine-1-carbonyl chloride | pyrrolidin-1-yl-[3-[4-(1H-pyrrolo[2,3-b]pyridin-3-yl)piperidin-1-yl]sulfonylazetidin-1-yl]methanone |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 88 | 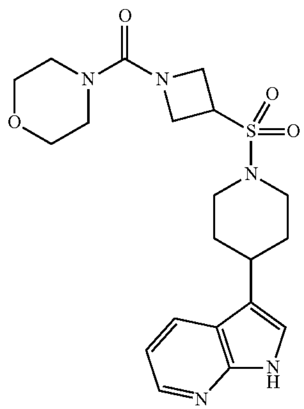 [SMILES: O=C(N1CCOCC1)N1CC(S(=O)(=O)N2CCC(c3c[nH]c4ncccc34)CC2)C1] | 434.1 | ¹H NMR (300 MHz, DMSO-d₆): δ = 11.36 (s, 1H), 8.17 (dd, J = 1.6, 4.7 Hz, 1H), 7.97 (dd, J = 1.5, 7.9 Hz, 1H), 7.24 (d, J = 2.3 Hz, 1H), 7.01 (dd, J = 4.7, 8.0 Hz, 1H), 4.42-4.30 (m, 1H), 4.21 (t, J = 8.6 Hz, 2H), 4.12-4.04 (m, 2H), 3.72 (d, J = 12.4 Hz, 2H), 3.55-3.49 (m, 4H), 3.24-3.16 (m, 4H), 3.03-2.84 (m, 3H), 2.07-1.96 (m, 2H), 1.62 (dd, J = 3.5, 12.2 Hz, 2H) ppm. | 1H-pyrrolo [2,3-b]pyridine | General method A2, B2, Ci using TFA, D using tert-butyl 3-chlorosulfonylaze-tidine-1-carboxylate, Cf using TFA, G1 using morpholine-4-carbonyl chloride | morpholin-4-yl-[3-[4-(1H-pyrrolo[2,3-b]pyridin-3-yl)piperidin-1-yl]sulfonylaze-tidin-1-yl]methanone |
| 89 | 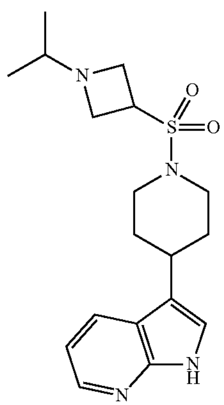 [SMILES: CC(C)N1CC(S(=O)(=O)N2CCC(c3c[nH]c4ncccc34)CC2)C1] | 363.1 | ¹H NMR (300 MHz, DMSO-d₆): δ = 11.37 (br. s., 1H), 8.17 (dd, J = 1.6, 4.7 Hz, 1H), 7.97 (dd, J = 1.1, 7.9 Hz, 1H), 7.24 (d, J = 2.3 Hz, 1H), 7.01 (dd, J = 4.7, 7.8 Hz, 1H), 4.18-4.04 (m, 1H), 3.68 (d, J = 12.2 Hz, 2H), 3.51 (t, J = 7.9 Hz, 2H), 3.22 (t, J = 7.7 Hz, 2H), 3.00-2.83 (m, 3H), 2.37-2.23 (m, 1H), 2.00 (d, J = 11.1 Hz, 2H), 1.71-1.53 (m, 2H), 0.87-0.80 (m, 6H) ppm. | 1H-pyrrolo [2,3-b]pyridine | General method A2, B2, Ci using TFA, D using tert-butyl 3-chlorosulfonylaze-tidine-1-carboxylate, Cf using TFA, J1 using 2-bromopropane | 3-[1-(1-propan-2-ylazetidin-3-yl)sulfonylpiperidin-4-yl]-1H-pyrrolo[2,3-b]pyridine |

Table with Representative Compounds of Formula (I):

| Cpd # | Structure | MS (m/z, ES+) | ¹H NMR Data | Starting Int/Cpd# | Sequence of Methods | Chemical Name |
|---|---|---|---|---|---|---|
| 90 | 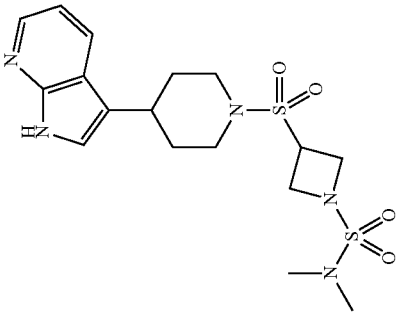 | 428.1 | ¹H NMR (300 MHz, DMSO-d₆): δ = 11.38 (br. s., 1H), 8.17 (dd, J = 1.5, 4.6 Hz, 1H), 7.97 (dd, J = 1.4, 7.8 Hz, 1H), 7.25 (d, J = 2.3 Hz, 1H), 7.01 (dd, J = 4.6, 7.9 Hz, 1H), 4.53-4.39 (m, 1H), 4.19-4.00 (m, 4H), 3.72 (d, J = 12.2 Hz, 2H), 3.05-2.83 (m, 3H), 2.79-2.69 (m, 6H), 2.01 (d, J = 11.1 Hz, 2H), 1.73-1.55 (m, 2H) ppm. | 1H-pyrrolo[2,3-b]pyridine | General method A2, B2, Ci using TFA, D using tert-butyl 3-chlorosulfonylazetidine-1-carboxylate, Cf using TFA, Df using N,N-dimethylsulfamoyl chloride | N,N-dimethyl-3-[4-(1H-pyrrolo[2,3-b]pyridin-3-yl)piperidin-1-yl]sulfonylazetidine-1-sulfonamide |
| 91 | 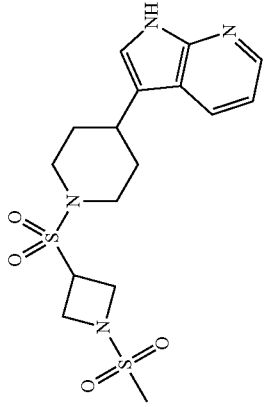 | 399 | ¹H NMR (600 MHz, DMSO-d₆): δ = 11.37 (br. s., 1H), 8.17 (dd, J = 1.6, 4.7 Hz, 1H), 7.97 (dd, J = 1.2, 7.8 Hz, 1H), 7.25 (d, J = 2.2 Hz, 1H), 7.01 (dd, J = 4.6, 7.9 Hz, 1H), 4.45-4.39 (m, 1H), 4.21 (t, J = 8.9 Hz, 2H), 4.11 (dd, J = 6.4, 9.2 Hz, 2H), 3.74 (d, J = 12.3 Hz, 2H), 3.06 (s, 3H), 3.01-2.95 (m, 2H), 2.94-2.88 (m, 1H), 2.01 (d, J = 11.4 Hz, 2H), 1.63 (dq, J = 4.0, 12.5 Hz, 2H) ppm. | 1H-pyrrolo[2,3-b]pyridine | General method A2, B2, Ci using TFA, D using tert-butyl 3-chlorosulfonylazetidine-1-carboxylate, Cf using TFA, Df using methanesulfonyl chloride | 3-[1-(1-methylsulfonylazetidin-3-yl)sulfonylpiperidin-4-yl]-1H-pyrrolo[2,3-b]pyridine |
| 92 | 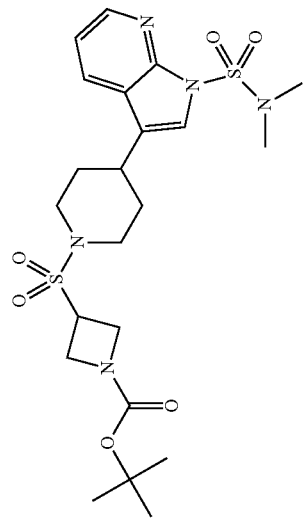 | 528.1 | ¹H NMR (300 MHz, DMSO-d₆): δ = 8.38 (dd, J = 1.39, 4.70 Hz, 1H), 8.16 (dd, J = 1.65, 7.93 Hz, 1H), 7.46 (s, 1H), 7.31 (dd, J = 4.79, 7.93 Hz, 1H), 4.27-4.37 (m, 1H), 4.12-4.23 (m, 2H), 3.93-4.02 (m, 2H), 3.69-3.78 (m, 2H), 2.92-3.03 (m, 3H), 2.91 (s, 6H), 1.97-2.08 (m, 2H), 1.54-1.71 (m, 2H), 1.38 (s, 9H) ppm. | 1H-pyrrolo[2,3-b]pyridine | General method A2, B2, Ci using TFA, D using tert-butyl 3-chlorosulfonylazetidine-1-carboxylate, P using N,N-dimethylsulfamoyl chloride | tert-butyl 3-[4-[1-(dimethylsulfamoyl)pyrrolo[2,3-b]pyridin-3-yl]piperidin-1-yl]sulfonylazetidine-1-carboxylate |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 93 | 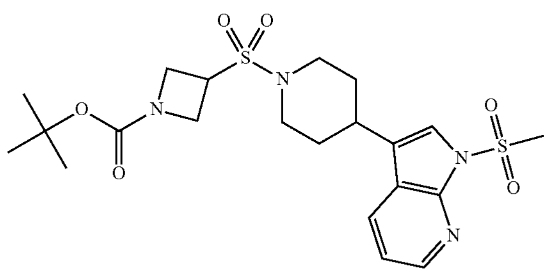 [SMILES: CC(C)(C)OC(=O)N1CC(S(=O)(=O)N2CCC(c3cn(S(C)(=O)=O)c4ncccc34)CC2)C1] | 499.2 | ¹H NMR (300 MHz, DMSO-d₆): δ = 8.43 (dd, J = 4.88 Hz, 1H), 8.21 (dd, J = 1.48, 7.93 Hz, 1H), 7.49 (s, 1H), 7.37 (dd, J = 4.79, 7.93 Hz, 1H), 4.28-4.38 (m, 1H), 4.12-4.24 (m, 2H), 3.92-4.03 (m, 2H), 3.70-3.79 (m, 2H), 3.69 (s, 3H), 2.90-3.04 (m, 3H), 1.97-2.09 (m, 2H), 1.54-1.71 (m, 2H), 1.37 (s, 9H) ppm. | 1H-pyrrolo[2,3-b]pyridine | General method A2, B2, Ci using TFA, D using tert-butyl 3-chlorosulfonylazetidine-1-carboxylate, P using methanesulfonyl chloride | tert-butyl 3-[4-(1-methylsulfonyl pyrrolo[2,3-b]pyridin-3-yl)piperidin-1-yl]sulfonylaze-tidine-1-carboxylate |
| 94 | 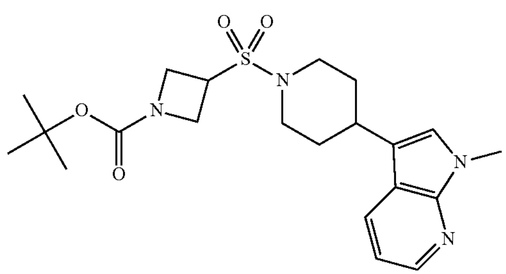 [SMILES: Cn1cc(C2CCN(S(=O)(=O)C3CN(C(=O)OC(C)(C)C)C3)CC2)c2cccnc21] | 435.1 | ¹H NMR (300 MHz, DMSO-d₆): δ = 8.22 (dd, J = 1.48, 4.62 Hz, 1H), 7.98 (dd, J = 1.57, 7.84 Hz, 1H), 7.31 (s, 1H), 7.04 (dd, J = 4.70, 7.84 Hz, 1H), 4.26-4.38 (m, 1H), 4.12-4.23 (m, 2H), 4.04 (m, 2H), 3.67-3.79 (m, 5H), 2.85-3.04 (m, 3H), 1.96-2.07 (m, 2H), 1.51-1.68 (m, 2H), 1.34-1.42 (m, 9H) ppm. | 1H-pyrrolo[2,3-b]pyridine | General method A2, B2, Ci using TFA, D using tert-butyl 3-chlorosulfonylazetidine-1-carboxylate, O using iodomethane | tert-butyl 3-[4-(1-methylpyrrolo[2,3-b]pyridin-3-yl)piperidin-1-yl]sulfonylaze-tidine-1-carboxylate |
| 95 | 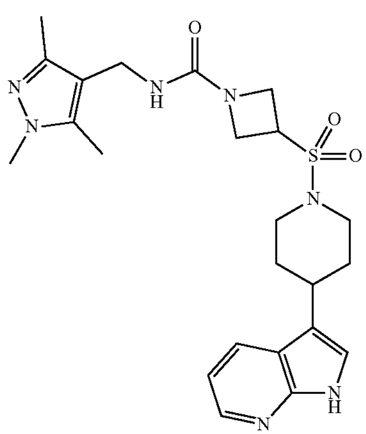 [SMILES: Cc1nn(C)c(C)c1CNC(=O)N1CC(S(=O)(=O)N2CCC(c3c[nH]c4ncccc34)CC2)C1] | 486.1 | ¹H NMR (300 MHz, DMSO-d₆): δ = 11.33-11.40 (m, 1H), 8.17 (dd, J = 1.48, 4.62 Hz, 1H), 7.97 (dd, J = 1.31, 7.93 Hz, 1H), 7.24 (d, J = 2.44 Hz, 1H), 6.96-7.04 (m, 2H), 6.58 (t, J = 5.23 Hz, 1H), 4.24-4.35 (m, 1H), 4.06 (t, J = 8.54 Hz, 2H), 3.87-3.98 (m, 4H), 3.71 (d, J = 11.67 Hz, 2H), 3.57 (s, 3H), 2.84-3.03 (m, 3H), 2.14 (s, 3H), 2.03 (s, 3H), 1.95-2.00 (m, 1H), 1.53-1.69 (m, 2H) ppm. | 1H-pyrrolo[2,3-b]pyridine | General method A2, B2, Ci using TFA, D using tert-butyl 3-chlorosulfonylazetidine-1-carboxylate, Cf using TFA, G4 using (1,3,5-trimethylpyrazol-4-yl)methanamine | 3-[4-(1H-pyrrolo[2,3-b]pyridin-3-yl)piperidin-1-yl]sulfonyl-N-[(1,3,5-trimethylpyrazol-4-yl)methyl]azeti dine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 96 | 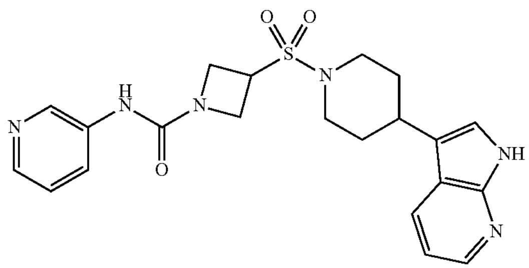 [SMILES: O=C(Nc1cccnc1)N1CC(S(=O)(=O)N2CCC(c3c[nH]c4ncccc34)CC2)C1] | 441.1 | ¹H NMR (300 MHz, DMSO-d₆): δ = 11.38 (br. s., 1H), 8.86 (s, 1H), 8.58-8.68 (m, 2H), 8.16 (br. s., 2H), 7.85-8.03 (m, 2H), 7.19-7.36 (m, 2H), 6.95-7.06 (m, 1H), 4.25-4.47 (m, 3H), 4.07-4.20 (m, 2H), 3.69-3.85 (m, 2H), 2.85-3.11 (m, 3H), 1.93-2.11 (m, 2H), 1.52-1.75 (m, 2H) ppm. | 1H-pyrrolo[2,3-b]pyridine | General method A2, B2, Ci using TFA, D using tert-butyl 3-chlorosulfonylazetidine-1-carboxylate, Cf using TFA, G2 using 3-isocyanatopyridine | N-pyridin-3-yl-3-[4-(1H-pyrrolo[2,3-b]pyridin-3-yl)piperidin-1-yl]sulfonylazetidine-1-carboxamide |
| 97 | 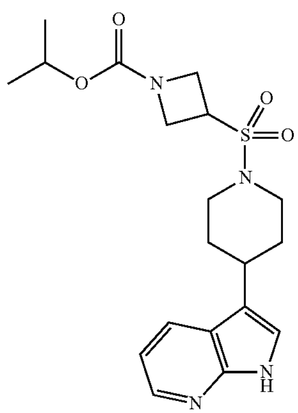 | 407.1 | ¹H NMR (300 MHz, DMSO-d₆): δ = 11.38 (s, 1H), 8.17 (dd, J = 1.57, 4.70 Hz, 1H), 7.96 (dd, J = 1.13, 7.93 Hz, 1H), 7.24 (d, J = 2.44 Hz, 1H), 7.01 (dd, J = 4.70, 7.84 Hz, 1H), 4.75 (quin, J = 6.23 Hz, 1H), 4.29-4.41 (m, 1H), 4.14-4.28 (m, 2H), 3.97-4.06 (m, 2H), 3.73 (d, J = 12.19 Hz, 2H), 2.83-3.05 (m, 3H), 1.96-2.07 (m, 2H), 1.52-1.71 (m, 2H), 1.16 (d, J = 6.27 Hz, 6H) ppm. | 1H-pyrrolo[2,3-b]pyridine | General method A2, B2, Ci using TFA, D using tert-butyl 3-chlorosulfonylazetidine-1-carboxylate, Cf using TFA, H1 using isopropyl carbonochloridate | propan-2-yl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 98 | 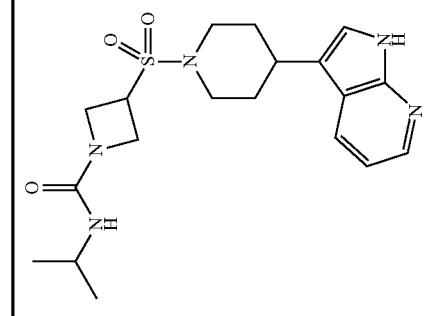 | 406.1 | ¹H NMR (300 MHz, DMSO-d₆): δ = 11.37 (br. s., 1H), 8.17 (dd, J = 1.48, 4.62 Hz, 1H), 7.97 (dd, J = 1.13, 7.93 Hz, 1H), 7.24 (d, J = 2.26 Hz, 1H), 7.01 (dd, J = 4.70, 7.84 Hz, 1H), 6.27 (d, J = 7.66 Hz, 1H), 4.25-4.36 (m, 1H), 4.07 (t, J = 8.54 Hz, 2H), 3.89-3.99 (m, 2H), 3.64-3.79 (m, 3H), 2.84-3.05 (m, 3H), 1.95-2.07 (m, 2H), 1.53-1.72 (m, 2H), 1.02 (d, J = 6.62 Hz, 6H) ppm. | 1H-pyrrolo [2,3-b]pyridine | General method A2, B2, Ci using TFA, D using tert-butyl 3-chlorosulfonylazetidine-1-carboxylate, Cf using TFA, G2 using 2-isocyanatopropane | N-propan-2-yl-3-[4-(1H-pyrrolo[2,3-b]pyridin-3-yl)piperidin-1-yl]sulfonylazetidine-1-carboxamide |
| 99 | 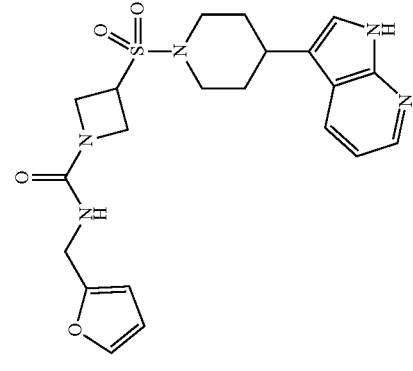 | 444.1 | ¹H NMR (300 MHz, DMSO-d₆): δ = 11.37 (s, 1H), 8.17 (dd, J = 1.57, 4.70 Hz, 1H), 7.97 (dd, J = 1.22, 8.01 Hz, 1H), 7.54 (dd, J = 0.78, 1.83 Hz, 1H), 7.24 (d, J = 2.26 Hz, 1H), 6.96-7.09 (m, 2H), 6.34-6.38 (m, 1H), 6.16-6.20 (m, 1H), 4.26-4.39 (m, 1H), 4.06-4.21 (m, 4H), 3.92-4.02 (m, 2H), 3.72 (d, J = 12.19 Hz, 2H), 2.85-3.05 (m, 3H), 1.93-2.07 (m, 2H), 1.53-1.71 (m, 2H) ppm. | 1H-pyrrolo [2,3-b]pyridine | General method A2, B2, Ci using TFA, D using tert-butyl 3-chlorosulfonylazetidine-1-carboxylate, Cf using TFA, G2 using 2-(isocyanatomethyl) furan | N-(furan-2-ylmethyl)-3-[4-(1H-pyrrolo[2,3-b]pyridin-3-yl)piperidin-1-yl]sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 100 | 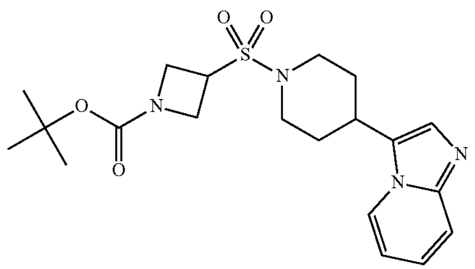 [SMILES: CC(C)(C)OC(=O)N1CC(S(=O)(=O)N2CCC(c3cnc4ccccn34)CC2)C1] | 421.1 | ¹H NMR (300 MHz, DMSO-d₆): δ = 8.41 (d, J = 6.97 Hz, 1H), 7.54 (td, J = 1.05, 9.06 Hz, 1H), 7.40 (s, 1H), 7.16-7.23 (m, 1H), 6.91 (dt, J = 1.13, 6.84 Hz, 1H), 4.28-4.39 (m, 1H), 4.18 (t, J = 8.80 Hz, 2H), 3.93-4.03 (m, 2H), 3.75 (d, J = 12.72 Hz, 2H), 3.09-3.21 (m, 1H), 2.96-3.08 (m, 2H), 2.08 (d, J = 11.32 Hz, 2H), 1.52-1.68 (m, 2H), 1.38 (s, 9H) ppm. | 3-bromoimidazo[1,2-a]pyridine | General method A1 using tert-butyl 4-(4,4,5,5-tetramethyl-1,3,2-dioxaborolan-2-yl)-3,6-dihydro-2H-pyridine-1-carboxylate, B2 (150% Pd/C), Ci using TFA, D using tert-butyl 3-chlorosulfonylazetidine-1-carboxylate | tert-butyl 3-(4-imidazo[1,2-a]pyridin-3-yl]piperidin-1-yl]sulfonylazetidine-1-carboxylate |
| 101 | 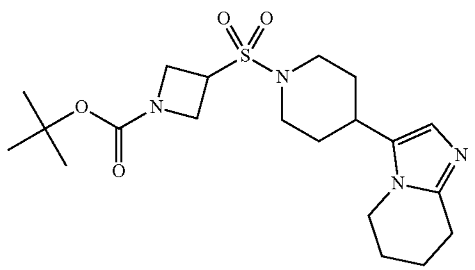 [SMILES: CC(C)(C)OC(=O)N1CC(S(=O)(=O)N2CCC(c3cnc4n3CCCC4)CC2)C1] | 425.1 | ¹H NMR (300 MHz, DMSO-d₆): δ = 8.41 (d, J = 6.97 Hz, 1H), 7.54 (td, J = 1.05, 9.06 Hz, 1H), 7.40 (s, 1H), 7.16-7.23 (m, 1H), 6.91 (dt, J = 1.13, 6.84 Hz, 1H), 4.28-4.39 (m, 1H), 4.18 (t, J = 8.80 Hz, 2H), 3.93-4.03 (m, 2H), 3.75 (d, J = 12.72 Hz, 2H), 3.09-3.21 (m, 1H), 2.96-3.08 (m, 2H), 2.08 (d, J = 11.32 Hz, 2H), 1.52-1.68 (m, 2H), 1.38 (s, 9H) ppm. | 3-bromoimidazo[1,2-a]pyridine | General method A1 using tert-butyl 4-(4,4,5,5-tetramethyl-1,3,2-dioxaborolan-2-yl)-3,6-dihydro-2H-pyridine-1-carboxylate, B1 using Pd/C then B2 (350% Pd/C), Ci using TFA, D using tert-butyl 3-chlorosulfonylazetidine-1-carboxylate | tert-butyl 3-[4-(5,6,7,8-tetrahydroimidazo[1,2-a]pyridin-3-yl]piperidin-1-yl]sulfonylazetidine-1-carboxylate |
| 102 | 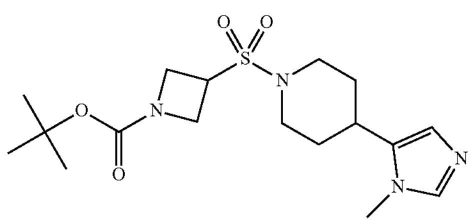 [SMILES: Cn1cncc1C1CCN(S(=O)(=O)C2CN(C(=O)OC(C)(C)C)C2)CC1] | 385.2 | ¹H NMR (300 MHz, DMSO-d₆): δ = 7.46 (s, 1H), 6.66 (s, 1H), 4.24-4.37 (m, 1H), 4.16 (t, J = 8.5 Hz, 2H), 3.88-4.03 (m, 2H), 3.68 (d, J = 12.2 Hz, 2H), 3.47-3.60 (m, 3H), 2.63-2.78 (m, 2H), 2.62-2.79 (m, 1H), 1.92 (d, J = 11.8 Hz, 2H), 1.42-1.55 (m, 2H), 1.30-1.42 ppm (s, 9H). | 4-(3-methyl-imidazol-4-yl)piperidine | General method D using tert-butyl 3-chlorosulfonylazetidine-1-carboxylate | tert-butyl 3-[4-(3-methylimidazol-4-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 103 | 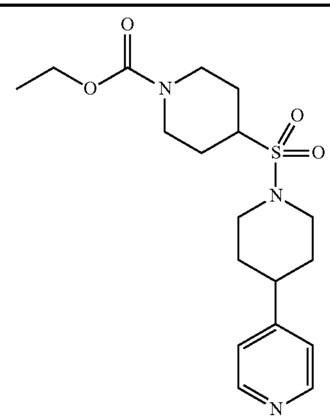 | 382.7 | ¹H NMR (500 MHz, CHLOROFORM-d): δ = 8.62-8.81 (m, 2H), 7.72-7.86 (m, 2H), 4.25-4.39 (m, 2H), 4.11-4.20 (m, 2H), 3.95-4.09 (m, 2H), 2.96-3.17 (m, 4H), 2.73-2.85 (m, 2H), 1.98-2.15 (m, 5H), 1.80-1.93 (m, 2H), 1.16-1.36 (m, 4H) ppm. | 4-(4-piperidyl) pyridine | General method D using tert-butyl 4-chlorosulfonylpiperidine-1-carboxylate, Cf using TFA, H1 using ethyl carbonochloridate | ethyl 4-(4-pyridin-4-yl)piperidin-1-yl)sulfonyl)piperidine-1-carboxylate |
| 104 | 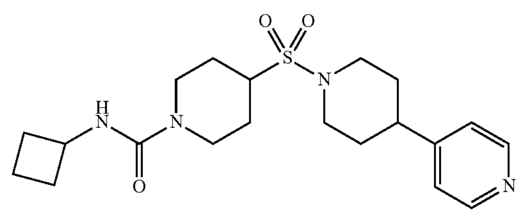 [SMILES: O=C(NC1CCC1)N1CCC(S(=O)(=O)N2CCC(c3ccncc3)CC2)CC1] | 407.7 | ¹H NMR (500 MHz, CHLOROFORM-d): δ = 8.65-8.72 (m, 2H), 7.92-7.99 (m, 2H), 4.20-4.29 (m, 1H), 3.94-4.02 (m, 2H), 3.78-3.88 (m, 2H), 3.05-3.24 (m, 5H), 2.91-3.00 (m, 1H), 2.03-2.41 (m, 11H), 1.69-1.85 (m, 4H) ppm. | 4-(4-piperidyl) pyridine | General method D using tert-butyl 4-chlorosulfonylpiperidine-1-carboxylate, Cf using TFA, G4 using cyclobutanamine | N-cyclobutyl-4-(4-pyridin-4-yl)piperidin-1-yl)sulfonyl)piperidine-1-carboxamide |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 105 | 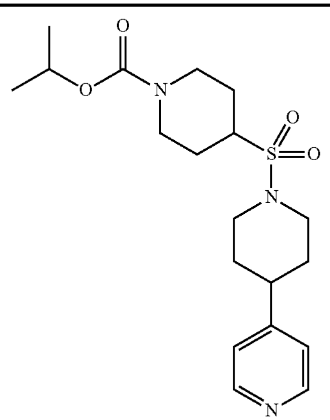 | 396.7 | 1H NMR (300 MHz, CHLOROFORM-d): δ = 8.60-8.69 (m, 2H), 7.49-7.57 (m, 2H), 4.90 (dt, J = 12.5, 6.2 Hz, 1H), 4.20-4.38 (m, 2H), 3.93-4.05 (m, 2H), 2.96-3.15 (m, 3H), 2.79-2.91 (m, 1H), 2.65-2.80 (m, 2H), 2.00-2.10 (m, 2H), 1.91-1.99 (m, 2H), 1.56-1.89 (m, 4H), 1.23 (d, J = 6.3 Hz, 6H) ppm. | 4-(4-piperidyl) pyridine | General method D using tert-butyl 4-chlorosulfonylpiperidine-1-carboxylate, Cf using TFA, H1 using isopropyl carbonochloridate | propan-2-yl 4-(4-pyridin-4-yl piperidin-1-yl)sulfonylpiperidine-1-carboxylate |
| 106 | 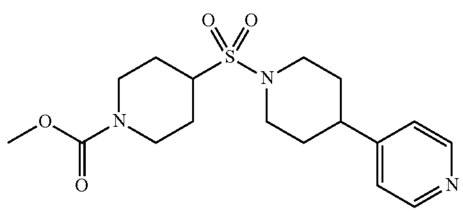 [SMILES: COC(=O)N1CCC(S(=O)(=O)N2CCC(c3ccncc3)CC2)CC1] | 368.6 | 1H NMR (300 MHz, CHLOROFORM-d): δ = 8.55-8.68 (m, 2H), 7.41-7.54 (m, 2H), 4.15-4.40 (br.s., 2H), 3.90-4.04 (m, 2H), 3.69 (s, 3H), 2.94-3.14 (m, 3H), 2.70-2.91 (m, 3H), 2.00-2.12 (m, 2H), 1.88-2.00 (m, 2H), 1.59-1.88 (m, 4H) ppm. | 4-(4-piperidyl) pyridine | General method D using tert-butyl 4-chlorosulfonylpiperidine-1-carboxylate, Cf using TFA, H1 using methyl carbonochloridate | methyl 4-(4-pyridin-4-yl piperidin-1-yl)sulfonylpiperidine-1-carboxylate |
| 107 | 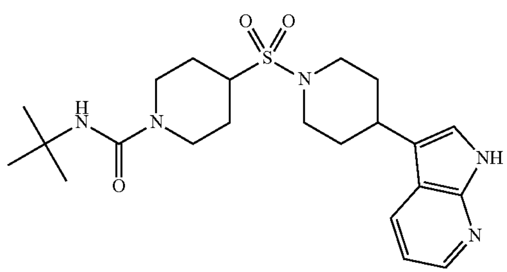 [SMILES: CC(C)(C)NC(=O)N1CCC(S(=O)(=O)N2CCC(c3c[nH]c4ncccc34)CC2)CC1] | 448.8 | 1H NMR (300 MHz, CHLOROFORM-d): δ =8.87 (s, 1H), 8.23-8.33 (m, 1H), 7.84-7.97 (m, 1H), 6.99-7.13 (m, 2H), 4.29 (s, 1H), 3.77-4.13 (m, 4H), 2.98-3.15 (m, 3H), 2.86-2.98 (m, 1H), 2.65-2.83 (m, 2H), 1.99-2.15 (m, 4H), 1.51-1.92 (m, 4H), 1.23-1.41 (m, 9H) ppm. | 3-(4-piperidyl)-1H-pyrrolo[2,3-b]pyridine | General method D using tert-butyl 4-chlorosulfonylpiperidine-1-carboxylate, Cf using TFA, G2 using 2-isocyanato-2-methyl-propane | N-tert-butyl-4-[4-(1H-pyrrolo[2,3-b]pyridin-3-yl)piperidin-1-yl]sulfonylpiperidine-1-carboxamide |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 108 | 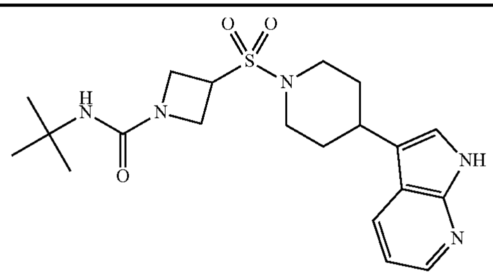 | 420.7 | ¹H NMR (300 MHz, CHLOROFORM-d): δ =9.07 (s, 1H), 8.22-8.35 (m, 1H), 7.86-7.93 (m, 1H), 6.92-7.13 (m, 2H), 4.09-4.27 (m, 4H), 3.88-4.02 (m, 4H), 2.84-3.08 (m, 3H), 2.03-2.16 (m, 2H), 1.71-1.92 (m, 2H), 1.32 (s, 9H) ppm. | 3-(4-piperidyl)-1H-pyrrolo[2,3-b]pyridine | General method D using tert-butyl 3-chlorosulfonylazetidine-1-carboxylate, Cf using TFA, G2 using 2-isocyanato-2-methyl-propane | N-tert-butyl-3-[4-(1H-pyrrolo[2,3-b]pyridin-3-yl)piperidin-1-yl]sulfonylazetidine-1-carboxamide |
| 109 | 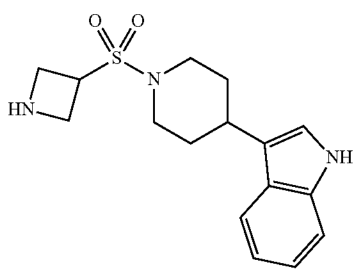 [SMILES: O=S(=O)(C1CNC1)N1CCC(c2c[nH]c3ccccc23)CC1] | 321.5 | ¹H NMR (300 MHz, CHLOROFORM-d): δ =9.23 (s, 1H), 8.26-8.32 (m, 1H), 7.87-7.93 (m, 1H), 6.96-7.11 (m, 2H), 4.07-4.27 (m, 3H), 3.87-3.97 (m, 2H), 3.74-3.85 (m, 2H), 2.77-3.02 (m, 3H), 2.03-2.15 (m, 2H), 1.74-1.93 (m, 3H) ppm. | 3-(4-piperidyl)-1H-pyrrolo[2,3-b]pyridine | General method D using tert-butyl 3-chlorosulfonylazetidine-1-carboxylate, Cf using TFA | 3-[1-(azetidin-3-ylsulfonyl)piperidin-4-yl]-1H-pyrrolo[2,3-b]pyridine |
| 110 | 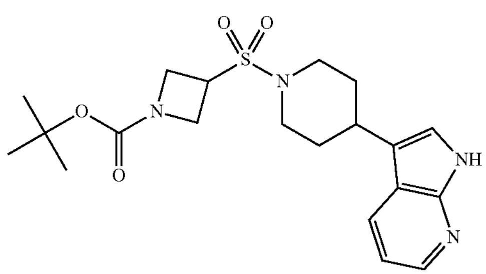 [SMILES: CC(C)(C)OC(=O)N1CC(S(=O)(=O)N2CCC(c3c[nH]c4ncccc34)CC2)C1] | 421.7 | ¹H NMR (300 MHz, CHLOROFORM-d): δ = 9.12 (s, 1H), 8.24-8.33 (m, 1H), 7.86-7.92 (m, 1H), 6.97-7.12 (m, 2H), 4.11-4.33 (m, 4H), 3.87-4.05 (m, 3H), 2.87-3.07 (m, 3H), 2.03-2.15 (m, 2H), 1.74-1.92 (m, 2H), 1.43 (s, 9H) ppm. | 3-(4-piperidyl)-1H-pyrrolo[2,3-b]pyridine | General method D using tert-butyl 3-chlorosulfonylazetidine-1-carboxylate | tert-butyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 111 | 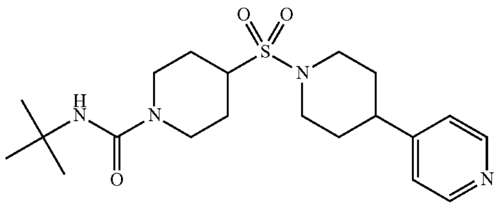 [SMILES: CC(C)(C)NC(=O)N1CCC(S(=O)(=O)N2CCC(c3ccncc3)CC2)CC1] | 409.2 | ¹H NMR (300 MHz, CHLOROFORM-d): δ =8.45-8.59 (m, 2H), 7.05-7.16 (m, 2H), 4.22-4.35 (s, 1H), 3.87-4.09 (m, 4H), 2.93-3.14 (m, 3H), 2.52-2.81 (m, 3H), 1.98-2.13 (m, 2H), 1.85-1.96 (m, 2H), 1.64-1.83 (m, 4H), 1.33 (s, 9H) ppm. | 4-(4-piperidyl)pyridine | General method D using tert-butyl 4-chlorosulfonylpiperidine-1-carboxylate, Cf using TFA, G2 using 2-isocyanato-2-methyl-propane | N-tert-butyl-4-(4-pyridin-4-yl)piperidin-1-yl]sulfonyl)piperidine-1-carboxamide |
| 112 | 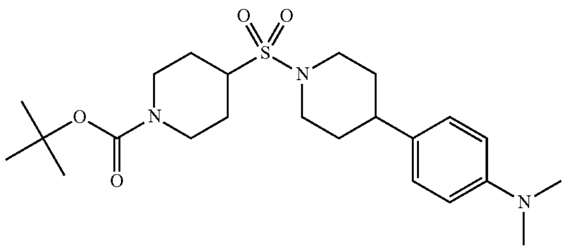 [SMILES: CN(C)c1ccc(C2CCN(S(=O)(=O)C3CCN(C(=O)OC(C)(C)C)CC3)CC2)cc1] | 452.3 | ¹H NMR (300 MHz, CHLOROFORM-d): δ = 7.02-7.09 (m, 2H), 6.64-6.72 (m, 2H), 4.23 (br.s., 2H), 3.85-3.95 (m, 2H), 2.94-3.11 (m, 3H), 2.90 (s, 6H), 2.61-2.78 (m, 2H), 2.44-2.60 (m, 1H), 1.98-2.12 (m, 2H), 1.81-1.91 (m, 2H), 1.61-1.80 (m, 4H), 1.45 (s, 9H)ppm. | tert-butyl 4-(4-aminophenyl)piperidine-1-carboxylate | General method T using formaldehyde, Ci using TFA, D using tert-butyl 4-[4-(dimethylamino)phenyl]piperidine-1-carboxylate | tert-butyl 4-[4-(dimethylamino)phenyl]piperidin-1-yl]sulfonyl)piperidine-1-carboxylate |
| 113 | 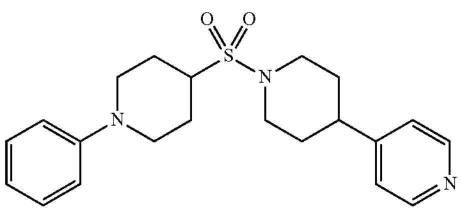 [SMILES: O=S(=O)(C1CCN(c2ccccc2)CC1)N1CCC(c2ccncc2)CC1] | 386.2 | ¹H NMR (300 MHz, CHLOROFORM-d): δ = 8.48-8.55 (m, 2H), 7.20-7.29 (m, 2H), 7.08-7.14 (m, 2H), 6.82-6.95 (m, 3H), 3.98 (d, J = 12.9 Hz, 2H), 3.79 (d, J = 12.7 Hz, 2H), 2.94-3.12 (m, 3H), 2.72 (td, J = 12.4, 2.4 Hz, 2H), 2.55-2.68 (m, 1H), 2.12-2.22 (m, 2H), 1.85-2.05 (m, 4H), 1.65-1.83 (m, 2H) ppm. | 4-(4-piperidyl)pyridine | General method D using tert-butyl 4-chlorosulfonylpiperidine-1-carboxylate, Cf using TFA, J4 using bromobenzene | 4-[1-(1-phenylpiperidin-4-yl)sulfonylpiperidin-4-yl]pyridine |
| 114 | 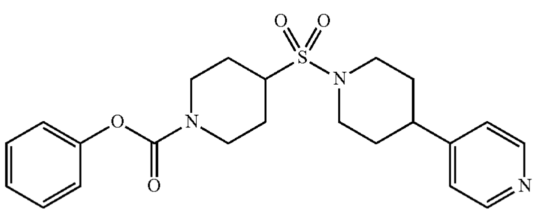 [SMILES: O=C(Oc1ccccc1)N1CCC(S(=O)(=O)N2CCC(c3ccncc3)CC2)CC1] | 430.2 | ¹H NMR (300 MHz, CHLOROFORM-d): δ = 8.49-8.55 (m, 2H), 7.30-7.38 (m, 2H), 7.15-7.22 (m, 1H), 7.04-7.14 (m, 4H), 4.35-4.51 (br. s., 2H), 3.93-4.02 (m, 2H), 3.08-3.18 (m, 1H), 2.95-3.07 (m, 3H), 2.78-2.93 (m, 1H), 2.59-2.71 (m, 1H), 2.09-2.20 (m, 2H), 1.73-1.96 (m, 6H) ppm. | 4-(4-piperidyl)pyridine | General method D using tert-butyl 4-chlorosulfonylpiperidine-1-carboxylate, Cf using TFA, H1 using phenyl carbonochloridate | phenyl 4-(4-pyridin-4-yl)piperidin-1-yl]sulfonyl)piperidine-1-carboxylate |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 115 | 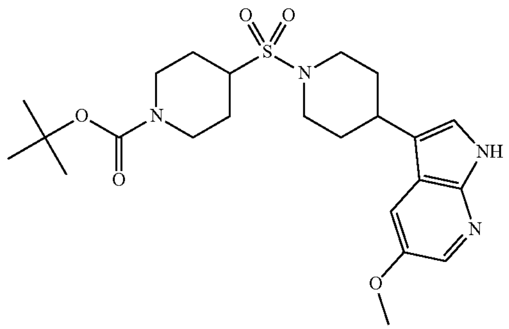 [SMILES: COc1cnc2[nH]cc(C3CCN(S(=O)(=O)C4CCN(C(=O)OC(C)(C)C)CC4)CC3)c2c1] | 479.2 | ¹H NMR (500 MHz, DMSO-d₆): δ = 11.20 (s., 1H), 7.93 (d, J = 2.75 Hz, 1H), 7.52 (d, J = 2.75 Hz, 1H), 7.21 (d, J = 2.44 Hz, 1H), 4.02 (d, J = 10.38 Hz, 2H), 3.82 (s, 3H), 3.74 (d, J = 12.51 Hz, 2H), 3.42 (1H), 3.04-3.12 (m, 2H), 2.89-2.97 (m, 1H), 2.78 (br. s., 2H), 1.93-2.05 (m, 4H), 1.59 (dq, J = 3.97, 12.41 Hz, 2H), 1.45 (dq, J = 4.20, 12.45 Hz, 2H), 1.40 (s, 9H) ppm | 3-bromo-5-methoxy-1H-pyrrolo[2,3-b]pyridine | General method E, A1 using Na₂CO₃, B1 using Pd/C, Ci using TFA, D using tert-butyl 4-chlorosulfonylpiperidine-1-carboxylate, then F | tert-butyl 4-[4-(5-methoxy-1H-pyrrolo[2,3-b]pyridin-3-yl)piperidin-1-yl]sulfonyl]piperidine-1-carboxylate |
| 116 | 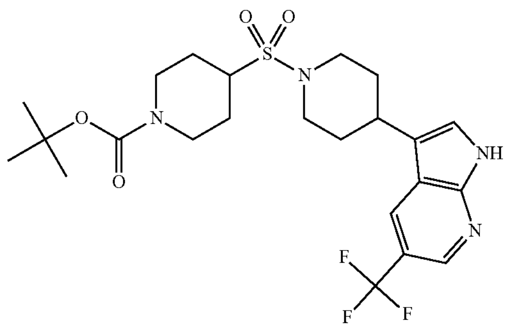 [SMILES: CC(C)(C)OC(=O)N1CCC(S(=O)(=O)N2CCC(c3c[nH]c4ncc(C(F)(F)F)cc34)CC2)CC1] | [M-56+H]⁺ 461.1 | ¹H NMR (500 MHz, DMSO-d₆): δ = 11.96 (br. s., 1H), 8.53 (d, J = 1.25 Hz, 1H), 8.41 (s, 1H), 7.50 (d, J = 1.53 Hz, 1H), 4.03 (d, J = 10.38 Hz, 2H), 3.74 (d, J = 12.51 Hz, 2H), 3.42 (1H), 3.01-3.15 (m, 3H), 2.79 (br. s., 2H), 1.93-2.07 (m, 4H), 1.62 (dq, J = 3.66, 12.41 Hz, 2H), 1.45 (dq, J = 4.20, 12.44 Hz, 2H), 1.40 (s, 9H) ppm | 5-(Trifluoromethyl)-1H-pyrrolo[2,3-b]pyridine | General method A2, B1 using Pd/C, Ci using TFA, then D using tert-butyl 4-chlorosulfonylpiperidine-1-carboxylate | tert-butyl 4-[4-[5-(trifluoromethyl)-1H-pyrrolo[2,3-b]pyridin-3-yl]piperidin-1-yl]sulfonyl]piperidine-1-carboxylate |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 117 | 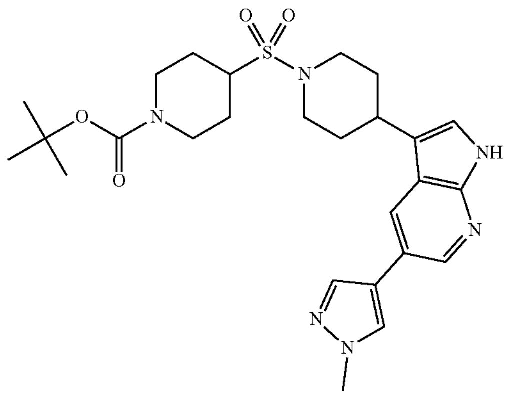 [SMILES: Cn1cc(-c2cnc3[nH]cc(C4CCN(S(=O)(=O)C5CCN(C(=O)OC(C)(C)C)CC5)CC4)c3c2)cn1] | 529.2 | ¹H NMR (600 MHz, DMSO-d₆): δ = 11.31 (d, J = 1.83 Hz, 1H), 8.42 (d, J = 2.02 Hz, 1H), 8.13 (s, 1H), 8.10 (d, J = 1.83 Hz, 1H), 7.88 (d, J = 0.73 Hz, 1H), 7.22 (d, J = 2.20 Hz, 1H), 4.02 (br. s., 2H), 3.86 (s, 3H), 3.74 (d, J = 12.47 Hz, 2H), 3.42 (m, 1H), 3.04-3.13 (m, 2H), 2.96 (tt, J = 3.16, 11.88 Hz, 1H), 2.78 (br. s., 2H), 2.04 (dd, J = 2.55, 13.40 Hz, 2H), 1.97 (dd, J = 1.65, 12.65 Hz, 2H), 1.61 (dq, J = 3.94, 12.44 Hz, 2H), 1.44 (dq, J = 4.49, 12.44 Hz, 2H), 1.39 (s, 9H) ppm | 5-(1-Methylpyrazol-4-yl)-3-(4-piperidyl)-1H-pyrrolo[2,3-b]pyridine | General method D using tert-butyl 4-chlorosulfonylpiperidine-1-carboxylate | tert-butyl 4-[4-[5-(1-methylpyrazol-4-yl)-1H-pyrrolo[2,3-b]pyridin-3-yl]piperidin-1-yl]sulfonylpiperidine-1-carboxylate |
| 118 | 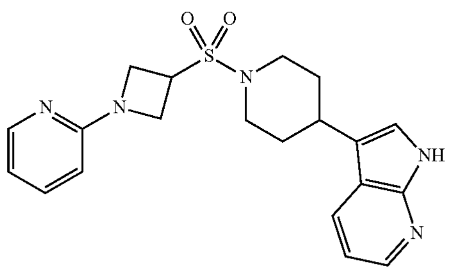 [SMILES: O=S(=O)(C1CN(c2ccccn2)C1)N1CCC(c2c[nH]c3ncccc23)CC1] | 398 | ¹H NMR (500 MHz, DMSO-d₆): δ = 11.38 (br. s., 1H), 8.18 (dd, J = 1.22, 4.58 Hz, 1H), 8.11 (dd, J = 0.92, 4.88 Hz, 1H), 7.97 (d, J = 7.93 Hz, 1H), 7.57 (dt, J = 1.83, 7.78 Hz, 1H), 7.24 (d, J = 2.44 Hz, 1H), 7.01 (dd, J = 4.73, 7.78 Hz, 1H), 6.72 (dd, J = 5.34, 6.87 Hz, 1H), 6.50 (d, J = 8.24 Hz, 1H), 4.50-4.58 (m, 1H), 4.29 (t, J = 8.54 Hz, 2H), 4.12 (dd, J = 5.80, 8.85 Hz, 2H), 3.77 (d, J = 12.21 Hz, 2H), 2.98-3.07 (m, 2H), 2.94 (tt, J = 3.05, 11.75 Hz, 1H), 2.03 (d, J = 11.29 Hz, 2H), 1.65 (dq, J = 3.97, 12.51 Hz, 2H) ppm | 1H-pyrrolo[2,3-b]pyridine | General method A2, B2, Ci using TFA, D using tert-butyl azetidine-1-carboxylate, Cf using TFA, then J3 using 2-fluoropyridine | 3-[1-(1-pyridin-2-ylazetidin-3-yl)sulfonylpiperidin-4-yl]-1H-pyrrolo[2,3-b]pyridine |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 119 | 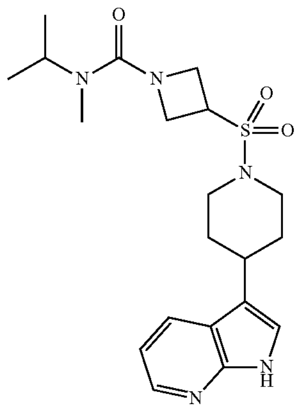 [SMILES: CC(C)N(C)C(=O)N1CC(S(=O)(=O)N2CCC(c3c[nH]c4ncccc34)CC2)C1] | 420.2 | ¹H NMR (600 MHz, DMSO-d₆): δ = 11.37 (br. s., 1H), 8.17 (dd, J = 4.55 Hz, 1H), 7.97 (d, J = 7.70 Hz, 1H), 7.24 (d, J = 2.02 Hz, 1H), 7.01 (dd, J = 4.68, 7.79 Hz, 1H), 4.30-4.37 (m, 1H), 4.16 (t, J = 8.62 Hz, 2H), 4.01-4.11 (m, 3H), 3.72 (d, J = 12.10 Hz, 2H), 2.94-3.01 (m, 2H), 2.87-2.94 (m, 1H), 2.58 (s, 3H), 2.02 (d, J = 11.92 Hz, 2H), 1.63 (dq, J = 3.58, 12.38 Hz, 2H), 1.02 (d, J = 6.79 Hz, 6H) ppm | 1H-pyrrolo [2,3-b]pyridine | General method A2, B2, Ci using TFA, D using tert-butyl 3-chlorosulfonyl azetidine-1-carboxylate, Cf using TFA, then G5 using N-isopropyl-N, 3-dimethyl-imidazol-1-ium-1-carboxamide-iodide | N-methyl-N-propan-2-yl-3-[4-(1H-pyrrolo[2,3-b]pyridin-3-yl)piperidin-1-yl]sulfonylazetidine-1-carboxamide |
| 120 | 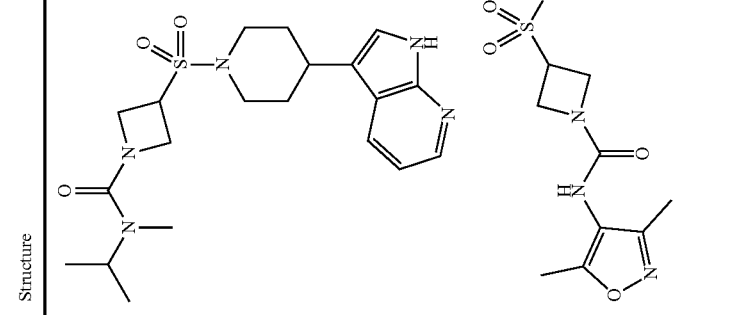 | 459.1 | ¹H NMR (600 MHz, DMSO-d₆): δ = 11.37 (s, 1H), 8.17 (dd, J = 1.56, 4.68 Hz, 1H), 8.02 (s, 1H), 7.97 (dd, J = 1.10, 7.89 Hz, 1H), 7.24 (d, J = 2.38 Hz, 1H), 7.01 (dd, J = 4.77, 7.89 Hz, 1H), 4.38 (tt, J = 5.41, 8.44 Hz, 1H), 4.26 (t, J = 8.71 Hz, 2H), 4.08 (dd, J = 5.50, 8.99 Hz, 2H), 3.75 (d, J = 12.29 Hz, 2H), 3.01 (dt, J = 2.11, 12.24 Hz, 2H), 2.93 (tt, J = 3.39, 11.92 Hz, 1H), 2.22 (s, 3H), 2.05 (s, 3H), 2.00-2.06 (m, 2H), 1.64 (dq, J = 3.94, 12.50 Hz, 2H) ppm | 1H-pyrrolo [2,3-b]pyridine | General method A2, B2, Ci using TFA, D using tert-butyl 3-chlorosulfonyl azetidine-1-carboxylate, Cf using TFA, then G2 using 4-isocyanato-3,5-dimethyl-isoxazole | N-(3,5-dimethyl-1,2-oxazol-4-yl)-3-[4-(1H-pyrrolo[2,3-b]pyridin-3-yl)piperidin-1-yl]sulfonylazetidine-1-carboxamide |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 121 | 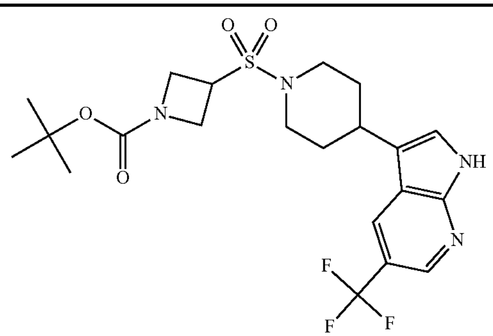 | 489 | ¹H NMR (500 MHz, DMSO-d₆): δ = 11.97 (br. s., 1H), 8.53 (d, J = 1.22 Hz, 1H), 8.42 (s, 1H), 7.50 (d, J = 1.83 Hz, 1H), 4.29-4.37 (m, 1H), 4.19 (br. s., 2H), 4.00 (br. s., 2H), 3.74 (d, J = 12.21 Hz, 2H), 2.93-3.06 (m, 3H), 2.04 (d, J = 11.60 Hz, 2H), 1.62 (dq, J = 3.66, 12.41 Hz, 2H), 1.39 (s, 9H) ppm | 5-(Trifluoromethyl)-1H-pyrrolo[2,3-b]pyridine | General method A2, B1 using Pd/C, Ci using TFA, then D using tert-butyl 3-chlorosulfonylazetidine-1-carboxylate | tert-butyl 3-[4-[5-(trifluoromethyl)-1H-pyrrolo[2,3-b]pyridin-3-yl]piperidin-1-yl]sulfonylazetidine-1-carboxylate |
| 122 | 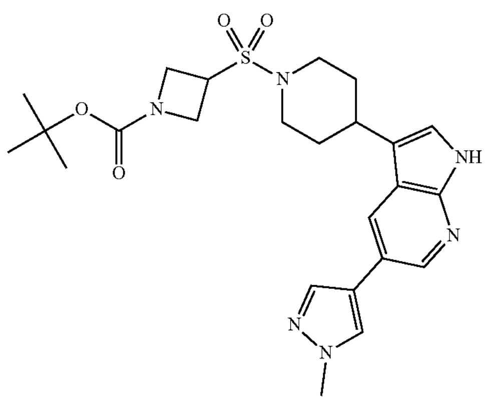 [SMILES: Cn1cc(-c2cnc3[nH]cc(C4CCN(S(=O)(=O)C5CN(C(=O)OC(C)(C)C)C5)CC4)c3c2)cn1] | 501 | ¹H NMR (500 MHz, DMSO-d₆): δ = 11.35 (s, 1H), 8.43 (d, J = 1.83 Hz, 1H), 8.15 (s, 1H), 8.11 (d, J = 1.53 Hz, 1H), 7.89 (s, 1H), 7.24 (d, J = 2.14 Hz, 1H), 4.30-4.38 (m, 1H), 4.20 (br. s., 2H), 4.01 (br. s., 2H), 3.87 (s, 3H), 3.75 (d, J = 12.21 Hz, 2H), 2.88-3.03 (m, 3H), 2.07 (d, J = 13.73 Hz, 2H), 1.63 (dq, J = 3.51, 12.36 Hz, 2H), 1.39 (s, 9H) ppm | 5-(1-Methylpyrazol-4-yl)-3-(4-piperidyl)-1H-pyrrolo[2,3-b]pyridine | General method D using tert-butyl 3-chlorosulfonylazetidine-1-carboxylate | tert-butyl 3-[4-[5-(1-methylpyrazol-4-yl)-1H-pyrrolo[2,3-b]pyridin-3-yl]piperidin-1-yl]sulfonylazetidine-1-carboxylate |

| Cpd # | MS (m/z ES+) | δ NMR Data | Starting Int/Cpd# | Sequence of Methods | Chemical Name |
|---|---|---|---|---|---|
| 123 | 451 | ¹H NMR (400 MHz, DMSO-d₆): δ = 11.21 (br. s., 1H), 7.92 (d, J = 2.81 Hz, 1H), 7.51 (d, J = 2.69 Hz, 1H), 7.21 (d, J = 2.57 Hz, 1H), 4.27-4.36 (m, 1H), 4.18 (br. s., 2H), 3.99 (br. s., 2H), 3.81 (s, 3H), 3.72 (d, J = 12.10 Hz, 2H), 2.83-3.02 (m, 3H), 2.02 (d, J = 10.88 Hz, 2H), 1.52-1.65 (m, 2H), 1.38 (s, 9H) ppm | 3-bromo-5-methoxy-1H-pyrrolo[2,3-b]pyridine | General method E, A1 using Na₂CO₃, B1 using Pd/C, C1 using TFA, D using tert-butyl 3-chlorosulfonylazetidine-1-carboxylate, then F | tert-butyl 3-[4-(5-methoxy-1H-pyrrolo[2,3-b]pyridin-3-yl)piperidin-1-yl]sulfonylazetidine-1-carboxylate |
| 124 | 422.2 | ¹H NMR (600 MHz, DMSO-d₆): δ = 8.21 (s, 1H), 8.07 (d, J = 1.6 Hz, 1H), 8.02 (s, 1H), 6.96 (d, J = 1.7 Hz, 1H), 4.29-4.37 (m, 1H), 4.19 (br. s., 2H), 3.99 (br. s., 2H), 3.76 (d, J = 11.6 Hz, 2H), 2.93 (t, J = 11.8 Hz, 2H), 2.82 (t, J = 12.2 Hz, 1H), 1.88 (d, J = 12.5 Hz, 2H), 1.61-1.74 (m, 2H), 1.38 (s, 9H) ppm | 5-bromofuro[2,3-b]pyridine | General method A1, B1 using Pd/C, C1 using TFA, D using tert-butyl 3-chlorosulfonylazetidine-1-carboxylate | tert-butyl 3-(4-furo[2,3-b]pyridin-5-yl)piperidin-1-yl)sulfonylazetidine-1-carboxylate |
| 125 | [M-56+H]⁺ 364.1 | ¹H NMR (600 MHz, DMSO-d₆): δ = 10.82 (s, 1H), 7.53 (d, J = 7.9 Hz, 1H), 7.32 (dt, J = 8.1, 0.8 Hz, 1H), 7.11 (d, J = 2.2 Hz, 1H), 7.05 (ddd, J = 8.1, 7.0, 1.1 Hz, 1H), 6.95 (ddd, J = 7.9, 7.0, 0.9 Hz, 1H), 4.31 (tt, J = 8.4, 5.5 Hz, 1H), 4.18 (br. s., 2H), 3.99 (br. s., 2H), 3.72 (d, J = 12.1 Hz, 2H), 2.98 (td, J = 12.2, 2.3 Hz, 2H), 2.91 (tt, J = 11.9, 3.5 Hz, 1H), 1.99-2.05 (m, 2H), 1.61 (qd, J = 12.5, 4.1 Hz, 2H), 1.38 (s, 9H) ppm | 3-(4-piperidyl)-1H-indole | General method D using tert-butyl 3-chlorosulfonylazetidine-1-carboxylate | tert-butyl 3-[4-(1H-indol-3-yl)piperidin-1-yl]sulfonylazetidine-1-carboxylate |

| Cpd # | Structure | MS (m/z, ES +) | δ NMR Data | Starting Int/Cpd# | Sequence of Methods | Chemical Name |
|---|---|---|---|---|---|---|
| 126 | 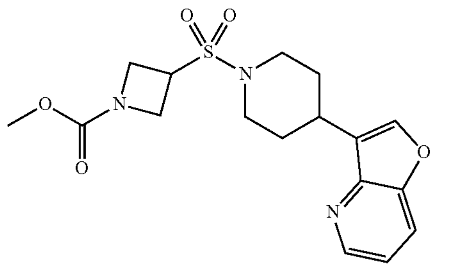 [SMILES: COC(=O)N1CC(S(=O)(=O)N2CCC(c3coc4cccnc34)CC2)C1] | 380.1 | ¹H NMR (600 MHz, DMSO-d₆): δ = 8.50 (d, J = 4.2 Hz, 1H), 8.11 (s, 1H), 7.98 (d, J = 8.3 Hz, 1H), 7.33 (dd, J = 8.3, 4.8 Hz, 1H), 4.32-4.42 (m, 1H), 4.27 (br. s., 2H), 4.05 (br. s., 2H), 3.73 (d, J = 11.9 Hz, 2H), 3.58 (s, 3H), 3.01 (t, J = 11.6 Hz, 3H), 2.12 (d, J = 12.5 Hz, 2H), 1.68-1.81 (m, 2H) ppm | 3-bromofuro[3,2-b]pyridine | General method A1 using Na₂CO₃, B1 using Pd/C, Ci using TFA, D using tert-butyl 3-chlorosulfonylazetidine-1-carboxylate, Cf using TFA, then H1 using methyl chloroformate | methyl 3-(4-furo[3,2-b]pyridin-3-yl)piperidin-1-yl)sulfonyl)azetidine-1-carboxylate |
| 127 | 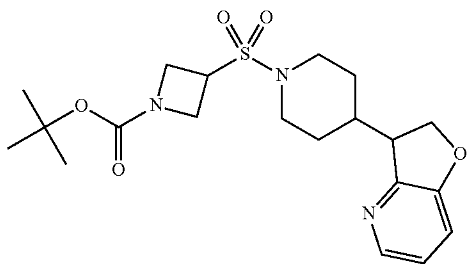 [SMILES: CC(C)(C)OC(=O)N1CC(S(=O)(=O)N2CCC(C3COc4cccnc43)CC2)C1] | 424.7 | ¹H NMR (600 MHz, DMSO-d₆): δ = 1.13 (qd, J = 12.5, 4.1 Hz, 1H), 1.38 (s, 9H), 1.40-1.52 (m, 2H), 1.78-1.88 (m, 1H), 1.97 (d, J = 13.2 Hz, 1H), 2.67-2.81 (m, 2H), 3.41 (dt, J = 9.7, 5.7 Hz, 1H), 3.62 (br.s., 2H), 3.93 (br.s., 2H), 4.13 (br.s., 2H), 4.23 (tt, J = 8.1, 5.1 Hz, 1H), 4.45 (dd, J = 9.4, 6.2 Hz, 1H), 4.64 (t, J = 9.5 Hz, 1H), 7.11 (dd, J = 8.1, 4.8 Hz, 1H), 7.14 (dd, J = 8.1, 1.1 Hz, 1H), 8.01 (dd, J = 4.6, 1.1 Hz, 1H) ppm | 3-bromofuro[3,2-b]pyridine | General method A1 using Na₂CO₃, B1 using Pd/C, Ci using TFA, D using tert-butyl 3-chlorosulfonylazetidine-1-carboxylate, by-product isolated | tert-butyl 3-[4-(2,3-dihydrofuro[3,2-b]pyridin-3-yl)piperidin-1-yl]sulfonylazetidine-1-carboxylate |
| 128 | 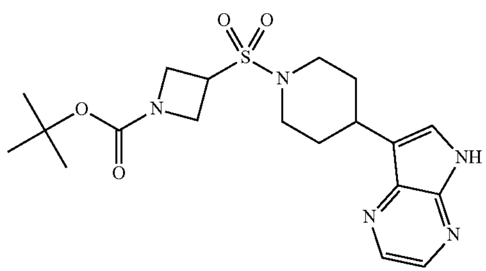 [SMILES: CC(C)(C)OC(=O)N1CC(S(=O)(=O)N2CCC(c3c[nH]c4nccnc34)CC2)C1] | 422.7 | ¹H NMR (400 MHz, DMSO-d₆): δ = 11.79 (br. s., 1H), 8.33 (d, J = 2.6 Hz, 1H), 8.20 (d, J = 2.4 Hz, 1H), 7.65 (d, J = 2.4 Hz, 1H), 4.26-4.35 (m, 1H), 4.13-4.24 (m, 2H), 3.93-4.03 (m, 2H), 3.71 (d, J = 12.0 Hz, 2H), 2.92-3.07 (m, 3H), 2.09 (d, J = 10.9 Hz, 2H), 1.75 (qd, J = 12.4, 3.9 Hz, 2H), 1.38 (s, 9H) ppm | 7-bromo-5H-pyrrolo[2,3-b]pyrazine | General method E, A1 using Na₂CO₃, B1 using Pd/C, Ci using TFA, D using tert-butyl 3-chlorosulfonylazetidine-1-carboxylate, then F | tert-butyl 3-[4-(5H-pyrrolo[2,3-b]pyrazin-7-yl)piperidin-1-yl]sulfonylazetidine-1-carboxylate |

TABLE with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 129 | 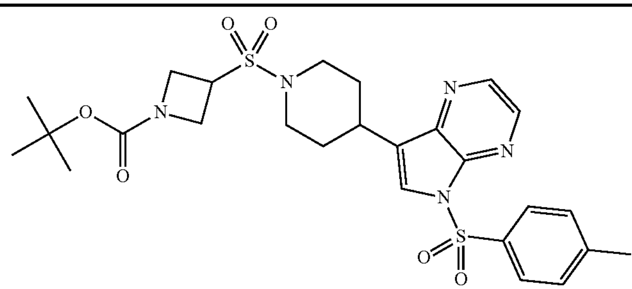 | 576.7 | ¹H NMR (600 MHz, DMSO-d₆): δ = 8.57 (d, J = 2.6 Hz, 1H), 8.41 (d, J = 2.6 Hz, 1H), 8.05 (s, 1H), 7.97-8.00 (m, 2H), 7.42 (d, J = 8.1 Hz, 2H), 4.28-4.34 (m, 1H), 4.18 (br. s., 2H), 3.98 (br. s., 2H), 3.72 (d, J = 12.3 Hz, 2H), 2.99-3.05 (m, 1H), 2.97 (td, J = 12.4, 2.2 Hz, 2H), 2.33 (s, 3H), 2.07 (d, J = 10.8 Hz, 2H), 1.71-1.80 (m, 2H), 1.38 (s, 9H). | 7-bromo-5H-pyrrolo[2,3-b]pyrazine | General method E, A1 using Na₂CO₃, B1 using Pd/C, Ci using TFA, D using tert-butyl 3-chlorosulfonylazetidine-1-carboxylate | tert-butyl 3-[4-[5-(4-methylphenyl)-sulfonylpyrrolo[2,3-b]pyrazin-7-yl]piperidin-1-yl]sulfonylazetidine-1-carboxylate |
| 130 | 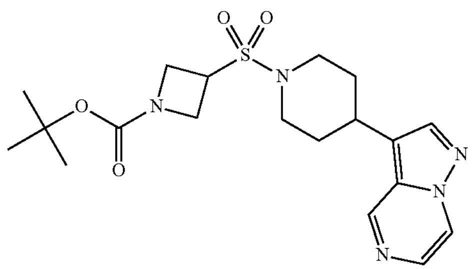 [SMILES: CC(C)(C)OC(=O)N1CC(S(=O)(=O)N2CCC(c3cnn4ccncc34)CC2)C1] | 422.7 | ¹H NMR (300 MHz, DMSO-d₆): δ = 9.22 (d, J = 1.4 Hz, 1H), 8.68 (dd, J = 4.7, 1.4 Hz, 1H), 8.08 (s, 1H), 7.83 (d, J = 4.7 Hz, 1H), 4.27-4.39 (m, 1H), 4.19 (t, J = 8.6 Hz, 2H), 3.93-4.05 (m, 2H), 3.74 (d, J = 12.5 Hz, 2H), 3.07-3.21 (m, 1H), 2.90-3.04 (m, 2H), 1.95-2.07 (m, 2H), 1.61-1.79 (m, 2H), 1.38 (s, 9H) ppm | 3-bromo pyrazolo[1,5-a]pyrazine | General method A1 using Na₂CO₃, B1 using Pd/C, Ci using TFA, D using tert-butyl 3-chlorosulfonylazetidine-1-carboxylate | tert-butyl 3-(4-pyrazolo[1,5-a]pyrazin-3-yl)piperidin-1-yl)sulfonylazetidine-1-carboxylate |
| 131 | 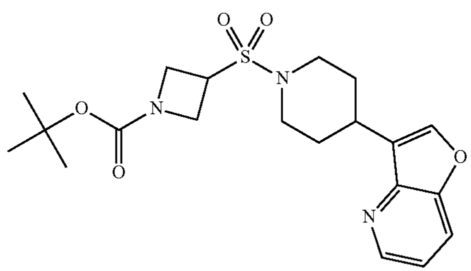 [SMILES: CC(C)(C)OC(=O)N1CC(S(=O)(=O)N2CCC(c3coc4cccnc34)CC2)C1] | 422.7 | ¹H NMR (300 MHz, DMSO-d₆): δ = 8.50 (dd, J = 4.7, 1.2 Hz, 1H), 8.11 (s, 1H), 7.98 (dd, J = 8.4, 1.1 Hz, 1H), 7.33 (dd, J = 8.4, 4.7 Hz, 1H), 4.25-4.38 (m, 1H), 4.19 (t, J = 8.4 Hz, 2H), 3.92-4.05 (m, 2H), 3.72 (d, J = 12.2 Hz, 2H), 3.00 (t, J = 11.2 Hz, 3H), 2.06-2.20 (m, 2H), 1.65-1.84 (m, 2H), 1.38 (s, 9H) ppm | 3-bromofuro[3,2-b]pyridine | General method A1 using Na₂CO₃, B1 using Pd/C, Ci using TFA, D using tert-butyl 3-chlorosulfonylazetidine-1-carboxylate | tert-butyl 3-(4-furo[3,2-b]pyridin-3-yl)piperidin-1-yl)sulfonylazetidine-1-carboxylate |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 132 | 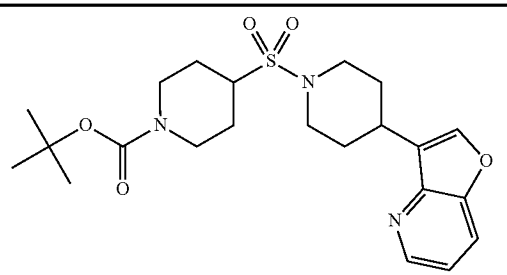 | 450.8 | ¹H NMR (300 MHz, DMSO-d₆): δ = 8.50 (dd, J = 4.8, 1.3 Hz, 1H), 8.11 (d, J = 0.7 Hz, 1H), 7.98 (dd, J = 8.4, 1.2 Hz, 1H), 7.33 (dd, J = 8.4, 4.7 Hz, 1H), 4.029 (d, J = 12.7 Hz, 2H), 3.73 (d, J = 12.7 Hz, 2H), 3.31-3.46 (m, 1H), 2.96-3.18 (m, 3H), 2.67-2.88 (m, 2H), 2.06-2.17 (m, 2H), 1.91-2.02 (m, 2H), 1.74 (qd, J = 12.3, 4.0 Hz, 2H), 1.35-1.52 (m, 2H), 1.39 (s, 9H) ppm | 3-bromofuro [3,2-b]pyridine | General method A1 using Na₂CO₃, B1 using Pd/C, Ci using TFA, D using tert-butyl 4-chlorosulfonylpiperidine-1-carboxylate | tert-butyl 4-(4-furo[3,2-b]pyridin-3-yl)piperidin-1-yl]sulfonyl)piperidine-1-carboxylate |
| 133 | 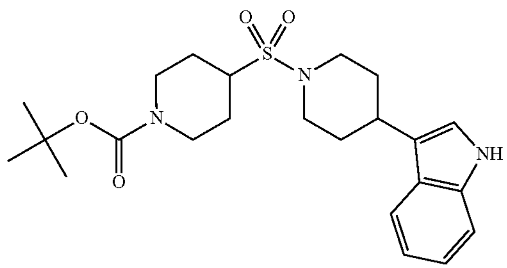 [SMILES: CC(C)(C)OC(=O)N1CCC(S(=O)(=O)N2CCC(c3c[nH]c4ccccc34)CC2)CC1] | 448.8 | ¹H NMR (300 MHz, DMSO-d₆): δ = 10.80 (s, 1H), 7.53 (d, J = 7.8 Hz, 1H), 7.32 (d, J = 8.0 Hz, 1H), 7.11 (d, J = 2.3 Hz, 1H), 7.01-7.08 (m, 1H), 6.92-6.99 (m, 1H), 4.02 (d, J = 13.2 Hz, 2H), 3.73 (d, J = 12.5 Hz, 2H), 3.33-3.46 (m, 1H), 3.02-3.16 (m, 2H), 2.88-3.01 (m, 1H), 2.68-2.87 (m, 2H), 1.91-2.07 (m, 4H), 1.61 (qd, J = 12.4, 3.8 Hz, 2H), 1.36-1.53 (m, 2H), 1.39 (s, 9H) ppm | 3-(4-piperidyl)-1H-indole | General method D using tert-butyl 4-chlorosulfonylpiperidine-1-carboxylate | tert-butyl 4-[4-(1H-indol-3-yl)piperidin-1-yl]sulfonyl)piperidine-1-carboxylate |
| 134 | 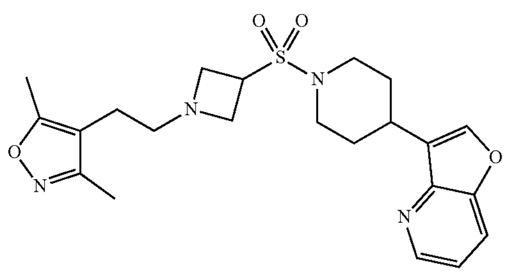 [SMILES: Cc1noc(C)c1CCN1CC(S(=O)(=O)N2CCC(c3coc4cccnc34)CC2)C1] | 445.8 | ¹H NMR (300 MHz, CHLOROFORM-d): δ =8.52 (dd, J = 1.3, 4.8 Hz, 1H), 7.72 (dd, J = 1.2, 8.4 Hz, 1H), 7.59 (d, J = 0.9 Hz, 1H), 7.19-7.25 (m, 1H), 3.94-4.03 (m, 1H), 3.90 (d, J = 12.2 Hz, 2H), 3.76 (br. s., 2H), 3.50 (t, J = 7.7 Hz, 2H), 3.06 (tt, J = 3.5, 11.8 Hz, 2H), 2.94 (dt, J = 2.2, 12.2 Hz, 2H), 2.60-2.68 (m, 1H), 2.59 (s, 2H), 2.35 (t, J = 7.5 Hz, 2H), 2.31 (s, 3H), 2.21 (s, 3H), 1.82 (qd, J = 3.8, 12.5 Hz, 2H) ppm. | 3-bromofuro [3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, J1 using 4-(2-chloroethyl)-3,5-dimethyl-isoxazole | 3-[1-[1-[2-(3,5-dimethyl-1,2-oxazol-4-yl)ethyl]azetidin-3-yl]sulfonylpiperidin-4-yl]furo[3,2-b]pyridine |

| Cpd # | Structure | MS (m/z, ES+) | δ NMR Data | Starting Int/Cpd# | Sequence of Methods | Chemical Name |
|---|---|---|---|---|---|---|
| 135 | 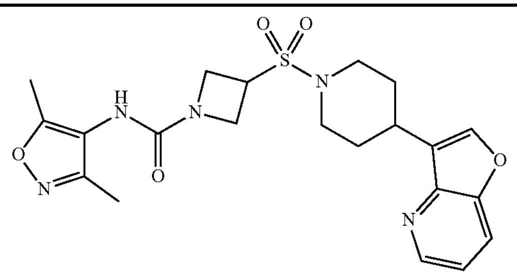 | 460.7 | ¹H NMR (400 MHz, CHLOROFORM-d): δ =8.51 (dd, J = 1.3, 4.8 Hz, 1H), 7.73 (dd, J = 1.2, 8.3 Hz, 1H), 7.60 (d, J = 0.9 Hz, 1H), 7.20-7.25 (m, 1H), 4.20-4.34 (m, 4H), 3.99-4.06 (m, 1H), 3.95 (d, J = 12.6 Hz, 2H), 3.09 (tt, J = 3.4, 12.1 Hz, 1H), 3.02 (dt, J = 2.3, 12.5 Hz, 2H), 2.31 (s, 3H), 2.25 (d, J = 10.9 Hz, 2H), 2.18 (s, 3H), 1.84 (qd, J = 3.9, 12.6 Hz, 2H) ppm. | 3-bromofuro [3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, G2 using 4-isocyanato-3,5-dimethyl-isoxazole | N-(3,5-dimethyl-1,2-oxazol-4-yl)-3-(4-furo[3,2-b]pyridin-3-yl)piperidin-1-ylsulfonyl)azetidine-carboxamide |
| 136 | 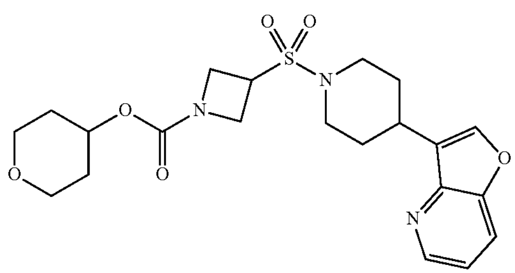 [SMILES: O=C(OC1CCOCC1)N1CC(S(=O)(=O)N2CCC(c3coc4cccnc34)CC2)C1] | 450.7 | ¹H NMR (300 MHz, CHLOROFORM-d): δ =8.52 (dd, J = 1.2, 4.9 Hz, 1H), 7.73 (dd, J = 1.0, 8.3 Hz, 1H), 7.60 (s, 1H), 7.19-7.26 (m, 1H), 4.81 (tt, J = 4.3, 8.7 Hz, 1H), 4.17-4.35 (m, 4H), 3.78-4.04 (m, 5H), 3.50 (ddd, J = 3.0, 9.1, 11.8 Hz, 2H), 2.94-3.17 (m, 3H), 2.26 (d, J = 11.1 Hz, 2H), 1.75-1.96 (m, 3H), 1.49-1.71 (m, 3H) ppm. | 3-bromofuro [3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, H3 using tetrahydropyran-4-ol | oxan-4-yl 3-(4-furo[3,2-b]pyridin-3-yl)piperidin-1-ylsulfonyl)azetidine-1-carboxylate |
| 137 | 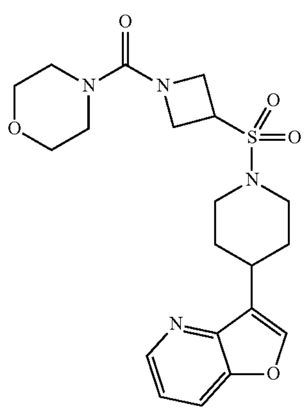 [SMILES: O=C(N1CCOCC1)N1CC(S(=O)(=O)N2CCC(c3coc4cccnc34)CC2)C1] | 435.7 | ¹H NMR (500 MHz, CHLOROFORM-d): δ =8.54 (dd, J = 0.8, 4.7 Hz, 1H), 7.75 (d, J = 8.2 Hz, 1H), 7.63 (s, 1H), 7.25 (dd, J = 4.7, 8.4 Hz, 1H), 4.28-4.33 (m, 2H), 4.23-4.28 (m, 2H), 4.01-4.06 (m, 1H), 3.98 (d, J = 12.5 Hz, 2H), 3.63-3.69 (m, 4H), 3.31-3.37 (m, 4H), 3.11 (tt, J = 3.3, 12.0 Hz, 1H), 3.05 (dt, J = 1.8, 12.5 Hz, 2H), 2.28 (d, J = 11.3 Hz, 2H), 1.86 (dq, J = 4.1, 12.6 Hz, 2H) ppm. | 3-bromofuro [3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, G1 using morpholine-4-carbonyl chloride | [3-(4-furo[3,2-b]pyridin-3-yl)piperidin-1-ylsulfonyl)azetidin-1-yl]-morpholin-4-ylmethanone |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 138 | 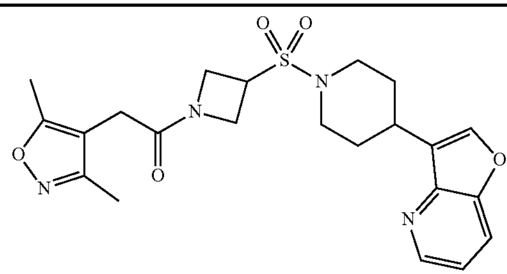 | 459.7 | ¹H NMR (500 MHz, CHLOROFORM-d): δ = 8.55 (d, J = 4.6 Hz, 1H), 7.79 (d, J = 8.2 Hz, 1H), 7.64 (s, 1H), 7.26-7.30 (m, 1H), 4.46-4.51 (m, 1H), 4.39-4.44 (m, 1H), 4.28-4.38 (m, 2H), 4.04 (tt, J = 5.8, 8.3 Hz, 1H), 3.97 (t, J = 11.7 Hz, 2H), 3.09-3.21 (m, 3H), 3.04 (dt, J = 1.8, 12.4 Hz, 2H), 2.35 (s, 3H), 2.23 (s, 3H), 1.80-1.92 (m, 2H) ppm. | 3-bromofuro[3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, I1 using 2-(3,5-dimethylisoxazol-4-yl)acetic acid | 2-(3,5-dimethyl-1,2-oxazol-4-yl)-1-[3-(4-furo[3,2-b]pyridin-3-yl)piperidin-1-yl]sulfonyl]azetidin-1-yl]ethanone |
| 139 | 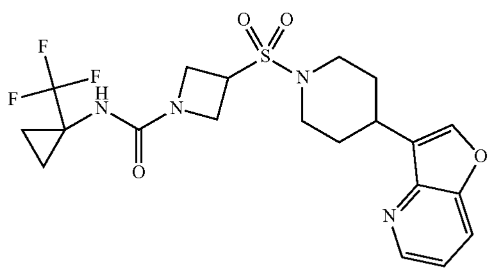 [SMILES: O=C(NC1(C(F)(F)F)CC1)N1CC(S(=O)(=O)N2CCC(c3coc4cccnc34)CC2)C1] | 473.7 | ¹H NMR (600 MHz, CHLOROFORM-d): δ = 8.51 (d, J = 4.2 Hz, 1H), 7.73 (d, J = 8.2 Hz, 1H), 7.59 (s, 1H), 7.22 (dd, J = 4.7, 8.3 Hz, 1H), 4.71 (s, 1H), 4.20-4.27 (m, 4H), 3.97-4.03 (m, 1H), 3.95 (d, J = 12.6 Hz, 2H), 3.09 (tt, J = 3.6, 11.8 Hz, 1H), 3.02 (dt, J = 2.1, 12.5 Hz, 2H), 2.25 (d, J = 11.2 Hz, 2H), 1.83 (dq, J = 3.9, 12.6 Hz, 2H), 1.26-1.31 (m, 2H), 1.07-1.14 (m, 2H) ppm. | 3-bromofuro[3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, G2 using 1-isocyanato-1-(trifluoromethyl)cyclopropane | 3-(4-furo[3,2-b]pyridin-3-yl)piperidin-3-yl]sulfonyl]-N-[1-(trifluoromethyl)cyclopropyl]azetidine-1-carboxamide |
| 140 | 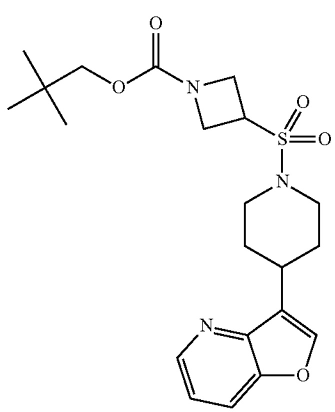 [SMILES: CC(C)(C)COC(=O)N1CC(S(=O)(=O)N2CCC(c3coc4cccnc34)CC2)C1] | 436.8 | ¹H NMR (600 MHz, CHLOROFORM-d): δ = 8.51 (d, J = 4.8 Hz, 1H), 7.72 (d, J = 8.2 Hz, 1H), 7.59 (s, 1H), 7.22 (dd, J = 4.8, 8.2 Hz, 1H), 4.29-4.34 (m, 2H), 4.23-4.28 (m, 2H), 3.93-4.02 (m, 3H), 3.74 (s, 2H), 3.09 (tt, J = 3.2, 11.8 Hz, 1H), 3.02 (dt, J = 1.8, 12.4 Hz, 2H), 2.26 (d, J = 11.7 Hz, 2H), 1.82 (dq, J = 3.8, 12.5 Hz, 2H), 0.90 (s, 9H) ppm. | 3-bromofuro[3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, H1 using neopentyl chloroformate | 2,2-dimethylpropyl 3-(4-furo[3,2-b]pyridin-3-yl)piperidin-1-yl]sulfonyl]azetidine-1-carboxylate |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 141 | 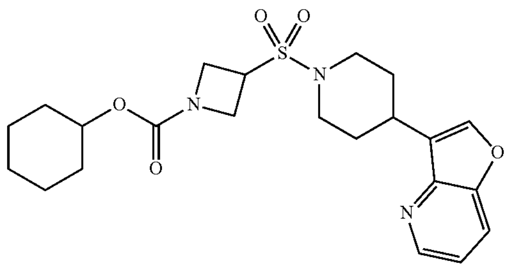 [SMILES: O=C(OC1CCCCC1)N1CC(S(=O)(=O)N2CCC(c3coc4cccnc34)CC2)C1] | 448.8 | ¹H NMR (600 MHz, CHLOROFORM-d): δ =8.52 (d, J = 4.8 Hz, 1H), 7.73 (d, J = 8.2 Hz, 1H), 7.60 (s, 1H), 7.22 (dd, J = 4.8, 8.2 Hz, 1H), 4.59-4.65 (m, 1H), 4.26-4.30 (m, 2H), 4.22 (t, J = 9.2 Hz, 2H), 3.93-4.00 (m, 3H), 3.09 (tt, J = 3.3, 12.0 Hz, 1H), 3.02 (dt, J = 2.0, 12.5 Hz, 2H), 2.26 (d, J = 11.5 Hz, 2H), 1.77-1.87 (m, 4H), 1.64-1.71 (m, 2H), 1.46-1.53 (m, 1H), 1.28-1.41 (m, 4H), 1.18-1.26 (m, 1H) ppm. | 3-bromofuro [3,2-b]pyridine | General method A1 using K₂CO₃, B1 using Pd/C, Ci using HCl in dioxane, D using tert-butyl 3-chlorosulfonyl azetidine-1-carboxylate, Cf using HCl in dioxane, H1 using cyclohexyl chloroformate | cyclohexyl 3-(4-furo[3,2-b]pyridin-3-yl)piperidin-1-yl)sulfonylazetidine-1-carboxylate |
| 142 | 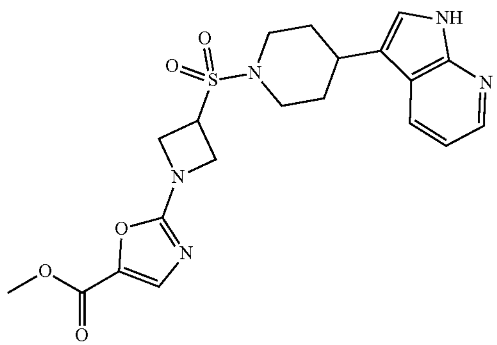 [SMILES: COC(=O)c1cnc(N2CC(S(=O)(=O)N3CCC(c4c[nH]c5ncccc45)CC3)C2)o1] | 446.7 | ¹H NMR (500 MHz, CHLOROFORM-d): δ= 9.19 (br. s., 1H), 8.32 (br. s., 1H), 7.95 (d, J = 7.9 Hz, 1H), 7.54 (s, 1H), 7.06-7.14 (m, 2H), 4.53-4.58 (m, 2H), 4.51 (t, J = 8.6 Hz, 2H), 4.17-4.25 (m, 1H), 4.01 (d, J = 12.2 Hz, 2H), 3.87 (s, 3H), 3.04 (t, J = 11.6 Hz, 2H), 2.97 (tt, J = 3.2, 11.9 Hz, 1H), 2.14 (d, J = 12.5 Hz, 2H), 1.84 (dq, J = 4.0, 12.5 Hz, 2H) ppm. | 3-(4-piperidyl)-1H-pyrrolo [2,3-b]pyridine | General method D using tert-butyl 3-chlorosulfonyl azetidine-1-carboxylate, E, Cf using TFA, I4 using ethyl 2-bromooxazole-5-carboxylate, F | methyl 2-[3-[4-(1H-pyrrolo [2,3-b]pyridin-3-yl)piperidin-1-yl]sulfonylazetidin-1-yl]-1,3-oxazole-5-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 143 | (structure) | 391.9 | 1H NMR (600 MHz, DMSO-d6): δ = 11.35 (br. s., 1H), 8.16 (dd, J = 4.68 Hz, 1H), 7.96 (dd, J = 1.10, 7.89 Hz, 1H), 7.24 (d, J = 2.38 Hz, 1H), 7.01 (dd, J = 4.58, 7.89 Hz, 1H), 4.22 (quin, J = 7.47 Hz, 1H), 3.68 (d, J = 11.92 Hz, 2H), 3.64 (t, J = 7.98 Hz, 2H), 3.33 (m, 2H), 2.85-2.97 (m, 3H), 2.21 (s, 2H), 2.00 (dd, J = 1.90, 13.00 Hz, 2H), 1.62 (dq, J = 3.94, 12.50 Hz, 2H), 0.81 (s, 9H) ppm | 3-(4-piperidyl)-1H-pyrrolo[2,3-b]pyridine | General method D using tert-butyl 3-chlorosulfonyl azetidine-1-carboxylate, Cf using TFA, then J2 using 2,2-dimethylpropanal | 3-[1-[1-(2,2-dimethylpropyl)azetidin-3-yl]sulfonyl]piperidin-4-yl]-1H-pyrrolo[2,3-b]pyridine |
| 144 | (structure) | 425.9 | 1H NMR (600 MHz, DMSO-d6): δ = 8.47 (d, J =3.30 Hz, 2H), 7.27 (d, J = 3.30 Hz, 2H), 4.31 (br. s., 1H), 4.17 (br. s., 2H), 3.97 (br. s., 2H), 3.73 (d, J = 10.82 Hz, 2H), 2.90 (t, J = 11.65 Hz, 2H), 2.67 (t, J = 10.30 Hz, 1H), 2.43 (br. s., 2H), 2.21 (br. s., 6H), 1.85 (d, J = 12.10 Hz, 2H), 1.58 (q, J = 10.80 Hz, 2H), 1.36 (br. s., 6H) ppm | 4-(4-piperidyl)pyridine | General method D using tert-butyl 3-chlorosulfonylazetidine-1-carboxylate, Cf using TFA, H3 using 1-(dimethylamino)-2-methyl-propan-2-ol | [1-(dimethylamino)-2-methylpropan-2-yl]3-(4-pyridin-4-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 145 | 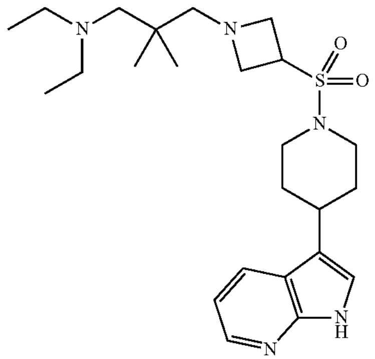 [SMILES: CCN(CC)CC(C)(C)CN1CC(S(=O)(=O)N2CCC(c3c[nH]c4ncccc34)CC2)C1] | 462.9 | ¹H NMR (600 MHz, DMSO-d₆): δ = 11.36 (br. s., 1H), 8.17 (dd, J = 4.60 Hz, 1H), 7.95 (d, J = 7.52 Hz, 1H), 7.23 (d, J = 2.02 Hz, 1H), 7.00 (dd, J = 4.68, 7.79 Hz, 1H), 4.21 (quin, J = 7.43 Hz, 1H), 3.68 (d, J = 11.92 Hz, 2H), 3.61 (t, J = 7.70 Hz, 2H), 3.32 (m, 2H), 2.84-2.98 (m, 3H), 2.44 (q, J = 7.09 Hz, 4H), 2.24 (s, 2H), 2.12 (s, 2H), 2.00 (d, J = 11.74 Hz, 2H), 1.62 (dq, J = 3.67, 12.41 Hz, 2H), 0.90 (t, J = 7.06 Hz, 6H), 0.72 (s, 6H) ppm | 3-(4-piperidyl)-1H-pyrrolo[2,3-b]pyridine | General method D using tert-butyl 3-chlorosulfonyl azetidine-1-carboxylate, Cf using TFA, then J2 using 3-(diethylamino)-2,2-dimethyl-propanal | N,N-diethyl-2,2-dimethyl-3-[3-[4-(1H-pyrrolo[2,3-b]pyridin-3-yl)piperidin-1-yl]sulfonylazetidin-1-yl]propan-1-amine |
| 146 | 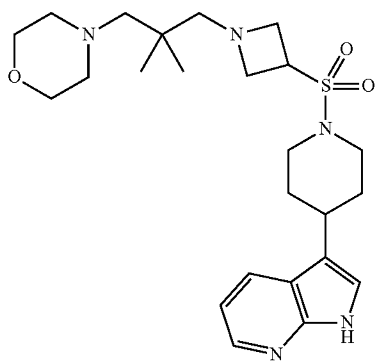 [SMILES: CC(C)(CN1CCOCC1)CN1CC(S(=O)(=O)N2CCC(c3c[nH]c4ncccc34)CC2)C1] | 476.9 | ¹H NMR (600 MHz, DMSO-d₆): δ = 11.36 (br. s., 1H), 8.17 (d, J = 4.03 Hz, 1H), 7.95 (d, J = 7.70 Hz, 1H), 7.24 (br. s., 1H), 7.01 (dd, J = 4.77, 7.52 Hz, 1H), 4.21 (quin, J = 7.34 Hz, 1H), 3.67 (d, J = 11.37 Hz, 2H), 3.62 (t, J = 7.52 Hz, 2H), 3.52 (br. s., 4H), 3.32 (2H), 2.83-2.98 (m, 3H), 2.39 (br. s., 4H), 2.27 (s, 2H), 2.06 (s, 2H), 2.00 (d, J = 12.47 Hz, 2H), 1.56-1.68 (m, 2H), 0.74 (s, 6H) ppm | 3-(4-piperidyl)-1H-pyrrolo[2,3-b]pyridine | General method D using tert-butyl 3-chlorosulfonyl azetidine-1-carboxylate, Cf using TFA, then J2 using 2,2-dimethyl-3-morpholino-propanal | 4-[2,2-dimethyl-3-[3-[4-(1H-pyrrolo[2,3-b]pyridin-3-yl)piperidin-1-yl]sulfonylazetidin-1-yl]propyl]morpholine |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 147 | 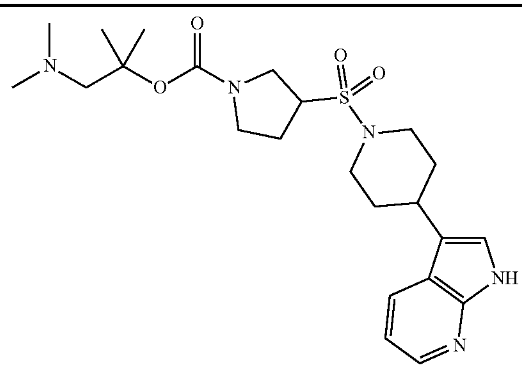 | 478.8 | ¹H NMR (600 MHz, DMSO-d₆): δ = 11.36 (br. s., 1H), 8.17 (dd, J = 4.68 Hz, 1H), 7.97 (dd, J = 1.38, 4.68 Hz, 1H), 7.24 (br. s., 1H), 7.01 (dd, J = 4.68, 7.79 Hz, 1H), 3.97-4.09 (m, 1H), 3.68-3.77 (m, 2H), 3.60 (dd, J = 8.16, 11.46 Hz, 1H), 3.41-3.52 (m, 2H), 3.20-3.31 (m, 1H), 2.98-3.09 (m, 2H), 2.94 (tt, J = 3.39, 11.83 Hz, 1H), 2.45 (d, J = 1.28 Hz, 2H), 2.22 (s, 6H), 2.07-2.28 (m, 2H), 2.02 (d, J = 12.47 Hz, 2H), 1.58-1.69 (m, 2H), 1.39 (s, 6H) ppm | 3-(4-piperidyl)-1H-pyrrolo[2,3-b]pyridine | General method D using tert-butyl 3-chlorosulfonyl pyrrolidine-1-carboxylate; racemate, Cf using TFA, then H3 using 1-(dimethylamino)-2-methyl-propan-2-ol | [1-(dimethylamino)-2-methylpropan-2-yl]3-[4-(1H-pyrrolo[2,3-b]pyridin-3-yl)piperidin-1-yl]sulfonyl]pyrrolidine-1-carboxylate |
| 148 | 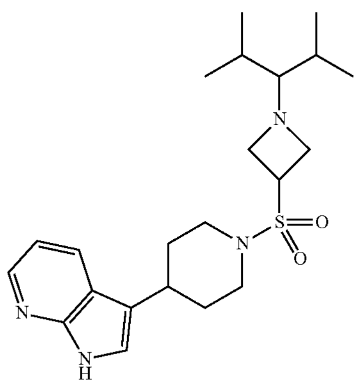 [SMILES: CC(C)C(C(C)C)N1CC(S(=O)(=O)N2CCC(c3c[nH]c4ncccc34)CC2)C1] | 419.9 | ¹H NMR (600 MHz, DMSO-d₆): δ = 11.36 (br. s., 1H), 8.17 (dd, J = 1.47, 4.58 Hz, 1H), 7.96 (dd, J = 1.10, 7.89 Hz, 1H), 7.24 (d, J = 2.38 Hz, 1H), 7.01 (dd, J = 4.68, 7.79 Hz, 1H), 4.21 (quin, J = 7.47 Hz, 1H), 3.68 (d, J = 12.10 Hz, 2H), 3.58 (t, J = 7.52 Hz, 2H), 3.31 (m, 2H), 2.95 (dt, J = 2.02, 12.10 Hz, 2H), 2.89 (tt, J = 3.37, 11.85 Hz, 1H), 2.00 (dd, J = 1.80, 13.20 Hz, 2H), 1.91 (t, J = 2.48 Hz, 1H), 1.73 (dtt, J = 2.40, 6.99, 14.10 Hz, 2H), 1.63 (dq, J = 3.94, 12.44 Hz, 2H), 0.86 (dd, J = 5.59, 7.06 Hz, 12H) ppm | 3-(4-piperidyl)-1H-pyrrolo[2,3-b]pyridine | General method D using tert-butyl 3-chlorosulfonyl azetidine-1-carboxylate, Cf using TFA, then J2 using 2,4-dimethylpentan-3-one | 3-[1-[1-(2,4-dimethylpentan-3-yl)azetidin-3-yl]sulfonylpiperidin-4-yl]-1H-pyrrolo[2,3-b]pyridine |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 149 | 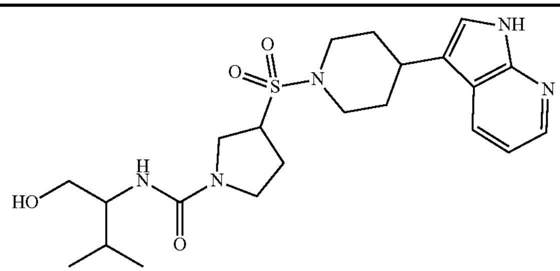 | 464.8 | mixture of diastereoisomers | 3-(4-piperidyl)-1H-pyrrolo[2,3-b]pyridine | General method D using tert-butyl 3-chlorosulfonyl pyrrolidine-1-carboxylate; racemate, Cf using TFA, then G6 using 2-amino-3-methyl-butan-1-ol(racemate) | N-(1-hydroxy-3-methylbutan-2-yl)-3-[4-(1H-pyrrolo[2,3-b]pyridin-3-yl)piperidin-1-yl]sulfonyl]pyrrolidine-1-carboxamide |
| 150 | 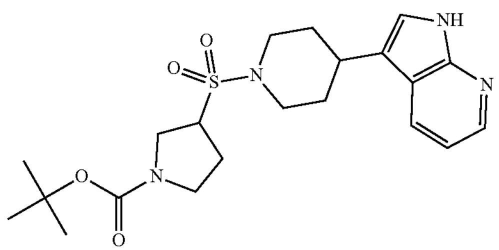 [SMILES: CC(C)(C)OC(=O)N1CCC(S(=O)(=O)N2CCC(c3c[nH]c4ncccc34)CC2)C1] | 435.8 | $^1$H NMR (600 MHz, DMSO-d$_6$): δ = 11.36 (br. s., 1H), 8.17 (dd, J = 1.56, 4.68 Hz, 1H), 7.98 (dd, J = 1.56, 7.79 Hz, 1H), 7.24 (s, 1H), 7.01 (dd, J = 4.68, 7.79 Hz, 1H), 3.97-4.08 (m, 1H), 3.69-3.77 (m, 2H), 3.60 (dd, J = 8.16, 11.28 Hz, 1H), 3.41-3.52 (m, 2H), 3.20-3.30 (m, 1H), 2.99-3.09 (m, 2H), 2.95 (tt, J = 3.39, 11.83 Hz, 1H), 2.20-2.28 (m, 1H), 2.08-2.20 (m, 1H), 1.99-2.06 (m, 2H), 1.64 (dq, J = 3.94, 12.44 Hz, 2H), 1.40 (s, 9H) ppm | 3-(4-piperidyl)-1H-pyrrolo[2,3-b]pyridine | General method D using tert-butyl 3-chlorosulfonyl pyrrolidine-1-carboxylate;racemate | tert-butyl 3-[4-(1H-pyrrolo[2,3-b]pyridin-3-yl)piperidin-1-yl]sulfonyl]pyrrolidine-1-carboxylate |
| 151 | 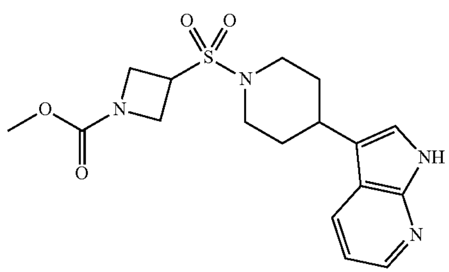 [SMILES: COC(=O)N1CC(S(=O)(=O)N2CCC(c3c[nH]c4ncccc34)CC2)C1] | 379.7 | $^1$H NMR (500 MHz, DMSO-d$_6$): δ = 11.37 (br. s., 1H), 8.18 (dd, J = 0.92, 4.58 Hz, 1H), 7.97 (d, J = 7.63 Hz, 1H), 7.25 (d, J = 2.14 Hz, 1H), 7.02 (dd, J = 4.73, 7.78 Hz, 1H), 4.33-4.40 (m, 1H), 4.27 (br. s., 2H), 4.06 (br. s., 2H), 3.74 (d, J = 12.21 Hz, 2H), 3.59 (s, 3H), 2.96-3.04 (m, 2H), 2.88-2.96 (m, 1H), 2.02 (d, J = 13.20 Hz, 2H), 1.63 (dq, J = 3.97, 12.51 Hz, 2H) ppm | 3-(4-piperidyl)-1H-pyrrolo[2,3-b]pyridine | General method D using tert-butyl 3-chlorosulfonyl azetidine-1-carboxylate, Cf using TFA, then H3 using 1-methoxy-2-methyl-propan-2-ol, isolated by-product | methyl 3-[4-(1H-pyrrolo[2,3-b]pyridin-3-yl)piperidin-1-yl]sulfonylazetidine-1-carboxylate |

| Cpd # | Structure | MS (m/z ES+) | δ NMR Data | Starting Int/Cpd# | Sequence of Methods | Chemical Name |
|---|---|---|---|---|---|---|
| 152 | 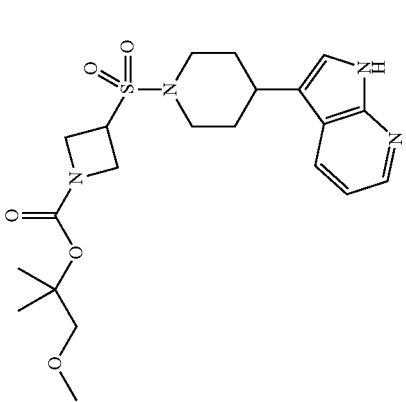 | 451.7 | ¹H NMR (500 MHz, DMSO-d₆): δ = 11.36 (br. s., 1H), 8.18 (dd, J = 4.60 Hz, 1H), 7.97 (d, J = 7.63 Hz, 1H), 7.25 (d, J = 2.14 Hz, 1H), 7.02 (dd, J = 4.73, 7.78 Hz, 1H), 4.29-4.37 (m, 1H), 4.19 (br. s., 2H), 4.00 (br. s., 2H), 3.73 (d, J = 11.90 Hz, 2H), 3.44 (s, 2H), 3.29 (s, 3H), 2.87-3.03 (m, 3H), 2.03 (d, J = 13.20 Hz, 2H), 1.63 (dq, J = 3.97, 12.51 Hz, 2H), 1.35 (s, 6H) ppm | 3-(4-piperidyl)-1H-pyrrolo[2,3-b]pyridine | General method D using tert-butyl 3-chlorosulfonyl azetidine-1-carboxylate, Cf using TFA, then H3 using 1-methoxy-2-methyl-propan-2-ol | (1-methoxy-2-methylpropan-2-yl) 3-[4-(1H-pyrrolo[2,3-b]pyridin-3-yl)piperidin-1-yl]sulfonylazetidine-1-carboxylate |
| 153 | 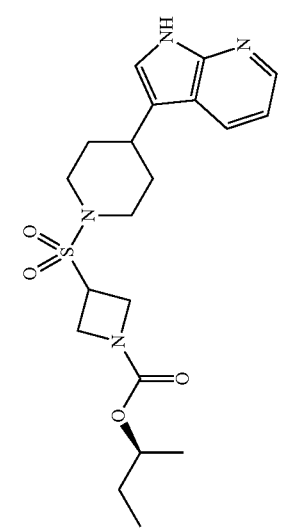 | 421.7 | ¹H NMR (500 MHz, DMSO-d₆): δ = 11.37 (br. s., 1H), 8.18 (dd, J = 4.60 Hz, 1H), 7.97 (d, J = 7.93 Hz, 1H), 7.25 (d, J = 2.14 Hz, 1H), 7.02 (dd, J = 4.73, 7.78 Hz, 1H), 4.59 (sxt, J = 6.29 Hz, 1H), 4.32-4.40 (m, 1H), 4.25 (br. s., 2H), 4.04 (br. s., 2H), 3.74 (d, J = 11.90 Hz, 2H), 2.99 (t, J = 11.60 Hz, 2H), 2.87-2.96 (m, 1H), 2.02 (d, J = 12.21 Hz, 2H), 1.63 (dq, J = 3.51, 12.36 Hz, 2H), 1.50 (dq, J = 7.10 Hz, 2H), 1.14 (d, J = 6.10 Hz, 3H), 0.84 (t, J = 7.48 Hz, 3H) ppm | 3-(4-piperidyl)-1H-pyrrolo[2,3-b]pyridine | General method D using tert-butyl 3-chlorosulfonyl azetidine-1-carboxylate, Cf using TFA, then H3 using (2S)-butan-2-ol | [(2S)-butan-2-yl] 3-[4-(1H-pyrrolo[2,3-b]pyridin-3-yl)piperidin-1-yl]sulfonylazetidine-1-carboxylate |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 154 | 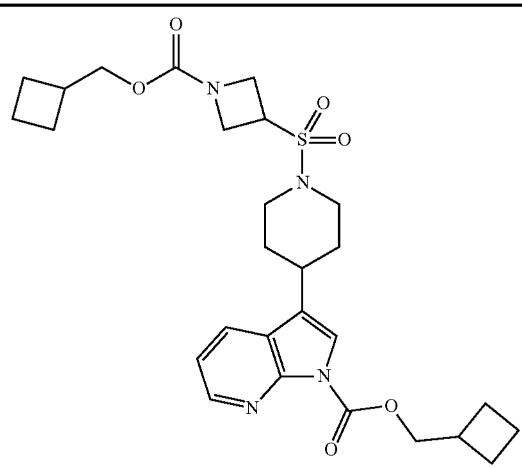 | 545.9 | ¹H NMR (500 MHz, DMSO-d₆): δ = 8.41 (dd, J = 0.92, 4.58 Hz, 1H), 8.13 (dd, J = 1.22, 7.93 Hz, 1H), 7.58 (s, 1H), 7.31 (dd, J = 4.88, 7.93 Hz, 1H), 4.37 (d, J = 6.50 Hz, 2H), 4.33-4.42 (m, 1H), 4.26 (br. s., 2H), 4.04 (br. s., 2H), 3.96 (d, J = 6.71 Hz, 2H), 3.76 (d, J = 12.51 Hz, 2H), 2.90-3.05 (m, 3H), 2.70-2.81 (m, 1H), 2.48-2.58 (m, 1H), 2.00-2.11 (m, 4H), 1.75-2.00 (m, 8H), 1.57-1.74 (m, 4H) ppm | 3-(4-piperidyl)-1H-pyrrolo[2,3-b]pyridine | General method D using tert-butyl 3-chlorosulfonyl azetidine-1-carboxylate, Cf using TFA, then H3 using cyclobutyl-methanol | cyclobutylmethyl 3-[1-[1-(cyclobutylmethoxycarbonyl)azetidin-3-yl]sulfonylpiperidin-4-yl]pyrrolo[2,3-b]pyridine-1-carboxylate |
| 155 | 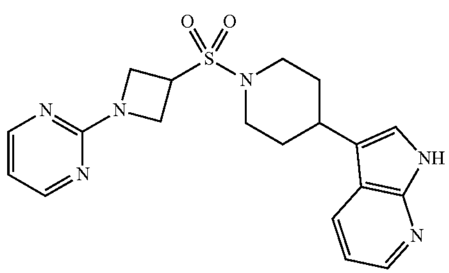 [SMILES: O=S(=O)(C1CN(c2ncccn2)C1)N1CCC(c2c[nH]c3ncccc23)CC1] | 399.7 | ¹H NMR (500 MHz, DMSO-d₆): δ = 11.37 (br. s., 1H), 8.41 (d, J = 4.88 Hz, 2H), 8.18 (dd, J = 1.22, 4.58 Hz, 1H), 7.97 (d, J = 7.63 Hz, 1H), 7.24 (d, J = 2.14 Hz, 1H), 7.01 (dd, J = 4.73, 7.78 Hz, 1H), 6.78 (t, J = 4.73 Hz, 1H), 4.48-4.55 (m, 1H), 4.39 (t, J = 8.70 Hz, 2H), 4.20 (dd, J = 5.49, 9.46 Hz, 2H), 3.77 (d, J =12.21 Hz, 2H), 2.99-3.07 (m, 2H), 2.90-2.98 (m, 1H), 2.03 (d, J = 11.60 Hz, 2H), 1.64 (dq, J = 3.81, 12.46 Hz, 2H) ppm | 3-(4-piperidyl)-1H-pyrrolo[2,3-b]pyridine | General method D using tert-butyl 3-chlorosulfonyl azetidine-1-carboxylate, Cf using TFA, then J3 using 2-fluoropyrimidine | 3-[1-(1-pyrimidin-2-ylazetidin-3-yl)sulfonylpiperidin-4-yl]-1H-pyrrolo[2,3-b]pyridine |

| Cpd # | Structure | MS (m/z, ES +) | δ NMR Data | Starting Int/Cpd# | Sequence of Methods | Chemical Name |
|---|---|---|---|---|---|---|
| 156 | 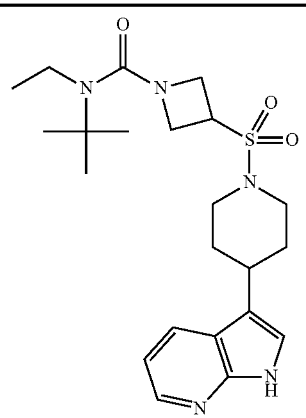 | 448.8 | ¹H NMR (600 MHz, DMSO-d₆): δ = 11.36 (s, 1H), 8.17 (dd, J = 1.47, 4.58 Hz, 1H), 7.97 (dd, J = 1.28, 7.89 Hz, 1H), 7.24 (d, J = 2.38 Hz, 1H), 7.01 (dd, J = 4.58, 7.89 Hz, 1H), 4.31 (tt, J = 5.89, 8.41 Hz, 1H), 4.13 (tt, J = 8.62 Hz, 2H), 4.00 (dd, J = 5.87, 8.80 Hz, 2H), 3.72 (d, J = 12.10 Hz, 2H), 3.12 (q, J = 7.09 Hz, 2H), 2.91 (tt, J = 3.35, 11.88 Hz, 1H), 2.02 (dd, J = 1.80, 13.20 Hz, 2H), 1.63 (dq, J = 3.94, 12.50 Hz, 2H), 1.31 (s, 9H), 1.08 (t, J = 6.97 Hz, 3H) ppm | 3-(4-piperidyl)-1H-pyrrolo[2,3-b]pyridine | General method D using tert-butyl 3-chlorosulfonyl azetidine-1-carboxylate, Cf using TFA, then G3 using N-ethyl-2-methyl-propan-2-amine | N-tert-butyl-N-ethyl-3-[4-(1H-pyrrolo[2,3-b]pyridin-3-yl)piperidin-1-yl]sulfonylazetidine-1-carboxamide |
| 157 | 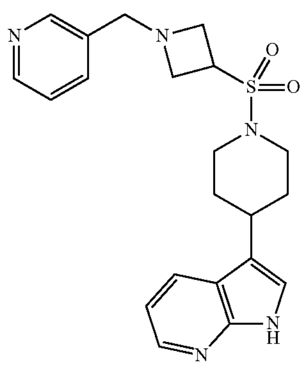 [SMILES: O=S(=O)(C1CN(Cc2cccnc2)C1)N1CCC(c2c[nH]c3ncccc23)CC1] | 412.7 | ¹H NMR (600 MHz, DMSO-d₆): δ = 11.36 (br. s., 1H), 8.48 (d, J = 2.02 Hz, 1H), 8.46 (dd, J = 1.65, 4.77 Hz, 1H), 8.16 (dd, J = 1.47, 4.58 Hz, 1H), 7.95 (dd, J = 1.19, 7.79 Hz, 1H), 7.68 (td, J = 1.83, 7.70 Hz, 1H), 7.34 (dd, J = 4.86, 7.79 Hz, 1H), 7.23 (d, J = 2.38 Hz, 1H), 7.00 (dd, J = 4.68, 7.79 Hz, 1H), 4.24 (quin, J = 7.47 Hz, 1H), 3.68 (d, J = 12.10 Hz, 2H), 3.64 (s, 2H), 3.59 (t, J = 7.98 Hz, 2H), 3.37 (t, J = 7.61 Hz, 2H), 2.85-2.95 (m, 3H), 1.99 (dd, J = 1.80, 13.20 Hz, 2H), 1.62 (dq, J = 4.03, 12.47 Hz, 2H) ppm | 3-(4-piperidyl)-1H-pyrrolo[2,3-b]pyridine | General method D using tert-butyl 3-chlorosulfonyl azetidine-1-carboxylate, Cf using TFA, then J2 using pyridine-3-carbaldehyde | 3-[1-[1-(pyridin-3-ylmethyl)azetidin-3-yl]sulfonylpiperidin-4-yl]-1H-pyrrolo[2,3-b]pyridine |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 158 | 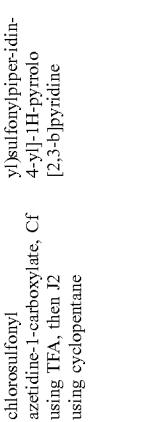 | 389.7 | ¹H NMR (600 MHz, DMSO-d₆): δ = 11.36 (br. s., 1H), 8.17 (d, J = 4.40 Hz, 1H), 7.96 (d, J = 7.70 Hz, 1H), 7.24 (s, 1H), 7.01 (dd, J = 4.68, 7.79 Hz, 1H), 4.13 (quin, J = 7.43 Hz, 2H), 3.69 (d, J = 11.92 Hz, 2H), 3.50 (t, J = 7.61 Hz, 2H), 3.21 (t, J = 7.24 Hz, 2H), 2.85-2.97 (m, 3H), 2.70-2.76 (m, 1H), 2.00 (d, J = 12.29 Hz, 2H), 1.63 (dq, J = 3.58, 12.44 Hz, 2H), 1.53-1.59 (m, 2H), 1.42-1.53 (m, 4H), 1.23-1.31 (m, 2H) ppm | 3-(4-piperidyl)-1H-pyrrolo[2,3-b]pyridine | General method D using tert-butyl 3-chlorosulfonyl azetidine-1-carboxylate, Cf using TFA, then J2 using cyclopentane | 3-[1-(1-cyclopentylazetidin-3-yl)sulfonylpiperidin-4-yl]-1H-pyrrolo[2,3-b]pyridine |
| 159 | 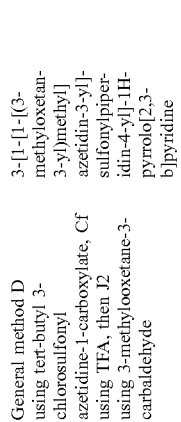 | 405.7 | ¹H NMR (600 MHz, DMSO-d₆): δ = 11.36 (br. s., 1H), 8.17 (dd, J = 1.47, 4.77 Hz, 1H), 7.96 (dd, J = 1.01, 7.79 Hz, 1H), 7.24 (d, J = 2.20 Hz, 1H), 7.01 (dd, J = 4.58, 7.89 Hz, 1H), 4.29 (d, J = 5.69 Hz, 2H), 4.23 (quin, J = 7.43 Hz, 1H), 4.13 (d, J = 5.50 Hz, 2H), 3.69 (d, J = 11.92 Hz, 2H), 3.65 (t, J = 7.89 Hz, 2H), 3.40 (t, J = 7.52 Hz, 2H), 2.85-2.97 (m, 3H), 2.63 (s, 2H), 2.00 (d, J = 11.37 Hz, 2H), 1.63 (dq, J = 3.85, 12.47 Hz, 2H), 1.19 (s, 3H) ppm | 3-(4-piperidyl)-1H-pyrrolo[2,3-b]pyridine | General method D using tert-butyl 3-chlorosulfonyl azetidine-1-carboxylate, Cf using TFA, then J2 using 3-methylooxetane-3-carbaldehyde | 3-[1-[[1-[(3-methyloxetan-3-yl)methyl]azetidin-3-yl]sulfonyl]piperidin-4-yl]-1H-pyrrolo[2,3-b]pyridine |
| 160 | 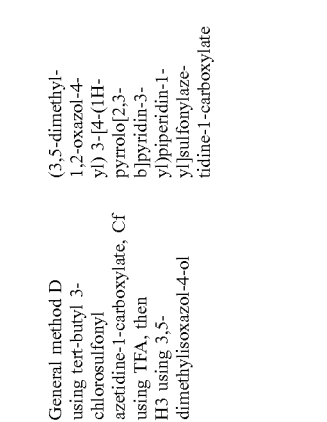 | 460.6 | ¹H NMR (600 MHz, DMSO-d₆): δ = 11.37 (s, 1H), 8.17 (dd, J = 1.56, 4.68 Hz, 1H), 7.97 (dd, J = 1.19, 7.98 Hz, 1H), 7.25 (d, J = 2.38 Hz, 1H), 7.01 (dd, J = 4.59, 7.89 Hz, 1H), 4.54-4.62 (m, 1H), 4.36-4.46 (m, 2H), 4.32 (br. s., 1H), 4.14 (br. s., 1H), 3.77 (d, J = 12.29 Hz, 2H), 3.02 (dt, J = 3.51, 11.81 Hz, 1H), 2.93 (tt, J = 3.51, 11.81 Hz, 1H), 2.27 (s, 3H), 2.09 (s, 3H), 2.03 (dd, J = 1.70, 13.20 Hz, 2H), 1.64 (dq, J = 4.03, 12.53 Hz, 2H) ppm | 3-(4-piperidyl)-1H-pyrrolo[2,3-b]pyridine | General method D using tert-butyl 3-chlorosulfonyl azetidine-1-carboxylate, Cf using TFA, then H3 using 3,5-dimethylisoxazol-4-ol | (3,5-dimethyl-1,2-oxazol-4-yl) 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 161 | 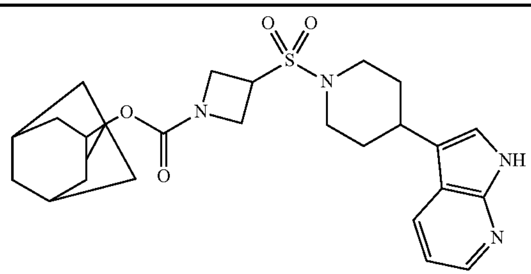 | 499.7 | ¹H NMR (500 MHz, DMSO-d₆): δ = 11.38 (br. s., 1H), 8.18 (dd, J = 0.70, Hz, 1H), 7.97 (d, J = 7.63 Hz, 1H), 7.25 (d, J = 1.83 Hz, 1H), 7.02 (dd, J = 4.58, 7.93 Hz, 1H), 4.28-4.36 (m, 1H), 4.19 (br. s., 2H), 3.99 (br. s., 2H), 3.73 (d, J = 11.90 Hz, 2H), 2.87-3.03 (m, 3H), 2.11 (br. s., 3H), 2.03 (d, 2H), 2.01 (br. s., 6H), 1.59 (br. s., 6H), 1.55-1.68 (m, 2H) ppm | 3-(4-piperidyl)-1H-pyrrolo[2,3-b]pyridine | General method D using tert-butyl 3-chlorosulfonyl azetidine-1-carboxylate, Cf using TFA, then H3 using adamantan-1-ol | 1-adamantyl 3-[4-(1H-pyrrolo[2,3-b]pyridin-3-yl)piperidin-1-yl]sulfonylazetidine-1-carboxylate |
| 162 | 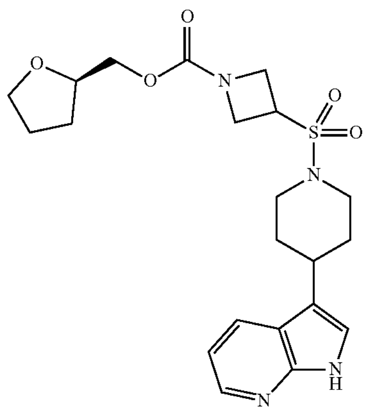 [SMILES: O=C(OC[C@H]1CCCO1)N1CC(S(=O)(=O)N2CCC(c3c[nH]c4ncccc34)CC2)C1] | 449.7 | ¹H NMR (600 MHz, DMSO-d₆): δ = 11.37 (s, 1H), 8.17 (dd, J = 1.47, 4.59 Hz, 1H), 7.96 (dd, J = 1.28, 7.89 Hz, 1H), 7.24 (d, J = 2.20 Hz, 1H), 7.01 (dd, J = 4.77, 7.89 Hz, 1H), 4.33-4.39 (m, 1H), 4.26 (br. s., 2H), 4.05 (br. s., 2H), 3.94-4.00 (m, 2H), 3.89-3.94 (m, 1H), 3.69-3.76 (m, 3H), 3.62 (dt, J = 6.24, 7.61 Hz, 1H), 2.99 (tt, J = 2.11, 12.24 Hz, 2H), 2.91 (tt, J = 3.46, 11.85 Hz, 1H), 2.02 (dd, J = 1.70, 13.15 Hz, 2H), 1.85-1.92 (m, 1H), 1.73-1.84 (m, 2H), 1.62 (dq, J = 3.94, 12.50 Hz, 2H), 1.49-1.57 (m, 1H) ppm | 3-(4-piperidyl)-1H-pyrrolo[2,3-b]pyridine | General method D using tert-butyl 3-chlorosulfonyl azetidine-1-carboxylate, Cf using TFA, then H3 using [(2R)-tetrahydrofuran-2-yl]methanol | [(2R)-oxolan-2-yl]methyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 163 | 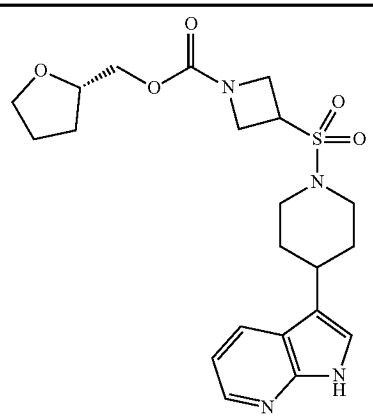 | 449.7 | ¹H NMR (600 MHz, DMSO-d₆): δ = 11.37 (s, 1H), 8.17 (dd, J = 1.56, 4.68 Hz, 1H), 7.96 (dd, J = 1.01, 7.79 Hz, 1H), 7.24 (d, J = 2.20 Hz, 1H), 7.01 (dd, J = 4.68, 7.79 Hz, 1H), 4.33-4.39 (m, 1H), 4.26 (br. s., 2H), 4.05 (br. s., 2H), 3.94-4.00 (m, 2H), 3.89-3.94 (m, 1H), 3.69-3.76 (m, 3H), 3.62 (dt, J = 6.33, 7.66 Hz, 1H), 2.99 (dt, J = 2.02, 12.29 Hz, 2H), 2.91 (tt, J = 3.46, 11.85 Hz, 1H), 2.02 (dd, J = 1.80, 13.12 Hz, 2H), 1.85-1.92 (m, 1H), 1.72-1.84 (m, 2H), 1.62 (dq, J = 4.03, 12.53 Hz, 2H), 1.49-1.57 (m, 1H) ppm | 3-(4-piperidyl)-1H-pyrrolo[2,3-b]pyridine | General method D using tert-butyl 3-chlorosulfonyl azetidine-1-carboxylate, Cf using TFA, then H3 using [(2S)-tetrahydrofuran-2-yl]methanol | [(2S)-oxolan-2-yl]methyl 3-[4-(1H-pyrrolo[2,3-b]pyridin-3-yl)piperidin-1-yl]sulfonylazetidine-1-carboxylate |
| 164 | 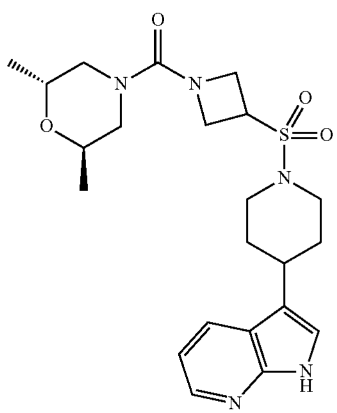 [SMILES: C[C@@H]1CN(C(=O)N2CC(S(=O)(=O)N3CCC(c4c[nH]c5ncccc45)CC3)C2)C[C@@H](C)O1] | 462.7 | ¹H NMR (500 MHz, DMSO-d₆): δ = 11.38 (br. s., 1H), 8.18 (d, J =2.60 Hz, 1H), 7.98 (d, J = 7.63 Hz, 1H), 7.25 (br. s., 1H), 6.97-7.07 (m, 1H), 4.31-4.42 (m, 1H), 4.17-4.29 (m, 2H), 4.03-4.15 (m, 1H), 3.87 (br. s., 2H), 3.73 (d, J = 10.99 Hz, 2H), 3.28 (d, J = 13.12 Hz, 2H), 2.86-3.03 (m, 5H), 2.03 (d, J = 12.21 Hz, 2H), 1.57-1.71 (m, 2H), 1.08 (d, J = 5.49 Hz, 6H) ppm | 3-(4-piperidyl)-1H-pyrrolo[2,3-b]pyridine | General method D using tert-butyl 3-chlorosulfonyl azetidine-1-carboxylate, Cf using TFA, then G3 using trans-2,6-dimethylmorpholine | [(2R,6R)-2,6-dimethylmorpholin-4-yl]-[3-[4-(1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 165 | 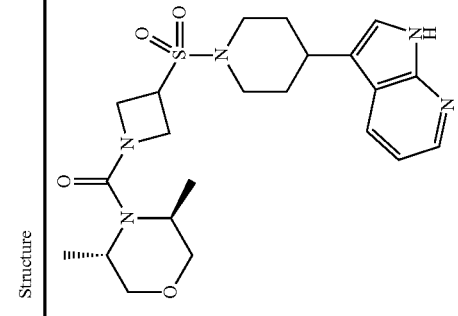 | 462.7 | 1H NMR (500 MHz, DMSO-d6): δ = 11.38 (br. s., 1H), 8.18 (d, J = 3.97 Hz, 1H), 7.98 (d, J = 7.63 Hz, 1H), 7.25 (s, 1H), 7.02 (dd, J = 4.88, 7.63 Hz, 1H), 4.32-4.44 (m, 2H), 4.15-4.26 (m, 1H), 4.02-4.12 (m, 1H), 3.90-3.98 (m, 1H), 3.74 (d, J = 10.38 Hz, 2H), 3.64 (dd, J = 2.44, 10.99 Hz, 2H), 3.26-3.38 (m, 4H), 2.86-3.04 (m, 3H), 2.03 (d, J = 12.51 Hz, 2H), 1.57-1.70 (m, 2H), 1.05 (d, J = 5.80 Hz, 6H) ppm | 3-(4-piperidyl)-1H-pyrrolo[2,3-b]pyridine | General method D using tert-butyl 3-chlorosulfonyl azetidine-1-carboxylate, Cf using TFA, then G3 using (3S,5S)-3,5-dimethylmorpholine, hydrochloride | [(3S,5S)-3,5-dimethylmorpholin-4-yl]-[3-[4-(1H-pyrrolo[2,3-b]pyridin-3-yl)piperidin-1-yl]sulfonylazetidin-1-yl]methanone |
| 166 | 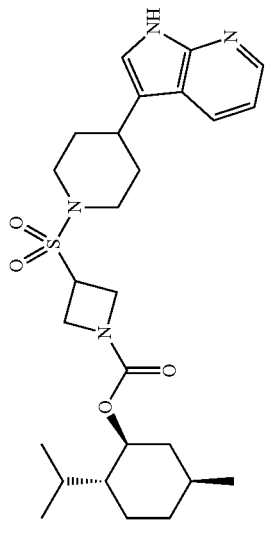 | 503 | 1H NMR (600 MHz, DMSO-d6): δ = 11.37 (d, J = 1.28 Hz, 1H), 8.17 (dd, J = 1.56, 4.68 Hz, 1H), 7.96 (dd, J = 1.10, 7.89 Hz, 1H), 7.24 (d, J = 2.38 Hz, 1H), 7.01 (dd, J = 4.58, 7.89 Hz, 1H), 4.42 (dt, J = 4.40, 10.91 Hz, 1H), 4.32-4.38 (m, 1H), 4.24 (br. s., 2H), 4.03 (br. s., 2H), 3.69-3.76 (m, 2H), 2.94-3.01 (m, 2H), 2.91 (tt, J = 3.12, 11.74 Hz, 1H), 2.01 (d, J =11.37 Hz, 2H), 1.80-1.90 (m, 2H), 1.57-1.67 (m, 4H), 1.37-1.46 (m, 1H), 1.27-1.34 (m, 1H), 1.01 (dq, J = 3.67, 13.02 Hz, 1H), 0.93 (q, J = 11.92 Hz, 1H), 0.85 (d, J = 7.03 Hz, 6H), 0.78-0.87 (m, 1H), 0.72 (d, J = 6.97 Hz, 3H) ppm | 3-(4-piperidyl)-1H-pyrrolo[2,3-b]pyridine | General method D using tert-butyl 3-chlorosulfonyl azetidine-1-carboxylate, Cf using TFA, then H1 using (1S)-(+)-menthyl chloroformate | [(1S,2R,5S)-5-methyl-2-propan-2-ylcyclohexyl] 3-[4-(1H-pyrrolo[2,3-b]pyridin-3-yl)piperidin-1-yl]sulfonylazetidine-1-carboxylate |

| Cpd # | Structure | MS (m/z, ES+) | δ NMR Data | Starting Int/Cpd# | Sequence of Methods | Chemical Name |
|---|---|---|---|---|---|---|
| 167 | 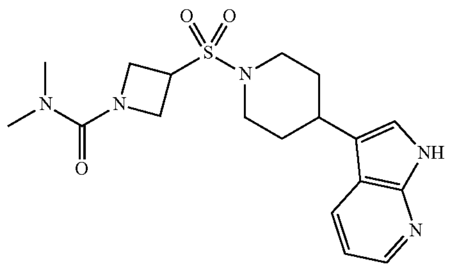 [SMILES: CN(C)C(=O)N1CC(S(=O)(=O)N2CCC(c3c[nH]c4ncccc34)CC2)C1] | 392 | ¹H NMR (600 MHz, DMSO-d₆): δ = 11.37 (s, 1H), 8.17 (dd, J = 1.56, 4.68 Hz, 1H), 7.97 (dd, J = 1.19, 7.98 Hz, 1H), 7.25 (d, J = 2.38 Hz, 1H), 7.01 (dd, J = 4.59, 7.89 Hz, 1H), 4.34 (tt, J = 6.08, 8.51 Hz, 1H), 4.17 (t, J = 8.71 Hz, 2H), 4.06 (dd, J = 6.14, 9.08 Hz, 2H), 3.72 (d, J = 12.29 Hz, 2H), 2.97 (dt, J = 2.29, 12.24 Hz, 2H), 2.91 (tt, J = 3.42, 11.90 Hz, 1H), 2.75 (s, 6H), 2.01 (dd, J = 1.90, 13.30 Hz, 2H), 1.63 (dq, J = 4.03, 12.47 Hz, 2H) ppm | 3-(4-piperidyl)-1H-pyrrolo[2,3-b]pyridine | General method D using tert-butyl 3-chlorosulfonyl azetidine-1-carboxylate, Cf using TFA, G1 using dimethylcarbamoyl chloride | N,N-dimethyl-3-[4-(1H-pyrrolo[2,3-b]pyridin-3-yl)piperidin-1-yl]sulfonylazetidine-1-carboxamide |
| 168 | 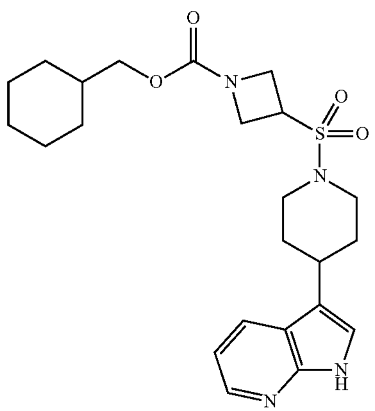 [SMILES: O=C(OCC1CCCCC1)N1CC(S(=O)(=O)N2CCC(c3c[nH]c4ncccc34)CC2)C1] | 461 | ¹H NMR (600 MHz, DMSO-d₆): δ = 11.36 (s, 1H), 8.17 (dd, J = 1.47, 4.59 Hz, 1H), 7.96 (dd, J = 1.28, 7.89 Hz, 1H), 7.23 (d, J = 2.38 Hz, 1H), 7.01 (dd, J = 4.68, 7.79 Hz, 1H), 4.32-4.38 (m, 1H), 4.25 (br. s., 2H), 4.03 (br. s., 2H), 3.79 (d, J = 6.60 Hz, 2H), 3.73 (d, J = 12.29 Hz, 2H), 2.98 (dt, J = 2.11, 12.24 Hz, 2H), 2.91 (tt, J = 3.48, 11.83 Hz, 1H), 2.01 (dd, J = 1.90, 13.30 Hz, 2H), 1.57-1.68 (m, 7H), 1.49-1.57 (m, 1H), 1.05-1.24 (m, 3H), 0.86-0.94 (m, 2H) ppm | 3-(4-piperidyl)-1H-pyrrolo[2,3-b]pyridine | General method D using tert-butyl 3-chlorosulfonyl azetidine-1-carboxylate, Cf using TFA, H2 using cyclohexylmethanol | cyclohexylmethyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 169 | 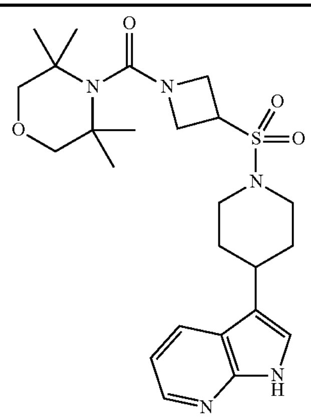 | 490 | ¹H NMR (600 MHz, DMSO-d₆): δ = 11.37 (s, 1H), 8.17 (dd, J = 1.47, 4.59 Hz, 1H), 7.97 (dd, J = 1.19, 7.79 Hz, 1H), 7.25 (d, J = 2.20 Hz, 1H), 7.01 (dd, J = 4.68, 7.79 Hz, 1H), 4.23-4.30 (m, 3H), 4.06-4.14 (m, 2H), 3.71 (d, J = 12.10 Hz, 2H), 3.29 (s, 4H), 2.97 (dt, J = 2.20, 12.20 Hz, 2H), 2.91 (tt, J = 3.35, 11.88 Hz, 1H), 2.02 (dd, J = 1.90, 13.30 Hz, 2H), 1.63 (dq, J = 3.94, 12.50 Hz, 2H), 1.15 (s, 12H) ppm | 3-(4-piperidyl)-1H-pyrrolo[2,3-b]pyridine | General method D using tert-butyl 3-chlorosulfonyl azetidine-1-carboxylate, Cf using TFA, then G3 using 3,3,5,5-tetramethylmorpholine, hydrochloride | [3-[4-(1H-pyrrolo[2,3-b]pyridin-3-yl)piperidin-1-yl]sulfonylazetidin-1-yl]-(3,3,5,5-tetramethylmorpholin-4-yl)methanone |
| 170 | 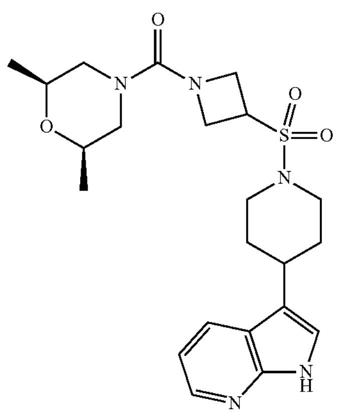 [SMILES: C[C@@H]1CN(C(=O)N2CC(S(=O)(=O)N3CCC(c4c[nH]c5ncccc45)CC3)C2)C[C@H](C)O1] | 462 | ¹H NMR (600 MHz, DMSO-d₆): δ = 11.37 (s, 1H), 8.17 (dd, J = 1.47, 4.59 Hz, 1H), 7.97 (dd, J = 1.28, 7.89 Hz, 1H), 7.24 (d, J = 2.20 Hz, 1H), 7.01 (dd, J = 4.58, 7.89 Hz, 1H), 4.32-4.39 (m, 1H), 4.21 (t, J = 8.80 Hz, 2H), 4.09 (dd, J = 6.05, 8.99 Hz, 2H), 3.72 (d, J = 12.29 Hz, 2H), 3.55 (dd, J = 1.20, 13.00 Hz, 2H), 3.39-3.46 (m, 2H), 2.97 (dt, J = 2.11, 12.24 Hz, 2H), 2.91 (tt, J = 3.44, 11.88 Hz, 1H), 2.42 (dd, J = 10.64, 13.20 Hz, 2H), 2.02 (dd, J = 1.90, 13.30 Hz, 2H), 1.63 (dq, J = 4.03, 12.53 Hz, 2H), 1.05 (d, J = 6.24 Hz, 6H) ppm | 3-(4-piperidyl)-1H-pyrrolo[2,3-b]pyridine | General method D using tert-butyl 3-chlorosulfonyl azetidine-1-carboxylate, Cf using TFA, then G3 using cis-2,6-dimethylmorpholine | [(2R,6S)-2,6-dimethylmorpholin-4-yl]-[3-[4-(1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 171 | 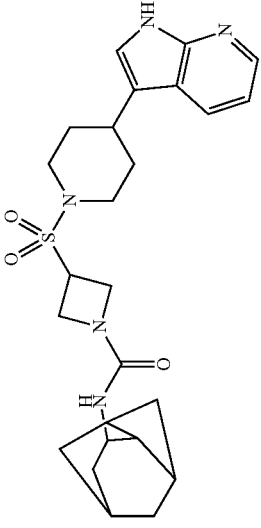 | 498 | ¹H NMR (500 MHz, DMSO-d₆): δ = 11.38 (br. s., 1H), 8.18 (dd, J = 1.37, 4.73 Hz, 1H), 7.98 (d, J = 7.93 Hz, 1H), 7.25 (d, J = 2.14 Hz, 1H), 7.02 (dd, J = 4.73, 7.78 Hz, 1H), 5.77 (s, 1H), 4.25-4.32 (m, 1H), 4.06 (t, J = 8.70 Hz, 2H), 3.94 (dd, J = 5.80, 8.85 Hz, 2H), 3.72 (d, J = 12.21 Hz, 2H), 2.88-3.02 (m, 3H), 2.03 (d, J = 12.96 Hz, 2H) 1.99 (br. s., 3H), 1.89 (br. s., 6H), 1.59 (br. s., 6H), 1.56-1.69 (m, 2H) ppm | 3-(4-piperidyl)-1H-pyrrolo[2,3-b]pyridine | General method D using tert-butyl 3-chlorosulfonyl azetidine-1-carboxylate, Cf using TFA, then G3 using 1-adamantanamine | N-(1-adamantyl)-3-[4-(1H-pyrrolo[2,3-b]pyridin-3-yl)piperidin-1-yl]sulfonyl]azetidine-1-carboxamide |
| 172 | 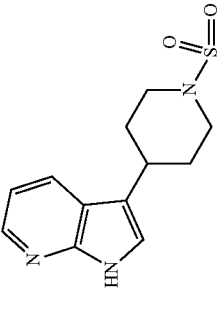 | 569 | ¹H NMR (300 MHz, DMSO-d₆): δ = 11.38 (br. s., 1H), 8.17 (dd, J = 1.57, 4.70 Hz, 1H), 7.96 (dd, J = 1.48, 7.93 Hz, 1H), 7.25 (s, 1H), 7.01 (dd, J = 4.70, 7.84 Hz, 1H), 4.38-4.50 (m, 1H), 4.15 (t, J = 8.36 Hz, 2H), 4.02-4.10 (m, 2H), 3.72 (d, J = 11.84 Hz, 2H), 3.35-3.43 (m, 4H), 3.09-3.17 (m, 4H), 2.84-3.06 (m, 3H), 1.95-2.06 (m, 2H), 1.55-1.72 (m, 2H), 1.40 (s, 9H) ppm | 3-(4-piperidyl)-1H-pyrrolo[2,3-b]pyridine | General method D using tert-butyl 3-chlorosulfonyl azetidine-1-carboxylate, Cf using TFA, then Df using tert-butyl 4-chlorosulfonyl piperazine-1-carboxylate | tert-butyl 4-[3-[4-(1H-pyrrolo[2,3-b]pyridin-3-yl)piperidin-3-yl]sulfonylazetidin-1-yl]sulfonyl]piperazine-1-carboxylate |

| Cpd # | Structure | MS (m/z, ES +) | δ NMR Data | Starting Int/Cpd# | Sequence of Methods | Chemical Name |
|---|---|---|---|---|---|---|
| 173 | 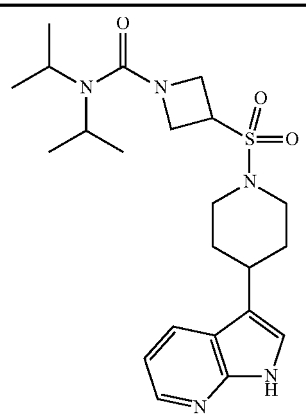 | 448.2 | ¹H NMR (600 MHz, DMSO-d₆): δ = 11.36 (s, 1H), 8.17 (dd, J = 1.56, 4.68 Hz, 1H), 7.97 (dd, J = 1.10, 7.89 Hz, 1H), 7.24 (d, J = 2.38 Hz, 1H), 7.01 (dd, J = 4.58, 7.89 Hz, 1H), 4.32 (tt, J = 6.21, 8.46 Hz, 2H), 4.10 (t, J = 8.62 Hz, 2H), 3.98 (dd, J = 6.14, 8.71 Hz, 2H), 3.72 (d, J = 12.29 Hz, 2H), 3.50 (spt, J = 6.63 Hz, 2H), 2.97 (dt, J = 3.42, 11.90 Hz, 1H), 2.91 (tt, J = 3.42, 11.90 Hz, 1H), 2.02 (d, J = 11.00 Hz, 2H), 1.63 (dq, J = 3.94, 12.50 Hz, 2H), 1.18 (d, J = 6.79 Hz, 12H) ppm | 3-(4-piperidyl)-1H-pyrrolo[2,3-b]pyridine | General method D using tert-butyl 3-chlorosulfonyl azetidine-1-carboxylate, Cf using TFA, then G1 using N,N-diisopropylcarbamoyl chloride | N,N-di(propan-2-yl)-3-[4-(1H-pyrrolo[2,3-b]pyridin-3-yl)piperidin-1-yl]sulfonylazetidine-1-carboxamide |
| 174 | 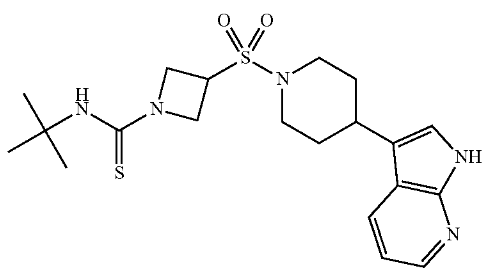 | 436.2 | ¹H NMR (600 MHz, DMSO-d₆): δ = 11.37 (br. s., 1H), 8.17 (dd, J = 1.38, 4.68 Hz, 1H), 7.97 (dd, J = 2.20, 7.85 Hz, 1H), 7.24 (d, J = 2.20 Hz, 1H), 7.01 (dd, J = 4.68, 7.79 Hz, 1H), 6.66 (s, 1H), 4.23-4.30 (m, 3H), 4.10-4.18 (m, 2H), 3.73 (d, J = 12.29 Hz, 2H), 2.97-3.04 (m, 2H), 2.89-2.96 (m, 1H), 2.03 (d, J = 11.55 Hz, 2H), 1.63 (dq, J = 3.67, 12.47 Hz, 2H), 1.44 (s, 9H) ppm | 3-(4-piperidyl)-1H-pyrrolo[2,3-b]pyridine | General method D using tert-butyl 3-chlorosulfonyl azetidine-1-carboxylate, Cf using TFA, then G2 using tert-butyl isothiocyanate | N-tert-butyl-3-[4-(1H-pyrrolo[2,3-b]pyridin-3-yl)piperidin-1-yl]sulfonylazetidine-1-carbothioamide |
| 175 | 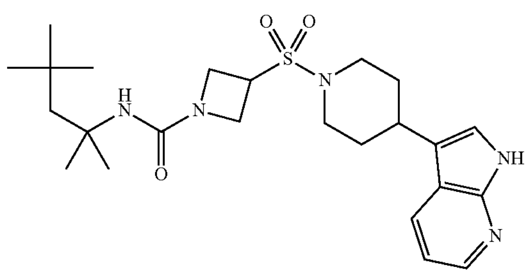 [SMILES: CC(C)(C)CC(C)(C)NC(=O)N1CC(S(=O)(=O)N2CCC(c3c[nH]c4ncccc34)CC2)C1] | 476.2 | ¹H NMR (600 MHz, DMSO-d₆): δ = 11.37 (d, J = 1.47 Hz, 1H), 8.17 (dd, J = 1.56, 4.68 Hz, 1H), 7.97 (dd, J = 1.10, 7.89 Hz, 1H), 7.24 (d, J = 2.38 Hz, 1H), 7.01 (dd, J = 4.59, 7.89 Hz, 1H), 5.75 (tt, J = 5.85, 8.37 Hz, 1H), 4.05 (t, J = 8.62 Hz, 2H), 3.95 (dd, J = 5.87, 8.99 Hz, 2H), 3.71 (d, J = 12.10 Hz, 2H), 2.87-3.00 (m, 3H), 2.01 (d, J = 11.00 Hz, 2H), 1.66 (s, 2H) 1.58-1.66 (m, 2H), 1.26 (s, 6H), 0.94 (s, 9H) ppm | 3-(4-piperidyl)-1H-pyrrolo[2,3-b]pyridine | General method D using tert-butyl 3-chlorosulfonyl azetidine-1-carboxylate, Cf using TFA, then G2 using 2-isocyanato-2,4,4-trimethyl-pentane | 3-[4-(1H-pyrrolo[2,3-b]pyridin-3-yl)piperidin-1-yl]sulfonyl-N-(2,4,4-trimethylpentan-2-yl)azetidine-1-carboxamide |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 176 | 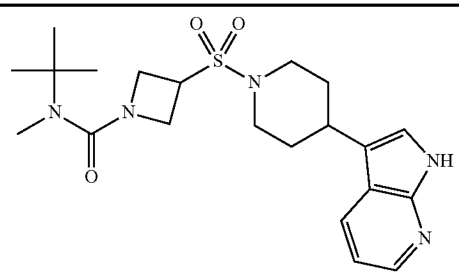 | 434.2 | ¹H NMR (300 MHz, DMSO-d₆): δ = 11.37 (s, 1H), 8.17 (dd, J = 1.51, 4.67 Hz, 1H), 7.97 (dd, J = 1.22, 7.84 Hz, 1H), 7.24 (d, J = 2.26 Hz, 1H), 7.01 (dd, J = 4.70, 7.84 Hz, 1H), 4.26-4.38 (m, 1H), 4.08 (t, J = 8.62 Hz, 2H), 3.91-4.01 (m, 2H), 3.72 (d, J = 11.84 Hz, 2H), 2.84-3.04 (m, 3H), 2.66 (s, 3H), 2.02 (d, J = 11.15 Hz, 2H), 1.63 (dq, J = 3.92, 12.40 Hz, 2H), 1.27 (s, 9H) ppm | 3-(4-piperidyl)-1H-pyrrolo[2,3-b]pyridine | General method D using tert-butyl 3-chlorosulfonyl azetidine-1-carboxylate, Cf using TFA, then G3 using N-methyl-tert-butylamine | N-tert-butyl-N-methyl-3-[4-(1H-pyrrolo[2,3-b]pyridin-3-yl)piperidin-1-yl]sulfonylazetidine-1-carboxamide |
| 177 | 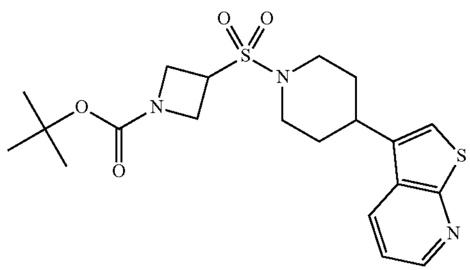 [SMILES: CC(C)(C)OC(=O)N1CC(S(=O)(=O)N2CCC(c3csc4ncccc34)CC2)C1] | 438.1 | ¹H NMR (300 MHz, DMSO-d₆): δ = 8.56 (dd, J = 1.39, 4.53 Hz, 1H), 8.29 (dd, J = 1.48, 8.10 Hz, 1H), 7.60 (s, 1H), 7.45 (dd, J = 4.53, 8.19 Hz, 1H), 4.27-4.40 (m, 1H), 4.19 (t, J = 8.27 Hz, 2H), 3.92-4.06 (m, 2H), 3.76 (d, J = 12.37 Hz, 2H), 2.93-3.18 (m, 3H), 2.01 (d, J = 11.84 Hz, 2H), 1.64 (dq, J = 3.92, 12.28 Hz, 2H), 1.38 (s, 9H) ppm | 3-bromothieno [3,2-b]pyridine | General method A1 using Na₂CO₃, B1 using Pd/C, then B2, Ci using TFA, then D using tert-butyl 3-chlorosulfonyl azetidine-1-carboxylate | tert-butyl 3-(4-thieno [3,2-b]pyridin-3-ylpiperidin-1-yl]sulfonylazetidine-1-carboxylate |
| 178 | 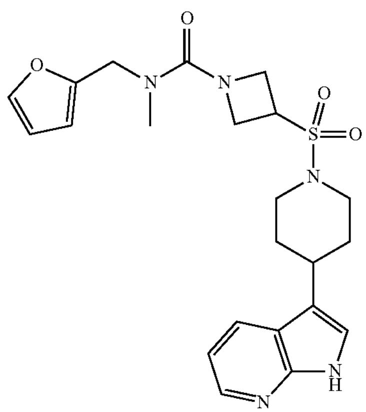 [SMILES: CN(Cc1ccco1)C(=O)N1CC(S(=O)(=O)N2CCC(c3c[nH]c4ncccc34)CC2)C1] | 458.1 | ¹H NMR (300 MHz, DMSO-d₆): δ = 11.37 (br. s., 1H), 8.17 (dd, J = 1.22, 4.53 Hz, 1H), 7.97 (d, J = 7.66 Hz, 1H), 7.59 (d, J = 1.05 Hz, 1H), 7.24 (d, J = 1.74 Hz, 1H), 7.01 (dd, J = 4.62, 7.93 Hz, 1H), 6.40 (dd, J = 1.92, 2.96 Hz, 1H), 6.30 (d, J = 2.96 Hz, 1H), 4.29-4.43 (m, 3H), 4.22 (t, J = 8.54 Hz, 2H), 4.05-4.16 (m, 2H), 3.72 (d, J = 12.02 Hz, 2H), 2.83-3.05 (m, 3H), 2.72 (s, 3H), 2.01 (d, J = 11.67 Hz, 2H), 1.52-1.73 (m, 2H) ppm | 3-(4-piperidyl)-1H-pyrrolo [2,3-b]pyridine | General method D using tert-butyl 3-chlorosulfonyl azetidine-1-carboxylate, Cf using TFA, then G5 using N-methylfurfurylamine | N-(furan-2-ylmethyl)-N-methyl-3-[4-(1H-pyrrolo[2,3-b]pyridin-3-yl)piperidin-1-yl]sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 179 | 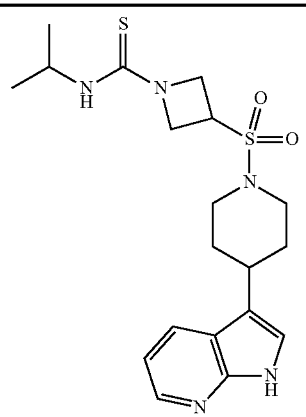 | 422.1 | ¹H NMR (500 MHz, DMSO-d₆): δ = 11.38 (br. s., 1H), 8.18 (dd, J = 4.58 Hz, 1H), 7.98 (d, J = 7.93 Hz, 1H), 7.44 (d, J = 7.93 Hz, 1H), 7.26 (d, J = 2.14 Hz, 1H), 7.02 (dd, J = 4.73, 7.78 Hz, 1H), 4.25-4.37 (m, 4H), 4.07-4.13 (m, 2H), 3.75 (d, J = 12.21 Hz, 2H), 2.98-3.07 (m, 2H), 2.90-2.98 (m, 1H), 2.03 (d, J = 11.29 Hz, 2H), 1.64 (dq, J = 3.97, 12.51 Hz, 2H), 1.11 (d, J = 6.41 Hz, 6H) ppm | 1H-pyrrolo [2,3-b]pyridine | General method A2, B1 using PtO2 (partial reduction), then B2, Ci using TFA, D using tert-butyl 3-chlorosulfonyl azetidine-1-carboxylate, Cf using TFA, then G2 using isopropyl isothiocyanate | N-propan-2-yl-3-[4-(1H-pyrrolo[2,3-b]pyridin-3-yl)piperidin-1-yl]sulfonylazetidine-1-carbothioamide |
| 180 | 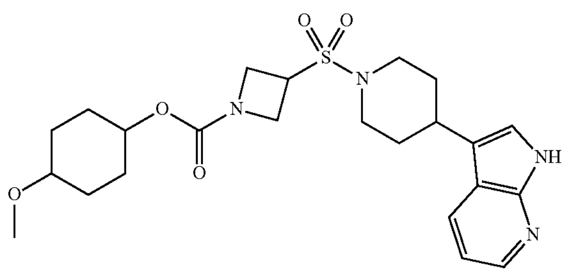 [SMILES: COC1CCC(OC(=O)N2CC(S(=O)(=O)N3CCC(c4c[nH]c5ncccc45)CC3)C2)CC1] | 477.2 | ¹H NMR (400 MHz, CHLOROFORM-d): δ = 8.94 (br. s., 1H), 8.29 (d, J = 4.9 Hz, 1H), 7.90 (d, J = 7.8 Hz, 1H), 7.03-7.09 (m, 2H), 4.65 (br.s, 1H), 4.26-4.33 (m, 2H), 4.17-4.25 (m, 2H), 3.92-4.00 (m, 3H), 3.31 (s, 3H), 3.14-3.25 (m, 1H), 2.87-3.04 (m, 3H), 2.11 (d, J = 12.6 Hz, 2H), 1.94 (d, J = 9.0 Hz, 3H), 1.74-1.88 (m, 3H), 1.61-1.69 (m, 2H), 1.36-1.43 (m, 2H) ppm. | 3-(4-piperidyl)-1H-pyrrolo [2,3-b]pyridine | General method D using tert-butyl 3-chlorosulfonyl azetidine-1-carboxylate, Cf using TFA, H3 using 4-methoxycyclohexanol | (4-methoxycyclohexyl) 3-[4-(1H-pyrrolo[2,3-b]pyridin-3-yl)piperidin-1-yl]sulfonylazetidine-1-carboxylate |
| 181 | 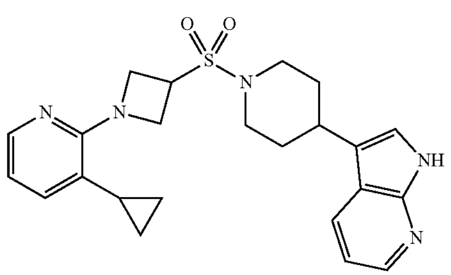 [SMILES: O=S(=O)(C1CN(c2ncccc2C2CC2)C1)N1CCC(c2c[nH]c3ncccc23)CC1] | 438.6 | ¹H NMR (500 MHz, DMSO-d₆): δ = 11.38 (br. s., 1H), 8.18 (d, J = 1.37, 4.73 Hz, 1H), 7.97-7.99 (m, 1H), 7.96 (d, J = 1.53 Hz, 1H), 7.26-7.27 (m, 1H), 7.23-7.26 (m, 1H), 7.00 (dd, J = 4.73, 7.78 Hz, 1H), 6.72 (dd, J = 4.88, 7.32 Hz, 1H), 4.48-4.54 (m, 1H), 4.42-4.48 (m, 2H), 4.33-4.38 (m, 2H), 3.78 (d, J = 12.21 Hz, 2H), 2.99-3.06 (m, 2H), 2.88-2.97 (m, 1H), 2.04 (d, J = 11.60 Hz, 2H), 1.77-1.84 (m, 1H), 1.66 (dq, J = 3.81, 12.46 Hz, 2H), 0.88-0.94 (m, 2H), 0.62-0.67 (m, 2H) ppm. | 3-(4-piperidyl)-1H-pyrrolo [2,3-b]pyridine | General method D using tert-butyl 3-chlorosulfonyl azetidine-1-carboxylate, Cf using TFA, J3 using 3-cyclopropyl-2-fluoro-pyridine | 3-[1-[1-(3-cyclopropylpyridin-2-yl)azetidin-3-yl]sulfonylpiperidin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 182 | 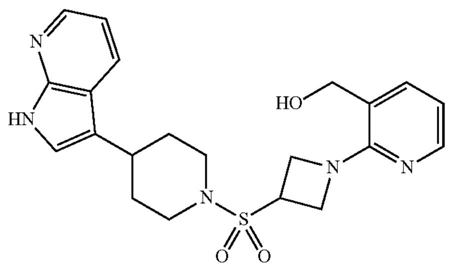 [SMILES: O=S(=O)(C1CN(c2ncccc2CO)C1)N1CCC(c2c[nH]c3ncccc23)CC1] | 428.8 | ¹H NMR (500 MHz, DMSO-d₆): δ = 11.36 (br. s., 1H), 8.17 (dd, J = 1.53, 4.58 Hz, 1H), 8.04 (dd, J = 1.53, 4.88 Hz, 1H), 7.97 (dd, J = 1.07, 7.78 Hz, 1H), 7.56 (dd, J = 1.53, 7.32 Hz, 1H), 7.23 (d, J = 2.44 Hz, 1H), 7.01 (dd, J = 4.73, 7.78 Hz, 1H), 6.78 (dd, J = 4.88, 7.32 Hz, 1H), 5.23 (t, J = 5.34 Hz, 1H), 4.44-4.53 (m, 2H), 4.33-4.41 (m, 4H), 4.26-4.33 (m, 2H), 3.76 (d, J = 11.90 Hz, 2H), 2.97-3.06 (m, 2H), 2.87-2.97 (m, 1H), 2.03 (d, J = 11.29 Hz, 2H), 1.60-1.70 (m, 2H) ppm. | 3-(4-piperidyl)-1H-pyrrolo[2,3-b]pyridine | General method D using tert-butyl 3-chlorosulfonylaze-tidine-1-carboxylate, Cf using TFA, J3 using (2-fluoro-3-pyridyl)-methanol | [2-[3-[4-(1H-pyrrolo[2,3-b]pyridin-3-yl)piperidin-1-yl]sulfonylaze-tidin-1-yl]pyridin-3-yl]methanol |
| 183 | 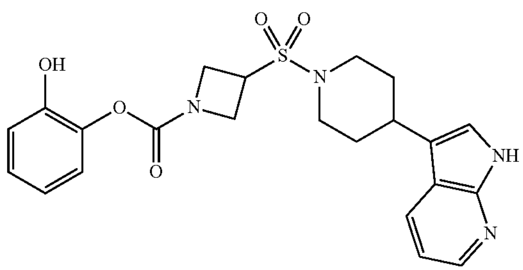 [SMILES: O=C(Oc1ccccc1O)N1CC(S(=O)(=O)N2CCC(c3c[nH]c4ncccc34)CC2)C1] | 457.8 | ¹H NMR (500 MHz, DMSO-d₆): δ = 11.39 (br. s., 1H), 9.61 (br. s., 1H), 8.18 (d, J = 4.27 Hz, 1H), 7.98 (d, J = 7.63 Hz, 1H), 7.27 (s, 1H), 7.00-7.08 (m, 2H), 6.98 (d, J = 7.93 Hz, 1H), 6.90 (d, J = 7.93 Hz, 1H), 6.76 (t, J = 7.63 Hz, 1H), 4.42-4.57 (m, 2H), 4.33 (br. s., 2H), 4.13 (br. s., 1H), 3.78 (d, J = 11.90 Hz, 2H), 3.03 (t, J = 11.75 Hz, 2H), 2.94 (t, J = 11.75 Hz, 1H), 2.05 (d, J = 12.21 Hz, 2H), 1.59-1.73 (m, 2H) ppm. | 3-(4-piperidyl)-1H-pyrrolo[2,3-b]pyridine | General method D using tert-butyl 3-chlorosulfonylaze-tidine-1-carboxylate, Cf using TFA, H3 using benzene-1,2-diol | (2-hydroxyphenyl) 3-[4-(1H-pyrrolo[2,3-b]pyridin-3-yl)piperidin-1-yl]sulfonylaze-tidine-1-carboxylate |
| 184 | 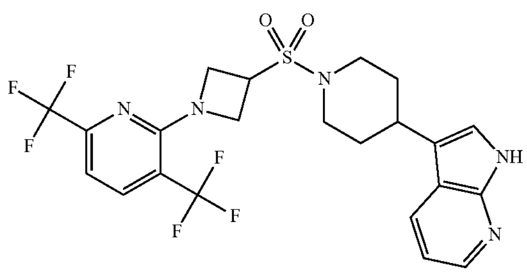 [SMILES: O=S(=O)(C1CN(c2nc(C(F)(F)F)ccc2C(F)(F)F)C1)N1CCC(c2c[nH]c3ncccc23)CC1] | 534.8 | ¹H NMR (300 MHz, DMSO-d₆): δ = 11.37 (br. s., 1H), 8.22 (d, J = 8.01 Hz, 1H), 8.17 (dd, J = 1.48, 4.62 Hz, 1H), 7.97 (d, J = 6.97 Hz, 1H), 7.29 (d, J = 7.66 Hz, 1H), 7.23 (d, J = 2.26 Hz, 1H), 7.00 (dd, J = 4.70, 7.84 Hz, 1H), 4.45-4.62 (m, 3H), 4.26-4.37 (m, 2H), 3.76 (d, J = 11.84 Hz, 2H), 2.86-3.12 (m, 3H), 1.99-2.10 (m, 2H), 1.64 (dq, J = 3.22, 12.28 Hz, 2H) ppm. | 3-(4-piperidyl)-1H-pyrrolo[2,3-b]pyridine | General method D using tert-butyl 3-chlorosulfonylaze-tidine-1-carboxylate, Cf using TFA, J3 using 2-chloro-3,6-bis(trifluoromethyl)pyridine | 3-[1-[1-[3,6-bis(trifluoromethyl)pyridin-2-yl]azetidin-3-yl]sulfonylpiper-idin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 185 | 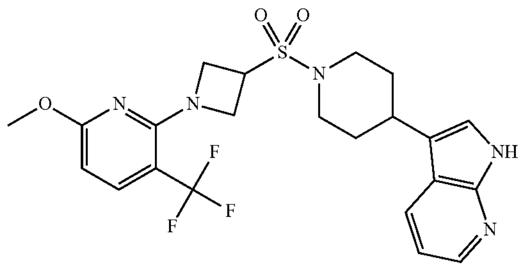 [SMILES: COc1ccc(C(F)(F)F)c(N2CC(S(=O)(=O)N3CCC(c4c[nH]c5ncccc45)CC3)C2)n1] | 496.8 | ¹H NMR (300 MHz, DMSO-d₆): δ = 11.37 (br. s., 1H), 8.17 (dd, J = 4.53 Hz, 1H), 7.96 (d, J = 6.79 Hz, 1H), 7.78 (d, J = 8.54 Hz, 1H), 7.23 (d, J = 2.09 Hz, 1H), 7.00 (dd, J = 4.62, 7.93 Hz, 1H), 6.22 (d, J = 8.36 Hz, 1H), 4.41-4.57 (m, 3H), 4.21-4.36 (m, 2H), 3.86 (s, 3H), 3.76 (d, J = 11.84 Hz, 2H), 2.85-3.10 (m, 3H), 1.98-2.10 (m, 2H), 1.64 (dq, J = 3.57, 12.28 Hz, 2H) ppm. | 3-(4-piperidyl)-1H-pyrrolo[2,3-b]pyridine | General method D using tert-butyl 3-chlorosulfonylaze-tidine-1-carboxylate, Cf using TFA, J3 using 2-chloro-6-methoxy-3-(trifluoromethyl)pyridine | 3-[1-[1-[6-methoxy-3-(trifluoromethyl)pyridin-2-yl]azetidin-3-yl]sulfonylpiperidin-4-yl]-1H-pyrrolo[2,3-b]pyridine |
| 186 | 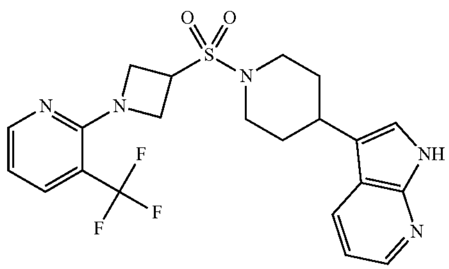 [SMILES: O=S(=O)(C1CN(c2ncccc2C(F)(F)F)C1)N1CCC(c2c[nH]c3ncccc23)CC1] | 466.8 | ¹H NMR (300 MHz, DMSO-d₆): δ = 11.37 (br. s., 1H), 8.40 (d, J = 3.83 Hz, 1H), 8.17 (dd, J = 1.31, 4.62 Hz, 1H), 7.91-8.00 (m, 2H), 7.23 (d, J = 2.09 Hz, 1H), 7.00 (dd, J = 4.62, 7.93 Hz, 1H), 6.89 (dd, J = 4.70, 7.49 Hz, 1H), 4.40-4.57 (m, 3H), 4.23-4.33 (m, 2H), 3.75 (d, J = 12.37 Hz, 2H), 2.86-3.11 (m, 3H), 1.97-2.10 (m, 2H), 1.55-1.73 (m, 2H) ppm. | 3-(4-piperidyl)-1H-pyrrolo[2,3-b]pyridine | General method D using tert-butyl 3-chlorosulfonylaze-tidine-1-carboxylate, Cf using TFA, J3 using 2-chloro-3-(trifluoromethyl)pyridine | 3-[1-[1-[3-(trifluoromethyl)pyridin-2-yl]azetidin-3-yl]sulfonylpiperidin-4-yl]-1H-pyrrolo[2,3-b]pyridine |
| 187 | 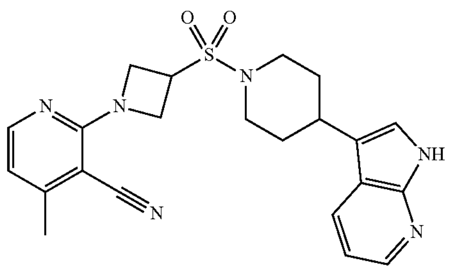 [SMILES: Cc1ccnc(N2CC(S(=O)(=O)N3CCC(c4c[nH]c5ncccc45)CC3)C2)c1C#N] | 437.8 | ¹H NMR (300 MHz, DMSO-d₆): δ = 11.37 (br. s., 1H), 8.22 (d, J = 5.05 Hz, 1H), 8.17 (dd, J = 1.48, 4.62 Hz, 1H), 7.97 (dd, J = 1.22, 7.84 Hz, 1H), 7.23 (d, J = 2.26 Hz, 1H), 7.00 (dd, J = 4.70, 7.84 Hz, 1H), 6.81 (d, J = 5.05 Hz, 1H), 4.46-4.63 (m, 3H), 4.32-4.40 (m, 2H), 3.76 (d, J = 12.02 Hz, 2H), 2.86-3.12 (m, 3H), 2.38 (s, 3H), 2.04 (d, J = 12.54 Hz, 2H), 1.54-1.74 (m, 2H) ppm. | 3-(4-piperidyl)-1H-pyrrolo[2,3-b]pyridine | General method D using tert-butyl 3-chlorosulfonylaze-tidine-1-carboxylate, Cf using TFA, J3 using 2-chloro-4-methyl-pyridine-3-carbonitrile | 4-methyl-2-[3-[4-(1H-pyrrolo[2,3-b]pyridin-3-yl)piperidin-1-yl]sulfonyl]aze-tidin-1-yl]pyridine-3-carbonitrile |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 188 | 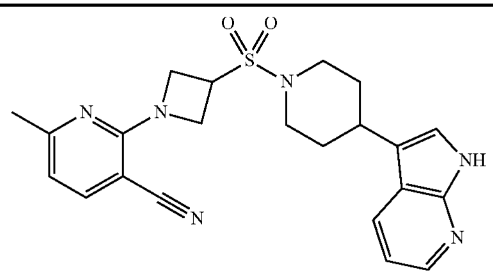 | 480.8 | ¹H NMR (300 MHz, DMSO-d₆): δ = 11.37 (br. s., 1H), 8.17 (dd, J = 4.62 Hz, 1H), 7.97 (dd, J = 1.22, 7.84 Hz, 1H), 7.81 (d, J = 7.84 Hz, 1H), 7.23 (d, J = 2.26 Hz, 1H), 7.00 (dd, J = 4.62, 7.93 Hz, 1H), 6.75 (d, J = 7.84 Hz, 1H), 4.37-4.57 (m, 3H), 4.21-4.32 (m, 2H), 3.75 (d, J = 12.37 Hz, 2H), 2.85-3.10 (m, 3H), 2.39 (s, 3H), 2.04 (d, J = 12.19 Hz, 2H), 1.54-1.74 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J3 using 2-chloro-6-methyl-3-(trifluoromethyl)pyridine | 3-[1-[6-methyl-3-(trifluoromethyl)pyridin-2-yl]azetidin-3-yl]sulfonyl]piperidin-4-yl]-1H-pyrrolo[2,3-b]pyridine |
| 189 | 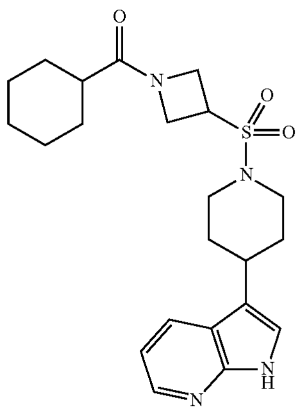 [SMILES: O=C(C1CCCCC1)N1CC(S(=O)(=O)N2CCC(c3c[nH]c4ncccc34)CC2)C1] | 431.8 | ¹H NMR (300 MHz, DMSO-d₆): δ = 11.38 (br. s., 1H), 8.17 (dd, J = 1.39, 4.70 Hz, 1H), 7.97 (d, J = 8.01 Hz, 1H), 7.25 (d, J = 2.09 Hz, 1H), 7.01 (dd, J = 4.62, 7.93 Hz, 1H), 4.44-4.56 (m, 1H), 4.27-4.41 (m, 2H), 4.09-4.19 (m, 1H), 3.96 (dd, J = 5.05, 9.93 Hz, 1H), 3.74 (d, J = 11.84 Hz, 2H), 2.85-3.05 (m, 3H), 2.21 (br. s., 1H), 2.02 (d, J = 12.19 Hz, 2H), 1.53-1.73 (m, 7H), 1.11-1.34 (m, 5H) ppm. | 3-(4-piperidyl)-1H-pyrrolo[2,3-b]pyridine | General method D using tert-butyl 3-chlorosulfonylazetidine-1-carboxylate, Cf using TFA, I2 using cyclohexanecarbonyl chloride | cyclohexyl-[3-[4-(1H-pyrrolo[2,3-b]pyridin-3-yl)piperidin-3-yl]sulfonyl]azetidin-1-yl]methanone |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 190 | 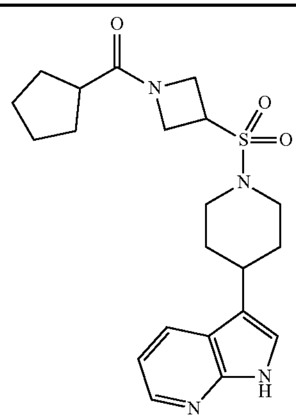 | 417.8 | ¹H NMR (300 MHz, DMSO-d₆): δ = 11.38 (br. s., 1H), 8.13-8.20 (m, 1H), 7.97 (d, J = 7.84 Hz, 1H), 7.25 (d, J = 2.44 Hz, 1H), 7.01 (dd, J = 4.70, 7.84 Hz, 1H), 4.44-4.53 (m, 1H), 4.26-4.42 (m, 2H), 4.16 (t, J = 8.88 Hz, 1H), 3.93-4.01 (m, 1H), 3.74 (d, J = 11.84 Hz, 2H), 2.85-3.05 (m, 3H), 2.57-2.69 (m, 1H), 1.96-2.08 (m, 2H), 1.67-1.79 (m, 2H), 1.41-1.67 (m, 8H) ppm. | 3-(4-piperidyl)-1H-pyrrolo[2,3-b]pyridine | General method D using tert-butyl 3-chlorosulfonylazetidine-1-carboxylate, Cf using TFA, 12 using cyclopentanecarbonyl chloride | cyclopentyl-[3-[4-(1H-pyrrolo[2,3-b]pyridin-3-yl)piperidin-1-yl]sulfonylazetidin-1-yl]methanone |
| 191 | 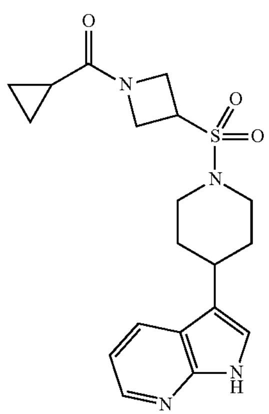 [SMILES: O=C(C1CC1)N1CC(S(=O)(=O)N2CCC(c3c[nH]c4ncccc34)CC2)C1] | 389.7 | ¹H NMR (300 MHz, DMSO-d₆): δ = 11.38 (br. s., 1H), 8.17 (dd, J = 1.39, 4.70 Hz, 1H), 7.97 (dd, J = 2.26 Hz, 1H), 7.25 (d, J = 1.22 Hz, 1H), 7.01 (dd, J = 4.62, 7.93 Hz, 1H), 4.54-4.64 (m, 1H), 4.34-4.46 (m, 2H), 4.13-4.23 (m, 1H), 3.98 (dd, J = 4.79, 10.19 Hz, 1H), 3.75 (d, J = 12.02 Hz, 2H), 2.86-3.07 (m, 3H), 2.02 (d, J = 11.67 Hz, 2H), 1.51-1.71 (m, 3H), 0.65-0.79 (m, 4H) ppm. | 3-(4-piperidyl)-1H-pyrrolo[2,3-b]pyridine | General method D using tert-butyl 3-chlorosulfonylazetidine-1-carboxylate, Cf using TFA, 12 using cyclopropanecarbonyl chloride | cyclopropyl-[3-[4-(1H-pyrrolo[2,3-b]pyridin-1-yl)piperidin-3-yl]sulfonylazetidin-1-yl]methanone |

| Cpd # | Structure | MS (m/z ES +) | δ NMR Data | Starting Int/Cpd# | Sequence of Methods | Chemical Name |
|---|---|---|---|---|---|---|
| 192 | 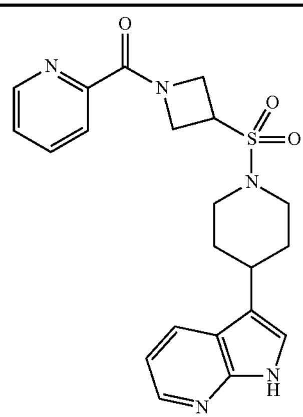 | 426.8 | ¹H NMR (300 MHz, DMSO-d₆): δ = 11.37 (br. s., 1H), 8.64 (dt, J = 4.70 Hz, 1H), 8.17 (dd, J = 1.48, 4.62 Hz, 1H), 7.93-8.02 (m, 3H), 7.52-7.61 (m, 1H), 7.23 (d, J = 2.09 Hz, 1H), 7.00 (dd, J = 4.70, 7.84 Hz, 1H), 4.9-5.00 (m, 1H), 4.72-4.80 (m, 1H), 4.39-4.50 (m, 2H), 4.18-4.28 (m, 1H), 3.76 (d, J = 10.10 Hz, 2H), 2.84-3.08 (m, 3H), 1.98-2.08 (m, 2H), 1.55-1.72 (m, 2H) ppm. | 3-(4-piperidyl)-1H-pyrrolo[2,3-b]pyridine | General method D using tert-butyl 3-chlorosulfonylazetidine-1-carboxylate, Cf using TFA, I1 using pyridine-2-carboxylic acid | pyridin-2-yl-[3-[4-(1H-pyrrolo[2,3-b]pyridin-3-yl)piperidin-1-yl]sulfonylazetidin-1-yl]methanone |
| 193 | 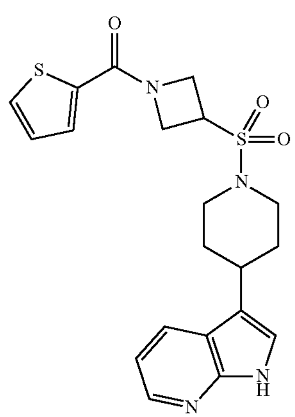 [SMILES: O=C(c1cccs1)N1CC(S(=O)(=O)N2CCC(c3c[nH]c4ncccc34)CC2)C1] | 431.7 | ¹H NMR (300 MHz, DMSO-d₆): δ = 11.37 (br. s., 1H), 8.17 (dd, J = 1.48, 4.62 Hz, 1H), 7.97 (dd, J = 1.22, 7.84 Hz, 1H), 7.86 (dd, J = 1.05, 4.88 Hz, 1H), 7.59 (dd, J = 1.05, 3.83 Hz, 1H), 7.24 (d, J = 2.26 Hz, 1H), 7.19 (dd, J = 3.74, 4.96 Hz, 1H), 7.01 (dd, J = 4.70, 7.84 Hz, 1H), 4.84 (br. s., 1H), 4.61 (br. s., 1H), 4.31-4.54 (m, 2H), 4.19 (br. s., 1H), 3.77 (d, J = 12.02 Hz, 2H), 2.86-3.10 (m, 3H), 2.02 (d, J = 11.50 Hz, 2H), 1.64 (dq, J = 3.75, 12.40 Hz, 2H) ppm. | 3-(4-piperidyl)-1H-pyrrolo[2,3-b]pyridine | General method D using tert-butyl 3-chlorosulfonylazetidine-1-carboxylate, Cf using TFA, I2 using thiophene-2-carbonyl chloride | [3-[4-(1H-pyrrolo[2,3-b]pyridin-3-yl)piperidin-1-yl]sulfonylazetidin-1-yl]-thiophen-2-ylmethanone |

| Cpd # | Structure | MS (m/z, ES +) | δ NMR Data | Starting Int/Cpd# | Sequence of Methods | Chemical Name |
|---|---|---|---|---|---|---|
| 194 | 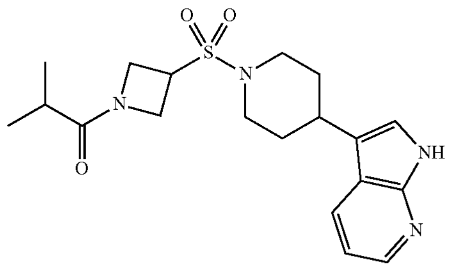 | 391.7 | ¹H NMR (300 MHz, DMSO-d₆): δ = 11.37 (br. s., 1H), 8.17 (dd, J = 1.48, 4.62 Hz, 1H), 7.97 (dd, J = 1.31, 7.75 Hz, 1H), 7.25 (d, J = 2.26 Hz, 1H), 7.01 (dd, J = 4.70, 7.84 Hz, 1H), 4.45-4.56 (m, 1H), 4.26-4.42 (m, 2H), 4.10-4.21 (m, 1H), 3.97 (dd, J = 5.05, 9.75 Hz, 1H), 3.75 (d, J = 12.37 Hz, 2H), 2.85-3.06 (m, 3H), 2.40-2.46 (m, 1H), 2.02 (d, J = 11.15 Hz, 2H), 1.62 (dq, J = 3.83, 12.43 Hz, 2H), 0.96 (dd, J = 1.57, 6.79 Hz, 6H) ppm. | 3-(4-piperidyl)-1H-pyrrolo[2,3-b]pyridine | General method D using tert-butyl 3-chlorosulfonylazetidine-1-carboxylate, Cf using TFA, I2 using 2-methylpropanoyl chloride | 2-methyl-1-[3-[4-(1H-pyrrolo[2,3-b]pyridin-3-yl)piperidin-1-yl]sulfonylazetidin-1-yl]propan-1-one |
| 195 | 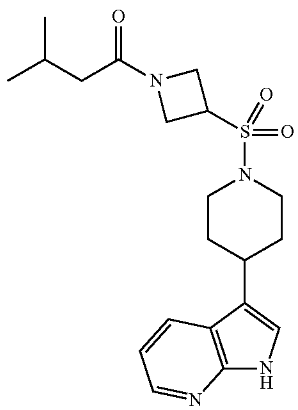 | 405.7 | ¹H NMR (300 MHz, DMSO-d₆): δ = 11.38 (br. s., 1H), 8.17 (dd, J = 1.48, 4.62 Hz, 1H), 7.97 (dd, J = 1.22, 7.84 Hz, 1H), 7.25 (d, J = 2.09 Hz, 1H), 7.01 (dd, J = 4.70, 7.84 Hz, 1H), 4.41-4.50 (m, 1H), 4.32-4.40 (m, 1H), 4.22-4.31 (m, 1H), 4.16 (t, J = 9.14 Hz, 1H), 3.98 (dd, J = 5.14, 10.02 Hz, 1H), 3.74 (d, J = 12.19 Hz, 2H), 2.85-3.05 (m, 3H), 2.02 (d, J = 11.84 Hz, 2H), 1.88-1.97 (m, 3H), 1.54-1.71 (m, 2H), 0.88 (d, J = 6.27 Hz, 6H) ppm. | 3-(4-piperidyl)-1H-pyrrolo[2,3-b]pyridine | General method D using tert-butyl 3-chlorosulfonylazetidine-1-carboxylate, Cf using TFA, I2 using 3-methylbutanoyl chloride | 3-methyl-1-[3-[4-(1H-pyrrolo[2,3-b]pyridin-3-yl)piperidin-1-yl]sulfonylazetidin-1-yl]butan-1-one |
| 196 | 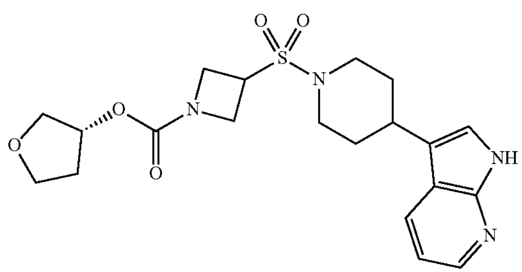 [SMILES: O=C(O[C@@H]1CCOC1)N1CC(S(=O)(=O)N2CCC(c3c[nH]c4ncccc34)CC2)C1] | 435.7 | ¹H NMR (300 MHz, DMSO-d₆): δ = 11.37 (br. s., 1H), 8.17 (dd, J = 1.48, 4.62 Hz, 1H), 7.96 (dd, J = 1.39, 7.84 Hz, 1H), 7.24 (d, J = 1.92 Hz, 1H), 7.01 (dd, J = 4.70, 7.84 Hz, 1H), 5.06-5.14 (m, 1H), 4.19-4.40 (m, 3H), 4.05 (br. s., 2H), 3.62-3.81 (m, 6H), 2.84-3.05 (m, 3H), 2.05-2.16 (m, 1H), 2.02 (d, J = 10.80 Hz, 2H), 1.80-1.92 (m, 1H), 1.52-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H3 using (3R)-tetrahydrofuran-3-ol | [(3R)-oxolan-3-yl]3-[4-(1H-pyrrolo[2,3-b]pyridin-3-yl)piperidin-1-yl]sulfonylazetidine-1-carboxylate |

| Cpd # | Structure | MS (m/z ES +) | δ NMR Data | Starting Int/Cpd# | Sequence of Methods | Chemical Name |
|---|---|---|---|---|---|---|
| 197 | 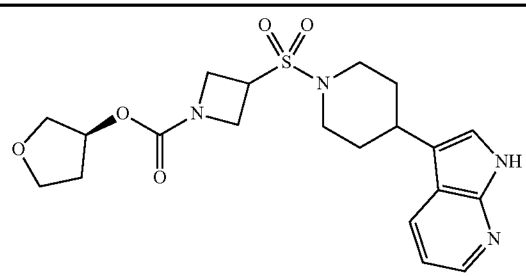 | 435.7 | ¹H NMR (300 MHz, DMSO-d₆): δ = 11.38 (br. s., 1H), 8.13-8.22 (m, 1H), 7.96 (dd, J = 1.39, 7.84 Hz, 1H), 7.24 (d, J = 2.09 Hz, 1H), 7.01 (dd, J = 4.70, 7.84 Hz, 1H), 5.07-5.17 (m, 1H), 4.17-4.42 (m, 3H), 4.05 (br. s., 2H), 3.58-3.82 (m, 6H), 2.82-3.07 (m, 3H), 1.95-2.18 (m, 3H), 1.78-1.92 (m, 1H), 1.52-1.71 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H3 using (3S)-tetrahydrofuran-3-ol | [(3S)-oxolan-3-yl]3-[4-(1H-pyrrolo[2,3-b]pyridin-3-yl)piperidin-1-yl]sulfonylazetidine-1-carboxylate |
| 198 | 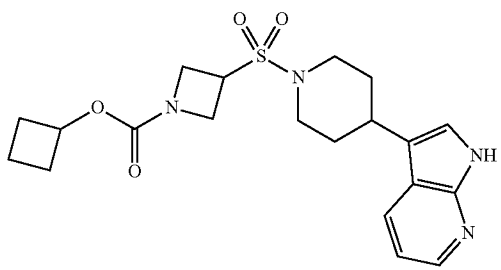 [SMILES: O=C(OC1CCC1)N1CC(S(=O)(=O)N2CCC(c3c[nH]c4ncccc34)CC2)C1] | 419.7 | ¹H NMR (300 MHz, DMSO-d₆): δ = 11.38 (br. s., 1H), 8.17 (dd, J = 1.57, 4.70 Hz, 1H), 7.96 (dd, J = 1.39, 7.84 Hz, 1H), 7.24 (d, J = 4.70, 7.84 Hz, 1H), 7.01 (dd, J = 1.57 Hz, 1H), 4.75-4.88 (m, 1H), 4.29-4.40 (m, 3H), 4.24 (br. s., 2H), 4.03 (br. s., 2H), 3.73 (d, J = 12.19 Hz, 2H), 2.85-3.04 (m, 3H), 2.15-2.30 (m, 2H), 1.90-2.07 (m, 4H), 1.45-1.76 (m, 4H) ppm. | 3-(4-piperidyl)-1H-pyrrolo[2,3-b]pyridine | General method D using tert-butyl 3-chlorosulfonylazetidine-1-carboxylate, Cf using TFA, H3 using cyclobutanol | cyclobutyl 3-[4-(1H-pyrrolo[2,3-b]pyridin-3-yl)piperidin-1-yl]sulfonylazetidine-1-carboxylate |
| 199 | 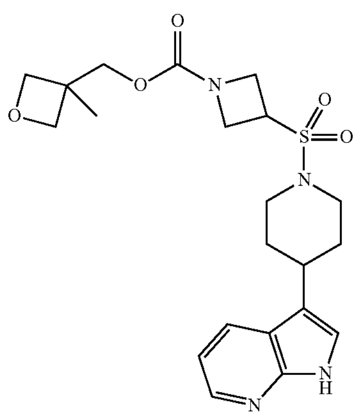 [SMILES: CC1(COC(=O)N2CC(S(=O)(=O)N3CCC(c4c[nH]c5ncccc45)CC3)C2)COC1] | 449.7 | ¹H NMR (500 MHz, DMSO-d₆): δ = 11.38 (br. s., 1H), 8.18 (d, J = 4.58 Hz, 1H), 7.97 (d, J = 7.63 Hz, 1H), 7.25 (d, J = 1.83 Hz, 1H), 7.02 (dd, J = 4.58, 7.93 Hz, 1H), 4.34-4.43 (m, 3H), 4.30 (br. s., 2H), 4.22 (d, J = 5.80 Hz, 2H), 4.09 (s, 4H), 3.74 (d, J = 12.21 Hz, 2H), 2.99 (t, J = 11.44 Hz, 2H), 2.87-2.95 (m, 1H), 2.03 (d, J = 11.90 Hz, 2H), 1.63 (dq, J = 3.66, 12.41 Hz, 2H), 1.24 (s, 3H) ppm. | 3-(4-piperidyl)-1H-pyrrolo[2,3-b]pyridine | General method D using tert-butyl 3-chlorosulfonylazetidine-1-carboxylate, Cf using TFA, H3 using (3-methyloxetan-3-yl)methanol | (3-methyloxetan-3-yl)methyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 200 | 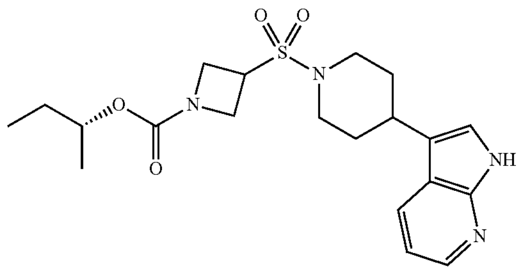 [SMILES: CC[C@@H](C)OC(=O)N1CC(S(=O)(=O)N2CCC(c3c[nH]c4ncccc34)CC2)C1] | 421.7 | ¹H NMR (300 MHz, DMSO-d₆): δ = 11.37 (br. s., 1H), 8.13-8.19 (m, 1H), 7.92-8.00 (m, 1H), 7.24 (br. s, 1H), 7.01 (dd, J = 4.70, 7.84 Hz, 1H), 4.52-4.65 (m, 1H), 4.29-4.43 (m, 1H), 4.15-4.29 (m, 2H), 3.94-4.08 (m, 2H), 3.73 (d, J = 11.84 Hz, 2H), 2.83-3.05 (m, 3H), 2.02 (d, J = 12.19 Hz, 2H), 1.53-1.70 (m, 2H), 1.49 (quin, J = 7.14 Hz, 2H), 1.13 (d, J = 6.27 Hz, 3H), 0.83 (t, J = 7.32 Hz, 3H) ppm. | 3-(4-piperidyl)-1H-pyrrolo[2,3-b]pyridine | General method D using tert-butyl 3-chlorosulfonylazetidine-1-carboxylate, Cf using TFA, H3 using (2R)-butan-2-ol | [(2R)-butan-2-yl]3-[4-(1H-pyrrolo[2,3-b]pyridin-3-yl)piperidin-1-yl]sulfonylazetidine-1-carboxylate |
| 201 | 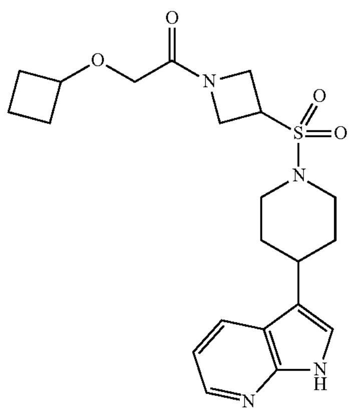 [SMILES: O=C(COC1CCC1)N1CC(S(=O)(=O)N2CCC(c3c[nH]c4ncccc34)CC2)C1] | 433.7 | ¹H NMR (300 MHz, DMSO-d₆): δ = 11.37 (br. s., 1H), 8.13-8.21 (m, 1H), 7.92-7.99 (m, 1H), 7.24 (br. s, 1H), 7.01 (dd, J = 4.70, 7.84 Hz, 1H), 4.16-4.30 (m, 2H), 3.98-4.10 (m, 2H), 3.96 (d, J = 6.62 Hz, 2H), 3.73 (d, J = 12.19 Hz, 2H), 2.83-3.05 (m, 3H), 2.62-2.51 (m, 1H), 1.88-2.07 (m, 4H), 1.52-1.88 (m, 6H) ppm. | 3-(4-piperidyl)-1H-pyrrolo[2,3-b]pyridine | General method D using tert-butyl 3-chlorosulfonylazetidine-1-carboxylate, Cf using TFA, H3 using cyclobutylmethanol | cyclobutylmethyl 3-[4-(1H-pyrrolo[2,3-b]pyridin-3-yl)piperidin-1-yl]sulfonylazetidine-1-carboxylate |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 202 | 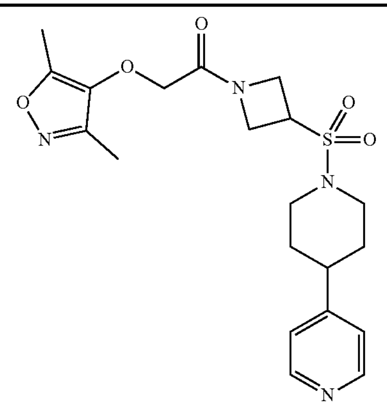 | 435.7 | ¹H NMR (300 MHz, DMSO-d₆): δ = 8.43-8.50 (m, 2H), 7.24-7.30 (m, 2H), 4.87 (s, 2H), 4.18-4.39 (m, 2H), 3.97-4.07 (m, 2H), 3.67-3.78 (m, 2H), 2.90 (t, J = 2.09 Hz, 2H), 2.59-2.74 (m, 1H), 2.37 (s, 3H), 2.19 (s, 3H), 1.82 (d, 2H), 1.48-1.66 (m, 2H) ppm. | 4-(4-piperidyl) pyridine | General method D using tert-butyl 3-chlorosulfonylaze- tidine-1-carboxylate, Cf using TFA, H2 using (3,5-dimethylisoxazol-4-yl)methanol | (3,5-dimethyl- 1,2-oxazol-4- yl)methyl 3-(4- pyridin-4-ylpiperidin-1-yl)sulfonylaze- tidine-1-carboxylate |
| 203 | 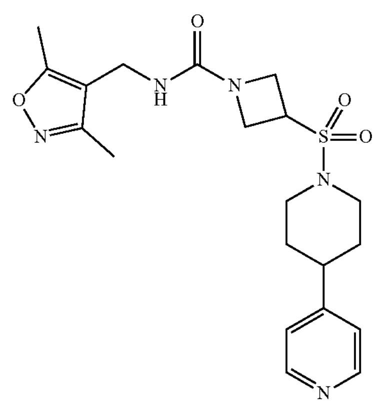 [SMILES: Cc1noc(C)c1CNC(=O)N1CC(S(=O)(=O)N2CCC(c3ccncc3)CC2)C1] | 434.7 | ¹H NMR (300 MHz, DMSO-d₆): δ = 8.43-8.51 (m, 2H), 7.24-7.31 (m, 2H), 6.85 (t, 1H), 4.24-4.36 (m, 1H), 4.09 (t, J = 8.62 Hz, 2H), 3.89-3.98 (m, 4H), 3.72 (d, J = 12.19 Hz, 2H), 2.83-2.97 (m, 2H), 2.60-2.76 (m, 1H), 2.32 (s, 3H), 2.16 (s, 3H), 1.84 (d, J = 10.45 Hz, 2H), 1.47-1.66 (m, 2H) ppm. | 4-(4-piperidyl) pyridine | General method D using tert-butyl 3-chlorosulfonylaze- tidine-1-carboxylate, Cf using TFA, G3 using (3,5-dimethylisoxazol-4-yl)methanamine | N-[(3,5-dimethyl-1,2- oxazol-4-yl)methyl]-3- (4-pyridin-4- ylpiperidin-1- yl)sulfonylaze- tidine-1-carboxamide |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 204 | 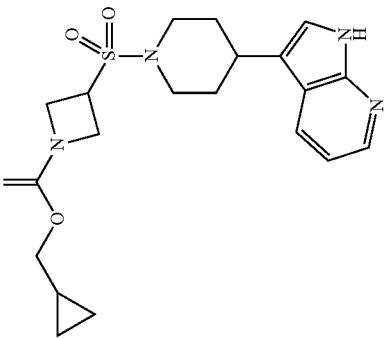 | 419.7 | 1H NMR (300 MHz, DMSO-d6): δ = 11.37 (s, 1H), 8.17 (dd, J = 1.48, 4.62 Hz, 1H), 7.93-8.00 (m, 1H), 7.24 (d, J = 2.44 Hz, 1H), 7.01 (dd, J = 4.62, 7.93 Hz, 1H), 4.31-4.43 (m, 1H), 4.19-4.31 (m, 2H), 4.05 (br. s., 2H), 3.82 (d, J = 7.32 Hz, 2H), 3.74 (d, J = 12.54 Hz, 2H), 2.85-3.05 (m, 3H), 2.02 (d, J = 11.32 Hz, 2H), 1.53-1.70 (m, 2H), 0.98-1.12 (m, 1H), 0.43-0.52 (m, 2H), 0.19-0.28 (m, 2H) ppm. | 3-(4-piperidyl)-1H-pyrrolo[2,3-b]pyridine | General method D using tert-butyl 3-chlorosulfonylazetidine-1-carboxylate, Cf using TFA, H2 using cyclopropylmethanol | cyclopropylmethyl 3-[4-(1H-pyrrolo[2,3-b]pyridin-3-yl)piperidin-1-yl]sulfonyl]azetidine-1-carboxylate |
| 205 | 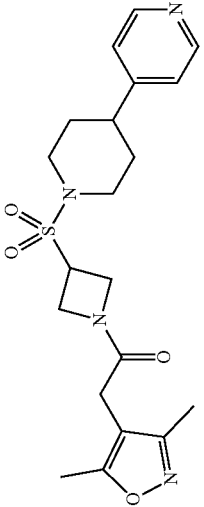 | 419.7 | 1H NMR (300 MHz, DMSO-d6): δ = 8.44-8.50 (m, 2H), 7.26-7.31 (m, 2H), 4.49-4.59 (m, 1H), 4.33-4.45 (m, 2H), 4.15-4.26 (m, 1H), 3.95-4.04 (m, 1H), 3.77 (d, J = 12.37 Hz, 2H), 3.26 (d, J = 2.61 Hz, 2H), 2.94 (t, J = 11.50 Hz, 2H), 2.63-2.76 (m, 1H), 2.27 (s, 3H), 2.08 (s, 3H), 1.86 (d, J = 12.72 Hz, 2H), 1.51-1.68 (m, 2H) ppm. | 4-(4-piperidyl)pyridine | General method D using tert-butyl 3-chlorosulfonylazetidine-1-carboxylate, Cf using TFA, I1 using 2-(3,5-dimethylisoxazol-4-yl)acetic acid | 2-(3,5-dimethyl-1,2-oxazol-4-yl)-1-[3-(4-pyridin-4-ylpiperidin-1-yl)sulfonyl]azetidin-1-yl]ethanone |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 206 | 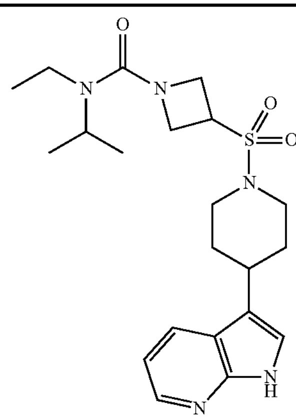 | 434.7 | ¹H NMR (600 MHz, CHLOROFORM-d): δ =9.15 (br. s., 1H), 8.29(d, J = 4.2 Hz, 1H), 7.90 (dd, J = 0.8, 7.9 Hz, 1H), 7.04-7.10 (m, 2H), 4.23-4.28 (m, 2H), 4.19 (t, J = 8.8 Hz, 2H), 3.93-4.02 (m, 4H), 3.10 (q, J = 7.1 Hz, 2H), 3.00 (td, J = 1.9, 12.6 Hz, 2H), 2.93 (tt, J = 3.4, 11.9 Hz, 1H), 2.10 (d, J = 13.1 Hz, 2H), 1.82 (qd, J = 3.9, 12.6 Hz, 2H), 1.10-1.16 (m, 9H) ppm. | 3-(4-piperidyl)-1H-pyrrolo[2,3-b]pyridine | General method D using tert-butyl 3-chlorosulfonyl azetidine-1-carboxylate, Cf using TFA, H3 using tertiary alcohol and DiPEA | N-ethyl-N-propan-2-yl-3-[4-(1H-pyrrolo[2,3-b]pyridin-3-yl)piperidin-1-yl]sulfonyl]azetidine-1-carboxamide |
| 207 | 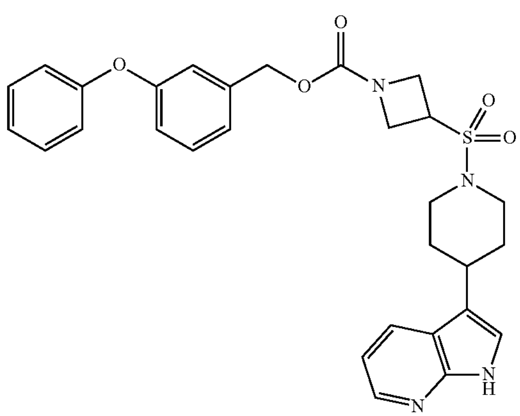 [SMILES: O=C(OCc1cccc(Oc2ccccc2)c1)N1CC(S(=O)(=O)N2CCC(c3c[nH]c4ncccc34)CC2)C1] | 547.7 | ¹H NMR (600 MHz, CHLOROFORM-d): δ =9.00 (br. s., 1H), 8.29 (d. J = 3.7 Hz, 1H), 7.89 (dd, J = 1.3, 7.9 Hz, 1H), 7.30-7.34 (m, 2H), 7.28 (t, J = 7.9 Hz, 1H), 7.08-7.12 (m, 1H), 7.02-7.07 (m, 3H), 6.96-7.01 (m, 3H), 6.92 (dd, J = 2.0, 8.0 Hz, 1H), 5.06 (br. s., 2H), 4.28-4.35 (m, 2H), 4.24 (t, J = 8.6 Hz, 2H), 3.92-4.00 (m, 3H), 2.97 (dt, J = 2.0, 12.4 Hz, 2H), 2.92 (tt, J = 3.5, 12.0 Hz, 1H), 2.09 (d, J = 11.2 Hz, 2H), 1.80 (dq, J = 4.0, 12.5 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using (3-phenoxyphenyl) methanol | (3-phenoxyphenyl) methyl 3-[4-(1H-pyrrolo[2,3-b]pyridin-3-yl)piperidin-1-yl]sulfonyl]azetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 208 | 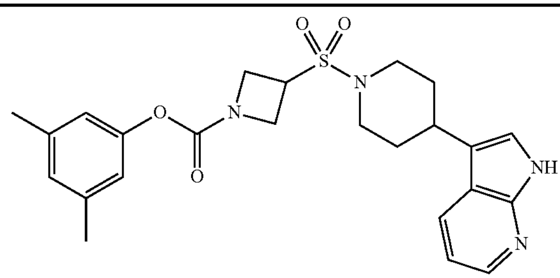 | 469.6 | ¹H NMR (600 MHz, CHLOROFORM-d): δ =9.03 (br. s., 1H), 8.28 (br. s., 1H), 7.91 (d, J = 7.7 Hz, 1H), 7.02-7.11 (m, 2H), 6.82 (s, 1H), 6.70 (s, 2H), 4.29-4.55 (m, 4H), 4.03-4.07 (m, 1H), 4.00 (d, J = 12.3 Hz, 2H), 3.02 (t, J = 11.5 Hz, 2H), 2.92-2.98 (m, 1H), 2.27 (s, 6H), 2.13 (d, J = 11.9 Hz, 2H), 1.84 (dq, J = 3.8, 12.47 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using 3,5-dimethylphenol | (3,5-dimethylphenyl) 3-[4-(1H-pyrrolo[2,3-b]pyridin-3-yl)piperidin-1-yl]sulfonylazetidine-1-carboxylate |
| 209 | 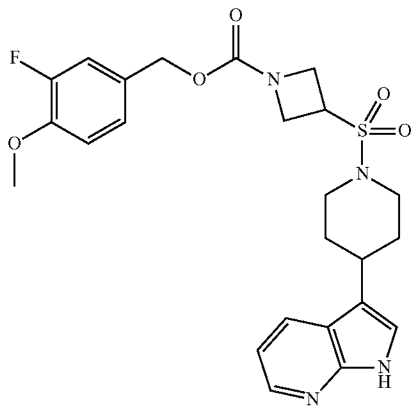 [SMILES: COc1ccc(COC(=O)N2CC(S(=O)(=O)N3CCC(c4c[nH]c5ncccc45)CC3)C2)cc1F] | 503.7 | ¹H NMR (600 MHz, CHLOROFORM-d): δ = 8.63 (br. s., 1H), 8.29 (d, J =4.2 Hz, 1H), 7.89 (d, J = 7.0 Hz, 1H), 7.01-7.10 (m, 4H), 6.89 (t, J = 8.4 Hz, 1H), 5.00 (br. s., 2H), 4.29-4.33 (m, 2H), 4.24 (t, J = 8.8 Hz, 2H), 3.92-4.00 (m, 3H), 3.86 (s, 3H), 2.97 (td, J = 1.8, 12.4 Hz, 2H), 2.91 (tt, J = 3.6, 11.9 Hz, 1H), 2.09 (d, J = 13.0 Hz, 2H), 1.80 (dq, J = 3.7, 12.5 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using (3-fluoro-4-methoxy-phenyl)methanol (15 min 0 C) | (3-fluoro-4-methoxyphenyl) methyl 3-[4-(1H-pyrrolo[2,3-b]pyridin-3-yl)piperidin-1-yl]sulfonylazetidine-1-carboxylate |
| 210 | 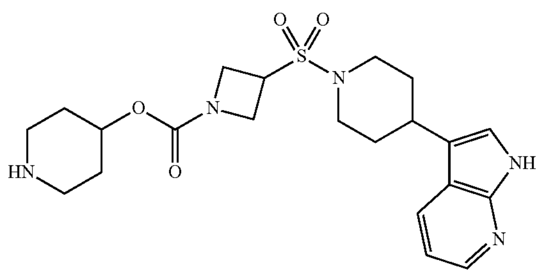 [SMILES: O=C(OC1CCNCC1)N1CC(S(=O)(=O)N2CCC(c3c[nH]c4ncccc34)CC2)C1] | 448.7 | ¹H NMR (600 MHz, CHLOROFORM-d): δ =8.89 (br. s., 1H), 8.28 (dd, J = 1.5, 4.8 Hz, 1H), 7.89 (dd, J = 1.5, 7.9 Hz, 1H), 7.04-7.08 (m, 2H), 4.74 (tt, J = 4.0, 8.6 Hz, 1H), 4.27-4.33 (m, 2H), 4.23 (t, J = 8.6 Hz, 2H), 3.93-4.00 (m, 3H), 3.05 (td, J = 4.7, 12.6 Hz, 2H), 2.99 (dt, J = 2.4, 12.5 Hz, 2H), 2.93 (tt, J = 3.5, 11.9 Hz, 1H), 2.69-2.76 (m, 2H), 2.11 (dd, J = 1.8, 13.0 Hz, 2H), 1.86-1.95 (m, 2H), 1.76-1.86 (m, 3H), 1.52-1.60 (m, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using tert-butyl 4-hydroxypiperidine-1-carboxylate, C using TFA | piperidin-4-yl 3-[4-(1H-pyrrolo[2,3-b]pyridin-3-yl)piperidin-1-yl]sulfonylazetidine-1-carboxylate |

| Cpd # | Structure | MS (m/z ES +) | δ NMR Data | Starting Int/Cpd# | Sequence of Methods | Chemical Name |
|---|---|---|---|---|---|---|
| 211 | 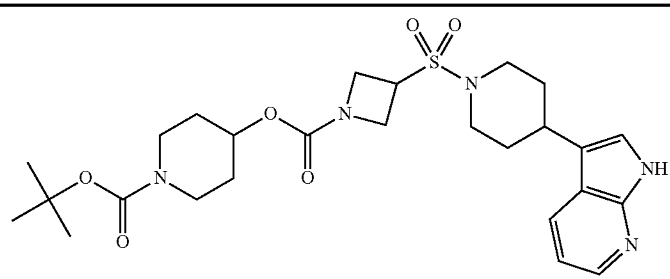 | 548.8 | ¹H NMR (400 MHz, CHLOROFORM-d): δ =9.08 (br. s., 1H), 8.30 (dd, J = 1.3, 4.7 Hz, 1H), 7.90 (dd, J = 1.2, 7.9 Hz, 1H), 7.03-7.09 (m, 1H), 4.27-4.34 (m, 2H), 4.23 (t, J = 8.5, 2H), 3.91-4.03 (m, 3H), 3.66 (d, J = 12.2 Hz, 2H), 3.12-3.2 (m, 2H), 2.87-3.05 (m, 3H), 2.11 (d, J = 11.1 Hz, 2H), 1.75-1.89 (m, 4H), 1.51-1.58 (m, 2H), 1.44 (s, 9H) ppm. | 3-(4-piperidyl)-1H-pyrrolo[2,3-b]pyridine | General method D using tert-butyl 3-chlorosulfonyl azetidine-1-carboxylate, Cf using TFA, H3 using tert-butyl 4-hydroxypiperidine-1-carboxylate | tert-butyl 4-[3-[4-(1H-pyrrolo[2,3-b]pyridin-3-yl)piperidin-1-yl]sulfonylazetidine-1-carbonyl]oxypiperidine-1-carboxylate |
| 212 | 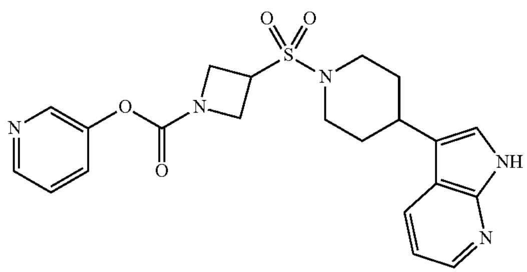 [SMILES: O=C(Oc1cccnc1)N1CC(S(=O)(=O)N2CCC(c3c[nH]c4ncccc34)CC2)C1] | 442.6 | ¹H NMR (400 MHz, CHLOROFORM-d): δ = 9.10 (br. s., 1H), 8.40-8.47 (m, 2H), 8.30 (d, J = 4.3 Hz, 1H), 7.91 (dd, J = 1.2, 7.9 Hz, 1H), 7.47-7.53 (m, 1H), 7.30 (dd, J = 4.7, 8.5 Hz, 1H), 7.04-7.11 (m, 2H), 4.29-4.62 (m, 4H), 4.04-4.13 (m, 1H), 4.00 (d, J = 12.7 Hz, 2H), 2.90-3.10 (m, 3H), 2.13 (d, J = 13.6 Hz, 2H), 1.83 (qd, J = 3.8, 12.7 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using pyridin-3-ol | pyridin-3-yl 3-[4-(1H-pyrrolo[2,3-b]pyridin-3-yl)piperidin-1-yl]sulfonylazetidine-1-carboxylate |
| 213 | 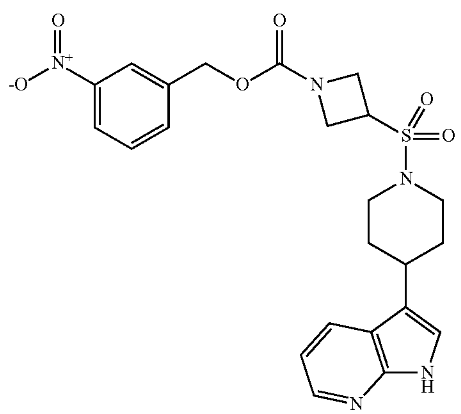 | 500.7 | ¹H NMR (500 MHz, CHLOROFORM-d): δ = 9.9 (br. s., 1H), 8.32 (d, J = 4.3 Hz, 1H), 8.22 (s, 1H), 8.19 (d, J = 8.2 Hz, 1H), 7.92 (d, J = 7.6 Hz, 1H), 7.67 (d, J = 7.6 Hz, 1H), 7.54 (t, J = 8.0 Hz, 1H), 7.05-7.12 (m, 2H), 5.21 (br. s., 2H), 4.25-4.45 (m, 4H), 3.94-4.07 (m, 3H), 2.91-3.07 (m, 3H), 2.14 (d, J = 12.5 Hz, 2H), 1.84 (dq, J = 3.4, 12.4 Hz, 2H) ppm. | 3-(4-piperidyl)-1H-[2,3-b]pyridine | General method D using tert-butyl 3-chlorosulfonyl azetidine-1-carboxylate, Cf using TFA, H3 using (3-nitrophenyl)methanol | (3-nitrophenyl)methyl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 214 | 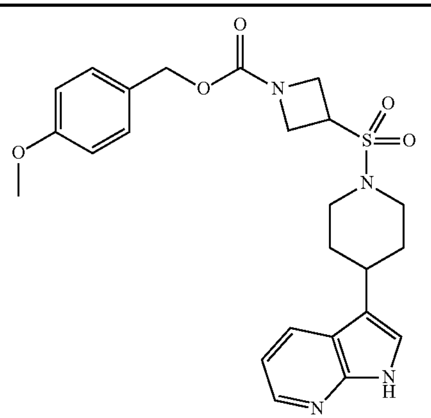 | 485.7 | ¹H NMR (500 MHz, CHLOROFORM-d): δ = 9.27 (br. s., 1H), 8.32 (d, J = 3.7 Hz, 1H), 7.92 (d, J = 7.6 Hz, 1H), 7.29 (d, J = 8.5 Hz, 2H), 7.07-7.11 (m, 2H), 6.88 (d, J = 8.5 Hz, 2H), 5.05 (s, 2H), 4.29-4.36 (m, 2H), 4.22-4.28 (m, 2H), 3.92-4.03 (m, 3H), 3.80 (s, 3H), 2.87-3.03 (m, 3H), 2.11 (d, J = 11.9 Hz, 2H), 1.76-1.90 (m, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using (4-methoxyphenyl) methanol (15 min 0C) | (4-methoxyphenyl) methyl 3-[4-(1H-pyrrolo[2,3-b]pyridin-3-yl)piperidin-1-yl]sulfonylazetidine-1-carboxylate |
| 215 | 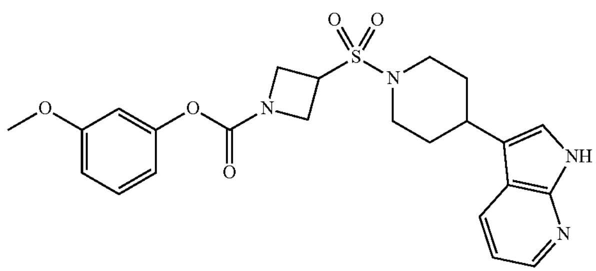 [SMILES: COc1cccc(OC(=O)N2CC(S(=O)(=O)N3CCC(c4c[nH]c5ncccc45)CC3)C2)c1] | 471.7 | ¹H MR (500 MHz, CHLOROFORM-d): δ = 9.27 (br. s., 1H), 8.33 (d, J = 4.6 Hz, 1H), 7.94 (d, J = 7.9 Hz, 1H), 7.21-7.26 (m, 1H), 7.07-7.12 (m, 2H), 6.77 (dd, J = 2.0, 8.4 Hz, 1H), 6.67-6.73 (m, 2H), 4.31-4.61 (m, 4H), 4.06-4.12 (m 1H), 4.03 (d, J = 12.5 Hz, 2H), 3.79 (s, 3H), 3.06 (t, J = 11.6 Hz, 2H), 2.98 (tt, J = 3.7, 11.6 Hz, 1H), 2.16 (d, J = 12.8 Hz, 2H), 1.87 (dq, J = 3.8, 12.5 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using 3-methoxyphenol | (3-methoxyphenyl) 3-[4-(1H-pyrrolo[2,3-b]pyridin-3-yl)piperidin-1-yl]sulfonylazetidine-1-carboxylate |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 216 | 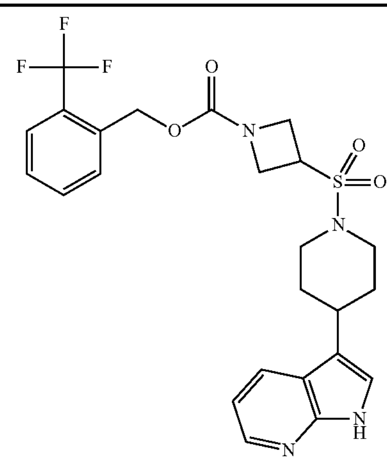 | 523.7 | ¹H NMR (400 MHz, CHLOROFORM-d): δ = 9.57 (br. s., 1H), 8.30 (d, J = 4.0 Hz, 1H), 7.90 (dd, J = 1.3, 7.9 Hz, 1H), 7.66 (d, J = 7.9 Hz, 1H), 7.48-7.56 (m, 2H), 7.37-7.44 (m, 1H), 7.03-7.10 (m, 1H), 5.28 (s, 2H), 4.31-4.38 (m, 2H), 4.27 (t, J = 8.3 Hz, 2H), 3.91-4.03 (m, 3H), 2.87-3.04 (m, 3H), 2.10 (d, J = 10.9 Hz, 2H), 1.80 (qd, J = 3.6, 12.3 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using (2-(trifluoromethyl) phenyl)methanol | [2-(trifluoromethyl) phenyl]methyl 3-[4-(1H-pyrrolo[2,3-b]pyridin-3-yl)piperidin-1-yl]sulfonylazetidine-1-carboxylate |
| 217 | 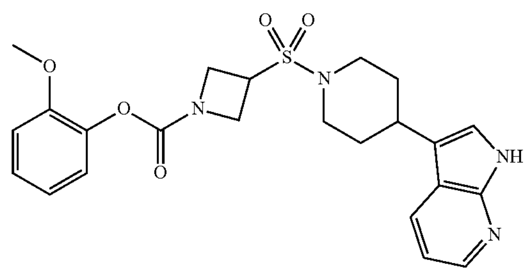 [SMILES: COc1ccccc1OC(=O)N1CC(S(=O)(=O)N2CCC(c3c[nH]c4ncccc34)CC2)C1] | 471.7 | ¹H NMR (400 MHz, CHLOROFORM-d): δ = 9.15 (br. s., 1H), 8.30 (dd, J = 1.4, 4.8 Hz, 1H), 7.91 (dd, J = 1.3, 7.9 Hz, 1H), 7.12-7.20 (m, 1H), 7.00-7.10 (m, 3H), 6.86-6.97 (m, 2H), 4.41 (br. s., 4H), 4.04-4.12 (m, 1H), 4.01 (d, J = 12.8 Hz, 2H), 3.81 (s, 3H), 3.03 (dt, J = 2.5, 12.4 Hz, 2H), 2.91-2.99 (m, 1H), 2.13 (d, J = 11.0 Hz, 2H), 1.77-1.91 (m, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using 2-methoxyphenol | (2-methoxyphenyl) 3-[4-(1H-pyrrolo[2,3-b]pyridin-3-yl)piperidin-1-yl]sulfonylazetidine-1-carboxylate |
| 218 | 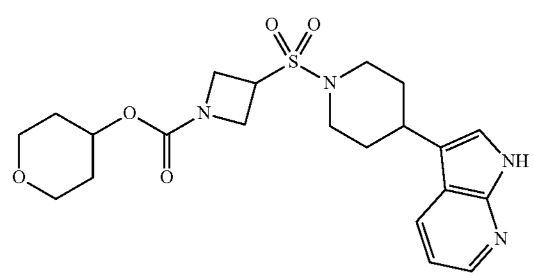 [SMILES: O=C(OC1CCOCC1)N1CC(S(=O)(=O)N2CCC(c3c[nH]c4ncccc34)CC2)C1] | 449.7 | ¹H NMR (400 MHz, CHLOROFORM-d): δ =9.03 (br. s., 1H), 7.90 (d, J = 6.7 Hz, 1H), 7.03-7.10 (m, 2H), 4.77-4.87 (m, 1H), 4.28-4.35 (m, 2H), 4.20-4.27 (m, 2H), 3.93-4.02 (m, 3H), 3.87 (td, J = 4.5, 11.9 Hz, 2H), 3.45-3.54 (m, 2H), 2.88-3.04 (m, 3H), 2.11 (d, J = 11.0 Hz, 2H), 1.75-1.93 (m, 4H), 1.60-1.69 (m, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using tetrahydropyran-4-ol | oxan-4-yl 3-[4-(1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 219 | 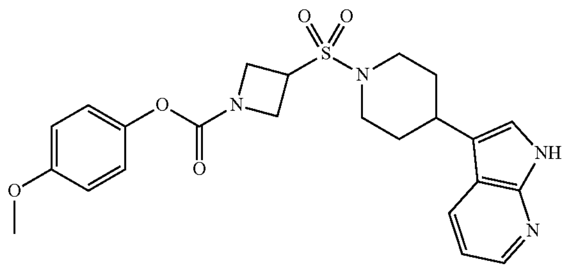 [SMILES: COc1ccc(OC(=O)N2CC(S(=O)(=O)N3CCC(c4c[nH]c5ncccc45)CC3)C2)cc1] | 471.7 | ¹H NMR (400 MHz, CHLOROFORM-d): δ = 9.03 (br. s., 1H), 8.30 (dd, J = 1.5, 4.6 Hz, 1H), 7.90 (d, J = 6.5 Hz, 1H), 7.03-7.10 (m, 2H), 6.94-7.02 (m, 2H), 6.79-6.87 (m, 2H), 4.41 (br. s., 4H), 3.95-4.10 (m, 3H), 3.77 (s, 3H), 2.99-3.07 (m, 2H), 2.95 (t, J = 12.0 Hz, 1H), 2.13 (d, J = 14.4 Hz, 2H), 1.76-1.90 (m, 2H) ppm. | 3-(4-piperidyl)-1H-pyrrolo[2,3-b]pyridine | General method D using tert-butyl 3-chlorosulfonyl azetidine-1-carboxylate, Cf using TFA, H3 using 4-methoxyphenol | (4-methoxyphenyl) 3-[4-(1H-pyrrolo[2,3-b]pyridin-3-yl)piperidin-1-yl]sulfonylazetidine-1-carboxylate |
| 220 | 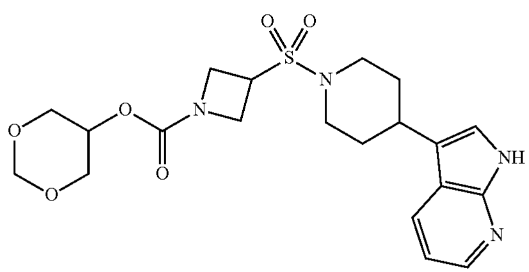 [SMILES: O=C(OC1COCOC1)N1CC(S(=O)(=O)N2CCC(c3c[nH]c4ncccc34)CC2)C1] | 451.7 | ¹H NMR (400 MHz, CHLOROFORM-d): δ =9.31 (br. s., 1H), 8.30 (br. s., 1H), 7.90 (d, J = 6.7 Hz, 1H), 7.03-7.10 (m, 2H), 5.00 (s, 1H), 4.87 (s, 1H), 4.19-4.37 (m, 4H), 4.05-4.18 (m, 2H), 3.92-4.02 (m, 4H), 3.66 (dd, J = 5.7, 8.5 Hz, 1H), 2.87-3.04 (m, 3H), 2.11 (d, J = 10.9 Hz, 2H), 1.81 (qd, J = 3.6, 12.6 Hz, 2H), 1.13 (d, J = 6.7 Hz, 1H) ppm. | 3-(4-piperidyl)-1H-pyrrolo[2,3-b]pyridine | General method D using tert-butyl 3-chlorosulfonyl azetidine-1-carboxylate, Cf using TFA, H3 using 1,3-dioxan-5-ol | 1,3-dioxan-5-yl 3-[4-(1H-pyrrolo[2,3-b]pyridin-3-yl)piperidin-1-yl]sulfonylazetidine-1-carboxylate |
| 221 | 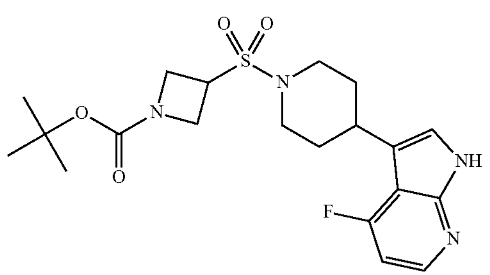 [SMILES: CC(C)(C)OC(=O)N1CC(S(=O)(=O)N2CCC(c3c[nH]c4nccc(F)c34)CC2)C1] | 439.2 | ¹H NMR (400 MHz, CHLOROFORM-d): δ = 9.42 (br. s., 1H), 8.17-8.28 (m, 1H), 7.02 (s, 1H), 6.78 (dd, J = 5.5, 10.8 Hz, 1H), 4.22-4.29 (m, 2H), 4.14-4.20 (m, 2H), 3.91-4.00 (m, 3H), 2.91-3.06 (m, 3H), 2.12 (d, J = 13.2 Hz, 2H), 1.67-1.81 (m, 2H), 1.43 (s, 9H) ppm. | 3-bromo-4-fluoro-1H-pyrrolo[2,3-b]pyridine | General method E, A1 using K₂CO₃, B1 using Pd/C, Ci using TFA, D using tert-butyl 3-chlorosulfonyl azetidine-1-carboxylate, F | tert-butyl 3-[4-(4-fluoro-1H-pyrrolo[2,3-b]pyridin-3-yl)piperidin-1-yl]sulfonylazetidine-1-carboxylate |

TABLE-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 222 | 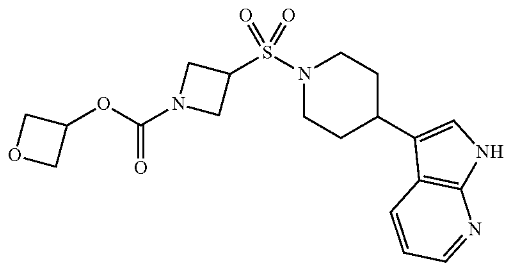 [SMILES: O=C(OC1COC1)N1CC(S(=O)(=O)N2CCC(c3c[nH]c4ncccc34)CC2)C1] | 421.1 | ¹H NMR (400 MHz, CHLOROFORM-d): δ = 9.16 (br. s., 1H), 8.30 (d, J = 3.8 Hz, 1H), 7.90 (d, J = 6.8 Hz, 1H), 1H-7.03-7.10 (m, 2H), 5.39 (quin, J = 5.8 Hz, 1H), 4.85 (t, J = 7.1 Hz, 2H), 4.58-4.65 (m, 2H), 4.31 (br. s., 4H), 3.92-4.03 (m, 3H), 2.88-3.04 (m, 3H), 2.12 (d, J = 12.7 Hz, 2H), 1.81 (dq, J = 4.2, 12.5 Hz, 2H) ppm. | 3-(4-piperidyl)-1H-pyrrolo[2,3-b]pyridine | General method D using tert-butyl 3-chlorosulfonyl azetidine-1-carboxylate, Cf using TFA, H2 using oxetan-3-ol | oxetan-3-yl 3-[4-(1H-pyrrolo[2,3-b]pyridin-3-yl)piperidin-1-yl]sulfonylazetidine-1-carboxylate |
| 223 | 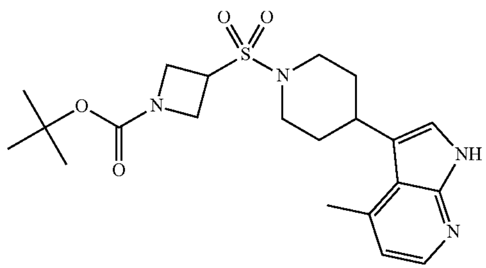 [SMILES: Cc1ccnc2[nH]cc(C3CCN(S(=O)(=O)C4CN(C(=O)OC(C)(C)C)C4)CC3)c12] | 435.1 | ¹H NMR (400 MHz, Chloroform-d): δ = 9.13 (s, 1H), 8.14 (d, J = 4.8 Hz, 1H), 7.04 (s, 1H), 6.82 (d, J = 5.0 Hz, 1H), 4.25 (dd, J = 9.4, 5.8 Hz, 2H), 4.17 (t, J = 8.8 Hz, 2H), 4.02-3.88 (m, 3H), 3.09 (tt, J = 12.0, 3.3 Hz, 1H), 2.96 (td, J = 12.3, 1.7 Hz, 2H), 2.66 (s, 3H), 2.11 (d, J = 13.1 Hz, 2H), 1.71 (qd, J = 12.8, 4.2 Hz, 2H), 1.43 (s, 9H) ppm. | 3-bromo-4-methyl-1H-pyrrolo[2,3-b]pyridine | General method E, A1 using K₂CO₃, B1 using Pd/C, Ci using TFA, D using tert-butyl 3-chlorosulfonyl azetidine-1-carboxylate, F | tert-butyl 3-[4-(4-methyl-1H-pyrrolo[2,3-b]pyridin-3-yl)piperidin-1-yl]sulfonylazetidine-1-carboxylate |
| 224 | 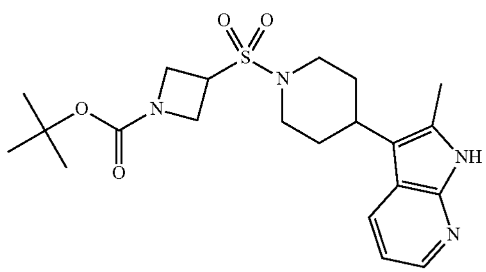 [SMILES: Cc1[nH]c2ncccc2c1C1CCN(S(=O)(=O)C2CN(C(=O)OC(C)(C)C)C2)CC1] | 435.1 | ¹H NMR (500 MHz, Chloroform-d): δ = 9.68 (s, 1H), 8.20 (d, J = 4.6 Hz, 1H), 7.90 (d, J = 7.8 Hz, 1H), 7.03 (dd, J = 7.9, 4.8 Hz, 1H), 4.31 (dd, J = 9.4, 5.8 Hz, 2H), 4.22 (t, J = 8.9 Hz, 2H), 4.06-3.94 (m, 3H), 2.93 (td, J = 12.5, 2.4 Hz, 2H), 2.86 (tt, J = 12.5, 3.8 Hz, 1H), 2.47 (s, 3H), 2.18 (qd, J = 12.8, 4.3 Hz, 2H), 1.87 (dd, J = 14.2, 3.5 Hz, 2H), 1.47 (s, 9H) ppm. | 2-methyl-1H-pyrrolo[2,3-b]pyridine | General method K, E, A1 using K₂CO₃, B1 using Pd/C, Ci using TFA, D using tert-butyl 3-chlorosulfonyl azetidine-1-carboxylate, F | tert-butyl 3-[4-(2-methyl-1H-pyrrolo[2,3-b]pyridin-3-yl)piperidin-1-yl]sulfonylazetidine-1-carboxylate |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 225 | 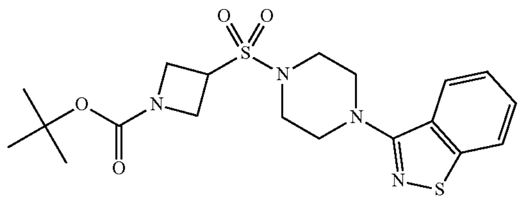 [SMILES: CC(C)(C)OC(=O)N1CC(S(=O)(=O)N2CCN(c3nsc4ccccc34)CC2)C1] | 439.1 | ¹H NMR (300 MHz, DMSO-d₆): δ = 8.07 (d, J = 9.2 Hz, 2H), 7.61-7.53 (m, 1H), 7.48-7.41 (m, 1H), 4.42-4.30 (m, 1H), 4.26-4.14 (m, 2H), 4.05-3.94 (m, 2H), 3.52-3.38 (m, 8H), 1.38 (s, 9H) ppm. | 3-piperazin-1-yl-1,2-benzothiazole | General method D using tert-butyl 3-chlorosulfonylaze-tidine-1-carboxylate | tert-butyl 3-[4-(1,H-benzothiazol-3-yl)piperazin-1-yl]sulfonylazetidine-1-carboxylate |
| 226 | 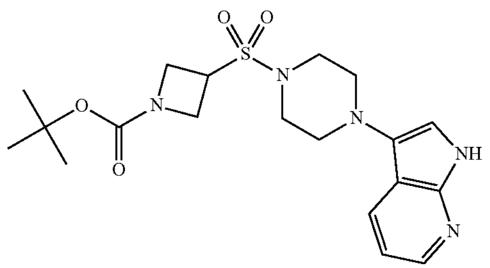 | 422.2 | ¹H NMR (600 MHz, DMSO-d₆): δ= 11.12 (d, J = 1.65 Hz, 1H), 8.17 (dd, J = 1.47, 4.59 Hz, 1H), 7.94 (dd, J = 1.01, 7.98 Hz, 1H), 6.99 (dd, J = 4.77, 7.89 Hz, 1H), 6.96 (d, J = 2.57 Hz, 1H), 4.35 (tt, J = 5.43, 8.41 Hz, 1H), 4.20 (br. s., 2H), 4.00 (br. s., 2H), 3.36-3.41 (m, 4H), 2.97-3.05 (m, 4H), 1.38 (s, 9H) ppm | 3-bromo-1H-pyrrolo[2,3-b]pyridine | General method R, Ci using TFA, D using tert-butyl 3-chlorosulfonylaze-tidine-1-carboxylate | tert-butyl 3-[4-(1H-pyrrolo[2,3-b]pyridin-3-yl)piperazin-1-yl]sulfonylazetidine-1-carboxylate |
| 227 | 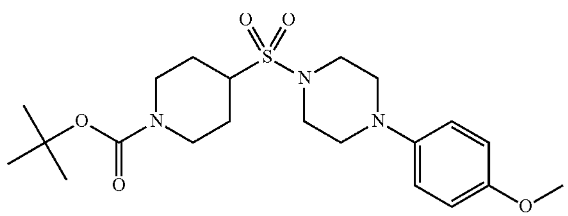 [SMILES: COc1ccc(N2CCN(S(=O)(=O)C3CCN(C(=O)OC(C)(C)C)CC3)CC2)cc1] | 440.2 | ¹H NMR (500 MHz, DMSO-d₆): δ = 6.89-6.94 (m, 2H), 6.81-6.85 (m, 2H), 3.89-4.10 (m, 2H), 3.68 (s, 3H), 3.40-3.48 (m, 1H), 3.36-3.40 (m, 4H), 2.97-3.09 (m, 4H), 2.66-2.88 (m, 2H), 2.01 (m, 2H), 1.46 (dd, J = 12.2, 4.3 Hz, 1H), 1.41 (dd, J= 12.1, 4.3 Hz, 1H), 1.39 (s, 9H) ppm | 1-(4-methoxyphenyl)piperazine | General method D using tert-butyl 4-chlorosulfonyl-piperidine-1-carboxylate | tert-butyl 4-[4-(4-methoxyphenyl)piperazin-1-yl]sulfonylpiperidine-1-carboxylate |
| 228 | 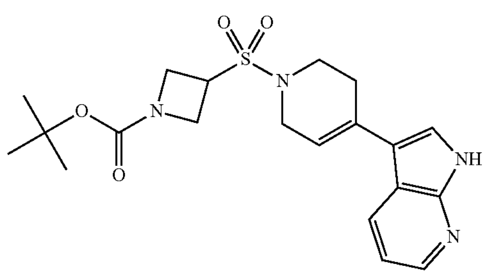 [SMILES: CC(C)(C)OC(=O)N1CC(S(=O)(=O)N2CC=C(c3c[nH]c4ncccc34)CC2)C1] | 419.1 | ¹H NMR (300 MHz, DMSO-d₆): δ = 11.72 (br. s., 1H), 8.17-8.26 (m, 2H), 7.56 (d, J = 2.44 Hz, 1H), 7.05-7.13 (m, 1H), 6.14-6.21 (m, 1H), 4.28-4.41 (m, 1H), 4.13 (t, J = 8.45 Hz, 2H), 3.91-4.05 (m, 4H), 3.48 (t, J = 5.84 Hz, 2H), 2.54-2.63 (m, 2H), 1.36 (s, 9H) ppm. | 1H-pyrrolo[2,3-b]pyridine | General method A2, Ci using TFA, D using tert-butyl 3-chlorosulfonylaze-tidine-1-carboxylate | tert-butyl 3-[[4-(1H-pyrrolo[2,3-b]pyridin-3-yl)-3,6-dihydro-2H-pyridin-1-yl]sulfonyl]azetidine-1-carboxylate |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 229 | 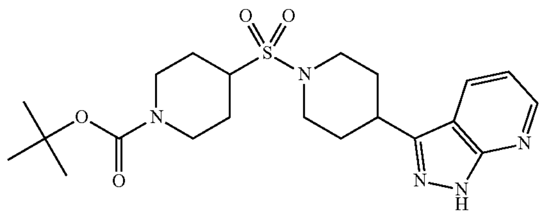 [SMILES: CC(C)(C)OC(=O)N1CCC(S(=O)(=O)N2CCC(c3n[nH]c4ncccc34)CC2)CC1] | 448.2 | ¹H NMR (400 MHz, Chloroform-d): δ = 11.39 (s, 1H), 8.58 (dd, J = 4.6, 1.5 Hz, 1H), 8.26 (dd, J = 8.2, 1.5 Hz, 1H), 7.19 (dd, J = 8.1, 4.6 Hz, 1H), 6.50-6.45 (m, 1H), 4.33-4.18 (m, 2H), 4.17-4.13 (m, 2H), 3.65 (t, J = 5.7 Hz, 2H), 3.09 (ddd, J = 12.0, 8.3, 3.7 Hz, 1H), 2.92-2.86 (m, 2H), 2.77-2.62 (m, 2H), 2.07 (d, J = 12.7 Hz, 2H), 1.74 (qd, J = 12.5, 4.6 Hz, 2H), 1.43 (s, 9H) ppm. | 3-bromo-1H-pyrazolo[3,4-b]pyridine | General method E, A1, Ci using HCl in dioxane, D using tert-butyl 4-chlorosulfonylpiperidine-1-carboxylate, F | tert-butyl 4-[[4-(1H-pyrazolo[3,4-b]pyridin-3-yl)-3,6-dihydro-2H-pyridin-1-yl]sulfonyl]piperidine-1-carboxylate |
| 230 | 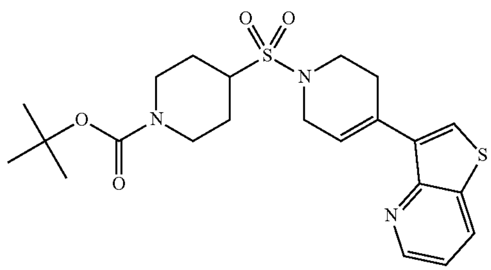 [SMILES: CC(C)(C)OC(=O)N1CCC(S(=O)(=O)N2CC=C(c3csc4cccnc34)CC2)CC1] | 464.1 | ¹H NMR (400 MHz, Chloroform-d): δ = 8.70 (dd, J = 4.6, 1.6 Hz, 1H), 8.16 (dd, J = 8.2, 1.6 Hz, 1H), 7.54 (s, 1H), 7.32-7.29 (m, 1H), 7.26 (dd, J = 8.2, 4.6 Hz, 1H), 4.30-4.17 (m, 2H), 4.16-4.13 (m, 2H), 3.68-3.63 (m, 2H), 3.13-3.03 (m, 1H), 2.79-2.61 (m, 4H), 2.07 (d, J = 13.1 Hz, 2H), 1.73 (qd, J = 12.5, 4.6 Hz, 2H), 1.43 (s, 9H) ppm. | 3-bromothieno[3,2-b]pyridine | General method A1, Ci using HCl in dioxane, D using tert-butyl 4-chlorosulfonylpiperidine-1-carboxylate | tert-butyl 4-[(4-thieno[3,2-b]pyridin-3-yl)-3,6-dihydro-2H-pyridin-1-yl]sulfonyl]piperidine-1-carboxylate |
| 231 | 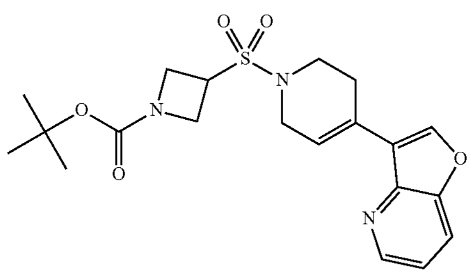 [SMILES: CC(C)(C)OC(=O)N1CC(S(=O)(=O)N2CC=C(c3coc4cccnc34)CC2)C1] | 420.5 | ¹H NMR (500 MHz, CHLOROFORM-d): δ = 8.60 (dd, J = 4.6, 1.2 Hz, 1H), 7.80 (s, 1H), 7.78 (dd, J = 8.4, 1.1 Hz, 1H), 7.34 (br. s., 1H), 7.27-7.31 (m, 1H), 4.28 (dd, J = 9.3, 5.6 Hz, 2H), 4.09-4.20 (m, 4H), 3.94-4.03 (m, 1H), 3.67 (t, J = 5.8 Hz, 2H), 2.63 (d, J = 2.1 Hz, 2H), 1.42 (s, 9H) ppm. | 3-bromofuro[3,2-b]pyridine | General method A1, Ci using HCl in dioxane, D using tert-butyl 3-chlorosulfonylazetidine-1-carboxylate | tert-butyl 3-[[4-furo[3,2-b]pyridin-3-yl)-3,6-dihydro-2H-pyridin-1-yl]sulfonyl]azetidine-1-carboxylate |

-continued

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 232 | 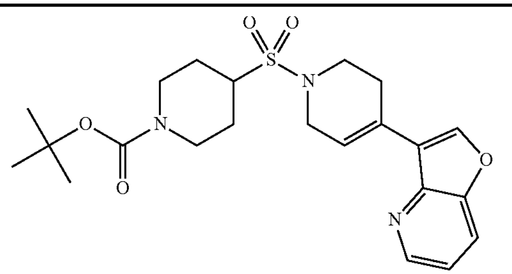 | 448.7 | ¹H NMR (400 MHz, CHLOROFORM-d): δ = 8.57 (dd, J = 4.8, 1.3 Hz, 1H), 7.77 (s, 1H), 7.74 (dt, J = 8.4, 1.3 Hz, 1H), 7.32 (dt, J = 3.4, 1.8 Hz, 1H), 7.22-7.27 (m, 1H), 4.22 (br. s., 2H), 4.09-4.15 (m, 2H), 3.63 (t, J = 5.7 Hz, 2H), 3.06 (tt, J = 12.0, 3.7 Hz, 1H), 2.68 (br. s., 2H), 2.56-2.63 (m, 2H), 2.05 (d, J = 16.6 Hz, 2H), 1.72 (qd, J = 12.4, 4.6 Hz, 2H), 1.42 (s, 9H) ppm. | 3-bromofuro [3,2-b]pyridine | General method A1, C1 using HCl in dioxane, D using tert-butyl 4-chlorosulfonylpiperidine-1-carboxylate | tert-butyl 4-[(4-furo[3,2-b]pyridin-3-yl-3,6-dihydro-2H-pyridin-1-yl)sulfonyl]piperidine-1-carboxylate |
| 233 | 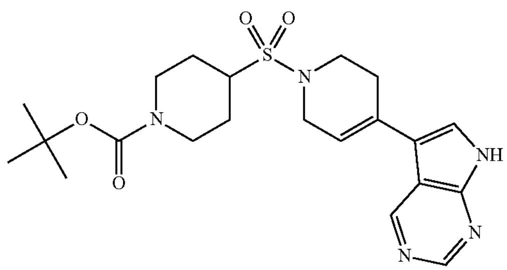 [SMILES: CC(C)(C)OC(=O)N1CCC(S(=O)(=O)N2CC=C(c3c[nH]c4ncncc34)CC2)CC1] | 448.7 | ¹H NMR (500 MHz, CHLOROFORM-d): δ = 10.17 (br. s., 1H), 9.24 (s, 1H), 8.93 (s, 1H), 7.33 (d, J = 1.8 Hz, 1H), 6.24 (br. s., 1H), 4.27 (br. s., 2H), 4.14 (d, J = 2.7 Hz, 2H), 3.67 (t, J = 5.6 Hz, 2H), 3.12 (tt, J = 11.9, 3.6 Hz, 1H), 2.73 (br. s., 2H), 2.66 (d, J = 1.5 Hz, 2H), 2.10 (d, J = 12.2 Hz, 2H), 1.71-1.82 (m, 2H), 1.45 (s, 9H) ppm. | 7-(p-tolyl-sulfonyl)-5-(4,4,5,5-tetramethyl-1,3,2-dioxaborolan-2-yl)pyrrolo[2,3-d]pyrimidine | General method A3, C1 using HCl in dioxane, D using tert-butyl 4-chlorosulfonylpiperidine-1-carboxylate | tert-butyl 4-[[4-(7H-pyrrolo[2,3-d]pyrimidin-5-yl)-3,6-dihydro-2H-pyridin-1-yl]sulfonyl]piperidine-1-carboxylate |
| 234 | 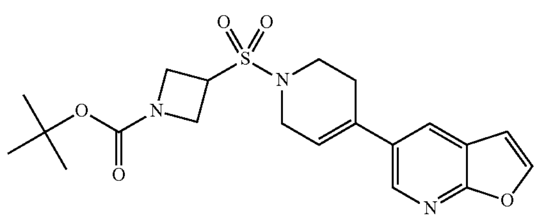 [SMILES: CC(C)(C)OC(=O)N1CC(S(=O)(=O)N2CC=C(c3cnc4occc4c3)CC2)C1] | 420.6 | ¹H NMR (300 MHz, DMSO-d₆): δ = 8.39 (d, J = 2.3 Hz, 1H), 8.15 (d, J = 2.3 Hz, 1H), 8.10 (d, J = 2.6 Hz, 1H), 7.01 (d, J = 2.6 Hz, 1H), 6.24 (s, 1H), 4.36 (s, 1H), 4.09-4.21 (m, 2H), 3.91-4.04 (m, 4H), 3.50 (t, J = 5.7 Hz, 2H), 2.63 (d, J = 1.4 Hz, 2H), 1.37 ppm (s, 9H) ppm. | 5-bromofuro [2,3-b]pyridine | General method A1, C1 using TFA, D using tert-butyl 3-chlorosulfonylazetidine-1-carboxylate | tert-butyl 3-[[(4-furo[2,3-b]pyridin-5-yl-3,6-dihydro-2H-pyridin-1-yl)sulfonyl]azetidine-1-carboxylate |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 235 | 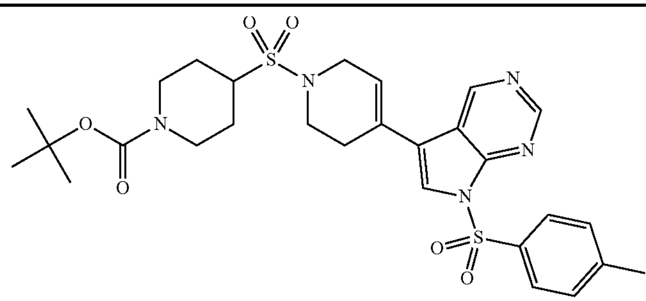 | 602.7 | ¹H NMR (300 MHz, CHLOROFORM-d): δ =9.13 (s, 1H), 9.00 (s, 1H), 8.03-8.11 (m, 2H), 7.65 (s, 1H), 7.30 (d, J = 8.0 Hz, 2H), 6.23 (s, 1H), 4.24 (d, J = 12.0 Hz, 2H), 4.09 (d, J = 2.8 Hz, 2H), 3.62 (t, J = 5.6 Hz, 2H), 3.00-3.14 (m, 1H), 2.56-2.79 (m, 4H), 2.38 (s, 3H), 1.99-2.10 (m, 2H), 1.72 (qd, J = 12.5, 4.6 Hz, 2H), 1.43 (s, 9H) ppm. | 7-(p-tolylsulfonyl)-5-(4,4,5,5-tetramethyl-1,3,2-dioxaborolan-2-yl)pyrrolo[2,3-d]pyrimidine | General method A3, Ci using HCl in dioxane, D using tert-butyl 4-chlorosulfonylpiperidine-1-carboxylate | tert-butyl 4-[[4-[7-(4-methylphenyl)sulfonylpyrrolo[2,3-d]pyrimidin-5-yl]-3,6-dihydro-2H-pyridin-1-yl]sulfonyl]piperidine-1-carboxylate |
| 236 | 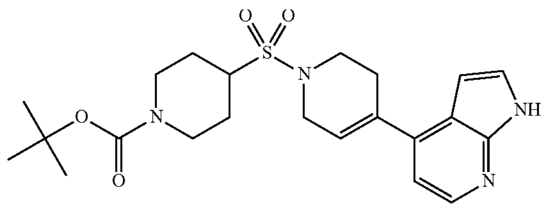 [SMILES: CC(C)(C)OC(=O)N1CCC(S(=O)(=O)N2CC=C(c3ccnc4[nH]ccc34)CC2)CC1] | 447.7 | ¹H NMR (500 MHz, CHLOROFORM-d): δ =9.92 (br. s., 1H), 8.30 (d, J = 5.1 Hz, 1H), 7.35-7.39 (m, 1H), 6.98 (d, J = 5.0 Hz, 1H), 6.60-6.63 (m, 1H), 6.29-6.33 (m, 1H), 4.28 (br. s., 2H), 4.12-4.19 (m, 2H), 3.68 (t, J = 5.4 Hz, 2H), 3.13 (tt, J = 12.0, 3.6 Hz, 1H), 2.61-2.82 (m, 4H), 2.11 (d, J = 12.5 Hz, 2H), 1.78 (dq, J = 12.5, 4.2 Hz, 2H), 1.47 (s, 9H) ppm. | 4-bromo-1-(p-tolylsulfonyl)pyrrolo[2,3-b]pyridine | General method A1, Ci using HCl in dioxane, D using tert-butyl 4-chlorosulfonylpiperidine-1-carboxylate, F | tert-butyl 4-[[4-(1H-pyrrolo[2,3-b]pyridin-4-yl)-3,6-dihydro-2H-pyridin-1-yl]sulfonyl]piperidine-1-carboxylate |
| 237 | 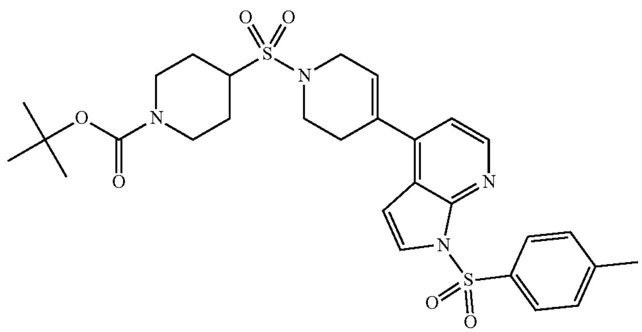 [SMILES: Cc1ccc(S(=O)(=O)n2ccc3c(C4=CCN(S(=O)(=O)C5CCN(C(=O)OC(C)(C)C)CC5)CC4)ccnc32)cc1] | 601.7 | ¹H NMR (400 MHz, CHLOROFORM-d): δ = 8.36 (d, J = 5.1 Hz, 1H), 8.05 (d, J = 8.4 Hz, 2H), 7.72 (d, J = 4.0 Hz, 1H), 7.25 (d, J = 7.8 Hz, 2H), 6.99 (d, J = 5.0 Hz, 1H), 6.65 (d, J = 4.0 Hz, 1H), 6.09-6.14 (m, 1H), 4.23 (br. s., 2H), 4.05-4.10 (m, 2H), 3.56-3.64 (m, 2H), 3.02-3.13 (m, 1H), 2.69 (br. s., 2H), 2.61 (d, J = 1.6 Hz, 2H), 2.35 (s, 3H), 2.05 (d, J = 15.3 Hz, 2H), 1.64-1.80 (m, 2H), 1.44 (s, 9H) ppm. | 4-bromo-1-(p-tolylsulfonyl)pyrrolo[2,3-b]pyridine | General method A1, Ci using HCl in dioxane, D using tert-butyl 4-chlorosulfonylpiperidine-1-carboxylate | tert-butyl 4-[[4-[1-(4-methylphenyl)sulfonylpyrrolo[2,3-b]pyridin-4-yl]-3,6-dihydro-2H-pyridin-1-yl]sulfonyl]piperidine-1-carboxylate |

| Cpd # | Structure | MS (m/z ES +) | δ NMR Data | Starting Int/Cpd# | Sequence of Methods | Chemical Name |
|---|---|---|---|---|---|---|
| 238 | 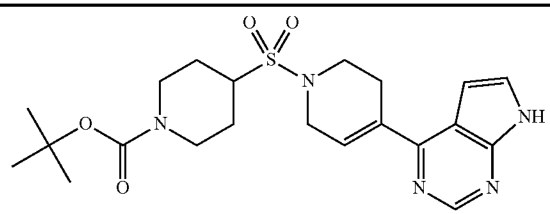 | 448.6 | ¹H NMR (400 MHz, CHLOROFORM-d): δ =9.24-9.44 (m, 1H), 7.81 (d, J = 6.8 Hz, 1H), 7.18 (br. s., 1H), 6.93 (br. s., 1H), 6.46 (br. s., 1H), 4.17-4.40 (m, 3H), 3.69-3.81 (m, 2H), 2.96-3.26 (m, 2H), 2.61-2.88 (m, 2H), 2.01-2.17 (m, 2H), 1.68-1.82 (m, 2H), 1.43 (s, 9H), 1.16-1.32 (m, 2H) ppm. | 4-chloro-7H-pyrrolo[2,3-d]pyrimidine | General method E, A1, Ci using HCl in dioxane, D using tert-butyl 4-chlorosulfonylpiperidine-1-carboxylate, F | tert-butyl 4-[[4-(7H-pyrrolo[2,3-d]pyrimidin-4-yl)-3,6-dihydro-2H-pyridin-1-yl]sulfonyl]piperidine-1-carboxylate |
| 239 | 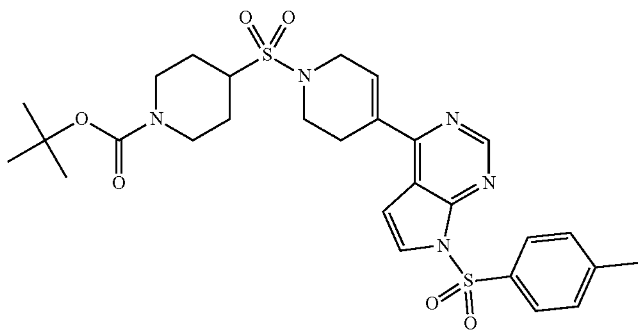 | 602.8 | ¹H NMR (600 MHz, CHLOROFORM-d): δ = 8.94-9.03 (m, 1H), 8.21 (d, J = 8.4 Hz, 1H), 8.08 (d, J = 7.9 Hz, 2H), 7.29-7.36 (m, 3H), 6.77-6.86 (m, 1H), 4.23 (br. s., 2H), 4.08-4.13 (m, 2H), 3.59-3.66 (m, 2H), 3.02-3.13 (m, 1H), 2.59-2.78 (m, 4H), 2.39 (s, 3H), 2.03 (d, J = 15.3 Hz, 2H), 1.65-1.76 (m, 2H), 1.43 (s, 9H) ppm. | 4-chloro-7H-pyrrolo[2,3-d]pyrimidine | General method E, A1, Ci using HCl in dioxane, D using tert-butyl 4-chlorosulfonylpiperidine-1-carboxylate | tert-butyl 4-[[4-[7-(4-methylphenyl)sulfonylpyrrolo[2,3-d]pyrimidin-4-yl]-3,6-dihydro-2H-pyridin-1-yl]sulfonyl]piperidine-1-carboxylate |
| 240 | 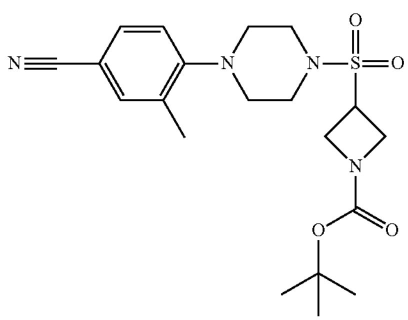 [SMILES: Cc1cc(C#N)ccc1N1CCN(S(=O)(=O)C2CN(C(=O)OC(C)(C)C)C2)CC1] | 421.9 | ¹H NMR (600 MHz, DMSO-d₆): δ= 7.61 (s, 1H), 7.60 (d, J = 8.07 Hz, 1H), 7.12 (d, J = 8.07 Hz, 1H), 4.31-4.39 (m, 1H), 4.20 (br. s., 2H), 3.98 (br. s., 2H), 3.34 (4H), 2.96 (t, J = 4.00 Hz, 4H), 2.26 (s, 3H), 1.38 (s, 9H) ppm | 4-fluoro-3-methyl-benzonitrile | General method S, D using tert-butyl 3-chlorosulfonylazetidine-1-carboxylate | tert-butyl 3-[4-(4-cyano-2-methylphenyl)piperazin-1-yl]sulfonylazetidine-1-carboxylate |

| Cpd # | Structure | MS (m/z, ES+) | δ NMR Data | Starting Int/Cpd# | Sequence of Methods | Chemical Name |
|---|---|---|---|---|---|---|
| 241 | 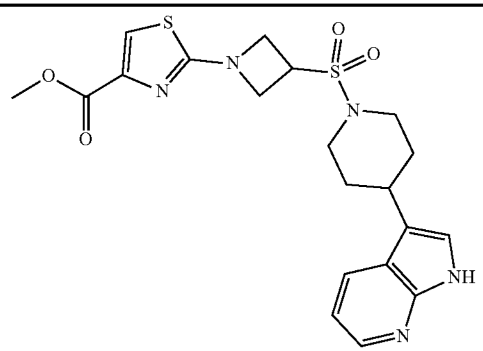 | 462.8 | ¹H NMR (500 MHz, CHLOROFORM-d): δ = 9.25 (br. s., 1H), 8.31 (d, J = 4.2 Hz, 1H), 7.93 (dd, J = 0.8, 8.1 Hz, 1H), 7.57 (s, 1H), 7.06-7.11 (m, 2H), 4.40-4.50 (m, 4H), 4.21-4.28 (m, 1H), 4.01 (d, J = 12.5 Hz, 2H), 3.90 (s, 3H), 3.04 (dd, J = 1.4, 12.6 Hz, 2H), 2.96 (tt, J = 3.3, 11.8 Hz, 1H), 2.13 (d, J = 13.7 Hz, 2H), 1.83 (qd, J = 3.6, 12.6 Hz, 2H) ppm. | 3-(4-piperidyl)-1H-pyrrolo[2,3-b]pyridine | General method D using tert-butyl 3-chlorosulfonyl azetidine-1-carboxylate, E, Ci using TFA, J3 using ethyl 2-bromothiazole-4-carboxylate, F | methyl 2-[3-[4-(1H-pyrrolo[2,3-b]pyridin-3-yl)piperidin-1-yl]sulfonylazetidin-1-yl]-1,3-thiazole-4-carboxylate |
| 242 | 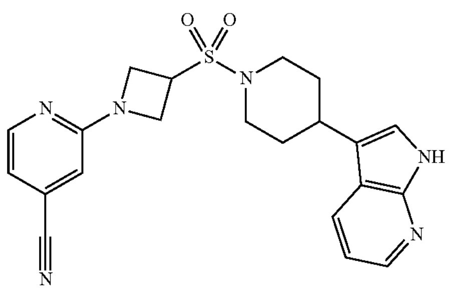 [SMILES: N#Cc1ccnc(N2CC(S(=O)(=O)N3CCC(c4c[nH]c5ncccc45)CC3)C2)c1] | 423.8 | ¹H NMR (300 MHz, DMSO-d₆): δ = 11.37 (br. s., 1H), 8.30 (d, J = 5.05 Hz, 1H), 8.17 (dd, J = 1.39, 4.70 Hz, 1H), 7.92-8.00 (m, 1H), 7.23 (d, J = 2.09 Hz, 1H), 6.96-7.07 (m, 3H), 4.48-4.61 (m, 1H), 4.35 (t, J = 8.71 Hz, 2H), 4.18 (dd, J = 5.57, 9.23 Hz, 2H), 3.77 (d, J = 12.19 Hz, 2H), 2.87-3.09 (m, 3H), 1.95-2.08 (m, 2H), 1.55-1.73 (m, 2H) ppm. | 3-(4-piperidyl)-1H-pyrrolo[2,3-b]pyridine | General method D using tert-butyl 3-chlorosulfonyl-tidine-1-carboxylate, Cf using TFA, J3 using 2-chloropyridine-4-carbonitrile | 2-[3-[4-(1H-pyrrolo[2,3-b]pyridin-3-yl)piperidin-1-yl]sulfonylazetidin-1-yl]pyridine-4-carbonitrile |

| Cpd # | Structure | MS (m/z, ES+) | δ NMR Data | Starting Int/Cpd# | Sequence of Methods | Chemical Name |
|---|---|---|---|---|---|---|
| 243 | 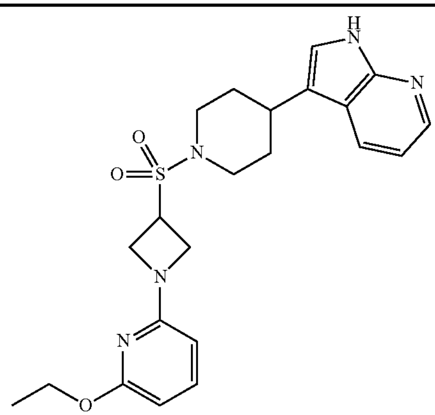 | 442.7 | ¹H NMR (600 MHz, DMSO-d₆): δ = 11.36 (br. s., 1H), 8.17 (dd, J = 1.65, 4.59 Hz, 1H), 7.96 (dd, J = 1.47, 7.89 Hz, 1H), 7.45 (t, J = 7.89 Hz, 1H), 7.23 (d, J = 2.02 Hz, 1H), 7.00 (dd, J = 4.77, 7.89 Hz, 1H), 6.06-6.08 (d, J = 1.47, 7.89 Hz, 1H), 5.97-5.99 (d, J = 1.47, 7.89 Hz, 1H), 4.48-4.55 (m, 1H), 4.17-4.29 (m, 2H), 4.09 (dd, J = 5.87, 8.80 Hz, 2H), 3.72-3.80 (m, 2H), 2.97-3.05 (m, 2H), 2.86-2.96 (m, 1H), 2.50-2.51 (m, 2H), 2.02 (d, J = 12.10 Hz, 2H), 1.64 (dq, J = 3.85, 12.41 Hz, 2H), 1.24-1.31 (m, 3H) ppm. | 3-(4-piperidyl)-1H-pyrrolo[2,3-b]pyridine | General method D using tert-butyl 3-chlorosulfonylazetidine-1-carboxylate, Cf using TFA, J3 using 2-chloro-6-ethoxy-pyridine | 3-[1-[1-(6-ethoxypyridin-2-yl)azetidin-3-yl]sulfonylpiperidin-4-yl]-1H-pyrrolo[2,3-b]pyridine |
| 244 | 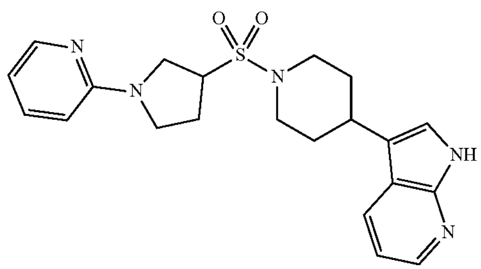 [SMILES: O=S(=O)(C1CCN(c2ccccn2)C1)N1CCC(c2c[nH]c3ncccc23)CC1] | 412.8 | ¹H NMR (600 MHz, DMSO-d₆): δ = 11.36 (br. s., 1H), 8.17 (d, J = 4.22 Hz, 1H), 8.08 (d, J = 3.85 Hz, 1H), 7.98 (d, J = 7.70 Hz, 1H), 7.51 (t, J = 7.52 Hz, 1H), 7.24 (br. s., 1H), 7.01 (dd, J = 4.86, 7.43 Hz, 1H), 6.59 (t, J = 5.87 Hz, 1H), 6.52 (d, J = 8.44 Hz, 1H), 4.17 (quin, J = 7.15 Hz, 1H), 3.72-3.84 (m, 3H), 3.65 (dd, J = 6.42, 11.00 Hz, 1H), 3.55-3.61 (m, 1H), 3.36-3.44 (m, 1H), 3.07 (t, J = 12.01 Hz, 2H), 2.96 (t, J = 11.65 Hz, 1H), 2.35-2.44 (m, 1H), 2.26-2.35 (m, 1H), 2.03 (d, J = 12.47 Hz, 2H), 1.59-1.72 (m, 2H) ppm | 3-(4-piperidyl)-1H-pyrrolo[2,3-b]pyridine | General method D using tert-butyl 3-chlorosulfonylpyrrolidine-1-carboxylate racemate, Cf using TFA, then J3 using 2-fluoropyridine | 3-[1-[1-(1-pyridin-2-ylpyrrolidin-3-yl)sulfonylpiperidin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 245 | 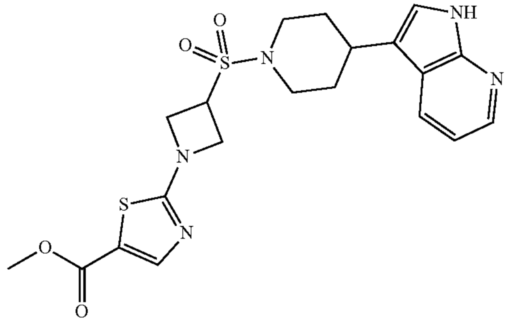 [SMILES: COC(=O)c1cnc(N2CC(S(=O)(=O)N3CCC(c4c[nH]c5ncccc45)CC3)C2)s1] | 462.7 | ¹H NMR (400 MHz, CHLOROFORM-d): δ = 9.05 (br. s., 1H), 8.29 (d, J = 4.5 Hz, 1H), 7.88 (dd, J = 1.1, 8.1 Hz, 1H), 7.86 (s, 1H), 7.02-7.08 (m, 2H), 4.37-4.47 (m, 4H), 4.19-4.27 (m, 1H), 3.99 (d, J = 12.5 Hz, 2H), 3.82 (s, 3H), 3.02 (td, J = 2.0, 12.6 Hz, 2H), 2.94 (tt, J = 3.3, 11.9 Hz, 1H), 2.11 (d, J = 13.5 Hz, 2H), 1.80 (qd, J = 3.8, 12.6 Hz, 2H) ppm. | 3-(4-piperidyl)-1H-pyrrolo[2,3-b]pyridine | General method D using tert-butyl 3-chlorosulfonyl azetidine-1-carboxylate, E, Ci using TFA, I3 using ethyl 2-bromothiazole-5-carboxylate, F | methyl 2-[3-[4-(1H-pyrrolo[2,3-b]pyridin-3-yl)piperidin-1-yl]sulfonylazetidin-1-yl]-1,3-thiazole-5-carboxylate |
| 246 | 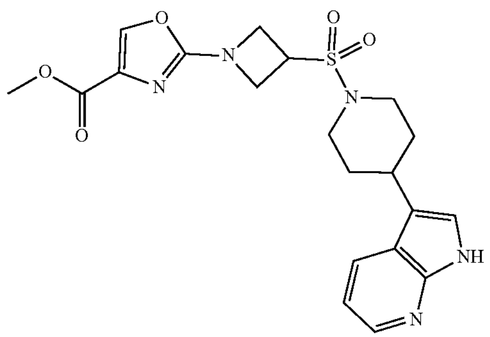 [SMILES: COC(=O)c1coc(N2CC(S(=O)(=O)N3CCC(c4c[nH]c5ncccc45)CC3)C2)n1] | 446.8 | | 3-(4-piperidyl)-1H-pyrrolo[2,3-b]pyridine | General method D using tert-butyl 3-chlorosulfonyl azetidine-1-carboxylate, E, Ci using TFA, I3 using ethyl 2-bromooxazole-4-carboxylate, F | methyl 2-[3-[4-(1H-pyrrolo[2,3-b]pyridin-3-yl)piperidin-1-yl]sulfonylazetidin-1-yl]-1,3-oxazole-4-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 247 | 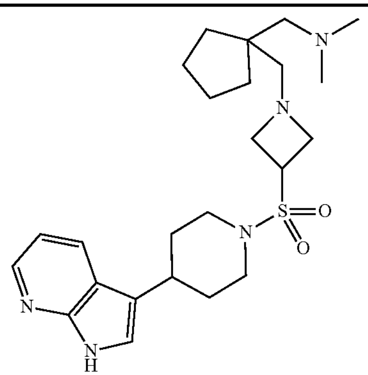 | 460.9 | ¹H NMR (500 MHz, DMSO-d₆) δ: 11.36 (br. s., 1H), 8.17 (d, J = 1.22, 4.88 Hz, 1H), 7.97 (d, J = 7.63 Hz, 1H), 7.24 (d, J = 1.83 Hz, 1H), 7.02 (dd, J = 4.73, 7.78 Hz, 1H), 4.20 (quin, J = 7.40 Hz, 1H), 3.69 (d, J = 11.90 Hz, 2H), 3.63 (t, J = 7.78 Hz, 2H), 3.39 (2H), 2.85-2.99 (m, 3H), 2.39 (s, 2H), 2.17 (s, 6H), 2.14 (s, 2H), 2.01 (d, J = 11.60 Hz, 2H), 1.63 (dq, J = 3.66, 12.41 Hz, 2H), 1.47-1.56 (m, 4H), 1.23-1.38 (m, 4H) ppm | 3-(4-piperidyl)-1H-pyrrolo[2,3-b]pyridine | General method D using tert-butyl 3-chlorosulfonylazetidine-1-carboxylate, Cf using TFA, then J2 using 1-[(dimethylamino)methyl] cyclopentanecarbaldehyde | N,N-dimethyl-1-[1-[[3-[4-(1H-pyrrolo[2,3-b]pyridin-3-yl)piperidin-1-yl]sulfonylazetidin-1-yl]methyl] cyclopentyl] methanamine |
| 248 | 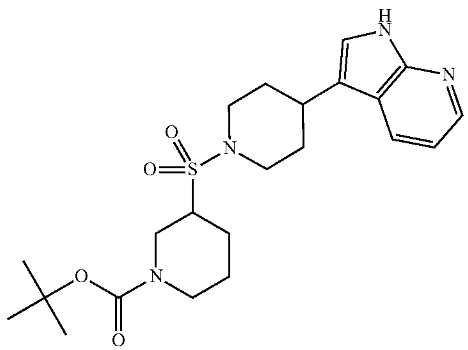 [SMILES: CC(C)(C)OC(=O)N1CCCC(S(=O)(=O)N2CCC(c3c[nH]c4ncccc34)CC2)C1] | 449.9 | ¹H NMR (80° C, 600 MHz, DMSO-d₆) δ: 11.09 (br. s., 1H), 8.17 (d, J = 4.59 Hz, 1H), 7.97 (dd, J = 7.89 Hz, 1H), 7.20 (d, J = 1.83 Hz, 1H), 7.00 (dd, J = 4.77, 7.89 Hz, 1H), 4.22 (d, J = 12.29 Hz, 1H), 3.75-3.85 (m, 3H), 3.18 (t, J = 3.97, 10.71 Hz, 1H), 3.08 (t, J = 12.29 Hz, 2H), 2.94-3.02 (m, 2H), 2.77-2.84 (m, 1H), 2.08-2.15 (m, 1H), 2.04 (d, J = 12.65 Hz, 2H), 1.65-1.79 (m, 4H), 1.40-1.49 (m, 1H), 1.42 (s, 9H) ppm | 3-(4-piperidyl)-1H-pyrrolo[2,3-b]pyridine | General method D using tert-butyl 3-chlorosulfonyl piperidine-1-carboxylate; racemate | tert-butyl 3-[4-(1H-pyrrolo[2,3-b]pyridin-3-yl)piperidin-1-yl]sulfonylpiperidine-1-carboxylate |
| 249 | 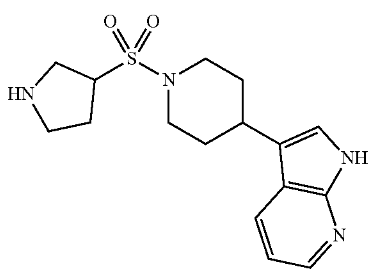 [SMILES: O=S(=O)(C1CCNC1)N1CCC(c2c[nH]c3ncccc23)CC1] | 335.7 | ¹H NMR (600 MHz, DMSO-d₆) δ: 11.35 (br. s., 1H), 8.17 (dd, J = 1.56, 4.68 Hz, 1H), 7.97 (dd, J = 1.10, 7.80 Hz, 1H), 7.24 (d, J = 2.20 Hz, 1H), 7.01 (dd, J = 4.77, 7.89 Hz, 1H), 3.67-3.76 (m, 3H), 3.10 (dd, J = 8.34, 11.83 Hz, 1H), 2.89-3.03 (m, 4H), 2.79-2.84 (m, 1H), 2.72-2.78 (m, 1H), 1.98-2.05 (m, 3H), 1.86-1.93 (m, 1H), 1.64 (dq, J = 4.31, 12.50 Hz, 2H) ppm | 3-(4-piperidyl)-1H-pyrrolo[2,3-b]pyridine | General method D using tert-butyl 3-chlorosulfonyl pyrrolidine-1-carboxylate; racemate, Cf using TFA | 3-[1-(pyrrolidin-3-ylsulfonyl)piperidin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 250 | 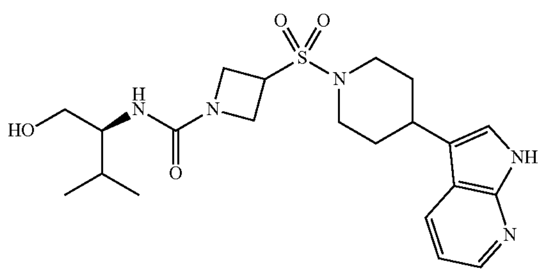 [SMILES: CC(C)[C@@H](CO)NC(=O)N1CC(S(=O)(=O)N2CCC(c3c[nH]c4ncccc34)CC2)C1] | 450.8 | 1H NMR (600 MHz, DMSO-d6) d: 11.37 (s, 1H), 8.17 (dd, J = 1.47, 4.58 Hz, 1H), 7.97 (dd, J = 1.10, 7.89 Hz, 1H), 7.24 (d, J = 2.38 Hz, 1H), 7.01 (dd, J = 4.68, 7.79 Hz, 1H), 6.03 (d, J = 8.44 Hz, 1H), 4.47 (br. s., 1H), 4.33 (tt, J = 5.73, 8.39 Hz, 1H), 4.13 (t, J = 8.62 Hz, 1H), 4.08 (t, J = 8.62 Hz, 1H), 4.02 (dd, J = 5.78, 8.89 Hz, 1H), 3.95 (dd, J = 5.69, 8.80 Hz, 1H), 3.72 (d, J = 10.64 Hz, 2H), 3.36-3.40 (m, 3H), 2.95-3.01 (m, 2H), 2.89-2.95 (m, 1H), 2.02 (d, J = 12.10 Hz, 2H), 1.78 (dd, J = 6.79, 13.02 Hz, 1H), 1.63 (q, J = 11.86 Hz, 2H), 0.83 (d, J = 6.97 Hz, 3H), 0.80 (d, J = 6.79 Hz, 3H) ppm | 3-(4-piperidyl)-1H-pyrrolo[2,3-b]pyridine | General method D using tert-butyl 3-chlorosulfonylazetidine-1-carboxylate, Cf using TFA, G6 using (S)-2-amino-3-methyl-butan-1-ol | N-[(2S)-1-hydroxy-3-methylbutan-2-yl]-3-[4-(1H-pyrrolo[2,3-b]pyridin-3-yl)piperidin-1-yl]sulfonylazetidine-1-carboxamide |
| 251 | 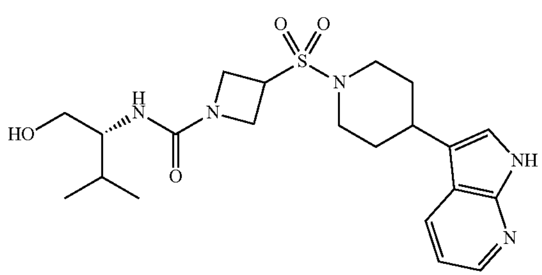 [SMILES: CC(C)[C@H](CO)NC(=O)N1CC(S(=O)(=O)N2CCC(c3c[nH]c4ncccc34)CC2)C1] | 450.8 | 1H NMR (500 MHz, DMSO-d6) d: 11.38 (br. s., 1H), 8.09-8.26 (m, 1H), 7.98 (d, J = 7.02 (dd, J = 4.58, 7.93 Hz, 1H), 6.04 (d, J = 7.93 Hz, 1H), 4.48 (br. s., 1H), 4.27-4.39 (m, 1H), 4.14 (t, J = 8.70 Hz, 1H), 4.09 (t, J = 8.54 Hz, 1H), 4.00-4.06 (m, 1H), 3.96 (dd, J = 5.65, 8.70 Hz, 1H), 3.73 (d, J = 11.60 Hz, 2H), 3.36-3.41 (m, 3H), 2.87-3.04 (m, 3H), 2.03 (d, J = 12.21 Hz, 2H), 1.79 (qd, J = 6.61, 13.12 Hz, 1H), 1.64 (q, J = 11.60 Hz, 2H), 0.84 (d, J = 6.71 Hz, 3H), 0.81 (d, J = 7.02 Hz, 3H) ppm | 3-(4-piperidyl)-1H-pyrrolo[2,3-b]pyridine | General method D using tert-butyl 3-chlorosulfonylazetidine-1-carboxylate, Cf using TFA, G6 using (R)-2-amino-3-methyl-butan-1-ol, (D-valinol) | N-[(2R)-1-hydroxy-3-methylbutan-2-yl]-3-[4-(1H-pyrrolo[2,3-b]pyridin-3-yl)piperidin-1-yl]sulfonylazetidine-1-carboxamide |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 252 | 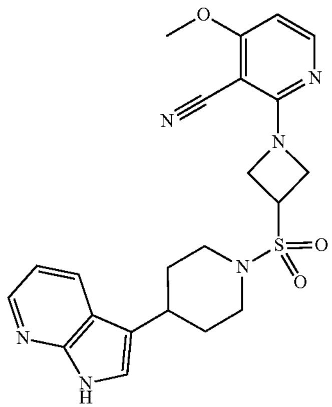 [SMILES: COc1ccnc(N2CC(S(=O)(=O)N3CCC(c4c[nH]c5ncccc45)CC3)C2)c1C#N] | 453.8 | ¹H NMR (300 MHz, DMSO-d₆) δ: 11.37 (br. s., 1H), 8.22 (d, J = 5.92 Hz, 1H), 8.17 (dd, J = 1.39, 4.70 Hz, 1H), 7.97 (d, J = 6.79 Hz, 1H), 7.22 (d, J = 2.26 Hz, 1H), 7.00 (dd, J = 4.62, 7.93 Hz, 1H), 6.64 (d, J = 5.92 Hz, 1H), 4.44-4.61 (m, 3H), 4.33 (dd, J = 4.18, 8.36 Hz, 2H), 3.92 (s, 3H), 3.76 (d, J = 11.84 Hz, 2H), 2.86-3.10 (m, 3H), 2.03 (d, J = 11.67 Hz, 2H), 1.54-1.73 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J3 using 2-chloro-4-methoxy-pyridine-3-carbonitrile | 4-methoxy-2-[3-[4-(1H-pyrrolo[2,3-b]pyridin-3-yl)piperidin-1-yl]sulfonylazetidin-1-yl]pyridine-3-carbonitrile |
| 253 | 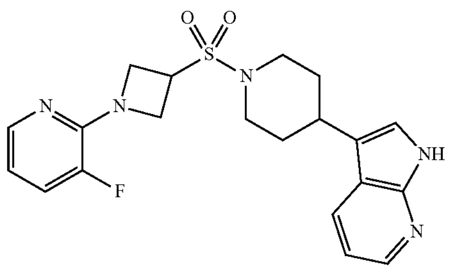 [SMILES: O=S(=O)(C1CN(c2ncccc2F)C1)N1CCC(c2c[nH]c3ncccc23)CC1] | 416.8 | ¹H NMR (300 MHz, DMSO-d₆) δ: 11.37 (br. s., 1H), 8.17 (dd, J = 1.22, 4.70 Hz, 1H), 7.92-7.99 (m, 2H), 7.49 (ddd, J = 1.13, 8.06, 12.41 Hz, 1H), 7.23 (d, J = 2.26 Hz, 1H), 7.00 (dd, J = 4.70, 7.66 Hz, 1H), 6.74-6.82 (m, 1H), 4.48-4.61 (m, 1H), 4.41 (t, J = 8.10 Hz, 2H), 4.18-4.29 (m, 2H), 3.76 (d, J = 12.02 Hz, 2H), 2.84-3.08 (m, 3H), 2.03 (d, J = 11.32 Hz, 2H), 1.54-1.73 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J3 using 2,3-difluoropyridine | 3-[1-[1-(3-fluoropyridin-2-yl)azetidin-3-yl]sulfonylpiperidin-4-yl]-1H-pyrrolo[2,3-b]pyridine |
| 254 | 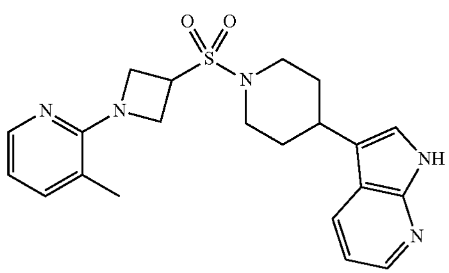 [SMILES: Cc1cccnc1N1CC(S(=O)(=O)N2CCC(c3c[nH]c4ncccc34)CC2)C1] | 412.8 | ¹H NMR (300 MHz, DMSO-d₆) δ: 11.36 (br. s., 1H), 8.17 (dd, J = 1.39, 4.70 Hz, 1H), 7.93-8.01 (m, 2H), 7.36 (d, J = 7.14 Hz, 1H), 7.24 (d, J = 2.26 Hz, 1H), 7.00 (dd, J = 4.70, 7.84 Hz, 1H), 6.73 (dd, J = 4.96, 7.23 Hz, 1H), 4.42-4.53 (m, 1H), 4.34 (t, J = 8.27 Hz, 2H), 4.21-4.29 (m, 2H), 3.76 (d, J = 12.02 Hz, 2H), 2.85-3.07 (m, 3H), 2.14 (s, 3H), 2.02 (d, J = 11.32 Hz, 2H), 1.55-1.73 (m, 2H) ppm. | 3-(4-piperidyl)-1H-pyrrolo[2,3-b]pyridine | General method D using tert-butyl 3-chlorosulfonylazetidine-1-carboxylate, Cf using TFA, J3 using 2-fluoro-3-methyl-pyridine | 3-[1-[1-(3-methylpyridin-2-yl)azetidin-3-yl]sulfonylpiperidin-4-yl]-1H-pyrrolo[2,3-b]pyridine |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 255 | 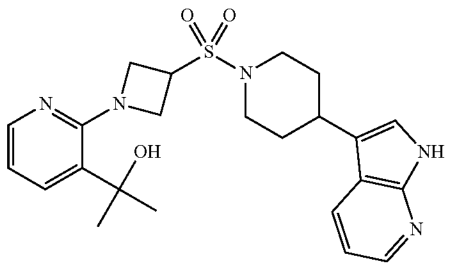 [SMILES: CC(C)(O)c1cccnc1N1CC(S(=O)(=O)N2CCC(c3c[nH]c4ncccc34)CC2)C1] | 456.9 | ¹H NMR (300 MHz, DMSO-d₆) δ: 11.37 (br. s., 1H), 8.17 (dd, J = 1.22, 4.53 Hz, 1H), 8.06 (dd, J = 1.57, 4.70 Hz, 1H), 7.98 (d, J = 6.62 Hz, 1H), 7.55 (dd, J = 1.65, 7.58 Hz, 1H), 7.24 (d, J = 2.26 Hz, 1H), 7.01 (dd, J = 4.70, 7.84 Hz, 1H), 6.75 (dd, J = 4.70, 7.49 Hz, 1H), 5.07 (s, 1H), 4.30-4.42 (m, 5H), 3.74 (d, J = 12.02 Hz, 2H), 2.87-3.08 (m, 3H), 2.03 (d, J = 11.32 Hz, 2H), 1.56-1.74 (m, 2H), 1.49 (s, 6H) ppm. | 3-(4-piperidyl)-1H-pyrrolo[2,3-b]pyridine | General method D using tert-butyl 3-chlorosulfonylazetidine-1-carboxylate, Cf using TFA, J3 using 2-(2-fluoro-3-pyridyl)propan-2-ol | 2-[2-[3-[4-(1H-pyrrolo[2,3-b]pyridin-3-yl)piperidin-1-yl]sulfonylazetidin-1-yl]pyridin-3-yl]propan-2-ol |
| 256 | 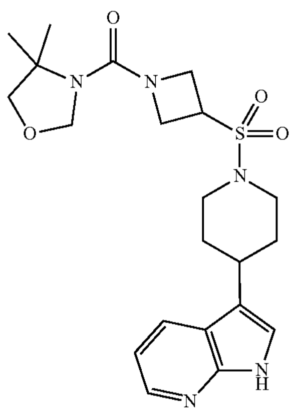 [SMILES: CC1(C)COCN1C(=O)N1CC(S(=O)(=O)N2CCC(c3c[nH]c4ncccc34)CC2)C1] | 448.7 | ¹H NMR (600 MHz, DMSO-d₆): δ = 11.37 (s, 1H), 8.17 (dd, J = 1.56, 4.68 Hz, 1H), 7.97 (dd, J = 1.28, 7.89 Hz, 1H), 7.24 (d, J = 2.20 Hz, 1H), 7.01 (dd, J = 4.58, 7.89 Hz, 1H), 4.74 (s, 2H), 4.31-4.39 (m, 1H), 4.11 (t, J = 8.71 Hz, 2H), 4.01 (dd, J = 6.14, 8.89 Hz, 2H), 3.72 (d, J = 12.29 Hz, 2H), 3.65 (s, 2H), 2.97 (dt, J = 2.20, 12.29 Hz, 2H), 2.91 (tt, J = 3.28, 11.85 Hz, 1H), 2.01 (d, J = 11.00 Hz, 2H), 1.63 (dq, J = 3.94, 12.44 Hz, 2H), 1.33 (s, 6H) ppm | 3-(4-piperidyl)-1H-pyrrolo[2,3-b]pyridine | General method D using tert-butyl 3-chlorosulfonylazetidine-1-carboxylate, Cf using TFA, then G3 using 4,4-dimethyl-1,3-oxazolidine | (4,4-dimethyl-1,3-oxazolidin-3-yl)-[3-[4-(1H-pyrrolo[2,3-b]pyridin-3-yl)piperidin-1-yl]sulfonylazetidin-1-yl]methanone |
| 257 | 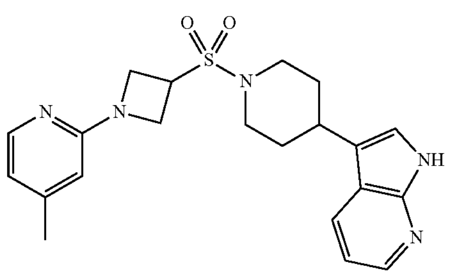 [SMILES: Cc1ccnc(N2CC(S(=O)(=O)N3CCC(c4c[nH]c5ncccc45)CC3)C2)c1] | 412.8 | ¹H NMR (600 MHz, CHLOROFORM-d) δ 9.34 (br. s., 1H), 8.26 (d, J = 4.58 Hz, 1H), 8.02 (d, J = 5.32 Hz, 1H), 7.93 (d, J = 7.70 Hz, 1H), 7.07 (dd, J = 4.86, 7.79 Hz, 1H), 7.04 (s, 1H), 6.53 (d, J = 5.32 Hz, 1H), 6.15 (s, 1H), 4.28-4.35 (m, 4H), 4.15-4.21 (m, 1H), 4.01 (d, J = 12.47 Hz, 2H), 3.02 (td, J = 1.72, 12.56 Hz, 2H), 2.93 (tt, J = 3.21, 11. + D3:D792 Hz, 1H), 2.26 (s, 3H), 2.08 (d, J = 12.10 Hz, 2H), 1.82 (dq, J = 4.03, 12.65 Hz, 2H) ppm | 3-(4-piperidyl)-1H-pyrrolo[2,3-b]pyridine | General method D using tert-butyl 3-chlorosulfonyl azetidine-1-carboxylate, E, Ci using TFA, I4 using 2-chloro-4-methyl-pyridine, F | 3-[1-[1-(4-methylpyridin-2-yl)azetidin-3-yl]sulfonylpiperidin-4-yl]-1H-pyrrolo[2,3-b]pyridine |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 258 | 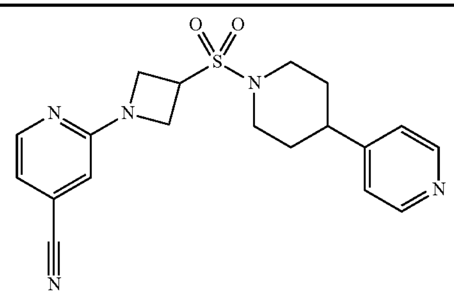 | 384.8 | ¹H NMR (600 MHz, CHLOROFORM-d) Shift 8.53 (d, J = 5.50 Hz, 2H), 8.27 (d, J = 5.13 Hz, 1H), 7.10 (d, J = 6.05 Hz, 2H), 6.84 (dd, J = 1.10, 5.14 Hz, 1H), 6.49 (s, 1H), 4.31-4.38 (m, 4H), 4.15-4.21 (m, 1H), 3.98-4.04 (m, 2H), 2.95 (dt, J = 2.20, 12.47 Hz, 2H), 2.64 (tt, J = 3.42, 12.17 Hz, 1H), 1.91-1.97 (m, 2H), 1.75 (dq, J = 4.13, 12.75 Hz, 2H) ppm | 4-(4-piperidyl)pyridine | General method D using tert-butyl 3-chlorosulfonylazetidine-1-carboxylate, Cf using TFA, J3 using 2-chloropyridine-4-carbonitrile | 2-[3-(4-pyridin-4-yl)piperidin-1-yl)sulfonylazetidin-1-yl]pyridine-4-carbonitrile |
| 259 | 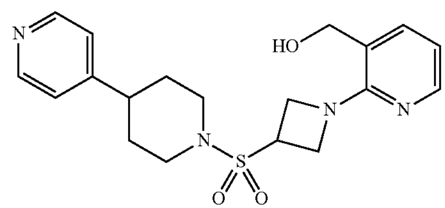 [SMILES: O=S(=O)(C1CN(c2ncccc2CO)C1)N1CCC(c2ccncc2)CC1] | 389.8 | ¹H NMR (600 MHz, CHLOROFORM-d) δ 8.50 (d, J = 4.59 Hz, 2H), 8.14 (dd, J = 1.28, 4.77 Hz, 1H), 7.49 (d, J = 6.60 Hz, 1H), 7.06 (d, J = 5.50 Hz, 2H), 6.75 (dd, J = 5.04, 7.24 Hz, 1H), 4.55 (s, 2H), 4.47-4.51 (m, 2H), 4.39-4.45 (m, 2H), 4.12-4.17 (m, 1H), 4.03 (d, J = 12.65 Hz, 2H), 2.96 (td, J = 1.62,12.68 Hz, 2H), 2.61 (tt, J = 3.08, 12.30 Hz, 1H), 1.91 (d, J = 12.29 Hz, 2H), 1.75 (dq, J = 3.85, 12.59 Hz, 2H) ppm | 4-(4-piperidyl)pyridine | General method D using tert-butyl 3-chlorosulfonylazetidine-1-carboxylate, Cf using TFA, J3 using (2-fluoro-3-pyridyl)methanol | [2-[3-(4-pyridin-4-yl)piperidin-1-yl)sulfonylazetidin-1-yl]pyridin-3-yl]methanol |

TABLE with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 260 | 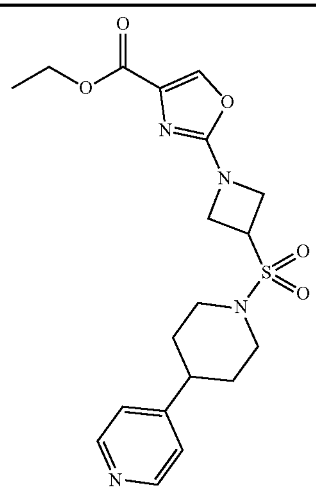 | 421.8 | CHLOROFORM-d δ 7.54-7.57 (m, 2H), 7.81 (s, 1H), 7.15-7.18 (m, 2H), 4.39-4.47 (m, 4H), 4.34 (q, J = 7.14 Hz, 2H), 4.12-4.18 (m, 1H), 3.97-4.03 (m, 2H), 2.95 (td, J = 2.19, 12.64 Hz, 2H), 2.67 (tt, J = 3.52, 12.25 Hz, 1H), 1.91-1.96 (m, 2H), 1.74 (qd, J = 4.08, 12.66 Hz, 2H), 1.33 (t, J = 7.14 Hz, 3H). | 4-(4-pyridyl)pyridine | General method D using tert-butyl 3-chlorosulfonylazetidine-1-carboxylate, Cf using TFA, J3 using ethyl 2-bromooxazole-4-carboxylate | ethyl 2-[3-(4-pyridin-4-ylpiperidin-1-yl)sulfonylazetidin-1-yl]-1,3-oxazole-4-carboxylate |
| 261 | 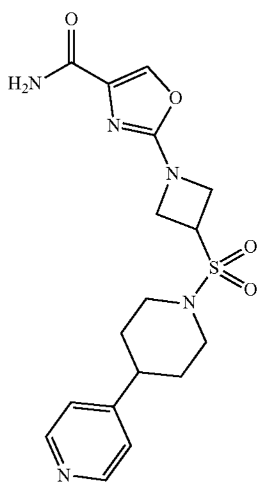 [SMILES: NC(=O)c1coc(N2CC(S(=O)(=O)N3CCC(c4ccncc4)CC3)C2)n1] | 392.8 | ¹H NMR (400 MHz, CHLOROFORM-d) δ 8.51-8.56 (m, 2H), 7.80 (s, 1H), 7.07-7.12 (m, 2H), 6.63 (br. s., 1H), 5.44 (br. s., 1H), 4.34-4.46 (m, 4H), 4.12-4.20 (m, 1H), 3.96-4.04 (m, 2H), 2.95 (dt, J = 2.38, 12.44 Hz, 2H), 2.64 (tt, J = 3.56, 12.03 Hz, 1H), 1.94 (d, J = 10.51 Hz, 2H), 1.75 (dq, J = 4.22, 12.61 Hz, 2H) ppm | 4-(4-piperidyl)pyridine | General method D using tert-butyl 3-chlorosulfonylazetidine-1-carboxylate, Cf using TFA, J3 using ethyl 2-bromooxazole-4-carboxylate, X | 2-[3-(4-pyridin-4-ylpiperidin-1-yl)sulfonylazetidin-1-yl]-1,3-oxazole-4-carboxamide |

Table with Representative Compounds of Formula (I): -continued

| Cpd # | Structure | MS (m/z ES +) | δ NMR Data | Starting Int/Cpd# | Sequence of Methods | Chemical Name |
|---|---|---|---|---|---|---|
| 262 | 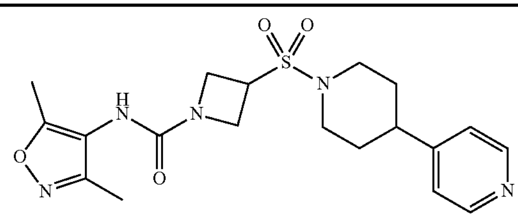 | 420.1 | ¹H NMR (600 MHz, CHLOROFORM-d) δ 8.53 (d, J = 4.40 Hz, 2H), 7.10 (d, J = 5.69 Hz, 2H), 5.35 (s, 1H), 4.25-4.30 (m, 2H), 4.18-4.24 (m, 2H), 3.94-4.02 (m, 3H), 2.92 (dt, J = 2.20, 12.47 Hz, 2H), 2.63 (tt, J = 3.48, 12.20 Hz, 1H), 2.31 (s, 3H), 2.18 (s, 3H), 1.94 (d, J = 13.10 Hz, 2H), 1.75 (dq, J = 4.22, 12.72 Hz, 2H) ppm | 4-(4-piperidyl)pyridine | General method D using tert-butyl 3-chlorosulfonylazetidine-1-carboxylate, Cf using TFA, G2 using 4-isocyanato-3,5-dimethyl-isoxazole | N-(3,5-dimethyl-1,2-oxazol-4-yl)-3-(4-pyridin-4-ylpiperidin-1-yl)sulfonylazetidine-1-carboxamide |
| 263 | 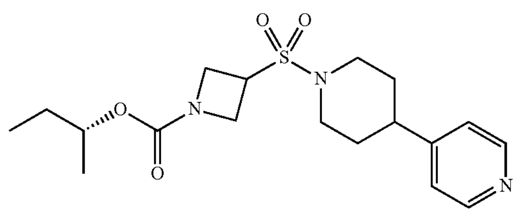 [SMILES: CC[C@@H](C)OC(=O)N1CC(S(=O)(=O)N2CCC(c3ccncc3)CC2)C1] | 382.1 | ¹H NMR (600 MHz, CHLOROFORM-d) δ 8.53 (d, J = 5.87 Hz, 2H), 7.10 (d, J = 6.05 Hz, 2H), 4.71 (sxt, J = 6.24 Hz, 1H), 4.24-4.28 (m, 2H), 4.18-4.23 (m, 2H), 3.92-4.01 (m, 3H), 2.92 (dt, J = 2.11, 12.52 Hz, 2H), 2.62 (tt, J = 3.46, 12.22 Hz, 1H), 1.93 (d, J = 6.24 Hz, 3H), 0.88 (t, J = 7.52 Hz, 3H) ppm | 4-(4-piperidyl)pyridine | General method D using tert-butyl 3-chlorosulfonylazetidine-1-carboxylate, Cf using TFA, H3 using (R)-butan-2-ol | [(2R)-butan-2-yl]3-(4-pyridin-4-ylpiperidin-1-yl)sulfonylazetidine-1-carboxylate |
| 264 | 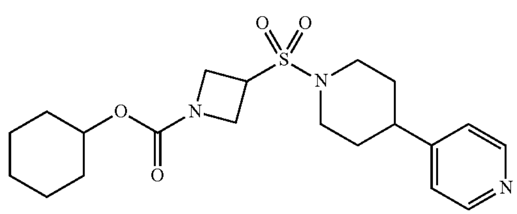 [SMILES: O=C(OC1CCCCC1)N1CC(S(=O)(=O)N2CCC(c3ccncc3)CC2)C1] | 408.8 | ¹H NMR (400 MHz, CHLOROFORM-d) δ 8.50-8.56 (m, 2H), 7.08-7.13 (m, 2H), 4.58-4.66 (m, 1H), 4.16-4.29 (m, 4H), 3.90-4.02 (m, 3H), 2.92 (dt, J = 2.26, 12.50 Hz, 2H), 2.63 (tt, J = 3.52, 12.13 Hz, 1H), 1.93 (d, J = 10.76 Hz, 2H), 1.66-1.86 (m, 6H), 1.46-1.55 (m, 1H), 1.18-1.43 (m, 5H) ppm | 4-(4-piperidyl)pyridine | General method D using tert-butyl 3-chlorosulfonylazetidine-1-carboxylate, Cf using TFA, H1 using cyclohexyl chloroformate | cyclohexyl 3-(4-pyridin-4-ylpiperidin-1-yl)sulfonylazetidine-1-carboxylate |
| 265 | 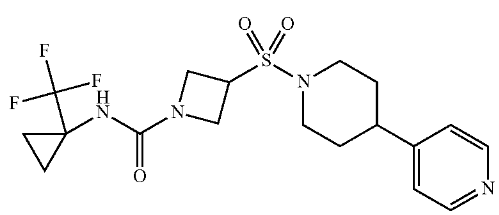 [SMILES: O=C(NC1(C(F)(F)F)CC1)N1CC(S(=O)(=O)N2CCC(c3ccncc3)CC2)C1] | 433.8 | ¹H NMR (600 MHz, CHLOROFORM-d) δ 8.50-8.54 (m, 2H), 7.08-7.12 (m, 2H), 4.81 (s, 1H), 4.17-4.25 (m, 4H), 3.94-4.00 (m, 3H), 2.93 (dt, J = 2.20, 12.47 Hz, 2H), 2.63 (tt, J = 3.51, 12.17 Hz, 1H), 1.93 (d, J = 13.29 Hz, 2H), 1.74 (dq, J = 4.13, 12.69 Hz, 2H), 1.27-1.31 (m, 2H), 1.09-1.13 (m, 2H) ppm | 4-(4-piperidyl)pyridine | General method D using tert-butyl 3-chlorosulfonylazetidine-1-carboxylate, Cf using TFA, G2 using 1-isocyanato-1-(trifluoromethyl)cyclopropane | 3-(4-pyridin-4-ylpiperidin-1-yl)sulfonyl-N-[1-(trifluoromethyl)cyclopropyl]azetidine-1-carboxamide |

| Cpd # | Structure | MS (m/z, ES+) | δ NMR Data | Starting Int/Cpd# | Sequence of Methods | Chemical Name |
|---|---|---|---|---|---|---|
| 266 | 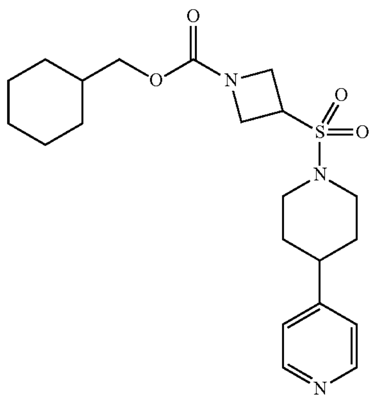 [SMILES: O=C(OCC1CCCCC1)N1CC(S(=O)(=O)N2CCC(c3ccncc3)CC2)C1] | 422.9 | ¹H NMR (600 MHz, CHLOROFORM-d) δ 8.53 (d, J = 5.87 Hz, 2H), 7.10 (d, J = 5.87 Hz, 2H), 4.25-4.30 (m, 2H), 4.19-4.24 (m, 2H), 3.93-4.01 (m, 3H), 3.86 (d, J = 6.60 Hz, 2H), 2.92 (dt, J = 2.11, 12.52 Hz, 2H), 2.63 (tt, J = 3.44, 12.24 Hz, 1H), 1.93 (d, J = 11.19 Hz, 2H), 1.63-1.79 (m, 8H), 1.09-1.24 (m, 3H), 0.92 (qd, J = 3.39, 11.89 Hz, 2H) ppm | 4-(4-piperidyl)pyridine | General method D using tert-butyl 3-chlorosulfonylazetidine-1-carboxylate, Cf using TFA, H3 using cyclohexylmethanol | cyclohexylmethyl 3-(4-pyridin-4-ylpiperidin-1-yl)sulfonylazetidine-1-carboxylate |
| 267 | 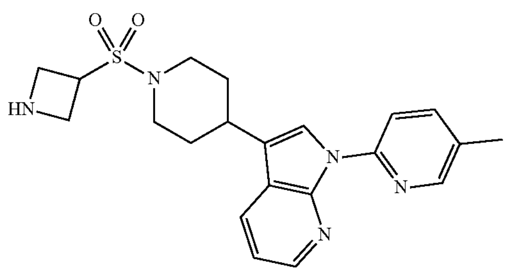 [SMILES: Cc1ccc(-n2cc(C3CCN(S(=O)(=O)C4CNC4)CC3)c3cccnc32)nc1] | 412.9 | ¹H NMR (300 MHz, DMSO-d₆): δ = 8.73 (d, J = 8.53 Hz, 1H), 8.38 (dd, J = 1.39, 4.70 Hz, 1H), 8.35-8.40 (m, 1H), 8.10-8.18 (m, 2H), 7.82 (dd, J = 2.00, 8.45 Hz, 1H), 7.24 (dd, J = 4.70, 7.84 Hz, 1H), 4.36-4.49 (m, 1H), 3.76-3.84 (m, 2H), 3.72 (d, J = 12.19 Hz, 2H), 3.56-3.66 (m, 2H), 2.88-3.05 (m, 3H), 2.33 (s, 3H), 2.08 (d, J = 11.50 Hz, 2H), 1.58-1.77 (m, 2H) ppm | 3-(4-piperidyl)-1H-pyrrolo[2,3-b]pyridine | General method D using tert-butyl 3-chlorosulfonylazetidine-1-carboxylate, E using 4-methyl-benzenesulfonyl chloride, Cf using TFA, then J4 using 2-chloro-5-methyl-pyridine. | 3-[1-(azetidin-3-ylsulfonyl)piperidin-4-yl]-1-(5-methylpyridin-2-yl)pyrrolo[2,3-b]pyridine |
| 268 | 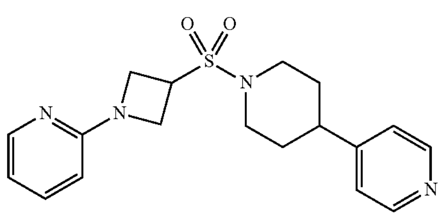 [SMILES: O=S(=O)(C1CN(c2ccccn2)C1)N1CCC(c2ccncc2)CC1] | 359.8 | ¹H NMR (300 MHz, DMSO-d₆): δ = 8.43-8.50 (m, 2H), 8.07-8.13 (m, 1H), 7.51-7.60 (m, 1H), 7.24 (d, J = 5.92 Hz, 2H), 6.67-6.74 (m, 1H), 6.48 (d, J = 8.19 Hz, 1H), 4.46-4.58 (m, 1H), 4.27 (t, J = 8.54 Hz, 2H), 4.09 (dd, J = 5.75, 8.71 Hz, 2H), 3.78 (d, J = 12.02 Hz, 2H), 2.89-3.02 (m, 2H), 2.62-2.76 (m, 1H), 1.85 (d, J = 12.02 Hz, 2H), 1.59 (dq, J = 3.83, 12.54 Hz, 2H) ppm | 4-(4-piperidyl)pyridine | General method D using tert-butyl 3-chlorosulfonylazetidine-1-carboxylate, Cf using TFA, then J3 using 2-fluoropyridine. | 2-[3-(4-pyridin-4-ylpiperidin-1-yl)sulfonylazetidin-1-yl]pyridine |

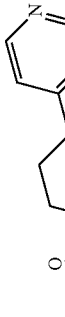

-continued

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 272 | AND Enantiomer 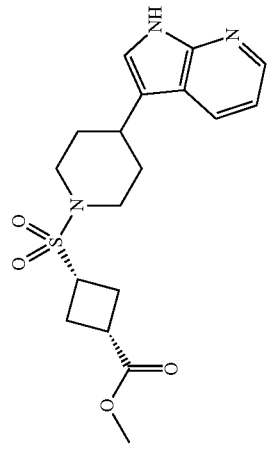 | 448.9 | ¹H NMR (300 MHz, DMSO-d₆): δ = 11.32-11.42 (m, 1H), 8.17 (dd, J = 1.31, 4.62 Hz, 1H), 7.98 (d, J = 6.62 Hz, 1H), 7.25 (d, J = 2.26 Hz, 1H), 7.01 (dd, J = 4.70, 7.84 Hz, 1H), 3.90-4.06 (m, 1H), 3.67-3.80 (m, 2H), 3.49-3.58 (m, 2H), 3.36-3.49 (m, 1H), 3.18-3.29 (m, 1H), 2.86-3.11 (m, 3H), 2.66 (s, 3H), 2.12-2.29 (m, 1H), 1.97-2.09 (m, 3H), 1.55-1.72 (m, 2H), 1.17-1.29 (s, 9H) ppm | 3-(4-piperidyl)-1H-pyrrolo[2,3-b]pyridine | General method D using tert-butyl 3-chlorosulfonylpyrrolidine-1-carboxylate, Cf using TFA, then G3 using N,2-dimethylpropan-2-amine. | N-tert-butyl-N-methyl-3-[4-(1H-pyrrolo[2,3-b]pyridin-3-yl)piperidin-1-yl]sulfonylpyrrolidine-1-carboxamide |
| 273 | 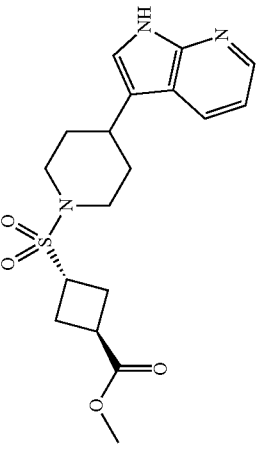 | 378.7 | ¹H NMR (300 MHz, DMSO-d6): δ = 11.37 (br. s., 1H), 8.17 (dd, J = 1.48, 4.62 Hz, 1H), 7.97 (d, J = 8.01 Hz, 1H), 7.24 (d, J = 2.26 Hz, 1H), 7.01 (dd, J = 4.62, 7.93 Hz, 1H), 3.98 (quin, J = 8.58 Hz, 1H), 3.67 (d, J = 12.02 Hz, 2H), 3.61 (s, 3H), 3.20 (quin, J = 9.14 Hz, 1H), 2.83-3.00 (m, 3H), 2.01 (d, J = 11.50 Hz, 2H), 1.53-1.72 (m, 2H) ppm | 3-(4-piperidyl)-1H-pyrrolo[2,3-b]pyridine | General method D using trans-methyl 3-chlorosulfonylcyclobutanecarboxylate (separation of isomers). | methyl cis-3-[4-(1H-pyrrolo[2,3-b]pyridin-3-yl)piperidin-1-yl]sulfonylcyclobutane-1-carboxylate |
| 274 | 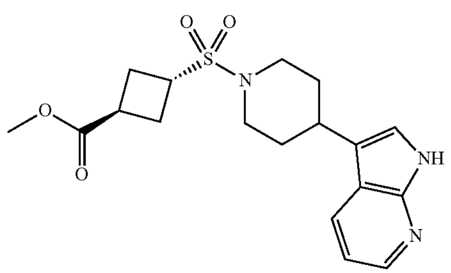 [SMILES: COC(=O)[C@H]1C[C@H](S(=O)(=O)N2CCC(c3c[nH]c4ncccc34)CC2)C1] | 378.7 | ¹H NMR (300 MHz, DMSO-d6): δ = 11.36 (br. s., 1H), 8.17 (d, J = 3.66 Hz, 1H), 7.96 (d, J = 7.84 Hz, 1H), 7.24 (d, J = 2.26 Hz, 1H), 7.01 (dd, J = 4.53, 7.84 Hz, 1H), 4.02 (quin, J = 7.93 Hz, 1H), 3.70 (d, J = 12.02 Hz, 2H), 3.64 (s, 3H), 3.18-3.29 (m, 1H), 2.85-3.02 (m, 3H), 2.53-2.63 (m, 4H), 2.00 (d, J = 11.84 Hz, 2H), 1.61 (dq, J = 3.66, 12.31 Hz, 2H) ppm | 3-(4-piperidyl)-1H-pyrrolo[2,3-b]pyridine | General method D using trans-methyl 3-chlorosulfonylcyclobutanecarboxylate (separation of isomers). | methyl trans-3-[4-(1H-pyrrolo[2,3-b]pyridin-3-yl)piperidin-1-yl]sulfonylcyclobutane-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 275 | 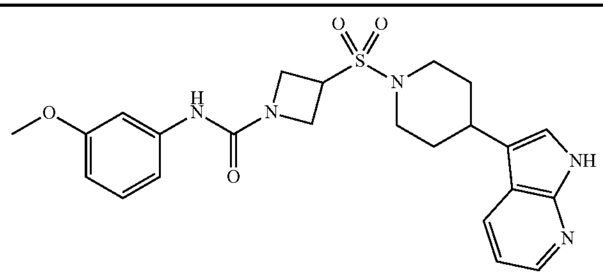 | 470.8 | ¹H NMR (300 MHz, DMSO-d6): δ = 11.38 (br. s., 1H), 8.61 (s, 1H), 8.17 (d, J = 3.66 Hz, 1H), 7.98 (d, J = 7.66 Hz, 1H), 7.25 (d, J = 2.09 Hz, 1H), 7.08-7.18 (m, 2H), 6.96-7.07 (m, 2H), 6.46-6.60 (m, 1H), 4.32-4.47 (m, 1H), 4.21-4.32 (m, 2H), 4.04-4.19 (m, 2H), 3.75 (d, J = 11.84 Hz, 2H), 3.69 (s, 3H), 2.83-3.12 (m, 3H), 2.03 (d, J = 12.02 Hz, 2H), 1.52-1.76 (m, 2H) ppm | 3-(4-piperidyl)-1H-pyrrolo[2,3-b]pyridine | General method D using tert-butyl 3-chlorosulfonylaze-tidine-1-carboxylate, Cf using TFA, then G2 using 1-isocyanato-3-methoxy-benzene. | N-(3-methoxyphenyl)-3-[4-(1H-pyrrolo[2,3-b]pyridin-3-yl)piperidin-1-yl]sulfonylaze-tidine-1-carboxamide |
| 276 | 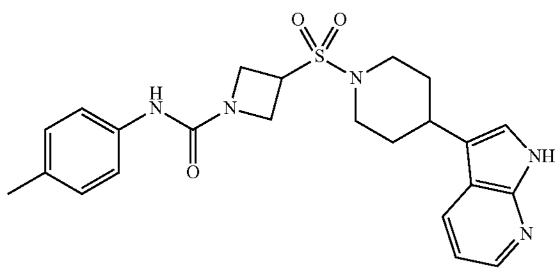 [SMILES: Cc1ccc(NC(=O)N2CC(S(=O)(=O)N3CCC(c4c[nH]c5ncccc45)CC3)C2)cc1] | 454.8 | ¹H NMR (300 MHz, DMSO-d6): δ = 11.37 (br. s., 1H), 8.53 (s, 1H), 8.13-8.21 (m, 1H), 7.97 (d, J = 6.79 Hz, 1H), 7.34 (d, J = 8.36 Hz, 2H), 7.24 (d, J = 2.26 Hz, 1H), 6.97-7.08 (m, 3H), 4.32-4.44 (m, 1H), 4.20-4.31 (m, 2H), 4.05-4.16 (m, 2H), 3.75 (d, J = 12.37 Hz, 2H), 2.84-3.09 (m, 3H), 2.21 (s, 3H), 2.03 (d, J = 11.15 Hz, 2H), 1.55-1.73 (m, 2H) ppm | 3-(4-piperidyl)-1H-pyrrolo[2,3-b]pyridine | General method D using tert-butyl 3-chlorosulfonylaze-tidine-1-carboxylate, Cf using TFA, then G2 using 1-isocyanato-4-methyl-benzene. | N-(4-methylphenyl)-3-[4-(1H-pyrrolo[2,3-b]pyridin-3-yl)piperidin-1-yl]sulfonylaze-tidine-1-carboxamide |
| 277 | 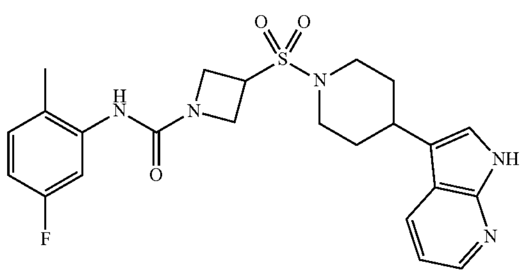 [SMILES: Cc1ccc(F)cc1NC(=O)N1CC(S(=O)(=O)N2CCC(c3c[nH]c4ncccc34)CC2)C1] | 472.8 | ¹H NMR (300 MHz, DMSO-d6): δ = 11.37 (br. s., 1H), 8.17 (d, J = 3.14 Hz, 1H), 8.05 (s, 1H), 7.98 (d, J = 7.14 Hz, 1H), 7.13-7.30 (m, 3H), 7.01 (dd, J = 4.70, 7.84 Hz, 1H), 6.85 (dt, J = 2.79, 8.45 Hz, 1H), 4.34-4.46 (m, 1H), 4.24-4.34 (m, 2H), 4.09-4.19 (m, 2H), 3.75 (d, J = 11.67 Hz, 2H), 2.86-3.09 (m, 3H), 2.16 (s, 3H), 2.03 (d, J = 11.32 Hz, 2H), 1.55-1.74 (m, 2H) ppm | 3-(4-piperidyl)-1H-pyrrolo[2,3-b]pyridine | General method D using tert-butyl 3-chlorosulfonylaze-tidine-1-carboxylate, Cf using TFA, then G2 using 4-fluoro-2-isocyanato-1-methyl-benzene. | N-(5-fluoro-2-methylphenyl)-3-[4-(1H-pyrrolo[2,3-b]pyridin-3-yl)piperidin-1-yl]sulfonylaze-tidine-1-carboxamide |

| Cpd # | Structure | MS (m/z, ES+) | δ NMR Data | Starting Int/Cpd# | Sequence of Methods | Chemical Name |
|---|---|---|---|---|---|---|
| 278 | 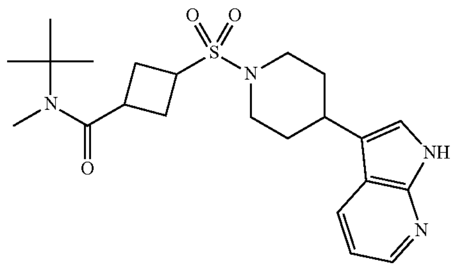 [SMILES: CN(C(=O)C1CC(S(=O)(=O)N2CCC(c3c[nH]c4ncccc34)CC2)C1)C(C)(C)C] | 433.9 | ¹H NMR (300 MHz, DMSO-d6) was recorded. Mixture of cis-and trans-configuration | 3-(4-piperidyl)-1H-pyrrolo[2,3-b]pyridine | General method D using trans-methyl 3-chlorosulfonylcyclobutanecarboxylate, V using NaOH, then I5 using N,2-dimethylpropan-2-amine. | N-tert-butyl-N-methyl-3-[4-(1H-pyrrolo[2,3-b]pyridin-3-yl)piperidin-1-yl]sulfonylcyclobutane-1-carboxamide |
| 279 | 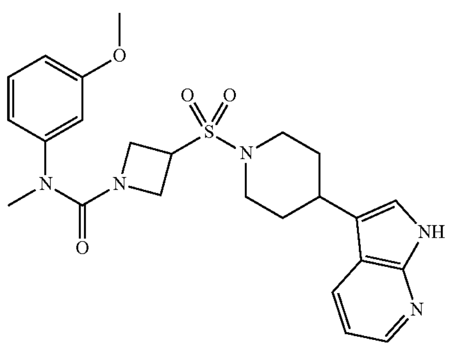 [SMILES: COc1cccc(N(C)C(=O)N2CC(S(=O)(=O)N3CCC(c4c[nH]c5ncccc45)CC3)C2)c1] | 484.8 | ¹H NMR (300 MHz, DMSO-d6): δ = 11.36 (s, 1H), 8.16 (dd, J = 1.57, 4.70 Hz, 1H), 7.95 (d, J = 6.79 Hz, 1H), 7.27-7.35 (m, 1H), 7.21 (d, J = 2.61 Hz, 1H), 7.00 (dd, J = 4.70, 7.84 Hz, 1H), 6.78-6.89 (m, 3H), 4.11-4.23 (m, 1H), 3.75 (s, 4H), 3.67-3.73 (m, 3H), 3.57-3.66 (m, 2H), 3.13 (s, 3H), 2.89 (t, J = 11.50 Hz, 3H), 1.97 (d, J = 11.50 Hz, 2H), 1.45-1.64 (m, 2H) ppm | 3-(4-piperidyl)-1H-pyrrolo[2,3-b]pyridine | General method D using tert-butyl 3-chlorosulfonylazetidine-1-carboxylate, E using 4-methylbenzenesulfonyl chloride, Cf using TFA, G2 using 1-isocyanato-3-methoxy-benzene, W using CH₃I, then F using Cs₂CO₃. | N-(3-methoxyphenyl)-N-methyl-3-[4-(1H-pyrrolo[2,3-b]pyridin-3-yl)piperidin-1-yl]sulfonylazetidine-1-carboxamide |
| 280 | 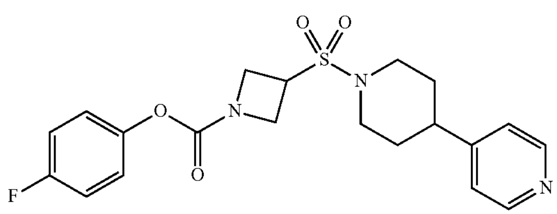 [SMILES: O=C(Oc1ccc(F)cc1)N1CC(S(=O)(=O)N2CCC(c3ccncc3)CC2)C1] | 420.8 | ¹H NMR (600 MHz, CHLOROFORM-d) δ 8.69 (d, J = 5.69 Hz, 2H), 7.74 (d, J = 5.69 Hz, 2H), 7.00-7.08 (m, 4H), 4.25-4.55 (m, 4H), 4.02-4.13 (m, 3H), 2.94-3.06 (m, 3H), 2.04 (d, J = 12.65 Hz, 2H), 1.87 (dq, J = 3.26, 12.55 Hz, 2H) ppm | 4-(4-piperidyl)pyridine | General method D using tert-butyl 3-chlorosulfonylazetidine-1-carboxylate, Cf using TFA, H1 using 4-fluorophenyl chloroformate | (4-fluorophenyl) 3-(4-pyridin-4-ylpiperidin-1-yl)sulfonylazetidine-1-carboxylate |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 281 | 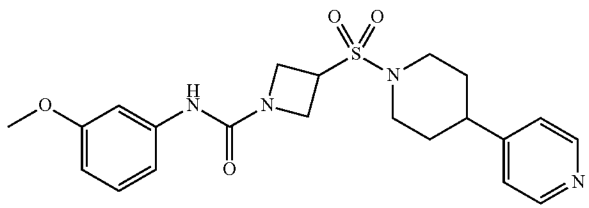 [SMILES: COc1cccc(NC(=O)N2CC(S(=O)(=O)N3CCC(c4ccncc4)CC3)C2)c1] | 431.8 | ¹H NMR (500 MHz, DMSO-d6) δ 8.62 (s, 1H), 8.44-8.47 (m, 2H), 7.28 (d, J = 5.80 Hz, 2H), 7.17 (t, J = 2.14 Hz, 1H), 7.14 (t, J = 8.28 Hz, 1H), 7.04-7.08 (m, 1H), 4.34-4.41 (m, 1H), 4.28 (t, J = 8.54 Hz, 2H), 4.11 (dd, J = 5.49, 9.16 Hz, 2H), 3.78 (d, J = 12.21 Hz, 2H), 3.70 (s, 3H), 2.96 (dt, J = 1.45, 12.60 Hz, 2H), 2.71 (tt, J = 3.09, 12.15 Hz, 1H), 1.87 (d, J = 11.90 Hz, 2H), 1.61 (dq, J = 3.97, 12.51 Hz, 2H) ppm | 4-(4-piperidyl) pyridine | General method D using tert-butyl 3-chlorosulfonylaze-tidine-1-carboxylate, Cf using TFA, G2 using 3-methoxyphenyl isocyanate | N-(3-methoxyphenyl)-3-(4-pyridin-4-yl)piperidin-1-yl)sulfonyl)aze-tidine-1-carboxamide |
| 282 | 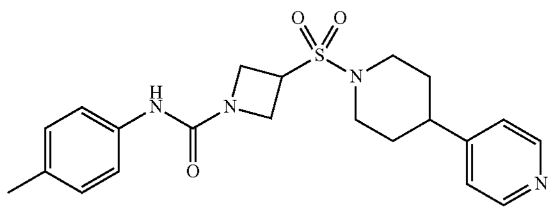 [SMILES: Cc1ccc(NC(=O)N2CC(S(=O)(=O)N3CCC(c4ccncc4)CC3)C2)cc1] | 415.8 | ¹H NMR (500 MHz, DMSO-d6) δ 8.54 (s, 1H), 8.45-8.47 (m, 2H), 7.36 (d, J = 8.54 Hz, 2H), 7.27 (d, J = 6.10 Hz, 2H), 7.05 (d, J = 8.24 Hz, 2H), 4.33-4.41 (m, 1H), 4.27 (t, J = 8.70 Hz, 2H), 4.10 (dd, J = 5.34, 9.00 Hz, 2H), 3.78 (d, J = 12.21 Hz, 2H), 2.96 (td, J = 1.46, 12.58 Hz, 2H), 2.71 (tt, J = 3.13, 12.19 Hz, 1H), 2.23 (s, 3H), 1.87 (d, J = 11.90 Hz, 2H), 1.61 (dq, J = 3.81, 12.56 Hz, 2H) ppm | 4-(4-piperidyl) pyridine | General method D using tert-butyl 3-chlorosulfonylaze-tidine-1-carboxylate, Cf using TFA, G2 using p-tolyl isocyanate | N-(4-methylphenyl)-3-(4-pyridin-4-yl)piperidin-1-yl)sulfonyl)aze-tidine-1-carboxamide |
| 283 | 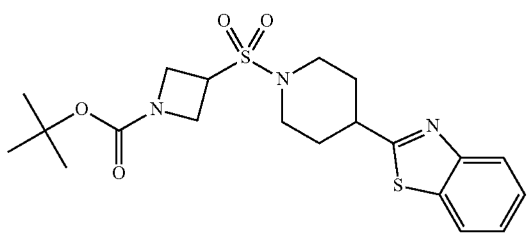 [SMILES: CC(C)(C)OC(=O)N1CC(S(=O)(=O)N2CCC(c3nc4ccccc4s3)CC2)C1] | 438.86 | ¹H NMR (500 MHz, DMSO-d6): δ = 8.08 (d, J = 7.93 Hz, 1H), 7.96 (d, J = 7.93 Hz, 1H), 7.47-7.53 (m, 1H), 7.39-7.45 (m, 1H), 4.29-4.37 (m, 1H), 4.17 (br. s., 2H), 3.98 (br. s., 2H), 3.73 (d, J = 12.51 Hz, 2H), 3.31 (m, 1H), 3.04 (t, J = 11.14 Hz, 2H), 2.21 (d, J = 11.29 Hz, 2H), 1.71-1.83 (m, 2H), 1.38 (s, 9H) ppm | 2-(4-piperidyl)-1,3-benzo-thiazole | General method D using tert-butyl 3-chlorosulfonylaze-tidine-1-carboxylate | tert-butyl 3-[4-(1,3-benzothiazol-2-yl)piperidin-1-yl]sulfonyl)aze-tidine-1-carboxylate |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 284 | 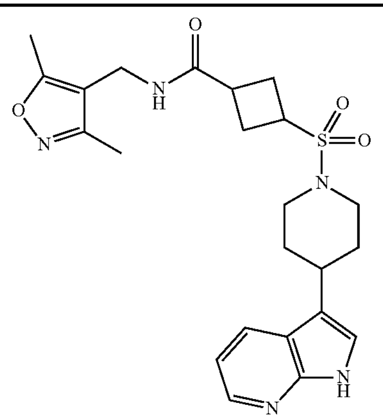 | 472.8 | 1H NMR (300 MHz, DMSO-d6) was recorded. Mixture of cis- and trans-configuration. | 3-(4-piperidyl)-1H-pyrrolo[2,3-b]pyridine | General method D using trans-methyl 3-chlorosulfonylcyclobutanecarboxylate, V using NaOH, then I5 using (3,5-dimethylisoxazol-4-yl)methanamine. | N-[(3,5-dimethyl-1,2-oxazol-4-yl)methyl]-3-[4-(1H-pyrrolo[2,3-b]pyridin-3-yl)piperidin-1-yl]sulfonylcyclobutane-1-carboxamide |
| 285 | 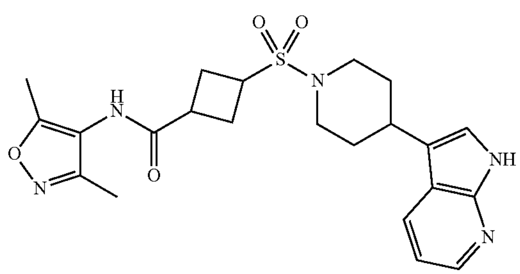 [SMILES: Cc1noc(C)c1NC(=O)C1CC(S(=O)(=O)N2CCC(c3c[nH]c4ncccc34)CC2)C1] | 458.8 | 1H NMR (300 MHz, DMSO-d6) was recorded. Mixture of cis- and trans-configuration. | 3-(4-piperidyl)-1H-pyrrolo[2,3-b]pyridine | General method D using trans-methyl 3-chlorosulfonylcyclobutanecarboxylate, V using NaOH, then I5 using 3,5-dimethylisoxazol-4-amine. | N-(3,5-dimethyl-1,2-oxazol-4-yl)-3-[4-(1H-pyrrolo[2,3-b]pyridin-3-yl)piperidin-1-yl]sulfonylcyclobutane-1-carboxamide |
| 286 | 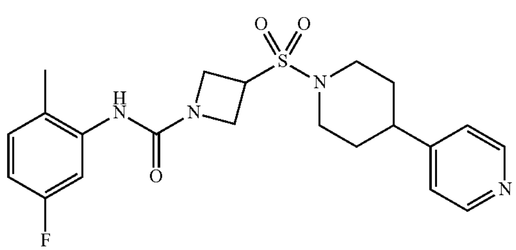 [SMILES: Cc1ccc(F)cc1NC(=O)N1CC(S(=O)(=O)N2CCC(c3ccncc3)CC2)C1] | 433.7 | 1H NMR (400 MHz, DMSO-d6) δ 8.43-8.48 (m, 2H), 8.06 (s, 1H), 7.24-7.30 (m, 3H), 7.18 (dd, J = 7.09, 7.95 Hz, 1H), 6.85 (dt, J = 2.87, 8.41 Hz, 1H), 4.35-4.44 (m, 1H), 4.29 (t, J = 8.62 Hz, 2H), 4.12 (dd, J = 5.44, 9.11 Hz, 2H), 3.77 (d, J = 12.23 Hz, 2H), 2.95 (dt, J = 1.96, 12.29 Hz, 2H), 2.70 (tt, J = 3.38, 12.13 Hz, 1H), 2.16 (s, 3H), 1.86 (d, J = 11.25 Hz, 2H), 1.60 (dq, J = 3.85, 12.53 Hz, 2H) ppm | 4-(4-piperidyl)pyridine | General method D using tert-butyl 3-chlorosulfonylazetidine-1-carboxylate, Cf using TFA, G2 using 5-fluoro-2-methylphenyl isocyanate | N-(5-fluoro-2-methylphenyl)-3-(4-pyridin-4-ylpiperidin-1-yl)sulfonylazetidine-1-carboxamide |

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 287 | 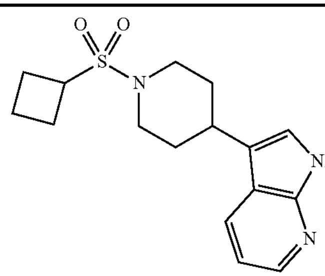 | 320.69 | 1H NMR (300 MHz, DMSO-d6): δ = 11.36 (br. s., 1H), 8.17 (d, J = 3.83 Hz, 1H), 7.96 (d, J = 7.66 Hz, 1H), 7.24 (br. s., 1H), 7.01 (dd, J = 4.62, 7.58 Hz, 1H), 4.03 (quin, J = 8.23 Hz, 1H), 3.67 (d, J = 11.15 Hz, 2H), 2.82-2.99 (m, 3H), 2.16-2.42 (m, 4H), 1.81-2.09 (m, 4H), 1.51-1.72 (m, 2H) ppm | 3-(4-piperidyl)-1H-pyrrolo[2,3-b]pyridine | General method D using cyclobutanesulfonyl chloride | 3-(1-cyclobutylsulfonylpiperidin-4-yl)-1H-pyrrolo[2,3-b]pyridine |
| 289 | 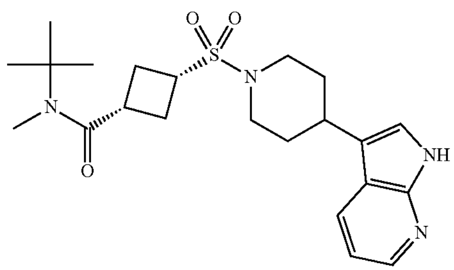 | 433.8 | 1H NMR (600 MHz, DMSO-d6): δ = 11.36 (br. s., 1H), 8.17 (d, J = 3.67 Hz, 1H), 7.97 (d, J = 7.52 Hz, 1H), 7.24 (d, J = 1.83 Hz, 1H), 7.01 (dd, J = 4.58, 7.89 Hz, 1H), 3.87 (quin, J = 8.67 Hz, 1H), 3.63-3.71 (m, 2H), 3.24 (quin, J = 8.99 Hz, 1H), 2.85-2.98 (m, 3H), 2.72-2.77 (m, 3H), 2.35-2.45 (m, 4H), 2.01 (d, J = 11.74 Hz, 2H), 1.57-1.68 (m, 2H), 1.32 (s, 9H) ppm | 3-(4-piperidyl)-1H-pyrrolo[2,3-b]pyridine | General method D using trans-methyl 3-chlorosulfonylcyclobutanecarboxylate, V using NaOH, then IS using N,2-dimethylpropan-2-amine (separation of isomers). | cis-N-tert-butyl-N-methyl-3-[4-(1H-pyrrolo[2,3-b]pyridin-3-yl)piperidin-1-yl]sulfonylcyclobutane-1-carboxamide |
| 290 | 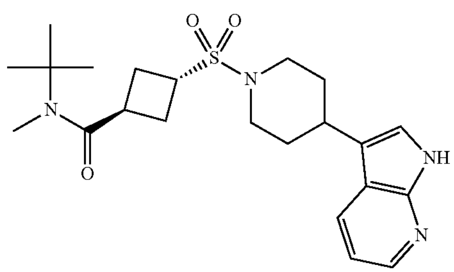 [SMILES: CN(C(=O)[C@H]1C[C@H](S(=O)(=O)N2CCC(c3c[nH]c4ncccc34)CC2)C1)C(C)(C)C] | 433.8 | 1H NMR (600 MHz, DMSO-d6): δ = 11.36 (br. s., 1H), 8.17 (d, J = 3.48 Hz, 1H), 7.97 (d, J = 7.52 Hz, 1H), 7.24 (d, J = 2.38 Hz, 1H), 7.01 (dd, J = 4.59, 7.89 Hz, 1H), 3.85 (quin, J = 7.79 Hz, 1H), 3.71 (d, J = 12.65 Hz, 2H), 3.34-3.41 (m, 1H), 2.87-2.98 (m, 3H), 2.72 (s, 3H), 2.51-2.52 (m, 4H), 2.00 (d, J = 11.37 Hz, 2H), 1.62 (dq, J = 3.85, 12.47 Hz, 2H), 1.34 (s, 9H) ppm | 3-(4-piperidyl)-1H-pyrrolo[2,3-b]pyridine | General method D using trans-methyl 3-chlorosulfonylcyclobutanecarboxylate, V using NaOH, then IS using N,2-dimethylpropan-2-amine (separation of isomers). | trans-N-tert-butyl-N-methyl-3-[4-(1H-pyrrolo[2,3-b]pyridin-3-yl)piperidin-1-yl]sulfonylcyclobutane-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 291 | 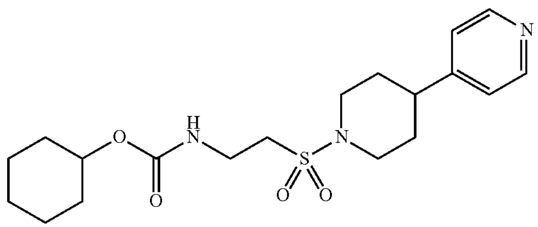 [SMILES: O=C(NCCS(=O)(=O)N1CCC(c2ccncc2)CC1)OC1CCCCC1] | 396.8 | ¹H NMR (600 MHz, CHLOROFORM-d) δ 8.52 (d, J = 5.69 Hz, 2H), 7.11 (d, J = 5.87 Hz, 2H), 5.26 (br. s., 1H), 4.62 (br. s., 1H), 3.93 (d, J = 12.44 Hz, 2H), 3.64 (q, J = 6.05 Hz, 2H), 3.14 (t, J = 5.96 Hz, 2H), 2.88 (dt, J = 1.83, 12.29 Hz, 2H), 2.61 (tt, J = 3.53, 12.24 Hz, 1H), 1.94 (d, J = 11.37 Hz, 2H), 1.82-1.87 (m, 2H), 1.79 (qd, J = 3.92, 12.69 Hz, 2H), 1.66-1.72 (m, 2H), 1.49-1.54 (m, 1H), 1.28-1.41 (m, 4H), 1.18-1.25 (m, 1H) ppm | 4-(4-piperidyl) pyridine | General method D using 2-phthalimidoethane sulfonyl chloride, Z, H1 using cyclohexyl chloroformate | cyclohexyl N-[2-[4-(4-pyridin-4-ylpiperidin-1-yl)sulfonylethyl] carbamate |
| 292 | 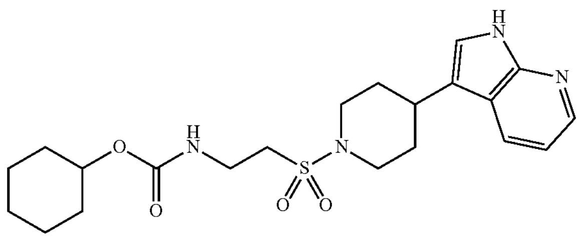 [SMILES: O=C(NCCS(=O)(=O)N1CCC(c2c[nH]c3ncccc23)CC1)OC1CCCCC1] | 435.8 | ¹H NMR (600 MHz, CHLOROFORM-d) δ 9.05 (br. s., 1H), 8.29 (dd, J = 1.17, 4.87 Hz, 1H), 7.91 (d, J = 7.89 Hz, 1H), 7.07 (s, 1H), 7.06 (dd, J = 4.70, 7.88 Hz, 1H), 5.31 (br. s., 1H), 4.62 (br. s., 1H), 3.92 (d, J = 12.29 Hz, 2H), 3.66 (q, J = 5.87 Hz, 2H), 3.15 (t, J = 5.96 Hz, 2H), 2.88-2.97 (m, 3H), 2.11 (d, J = 11.00 Hz, 2H), 1.80-1.91 (m, 4H), 1.66-1.73 (m, 2H), 1.48-1.55 (m, 1H), 1.28-1.41 (m, 4H), 1.16-1.26 (m, 1H) ppm | 3-(4-piperidyl)-1H-pyrrolo[2,3-b]pyridine | General method D using 2-phthalimidoethane sulfonyl chloride, Z, H1 using cyclohexyl chloroformate | cyclohexyl N-[2-[4-(1H-pyrrolo[2,3-b]pyridin-3-yl)piperidin-1-yl]sulfonylethyl] carbamate |
| 293 | 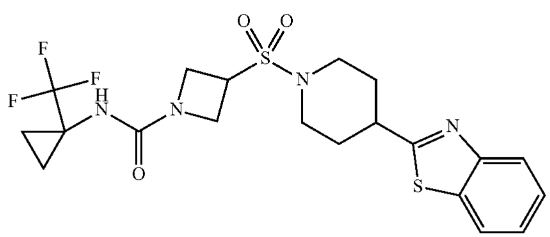 [SMILES: O=C(NC1(C(F)(F)F)CC1)N1CC(S(=O)(=O)N2CCC(c3nc4ccccc4s3)CC2)C1] | 489.7 | ¹H NMR (300 MHz, DMSO-d6): δ = 8.07 (d, J = 7.84 Hz, 1H), 7.95 (d, J = 8.36 Hz, 1H), 7.45-7.54 (m, 1H), 7.37-7.45 (m, 2H), 4.26-4.38 (m, 1H), 4.10 (t, J = 8.62 Hz, 2H), 3.90-3.99 (m, 2H), 3.72 (d, J = 12.89 Hz, 2H), 2.96-3.11 (m, 2H), 2.19 (d, J = 10.97 Hz, 2H), 1.66-1.84 (m, 2H), 1.12-1.23 (m, 2H), 0.93-1.03 (m, 2H) ppm | 2-(4-piperidyl)-1,3-benzothiazole | General method D using tert-butyl 3-chlorosulfonylazetidine-1-carboxylate, Cf using TFA, then G2 using 1-isocyanato-1-(trifluoromethyl)cyclopropane. | 3-[4-(1,3-benzothiazol-2-yl)piperidin-1-yl]sulfonyl-N-[1-(trifluoromethyl)cyclopropyl] azetidine-1-carboxamide |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 294 | 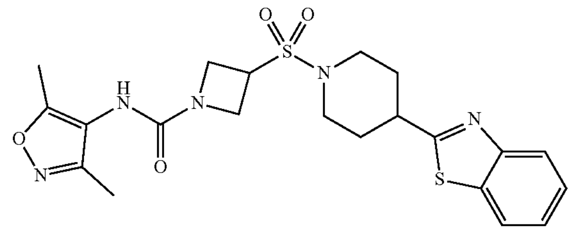 [SMILES: Cc1noc(C)c1NC(=O)N1CC(S(=O)(=O)N2CCC(c3nc4ccccc4s3)CC2)C1] | 476.7 | $^1$H NMR (300 MHz, DMSO-d6): δ = 8.05-8.10 (m, 1H), 8.02 (s, 1H), 7.92-7.98 (m, 1H), 7.49 (dt, J = 1.31, 7.62 Hz, 1H), 7.37-7.45 (m, 1H), 4.33-4.45 (m, 1H), 4.24 (t, J = 8.62 Hz, 2H), 4.02-4.10 (m, 2H), 3.75 (d, J = 12.37 Hz, 2H), 3.00-3.14 (m, 2H), 2.16-2.28 (m, 2H), 2.21 (s, 3H), 2.05 (s, 3H), 1.78 (d, J = 8.88 Hz, 2H) ppm | 2-(4-piperidyl)-1,3-benzothiazole | General method D using tert-butyl 3-chlorosulfonylazetidine-1-carboxylate, Cf using TFA, then G2 using 4-isocyanato-3,5-dimethyl-isoxazole. | 3-[4-(1,3-benzothiazol-2-yl)piperidin-1-yl]sulfonyl-N-(3,5-dimethyl-1,2-oxazol-4-yl)azetidine-1-carboxamide |
| 295 | 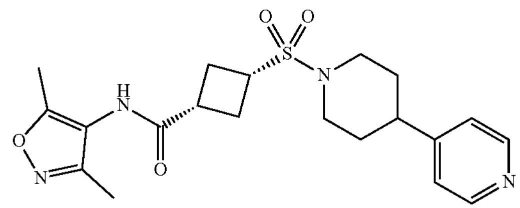 [SMILES: Cc1noc(C)c1NC(=O)[C@H]1C[C@@H](S(=O)(=O)N2CCC(c3ccncc3)CC2)C1] | 419.7 | $^1$H NMR (600 MHz, CHLOROFORM-d) δ 8.48-8.55 (m, 2H), 7.10-7.12 (m, 2H), 7.06 (br.s., 1H), 3.93-4.00 (m, 2H), 3.81 (quin, J = 8.57 Hz, 1H), 3.18 (quin, J = 8.89 Hz, 1H), 2.95 (dt, J = 2.29, 12.43 Hz, 2H), 2.78-2.85 (m, 2H), 2.66-2.72 (m, 2H), 2.62 (tt, J = 3.65, 12.22 Hz, 1H), 2.30 (s, 3H), 2.17 (s, 3H), 1.91 (d, J = 13.36 Hz, 2H), 1.78 (dq, J = 4.03, 12.65 Hz, 2H) ppm | 4-(4-piperidyl)pyridine | General method D using methyl 3-chlorosulfonylcyclobutanecarboxylate,V, then II using 3,5-dimethylisoxazol-4-amine. | cis-N-(3,5-dimethyl-1,2-oxazol-4-yl)-3-(4-pyridin-4-ylpiperidin-1-yl)sulfonylcyclobutane-1-carboxamide |
| 296 | 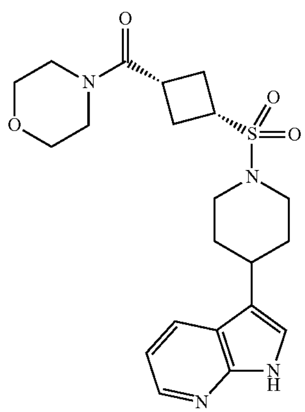 [SMILES: O=C([C@H]1C[C@@H](S(=O)(=O)N2CCC(c3c[nH]c4ncccc34)CC2)C1)N1CCOCC1] | 433.7 | $^1$H NMR (600 MHz, DMSO-d6): δ = 11.36 (s, 1H), 8.17 (dd, J = 1.47, 4.77 Hz, 1H), 7.97 (dd, J = 1.19, 7.79 Hz, 1H), 7.24 (d, J = 2.20 Hz, 1H), 7.01 (dd, J = 4.77, 7.89 Hz, 1H), 3.87-3.96 (m, 1H), 3.68 (d, J = 11.92 Hz, 2H), 3.53 (t, J = 4.86 Hz, 4H), 3.39-3.45 (m, 2H), 3.25-3.30 (m, 1H), 2.86-2.98 (m, 3H), 2.50-2.55 (m, 4H), 2.39-2.46 (m, 2H), 2.01 (d, J = 10.82 Hz, 2H), 1.63 (dq, J = 3.94, 12.44 Hz, 2H) ppm | 3-(4-piperidyl)-1H-pyrrolo[2,3-b]pyridine | General method D using trans-methyl 3-chlorosulfonylcyclobutanecarboxylate, V using NaOH, then IS using morpholine (separation of isomers). | cis-morpholin-4-yl-[3-[4-(1H-pyrrolo[2,3-b]pyridin-3-yl)piperidin-1-yl]sulfonylcyclobutyl]methanone |

| Cpd # | Structure | MS (m/z, ES +) | δ NMR Data | Starting Int/Cpd# | Sequence of Methods | Chemical Name |
|---|---|---|---|---|---|---|
| 297 | 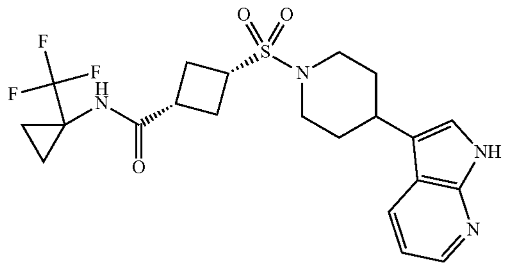 [SMILES: O=C(NC1(C(F)(F)F)CC1)[C@H]1C[C@@H](S(=O)(=O)N2CCC(c3c[nH]c4ncccc34)CC2)C1] | 471.7 | ¹H NMR (600 MHz, DMSO-d6): δ = 11.35 (s, 1H), 8.60 (s, 1H), 8.17 (dd, J = 1.56, 4.68 Hz, 1H), 7.98 (dd, J = 1.19, 7.79 Hz, 1H), 7.24 (d, J = 2.20 Hz, 1H), 7.01 (dd, J = 4.77, 7.89 Hz, 1H), 3.91-3.98 (m, 1H), 3.66 (d, J = 12.29 Hz, 2H), 2.86-2.99 (m, 3H), 2.30-2.45 (m, 4H), 2.00 (d, J = 11.55 Hz, 2H), 1.63 (dq, J = 3.94, 12.44 Hz, 2H), 1.18-1.23 (m, 2H), 0.96-1.01 (m, 2H) ppm | 3-(4-piperidyl)-1H-pyrrolo[2,3-b]pyridine | General method D using trans-methyl 3-chlorosulfonylcyclobutanecarboxylate, V using NaOH, then I5 using 1-(trifluoromethyl)cyclopropanamine (separation of isomers). | cis-3-[4-(1H-pyrrolo[2,3-b]pyridin-3-yl)piperidin-1-yl]sulfonyl-N-[1-(trifluoromethyl)cyclopropyl]cyclobutane-1-carboxamide |
| 298 | 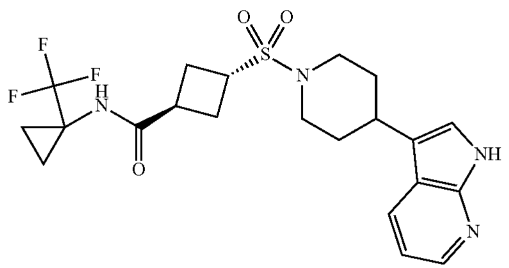 [SMILES: O=C(NC1(C(F)(F)F)CC1)[C@H]1C[C@H](S(=O)(=O)N2CCC(c3c[nH]c4ncccc34)CC2)C1] | 471.7 | ¹H NMR (600 MHz, DMSO-d6): δ = 11.36 (s, 1H), 8.59-8.65 (m, 1H), 8.17 (dd, J = 1.56, 4.68 Hz, 1H), 7.96 (dd, J = 1.47, 7.89 Hz, 1H), 7.23 (d, J = 1.83 Hz, 1H), 7.01 (dd, J = 4.68, 7.79 Hz, 1H), 3.89-3.97 (m, 1H), 3.69 (d, J = 12.10 Hz, 2H), 3.10 (quin, J = 7.66 Hz, 1H), 2.87-2.99 (m, 3H), 2.42-2.47 (m, 4H), 2.00 (d, J = 10.64 Hz, 2H), 1.61 (dq, J = 4.13, 12.50 Hz, 2H), 1.18-1.24 (m, 2H), 0.98-1.03 (m, 2H) ppm | 3-(4-piperidyl)-1H-pyrrolo[2,3-b]pyridine | General method D using trans-methyl 3-chlorosulfonylcyclobutanecarboxylate, V using NaOH, then I5 using 1-(trifluoromethyl)cyclopropanamine (separation of isomers). | trans-3-[4-(1H-pyrrolo[2,3-b]pyridin-3-yl)piperidin-1-yl]sulfonyl-N-[1-(trifluoromethyl)cyclopropyl]cyclobutane-1-carboxamide |
| 299 | 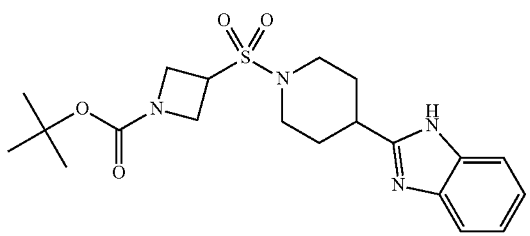 [SMILES: CC(C)(C)OC(=O)N1CC(S(=O)(=O)N2CCC(c3nc4ccccc4[nH]3)CC2)C1] | 421.7 | ¹H NMR (500 MHz, DMSO-d6): δ = 12.20 (br.s, 1H), 7.44-7.50 (m, 2H), 7.08-7.14 (m, 2H), 4.25-4.40 (m, 1H), 4.18 (br. s., 2H), 3.98 (br. s., 2H), 3.71 (d, J = 12.51 Hz, 2H), 3.02 (t, J = 11.14 Hz, 3H), 2.04-2.17 (m, 2H), 1.72-1.85 (m, 2H), 1.39 (s, 9H) ppm | 2-(4-piperidyl)-1H-benzimidazole | General method D using tert-butyl 3-chlorosulfonylazetidine-1-carboxylate. | tert-butyl 3-[4-(1H-benzimidazol-2-yl)piperidin-1-yl]sulfonylazetidine-1-carboxylate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 300 | 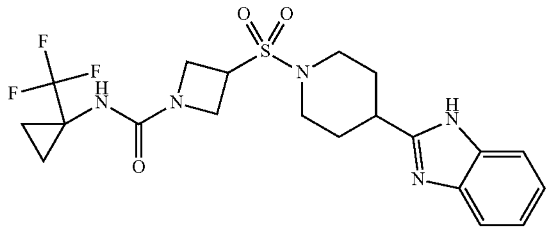 [SMILES: O=C(NC1(C(F)(F)F)CC1)N1CC(S(=O)(=O)N2CCC(c3nc4ccccc4[nH]3)CC2)C1] | 472.7 | ¹H NMR (300 MHz, DMSO-d6): δ = 12.21 (s, 1H), 7.48-7.57 (m, 1H), 7.36-7.44 (m, 2H), 7.05-7.18 (m, 2H), 4.25-4.39 (m, 1H), 4.11 (t, J = 8.62 Hz, 2H), 3.95 (dd, J = 5.57, 9.06 Hz, 2H), 3.69 (d, J = 12.19 Hz, 2H), 2.92-3.12 (m, 3H), 2.09 (d, J = 10.63 Hz, 2H), 1.68-1.87 (m, 2H), 1.13-1.24 (m, 2H), 0.94-1.03 (m, 2H) ppm | 2-(4-piperidyl)-1H-benzimidazole | General method D using tert-butyl 3-chlorosulfonylaze-tidine-1-carboxylat, Cf using TFA, then G2 using 1-isocyanato-1-(trifluoromethyl) cyclopropane. | 3-[4-(1H-benzimidazol-2-yl)piperidin-1-yl]sulfonyl-N-[1-(trifluoromethyl) cyclopropyl] azetidine-1-carboxamide |
| 301 | 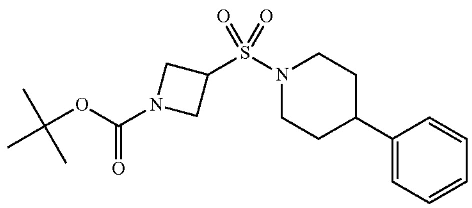 | 349.72 (M + H − 56)⁺ | ¹H NMR (300 MHz, DMSO-d6): d = 1.38 (s, 9 H), 1.58 (qd, J = 12.6, 4.4 Hz, 2 H), 1.82 (d, J = 11.0 Hz, 2 H), 2.56-2.74 (m, 1 H), 2.84-2.96 (m, 2H), 3.73 (d, J = 12.4 Hz, 2 H), 3.92-4.02 (m, 2 H), 4.17 (t, J = 8.3 Hz, 2 H), 4.25-4.37 (m, 1 H), 7.15-7.34 (m, 5H) ppm | 4-phenyl-piperidine | General method D using tert-butyl 3-chlorosulfonylaze-tidine-1-carboxylate | tert-butyl 3-(4-phenylpiperidin-1-yl)sulfonylaze-tidine-1-carboxylate |
| 302 | 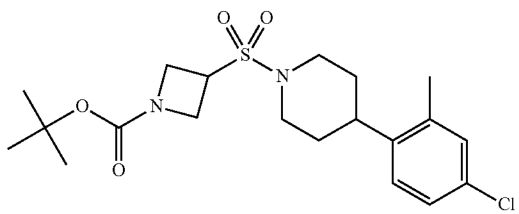 [SMILES: Cc1cc(Cl)ccc1C1CCN(S(=O)(=O)C2CN(C(=O)OC(C)(C)C)C2)CC1] | 373.66 (M + H − 56)⁺ | ¹H NMR (400 MHz, DMSO-d6): d = 1.35-1.40 (m, 9 H), 1.48-1.61 (m, 2H), 1.73 (d, J = 12.0 Hz, 2 H), 2.29 (s, 3 H), 2.76-2.86 (m, 1 H), 2.89-2.98 (m, 2 H), 3.72 (d, J = 12.6 Hz, 2 H), 3.98 (br. s., 2 H), 4.18 (br. s., 2 H), 4.26-4.35 (m, 1 H), 7.16-7.25 (m, 3H) ppm | 4-(4-chloro-2-methyl-phenyl) piperidine | General method D using tert-butyl 3-chlorosulfonylaze-tidine-1-carboxylate | tert-butyl 3-[4-(4-chloro-2-methylphenyl) piperidin-1-yl]sulfonylaze-tidine-1-carboxylate |
| 303 | 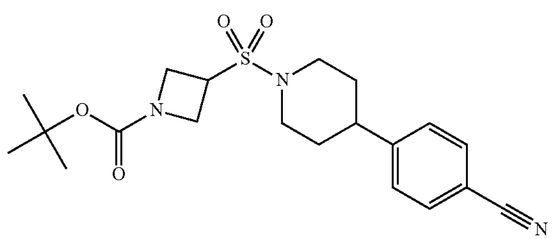 [SMILES: CC(C)(C)OC(=O)N1CC(S(=O)(=O)N2CCC(c3ccc(C#N)cc3)CC2)C1] | 350.66 (M + H − 56)⁺ | ¹H NMR (400 MHz, DMSO-d6): d = 1.38 (s, 9 H), 1.52-1.66 (m, 2 H), 1.83 (d, J = 11.5 Hz, 2 H), 2.71-2.80 (m, 1H), 2.86-2.95 (m, 2 H), 3.74 (d, J = 12.6 Hz, 2 H), 3.97 (br. s., 2 H), 4.18 (br. s., 2 H), 4.26-4.37 (m, 1 H), 7.47 (d, J = 8.2 Hz, 2 H), 7.73-7.80 (m, 2H) ppm | 4-(4-piperidyl) benzonitrile | General method D using tert-butyl 3-chlorosulfonylaze-tidine-1-carboxylate | tert-butyl 3-[4-(4-cyanophenyl) piperidin-1-yl]sulfonylaze-tidine-1-carboxylate |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 304 | 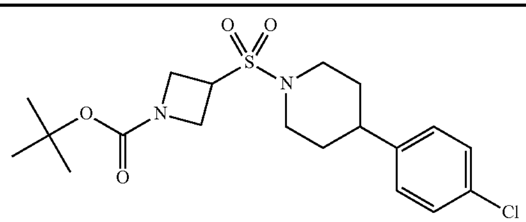 | 359.62 (M+H-56)+ | 1H NMR (400 MHz, DMSO-d6): d = 1.38 (s, 9 H), 1.49-1.63 (m, 2 H), 1.81 (d, J = 12.8 Hz, 2 H), 2.59-2.71 (m, 1H), 2.89 (t, J = 12.1 Hz, 2H), 3.72 (d, J = 11.4 Hz, 2 H), 3.97 (m, 2 H), 4.17 (br. s., 2 H), 4.30 (d, J = 6.7 Hz, 1 H), 7.21-7.39 (m, 4 H) ppm | 4-(4-chloro-phenyl)piperidine | General method D using tert-butyl 3-chlorosulfonylaze-tidine-1-carboxylate | tert-butyl 3-[4-(4-chlorophenyl)piperidin-1-yl]sulfonylaze-tidine-1-carboxylate |
| 305 | 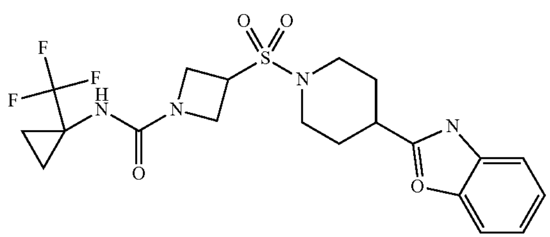 | 473.7 | 1H NMR (400 MHz, DMSO-d6): δ = 7.63-7.76 (m, 2H), 7.39-7.42 (m, 1H), 7.29-7.38 (m, 2H), 4.24-4.38 (m, 1H), 4.09 (t, J = 7.95 Hz, 2H), 3.89-3.96 (m, 2H), 3.65 (d, J = 9.05 Hz, 2H), 3.14-3.27 (m, 1H), 3.06 (t, J = 10.82 Hz, 2H), 2.18 (d, J = 13.45 Hz, 2H), 1.71-1.84 (m, 2H), 1.17 (br. s., 2H), 0.98 (br. s., 2H) ppm | 2-(4-piperidyl)-1,3-benzoxazole | General method D using tert-butyl 3-chlorosulfonylaze-tidine-1-carboxylate, Cf using TFA, then G2 using 1-isocyanato-1-(trifluoromethyl)cyclopropane. | 3-[4-(1,3-benzoxazol-2-yl)piperidin-1-yl]sulfonyl-N-[1-(trifluoromethyl)cyclopropyl]azetidine-1-carboxamide |
| 306 | 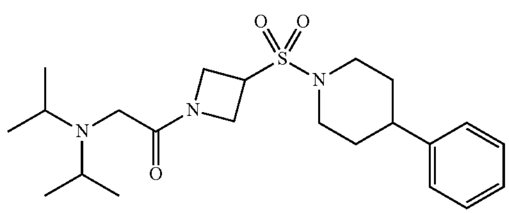 [SMILES: CC(C)N(CC(=O)N1CC(S(=O)(=O)N2CCC(c3ccccc3)CC2)C1)C(C)C] | 422.8 | 1H NMR (400 MHz, DMSO-d6): d = 0.96 (br. s., 12 H), 1.50-1.65 (m, 2 H), 1.83 (d, J = 13.6 Hz, 2 H), 2.65 (m, 1 H), 2.87-2.98 (m, 4 H), 3.06-3.21 (m, 2 H), 3.73 (d, J = 11.5 Hz, 2 H), 3.99 (m, 1 H), 4.12-4.21 (m, 1 H), 4.36 (m, 1 H), 4.48 (m, 1 H), 4.54-4.62 (m, 1 H), 7.12-7.37 (m, 5 H) ppm | 4-phenyl-piperidine | General method D using tert-butyl 3-chlorosulfonylaze-tidine-1-carboxylate, Cf using TFA, I1 using 2-(diisopropylamino)acetic acid | 2-[di(propan-2-yl)amino]-1-[3-(4-phenylpiperidin-1-yl)sulfonylaze-tidin-1-yl]ethanone |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 307 | 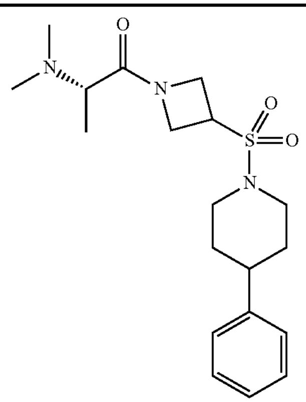 | 380.79 | ¹H NMR (400 MHz, DMSO-d₆): d = 1.00 (d, J = 7.3 Hz, 3 H), 1.59 (d, J = 12.5 Hz, 2 H), 1.83 (d, J = 12.2 Hz, 2 H), 2.14 (br. s., 6 H), 2.64 (br. s., 1 H), 2.86-2.98 (m, 2 H), 3.17 (br. s., 1 H), 3.74 (d, J = 12.1 Hz, 2 H), 4.00 (d, J = 4.2 Hz, 1H), 4.17 (t, J = 8.7 Hz, 1H), 4.37 (br. s., 2 H), 4.53 (d, J = 9.9 Hz, 1 H), 7.16-7.34 (m, 5 H) ppm | 4-phenylpiperidine | General method D using tert-butyl 3-chlorosulfonylazetidine-1-carboxylate, Cf using TFA, I1 using 2-(dimethylamino) propanoic acid | 2-(dimethylamino)-1-[3-(4-phenyl-piperidin-1-yl)sulfonylazetidin-1-yl]propan-1-one |
| 308 | 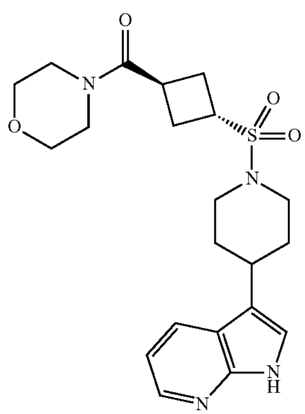 [SMILES: O=C([C@H]1C[C@H](S(=O)(=O)N2CCC(c3c[nH]c4ncccc34)CC2)C1)N1CCOCC1] | 433.7 | ¹H NMR (600 MHz, DMSO-d6): δ = 11.36 (br. s., 1H), 8.17 (dd, J = 4.58 Hz, 1H), 7.96 (dd, J = 1.10, 7.89 Hz, 1H), 7.24 (dd, J = 2.20 Hz, 1H), 7.01 (dd, J = 4.58, 7.89 Hz, 1H), 3.85-3.95 (m, 1H), 3.70 (d, J = 12.10 Hz, 2H), 3.50-3.56 (m, 4H), 3.39-3.47 (m, 3H), 3.23-3.29 (m, 2H), 2.86-2.99 (m, 3H), 2.52-2.62 (m, 4H), 2.00 (d, J = 11.19 Hz, 2H), 1.62 (dq, J = 3.94, 12.44 Hz, 2H) ppm | 3-(4-piperidyl)-1H-pyrrolo [2,3-b]pyridine | General method D using trans-methyl 3-chlorosulfonylcyclobutanecarboxylate, V using NaOH, then I5 using morpholine (separation of isomers). | trans-morpholin-4-yl-[3-[4-(1H-pyrrolo [2,3-b]pyridin-3-yl)piperidin-1-yl]sulfonyl-cyclobutyl] methanone |

| Cpd # | Structure | MS (m/z, ES +) | δ NMR Data | Starting Int/Cpd# | Sequence of Methods | Chemical Name |
|---|---|---|---|---|---|---|
| 309 | 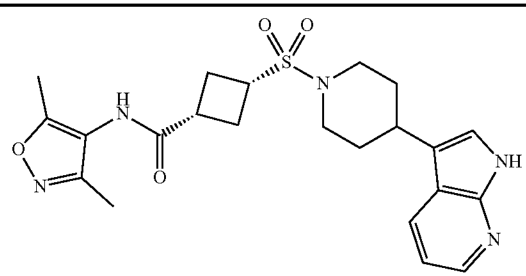 | 458.8 | ¹H NMR (600 MHz, DMSO-d6): δ = 11.36 (s, 1H), 9.26 (s, 1H), 8.17 (dd, J = 1.56, 4.68 Hz, 1H), 7.98 (dd, J = 1.01, 7.79 Hz, 1H), 7.24 (d, J = 2.20 Hz, 1H), 7.00 (dd, J = 4.68, 7.79 Hz, 1H), 3.99-4.06 (m, 1H), 3.69 (d, J = 12.10 Hz, 2H), 3.16-3.23 (m, 1H), 2.87-3.00 (m, 3H), 2.42-2.47 (m, 4H), 2.22 (s, 3H), 2.05 (s, 3H), 2.02 (d, J = 11.19 Hz, 2H), 1.65 (dq, J = 4.13, 12.44 Hz, 2H) ppm | 3-(4-piperidyl)-1H-pyrrolo[2,3-b]pyridine | General method D using trans-methyl 3-chlorosulfonylcyclobutanecarboxylate, V using NaOH, then I5 using 3,5-dimethylisoxazol-4-amine (separation of isomers). | cis-N-(3,5-dimethyl-1,2-oxazol-4-yl)-3-[4-(1H-pyrrolo[2,3-b]pyridin-3-yl)piperidin-1-yl]sulfonylcyclobutane-1-carboxamide |
| 310 | 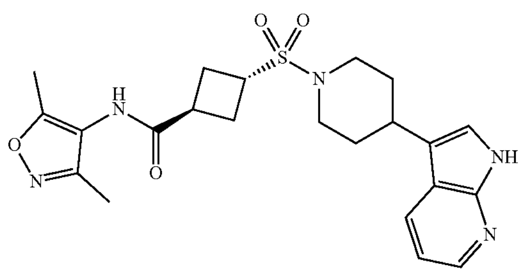 [SMILES: Cc1noc(C)c1NC(=O)[C@H]1C[C@H](S(=O)(=O)N2CCC(c3c[nH]c4ncccc34)CC2)C1] | 458.8 | ¹H NMR (600 MHz, DMSO-d6): δ = 11.36 (s, 1H), 9.30 (s, 1H), 8.17 (dd, J = 1.47, 4.58 Hz, 1H), 7.97 (dd, J = 1.19, 7.98 Hz, 1H), 7.24 (d, J = 2.38 Hz, 1H), 7.01 (dd, J = 4.68, 7.79 Hz, 1H), 3.96-4.03 (m, 1H), 3.72 (d, J = 12.29 Hz, 2H), 3.32-3.39 (m, 1H), 2.89-3.02 (m, 3H), 2.55-2.64 (m, 4H), 2.24 (s, 3H), 2.07 (s, 3H), 2.01 (d, J = 10.45 Hz, 2H), 1.63 (dq, J = 3.85, 12.47 Hz, 2H) ppm | 3-(4-piperidyl)-1H-pyrrolo[2,3-b]pyridine | General method D using trans-methyl 3-chlorosulfonylcyclobutanecarboxylate, V using NaOH, then I5 using 3,5-dimethylisoxazol-4-amine (separation of isomers). | trans-N-(3,5-dimethyl-1,2-oxazol-4-yl)-3-[4-(1H-pyrrolo[2,3-b]pyridin-3-yl)piperidin-1-yl]sulfonylcyclobutane-1-carboxamide |
| 311 | 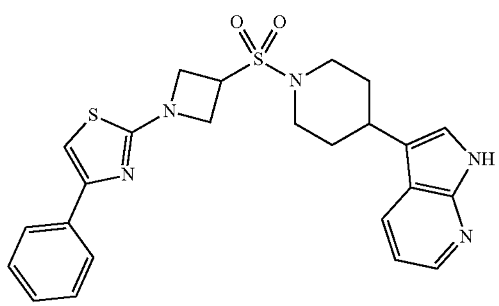 [SMILES: O=S(=O)(C1CN(c2nc(-c3ccccc3)cs2)C1)N1CCC(c2c[nH]c3ncccc23)CC1] | 480.7 | ¹H NMR (600 MHz, DMSO-d6): δ = 11.37 (br. s., 1H), 8.17 (dd, J = 1.5, 4.7 Hz, 1H), 7.98 (dd, J = 0.9, 7.8 Hz, 1H), 7.84 (d, J = 7.1 Hz, 2H), 7.39 (t, J = 7.8 Hz, 2H), 7.36 (s, 1H), 7.27-7.30 (m, 1H), 7.25 (d, J = 2.3 Hz, 1H), 7.00 (dd, J = 4.7, 8.0 Hz, 1H), 4.60-4.66 (m, 1H), 4.45 (t, J = 8.5 Hz, 2H), 4.23 (dd, J = 5.6, 8.8 Hz, 2H), 3.75-3.80 (m, 2H), 3.00-3.06 (m, 2H), 2.90-2.96 (m, 2H), 2.00-2.05 (m, 2H), 1.60-1.70 (m, 2H) ppm | 3-(4-piperidyl)-1H-pyrrolo[2,3-b]pyridine | General method D using tert-butyl 3-chlorosulfonylazetidine-1-carboxylate, Cf using TFA, then I3 using 2-bromo-4-phenyl-thiazole | 4-phenyl-2-[3-[4-(1H-pyrrolo[2,3-b]pyridin-3-yl)piperidin-1-yl]sulfonylazetidin-1-yl]-1,3-thiazole |

| Cpd # | Structure | MS (m/z, ES+) | δ NMR Data | Starting Int/Cpd# | Sequence of Methods | Chemical Name |
|---|---|---|---|---|---|---|
| 312 | 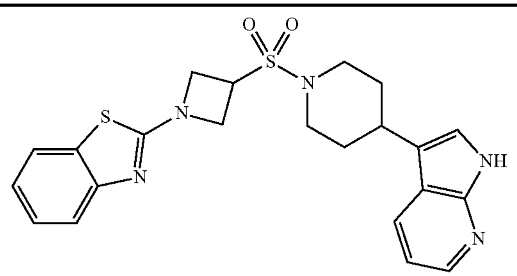 | 454.6 | ¹H NMR (600 MHz, DMSO-d6): δ = 11.37 (br. s., 1H), 8.16 (dd, J = 1.5, 4.7 Hz, 1H), 7.96 (dd, J = 1.1, 8.0 Hz, 1H), 7.82 (dd, J = 0.8, 8.0 Hz, 1H), 7.53 (dd, J = 0.5, 8.0 Hz, 1H), 7.30-7.33 (m, 1H), 7.23 (d, J = 2.6 Hz, 1H), 7.11-7.14 (m, 1H), 7.00 (dd, J = 4.7, 8.0 Hz, 1H), 4.60-4.68 (m, 1H), 4.51 (t, J = 8.5 Hz, 2H), 4.29 (dd, J = 5.6, 8.8 Hz, 2H), 3.75-3.80 (m, 2H), 3.00-3.06 (m, 2H), 2.90-2.96 (m, 2H), 2.00-2.05 (m, 2H), 1.60-1.70 (m, 2H) ppm | 3-(4-piperidyl)-1H-pyrrolo[2,3-b]pyridine | General method D using tert-butyl 3-chlorosulfonylazetidine-1-carboxylate, Cf using TFA, then J3 using 2-chloro-1,3-benzothiazole | 2-[3-[4-(1H-pyrrolo[2,3-b]pyridin-3-yl)piperidin-1-yl]sulfonylazetidin-1-yl]-1,3-benzothiazole |
| 313 | 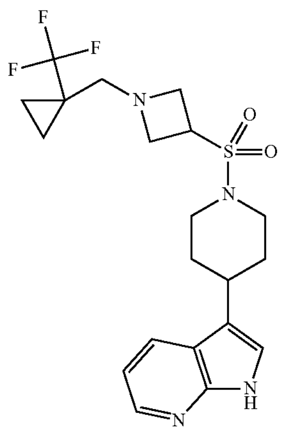 [SMILES: O=S(=O)(C1CN(CC2(C(F)(F)F)CC2)C1)N1CCC(c2c[nH]c3ncccc23)CC1] | 443.7 | ¹H NMR (400 MHz, DMSO-d6): δ = 11.36 (br. s., 1H), 8.16 (dd, J = 1.5, 4.7 Hz, 1H), 7.96 (dd, J = 1.2, 7.8 Hz, 1H), 7.23 (d, J = 2.3 Hz, 1H), 7.00 (dd, J = 4.7, 8.6 Hz, 1H), 4.18-4.29 (m, 1H), 3.60-3.72 (m, 4H), 3.33 (m, 2H, under water), 2.85-2.97 (m, 3H), 2.64 (s, 2H), 1.95-2.05 (m, 2H), 1.56-1.68 (m, 2H), 0.84-0.88 (m, 2H), 0.73-0.77 (m, 2H) ppm | 3-(4-piperidyl)-1H-pyrrolo[2,3-b]pyridine | General method D using tert-butyl 3-chlorosulfonylazetidine-1-carboxylate, Cf using TFA, then J1 using 1-(bromomethyl)-1-(trifluoromethyl) cyclopropane | 3-[1-[[1-(trifluoromethyl)cyclopropyl]methyl]azetidin-3-yl]sulfonylpiperidin-4-yl]-1H-pyrrolo[2,3-b]pyridine |
| 314 | 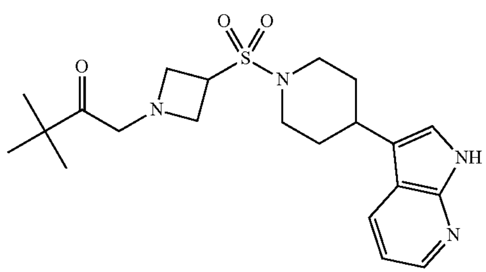 [SMILES: CC(C)(C)C(=O)CN1CC(S(=O)(=O)N2CCC(c3c[nH]c4ncccc34)CC2)C1] | 419.8 | ¹H NMR (400 MHz, DMSO-d6): δ = 11.36 (br. s., 1H), 8.16 (dd, J = 1.5, 4.7 Hz, 1H), 7.96 (dd, J = 1.2, 7.8 Hz, 1H), 7.23 (d, J = 2.0 Hz, 1H), 7.00 (dd, J = 4.7, 8.0 Hz, 1H), 4.20-4.29 (m, 1H), 3.62-3.70 (m, 4H), 3.58 (s, 2H), 3.33 (m, 2H, under water), 2.84-2.98 (m, 3H), 1.96-2.04 (m, 2H), 1.56-1.68 (m, 2H), 1.04 (s, 9H) ppm | 3-(4-piperidyl)-1H-pyrrolo[2,3-b]pyridine | General method D using tert-butyl 3-chlorosulfonylazetidine-1-carboxylate, Cf using TFA, then J1 using 1-bromo-3,3-dimethyl-butan-2-one | 3,3-dimethyl-1-[3-[4-(1H-pyrrolo[2,3-b]pyridin-3-yl)piperidin-1-yl]sulfonylazetidin-1-yl]butan-2-one |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 315 | 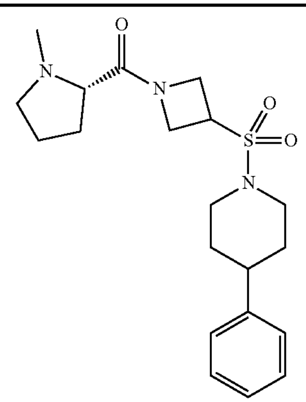 | 392.7 | ¹H NMR (400 MHz, DMSO-d₆): d = 1.52-1.79 (m, 5 H), 1.83 (d, J = 12.3 Hz, 2 H), 1.97-2.06 (m, 1 H), 2.09-2.17 (m, 1 H), 2.21 (s, 3 H), 2.59-2.70 (m, 1 H), 2.75-2.82 (m, 1 H), 2.87-2.99 (m, 3 H), 3.74 (d, J = 11.9 Hz, 2 H), 3.95-4.04 (m, 1 H), 4.14-4.23 (m, 1 H), 4.29-4.44 (m, 2 H), 4.53-4.62 (m, 1 H), 7.16-7.33 (m, 5 H) ppm | 4-phenyl-piperidine | General method D using tert-butyl 3-chlorosulfonylazetidine-1-carboxylate, Cf using TFA, I1 using (2S)-1-methylpyrrolidine-2-carboxylic acid | [(2S)-1-methyl-pyrrolidin-2-yl]-[3-(4-phenylpiperidin-1-yl)sulfonylazetidin-1-yl]methanone |
| 316 | 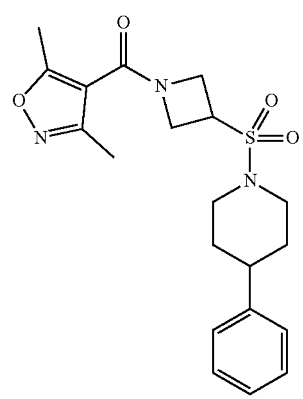 [SMILES: Cc1noc(C)c1C(=O)N1CC(S(=O)(=O)N2CCC(c3ccccc3)CC2)C1] | 404.6 | ¹NMR (400 MHz, DMSO-d₆): d = 1.53-1.65 (m, 2 H), 1.82 (d, J = 13.6 Hz, 2 H), 2.22 (s, 3 H), 2.45 (s, 3 H), 2.58-2.68 (m, 1 H), 2.87-2.98 (m, 2 H), 3.74 (d, J = 11.5 Hz, 2 H), 4.14 (d, J = 4.2 Hz, 2 H), 4.39 (br. s., 3 H), 7.16-7.33 (m, 5 H) ppm | 4-phenyl-piperidine | General method D using tert-butyl 3-chlorosulfonylazetidine-1-carboxylate, Cf using TFA, I4 using 3,5-dimethylisoxazole-4-carboxylic acid | (3,5-dimethyl-1,2-oxazol-4-yl)-[3-(4-phenylpiperidin-1-yl)sulfonylazetidin-1-yl]methanone |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 317 | 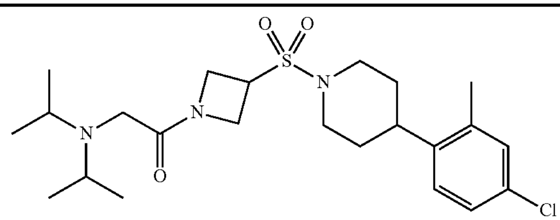 | 470.7 | ¹H NMR (400 MHz, DMSO-d₆): d = 0.95 (t, J = 6.1 Hz, 12 H), 1.46-1.62 (m, 2 H), 1.74 (d, J = 11.6 Hz, 2 H), 2.27-2.33 (s, 3 H), 2.83 (m, 1 H), 2.88-3.01 (m, 4 H), 3.13 (q, J = 15.3 Hz, 2 H), 3.73 (d, J = 11.0 Hz, 2 H), 3.97 (dd, J = 10.2, 5.4 Hz, 1 H), 4.17 (t, J = 9.5 Hz, 1 H), 4.30-4.39 (m, 1 H), 4.48 (m, 1 H), 4.54-4.62 (m, 1 H), 7.16-7.24 (m, 3 H) ppm | 4-(4-chloro-2-methylphenyl) piperidine | General method D using tert-butyl 3-chlorosulfonylazetidine-1-carboxylate, Cf using TFA, I4 using 2-(diisopropylamino) acetic acid | 1-[3-[4-(4-chloro-2-methylphenyl) piperidin-1-yl]sulfonylazetidin-1-yl]-2-[di(propan-2-yl)amino] ethanone |
| 318 | 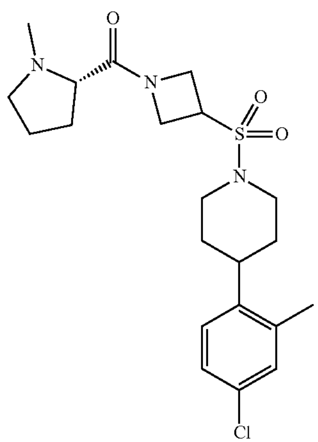 [SMILES: Cc1cc(Cl)ccc1C1CCN(S(=O)(=O)C2CN(C(=O)[C@@H]3CCCN3C)C2)CC1] | 440.6 | ¹H NMR (400 MHz, DMSO-d₆): d = 1.48-1.64 (m, 2 H), 1.66-1.80 (m, 5H,), 1.95-2.07 (m, 1 H, ), 2.13 (m, 1H, ), 2.22 (s, 3 H), 2.27-2.33 (s, 3 H),2.74-2.87 (m, 2 H, ), 2.95 (t, J = 9.9Hz, 3 H,), 3.73 (d, J = 12.0 Hz, 2 H), 3.95-4.04 (m, 1 H,), 4.15-4.25 (m, 1H, ), 4.29-4.44 (m, 2 H, ), 4.53-4.62 (m, 1 H,), 7.16-7.25 (m, 3 H) ppm | 4-(4-chloro-2-methyl-phenyl) piperidine | General method D using tert-butyl 3-chlorosulfonylazetidine-1-carboxylate, Cf using TFA, I1 using (2S)-1-methylpyrrolidine-2-carboxylic acid | [3-[4-(4-chloro-2-methylphenyl) piperidin-1-yl]sulfonylazetidin-1-yl]-[(2S)-1-methylpyrrolidin-2-yl]methanone |
| 319 | 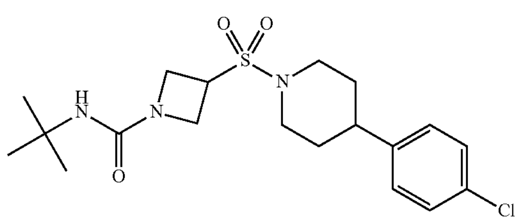 [SMILES: CC(C)(C)NC(=O)N1CC(S(=O)(=O)N2CCC(c3ccc(Cl)cc3)CC2)C1] | 414.7 | ¹H NMR (400 MHz, DMSO-d₆): d = 1.38 (s, 9 H), 1.49-1.63 (m, 2 H), 1.81 (d, J = 12.8 Hz, 2 H), 2.60-2.71 (m, 1 H), 2.89 (t, J= 12.1 Hz, 2 H), 3.72 (d, J= 11.4 Hz, 2 H), 3.93 (m, 2 H), 4.00-4.09 (m, 2 H), 4.22-4.31 (m, 1 H), 5.88 (s, 1H), 7.24-7.38 (m, 4 H) ppm | 4-(4-chlorophenyl) piperidine | General method D using tert-butyl 3-chlorosulfonylazetidine-1-carboxylate, Cf using TFA, G2 using 2-isocyanato-2-methyl-propane | N-tert-butyl-3-[4-(4-chlorophenyl) piperidin-1-yl]sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 320 | 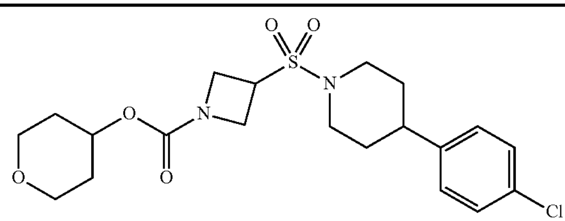 | 443.6 | ¹H NMR (300 MHz, DMSO-$d_6$): d = 1.41-1.64 (m, 4 H, ), 1.81 (d, J = 11.0 Hz, 4 H, ), 2.58-2.75 (m, 1 H, ), 2.83-2.98 (m, 2 H,), 3.36-3.48 (m, 2 H), 3.67-3.81 (m, 4 H,), 4.04 (br. s., 2 H, ), 4.17-4.41 (m, 3 H, ), 4.71 (tt, J = 8.6, 4.1 Hz, 1 H), 7.23-7.38 (m, 4 H) ppm | 4-(4-chlorophenyl) piperidine | General method D using tert-butyl 3-chlorosulfonylazetidine-1-carboxylate, Cf using TFA, H3 using tetrahydropyran-4-ol | oxan-4-yl 3-[4-(4-chlorophenyl) piperidin-1-yl]sulfonylazetidine-1-carboxylate |
| 321 | 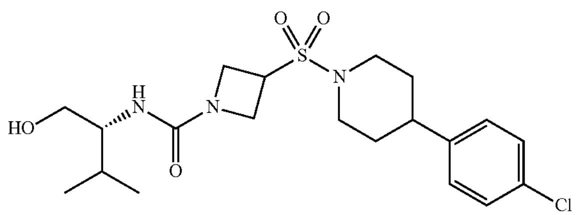 [SMILES: CC(C)[C@H](CO)NC(=O)N1CC(S(=O)(=O)N2CCC(c3ccc(Cl)cc3)CC2)C1] | 444.6 | ¹H NMR (300 MHz, DMSO-$d_6$): d = 0.81 (dd, J = 8.6, 6.9 Hz, 5 H), 1.46-1.67 (m, 2 H), 1.71-1.87 (m, 3 H), 2.26 (t, J = 1.7 Hz, 1 H), 2.90 (t, J = 11.7 Hz, 2 H), 3.34-3.40 (m, 3 H), 3.73 (d, J = 11.8 Hz, 2 H), 3.89-4.16 (m, 4 H), 4.31 (s, 1 H), 4.44-4.50 (m, 1 H), 6.03 (d, J = 8.0 Hz, 1 H), 7.24-7.38 (m, 4 H) ppm | 4-(4-chlorophenyl) piperidine | General method D using tert-butyl 3-chlorosulfonylazetidine-1-carboxylate, Cf using TFA, G6 using (2R)-2-amino-3-methyl-butan-1-ol | 3-[4-(4-chlorophenyl) piperidin-1-yl]sulfonyl-N-[(2R)-1-hydroxy-3-methylbutan-2-yl]azetidine-1-carboxamide |
| 322 | 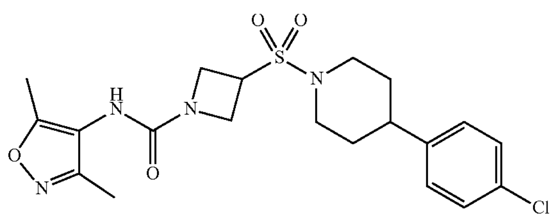 [SMILES: Cc1noc(C)c1NC(=O)N1CC(S(=O)(=O)N2CCC(c3ccc(Cl)cc3)CC2)C1] | 453.7 | ¹H NMR (300 MHz, DMSO-$d_6$): d = 1.48-1.66 (m, 2 H), 1.82 (d, J = 11.3 Hz, 2 H), 2.05 (s, 3 H), 2.22 (s, 3 H), 2.67 (t, J = 12.5 Hz, 1 H), 2.93 (t, J = 11.4 Hz, 2 H), 3.75 (d, J = 12.2 Hz, 2 H), 4.02-4.11 (m, 2 H), 4.25 (t, J = 8.4 Hz, 2 H), 4.31-4.45 (m, 1 H), 7.23-7.38 (m, 4 H), 8.03 (s, 1 H) ppm | 4-(4-chlorophenyl) piperidine | General method D using tert-butyl 3-chlorosulfonylazetidine-1-carboxylate, Cf using TFA, G2 using 4-isocyanato-3,5-dimethyl-isoxazole | 3-[4-(4-chlorophenyl) piperidin-1-yl]sulfonyl-N-(3,5-dimethyl-1,2-oxazol-4-yl)azetidine-1-carboxamide |
| 323 | 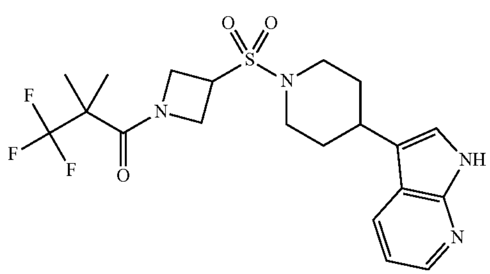 [SMILES: CC(C)(C(=O)N1CC(S(=O)(=O)N2CCC(c3c[nH]c4ncccc34)CC2)C1)C(F)(F)F] | 459.7 | ¹H NMR (300 MHz, DMSO-$d_6$): d = 1.35 (s, 6 H), 1.63 (dd, J = 12.2, 8.9 Hz, 2 H), 2.02 (d, J = 10.6 Hz, 2 H), 2.84-3.08 (m, 3 H), 3.74 (d, J = 11.8 Hz, 2 H), 4.05 (br. s., 1 H), 4.24 (d, J = 7.8 Hz, 1 H), 4.31-4.44 (m, 1 H), 4.5 (br. s., 1 H), 4.77 (br. s., 1 H), 7.01 (dd, J = 7.9, 4.6 Hz, 1 H), 7.25 (d, J = 2.4 Hz, 1 H), 7.93-7.99 (m, 1 H), 8.17 (dd, J = 4.7, 1.6 Hz, 1 H), 11.38 (br. s., 1 H) ppm | 3-(4-piperidyl)-1H-pyrrolo[2,3-b]pyridine | General method D using tert-butyl 3-chlorosulfonylazetidine-1-carboxylate, Cf using TFA, I2 using 3,3,3-trifluoro-2,2-dimethyl-propanoyl chloride | 3,3,3-trifluoro-2,2-dimethyl-1-[3-[4-(1H-pyrrolo[2,3-b]pyridin-3-yl)piperidin-1-yl]sulfonylazetidin-1-yl]propan-1-one |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 324 | 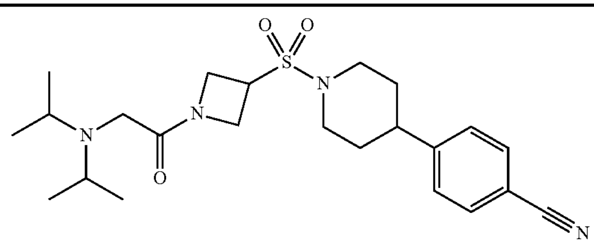 | 447.8 | ¹H NMR (400 MHz, DMSO-d₆): d = 1.05-0.87 (s, 12 H), 1.69-1.52 (m, 2 H), 1.96-1.76 (m, 2 H), 3.23-2.71 (m, 7 H), 4.72-3.65 (m, 7H), 7.10-8.08 (m, 4 H) ppm | 4-(4-piperidyl)benzonitrile | General method D using tert-butyl 3-chlorosulfonylazetidine-1-carboxylate, Cf using TFA, I1 using 2-(diisopropylamino)acetic acid | 4-[1-[2-[di(propan-2-yl)amino]acetyl]azetidin-3-yl]sulfonyl]piperidin-4-yl]benzonitrile |
| 325 | 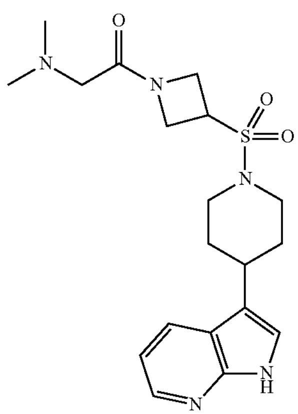 [SMILES: CN(C)CC(=O)N1CC(S(=O)(=O)N2CCC(c3c[nH]c4ncccc34)CC2)C1] | 406.8 | ¹H NMR (300 MHz, DMSO-d₆): d = 1.53-1.72 (m, 2 H), 2.03 (d, J = 11.5 Hz, 2 H), 2.23-2.29 (m, 1 H), 2.69-2.75 (m, 2 H), 2.86-3.07 (m, 3 H), 3.55 (br. s., 3 H), 3.74 (d, J = 12.5 Hz, 3 H), 4.07 (d, J = 9.8 Hz, 1 H), 4.27 (t, J = 8.8 Hz, 2 H), 4.33-4.56 (m, 3 H), 7.02 (dd, J = 7.8, 4.7 Hz, 1 H), 7.25 (d, J = 2.4 Hz, 1 H), 7.97 (d, J = 6.8 Hz, 1 H), 8.17 (dd, J = 4.8, 1.5 Hz, 1 H), 11.39 (s, 1 H) ppm | 3-(4-piperidyl)-1H-pyrrolo[2,3-b]pyridine | General method D using tert-butyl 3-chlorosulfonylazetidine-1-carboxylate, Cf using TFA, I1 using 2-(dimethylamino)acetic acid | 2-(dimethylamino)-1-[3-[4-(1H-pyrrolo[2,3-b]pyridin-3-yl)piperidin-1-yl]sulfonylazetidin-1-yl]ethanone |
| 326 | 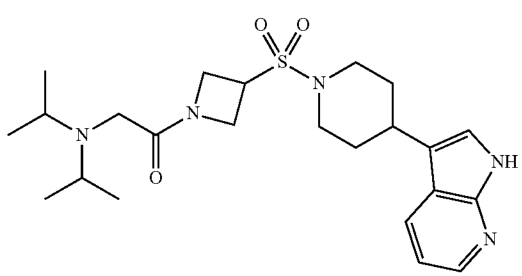 [SMILES: CC(C)N(CC(=O)N1CC(S(=O)(=O)N2CCC(c3c[nH]c4ncccc34)CC2)C1)C(C)C] | 462.8 | ¹H NMR (300 MHz, DMSO-d₆): d = 0.79-1.09 (m, 12 H), 1.62 (d, J = 11.0 Hz, 2 H), 2.02 (d, J = 11.3 Hz, 2 H), 2.80-3.21 (m, 7 H), 3.73 (d, J = 10.8 Hz, 2 H), 4.00 (d, J = 5.1 Hz, 1 H), 4.17 (t, J = 9.0 Hz, 1 H), 4.28-4.67 (m, 3 H), 6.94-7.09 (m, 1 H), 7.24 (br. s., 1 H), 7.97 (d, J = 7.5 Hz, 1 H), 8.17 (d, J = 4.0 Hz, 1 H), 11.37 (br. s., 1 H) ppm | 3-(4-piperidyl)-1H-pyrrolo[2,3-b]pyridine | General method D using tert-butyl 3-chlorosulfonylazetidine-1-carboxylate, Cf using TFA, I1 using 2-(diisopropylamino)acetic acid | 2-[di(propan-2-yl)amino]-1-[3-[4-(1H-pyrrolo[2,3-b]pyridin-3-yl)piperidin-1-yl]sulfonylazetidin-1-yl]ethanone |

-continued

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 327 | 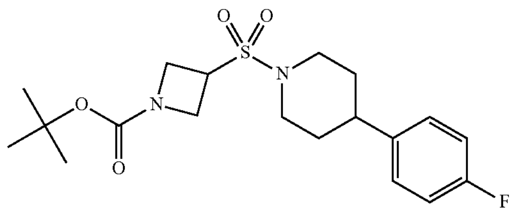 [SMILES: CC(C)(C)OC(=O)N1CC(S(=O)(=O)N2CCC(c3ccc(F)cc3)CC2)C1] | 343.5 (M + H - 56)+ | ¹H NMR (300 MHz, DMSO-d₆): d = 1.38 (s, 9 H), 1.55 (qd, J = 12.5, 4.0 Hz, 2 H), 1.81 (d, J = 10.8 Hz, 2 H), 2.58-2.73 (m, 1 H), 2.82-2.96 (m, 2 H), 3.72 (d, J = 11.8 Hz, 2 H), 3.97 (dd, J = 8.6, 5.5 Hz, 2 H), 4.17 (t, J = 8.4 Hz, 2 H), 4.25-4.36 (m, 1 H), 7.06-7.16(m, 2 H), 7.23-7.32(m, 2 H) ppm | 4-(4-fluoro-phenyl) piperidine | General method D using tert-butyl 3-chlorosulfonylaze-tidine-1-carboxylate | tert-butyl 3-[4-(4-fluorophenyl) piperidin-1-yl]sulfonylaze-tidine-1-carboxylate |
| 328 | 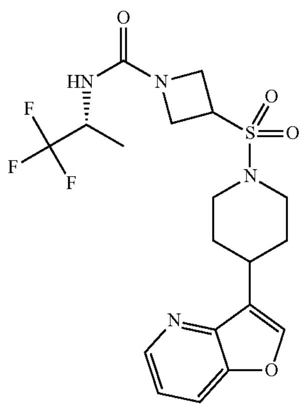 [SMILES: C[C@@H](NC(=O)N1CC(S(=O)(=O)N2CCC(c3coc4cccnc34)CC2)C1)C(F)(F)F] | 461.7 | ¹H NMR (300 MHz, DMSO-d₆): d = 1.21 (d, J = 7.0 Hz, 3 H), 1.67-1.84 (m, 2 H), 2.13 (d, J = 10.8 Hz, 2 H), 3.01 (t, J = 11.7 Hz, 3 H), 3.72 (d, J = 12.2 Hz, 2 H), 3.92-4.09 (m, 2 H), 4.11-4.24 (m, 2 H), 4.27-4.48 (m, 2 H), 7.03 (d, J = 9.1 Hz, 1 H), 7.33 (dd, J = 8.4, 4.7 Hz, 1 H), 7.98 (dd, J = 8.4, 1.2 Hz, 1 H), 8.11 (s, 1 H), 8.50 (dd, J = 4.7, 1.2 Hz, 1 H) ppm | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, G6 using (2R)-1,1,1-trifluoropropan-2-amine | 3-(4-furo[3,2-b]pyridin-3-ylpiperidin-1-yl)sulfonyl-N-[(2R)-1,1,1-trifluoropropan-2-yl]azetidine-1-carboxamide |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 329 | 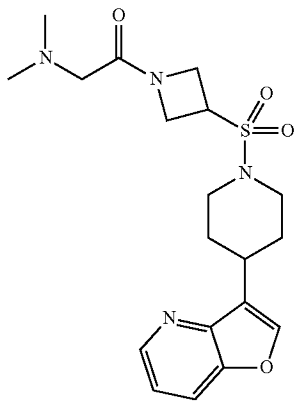 [SMILES: CN(C)CC(=O)N1CC(S(=O)(=O)N2CCC(c3coc4cccnc34)CC2)C1] | 407.8 | ¹H NMR (300 MHz, DMSO-d₆): d = 1.73 (s, 2 H), 2.15 (d, J = 11.1 Hz, 2 H), 2.79 (s, 6 H), 2.96-3.13 (m, 3 H), 3.75 (d, J = 12.4 Hz, 2 H), 3.92-4.16 (m, 3 H), 4.30-4.56 (m, 4 H), 7.34 (dd, J = 8.2, 4.7 Hz, 1 H), 7.99 (dd, J = 8.4, 1.1 Hz, 1 H), 8.12 (s, 1 H), 8.51 (dd, J = 4.6, 1.3 Hz, 1 H), 9.72 (s, 1 H) ppm | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, I1 using 2-(dimethylamino) acetic acid | 2-(dimethylamino)-1-[3-(4-furo[3,2-b]pyridin-3-yl)piperidin-1-yl]sulfonylazetidin-1-yl]ethanone |
| 330 | 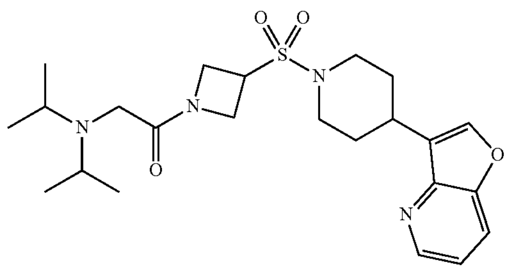 [SMILES: CC(C)N(CC(=O)N1CC(S(=O)(=O)N2CCC(c3coc4cccnc34)CC2)C1)C(C)C] | 463.8 | ¹H NMR (300 MHz, DMSO-d₆): d = 0.95 (dd, J = 6.5, 3.7 Hz, 12 H), 1.76 (qd, J = 12.3, 4.1 Hz, 2 H), 2.12 (d, J = 13.4 Hz, 2 H), 2.84-3.08 (m, 4 H), 3.14 (d, J = 9.2 Hz, 2 H), 3.72 (d, J = 11.7 Hz, 1 H), 3.98 (dd, J = 9.8, 5.6 Hz, 1 H), 4.18 (t, J = 9.3 Hz, 1 H), 4.29-4.41 (m, 1 H), 4.44-4.53 (m, 1 H), 4.55-4.64 (m, 1 H), 7.30-7.36 (m, 1 H), 7.98 (dd, J = 8.4, 1.4 Hz, 1 H), 8.11 (d, J = 0.7 Hz, 1 H), 8.50 (dd, J = 4.8, 1.3 Hz, 1 H) ppm | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, I1 using 2-(diisopropylamino) acetic acid | 2-[di(propan-2-yl)amino]-1-[3-(4-furo[3,2-b]pyridin-3-yl)piperidin-1-yl)sulfonylazetidin-1-yl]ethanone |
| 331 | 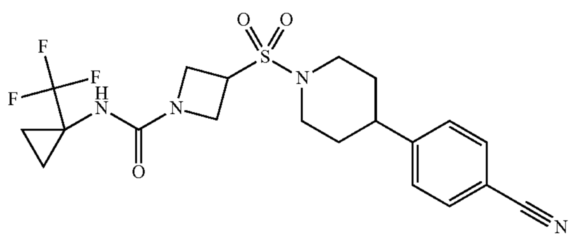 [SMILES: N#Cc1ccc(C2CCN(S(=O)(=O)C3CN(C(=O)NC4(C(F)(F)F)CC4)C3)CC2)cc1] | 457.7 | ¹H NMR (300 MHz, DMSO-d₆): d = 0.94-1.05 (m, 2 H), 1.14-1.22 (m, 2 H), 1.50-1.67 (m, 2 H), 1.83 (d, J = 11.5 Hz, 2 H), 2.68-2.83 (m, 1 H), 2.85-2.98 (m, 2 H), 3.73 (d, J = 12.2 Hz, 2 H), 3.94 (dd, J = 9.1, 5.6 Hz, 2 H, ), 4.12 (t, J = 8.6 Hz, 2 H, ), 4.24-4.38 (m, 1 H), 7.34-7.51 (m, 3 H), 7.70-7.83 (m, 2 H) ppm | 4-(4-piperidyl) benzonitrile | General method D using tert-butyl 3-chlorosulfonylaze-tidine-1-carboxylate, Cf using TFA, G2 using 1-isocyanato-1-(trifluoromethyl) cyclopropane | 3-[4-(4-cyanophenyl) piperidin-1-yl]sulfonyl-N-[1-(trifluoromethyl) cyclopropyl] azetidine-1-carboxamide |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 332 | 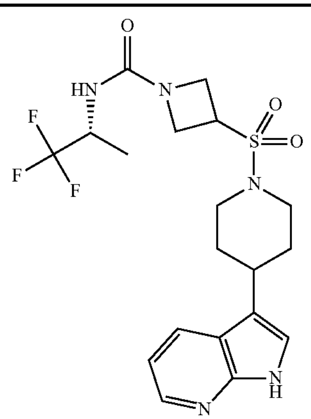 | 460.5 | ¹H NMR (300 MHz, DMSO-d₆): d = 1.48-1.66 (m, 2 H), 1.82 (d, J = 11.3 Hz, 2 H), 2.05 (s, 3 H), 2.22 (s, 3 H), 2.67 (t, J = 12.5 Hz, 1 H), 2.93 (t, J = 11.4 Hz, 2 H), 3.75 (d, J = 12.2 Hz, 2 H), 4.02-4.11 (m, 2 H), 4.25 (t, J = 8.4 Hz, 2 H), 4.31-4.45 (m, 1 H), 7.23-7.38 (m, 4 H), 8.03 (s, 1 H) ppm | 3-(4-piperidyl)-1H-pyrrolo[2,3-b]pyridine | General method D using tert-butyl 3-chlorosulfonylazetidine-1-carboxylate, Cf using TFA,G6 using (2R)-1,1,1-trifluoropropan-2-amine | 3-[4-(1H-pyrrolo[2,3-b]pyridin-3-yl)piperidin-1-yl]sulfonyl-N-[(2R)-1,1,1-trifluoropropan-2-yl]azetidine-1-carboxamide |
| 333 | 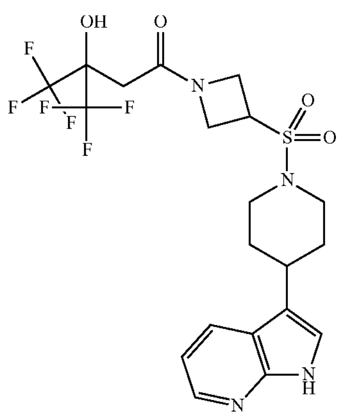 [SMILES: O=C(CC(O)(C(F)(F)F)C(F)(F)F)N1CC(S(=O)(=O)N2CCC(c3c[nH]c4ncccc34)CC2)C1] | 529.6 | ¹H NMR (300 MHz, DMSO-d₆) d 11.38 (s, 1H), 8.53 (br. s.., 1H), 8.17 (dd, J = 1.48, 4.79 Hz, 1H), 7.97 (dd, J = 1.31, 7.93 Hz, 1H), 7.25 (d, J = 2.26 Hz, 1H), 7.01 (dd, J = 4.70, 7.84 Hz, 1H), 4.54-4.63 (m, 1H), 4.35-4.52 (m, 2H), 4.27 (dd, J = 8.19, 10.28 Hz, 1H), 4.06 (dd, J = 5.40, 10.10 Hz, 1H), 3.74 (d, J = 12.19 Hz, 2H), 2.86-3.07 (m, 3H), 2.83 (d, J = 3.66 Hz, 2H), 2.02 (d, J = 11.32 Hz, 2H), 1.63 (q, J = 12.31 Hz, 2H) ppm | 3-(4-piperidyl)-1H-pyrrolo[2,3-b]pyridine | General method D using tert-butyl 3-chlorosulfonylazetidine-1-carboxylate, Cf using TFA, I3 using 4,4,4-trifluoro-3-hydroxy-3-(trifluoromethyl)butanoic acid | 4,4,4-trifluoro-3-hydroxy-1-[3-[4-(1H-pyrrolo[2,3-b]pyridin-3-yl)piperidin-1-yl]sulfonylazetidin-1-yl]-3-(trifluoromethyl)butan-1-one |

| Cpd # | Structure | MS (m/z, ES+) | δ NMR Data | Starting Int/Cpd# | Sequence of Methods | Chemical Name |
|---|---|---|---|---|---|---|
| 334 | 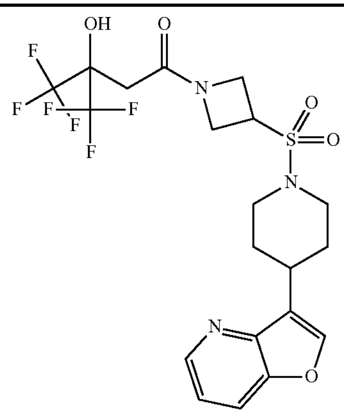 | 530.6 | ¹H NMR (300 MHz, DMSO-d₆) δ 8.50 (dd, J = 1.22, 4.70 Hz, 2H), 8.12 (s, 1H), 7.99 (dd, J = 1.22, 8.36 Hz, 1H), 7.30-7.37 (m, 1H), 4.54-4.64 (m, 1H), 4.36-4.50 (m, 2H), 4.29 (dd, J = 8.19, 10.45 Hz, 1H), 4.06 (dd, J = 5.31, 10.02 Hz, 1H), 3.74 (d, J = 11.84 Hz, 2H), 3.03 (t, J = 11.32 Hz, 3H), 2.82 (d, J = 4.53 Hz, 2H), 2.13 (d, J = 12.02 Hz, 2H), 1.76 (q, J = 12.95 Hz, 2H) ppm | 3-bromofuro[3,2-b]pyridine | General method A1 using K2CO3, B1 using Pd/C, Ci using TFA, D using tert-butyl 3-chlorosulfonyl azetidine-1-carboxylate, Cf using TFA, I3 using 4,4,4-trifluoro-3-hydroxy-3-(trifluoromethyl) butanoic acid | 4,4,4-trifluoro-1-[3-(4-furo[3,2-b]pyridin-3-yl)piperidin-1-yl]sulfonylazetidin-1-yl]-3-hydroxy-3-(trifluoromethyl)butan-1-one |
| 335 | 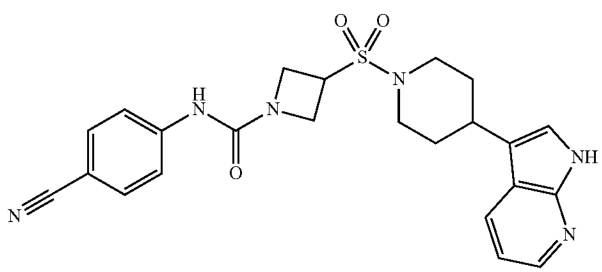 [SMILES: N#Cc1ccc(NC(=O)N2CC(S(=O)(=O)N3CCC(c4c[nH]c5ncccc45)CC3)C2)cc1] | 465.6 | ¹H NMR (300 MHz, DMSO-d₆) δ 11.38 (br. s., 1H), 9.11 (s, 1H), 8.17 (d, J = 3.31 Hz, 1H), 7.97 (d, J = 7.14 Hz, 1H), 7.68 (s, 4H), 7.24 (d, J = 2.09 Hz, 1H), 7.01 (dd, J = 4.70, 7.84 Hz, 1H), 4.27-4.45 (m, 3H), 4.16 (d, J = 3.83 Hz, 2H), 3.76 (d, J = 11.15 Hz, 2H), 2.83-3.14 (m, 3H), 2.03 (d, J = 11.50 Hz, 2H), 1.52-1.77 (m, 2H) ppm | 3-(4-piperidyl)-1H-pyrrolo[2,3-b]pyridine | General method D using tert-butyl 3-chlorosulfonylazetidine-1-carboxylate, Cf using TFA, G2 using 4-isocyanatobenzonitrile | N-(4-cyanophenyl)-3-[4-(1H-pyrrolo[2,3-b]pyridin-3-yl)piperidin-1-yl]sulfonylazetidine-1-carboxamide |

| Cpd # | Structure | MS (m/z, ES +) | δ NMR Data | Starting Int/Cpd# | Sequence of Methods | Chemical Name |
|---|---|---|---|---|---|---|
| 336 | 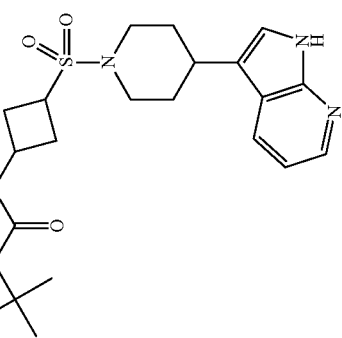 | 435.7 | ¹H NMR (500 MHz, CHLOROFORM-d) δ 9.08 (br. s., 2H), 8.32 (d, J = 4.88 Hz, 2H), 7.93 (d, J = 7.93 Hz, 2H), 7.06-7.11 (m, 4H), 4.95 (d, J = 8.24 Hz, 1H), 4.81 (d, J = 6.41 Hz, 1H), 4.27-4.37 (m, 1H), 4.15-4.27 (m, 1H), 3.88-4.00 (m, 4H), 3.78 (td, J = 4.46, 9.08 Hz, 1H), 3.47 (quin, J = 8.44 Hz, 1H), 2.83-3.02 (m, 8H), 2.72-2.82 (m, 2H), 2.50 (br. s., 2H), 2.35-2.44 (m, 2H), 2.10 (d, J = 13.43 Hz, 4H), 1.84 (dq, J = 3.66, 12.51 Hz, 4H), 1.46 (s, 9H), 1.45 (s, 9H) ppm | 3-(4-piperidyl)-1H-pyrrolo[2,3-b]pyridine | General method U using trans-tert-butyl-N-(3-sulfanylcyclobutyl) carbamate. | tert-butyl N-[3-[4-(1H-pyrrolo[2,3-b]pyridin-3-yl)piperidin-1-yl]sulfonylcyclobutyl] carbamate |
| 337 | 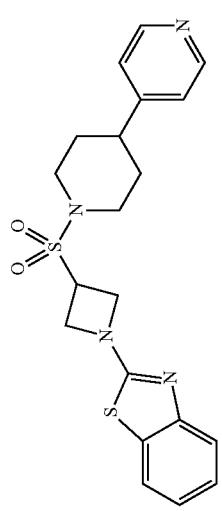 | 415.6 | 1H NMR (500 MHz, CHLOROFORM-d) δ 8.42-8.45 (m, 2H), 7.66 (dd, J = 3.97, 7.93 Hz, 2H), 7.35-7.39 (m, 1H), 7.16-7.20 (m, 1H), 6.98 (d, J = 6.10 Hz, 2H), 4.45-4.53 (m, 4H), 4.24-4.32 (m, 1H), 4.05 (d, J = 12.82 Hz, 2H), 3.01 (dt, J = 1.98, 12.59 Hz, 2H), 2.63 (tt, J = 3.36, 12.21 Hz, 1H), 1.94 (d, J = 12.82 Hz, 2H), 1.74 (dq, J = 4.12, 12.66 Hz, 2H) ppm | 4-(4-piperidyl)pyridine | General method D using tert-butyl 3-chlorosulfonylazetidine-1-carboxylate, Cf using TFA, I3 using 2-chloro-1,3-benzothiazole | 2-[3-[4-(4-pyridin-4-yl)piperidin-1-yl]sulfonylazetidin-1-yl]-1,3-benzothiazole |
| 338 | 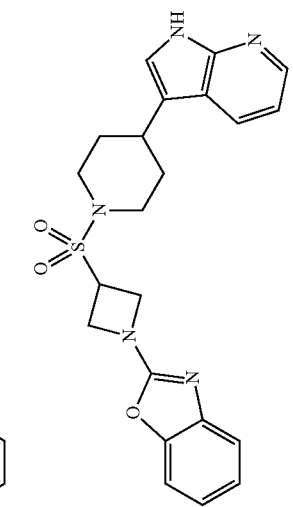 | 438.6 | 1H NMR (500 MHz, CHLOROFORM-d) δ 8.76 (br. s., 1H), 8.31 (dd, J = 1.07, 4.73 Hz, 1H), 7.91 (dd, J = 1.07, 7.78 Hz, 1H), 7.43 (d, J = 7.63 Hz, 1H), 7.31 (d, J = 7.93 Hz, 1H), 7.23 (dt, J = 0.92, 7.63 Hz, 1H), 7.11 (dt, J = 1.04, 7.78 Hz, 1H), 7.06 (dd, J = 4.88, 7.93 Hz, 1H), 6.96 (s, 1H), 4.53-4.62 (m, 4H), 4.22-4.30 (m, 1H), 4.04 (d, J = 12.51 Hz, 2H), 3.08 (td, J = 1.81, 12.59 Hz, 2H), 2.96 (tt, J = 3.37, 12.00 Hz, 1H),2.13 (d, J = 11.60 Hz, 2H), 1.82 (dq, J = 3.97, 12.61 Hz, 2H) ppm | 3-(4-piperidyl)-1H-pyrrolo[2,3-b]pyridine | General method D using tert-butyl 3-chlorosulfonylazetidine-1-carboxylate, Cf using TFA, I3 using 2-chloro-1,3-benzoxazole | 2-[3-[4-(1H-pyrrolo[2,3-b]pyridin-3-yl)piperidin-1-yl]sulfonylazetidin-1-yl]-1,3-benzoxazole |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 339 | 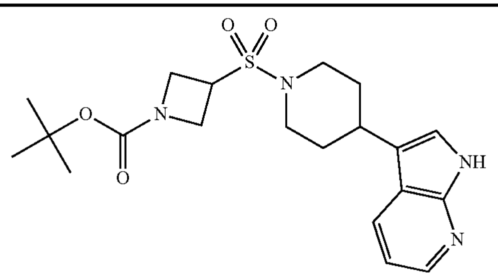 | 421.7 | 1H NMR (300 MHz, DMSO-d6): δ = 11.35 (br. s., 1H), 8.68 (d, J = 1.05 Hz, 1H), 8.05 (d, J = 5.40 Hz, 1H), 7.52 (d, J = 5.23 Hz, 1H), 7.39 (d, J = 2.26 Hz, 1H), 4.26-4.37 (m, 1H), 4.09-4.25 (m, 2H), 3.93-4.05 (m, 2H), 3.72 (d, J = 12.37 Hz, 2H), 2.84-3.05 (m, 3H), 1.95-2.06 (m, 2H), 1.53-1.72 (m, 2H), 1.38 (s, 9H) ppm | 1H-pyrrolo[2,3-c]pyridine | General method A2 using KOH, B2 using Pd/C, Ci using TFA, then method D using tert-butyl 3-chlorosulfonylazetidine-1-carboxylate. | tert-butyl 3-[4-(1H-pyrrolo[2,3-c]pyridin-3-yl)piperidin-1-yl]sulfonylazetidine-1-carboxylate |
| 340 | 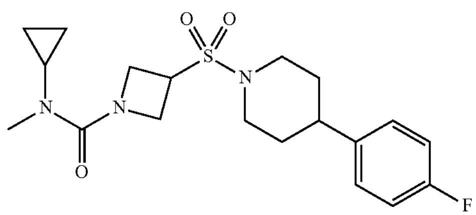 [SMILES: CN(C(=O)N1CC(S(=O)(=O)N2CCC(c3ccc(F)cc3)CC2)C1)C1CC1] | 396.7 | 1H NMR (300 MHz, DMSO-d6): d = 0.58-078 (m, 2H), 1.48-1.65 (m, 2 H), 1.76-1.87 (m, 2 H), 2.56-2.67 (m, 2 H), 2.89 (t, J = 12.9 Hz, 2 H), 3.67-3.77 (d, J = 12.3 Hz, 2 H), 4.07-4.16 (m, 2 H), 4.18-4.26 (t, J = 8.17 Hz, 2 H), 4.27-4.40 (m, 1 H), 7.06-7.16 (m, 2H), 7.24-7.33 (m, 2H) ppm | 4-(4-fluorophenyl)piperidine | General method D using tert-butyl 3-chlorosulfonylazetidine-1-carboxylate, Cf using TFA, G6 using N-methylcyclopropanamine | N-cyclopropyl-3-[4-(4-fluorophenyl)piperidin-1-yl]sulfonyl-N-methylazetidine-1-carboxamide |
| 341 | 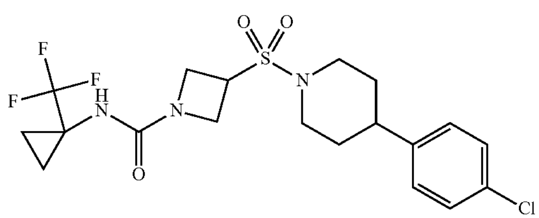 [SMILES: O=C(NC1(C(F)(F)F)CC1)N1CC(S(=O)(=O)N2CCC(c3ccc(Cl)cc3)CC2)C1] | 466.6 | 1H NMR (300 MHz, DMSO-d6): d = 7.42 (s, 1H), 7.35 (d, J = 9.03 Hz, 2H), 7.28 (d, J = 8.49 Hz, 2H), 4.25-4.36 (m, 1H), 4.11 (t, J = 8.76 Hz, 2H), 3.89-3.98 (m, 2H), 3.71 (d, J = 13.4 Hz, 2H), 2.90 (t, J = 12.3 Hz, 2H), 2.59-2.73 (m, 1H), 1.81 (d, J = 12.59 Hz, 2H), 1.46-1.64 (m, 2H), 1.12-1.21 (m, 2H), 0.95-1.04 (m, 2H) ppm | 4-(4-chlorophenyl)piperidine | General method D using tert-butyl 3-chlorosulfonylazetidine-1-carboxylate, Cf using TFA, G2 using 1-isocyanato-1-(trifluoromethyl)cyclopropane | 3-[4-(4-chlorophenyl)piperidin-1-yl]sulfonyl-N-[1-(trifluoromethyl)cyclopropyl]azetidine-1-carboxamide |
| 342 | 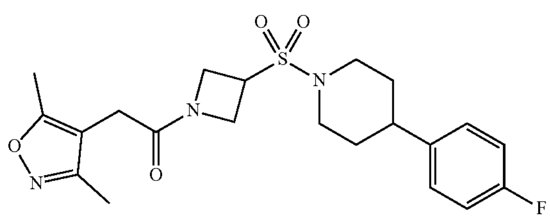 [SMILES: Cc1noc(C)c1CC(=O)N1CC(S(=O)(=O)N2CCC(c3ccc(F)cc3)CC2)C1] | 436.7 | 1H NMR (300 MHz, DMSO-d6): d = 7.24-7.32 (m, 2H), 7.06-7.16 (m, 2H), 4.49-4.59 (t, J = 10.26 Hz, 1H), 4.33-4.44 (m, 2H), 4.19 (t, J = 10.26 Hz, 1H), 3.96-4.04 (m, 1H), 3.75 (d, J = 12.45 Hz, 2H), 3.26 (d, J = 2.84 Hz, 2H), 2.92 (t, J = 12.44, 2H), 2.60-2.73 (m, 1H), 2.27 (s, 3H), 2.08 (s, 3H), 1.82 (d, J = 1.80 Hz, 2H), 1.48-1.65 (m, 2H) ppm | 4-(4-fluorophenyl)piperidine | General method D using tert-butyl 3-chlorosulfonylazetidine-1-carboxylate, Cf using TFA, I1 using 2-(3,5-dimethylisoxazol-4-yl)acetic acid | 2-(3,5-dimethyl-1,2-oxazol-4-yl)-1-[3-[4-(4-fluorophenyl)piperidin-1-yl]sulfonylazetidin-1-yl]ethanone |

TABLE with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 343 | 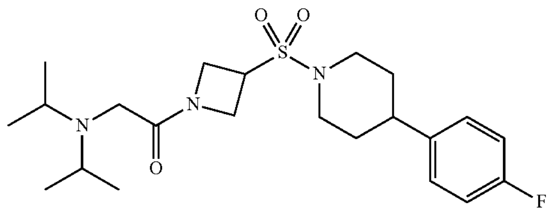 [SMILES: CC(C)N(CC(=O)N1CC(S(=O)(=O)N2CCC(c3ccc(F)cc3)CC2)C1)C(C)C] | 440.8 | ¹H NMR (300 MHz, DMSO-d₆): δ = 0.92-1.00 (m, 2 H), 1.47-1.64 (m, 2H), 1.81 (d, J = 12.28 Hz, 2 H), 2.59-2.74 (m, 2 H), 2.85-2.99 (m, 4 H), 3.13 (d, J= 9.06 Hz, 1 H), 3.73 (d, J= 11.88 Hz, 2 H), 3.93-4.01 (m, 1H), 4.16 (t, J = 10.07 Hz, 1 H), 4.29-4.41(m, 1H), 4.43-4.51 (m, 1H), 4.58 (t, J = 8.86 Hz, 1H), 7.06-7.16 (m, 2H), 7.24-7.32 8m, 2H) ppm | 4-(4-fluoro-phenyl) piperidine | General method D using tert-butyl 3-chlorosulfonylaze-tidine-1-carboxylate, Cf using TFA, I1 using 2-(diisopropylamino) acetic acid | 2-[di(propan-2-yl)amino]-1-[3-[4-(4-fluorophenyl) piperidin-1-yl]sulfonylaze-tidin-yl]ethanone |
| 344 | AND Enantiomer | 428.7 | ¹H NMR (300 MHz, DMSO-d₆): δ = 0.76-0.87 (m, 6H), 1.48-1.66 (m, 2H), 1.70-1.87 (m, 3H), 2.58-2.70 (m, 1H), 2.90 (t, J = 2.90 Hz, 2H), 3.36 (d, J = 5.05 Hz, 3H), 3.72 (d, J= 12.03 Hz, 2H), 3.89-4.17 (m, 4H), 4.26-4.37 (m, 1H), 4.47 (t, J= 4.66 Hz, 1H), 6.04 (d, J= 8.15 Hz, 1H), 7.06-7.16 (m, 2H), 7.24-7.33 (m, 2H) ppm | 4-(4-fluoro-phenyl) piperidine | General method D using tert-butyl 3-chlorosulfonylaze-tidine-1-carboxylate, Cf using TFA, G6 using 2-amino-3-methyl-butan-1-ol | 3-[4-(4-fluorophenyl) piperidin-1-yl]sulfonyl-N-[1-hydroxy-3-methylbutan-2-yl] azetidine-1-carboxamide |
| 345 | 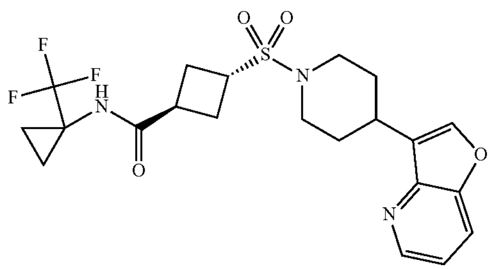 [SMILES: O=C(NC1(C(F)(F)F)CC1)[C@H]1C[C@H](S(=O)(=O)N2CCC(c3coc4cccnc34)CC2)C1] | 472.6 | ¹H NMR (600 MHz, CHLOROFORM-d) δ d 8.51 (d, J = 4.77 Hz, 1H), 7.72 (d, J = 8.25 Hz, 1H), 7.58 (s, 1H), 7.21 (dd, J = 4.77, 8.44 Hz, 1H), 5.80 (s, 1H), 3.85-3.93 (m, 3H), 3.02-3.10 (m, 2H), 2.97 (t, J = 11.55 Hz, 2H), 2.67-2.74 (m, 2H), 2.58-2.65 (m, 2H), 2.24 (d, J = 11.92 Hz, 2H), 1.80 (dq, J = 4.03, 12.41 Hz, 2H), 1.31-1.35 (m, 2H), 1.07-1.13 (m, 2H) ppm | 3-bromofuro [3,2-b]pyridine | General method A1 using K2CO3, B1 using Pd/C, Ci using TFA, D using methyl 3-chlorosulfonylcyclobutane carboxylate (separation of isomers), V using NaOH, I5 using 1-(trifluoromethyl) cyclopropanamine | trans-3-(4-furo[3,2-b]pyridin-3-yl)piperidin-1-yl)sulfonyl-N-[1-(trifluoromethyl) cyclopropyl] cyclobutane-1-carboxamide |

Table with Representative Compounds of Formula (I): -continued

| Cpd # | Structure | MS (m/z ES+) | δ NMR Data | Starting Int/Cpd# | Sequence of Methods | Chemical Name |
|---|---|---|---|---|---|---|
| 346 | 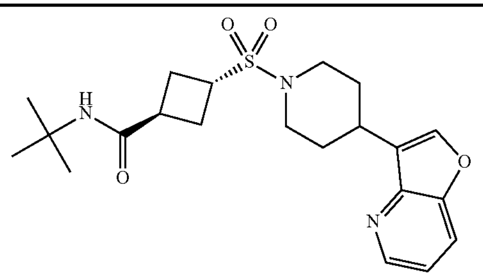 | 420.7 | ¹H NMR (600 MHz, CHLOROFORM-d) d 8.51 (d, J = 4.77 Hz, 1H), 7.71 (d, J = 8.25 Hz, 1H), 7.58 (s, 1H), 7.21 (dd, J = 4.77, 8.25 Hz, 1H), 5.18 (br. s., 1H), 3.86-3.95 (m, 3H), 3.05 (t, J = 11.92 Hz, 1H), 2.92-3.00 (m, 1H), 2.63-2.70 (m, 2H), 2.55-2.62 (m, 2H), 2.24 (d, J = 13.20 Hz, 2H), 1.79 (dq, J = 3.94, 12.44 Hz, 2H), 1.34 (s, 9H) ppm | 3-bromofuro[3,2-b]pyridine | General method A1 using K2CO3, B1 using Pd/C, Ci using TFA, D using methyl 3-chlorosulfonylcyclobutane carboxylate (separation of isomers), V using NaOH, I5 using 2-methylpropan-2-amine | trans-N-tert-butyl-3-(4-furo[3,2-b]pyridin-3-yl)piperidin-1-yl)sulfonyl)cyclobutane-1-carboxamide |
| 347 | 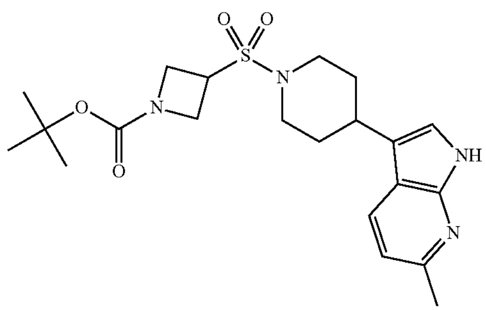 [SMILES: Cc1ccc2c(C3CCN(S(=O)(=O)C4CN(C(=O)OC(C)(C)C)C4)CC3)c[nH]c2n1] | 435.7 | ¹H NMR (600 MHz, CHLOROFORM-d) δ 9.53 (br. s., 1H), 7.79 (d, J = 8.07 Hz, 1H), 6.98 (s, 1H), 6.93 (d, J = 7.89 Hz, 1H), 4.22-4.27 (m, 2H), 4.16 (t, J = 8.89 Hz, 2H), 3.90-3.98 (m, 3H), 2.97 (t, J = 12.29 Hz, 2H), 2.90 (t, J = 12.01 Hz, 1H), 2.62 (s, 3H), 2.09 (d, J = 13.39 Hz, 2H), 1.80 (q, J = 12.23 Hz, 2H), 1.43 (s, 9H) ppm | 6-methyl-1H-pyrrolo[2,3-b]pyridine | General method A2 using KOtBu, B1 using Pd/C, Ci using TFA, D using tert-butyl 3-chlorosulfonyl azetidine-1-carboxylate | tert-butyl 3-[4-(6-methyl-1H-pyrrolo[2,3-b]pyridin-3-yl)piperidin-1-yl]sulfonylazetidine-1-carboxylate |
| 348 | 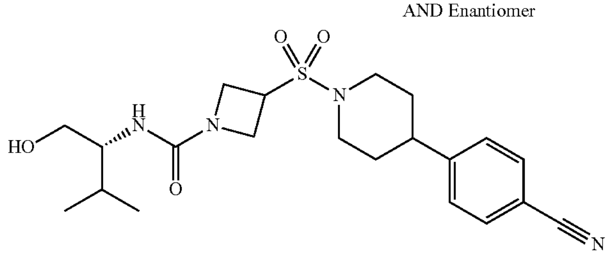 [SMILES: CC(C)[C@H](CO)NC(=O)N1CC(S(=O)(=O)N2CCC(c3ccc(C#N)cc3)CC2)C1] | 435.7 | ¹H NMR (300 MHz, DMSO-d6): δ = 7.77 (d, J = 8.36 Hz, 2H), 7.47 (d, J = 8.36 Hz, 2H), 6.04 (d, J = 8.01 Hz, 1H), 4.42-4.52 (m, 1H), 4.25-4.38 (m, 1H), 4.10 (td, J = 8.47, 12.85 Hz, 2H), 3.99-4.03 (m, 1H), 3.89-3.98 (m, 1H), 3.74 (d, J = 11.15 Hz, 2H), 3.33-3.42 (m, 3H), 2.84-2.98 (m, 2H), 2.68-2.84 (m, 1H), 1.70-1.90 (m, 3H), 1.51-1.69 (m, 2H), 0.81 (dd, J = 6.88, 8.62 Hz, 6H) ppm | 4-(4-piperidyl)benzonitrile | General method D using tert-butyl 3-chlorosulfonylazetidine-1-carboxylate, Cf using TFA, then G6 using 2-amino-3-methyl-butan-1-ol. | 3-[4-(4-cyanophenyl)piperidin-1-yl]sulfonyl-N-[1-hydroxy-3-methylbutan-2-yl]azetidine-1-carboxamide |

AND Enantiomer

Table with Representative Compounds of Formula (I):

| Cpd # | Structure | MS (m/z ES+) | δ NMR Data | Starting Int/Cpd# | Sequence of Methods | Chemical Name |
|---|---|---|---|---|---|---|
| 349 | 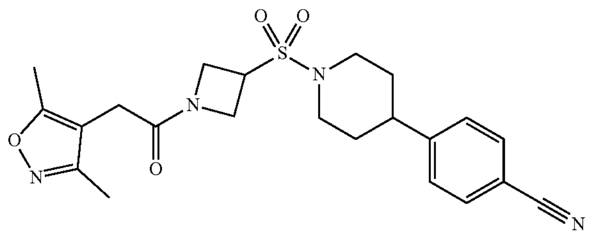 [SMILES: Cc1noc(C)c1CC(=O)N1CC(S(=O)(=O)N2CCC(c3ccc(C#N)cc3)CC2)C1] | 443.7 | ¹H NMR (300 MHz, DMSO-d6): δ = 7.77 (d, J = 8.36 Hz, 2H), 7.47 (d, J = 8.36 Hz, 2H), 4.48-4.59 (m, 1H), 4.33-4.45 (m, 2H), 4.14-4.26 (m, 1H), 4.00 (dd, J = 4.53, 10.28 Hz, 1H), 3.77 (d, J = 12.19 Hz, 2H), 3.26 (d, J = 2.96 Hz, 2H), 2.94 (t, J = 11.41 Hz, 2H), 2.67-2.84 (m, 1H), 2.27 (s, 3H), 2.08 (s, 3H), 1.85 (d, J = 13.41 Hz, 2H), 1.51-1.71 (m, 2H) ppm | 4-(4-piperidyl) benzonitrile | General method D using tert-butyl 3-chlorosulfonylazetidine-1-carboxylate, Cf using TFA, then I1 using 2-(3,5-dimethylisoxazol-4-yl)acetic acid. | 4-[1-[2-(3,5-dimethyl-1,2-oxazol-4-yl)acetyl]azetidin-3-yl]sulfonylpiperidin-4-yl]benzonitrile |
| 350 | 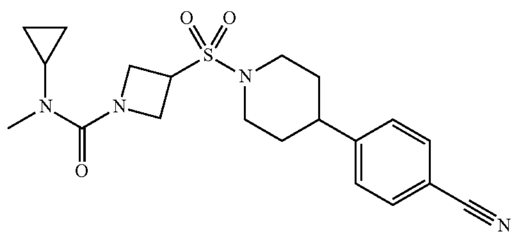 [SMILES: CN(C(=O)N1CC(S(=O)(=O)N2CCC(c3ccc(C#N)cc3)CC2)C1)C1CC1] | 403.7 | ¹H NMR (300 MHz, DMSO-d6): δ = 7.77 (d, J = 8.36 Hz, 2H), 7.47 (d, J = 8.36 Hz, 2H), 4.28-4.40 (m, 1H), 4.22 (t, J = 8.36 Hz, 2H), 4.06-4.16 (m, 2H), 3.74 (d, J = 12.54 Hz, 2H), 2.84-2.97 (m, 2H), 2.72 (s, 3H), 2.69-2.82 (m, 1H), 2.55-2.65 (m, 1H), 1.83 (d, J = 12.54 Hz, 2H), 1.51-1.71 (m, 2H), 0.68-0.80 (m, 2H), 0.57-0.67 (m, 2H) ppm | 4-(4-piperidyl) benzonitrile | General method D using tert-butyl 3-chlorosulfonylazetidine-1-carboxylate, Cf using TFA, then G6 using N-methylcyclopropanamine. | 3-[4-(4-cyanophenyl) piperidin-1-yl]sulfonyl-N-cyclopropyl-N-methylazetidine-1-carboxamide |
| 351 | 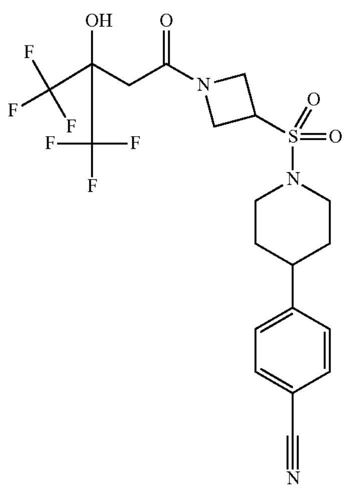 [SMILES: N#Cc1ccc(C2CCN(S(=O)(=O)C3CN(C(=O)CC(O)(C(F)(F)F)C(F)(F)F)C3)CC2)cc1] | 512.6 (m/z, ES-) | 1H NMR (300 MHz, DMSO-d6): δ = 8.52 (br. s., 1H), 7.77 (d, J = 8.36 Hz, 2H), 7.48 (d, J = 8.19 Hz, 2H), 4.52-4.64 (m, 1H), 4.34-4.50 (m, 2H), 4.21-4.33 (m, 1H), 4.05 (dd, J = 5.05, 10.10 Hz, 1H), 3.76 (d, J = 12.54 Hz, 2H), 2.94 (t, J = 12.11 Hz, 2H), 2.82 (d, J = 3.48 Hz, 2H), 2.69-2.78 (m, 1H), 1.84 (d, J = 10.97 Hz, 2H), 1.52-1.71 (m, 2H) ppm | 4-(4-piperidyl) benzonitrile | General method D using tert-butyl 3-chlorosulfonylazetidine-1-carboxylate, Cf using TFA, then I3 using 4,4,4-trifluoro-3-hydroxy-3-(trifluoromethyl) butanoic acid. | 4-[1-[4,4,4-trifluoro-3-hydroxy-3-(trifluoromethyl) butanoyl]azetidin-3-yl]sulfonylpiperidin-4-yl]benzonitrile |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 352 | (structure) | 405.7 | 1H NMR (300 MHz, DMSO-d6): δ = 7.77 (d, J = 8.36 Hz, 2H), 7.47 (d, J = 8.19 Hz, 2H), 5.89 (s, 1H), 4.21-4.35 (m, 1H), 4.05 (t, J = 8.54 Hz, 2H), 3.88-3.97 (m, 2H), 3.73 (d, J = 12.54 Hz, 2H), 2.83-2.98 (m, 2H), 2.68-2.83 (m, 1H), 1.84 (d, J = 11.50 Hz, 2H), 1.60 (dd, J = 3.57, 12.45 Hz, 2H), 1.22 (s, 9H) ppm | 4-(4-piperidyl)benzonitrile | General method D using tert-butyl 3-chlorosulfonylazetidine-1-carboxylate, Cf using TFA, then G2 using 2-isocyanato-2-methyl-propane. | N-tert-butyl-3-[4-(4-cyanophenyl)piperidin-1-yl]sulfonylazetidine-1-carboxamide |
| 353 | (structure) | 437 | 1H NMR (300 MHz, DMSO-d6): d = 1.49-1.67 (m, 2H), 1.80 (d, J = 13.58 Hz, 2H), 2.54-2.74 (m, 2H), 2.86 (t, J = 11.98 Hz, 2H), 3.38 (t, J = 7.41 Hz, 2H), 3.55-3.76 (m, 6H), 4.16-4.30 (m, 1H), 7.13-7.46 (m, 9H) ppm | 4-phenyl-piperidine | General method D using tert-butyl 3-chlorosulfonylazetidine-1-carboxylate, Cf using TFA, J using 1-(bromomethyl)-2-(difluoromethoxy) benzene | 1-[1-[[2-(difluoromethoxy)phenyl]methyl]azetidin-3-yl]sulfonyl-4-phenylpiperidine |
| 354 | (structure) | 353.0 (M + H - tBu) + | 1H NMR (600 MHz, CHLOROFORM-d) δ 7.02-7.05 (m, 2H), 6.95-7.00 (m, 2H), 4.21-4.27 (m, 2H), 4.16 (t, J = 8.65 Hz, 2H), 3.97 (d, J = 11.92 Hz, 2H), 3.89-3.95 (m, 1H), 2.90 (t, J = 12.38 Hz, 2H), 2.77 (t, J = 11.92 Hz, 1H), 2.28 (s, 3H), 2.27 (s, 3H), 1.82 (d, J = 13.34 Hz, 2H), 1.72 (qd, J = 2.60, 12.58 Hz, 2H), 1.43 (s, 9H). | (2,4-dimethylphenyl) boronic acid | General method A3, B1 using Pd/C, Ci using TFA, D using tert-butyl 3-chlorosulfonyl azetidine-1-carboxylate | tert-butyl 3-[4-(2,4-dimethylphenyl)piperidin-1-yl]sulfonylazetidine-1-carboxylate |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 355 | 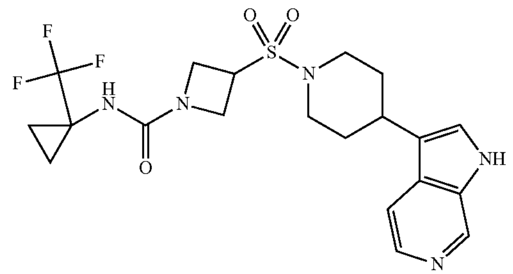 [SMILES: O=C(NC1(C(F)(F)F)CC1)N1CC(S(=O)(=O)N2CCC(c3c[nH]c4cnccc34)CC2)C1] | 472.1 | 1H NMR (300 MHz, DMSO-d6): δ = 11.36 (s, 1H), 8.68 (d, J = 0.70 Hz, 1H), 8.05 (d, J = 5.57 Hz, 1H), 7.48-7.56 (m, 1H), 7.40 (d, J = 10.97 Hz, 2H), 4.25-4.39 (m, 1H), 4.12 (t, J = 8.62 Hz, 2H), 3.96 (dd, J = 5.57, 9.06 Hz, 2H), 3.72 (d, J = 12.02 Hz, 2H), 2.86-3.05 (m, 3H), 2.01 (d, J = 11.15 Hz, 2H), 1.52-1.72 (m, 2H), 1.12-1.24 (m, 2H), 0.94-1.03 (m, 2H) ppm | 1H-pyrrolo [2,3-c]pyridine | General method A2 using KOH, B2 using Pd/C, E using 4-methylbenzenesulfonyl chloride, Ci using TFA, method D using tert-butyl 3-chlorosulfonylazetidine-1-carboxylate, Cf using TFA, G2 using 1-isocyanato-1-(trifluoromethyl) cyclopropane, then F using Cs₂CO₃. | 3-[4-(1H-pyrrolo[2,3-c]pyridin-3-yl)piperidin-1-yl]sulfonyl-N-[1-(trifluoromethyl) cyclopropyl] azetidine-1-carboxamide |
| 356 | 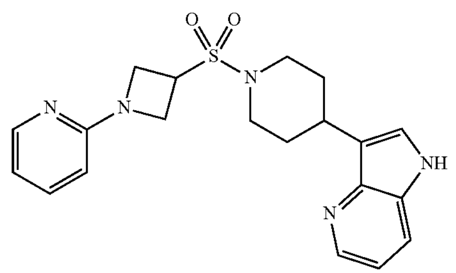 [SMILES: O=S(=O)(C1CN(c2ccccn2)C1)N1CCC(c2c[nH]c3cccnc23)CC1] | 398.15 | ¹H NMR (300 MHz, DMSO-d₆): d = 1.71-1.88 (m, 2H), 2.15 (d, J = 13.19 Hz, 2H), 2.95 (t, J = 12.53 Hz, 2H), 3.05-3.17 (m, 1H), 3.62-3.75 (m, 4H), 3.83 (t, J = 8.08 Hz, 2H), 4.35-4.48 (m, 1H), 7.22-7.32 (m, 2H), 7.81 (d, J = 8.62 Hz, 1H), 7.94-8.02 (m, 1H), 8.17 (s, 1H), 8.43 (dd, J = 4.71, 1.21 Hz, 1H), 8.55 (dd, J = 4.58, 1.35 Hz, 1H), 8.75 (dd, J = 8.49, 1.48 Hz, 1H) ppm | 1H-pyrrolo [3,2-b]pyridine | General method A2 using KOH, B2 using ammonium formate, Ci using TFA, D using tert-butyl 3-chlorosulfonyl azetidine-1-carboxylate, Cf using TFA, J3 using 2-fluoropyridine | 3-[1-(1-pyridin-2-yl)azetidin-3-yl]sulfonyl]piperidin-4-yl]-1H-pyrrolo[3,2-b]pyridine |
| 357 | 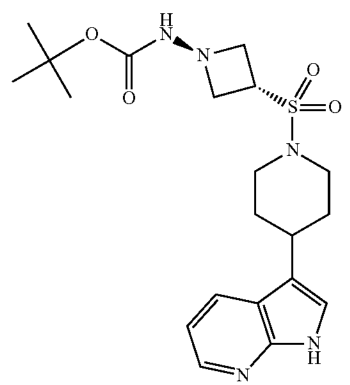 | 435.1 | 1H NMR (600 MHz, CHLOROFORM-d) δ 8.89 (br. s., 1H), 8.29 (d, J = 4.40 Hz, 1H), 7.90 (d, J = 7.89 Hz, 1H), 7.02-7.09 (m, 2H), 4.76 (br. s., 1H), 4.29 (d, J = 6.60 Hz, 1H), 3.94 (d, J = 11.92 Hz, 2H), 3.75 (br. s., 1H), 2.79-3.00 (m, 5H), 2.47 (br. s., 2H), 2.07 (d, J = 12.84 Hz, 2H), 1.81 (q, J = 11.87 Hz, 2H), 1.43 (s, 9H). | 3-(4-piperidyl)-1H-pyrrolo [2,3-b]pyridine | General method U using cis-tert-butyl N-(3-sulfanylcyclobutyl) carbamate. | trans-tert-butyl N-[3-[4-(1H-pyrrolo[2,3-b]pyridin-3-yl)piperidin-1-yl] sulfonylcyclobutyl] carbamate |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 358 | 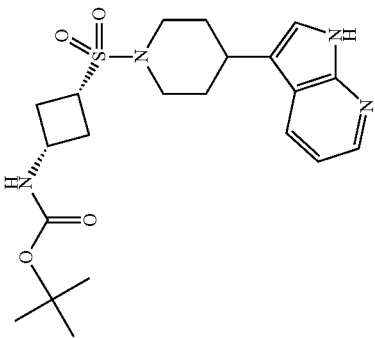 | 435.2 | 1H NMR (600 MHz, CHLOROFORM-d) δ 9.04 (br. s., 1H), 8.29 (d, J = 4.58 Hz, 1H), 7.90 (d, J = 7.89 Hz, 1H), 7.02-7.09 (m, 2H), 4.92 (d, J = 7.89 Hz, 1H), 4.19 (d, J = 7.34 Hz, 1H), 3.89 (d, J = 11.55 Hz, 2H), 3.44 (quin, J = 8.39 Hz, 1H), 2.90 (t, J = 12.10 Hz, 3H), 2.74 (d, J = 8.25 Hz, 2H), 2.33-2.41 (m, 2H), 2.08 (d, J = 13.02 Hz, 2H), 1.82 (qd, J = 3.01, 12.66 Hz, 2H), 1.42 (s, 9H). | 3-(4-piperidyl)-1H-pyrrolo[2,3-b]pyridine | General method U using cis-tert-butyl-N-(3-sulfanylcyclobutyl) carbamate. | cis-tert-butyl N-[3-[4-(1H-pyrrolo[2,3-b]pyridin-3-yl)piperidin-1-yl]sulfonyl-cyclobutyl) carbamate |
| 359 | 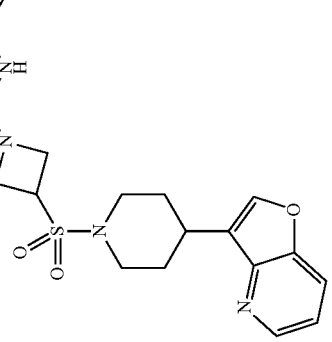 | 511 | 1H NMR (600 MHz, DMSO-d6) δ 8.50 (d, J = 4.58 Hz, 1H), 8.34 (s, 1H), 8.10 (s, 1H), 7.98 (d, J = 8.25 Hz, 1H), 7.57-7.63 (m, 2H), 7.37 (d, J = 8.80 Hz, 1H), 7.33 (dd, J = 4.95, 8.07 Hz, 1H), 4.36-4.44 (m, 1H), 4.31 (t, J = 8.62 Hz, 2H), 4.11-4.18 (m, 2H), 3.74 (d, J = 11.74 Hz, 2H), 2.96-3.09 (m, 3H), 2.14 (d, J = 13.02 Hz, 2H), 1.77 (q, J = 12.10 Hz, 2H). | 3-bromofuro[3,2-b]pyridine | General method A1 using K2CO3, B1 using Pd/C, Ci using HCl in dioxane, D using tert-butyl 3-chlorosulfonyl azetidine-1-carboxylate, Cf using HCl in dioxane, G2 using 2,4-dichlorophenyl isocyanate | N-(2,4-dichlorophenyl)-3-(4-furo[3,2-b]pyridin-3-ylpiperidin-1-yl)sulfonylazetidine-1-carboxamide |

| Cpd # | Structure | MS (m/z, ES+) | δ NMR Data | Starting Int/Cpd# | Sequence of Methods | Chemical Name |
|---|---|---|---|---|---|---|
| 360 | 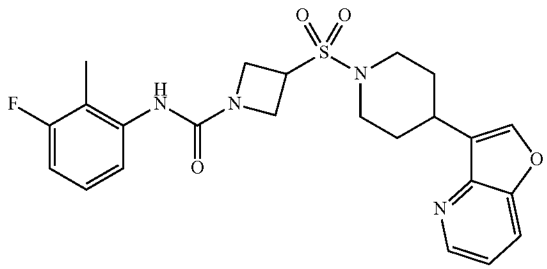 [SMILES: Cc1c(F)cccc1NC(=O)N1CC(S(=O)(=O)N2CCC(c3coc4cccnc34)CC2)C1] | 473.1 | 1H NMR (600 MHz, DMSO-d6) δ 8.50 (d, J = 4.58 Hz, 1H), 8.26 (s, 1H), 8.11 (s, 1H), 7.98 (d, J = 8.44 Hz, 1H), 7.33 (dd, J = 5.04, 7.98 Hz, 1H), 7.10-7.19 (m, 2H), 6.89-6.98 (m, 1H), 4.35-4.43 (m, 1H), 4.29 (t, J = 8.71 Hz, 2H), 4.10-4.16 (m, 2H), 3.75 (d, J = 11.92 Hz, 2H), 2.98-3.07 (m, 3H), 2.15 (d, J = 13.02 Hz, 2H), 2.07 (s, 3H), 1.77 (q, J = 12.17 Hz, 2H). | 3-bromofuro [3,2-b]pyridine | General method A1 using K2CO3, B1 using Pd/C, Ci using HCl in dioxane, D using tert-butyl 3-chlorosulfonyl azetidine-1-carboxylate, Cf using HCl in dioxane, G2 using 3-fluoro-2-methylphenyl isocyanate | N-(3-fluoro-2-methylphenyl)-3-(4-furo[3,2-b]pyridin-3-ylpiperidin-1-yl)sulfonylazetidine-1-carboxamide |
| 361 | 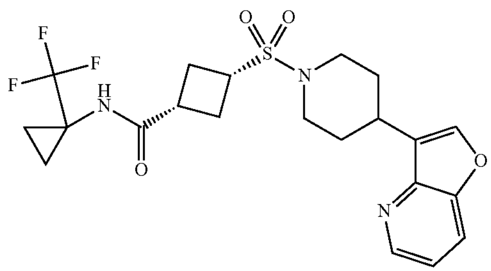 [SMILES: O=C(NC1(C(F)(F)F)CC1)[C@H]1C[C@@H](S(=O)(=O)N2CCC(c3coc4cccnc34)CC2)C1] | 472.6 | 1H NMR (600 MHz, CHLOROFORM-d) d 8.51 (d, J = 4.77 Hz, 1H), 7.72 (d, J = 8.07 Hz, 1H), 7.60-7.63 (m, 1H), 7.21 (dd, J = 4.68, 8.53 Hz, 1H), 6.12-6.21 (m, 1H), 3.92 (d, J = 13.02 Hz, 2H), 3.65-3.80 (m, 1H), 2.91-3.14 (m, 4H), 2.66-2.74 (m, 2H), 2.52-2.61 (m, 2H), 2.24 (d, J = 12.29 Hz, 2H), 1.78-1.87 (m, 2H), 1.30-1.35 (m, 2H), 1.11 (s, 2H) ppm | 3-bromofuro [3,2-b]pyridine | General method A1 using K2CO3, B1 using Pd/C, Ci using TFA, D using methyl 3-chlorosulfonylcyclobutane carboxylate (separation of isomers), V using NaOH, I5 using 1-(trifluoromethyl) cyclopropanamine | cis-3-(4-furo[3,2-b]pyridin-3-ylpiperidin-1-yl)sulfonyl-N-[1-(trifluoromethyl) cyclopropyl] cyclobutane-1-carboxamide |
| 362 | 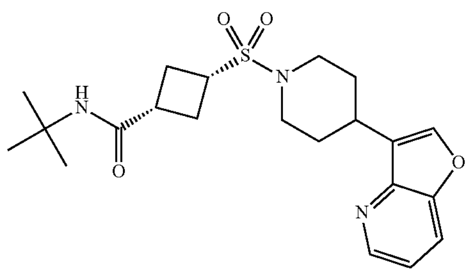 [SMILES: CC(C)(C)NC(=O)[C@H]1C[C@@H](S(=O)(=O)N2CCC(c3coc4cccnc34)CC2)C1] | 420.7 | 1H NMR (600 MHz, CHLOROFORM-d) d 8.51 (d, J = 4.58 Hz, 1H), 7.71 (d, J = 8.25 Hz, 1H), 7.61 (s, 1H), 7.21 (dd, J = 4.77, 8.25 Hz, 1H), 5.37 (br: s., 1H), 3.92 (d, J = 12.29 Hz, 2H), 3.69 (quin, J = 8.71 Hz, 1H), 3.08 (t, J = 11.92 Hz, 1H), 3.01 (t, J = 12.38 Hz, 2H), 2.81-2.89 (m, 1H), 2.65-2.73 (m, 2H), 2.45-2.52 (m, 2H), 2.23 (d, J = 12.47 Hz, 2H), 1.82 (dq, J = 3.85, 12.47 Hz, 2H), 1.33 (s, 9H) ppm | 3-bromofuro [3,2-b]pyridine | General method A1 using K2CO3, B1 using Pd/C, Ci using TFA, D using methyl 3-chlorosulfonylcyclobutane carboxylate (separation of isomers), V using NaOH, I5 using 2-methylpropan-2-amine | cis-N-tert-butyl-3-(4-furo[3,2-b]pyridin-3-ylpiperidin-1-yl) sulfonylcyclobutane-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 363 | 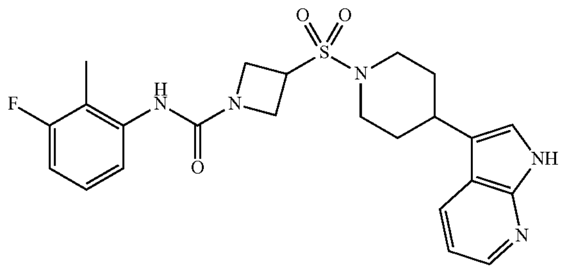 [SMILES: Cc1c(F)cccc1NC(=O)N1CC(S(=O)(=O)N2CCC(c3c[nH]c4ncccc34)CC2)C1] | 472.1 | 1H NMR (300 MHz, DMSO-d6) δ 11.38 (s, 1H), 8.27 (s, 1H), 8.17 (dd, J = 1.48, 4.62 Hz, 1H), 7.98 (dd, J = 1.39, 7.84 Hz, 1H), 7.24 (d, J = 1.74 Hz, 1H), 7.12-7.16 (m, 2H), 6.89-7.04 (m, 2H), 4.35-4.45 (m, 1H), 4.28 (t, J = 8.54 Hz, 2H), 4.08-4.17 (m, 2H), 3.76 (d, J = 12.37 Hz, 2H), 2.87-3.08 (m, 3H), 2.07 (d, J = 2.26 Hz, 4H), 2.01 (br. s., 1H), 1.56-1.73 (m, 2H) ppm | 3-(4-piperidyl)-1H-pyrrolo[2,3-b]pyridine | General method D using tert-butyl 3-chlorosulfonylazetidine-1-carboxylate, Cf using TFA, G2 using 4-fluoro-2-isocyanato-1-methyl-benzene | N-(3-fluoro-2-methylphenyl)-3-[4-(1H-pyrrolo[2,3-b]pyridin-3-yl)piperidin-1-yl]sulfonylazetidine-1-carboxamide |
| 364 | 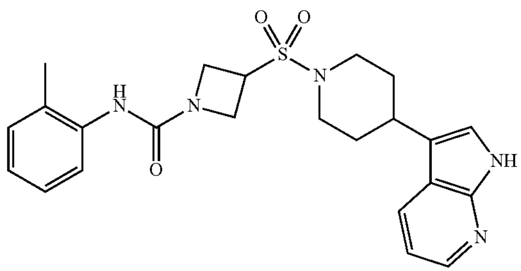 [SMILES: Cc1ccccc1NC(=O)N1CC(S(=O)(=O)N2CCC(c3c[nH]c4ncccc34)CC2)C1] | 454.14 | 1H NMR (300 MHz, DMSO-d6) δ 11.38 (br. s., 1H), 8.17 (d, J = 3.14 Hz, 1H), 8.05 (s, 1H), 7.98 (d, J = 7.14 Hz, 1H), 7.22-7.30 (m, 2H), 7.08-7.21 (m, 2H), 6.96-7.08 (m, 2H), 4.38 (d, J = 8.71 Hz, 1H), 4.26 (t, J = 8.71 Hz, 2H), 4.06-4.16 (m, 2H), 3.75 (d, J = 12.72 Hz, 2H), 2.87-3.08 (m, 3H), 2.18 (s, 3H), 1.97-2.09 (m, 2H), 1.55-1.74 (m, 2H) ppm | 3-(4-piperidyl)-1H-pyrrolo[2,3-b]pyridine | General method D using tert-butyl 3-chlorosulfonylazetidine-1-carboxylate, Cf using TFA, G2 using 1-isocyanato-2-methyl-benzene | N-(2-methylphenyl)-3-[4-(1H-pyrrolo[2,3-b]pyridin-3-yl)piperidin-1-yl]sulfonylazetidine-1-carboxamide |
| 365 | 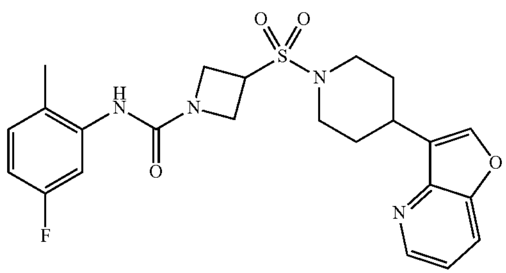 [SMILES: Cc1ccc(F)cc1NC(=O)N1CC(S(=O)(=O)N2CCC(c3coc4cccnc34)CC2)C1] | 473.1 | 1H NMR (600 MHz, DMSO-d6) δ 8.46-8.54 (m, 1H), 8.10 (s, 1H), 8.05 (s, 1H), 7.98 (d, J = 8.25 Hz, 1H), 7.33 (dd, J = 4.77, 8.07 Hz, 1H), 7.26 (d, J = 11.00 Hz, 1H), 7.18 (t, J = 7.43 Hz, 1H), 6.80-6.88 (m, 1H), 4.36-4.42 (m, 1H), 4.30 (t, J = 8.62 Hz, 2H), 4.11-4.18 (m, 2H), 3.75 (d, J = 11.74 Hz, 2H), 2.98-3.08 (m, 3H), 2.10-2.18 (m, 5H), 1.77 (qd, J = 2.80, 12.66, 2H). | 3-bromofuro[3,2-b]pyridine | General method A1 using K2CO3, B1 using Pd/C, Ci using HCl in dioxane, D using tert-butyl 3-chlorosulfonyl azetidine-1-carboxylate, Cf using HCl in dioxane, G2 using 5-fluoro-2-methylphenyl isocyanate | N-(5-fluoro-2-methylphenyl)-3-(4-furo[3,2-b]pyridin-3-ylpiperidin-1-yl)sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 366 | 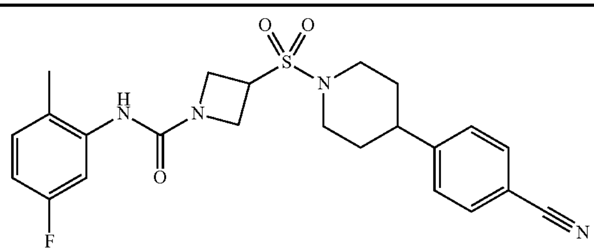 | 457.13 | ¹H NMR (300 MHz, DMSO-d₆): d = 1.53-1.70 (m, 2 H), 1.85 (d, J = 12.5 Hz, 2 H), 2.16 (s, 2 H), 2.70-2.85 (m, 1 H), 2.95 (t, J = 12.5, 2 H), 3.77 (d, J = 13.4 Hz, 1 H), 4.08-4.18 (m, 2 H), 4.29 (t, J = 9.6, 2 H), 4.33-4.45 (m, 1H), 6.85 (dt, J = 2.97, 8.45, 1H) 7.17 (m, 1 H), 7.26 (dd, J = 2.76, 11.29, 1 H), 7.46 (d, J = 8.03, 2H), 7.75 (d, J = 9.24, 2H), 8.06 (s, 1 H) ppm | 4-(4-piperidyl) benzonitrile | General method D using tert-butyl 3-chlorosulfonylazetidine-1-carboxylate, Cf using TFA, G2 using 4-fluoro-2-isocyanato-1-methyl-benzene | 3-[4-(4-cyanophenyl) piperidin-1-yl]sulfonyl-N-(5-fluoro-2-methylphenyl) azetidine-1-carboxamide |
| 367 | 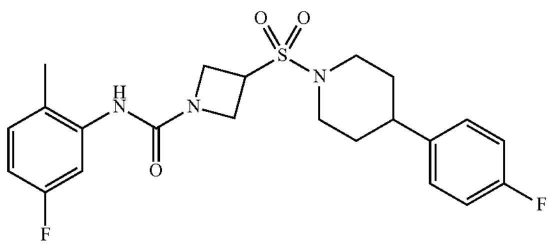 [SMILES: Cc1ccc(F)cc1NC(=O)N1CC(S(=O)(=O)N2CCC(c3ccc(F)cc3)CC2)C1] | 450.1 | 1H NMR (300 MHz, DMSO-d6): δ = 8.06 (s, 1H), 7.23-7.32 (m, 3H), 7.14-7.22 (m, 1H), 7.04-7.13 (m, 2H), 6.85 (dt, J = 2.70, 8.40 Hz, 1H), 4.33-4.45 (m, 1H), 4.23-4.33 (m, 2H), 4.08-4.17 (m, 2H), 3.75 (d, J = 12.02 Hz, 2H), 2.87-3.00 (m, 2H), 2.59-2.75 (m, 1H), 2.16 (s, 3H), 1.81 (d, J = 12.02 Hz, 2H), 1.48-1.66 (m, 2H) ppm | 4-(4-fluoro-phenyl) piperidine | General method D using tert-butyl 3-chlorosulfonylazetidine-1-carboxylate, Cf using TFA, then G2 using 4-fluoro-2-isocyanato-1-methyl-benzene. | N-(5-fluoro-2-methylphenyl)-3-[4-(4-fluorophenyl) piperidin-1-yl]sulfonylazetidine-1-carboxamide |
| 368 | 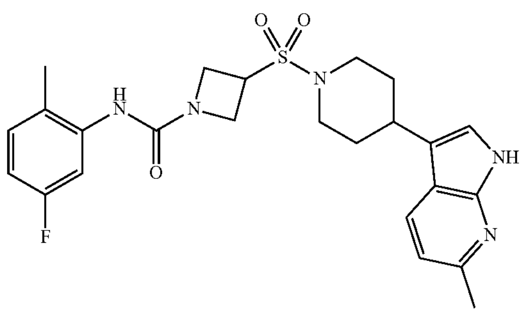 [SMILES: Cc1ccc2c(C3CCN(S(=O)(=O)C4CN(C(=O)Nc5cc(F)ccc5C)C4)CC3)c[nH]c2n1] | 486.1 | 1H NMR (500 MHz, DMSO-d6) δ 11.16 (s, 1H), 8.06 (s, 1H), 7.86 (d, J = 7.93 Hz, 1H), 7.27 (dd, J = 2.44, 10.99 Hz, 1H), 7.16-7.22 (m, 1H), 7.13 (d, J = 2.14 Hz, 1H), 6.89 (d, J = 7.93 Hz, 1H), 6.86 (td, J = 2.80, 8.53 Hz, 1H), 4.36-4.44 (m, 1H), 4.30 (t, J = 8.70 Hz, 2H), 4.15 (dd, J = 5.49, 8.85 Hz, 2H), 3.75 (d, J = 12.21 Hz, 2H), 3.01 (td, J = 1.58, 12.47 Hz, 2H), 2.90 (tt, J = 3.10, 11.85 Hz, 1H), 2.47 (s, 3H), 2.17 (s, 3H), 2.03 (d, J = 11.90 Hz, 2H), 1.63 (dq, J = 3.81, 12.46 Hz, 2H). | 6-methyl-1H-pyrrolo[2,3-b]pyridine | General method A2 using KOtBu, B1 using Pd/C, Ci using TFA, D using tert-butyl 3-chlorosulfonylazetidine-1-carboxylate, Cf using TFA, G2 using 5-fluoro-2-methylphenyl isocyanate | N-(5-fluoro-2-methylphenyl)-3-[4-(6-methyl-1H-pyrrolo[2,3-b]pyridin-3-yl)piperidin-1-yl]sulfonylazetidine-1-carboxamide |

| Cpd # | Structure | MS (m/z, ES +) | δ NMR Data | Starting Int/Cpd# | Sequence of Methods | Chemical Name |
|---|---|---|---|---|---|---|
| 369 | 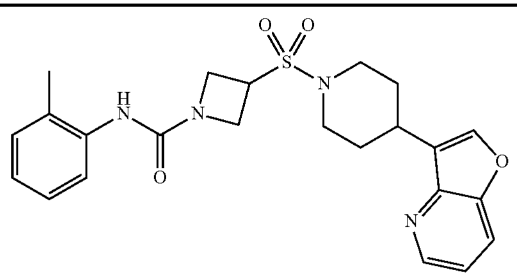 | 455.1 | 1H NMR (600 MHz, DMSO-d6) δ 8.47-8.54 (m, 1H), 8.05 (s, 1H), 7.98 (d, J = 8.44 Hz, 1H), 7.33 (dd, J = 4.95, 7.89 Hz, 1H), 7.26 (d, J = 7.89 Hz, 1H), 7.17 (d, J = 7.34 Hz, 1H), 7.12 (t, J = 7.52 Hz, 1H), 7.00-7.06 (m, 1H), 4.35-4.42 (m, 1H), 4.26 (t, J = 8.62 Hz, 2H), 4.06-4.15 (m, 2H), 3.75 (d, J = 11.92 Hz, 2H), 2.97-3.08 (m, 3H), 2.18 (s, 3H), 2.15 (d, J = 12.84 Hz, 2H), 1.77 (q, J = 12.17 Hz, 2H). | 3-bromofuro [3,2-b]pyridine | General method A1 using K2CO3, B1 using Pd/C, Ci using HCl in dioxane, D using tert-butyl 3-chlorosulfonyl azetidine-1-carboxylate, Cf using HCl in dioxane, G2 using 2-methylphenyl isocyanate | 3-(4-furo[3,2-b]pyridin-3-yl)piperidin-1-yl)sulfonyl-N-(2-methylphenyl) azetidine-1-carboxamide |
| 370 | 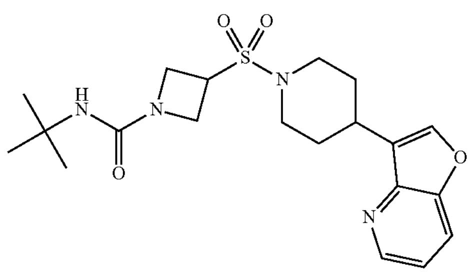 [SMILES: CC(C)(C)NC(=O)N1CC(S(=O)(=O)N2CCC(c3coc4cccnc34)CC2)C1] | 421.2 | 1H NMR (600 MHz, DMSO-d6) δ 8.50 (d, J = 3.85 Hz, 1H), 8.11 (s, 1H), 7.98 (d, J = 8.25 Hz, 1H), 7.33 (dd, J = 5.04, 7.98 Hz, 1H), 5.88 (s, 1H), 4.28 (quin, J = 7.06 Hz, 1H), 4.06 (t, J = 8.62 Hz, 2H), 3.91-3.96 (m, 2H), 3.71 (d, J = 12.10 Hz, 2H), 2.99 (t, J = 11.83 Hz, 3H), 2.13 (d, J = 13.20 Hz, 2H), 1.75 (q, J = 12.41 Hz, 2H), 1.22 (s, 9H). | 3-bromofuro [3,2-b]pyridine | General method A1 using K2CO3, B1 using Pd/C, Ci using HCl in dioxane, D using tert-butyl 3-chlorosulfonyl azetidine-1-carboxylate, Cf using HCl in dioxane, G2 using tert-butyl isocyanate | N-tert-butyl-3-(4-furo[3,2-b]pyridin-3-yl)piperidin-1-yl)sulfonylaze-tidine-1-carboxamide |
| 371 | 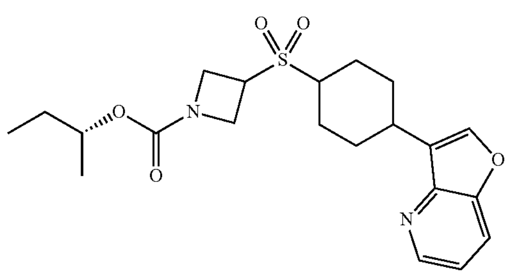 [SMILES: CC[C@@H](C)OC(=O)N1CC(S(=O)(=O)C2CCC(c3coc4cccnc34)CC2)C1] | 422.1 | 1H NMR (300 MHz, DMSO-d6): δ = 8.50 (dd, J = 1.05, 4.70 Hz, 1H), 8.11 (s, 1H), 7.98 (dd, J = 1.13, 8.45 Hz, 1H), 7.33 (dd, J = 4.79, 8.45 Hz, 1H), 4.58 (q, J = 6.15 Hz, 1H), 4.30-4.41 (m, 1H), 4.24 (br. s., 2H), 4.03 (br. s., 2H), 3.72 (d, J = 12.02 Hz, 2H), 3.00 (t, J = 12.19 Hz, 3H), 2.13 (d, J = 10.63 Hz, 2H), 1.65-1.83 (m, 2H), 1.41-1.56 (m, 2H), 1.13 (d, J = 6.10 Hz, 3H), 0.83 (t, J = 7.40 Hz, 3H) ppm | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, then G3 using (2R)-butan-2-ol. | [(2R)-butan-2-yl]3-(4-furo[3,2-b]pyridin-3-yl)piperidin-1-yl)sulfonylaze-tidine-1-carboxylate |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 372 | 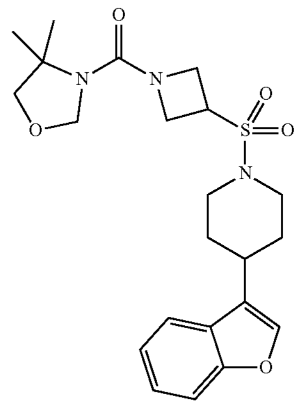 [SMILES: CC1(C)COCN1C(=O)N1CC(S(=O)(=O)N2CCC(c3coc4ccccc34)CC2)C1] | 449.1 | 1H NMR (300 MHz, DMSO-d6): δ = 8.50 (dd, J = 1.31, 4.79 Hz, 1H), 8.11 (s, 1H), 7.98 (dd, J = 1.39, 8.36 Hz, 1H), 7.33 (dd, J = 4.70, 8.36 Hz, 1H), 4.74 (s, 2H), 4.29-4.42 (m, 1H), 4.12 (t, J = 8.62 Hz, 2H), 3.94-4.06 (m, 2H), 3.72 (d, J = 12.19 Hz, 2H), 3.65 (s, 2H), 2.92-3.08 (m, 3H), 2.13 (d, J = 10.80 Hz, 2H), 1.66-1.84 (m, 2H), 1.29-1.38 (m, 6H) ppm | 3-bromofuro [3,2-b]pyridine | General method A1 using K$_2$CO$_3$, B1 using Pd/C, Ci using TFA, D using tert-butyl 3-chlorosulfonylazetidine-1-carboxylate, Cf using TFA, then G3 using 4,4-dimethyloxazolidine. | (4,4-dimethyl-1,3-oxazolidin-3-yl)-[3-(4-furo[3,2-b]pyridin-3-yl)piperidin-1-yl)sulfonylazetidin-1-yl]methanone |
| 373 | 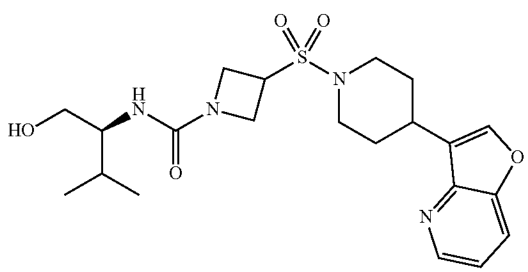 [SMILES: CC(C)[C@@H](CO)NC(=O)N1CC(S(=O)(=O)N2CCC(c3coc4cccnc34)CC2)C1] | 451.1 | 1H NMR (300 MHz, DMSO-d6): δ = 8.50 (dd, J = 1.39, 4.70 Hz, 1H), 8.11 (s, 1H), 7.98 (dd, J = 1.39, 8.36 Hz, 1H), 7.30-7.37 (m, 1H), 6.03 (d, J = 8.19 Hz, 1H), 4.43-4.51 (m, 1H), 4.26-4.38 (m, 1H), 4.11 (td, J = 8.47, 12.67 Hz, 2H), 4.00-4.05 (m, 1H), 3.89-3.99 (m, 1H), 3.72 (d, J = 11.50 Hz, 2H), 3.33-3.41 (m, 3H), 2.93-3.09 (m, 3H), 2.13 (d, J = 11.50 Hz, 2H), 1.65-1.85 (m, 3H), 0.75-0.85 (m, 6H) ppm | 3-bromofuro [3,2-b]pyridine | General method A1 using K$_2$CO$_3$, B1 using Pd/C, Ci using TFA, D using tert-butyl 3-chlorosulfonyl-azetidine-1-carboxylate, Cf using TFA, then G6 using (2S)-2-amino-3-methyl-butan-1-ol. | 3-(4-furo[3,2-b]pyridin-3-ylpiperidin-1-yl)sulfonyl-N-[(2S)-1-hydroxy-3-methylbutan-2-yl]azetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 374 | 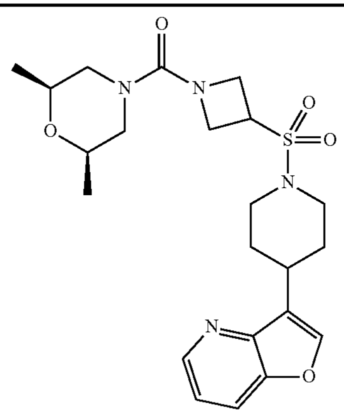 | 463.1 | 1H NMR (300 MHz, DMSO-d6): δ = 8.50 (dd, J = 1.39, 4.70 Hz, 1H), 8.11 (s, 1H), 7.98 (dd, J = 1.39, 8.36 Hz, 1H), 7.33 (dd, J = 4.88, 8.36 Hz, 1H), 4.29-4.43 (m, 1H), 4.22 (t, J = 8.62 Hz, 2H), 4.04-4.14 (m, 2H), 3.72 (d, J = 12.37 Hz, 2H), 3.54 (d, J = 12.89 Hz, 2H), 3.37-3.49 (m, 2H), 2.92-3.07 (m, 3H), 2.36-2.46 (m, 2H), 2.13 (d, J = 10.63 Hz, 2H), 1.66-1.84 (m, 2H), 1.05 (d, J = 6.27 Hz, 6H) ppm | 3-bromofuro [3,2-b]pyridine | General method A1 using K₂CO₃, B1 using Pd/C, Ci using TFA, D using tert-butyl 3-chlorosulfonyl azetidine-1-carboxylate, Cf using TFA, then G3 using cis-2,6-dimethylmorpholine. | [(2R,6S)-2,6-dimethylmorpholin-4-yl]-[3-(4-furo[3,2-b]pyridin-3-yl)piperidin-1-yl)sulfonyl]azetidin-1-yl]methanone |
| 375 | 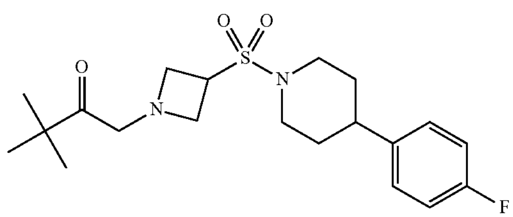 [SMILES: CC(C)(C)C(=O)CN1CC(S(=O)(=O)N2CCC(c3ccc(F)cc3)CC2)C1] | 397.1 | 1H NMR (300 MHz, DMSO-d6): δ = 7.23-7.32 (m, 2H), 7.05-7.16 (m, 2H), 4.16-4.29 (m, 1H), 3.60-3.72 (m, 4H), 3.59 (s, 2H), 3.27-3.36 (m, 2H), 2.80-2.93 (m, 2H), 2.56-2.70 (m, 1H), 1.80 (d, J = 10.80 Hz, 2H), 1.49-1.66 (m, 2H), 1.05 (s, 9H) ppm | 4-(4-fluorophenyl) piperidine | General method D using tert-butyl 3-chlorosulfonylazetidine-1-carboxylate, Cf using TFA, then J1 using 1-bromo-3,3-dimethyl-butan-2-one. | 1-[3-[4-(4-fluorophenyl) piperidin-1-yl]sulfonylazetidin-1-yl]-3,3-dimethylbutan-2-one |
| 376 | 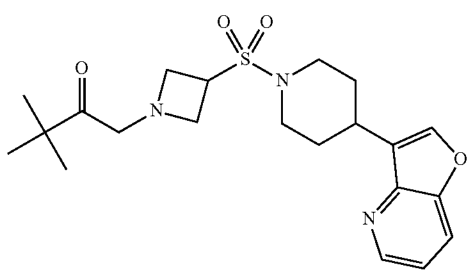 [SMILES: CC(C)(C)C(=O)CN1CC(S(=O)(=O)N2CCC(c3coc4cccnc34)CC2)C1] | 420.2 | ¹H NMR (300 MHz, DMSO-d₆) d 8.50 (dd, J = 1.42, 4.71 Hz, 2H), 8.12 (s, 1H), 7.99 (dd, J = 1.69, 8.49 Hz, 1H), 7.29-7.37 (m, 1H), 4.20-4.33 (m, 1H), 3.61-3.81 (m, 6H), 3.37-3.47 (m, 2H), 2.98 (t, J = 11.9 Hz, 4H), 2.11 (d, J = 13.7 Hz, 2H), 1.67-1.84 (m, 2H), 1.05 (s, 9H) ppm | 3-bromofuro [3,2-b]pyridine | General method A1 using K2CO3, B1 using Pd/C, Ci using TFA, D using tert-butyl 3-chlorosulfonylazetidine-1-carboxylate, Cf using TFA, J1 using 1-bromo-3,3-dimethyl-butan-2-one | 1-[3-[4-(4-furo[3,2-b]pyridin-3-yl)piperidin-1-yl]sulfonylazetidin-1-yl]-3,3-dimethylbutan-2-one |

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 377 | 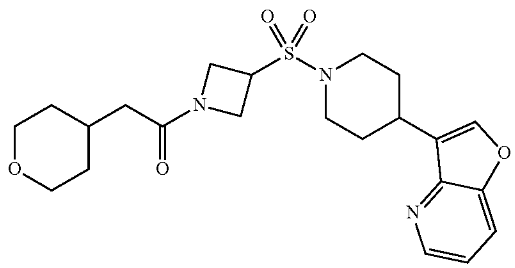 [SMILES: O=C(CC1CCOCC1)N1CC(S(=O)(=O)N2CCC(c3coc4cccnc34)CC2)C1] | 448.2 | ¹H NMR (300 MHz, DMSO-d₆): d = 1.09-1.27 (m, 2 H), 1.54 (d, J = 14.03 Hz, 2 H), 1.65-1.91 (m, 4 H), 1.98-2.04 (m, 2H), 2.13 (d, J = 10.9 Hz, 2 H), 3.01 (t, J = 11.9 Hz, 3 H), 3.20-3.30 (m, 1H), 3.76 (t, J = 13.8 Hz, 4 H), 3.93-4.00 (m, 1H), 4.16 (t, J = 9.1 Hz, 1 H), 4.25-4.39 (m, 2 H), 4.47 (t, J = 7.80 Hz, 1 H), 7.30-7.36 (m, 1H), 7.99 (dd, J = 1.49, 8.40 Hz, 1H), 8.11 (s, 1H), 8.50 (dd, J = 1.40, 4.65, 1H) ppm | 3-bromofuro [3,2-b]pyridine | General method A1 using K2CO3, B1 using Pd/C, Ci using TFA, D using tert-butyl 3-chlorosulfonylazetidine-1-carboxylate, Cf using TFA, I4 using 2-tetrahydropyran-4-ylacetic acid | 1-[3-(4-furo[3,2-b]pyridin-3-ylpiperidin-1-yl)sulfonylazetidin-1-yl]-2-(oxan-4-yl)ethanone |
| 378 | 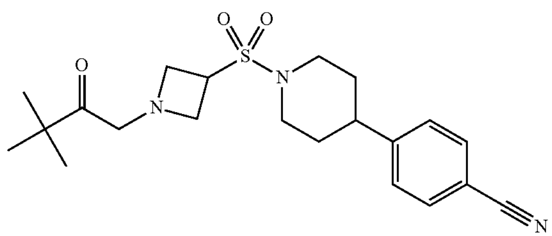 [SMILES: CC(C)(C)C(=O)CN1CC(S(=O)(=O)N2CCC(c3ccc(C#N)cc3)CC2)C1] | 404.2 | ¹H NMR (600 MHz, DMSO-d) Shift = 1.05 (s, 9 H), 1.57-1.66 (m, 2 H), 1.82 (d, J = 14.2 Hz, 2 H), 2.72-2.78 (m, 1 H), 2.88 (t, J = 12.1 Hz, 2H), 3.33 (d, J = 8.35 Hz, 2H), 3.58 (s, 2 H), 3.64 (t, J = 8.77 Hz, 2 H), 3.69 (d, J = 12.52 Hz, 2 H), 4.20-4.27 (m, 1H), 7.47 (d, J = 7.93 Hz, 2 H), 7.76 (d, J = 9.59 Hz, 2 H) ppm | 4-(4-piperidyl) benzonitrile | General method D using tert-butyl 3-chlorosulfonylazetidine-1-carboxylate, Cf using TFA, J1 using 1-bromo-3,3-dimethyl-butan-2-one | 4-[1-[1-(3,3-dimethyl-2-oxobutyl) azetidin-3-yl] sulfonylpiperidin-4-yl]benzonitrile |
| 379 | 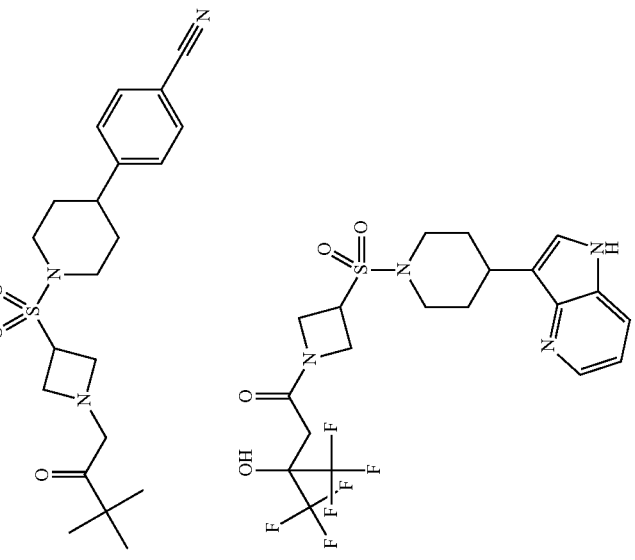 | 527.1 (m/z, ES-) | ¹H NMR FID1193-017A1 (300 MHz, DMSO-d₆) d 11.04 (s, 1H), 8.52 (s, 1H), 8.27 (d, J = 4.75 Hz, 1H), 7.69 (d, J = 18.41 Hz, 1H), 7.40 (s, 1H), 7.02-7.11 (m, 1H), 4.53-4.65 (m, 1H), 4.35-4.52 (m, 1H), 4.24-4.34 (m, 1H), 4.02-4.12 (m, 1H), 3.74 (d, J = 10.97 Hz, 2H), 2.94-3.12 (m, 3H), 2.83 (d, J = 4.39 Hz, 2H), 2.10 (d, J = 12.80 Hz, 2H), 1.65-1.84 (m, 2H) ppm | 1H-pyrrolo [3,2-b]pyridine | General method A2 using KOH, B2 using ammonium formate, D using tert-butyl 3-chlorosulfonyl-azetidine-1-carboxylate, Cf using TFA, I3 using 4,4,4-trifluoro-3-hydroxy-3-(trifluoromethyl) butanoic acid | 4,4,4-trifluoro-1-[3-[4-(1H-pyrrolo[3,2-b]pyridin-3-yl)piperidin-1-yl]sulfonylazetidin-1-yl]-3-(trifluoromethyl) butan-1-one |

| Cpd # | Structure | MS (m/z, ES+) | δ NMR Data | Starting Int/Cpd# | Sequence of Methods | Chemical Name |
|---|---|---|---|---|---|---|
| 380 | 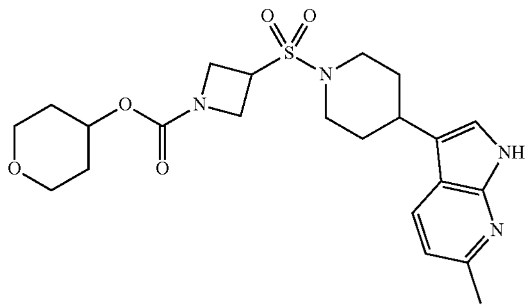 [SMILES: Cc1ccc2c(C3CCN(S(=O)(=O)C4CN(C(=O)OC5CCOCC5)C4)CC3)c[nH]c2n1] | 463.1 | 1H NMR (600 MHz, CHLOROFORM-d) δ 9.35 (br. s., 1H), 7.83 (d, J = 8.07 Hz, 1H), 6.99 (s, 1H), 6.95 (d, J = 8.07 Hz, 1H), 4.78-4.85 (m, 1H), 4.28-4.34 (m, 2H), 4.20-4.26 (m, 2H), 3.93-4.01 (m, 3H), 3.83-3.90 (m, 2H), 3.49 (t, J = 10.45 Hz, 2H), 2.98 (t, J = 12.38 Hz, 2H), 2.91 (t, J = 11.74 Hz, 1H), 2.64 (s, 3H), 2.10 (d, J = 13.39 Hz, 2H), 1.89 (d, J = 12.29 Hz, 2H), 1.80 (q, J = 12.47 Hz, 2H), 1.59-1.68 (m, 2H). | 6-methyl-1H-pyrrolo[2,3-b]pyridine | General method A2 using KOtBu, B1 using Pd/C, Ci using TFA, D using tert-butyl 3-chlorosulfonyl azetidine-1-carboxylate, Cf using TFA, H3 using tetrahydropyran-4-ol | oxan-4-yl 3-[4-(6-methyl-1H-pyrrolo[2,3-b]pyridin-3-yl)piperidin-1-yl]sulfonylazetidine-1-carboxylate |
| 381 | 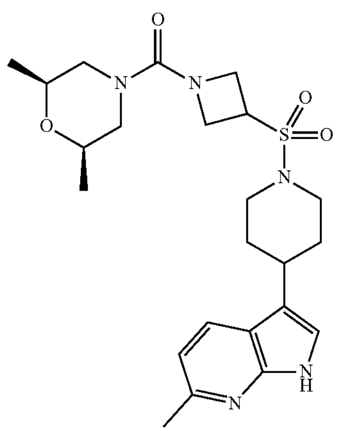 [SMILES: Cc1ccc2c(C3CCN(S(=O)(=O)C4CN(C(=O)N5C[C@@H](C)O[C@@H](C)C5)C4)CC3)c[nH]c2n1] | 476 | 1H NMR (500 MHz, DMSO-d6) δ 11.16 (s, 1H), 7.85 (d, J = 7.93 Hz, 1H), 7.12 (d, J = 2.14 Hz, 1H), 6.89 (d, J = 7.93 Hz, 1H), 4.32-4.40 (m, 1H), 4.22 (t, J = 8.70 Hz, 2H), 4.09 (dd, J = 6.10, 8.85 Hz, 2H), 3.72 (d, J = 12.21 Hz, 2H), 3.56 (d, J = 12.51 Hz, 2H), 3.39-3.47 (m, 2H), 2.96 (qd, J = 1.49, 12.44, 2H), 2.87 (tt, J = 3.10, 11.85 Hz, 1H), 2.47 (s, 3H), 2.43 (dd, J = 10.68, 13.12 Hz, 2H), 2.02 (d, J = 11.60 Hz, 2H), 1.62 (dq, J = 3.81, 12.46 Hz, 2H), 1.06 (s, 3H), 1.05 (s, 3H). | 6-methyl-1H-pyrrolo[2,3-b]pyridine | General method A2 using KOtBu, B1 using Pd/C, Ci using TFA, D using tert-butyl 3-chlorosulfonylazetidine-1-carboxylate, Cf using TFA, G7 using cis-2,6-dimethylmorpholine | [(2R,6S)-2,6-dimethylmorpholin-4-yl]-[3-[4-(6-methyl-1H-pyrrolo[2,3-b]pyridin-3-yl)piperidin-1-yl]sulfonylazetidin-1-yl]methanone |

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 382 | 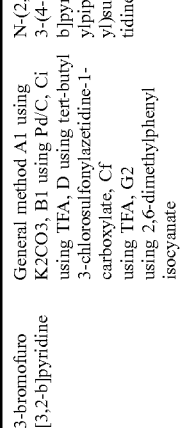 | 469.1 | 1H NMR (500 MHz, DMSO-d6) δ 8.51 (dd, J = 1.07, 4.73 Hz, 1H), 8.13 (s, 1H), 7.96-8.03 (m, 2H), 7.34 (dd, J = 4.73, 8.39 Hz, 1H), 7.05 (s, 3H), 4.36-4.45 (m, 1H), 4.24 (t, J = 7.78 Hz, 2H), 4.03-4.15 (m, 2H), 3.75 (d, J = 12.21 Hz, 2H), 2.97-3.09 (m, 3H), 2.16 (s, 8H), 1.78 (dq, J = 3.81, 12.36 Hz, 2H). | 3-bromofuro [3,2-b]pyridine | General method A1 using K2CO3, B1 using Pd/C, Ci using TFA, D using tert-butyl 3-chlorosulfonylazetidine-1-carboxylate, Cf using TFA, G2 using 2,6-dimethylphenyl isocyanate | N-(2,6-dimethylphenyl)-3-(4-furo[3,2-b]pyridin-3-ylpiperidin-1-yl)sulfonylazetidine-1-carboxamide |
| 383 | 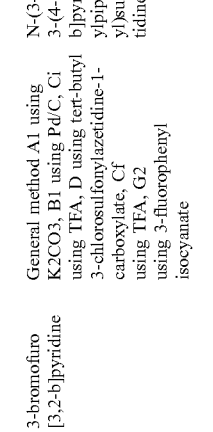 | 459.1 | 1H NMR (500 MHz, DMSO-d6) δ 8.86 (s, 1H), 8.51 (dd, J = 0.92, 4.58 Hz, 1H), 8.11 (s, 1H), 7.99 (dd, J = 1.22, 8.24 Hz, 1H), 7.46 (d, J = 12.21 Hz, 1H), 7.34 (dd, J = 4.73, 8.39 Hz, 1H), 7.20-7.31 (m, 2H), 6.72-6.79 (m, 1H), 4.35-4.42 (m, 1H), 4.28-4.35 (m, 2H), 4.14 (dd, J = 5.19, 8.85 Hz, 2H), 3.76 (d, J = 12.21 Hz, 2H), 2.98-3.10 (m, 3H), 2.15 (d, J = 11.60 Hz, 2H), 1.77 (dq, J = 3.81, 12.36 Hz, 2H). | 3-bromofuro [3,2-b]pyridine | General method A1 using K2CO3, B1 using Pd/C, Ci using TFA, D using tert-butyl 3-chlorosulfonylazetidine-1-carboxylate, Cf using TFA, G2 using 3-fluorophenyl isocyanate | N-(3-fluorophenyl)-3-(4-furo[3,2-b]pyridin-3-ylpiperidin-1-yl)sulfonylazetidine-1-carboxamide |
| 384 | 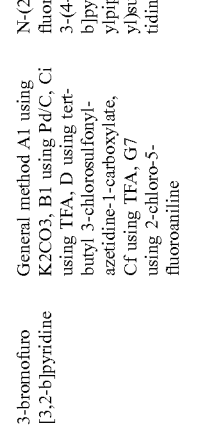 | 495 | 1H NMR (500 MHz, DMSO-d6) δ 8.51 (dd, J = 1.07, 4.73 Hz, 1H), 8.30 (s, 1H), 8.11 (s, 1H), 7.99 (dd, J = 1.07, 8.39 Hz, 1H), 7.59 (dd, J = 3.05, 10.68 Hz, 1H), 7.50 (dd, J = 5.80, 8.85 Hz, 1H), 7.00 (dt, J = 3.05, 8.39 Hz, 1H), 4.38-4.45 (m, 1H), 4.31-4.37 (m, 2H), 4.18 (dd, J = 5.19, 8.54 Hz, 2H), 3.76 (d, J = 12.21 Hz, 2H), 2.97-3.09 (m, 3H), 2.15 (d, J = 11.60 Hz, 2H), 1.78 (dq, J = 3.81, 12.36 Hz, 2H). | 3-bromofuro [3,2-b]pyridine | General method A1 using K2CO3, B1 using Pd/C, Ci using TFA, D using tert-butyl 3-chlorosulfonyl-azetidine-1-carboxylate, Cf using TFA, G7 using 2-chloro-5-fluoroaniline | N-(2-chloro-5-fluorophenyl)-3-(4-furo[3,2-b]pyridin-3-ylpiperidin-1-yl)sulfonylazetidine-1-carboxamide |

-continued

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 385 | 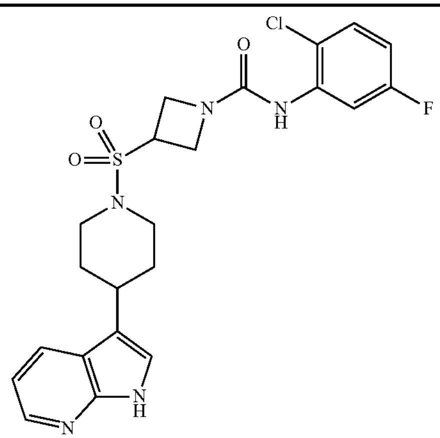 | 492.7 | 1H NMR (600 MHz, DMSO-d6) δ 11.37 (s, 1H), 8.29 (s, 1H), 8.17 (d, J = 4.58 Hz, 1H), 7.97 (d, J = 7.89 Hz, 1H), 7.58 (dd, J = 3.12, 10.82 Hz, 1H), 7.50 (dd, J = 5.96, 8.89 Hz, 1H), 7.24 (d, J = 2.38 Hz, 1H), 6.96-7.03 (m, 2H), 4.37-4.44 (m, 1H), 4.33 (t, J = 8.62 Hz, 2H), 4.15-4.21 (m, 2H), 3.75 (d, J = 12.10 Hz, 2H), 3.01 (t, J = 12.50 Hz, 2H), 2.93 (tt, J = 3.32, 12.29 Hz, 1H), 2.03 (d, J = 12.84 Hz, 2H), 1.64 (qd, J = 3.39, 12.43 Hz, 2H). | 3-(4-piperidyl)-1H-pyrrolo[2,3-b]pyridine | General method D using tert-butyl 3-chlorosulfonylazetidine-1-carboxylate, Cf using TFA, G7 using 2-chloro-5-fluoroaniline | N-(2-chloro-5-fluorophenyl)-3-[4-(1H-pyrrolo[2,3-b]pyridin-3-yl)piperidin-1-yl]sulfonylazetidine-1-carboxamide |
| 386 | 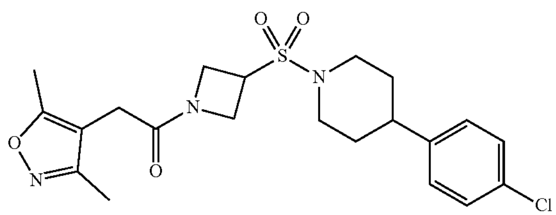 [SMILES: Cc1noc(C)c1CC(=O)N1CC(S(=O)(=O)N2CCC(c3ccc(Cl)cc3)CC2)C1] | 452.7 | 1H NMR (300 MHz, DMSO-d6): δ = 7.25-7.38 (m, 4H), 4.49-4.58 (m, 1H), 4.33-4.44 (m, 2H), 4.19 (t, J = 10.3 Hz, 1H), 3.96-4.04 (m, 1H), 3.75 (d, J = 12.97 Hz, 2H), 3.26 (d, J = 2.86 Hz, 2H), 2.93 (t, J = 12.01, 2H), 2.65-2.73 (m, 1H), 2.27 (s, 3H), 2.08 (s, 3H), 1.82 (d, J = 13.16 Hz, 2H), 1.48-1.65 (m, 2H) ppm. | 4-(4-chlorophenyl)piperidine | General method D using tert-butyl 3-chlorosulfonylazetidine-1-carboxylate, Cf using TFA, I1 using 2-(3,5-dimethylisoxazol-4-yl)acetic acid | 1-[3-[4-(4-chlorophenyl)piperidin-1-yl]sulfonylazetidin-1-yl]-2-(3,5-dimethyl-1,2-oxazol-4-yl)ethanone |
| 387 | 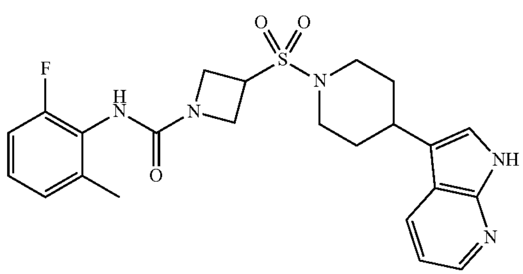 [SMILES: Cc1cccc(F)c1NC(=O)N1CC(S(=O)(=O)N2CCC(c3c[nH]c4ncccc34)CC2)C1] | 472.7 | 1H NMR (500 MHz, DMSO-d6) δ 11.39 (s, 1H), 8.18 (br. s., 2H), 7.99 (dd, J = 0.85, 7.99 Hz, 1H), 7.26 (d, J = 2.14 Hz, 1H), 7.13-7.19 (m, 1H), 6.99-7.08 (m, 3H), 4.38-4.44 (m, 1H), 4.26 (t, J = 8.70 Hz, 2H), 4.11 (dd, J = 5.49, 8.85 Hz, 2H), 3.76 (d, J = 12.21 Hz, 2H), 3.02 (td, J = 1.37, 12.36 Hz, 2H), 2.94 (tt, J = 3.13, 11.88 Hz, 1H), 2.19 (s, 3H), 2.04 (d, J = 11.29 Hz, 2H), 1.65 (dq, J = 3.81, 12.46 Hz, 2H). | 3-(4-piperidyl)-1H-pyrrolo[2,3-b]pyridine | General method D using tert-butyl 3-chlorosulfonylazetidine-1-carboxylate, Cf using TFA, G7 using 2-fluoro-6-methylaniline | N-(2-fluoro-6-methylphenyl)-3-[4-(1H-pyrrolo[2,3-b]pyridin-3-yl)piperidin-1-yl]sulfonylazetidine-1-carboxamide |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 388 | (structure) | 461.1 | ¹H NMR (300 MHz, DMSO-d₆): δ 11.37 (br. s., 1H), 8.17 (d, J = 4.62 Hz, 1H), 7.97 (d, J = 6.62 Hz, 1H), 7.24 (d, J = 1.74 Hz, 1H), 6.89-7.07 (m, 2H), 4.67-4.81 (m, 1H), 4.50-4.62 (m, 1H), 4.31-4.47 (m, 1H), 4.17-4.31 (m, 1H), 3.99-4.09 (m, 1H), 3.72 (d, J = 11.67 Hz, 2H), 2.83-3.08 (m, 3H), 1.94-2.10 (m, 2H), 1.51-1.74 (m, 2H), 1.47 (s, 3H) ppm | 3-(4-piperidyl)-1H-pyrrolo[2,3-b]pyridine | General method D using tert-butyl 3-chlorosulfonylazetidine-1-carboxylate, Cf using TFA, then II using (2S)-3,3,3-trifluoro-2-hydroxy-2-methyl-propanoic acid. | (2S)-3,3,3-trifluoro-2-hydroxy-2-methyl-1-[3-[4-(1H-pyrrolo[2,3-b]pyridin-3-yl)piperidin-1-yl]sulfonyl]azetidin-1-yl]propan-1-one |
| 389 | (structure) | 458.7 | 1H NMR (600 MHz, DMSO-d6) δ 11.37 (s, 1H), 8.85 (s, 1H), 8.17 (dd, J = 1.38, 4.68 Hz, 1H), 7.97 (d, J = 7.89 Hz, 1H), 7.45 (td, J = 2.11, 12.10 Hz, 1H), 7.21-7.30 (m, 3H), 7.01 (dd, J = 4.68, 7.79 Hz, 1H), 6.73-6.78 (m, 1H), 4.35-4.41 (m, 1H), 4.31 (t, J = 8.71 Hz, 2H), 4.13 (dd, J = 5.32, 8.99 Hz, 2H), 3.76 (d, J = 12.29 Hz, 2H), 3.01 (td, J = 1.57, 12.49 Hz, 2H), 2.93 (tt, J = 3.31, 12.03 Hz, 1H), 2.03 (d, J = 11.19 Hz, 2H), 1.64 (dq, J = 3.76, 12.50 Hz, 2H). | 3-(4-piperidyl)-1H-pyrrolo[2,3-b]pyridine | General method D using tert-butyl 3-chlorosulfonylazetidine-1-carboxylate, Cf using TFA, G2 using 3-fluorophenyl isocyanate | N-(3-fluorophenyl)-3-[4-(1H-pyrrolo[2,3-b]pyridin-3-yl)piperidin-1-yl]sulfonyl]azetidine-1-carboxamide |
| 390 | (structure) | 476.7 | 1H NMR (500 MHz, DMSO-d6) δ 11.39 (br. s., 1H), 8.44 (s, 1H), 8.18 (dd, J = 1.22, 4.58 Hz, 1H), 7.99 (d, J = 7.63 Hz, 1H), 7.27-7.35 (m, 1H), 7.26 (d, J = 2.14 Hz, 1H), 7.13 (t, J = 7.93 Hz, 2H), 7.02 (dd, J = 4.58, 7.93 Hz, 1H), 4.39-4.47 (m, 1H), 4.29 (t, J = 8.70 Hz, 2H), 4.13 (dd, J = 5.49, 8.85 Hz, 2H), 3.76 (d, J = 12.21 Hz, 2H), 3.02 (td, J = 1.28, 12.45 Hz, 2H), 2.94 (tt, J = 3.00, 11.81 Hz, 1H), 2.04 (d, J = 11.60 Hz, 2H), 1.65 (dq, J = 3.81, 12.46 Hz, 2H). | 3-(4-piperidyl)-1H-pyrrolo[2,3-b]pyridine | General method D using tert-butyl 3-chlorosulfonylazetidine-1-carboxylate, Cf using TFA, G2 using 2,6-difluorophenyl isocyanate | N-(2,6-difluorophenyl)-3-[4-(1H-pyrrolo[2,3-b]pyridin-3-yl)piperidin-1-yl]sulfonyl]azetidine-1-carboxamide |

| Cpd # | Structure | MS (m/z, ES+) | δ NMR Data | Starting Int/Cpd# | Sequence of Methods | Chemical Name |
|---|---|---|---|---|---|---|
| 391 | 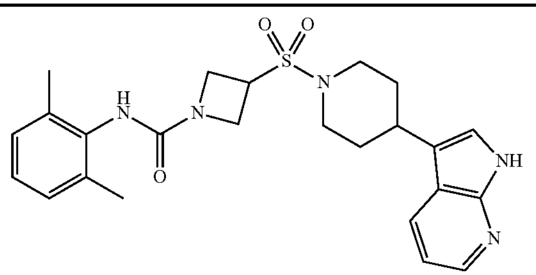 | 468.8 | 1H NMR (500 MHz, DMSO-d6) δ 11.39 (br. s., 1H), 8.18 (d, J = 3.66 Hz, 1H), 7.96-8.03 (m, 2H), 7.26 (d, J = 1.83 Hz, 1H), 7.05 (s, 3H), 7.02 (dd, J = 4.83, 8.04 Hz, 1H), 4.37-4.45 (m, 1H), 4.18-4.29 (m, 2H), 4.05-4.16 (m, 2H), 3.75 (d, J = 12.21 Hz, 2H), 3.01 (t, J = 11.75 Hz, 2H), 2.94 (tt, J = 3.11, 11.90 Hz, 1H), 2.16 (s, 6H), 2.04 (d, J = 11.29 Hz, 2H), 1.65 (dq, J = 3.66, 12.41 Hz, 2H). | 3-(4-piperidyl)-1H-pyrrolo[2,3-b]pyridine | General method D using tert-butyl 3-chlorosulfonylaze-tidine-1-carboxylate, Cf using TFA, G2 using 2,6-dimethylphenyl isocyanate | N-(2,6-dimethylphenyl)-3-[4-(1H-pyrrolo[2,3-b]pyridin-3-yl)piperidin-1-yl]sulfonylaze-tidine-1-carboxamide |
| 392 | 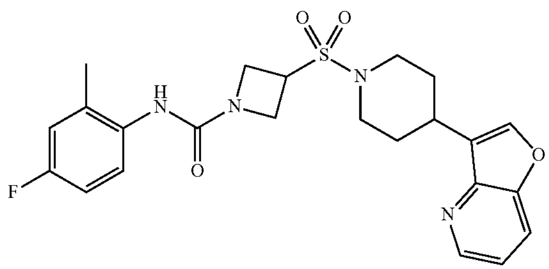 [SMILES: Cc1cc(F)ccc1NC(=O)N1CC(S(=O)(=O)N2CCC(c3coc4cccnc34)CC2)C1] | 473.7 | 1H NMR (500 MHz, DMSO-d6) δ 8.51 (dd, J = 1.07, 4.73 Hz, 1H), 8.12 (s, 1H), 8.10 (s, 1H), 8.00 (dd, J = 1.22, 8.24 Hz, 1H), 7.34 (dd, J = 4.73, 8.39 Hz, 1H), 7.23 (dd, J = 5.65, 8.70 Hz, 1H), 7.05 (dd, J = 2.90, 9.61 Hz, 1H), 6.96 (dt, J = 2.90, 8.62 Hz, 1H), 4.43 (m, 1H), 4.27 (t, J = 8.70 Hz, 2H), 4.11 (dd, J = 5.49, 9.16 Hz, 2H), 3.75 (d, J = 12.21 Hz, 2H), 2.97-3.09 (m, 3H), 2.18 (s, 3H), 2.15 (d, 2H), 1.78 (dq, J = 3.81, 12.36 Hz, 2H). | 3-bromofuro[3,2-b]pyridine | General method A1 using K2CO3, B1 using Pd/C, Ci using TFA, D using tert-butyl 3-chlorosulfonylaze-tidine-1-carboxylate, Cf using TFA, G7 using 4-fluoro-2-methylaniline | N-(4-fluoro-2-methylphenyl)-3-[4-(4-furo[3,2-b]pyridin-3-yl)piperidin-1-yl]sulfonylaze-tidine-1-carboxamide |
| 393 | 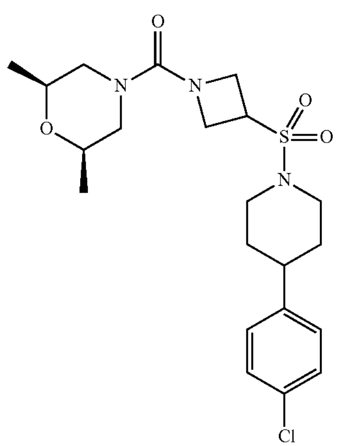 [SMILES: C[C@@H]1CN(C(=O)N2CC(S(=O)(=O)N3CCC(c4ccc(Cl)cc4)CC3)C2)C[C@H](C)O1] | 456.7 | 1H NMR (400 MHz, DMSO-d6): δ = 1.05 (d, J = 6.1 Hz, 6H), 1.50-1.63 (m, 2H), 1.82 (d, J = 13.3 Hz, 2 H), 2.38-2.46 (m, 2H), 2.60-2.70 (m, 1 H), 2.88 (t, J = 12.0, 2 H), 3.38-3.48 (m, 2 H), 3.55 (d, J = 13.7 Hz, 2 H), 3.72 (d, J = 11.7 Hz, 2 H), 4.04-4.10 (m, 2 H), 4.20 (t, J = 8.7 Hz, 2 H), 4.30-4.38 (m, 1 H), 7.27 (d, J = 8.7 Hz, 2 H), 7.35 (d, J = 8.7 Hz, 2 H), ppm. | 4-(4-chloro-phenyl)piperidine | General method D using tert-butyl 3-chlorosulfonylaze-tidine-1-carboxylate, Cf using TFA, G7using cis-2,6-dimethylmorpholine | [3-[4-(4-chlorophenyl)piperidin-1-yl]sulfonylaze-tidin-1-yl]-[(2R,6S)-2,6-dimethylmorpholin-4-yl]methanone |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 394 | | 472.7 | 1H NMR (600 MHz, DMSO-d6) δ 11.37 (s, 1H), 8.17 (dd, J = 1.38, 4.68 Hz, 1H), 8.09 (s, 1H), 7.98 (d, J = 7.89 Hz, 1H), 7.24 (d, J = 2.40 Hz, 1H), 7.22 (dd, J = 5.71, 8.74 Hz, 1H), 7.04 (dd, J = 2.84, 9.63 Hz, 1H), 7.01 (dd, J = 4.58, 7.89 Hz, 1H), 6.95 (dt, J = 3.03, 8.57 Hz, 1H), 4.36-4.42 (m, 1H), 4.25 (t, J = 8.71 Hz, 2H), 4.10 (dd, J = 5.41, 8.89 Hz, 2H), 3.75 (d, J = 12.29 Hz, 2H), 3.01 (td, J = 1.51, 12.60 Hz, 2H), 2.93 (t, J = 3.28, 11.92 Hz, 1H), 2.18 (s, 3H), 2.03 (d, J = 11.55 Hz, 2H), 1.64 (dq, J = 4.13, 12.50 Hz, 2H). | 3-(4-piperidyl)-1H-pyrrolo[2,3-b]pyridine | General method D using tert-butyl 3-chlorosulfonylazetidine-1-carboxylate, Cf using TFA, G7 using 4-fluoro-2-methylaniline | N-(4-fluoro-2-methylphenyl)-3-[4-(1H-pyrrolo[2,3-b]pyridin-3-yl)piperidin-1-yl]sulfonylazetidine-1-carboxamide |
| 395 | 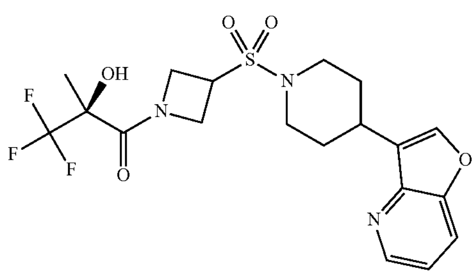 [SMILES: C[C@](O)(C(=O)N1CC(S(=O)(=O)N2CCC(c3coc4cccnc34)CC2)C1)C(F)(F)F] | 462.7 | 1H NMR (300 MHz, DMSO-d6) δ 8.50 (d, J = 4.70 Hz, 1H), 8.12 (s, 1H), 7.98 (dd, J = 1.22, 8.36 Hz, 1H), 7.33 (dd, J = 4.70, 8.36 Hz, 1H), 6.98 (br. s., 1H), 4.73 (dd, J = 5.31, 8.45 Hz, 1H), 4.50-4.62 (m, 1H), 4.32-4.46 (m, 1H), 4.20-4.32 (m, 1H), 3.99-4.09 (m, 1H), 3.72 (d, J = 11.50 Hz, 2H), 2.13 (d, J = 11.50 Hz, 2H), 1.66-1.85 (m, 2H), 1.47 (s, 3H) ppm | 3-bromofuro[3,2-b]pyridine | General method A1 using K2CO3, B1 using Pd/C, Ci using TFA, D using tert-butyl 3-chlorosulfonylazetidine-1-carboxylate, Cf using TFA, then I1 using (2S)-3,3,3-trifluoro-2-hydroxy-2-methylpropanoic acid. | (2S)-3,3,3-trifluoro-1-[3-(4-furo[3,2-b]pyridin-3-ylpiperidin-1-yl)sulfonylazetidin-1-yl]-2-hydroxy-2-methylpropan-1-one |
| 396 | 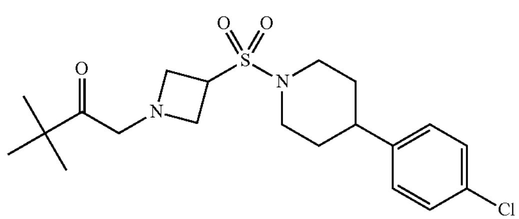 [SMILES: CC(C)(C)C(=O)CN1CC(S(=O)(=O)N2CCC(c3ccc(Cl)cc3)CC2)C1] | 413.6 | 1H NMR (300 MHz, DMSO-d) δ = 1.05 (s, 9 H), 1.47-1.67 (m, 2 H), 1.80 (d, J = 13.1 Hz, 2 H), 2.58-2.75 (m, 3H), 2.87 (t, J = 11.4 Hz, 2 H), 3.54-3.80 (m, 6H), 4.17-4.35 (m, 1H), 7.21-7.42 (m, 4 H) ppm. | 4-(4-chlorophenyl)piperidine | General method D using tert-butyl 3-chlorosulfonylazetidine-1-carboxylate, Cf using TFA, I1 using 1-bromo-3,3-dimethyl-butan-2-one | 1-[3-[4-(4-chlorophenyl)piperidin-1-yl]sulfonylazetidin-1-yl]-3,3-dimethylbutan-2-one |

| Cpd # | Structure | MS (m/z, ES+) | δ NMR Data | Starting Int/Cpd# | Sequence of Methods | Chemical Name |
|---|---|---|---|---|---|---|
| 397 | 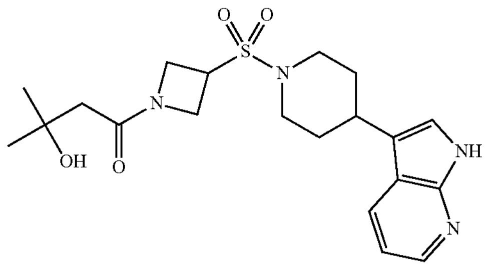 [SMILES: CC(C)(O)CC(=O)N1CC(S(=O)(=O)N2CCC(c3c[nH]c4ncccc34)CC2)C1] | 421.2 | ¹H NMR (300 MHz, DMSO-d₆) δ 11.38 (br. s., 1H), 8.17 (dd, J = 4.62 Hz, 1H), 7.90-8.03 (m, 1H), 7.25 (d, J = 2.44 Hz, 1H), 7.01 (dd, J = 4.70, 7.84 Hz, 1H), 4.62 (s, 1H), 4.44-4.56 (m, 1H), 4.27-4.41 (m, 2H), 4.09-4.23 (m, 1H), 3.93-4.03 (m, 1H), 3.74 (d, J = 12.02 Hz, 2H), 2.85-3.06 (m, 3H), 2.18 (s, 2H), 2.02 (d, J = 11.50 Hz, 2H), 1.53-1.73 (m, 2H), 1.16 (s, 6H) ppm | 3-(4-piperidyl)-1H-pyrrolo[2,3-b]pyridine | General method D using tert-butyl 3-chlorosulfonylazetidine-1-carboxylate, Cf using TFA, then I1 using 3-hydroxy-3-methyl-butanoic acid. | 3-hydroxy-3-methyl-1-[3-[4-(1H-pyrrolo[2,3-b]pyridin-3-yl)piperidin-3-yl]sulfonyl]azetidin-1-yl]butan-1-one |
| 398 | 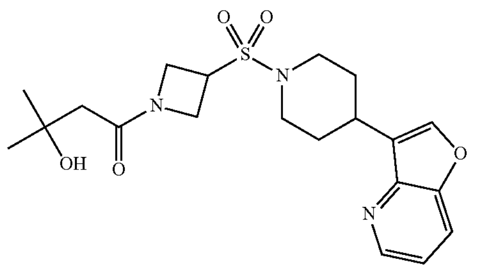 [SMILES: CC(C)(O)CC(=O)N1CC(S(=O)(=O)N2CCC(c3coc4cccnc34)CC2)C1] | 422.8 | ¹H NMR (300 MHz, DMSO-d₆) δ 8.48-8.53 (m, 1H), 8.12 (s, 1H), 7.95-8.02 (m, 1H), 7.33 (dd, J = 4.70, 8.36 Hz, 1H), 4.62 (s, 1H), 4.45-4.56 (m, 1H), 4.27-4.40 (m, 2H), 4.12-4.22 (m, 1H), 3.92-4.04 (m, 1H), 3.74 (d, J = 12.19 Hz, 2H), 3.02 (t, J = 12.02 Hz, 3H), 2.18 (s, 2H), 2.13 (d, J = 12.72 Hz, 2H), 1.66-1.85 (m, 2H), 1.16 (s, 6H) ppm | 3-bromofuro[3,2-b]pyridine | General method A1 using K₂CO₃, B1 using Pd/C, Ci using TFA, D using tert-butyl 3-chlorosulfonylazetidine-1-carboxylate, Cf using TFA, then I1 using 3-hydroxy-3-methyl-butanoic acid. | 1-[3-(4-furo[3,2-b]pyridin-3-yl)piperidin-1-yl]sulfonyl]azetidin-1-yl]-3-hydroxy-3-methylbutan-1-one |
| 399 | 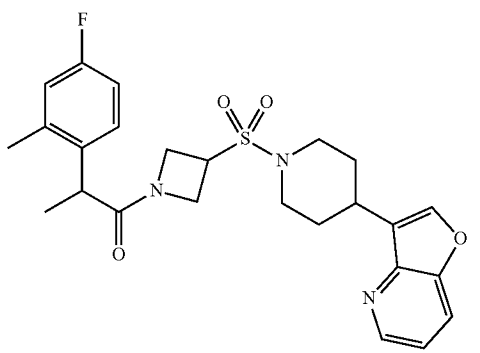 [SMILES: Cc1cc(F)ccc1C(C)C(=O)N1CC(S(=O)(=O)N2CCC(c3coc4cccnc34)CC2)C1] | 487.7 | 1H NMR (500 MHz, CHLOROFORM-d) δ 8.54 (dd, J = 0.92, 4.88 Hz, 1H), 7.76 (d, J = 8.24 Hz, 1H), 7.61 (s, 1H), 7.23-7.26 (m, 1H), 7.17 (dd, J = 5.49, 8.54 Hz, 1H), 6.97 (dd, J = 2.90, 9.00 Hz, 1H), 6.92 (dt, J = 2.75, 8.24 Hz, 1H), 3.65-3.94 (m, 7H), 3.14 (s, 3H), 3.09 (t, J = 11.75 Hz, 1H), 2.94 (dt, J = 1.98, 12.44 Hz, 2H), 2.27 (s, 3H), 2.24 (d, J = 13.24 Hz, 2H), 1.78 (dq, J = 4.12, 12.56 Hz, 2H). | 3-bromofuro[3,2-b]pyridine | General method A1 using K2CO3, B1 using Pd/C, Ci using TFA, D using tert-butyl 3-chlorosulfonyl-azetidine-1-carboxylate, Cf using TFA, G7 using 4-fluoro-2-methylaniline, W using methyl iodide | N-(4-fluoro-2-methylphenyl)-3-(4-furo[3,2-b]pyridin-3-yl)piperidin-3-yl]sulfonyl]-N-methylazetidine-1-carboxamide |

-continued

Table with Representative Compounds of Formula (I):

| Cpd # | Structure | MS (m/z, ES+) | δ NMR Data | Starting Int/Cpd# | Sequence of Methods | Chemical Name |
|---|---|---|---|---|---|---|
| 400 | 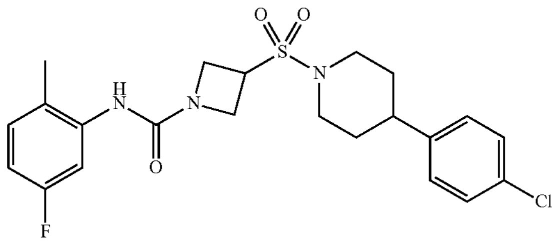 [SMILES: Cc1ccc(F)cc1NC(=O)N1CC(S(=O)(=O)N2CCC(c3ccc(Cl)cc3)CC2)C1] | 466 | 1H NMR (300 MHz, DMSO-d6): δ = 1.49-1.66 (m, 2 H), 1.82 (d, J = 16.5 Hz, 2 H), 2.16 (s, 3 H), 2.64-2.745 (m, 1 H), 2.94 (t, J = 12.0, 2 H), 3.76 (d, J = 13.0 Hz, 2 H), 4.08-4.16 (m, 2 H), 4.29 (t, J = 8.0, 2 H), 4.33-4.42 (m, 1 H), 6.85 (dt, J = 3.6, 8.0, 1H) 7.18 (m, 1 H), 7.24-7.37 (m, 5 H), 8.06 (s, 1 H) ppm. | 4-(4-chloro-phenyl)piperidine | General method D using tert-butyl 3-chlorosulfonylaze-tidine-1-carboxylate, Cf using TFA, G2 using 4-fluoro-2-isocyanato-1-methyl-benzene | 3-[4-(4-chlorophenyl)piperidin-1-yl]sulfonyl-N-(5-fluoro-2-methylphenyl)azetidine-1-carboxamide |
| 401 | 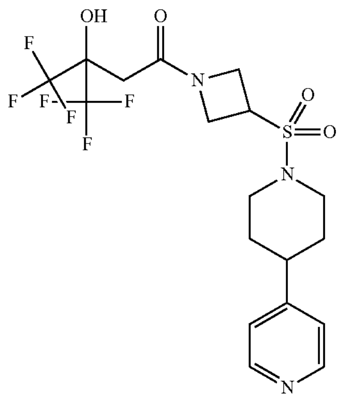 [SMILES: O=C(CC(O)(C(F)(F)F)C(F)(F)F)N1CC(S(=O)(=O)N2CCC(c3ccncc3)CC2)C1] | 490.7 | 1H NMR (300 MHz, DMSO-d6) δ = 8.50 (s, 1H), 8.47 (d, J = 5.32 Hz, 1H), 7.28 (d, J = 6.16 Hz, 1H), 4.53-4.65 (m, 1H), 4.35-4.52 (m, 2H), 4.244.34 (m, 1H), 4.02-4.12 (m, 1H), 3.74 (d, J = 13.43 Hz, 2H), 2.94 (t, J = 13.43 Hz, 3H), 2.83 (d, J = 3.36 Hz, 2H), 2.67-2.78 (m, 2H), 1.85 (d, J = 12.59 Hz, 2H), 1.51-1.68 (m, 2H) ppm. | 4-(4-piperidyl)pyridine | General method D using tert-butyl 3-chlorosulfonylaze-tidine-1-carboxylate, Cf using TFA, I3 using 4,4,4-trifluoro-3-hydroxy-3-(trifluoromethyl) butanoic acid | 4,4,4-trifluoro-3-hydroxy-1-[3-(4-pyridin-4-ylpiperidin-1-yl)sulfonylazetidin-1-yl]-3-(trifluoromethyl)butan-1-one |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 402 | 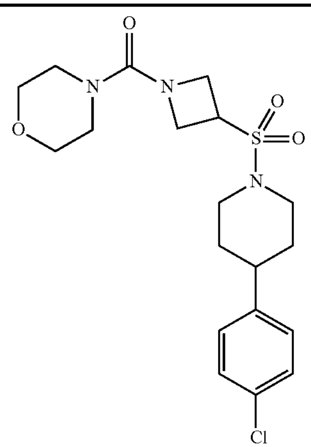 | 428.6 | 1H NMR (300 MHz, DMSO-d) δ = 1.47-1.65 (m, 2 H), 1.81 (d, J = 13.2 Hz, 2 H), 2.59-2.74 (m, 1 H), 2.89 (t, J = 13.6 Hz, 2 H), 3.20 (t, J = 5.0 Hz, 4 H), 3.52 (t, J = 5.0 Hz, 4 H), 3.72 (d, J = 12.2 Hz, 2 H), 4.03-4.11 (m, 2 H), 4.20 (t, J = 9.3 Hz, 2H), 4.30-4.42 (m,1 H), 7.24-7.38 (m, 4H) ppm. | 4-(4-chlorophenyl) piperidine | General method D using tert-butyl 3-chlorosulfonylazetidine-1-carboxylate, Cf using TFA, G1 using morpholine 4-carbonyl chloride | [3-[4-(4-chlorophenyl) piperidin-1-yl]sulfonylazetidin-1-yl]-morpholin-4-ylmethanone |
| 403 | 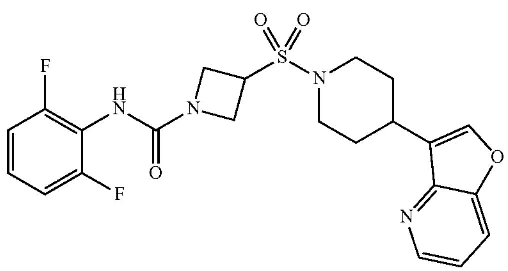 [SMILES: O=C(Nc1c(F)cccc1F)N1CC(S(=O)(=O)N2CCC(c3coc4cccnc34)CC2)C1] | 477.7 | 1H NMR (600 MHz, DMSO-d6) δ 8.51 (dd, J = 1.28, 4.77 Hz, 1H), 8.43 (s, 1H), 8.11 (d, J = 0.73 Hz, 1H), 7.98 (dd, J = 1.28, 8.25 Hz, 1H), 7.33 (dd, J = 4.77, 8.41 Hz, 1H), 7.27-7.32 (m, 1H), 7.09-7.15 (m, 2H), 4.39-4.44 (m, 1H), 4.29 (t, J = 8.71 Hz, 2H), 4.12 (dd, J = 5.50, 8.99 Hz, 2H), 3.75 (d, J = 12.29 Hz, 2H), 2.99-3.07 (m, 3H), 2.14 (dd, J = 2.13, 13.44 Hz, 2H), 1.77 (dq, J = 3.94, 12.44 Hz, 2H). | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, G2 using 2,6-difluorophenyl isocyanate | N-(2,6-difluorophenyl)-3-(4-furo[3,2-b]pyridin-3-ylpiperidin-3-yl)sulfonylazetidine-1-carboxamide |
| 404 | 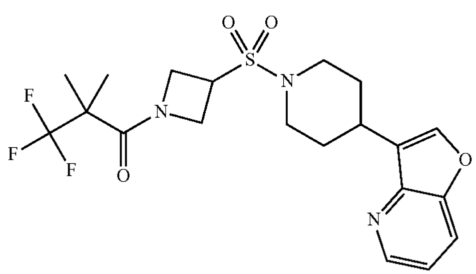 [SMILES: CC(C)(C(=O)N1CC(S(=O)(=O)N2CCC(c3coc4cccnc34)CC2)C1)C(F)(F)F] | 460.7 | 1H NMR (300 MHz, DMSO-d6) δ 8.50 (dd, J = 1.13, 4.79 Hz, 1H), 8.12 (s, 1H), 7.99 (dd, J = 1.13, 8.27 Hz, 1H), 7.33 (dd, J = 4.79, 8.27 Hz, 1H), 4.69-4.86 (m, 1H), 4.46-4.60 (m, 1H), 4.32-4.45 (m, 1H), 4.16-4.30 (m, 1H), 3.96-4.09 (m, 1H), 3.73 (d, J = 12.37 Hz, 2H), 2.93-3.10 (m, 3H), 2.13 (d, J = 11.15 Hz, 2H), 1.67-1.85 (m, 2H), 1.36 (s, 6H) ppm | 3-bromofuro [3,2-b]pyridine | General method A1 using K2CO3, B1 using Pd/C, Ci using TFA, D using tert-butyl 3-chlorosulfonyl azetidine-1-carboxylate, Cf using TFA, then I1 using 3,3,3-trifluoro-2,2-dimethyl-propanoic acid. | 3,3,3-trifluoro-1-[3-(4-furo[3,2-b]pyridin-3-ylpiperidin-1-yl)sulfonylazetidin-1-yl]-2,2-dimethylpropan-1-one |

Table with Representative Compounds of Formula (I):

| Cpd # | Structure | MS (m/z, ES +) | δ NMR Data | Starting Int/Cpd# | Sequence of Methods | Chemical Name |
|---|---|---|---|---|---|---|
| 405 | 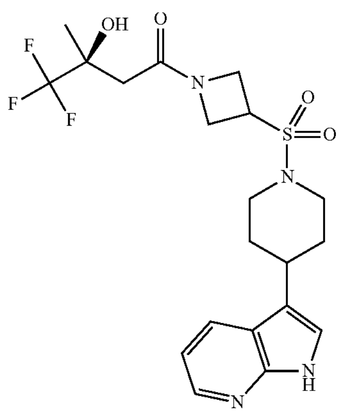 [SMILES: C[C@](O)(CC(=O)N1CC(S(=O)(=O)N2CCC(c3c[nH]c4ncccc34)CC2)C1)C(F)(F)F] | 475.7 | ¹H NMR (300 MHz, DMSO-d₆) δ 11.37 (s, 1H), 8.17 (dd, J = 1.31, 4.62 Hz, 1H), 7.97 (d, J = 6.79 Hz, 1H), 7.25 (s, 1H), 7.01 (dd, J = 4.53, 7.84 Hz, 1H), 6.24 (s, 1H), 4.30-4.59 (m, 3H), 4.13-4.26 (m, 1H), 3.95-4.07 (m, 1H), 3.73 (d, J = 12.19 Hz, 2H), 2.85-3.08 (m, 3H), 2.51-2.57 (m, 1H), 2.19-2.30 (m, 1H), 1.95-2.09 (m, 2H), 1.54-1.72 (m, 2H), 1.39 (s, 3H) ppm | 3-(4-piperidyl)-1H-pyrrolo [2,3-b]pyridine | General method D using tert-butyl 3-chlorosulfonylazetidine-1-carboxylate, Cf using TFA, then I1 using 4,4,4-trifluoro-3-hydroxy-3-methyl-butanoic acid. | 4,4,4-trifluoro-3-hydroxy-3-methyl-1-[3-[4-(1H-pyrrolo[2,3-b]pyridin-3-yl)piperidin-1-yl]sulfonylazetidin-1-yl]butan-1-one |
| 406 | 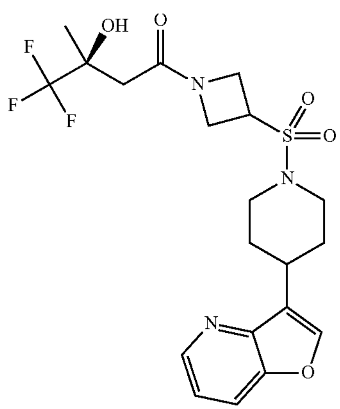 [SMILES: C[C@](O)(CC(=O)N1CC(S(=O)(=O)N2CCC(c3coc4cccnc34)CC2)C1)C(F)(F)F] | 476.7 | ¹H NMR (300 MHz, DMSO-d₆) δ 8.47-8.54 (m, 1H), 8.12 (s, 1H), 7.95-8.01 (m, 1H), 7.33 (dd, J = 4.88, 8.36 Hz, 1H), 6.24 (d, J = 8.19 Hz, 1H), 4.30-4.61 (m, 3H), 4.15-4.26 (m, 1H), 3.96-4.07 (m, 1H), 3.73 (d, J = 11.67 Hz, 2H), 2.94-3.09 (m, 3H), 2.51-2.56 (m, 1H), 2.19-2.30 (m, 1H), 2.13 (d, J = 13.24 Hz, 2H), 1.67-1.84 (m, 2H), 1.39 (s, 3H) ppm | 3-bromofuro [3,2-b]pyridine | General method A1 using K₂CO₃, B1 using Pd/C, Ci using TFA, D using tert-butyl 3-chlorosulfonylazetidine-1-carboxylate, Cf using TFA, then I1 using 4,4,4-trifluoro-3-hydroxy-3-methyl-butanoic acid. | 4,4,4-trifluoro-1-[3-(4-furo[3,2-b]pyridin-3-ylpiperidin-1-yl)sulfonylazetidin-1-yl]-3-hydroxy-3-methylbutan-1-one |

Table with Representative Compounds of Formula (I): -continued

| Cpd # | Structure | MS (m/z, ES +) | δ NMR Data | Starting Int/Cpd# | Sequence of Methods | Chemical Name |
|---|---|---|---|---|---|---|
| 407 | 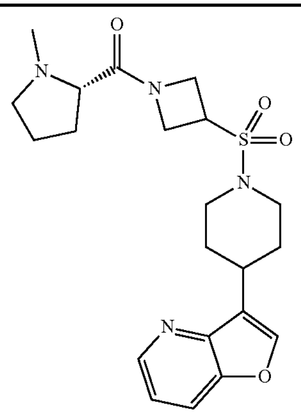 | 433.8 | ¹H NMR (300 MHz, DMSO-d₆) δ 8.46-8.54 (m, 1H), 8.12 (s, 1H), 7.95-8.01 (m, 1H), 7.33 (dd, J = 4.70, 8.36 Hz, 1H), 4.52-4.64 (m, 1H), 4.28-4.45 (m, 2H), 4.13-4.26 (m, 1H), 3.94-4.06 (m, 1H), 3.73 (d, J = 12.19 Hz, 2H), 2.91-3.09 (m, 4H), 2.68-2.84 (m, 1H), 2.21 (s, 3H), 2.13 (d, J = 10.45 Hz, 3H), 1.92-2.07 (m, 1H), 1.62-1.84 (m, 5H) ppm | 3-bromofuro [3,2-b]pyridine | General method A1 using K₂CO₃, B1 using Pd/C, Ci using TFA, D using tert-butyl 3-chlorosulfonylazetidine-1-carboxylate, Cf using TFA, then I1 using (2S)-1methyl-pyrrolidine 2-carboxylic acid. | [3-(4-furo[3,2-b]pyridin-3-yl)piperidin-1-yl)sulfonylazetidin-1-yl]-[(2S)-methylpyrrolidin-2-yl]methanone |
| 408 | 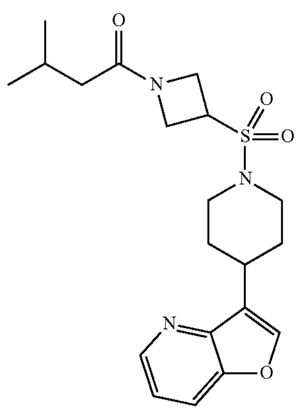 | 406.8 | ¹H NMR (300 MHz, DMSO-d₆) δ 8.50 (dd, J = 1.05, 4.70 Hz, 1H), 8.12 (s, 1H), 7.98 (dd, J = 1.13, 8.27 Hz, 1H), 7.33 (dd, J = 4.70, 8.36 Hz, 1H), 4.41-4.50 (m, 1H), 4.31-4.40 (m, 1H), 4.23-4.31 (m, 1H), 4.12-4.21 (m, 1H), 3.98 (dd, J = 5.05, 10.10 Hz, 1H), 3.74 (d, J = 12.19 Hz, 2H), 3.01 (t, J = 11.24 Hz, 3H), 2.07-2.19 (m, 2H), 1.88-2.00 (m, 3H), 1.65-1.84 (m, 2H), 0.82-0.94 (m, 6H) ppm | 3-bromofuro [3,2-b]pyridine | General method A1 using K₂CO₃, B1 using Pd/C, Ci using TFA, D using tert-butyl 3-chlorosulfonylazetidine-1-carboxylate, Cf using TFA, then I2 using 3-methylbutanoyl chloride. | 1-[3-(4-furo[3,2-b]pyridin-3-yl)piperidin-1-yl)sulfonylazetidin-1-yl]-3-methylbutan-1-one |

-continued

Table with Representative Compounds of Formula (I):

| Cpd # | Structure | MS (m/z ES +) | δ NMR Data | Starting Int/Cpd# | Sequence of Methods | Chemical Name |
|---|---|---|---|---|---|---|
| 409 | 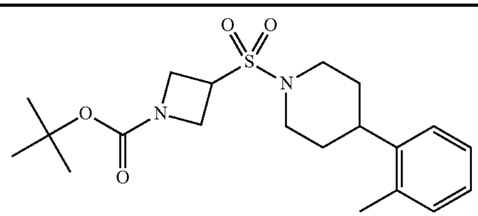 | 295.7 | | 4-(o-tolyl)piperidine | General method D using tert-butyl 3-chlorosulfonylazetidine-1-carboxylate. | tert-butyl 3-[4-(2-methylphenyl)piperidin-1-yl]sulfonylazetidine-1-carboxylate |
| 410 | 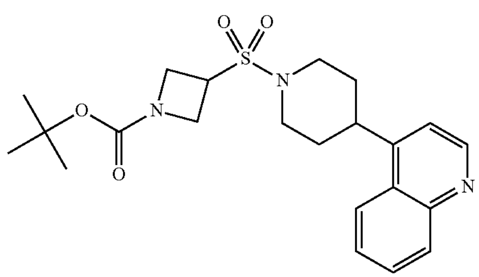 [SMILES: CC(C)(C)OC(=O)N1CC(S(=O)(=O)N2CCC(c3ccnc4ccccc34)CC2)C1] | 432.8 | 1H NMR (300 MHz, DMSO-d6) δ 8.83 (d, J = 4.53 Hz, 1H), 8.24 (d, J = 8.36 Hz, 1H), 8.03 (d, J = 7.66 Hz, 1H), 7.76 (t, J = 7.05 Hz, 1H), 7.59-7.69 (m, 1H), 7.43 (d, J = 4.53 Hz, 1H), 4.29-4.42 (m, 1H), 4.21 (br. s., 2H), 4.02 (d, J = 5.05 Hz, 2H), 3.80 (d, J = 12.37 Hz, 2H), 3.59(t, J = 11.93 Hz, 1H), 3.05-3.20 (m, 2H), 1.95 (d, J = 12.02 Hz, 2H), 1.63-1.82 (m, 2H), 1.39 (s, 9H) ppm | 4-(4-piperidyl)quinoline; dihydrochloride | General method D using tert-butyl 3-chlorosulfonylazetidine-1-carboxylate. | tert-butyl 3-[4-(4-quinolin-4-ylpiperidin-1-yl)sulfonylazetidine-1-carboxylate |
| 411 | 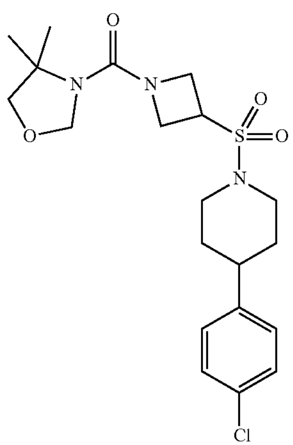 [SMILES: CC1(C)COCN1C(=O)N1CC(S(=O)(=O)N2CCC(c3ccc(Cl)cc3)CC2)C1] | 442.7 | 1H NMR (300 MHz, DMSO-d6): δ = 1.33 (s, 6H), 1.48-1.65 (m, 2 H), 1.81 (d, J = 12.5 Hz, 2 H), 2.59-2.73 (m, 1 H), 2.89 (t, J = 11.4 Hz, 2 H), 3.64 (s, 2 H), 3.73 (d, J = 11.4 Hz, 2 H), 3.95-4.04 (m, 2H), 4.10 (t, J = 9.02 Hz, 2 H), 4.30-4.38 (m, 1 H), 4.73 (s, 2 H), 7.24-7.38 (m, 2H) ppm. | 4-(4-chlorophenyl)piperidine | General method D using tert-butyl 3-chlorosulfonylazetidine-1-carboxylate, Cf using TFA, G7 using 4,4-dimethyloxazolidine | [3-[4-(4-chlorophenyl)piperidin-1-yl]sulfonylazetidin-1-yl]-(4,4-dimethyl-1,3-oxazolidin-3-yl)methanone |

Biological Assays

The potential for a compound of formula (I) obtained by the process of the present invention to act as a Hh modulator may be demonstrated in vitro.

Example 1

In Vitro Screening Protocol (C3H Assay)
Differentiation of C3H10T1/2 Cells by Mouse Sonic Hedgehog Ligand (mSHH)—Measurement of Alkaline Phosphatase.

The procedure is based upon that described in Schaefer G I et al (J Am Chem Soc. 2013; 135(26):9675-80). In response to activation of the Hedgehog pathway with one of the PTCH1 ligands, e.g. mSHH, mouse C3H10T1/2 embryonic sarcoma cells differentiate and start to express alkaline phosphatase. Inhibitors of the pathway block differentiation and alkaline phosphatase expression.

C3H10T1/2 cells are seeded into a black 384-well plate and cultured for 24-hours until they have reached confluency. The media is replaced with a reduced serum media and the cells are then stimulated with mSHH for 72 hours at 37° C. in the presence or absence of test compound.

All media is removed and cell viability is determined by incubating the cells for 1 hour at 37° C. in the presence of Promega Cell Titer-Blue® reagent and measuring the fluorescence at $560_{EX}/590_{EM}$.

The Cell Titer-Blue® reagent is then removed and alkaline phosphatase activity is measured using the phosphatase substrate 4-methylumbelliferyl phosphate. The cells are incubated in the dark in the presence of the substrate for 1½-2 hours at room temperature and substrate conversion is determined by detecting fluorescence at $360_{EX}/449_{EM}$.

IC50 ranges for compounds of the invention are presented in Table 2, whereby the IC50 ranges are as follows:
A: $IC_{50} \leq 10$ nM
B: $IC_{50} = 10\text{-}100$ nM
C: $IC_{50} = 100\text{-}1000$ nM
D: $IC_{50} = 1000\text{-}10000$ nM For reference both Sonidegib and Vismodegib were also run in the C3H assay, whereby the mean IC50 values were 11 nM and 6.3 nM, respectively.

TABLE 2

| Cpd# | IC$_{50}$ Ranges |
| --- | --- |
| 1 | C |
| 2 | D |
| 3 | C |
| 4 | D |
| 5 | D |
| 6 | C |
| 7 | C |
| 8 | B |
| 9 | D |
| 10 | D |
| 11 | C |
| 12 | C |
| 13 | C |
| 14 | C |
| 15 | D |
| 16 | C |
| 17 | B |
| 18 | B |
| 19 | B |
| 20 | D |
| 21 | D |
| 22 | C |
| 23 | C |
| 24 | C |
| 25 | D |
| 26 | B |
| 27 | B |
| 28 | C |
| 29 | D |
| 30 | D |
| 31 | C |
| 32 | C |
| 33 | B |
| 34 | B |
| 35 | C |
| 36 | D |
| 37 | D |
| 38 | C |
| 39 | B |
| 40 | D |
| 41 | B |
| 42 | D |
| 43 | B |
| 44 | B |
| 45 | B |
| 46 | D |
| 47 | D |
| 48 | C |
| 49 | B |
| 50 | B |
| 51 | C |
| 52 | C |
| 53 | D |
| 54 | B |
| 55 | B |
| 56 | B |
| 57 | A |
| 58 | C |
| 59 | B |
| 60 | B |
| 61 | D |
| 62 | B |
| 63 | B |
| 64 | B |
| 65 | C |
| 66 | B |
| 67 | B |
| 68 | C |
| 69 | C |
| 70 | C |
| 71 | D |
| 72 | D |
| 73 | C |
| 74 | D |
| 75 | B |
| 76 | B |
| 77 | B |
| 78 | C |
| 79 | D |
| 80 | C |
| 81 | C |
| 82 | C |
| 83 | D |
| 84 | B |
| 85 | B |
| 86 | C |
| 87 | C |
| 88 | C |
| 89 | D |
| 90 | C |
| 91 | C |
| 92 | D |
| 93 | D |
| 94 | C |
| 95 | C |
| 96 | B |
| 97 | C |
| 98 | C |
| 99 | C |

TABLE 2-continued

| Cpd# | IC$_{50}$ Ranges |
|---|---|
| 100 | C |
| 101 | D |
| 102 | D |
| 103 | D |
| 104 | D |
| 105 | D |
| 106 | D |
| 107 | B |
| 108 | B |
| 109 | C |
| 110 | B |
| 111 | C |
| 112 | C |
| 113 | D |
| 114 | D |
| 115 | C |
| 116 | C |
| 117 | D |
| 118 | B |
| 119 | B |
| 120 | B |
| 121 | D |
| 122 | C |
| 123 | C |
| 124 | B |
| 125 | B |
| 126 | C |
| 127 | C |
| 128 | B |
| 129 | D |
| 130 | D |
| 131 | B |
| 132 | C |
| 133 | C |
| 134 | C |
| 135 | A |
| 136 | B |
| 137 | C |
| 138 | A |
| 139 | B |
| 140 | B |
| 141 | B |
| 142 | C |
| 143 | C |
| 144 | C |
| 145 | D |
| 146 | D |
| 147 | B |
| 148 | D |
| 149 | B |
| 150 | B |
| 151 | C |
| 152 | A |
| 153 | B |
| 154 | B |
| 155 | C |
| 156 | A |
| 157 | D |
| 158 | D |
| 159 | D |
| 160 | A |
| 161 | B |
| 162 | B |
| 163 | B |
| 164 | B |
| 165 | C |
| 166 | A |
| 167 | D |
| 168 | B |
| 169 | B |
| 170 | B |
| 171 | A |
| 172 | B |
| 173 | C |
| 174 | B |
| 175 | A |
| 176 | A |

TABLE 2-continued

| Cpd# | IC$_{50}$ Ranges |
|---|---|
| 177 | B |
| 178 | B |
| 179 | B |
| 180 | B |
| 181 | B |
| 182 | B |
| 183 | C |
| 184 | C |
| 185 | C |
| 186 | C |
| 187 | C |
| 188 | C |
| 189 | B |
| 190 | B |
| 191 | C |
| 192 | C |
| 193 | B |
| 194 | C |
| 195 | B |
| 196 | C |
| 197 | B |
| 198 | B |
| 199 | B |
| 200 | B |
| 201 | B |
| 202 | C |
| 203 | D |
| 204 | B |
| 205 | B |
| 206 | B |
| 207 | B |
| 208 | C |
| 209 | B |
| 210 | C |
| 211 | B |
| 212 | B |
| 213 | A |
| 214 | B |
| 215 | B |
| 216 | A |
| 217 | A |
| 218 | B |
| 219 | B |
| 220 | B |
| 221 | C |
| 222 | C |
| 223 | B |
| 224 | D |
| 225 | D |
| 226 | D |
| 227 | D |
| 228 | C |
| 229 | D |
| 230 | C |
| 231 | C |
| 232 | C |
| 233 | D |
| 234 | C |
| 235 | C |
| 236 | D |
| 237 | C |
| 238 | D |
| 239 | C |
| 240 | D |
| 241 | C |
| 242 | B |
| 243 | B |
| 244 | C |
| 245 | C |
| 246 | C |
| 247 | D |
| 248 | C |
| 249 | D |
| 250 | B |
| 251 | B |
| 252 | C |
| 253 | B |

TABLE 2-continued

| Cpd# | IC$_{50}$ Ranges |
|---|---|
| 254 | B |
| 255 | B |
| 256 | B |
| 257 | B |
| 258 | D |
| 259 | D |
| 260 | D |
| 261 | D |
| 262 | C |
| 263 | C |
| 264 | C |
| 265 | C |
| 266 | C |
| 267 | D |
| 268 | D |
| 269 | C |
| 270 | C |
| 271 | C |
| 272 | B |
| 273 | C |
| 274 | C |
| 275 | C |
| 276 | C |
| 277 | B |
| 278 | B |
| 279 | D |
| 280 | D |
| 281 | D |
| 282 | D |
| 283 | C |
| 284 | C |
| 285 | B |
| 286 | D |
| 287 | D |
| 289 | B |
| 290 | C |
| 291 | D |
| 292 | C |
| 293 | B |
| 294 | C |
| 295 | D |
| 296 | C |
| 297 | B |
| 298 | C |
| 299 | D |
| 300 | D |
| 301 | C |
| 302 | C |
| 303 | C |
| 304 | C |
| 305 | D |
| 306 | C |
| 307 | D |
| 308 | C |
| 309 | B |
| 310 | C |
| 311 | B |
| 312 | B |
| 313 | C |
| 314 | B |
| 315 | D |
| 316 | D |
| 317 | C |
| 318 | D |
| 319 | B |
| 320 | C |
| 321 | B |
| 322 | B |
| 323 | B |
| 324 | B |
| 325 | D |
| 326 | B |
| 327 | C |
| 328 | B |
| 329 | D |
| 330 | B |
| 331 | B |

TABLE 2-continued

| Cpd# | IC$_{50}$ Ranges |
|---|---|
| 332 | B |
| 333 | B |
| 334 | B |
| 335 | B |
| 336 | B |
| 337 | C |
| 338 | B |
| 339 | D |
| 340 | D |
| 341 | B |
| 342 | B |
| 343 | C |
| 344 | C |
| 345 | C |
| 346 | D |
| 347 | B |
| 348 | C |
| 349 | B |
| 350 | D |
| 351 | C |
| 352 | C |
| 353 | D |
| 354 | D |
| 355 | D |
| 356 | D |
| 357 | B |
| 358 | B |
| 359 | B |
| 360 | B |
| 361 | B |
| 362 | B |
| 363 | B |
| 364 | B |
| 365 | B |
| 366 | C |
| 367 | D |
| 368 | D |
| 369 | C |
| 370 | B |
| 371 | B |
| 372 | B |
| 373 | B |
| 374 | A |
| 375 | C |
| 376 | B |
| 377 | B |
| 378 | C |
| 379 | B |
| 380 | A |
| 381 | A |
| 382 | B |
| 383 | B |
| 384 | B |
| 385 | B |
| 386 | B |
| 387 | B |
| 388 | B |
| 389 | B |
| 390 | B |
| 391 | B |
| 392 | B |
| 393 | B |
| 394 | B |
| 395 | C |
| 396 | C |
| 397 | C |
| 398 | C |
| 399 | C |
| 400 | C |
| 401 | C |
| 402 | C |
| 403 | B |
| 404 | B |
| 405 | B |
| 406 | B |
| 407 | C |
| 408 | C |

TABLE 2-continued

| Cpd# | IC$_{50}$ Ranges |
|---|---|
| 409 | D |
| 410 | C |
| 411 | B |

Example 2

Loss of Potency in C3H10T1/2 Cell Differentiation Assay Associated with Presence of SMO L416F Mutation.

Table 3 below details the number of fold reduction in potency of a range of compounds of the invention when applied to the SMO L416F mutant cell line compared to the wild type. SMO mutation has been described in the literature (Pricl, Sabrina, et al.) as a key mutation causative of vismodegib resistance in the clinic by interfering with drug binding. As can observed from the data in Table 3, the loss of potency observed for compounds of the invention is less than that of vismodegib, which is considered to reflect the potential for overcoming resistance associated with vismodegib. Such data are also reflected in the graph of FIG. 1, whereby a lower concentration of compound 174 is required to achieve the same percent inhibition of differentiation.

TABLE 3

| Compound | Fold reduction in potency in SMO L416F mutant cell line |
|---|---|
| Vismodegib | 202 |
| 177 | 37 |
| 175 | 40 |
| 171 | 38 |
| 166 | 51 |
| 217 | 34 |
| 160 | 29 |
| 26 | 67 |
| 154 | 28 |
| 143 | 21 |
| 250 | 29 |
| 248 | 10 |
| 107 | 56 |
| 124 | 64 |
| 216 | 47 |
| 120 | 38 |
| 88 | 27 |
| 84 | 50 |
| 75 | 60 |
| 223 | 26 |
| 168 | 33 |

Example 3

Differential Potencies Between SMO Binding Affinity and C3H10T1/2 Cell Differentiation Standard Protocol for Smoothened (SMO) Binding Fluorescence Polarisation Assay.

The assay measures the ability of the test compounds to compete with a fluorescently-labelled version of the known ligand, cyclopamine, for binding to SMO. The fluorescent tag used is BODIPY (boron dipyrromethene).

An aliquot of a membrane preparation from a SMO-overexpressing HEK293 cell line is diluted to protein concentration of 0.117 mg/ml in assay buffer (25 mM HEPES, 2 mM EDTA, 0.05% γ-globulin, 0.01% pluronic acid pH7.4, plus protease Inhibitor cocktail). 8.5 µl of the membrane suspension is added to each well of a black, low volume 384 well microtitre plate.

Test compounds are added in a seven point dilution range to the wells containing the membrane preparation. The final DMSO solvent concentration in the wells is maintained at 0.3%. 6.5 µl of a 6.9 nM BODIPY-cyclopamine solution is added to each of the wells (final assay concentration 3 nM).

The plate is sealed and stored in the dark at room temperature for 24 hours prior to measurement of the fluorescence polarisation signal on a Perkin Elmer Envision multi-label reader.

Table 4 below details the ratio of SMO binding compared to the potency in the C3H10T1/2 cellular assay. The small ratio between SMO binding and potency for vismodegib is considered to be reflective of the fact vismodegib acts mainly through inhibition of the SMO protein. The larger ratios for the compound of the invention are considered to be reflective of alternate actions outside of direct SMO inhibition.

TABLE 4

| Compound | Ratio of potency in SMO binding assay to potency in C3H10T1/2 cellular assay |
|---|---|
| Vismodegib | 2.2 |
| 112 | 42 |
| 107 | 20 |
| 239 | >37 |
| 131 | 84 |
| 124 | 82 |
| 16 | >78 |
| 122 | >55 |
| 228 | 20 |
| 97 | 22 |
| 116 | 21 |
| 115 | 20 |
| 67 | 45 |
| 223 | 21 |
| 162 | 20 |
| 34 | 21 |
| 154 | 66 |
| 143 | >17 |
| 255 | 21 |
| 256 | 2.7 |
| 265 | 3.9 |
| 274 | >10 |
| 284 | 2.3 |
| 285 | 2.9 |
| 292 | 4.3 |
| 294 | 5.0 |
| 296 | 3.8 |
| 298 | 4.9 |
| 308 | 4.8 |
| 313 | 2.7 |
| 314 | 6.7 |
| 319 | 2.9 |
| 328 | 3.2 |
| 333 | 2.5 |
| 334 | 2.6 |
| 347 | 3.8 |
| 388 | 5.4 |
| 395 | 2.6 |
| 396 | 2.5 |
| 397 | 3.6 |
| 401 | 3.0 |
| 410 | 3.1 |

Example 4

In Vivo Protocol:
Evaluation of the Pharmacodynamic (PD) Effect of Compounds of Formula I and
Sonidegib on a Subcutaneous Calu-6 Xenograft Model.
The objective of this study is to assess the pharmacodynamic (PD) effect of three novel inhibitors of the hedgehog pathway (of Formula I) and Sonidegib, on a subcutaneous Calu-6 xenograft model.
  Calu-6 tumour cells to be implanted into the flank of Balb/c mice and treatment commenced once tumours reach a mean volume of ~300-400 mm$^3$
  The animals to be dosed for 4 days and terminated at 4 hours after the final dose
  Tumour samples to be collected and Gli1 expression levels to be measured as a readout of Hedgehog pathway activity

REFERENCES

Alcedo J, Ayzenzon M, Von Ohlen T, Noll M & Hooper J E (1996). The *Drosophila* smoothened Gene Encodes a Seven-Pass Membrane Protein, a Putative Receptor for the Hedgehog Signal. *Cell* 86, 221-232.

Berman D M, Karhadkar S S, Hallahan A R, Pritchard J I, Eberhart C G, Watkins D N, Chen J K, Cooper M K, Taipale J, Olson J M & Beachy P A (2002). Medulloblastoma Growth Inhibition by Hedgehog Pathway Blockade. *Science* (80-).

Bitgood M J, Shen L & McMahon A P (1996). Sertoli cell signaling by Desert hedgehog regulates the male germline. *Curr Biol* 6, 298-304.

Chen J K, Taipale J, Cooper M K & Beachy P A (2002). Inhibition of Hedgehog signaling by direct binding of cyclopamine to Smoothened. *Genes Dev* 16, 2743.

Chen Y, Sasai N, Ma G, Yue T, Jia J, Briscoe J & Jiang J (2011). Sonic Hedgehog Dependent Phosphorylation by CK1α and GRK2 Is Required for Ciliary Accumulation and Activation of Smoothened. *PLoS Biol*; DOI: 10.1371/journal.pbio.1001083.

Chiang C, Litingtung Y, Lee E, Young K E, Corden J L, Westphal H & Beachy P A (1996). Cyclopia and defective axial patterning in mice lacking Sonic hedgehog gene function. *Nature* 383, 407-413.

Coon V, Laukert T, Pedone C A, Laterra J, Kim K J & Fults D W (2010). Molecular Therapy Targeting Sonic Hedgehog and Hepatocyte Growth Factor Signaling in a Mouse Model of Medulloblastoma. *Mol Cancer Ther.*

Dierks C, Beigi R, Guo G-R, Zirlik K, Stegert M R, Manley P, Trussell C, Schmitt-Graeff A, Landwerlin K, Veelken H & Warmuth M (2008). Expansion of Bcr-Abl-Positive Leukemic Stem Cells Is Dependent on Hedgehog Pathway Activation. *Cancer Cell* 14, 238-249.

Echelard Y, Epstein D J, St-Jacques B, Shen L, Mohler J, McMahon J A & McMahon A P (1993). Sonic hedgehog, a member of a family of putative signaling molecules, is implicated in the regulation of CNS polarity. *Cell* 75, 1417-1430.

Epstein E H (2008). Basal cell carcinomas: attack of the hedgehog. *Nat Rev Cancer* 8, 743.

Hui C & Angers S (2011). Gli Proteins in Development and Disease. *Annu Rev Cell Dev Biol* 27, 513-537.

Incardona J P, Lee J H, Robertson C P, Enga K, Kapur R P & Roelink H (2000). Receptor-mediated endocytosis of soluble and membrane-tethered Sonic hedgehog by Patched-1. *Proc Natl Acad Sci USA* 97, 12044.

Ingham P W & McMahon A P (2001). Hedgehog signaling in animal development: paradigms and principles. *Genes Dev* 15, 3059-3087.

Kimonis V, Goldstein A, Pastakia b & Bale s (1997). Clinical manifestations in 105 persons with nevoid basal cell carcinoma syndrome.—PubMed—NCBI. *Am J Med Genet* 69, 299-308.

Kool M, Koster J, Bunt J, Hasselt N E, Lakeman A, Sluis P van, Troost D, Meeteren N S, Caron H N, Cloos J, Mršić A, Ylstra B, Grajkowska W, Hartmann W, Pietsch T, Ellison D, Clifford S C & Versteeg R (2008). Integrated Genomics Identifies Five Medulloblastoma Subtypes with Distinct Genetic Profiles, Pathway Signatures and Clinicopathological Features. *PLoS One*; DOI: 10.1371/journal.pone.0003088.

Kubo M, Nakamura M, Tasaki A, Yamanaka N, Nakashima H, Nomura M, Kuroki S & Katano M (2004). Hedgehog Signaling Pathway is a New Therapeutic Target for Patients with Breast Cancer. *Cancer Res.*

Lai K, Kaspar B K, Gage F H & Schaffer D V. (2002). Sonic hedgehog regulates adult neural progenitor proliferation in vitro and in vivo. *Nat Neurosci* 6, 21-27.

Levy V, Lindon C, Harfe B D & Morgan B A (2005). Distinct Stem Cell Populations Regenerate the Follicle and Interfollicular Epidermis. *Dev Cell* 9, 855-861.

List A, Beran M, DiPersio J, Slack J, Vey N, Rosenfeld C S & Greenberg P (2003). Opportunities for Trisenox® (arsenic trioxide) in the treatment of myelodysplastic syndromes. *Leukemia* 17, 1499-1507.

Metcalfe C & de Sauvage F J (2011). Hedgehog Fights Back: Mechanisms of Acquired Resistance against Smoothened Antagonists. *Cancer Res.*

Mimeault M, Johansson S L, Henichart J-P, Depreux P & Batra S K (2010). Cytotoxic effects induced by docetaxel, gefitinib and cyclopamine on side population and non-side population cell fractions from human invasive prostate cancer cells. *Mol Cancer Ther* 9, 617.

Mohler J & Vani K (1992). Molecular organization and embryonic expression of the hedgehog gene involved in cell-cell communication in segmental patterning of *Drosophila. Development.*

Murone M, Rosenthal A & de Sauvage F J (1999). Sonic hedgehog signaling by the Patched-Smoothened receptor complex. *Curr Biol* 9, 76-84.

Nusslein-Volhard C & Wieschaus E (1980). Mutations affecting segment number and polarity in *Drosophila*.—PubMed—NCBI. *Nature* 287, 795-801.

Pak E & Segal R A (2016). Hedgehog Signal Transduction: Key Players, Oncogenic Drivers, and Cancer Therapy. *Dev Cell* 38, 333-344.

Pan S et al. (2010). Discovery of NVP-LDE225, a Potent and Selective Smoothened Antagonist. *ACS Med Chem Lett* 1, 130.

Pathi S, Pagan-Westphal S, Baker D P, Garber E A, Rayhorn P, Bumcrot D, Tabin C J, Blake Pepinsky R & Williams K P (2001). Comparative biological responses to human Sonic, Indian, and Desert hedgehog. *Mech Dev* 106, 107-117.

Perler F B (1998). Protein Splicing of Inteins and Hedgehog Autoproteolysis: Structure, Function, and Evolution. *Cell* 92, 1-4.

Petrova E, Rios-Esteves J, Ouerfelli O, Glickman J F & Resh M D (2013). Inhibitors of Hedgehog Acyltransferase Block Sonic Hedgehog Signaling. *Nat Chem Biol* 9, 247.

Rimkus T K, Carpenter R L, Qasem S, Chan M & Lo H-W (2016). Targeting the Sonic Hedgehog Signaling Pathway: Review of Smoothened and GLI Inhibitors. *Cancers (Basel)*; DOI: 10.3390/cancers8020022.

Robarge K D et al. (2009). *GDC-0449—A potent inhibitor of the hedgehog pathway.*

Ruiz i Altaba A (1999). Gli proteins encode context-dependent positive and negative functions: implications for development and disease. *Development.*

Sanchez P, Hernández A M, Stecca B, Kahler A J, DeGueme A M, Barrett A, Beyna M, Datta M W, Datta S & Altaba A R i (2004). Inhibition of prostate cancer proliferation by interference with SONIC HEDGEHOG-GLI1 signaling. *Proc Natl Acad Sci USA* 101, 12561.

Sekulic A, Migden M R, Oro A E, Dirix L, Lewis K D, Hainsworth J D, Solomon J A, Yoo S, Arron S T, Friedlander P A, Marmur E, Rudin C M, Chang A L S, Low J A, Mackey H M, Yauch R L, Graham R A, Reddy J C & Hauschild A (2012). Efficacy and Safety of Vismodegib in Advanced Basal-Cell Carcinoma. *N Engl J Med* 366, 2171-2179.

Sharpe H J et al. (2015). Genomic Analysis of Smoothened Inhibitor Resistance in Basal Cell Carcinoma. *Cancer Cell* 27, 327-341.

St-Jacques B, Hammerschmidt M & McMahon A P (1999). Indian hedgehog signaling regulates proliferation and differentiation of chondrocytes and is essential for bone formation. *Genes Dev* 13, 2072.

Stone D M, Hynes M, Armanini M, Swanson T A, Gu Q, Johnson R L, Scott M P, Pennica D, Goddard A, Phillips H, Noll M, Hooper J E, de Sauvage F & Rosenthal A (1996). The tumour-suppressor gene patched encodes a candidate receptor for Sonic hedgehog. *Nature* 384, 129-134.

Taipale J, Cooper M K, Maiti T & Beachy P A (2002). Patched acts catalytically to suppress the activity of Smoothened. *Nature* 418, 892-896.

Thayer S P, Magliano M P di, Heiser P W, Nielsen C M, Roberts D J, Lauwers G Y, Qi Y P, Gysin S, Castillo C F, Yajnik V, Antoniu B, McMahon M, Warshaw A L & Hebrok M (2003). Hedgehog is an early and late mediator of pancreatic cancer tumorigenesis. *Nature* 425, 851.

Tojo M, Kiyosawa H, Iwatsuki K & Kaneko F (2002). Expression of a sonic hedgehog signal transducer, hedgehog-interacting protein, by human basal cell carcinoma. *Br J Dermatol* 146, 69-73.

Varnat F, Duquet A, Malerba M, Zbinden M, Mas C, Gervaz P & Altaba A R i (2009). Human colon cancer epithelial cells harbour active HEDGEHOG-GLI signalling that is essential for tumour growth, recurrence, metastasis and stem cell survival and expansion. *EMBO Mol Med* 1, 338.

Watkins D N, Berman D M, Burkholder S G, Wang B, Beachy P A & Baylin S B (2003). Hedgehog signalling within airway epithelial progenitors and in small-cell lung cancer. *Nature* 422, 313-317.

Yauch R L, Gould S E, Scales S J, Tang T, Tian H, Ahn C P, Marshall D, Fu L, Januario T, Kallop D, Nannini-Pepe M, Kotkow K, Marsters J C, Rubin L L & de Sauvage F J (2008). A paracrine requirement for hedgehog signalling in cancer. *Nature* 455, 406-410.

Zhao C, Chen A, Jamieson C H, Fereshteh M, Abrahamsson A, Blum J, Kwon H Y, Kim J, Chute J P, Rizzieri D, Munchhof M, VanArsdale T, Beachy P A & Reya T (2009). Hedgehog signalling is essential for maintenance of cancer stem cells in myeloid leukaemia. *Nature* 458, 776.

Zhao Y, Tong C & Jiang J (2007). Hedgehog regulates smoothened activity by inducing a conformational switch. *Nature* 450, 252-258.

Zerr, Pawel, et al. "Inhibition of hedgehog signalling for the treatment of murine sclerodermatous chronic graft-versus-host disease." *Blood* 120.14 (2012): 2909-2917.

Pricl, Sabrina, et al. "Smoothened (SMO) receptor mutations dictate resistance to vismodegib in basal cell carcinoma." *Molecular oncology* 9.2 (2015): 389-397.

Rimkus, Tadas K., et al. "Targeting the Sonic Hedgehog Signaling Pathway: Review of Smoothened and GLI Inhibitors." *Cancers* 8.2 (2016): 22.

The invention claimed is:

1. A compound according to Formula (I):

$$R^2-X-Y\begin{pmatrix}(CH_2)_n\\(CH_2)_m\end{pmatrix}\overset{O}{\underset{O}{\overset{\parallel}{\underset{\parallel}{S}}}}-W^1\begin{pmatrix}W^{3B}-W^{4B}\\W^{3A}-W^{4A}\end{pmatrix}W^2-R^1 \quad (I)$$

or a salt, or a solvate, or a solvate of the salt thereof, wherein, integers n and m are selected from:
  (i) 1, 2 and 3, provided that sum of n and m is 2, 3 or 4; or
  (ii) 0 and 1, provided that the sum of n and m is 1;

Y is N;

$W^1$ is N;

$W^2$ is C, provided that one of $W^{4A}$ and $W^{4B}$ is —CH— and is connected to $W^2$ by a double bond and the other is —CH$_2$—

$W^{3A}$ and $W^{3B}$ are —CH$_2$— or —CH(R$^3$)—, wherein R$^3$ is methyl;

$W^{4A}$ and $W^{4B}$ are —CH$_2$— or —CH—, provided that when one of $W^{4A}$ and $W^{4B}$ is —CH— the other is —CH$_2$—;

$R^1$ is selected from:
  (i) a fused 9-10 membered bicyclic heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(═O)OC$_{1-6}$alkyl, —O(C═O)C$_{1-6}$alkyl, —C(═O)O—C$_{0-4}$alkyl-cycloalkyl, C$_{0-6}$alkyl-phenyl (wherein phenyl may be optionally substituted by C$_{1-4}$alkyl), —C(═O)NHC$_{1-6}$alkyl, —NHC(═O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$ alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(═O)C$_{1-6}$alkyl, —OC(═O)C$_{1-6}$ alkyl, —C(═O)OH, —C(═O)OC$_{1-6}$alkyl, —C(═O)NHC$_{1-6}$alkyl and —NHC(═O)C$_{1-6}$alkyl, provided that when $W^1$ is N, $W^{3A}$, $W^{3B}$, $W^{4A}$, and $W^{4B}$ are —CH$_2$—, n and m are 1 or 2, sum of n and m is 3, X is —(CH$_2$)x$^1$, x$^1$ is 1, and R$^2$ is unsubstituted phenyl, then R$^1$ cannot represent benzothiazole-2-yl;
  (ii) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(═O)C$_{1-6}$alkyl, —C(═O)OH, —C(=O)OC$_{1-6}$alkyl, —O(C=O)C$_{1-6}$alkyl, —C(=O)O—C$_{0-4}$alkyl-cycloalkyl, C$_{0-6}$alkyl-phenyl (wherein phenyl may be optionally substituted by C$_{1-4}$alkyl), —C(=O)NHC$_{1-6}$alkyl, —NHC(=O)C$_{1-6}$alkyl, —SO$_2$—C$_{1-6}$alkyl, —SO$_2$—N(C$_{1-6}$ alkyl)$_2$, —SO$_2$-phenyl, and 5-6-membered heteroaryl wherein phenyl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

(iii) 6-10 membered aryl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$ alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$ alkyl and —NHC(=O)C$_{1-6}$alkyl;

(iv) a fused 8-10 membered partially unsaturated bicyclic heterocyclyl optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl; and (v) a 5-6 membered monocyclic heterocycloalkyl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

X is absent or a bivalent group selected from:
(a) —(CH$_2$)x$^1$-, wherein x$^1$ is 1, 2 or 3;
(b) —(CH$_2$)x$^2$-C(CH$_3$)$_2$—(CH$_2$)x$^3$-, wherein x$^2$ is 1 or 2 and x$^3$ is 1;
(c) —C(=O)—(CH$_2$)x$^4$-, wherein x$^4$ is zero, 1 or 2;
(d) —C(=O)O—(CH$_2$)x$^5$-, wherein x$^5$ is zero, 1, 2 or 3;
(e) —C(=O)NR$^x$—(CH$_2$)x$^6$-, wherein
  (e.i) x$^6$ is zero, 1 or 2 and R$^x$ is H or C$_{1-4}$alkyl, or
  (e.ii) x$^6$ is zero and R$^x$ together with R$^2$ and with nitrogen to which R$^x$ and R$^2$ are attached form a heterocycloalkyl ring which may have one additional heteroatom selected from O or N, and said heterocycloalkyl may be optionally substituted by one or more C$_{1-4}$alkyl groups;
(f) —C(=S)NR$^y$—, wherein R$^y$ is H or C$_{1-4}$alkyl; and
(g) —SO$_2$—;

R$^2$ is selected from:
(i) C$_{1-10}$alkyl optionally substituted by one or more groups independently selected from OH, —OC$_{1-4}$alkyl, —NHC$_{1-4}$alkyl, and —N(C$_{1-4}$alkyl)$_2$;
(ii) —NHC$_{1-4}$alkyl, —N(C$_{1-4}$alkyl)$_2$;
(iii) 3-10 membered cycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-NH—C$_{1-6}$alkyl and —C$_{0-6}$alkyl-N(C$_{1-6}$alkyl)$_2$;

(iv) 5-6 membered heterocycloalkyl optionally substituted by one or more groups independently selected from OH, halogen, CN, NH$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, and —C(=O)NH$_2$;

(v) 6-membered aryl (phenyl) optionally substituted by one or more groups independently selected from halogen, CN, OH, NO$_2$, C$_{1-6}$alkyl, C$_{2-6}$alkenyl, C$_{2-6}$alkynyl, —OC$_{1-6}$alkyl, O-phenyl, haloC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —C(=O)OH, —O(C=O)C$_{1-6}$alkyl, —C(=O)OC$_{1-6}$alkyl, —C(=O)NHC$_{1-6}$alkyl and —NHC(=O)C$_{1-6}$alkyl, provided when X is bivalent group —C(=O)O—(CH$_2$)x$^5$-, x$^5$ is 1, and R$^2$ is unsubstituted phenyl, W$^1$ is N, W$^2$ is CH or N, W$^{3A}$, W$^{3B}$, W$^{4A}$, and W$^{4B}$ are —CH$_2$—, sum of n and m is 4, then R$^1$ is other than phenyl optionally substituted by C$_{1-6}$ alkyl or —OC$_{1-6}$alkyl, and pyridyl optionally substituted by halogen;

(vi) 5-6 membered heteroaryl optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$ alkyl, —C(=O)OH, —C(=O)OC$_{1-6}$alkyl, —C(=O)NHC$_{1-6}$alkyl, —NHC(=O)C$_{1-6}$alkyl, and 3-6-membered cycloalkyl wherein said cycloalkyl may optionally be substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alky; and (vii) H and X is absent, provided that when W$^1$ is N, W$^2$ is CH, W$^{3A}$, W$^{3B}$, W$^{4A}$, and W$^{4B}$ are —CH$_2$—, sum of n and m is 3 or 4, then R$^1$ cannot represent piperidinyl, and when W$^1$ and W$^2$ are N, W$^{3A}$, W$^{3B}$, W$^{4A}$ and W$^{4B}$ are —CH$_2$—, sum of n and m is 3 or 4, then R$^1$ cannot represent phenyl optionally substituted by CH$_3$ or halogen, pyridinyl, pyrimidinyl or thiazolyl;

provided that when X is —(C=O)(CH$_2$)x$^4$, x$^4$ is zero, R$^2$ is unsubstituted cyclopentyl or phenyl optionally substituted by halogen, W$^1$ is N, W$^2$ is CH or N, W$^{3A}$ and W$^{3B}$ are —CH$_2$— or —CH(R$^3$)—, R$^3$ is CH$_3$, W$^{4A}$, and W$^{4B}$ are —CH$_2$—, then R$^1$ is a fused 9-10 membered bicyclic heteroaryl or a fused 8-10 membered partially unsaturated bicyclic heterocyclyl;

or a pharmaceutically acceptable salt or a solvate thereof.

2. The compound according to claim 1, wherein integers n and m are selected from 1, 2 and 3, provided that sum of n and m is 4.

3. The compound according to claim 1, wherein ring:

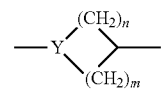

represents

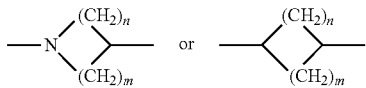

in which n and m are each as herein defined.

4. The compound according to claim 1, wherein the ring is:

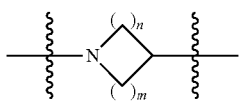

and the ring is selected from:

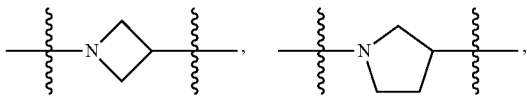

5. The compound according to claim 1, wherein subunit

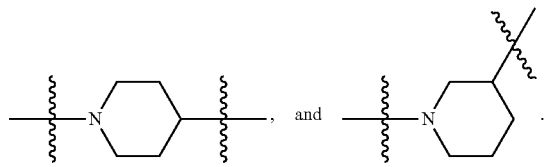

is:

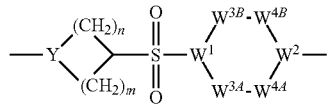

6. The compound according to claim 1, wherein subunit

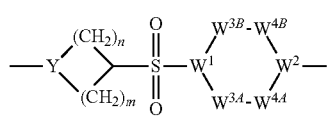

is:

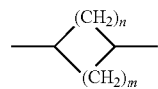

7. The compound according to claim 1, wherein the ring is:

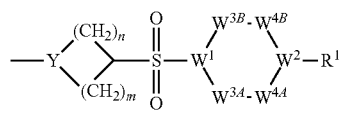

the ring is:

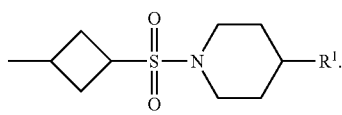

8. The compound according to claim 1, wherein subunit is

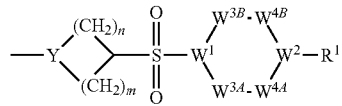

9. The compound according to claim 1, wherein subunit

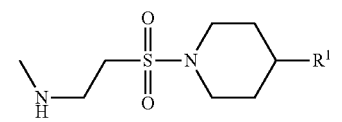

is wherein $R^1$ is as defined in claim 1.

10. The compound according to claim 1, which comprises a compound of formula (Ia):

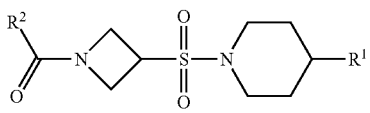
(Ia)

in which R¹ is selected from the group consisting of:

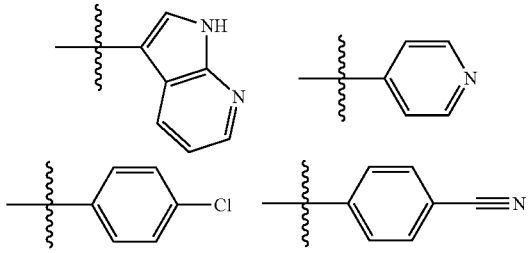

and R² is selected from the group consisting of:

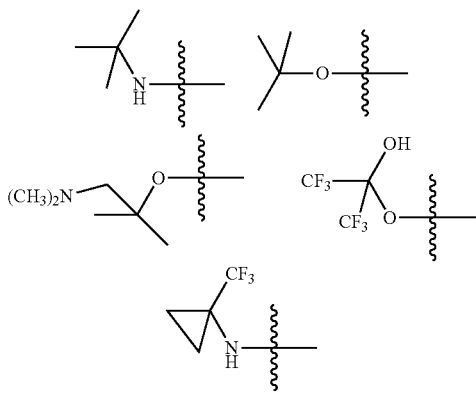

or a pharmaceutically acceptable salt or a solvate thereof.

11. The compound according to claim 1, wherein R¹ is selected from: a fused 9-10 membered bicyclic heteroaryl, 5-6 membered heteroaryl, 6-10 membered aryl, and a fused 8-10 membered partially unsaturated bicyclic heterocyclyl.

12. The compound according to claim 1, wherein R¹ is a fused 9-10 membered bicyclic heteroaryl or 5-6 membered heteroaryl.

13. The compound according to claim 1, wherein R¹ is a fused 9-10 membered bicyclic heteroaryl or a fused 8-10 membered partially unsaturated bicyclic heterocyclyl.

14. The compound according to claim 1, wherein X is absent and R² is hydrogen.

15. The compound according to claim 1, wherein X is absent and R² is selected from $C_{1-10}$alkyl, 3-10 membered cycloalkyl, 6-membered aryl (phenyl) and 5-6 membered heteroaryl.

16. The compound according to claim 1, wherein X is —(CH₂)x¹-, integer x¹ is 1, 2 or 3 and R² is selected from $C_{1-10}$alkyl, —NHC$_{1-4}$alkyl, —N(C$_{1-4}$alkyl)₂, 3-10 membered cycloalkyl, 5-6 membered heterocycloalkyl, 6-membered aryl (phenyl) and 5-6 membered heteroaryl.

17. The compound according to claim 1, wherein X is —(CH₂)x²-C(CH₃)₂—(CH₂)x³-, integer x² is 1 or 2, integer x³ is 1 and R² is selected from $C_{1-10}$alkyl, —NHC$_{1-4}$alkyl, —N(C$_{1-4}$alkyl)₂, 3-10 membered cycloalkyl, 5-6 membered heterocycloalkyl, 6-membered aryl (phenyl) and 5-6 membered heteroaryl.

18. The compound according to claim 1, wherein the compound is selected from the group consisting of:
tert-butyl 3-[4-(5-fluoro-1H-pyrrolo[2,3-b]pyridin-3-yl)piperidin-1-yl]sulfonylazetidine-1-carboxylate; [1]
tert-butyl 3-[4-(5-methyl-1H-pyrrolo[2,3-b]pyridin-3-yl)piperidin-1-yl]sulfonylazetidine-1-carboxylate; [2]
tert-butyl 3-[4-(3-benzylimidazol-4-yl)piperidin-1-yl]sulfonylazetidine-1-carboxylate; [3]
tert-butyl 3-[1-[1-[(2-methylpropan-2-yl)oxycarbonyl]azetidin-3-yl]sulfonylpiperidin-4-yl]-6,8-dihydro-5H-imidazo[1,2-a]pyrazine-7-carboxylate; [4]
tert-butyl 3-[4-(6,7-dihydro-5H-pyrrolo[1,2-a]imidazol-3-yl)piperidin-1-yl] sulfonylazetidine-1-carboxylate; [5]
tert-butyl 3-[4-(4-methoxyphenyl)piperidin-1-yl]sulfonylazetidine-1-carboxylate; [6]
tert-butyl 4-[4-(1H-pyrrolo[2,3-b]pyridin-4-yl)piperidin-1-yl]sulfonylpiperidine-1-carboxylate; [7]
tert-butyl 4-[4-[1-(4-methylphenyl)sulfonylpyrrolo[2,3-b]pyridin-4-yl]piperidin-1-yl]sulfonylpiperidine-1-carboxylate; [8]
tert-butyl 4-[4-(2,4-dimethylphenyl)piperidin-1-yl]sulfonylpiperidine-1-carboxylate; [9]
tert-butyl 3-[4-(7H-pyrrolo[2,3-d]pyrimidin-4-yl)piperidin-1-yl]sulfonylpiperidine-1-carboxylate; [10]
tert-butyl 4-(4-quinolin-4-ylpiperidin-1-yl)sulfonylpiperidine-1-carboxylate; [11]
tert-butyl 4-[4-[7-(4-methylphenyl)sulfonylpyrrolo[2,3-d]pyrimidin-4-yl]piperidin-1-yl]sulfonylpiperidine-1-carboxylate; [12]
tert-butyl 4-[4-(4-methoxyphenyl)piperidin-1-yl]sulfonylpiperidine-1-carboxylate; [13]
tert-butyl 4-(4-phenylpiperidin-1-yl)sulfonylpiperidine-1-carboxylate; [14]methyl 3-[1-[1-[(2-methylpropan-2-yl)oxycarbonyl]azetidin-3-yl]sulfonylpiperidin-4-yl]-1H-pyrrolo[2,3-b]pyridine-5-carboxylate; [15]methyl 3-[1-[1-[(2-methylpropan-2-yl)oxycarbonyl]piperidin-4-yl]sulfonylpiperidin-4-yl]-1H-pyrrolo[2,3-b]pyridine-5-carboxylate; [16]
tert-butyl 3-(4-thieno[3,2-b]pyridin-3-ylpiperidin-1-yl)sulfonylazetidine-1-carboxylate; [17]
tert-butyl 4-(4-thieno[3,2-b]pyridin-3-ylpiperidin-1-yl)sulfonylpiperidine-1-carboxylate; [18]
tert-butyl 4-[4-(1H-pyrrolo[2,3-b]pyridin-3-yl)piperidin-1-yl]sulfonylpiperidine-1-carboxylate; [19]
tert-butyl 4-[4-(oxan-4-yl)piperidin-1-yl]sulfonylpiperidine-1-carboxylate; [20]
N-phenyl-4-(4-pyridin-4-ylpiperidin-1-yl)sulfonylpiperidine-1-carboxamide; [21]
tert-butyl 3-(4-pyridin-4-ylpiperidin-1-yl)sulfonylazetidine-1-carboxylate; [22]
tert-butyl 4-(4-pyridin-4-ylpiperidin-1-yl)sulfonylpiperidine-1-carboxylate; [23]3-(4-pyridin-4-ylpiperidin-1-yl)sulfonyl-N-[1-hydroxy-3-methylbutan-2-yl]azetidine-1-carboxamide; [24]
N-(3,5-dimethyl-1,2-oxazol-4-yl)-3-(4-pyridazin-3-ylpiperidin-1-yl)sulfonylazetidine-1-carboxamide; [25]
3-[4-(1H-pyrrolo[2,3-b]pyridin-3-yl)piperidin-1-yl]sulfonyl-N-[1-hydroxy-3-methylbutan-2-yl]azetidine-1-carboxamide; [26]
(2-methoxyphenyl) 3-(4-pyridin-4-ylpiperidin-1-yl)sulfonylazetidine-1-carboxylate; [27]
(4-methoxycyclohexyl) 3-(4-pyridin-4-ylpiperidin-1-yl) sulfonylazetidine-1-carboxylate; [28]oxan-4-yl 3-(4-pyridin-4-ylpiperidin-1-yl)sulfonylazetidine-1-carboxylate; [29]

(oxolan-2-yl)methyl 3-(4-pyridin-4-ylpiperidin-1-yl)sulfonylazetidine-1-carboxylate; [30]
N-tert-butyl-N-methyl-3-(4-pyridin-4-ylpiperidin-1-yl)sulfonylazetidine-1-carboxamide; [31]
[3-(4-pyridin-4-ylpiperidin-1-yl)sulfonylazetidin-1-yl]-(3,3,5,5-tetramethylmorpholin-4-yl)methanone; [32]
3-(4-pyridin-4-ylpiperidin-1-yl)sulfonyl-N-(2,4,4-trimethylpentan-2-yl)azetidine-1-carboxamide; [33]
[3-(4-furo[2,3-b]pyridin-5-ylpiperidin-1-yl)sulfonylazetidin-1-yl]-(3,3,5,5-tetramethylmorpholin-4-yl)methanone; [34]
[(2R,6S)-2,6-dimethylmorpholin-4-yl]-[3-(4-furo[2,3-b]pyridin-5-ylpiperidin-1-yl) sulfonylazetidin-1-yl]methanone; [35]
3-[4-(2,3-dihydrofuro[2,3-b]pyridin-5-yl)piperidin-1-yl]sulfonyl-N-(3,5-dimethyl-1,2-oxazol-4-yl)azetidine-1-carboxamide; [36]
N-(3,5-dimethyl-1,2-oxazol-4-yl)-3-(4-furo[2,3-b]pyridin-5-ylpiperidin-1-yl) sulfonylazetidine-1-carboxamide; [37]
cyclohexyl 3-(4-furo[2,3-b]pyridin-5-ylpiperidin-1-yl)sulfonylazetidine-1-carboxylate; [38]
N-(3,5-dimethyl-1,2-oxazol-4-yl)-3-[4-(1H-pyrrolo[3,2-b]pyridin-3-yl)piperidin-1-yl]sulfonylazetidine-1-carboxamide; [39]
cyclohexyl 3-[1-(1-cyclohexyloxycarbonylazetidin-3-yl)sulfonylpiperidin-4-yl] pyrrolo [3,2-b]pyridine-1-carboxylate; [40]
cyclohexyl 3-[4-(1H-pyrrolo[3,2-b]pyridin-3-yl)piperidin-1-yl]sulfonylazetidine-1-carboxylate; [41]
N-(3,5-dimethyl-1,2-oxazol-4-yl)-3-[4-(5-methylpyrrolo[2,3-b]pyrazin-7-yl)piperidin-1-yl]sulfonylazetidine-1-carboxamide; [42]
N-(3,5-dimethyl-1,2-oxazol-4-yl)-3-[4-(5H-pyrrolo[2,3-b]pyrazin-7-yl)piperidin-1-yl]sulfonylazetidine-1-carboxamide; [43]
cyclohexyl 3-[4-(5H-pyrrolo[2,3-b]pyrazin-7-yl)piperidin-1-yl]sulfonylazetidine-1-carboxylate; [44]
tert-butyl 3-[(2R)-2-methyl-4-(1H-pyrrolo[2,3-b]pyridin-3-yl)piperidin-1-yl] sulfonylazetidine-1-carboxylate; [45]
tert-butyl 3-[2-methyl-4-(1H-pyrrolo[2,3-b]pyridin-3-yl)piperidin-1-yl]sulfonylazetidine-1-carboxylate; [46]
tert-butyl 3-[4-(5-methoxypyridin-2-yl)piperidin-1-yl] sulfonylazetidine-1-carboxylate; [47]
tert-butyl 3-[4-(6-methoxypyridin-3-yl)piperidin-1-yl] sulfonylazetidine-1-carboxylate; [48]
tert-butyl 3-[4-(1H-pyrrolo[3,2-b]pyridin-3-yl)piperidin-1-yl]sulfonylazetidine-1-carboxylate; [49]
[1-(dimethylamino)-2-methylpropan-2-yl] 3-[4-(1H-pyrrolo[2,3-b]pyridin-3-yl)piperidin-1-yl]sulfonylazetidine-1-carboxylate; [50]
(1-methylpiperidin-4-yl)methyl 3-[4-(1H-pyrrolo[2,3-b]pyridin-3-yl)piperidin-1-yl]sulfonylazetidine-1-carboxylate; [51]
2-(diethylamino)ethyl 3-[4-(1H-pyrrolo[2,3-b]pyridin-3-yl)piperidin-1-yl] sulfonylazetidine-1-carboxylate; [52]
3-(4-methylpiperazin-1-yl)propyl 3-[4-(1H-pyrrolo[2,3-b]pyridin-3-yl)piperidin-1-yl]sulfonylazetidine-1-carboxylate; [53]
2-morpholin-4-ylethyl 3-[4-(1H-pyrrolo[2,3-b]pyridin-3-yl)piperidin-1-yl] sulfonylazetidine-1-carboxylate; [54]
N-[(3,5-dimethyl-1,2-oxazol-4-yl)methyl]-3-[4-(1H-pyrrolo[2,3-b]pyridin-3-yl)piperidin-1-yl]sulfonylazetidine-1-carboxamide; [55]
3,5-dimethyl-4-[2-[3-[4-(1H-pyrrolo[2,3-b]pyridin-3-yl)piperidin-1-yl]sulfonylazetidin-1-yl]ethyl]-1,2-oxazole; [56]
3-[4-(1H-pyrrolo[2,3-b]pyridin-3-yl)piperidin-1-yl]sulfonyl-N-[1-(trifluoromethyl) cyclopropyl]azetidine-1-carboxamide; [57]
3-piperidin-1-ylpropyl 3-[4-(1H-pyrrolo[2,3-b]pyridin-3-yl)piperidin-1-yl] sulfonylazetidine-1-carboxylate; [58]
2-piperidin-1-ylethyl 3-[4-(1H-pyrrolo[2,3-b]pyridin-3-yl)piperidin-1-yl]sulfonylazetidine-1-carboxylate; [59]
2-(oxan-4-yl)ethyl 3-[4-(1H-pyrrolo[2,3-b]pyridin-3-yl)piperidin-1-yl]sulfonylazetidine-1-carboxylate; [60]
3,5-dimethyl-4-[[3-[4-(1H-pyrrolo[2,3-b]pyridin-3-yl)piperidin-1-yl]sulfonylazetidin-1-yl]methyl]-1,2-oxazole; [61]
(3,5-dimethyl-1,2-oxazol-4-yl)methyl 3-[4-(1H-pyrrolo[2,3-b]pyridin-3-yl)piperidin-1-yl]sulfonylazetidine-1-carboxylate; [62]
2-(3,5-dimethyl-1,2-oxazol-4-yl)-1-[3-[4-(1H-pyrrolo[2,3-b]pyridin-3-yl)piperidin-1-yl]sulfonylazetidin-1-yl]ethanone; [63]
[3-[4-(1H-pyrrolo[2,3-b]pyridin-3-yl)piperidin-1-yl] sulfonylazetidin-1-yl]-(2,2,6,6-tetramethylpiperidin-1-yl)methanone; [64]
2-methoxyethyl 3-[4-(1H-pyrrolo[2,3-b]pyridin-3-yl)piperidin-1-yl]sulfonylazetidine-1-carboxylate; [65]
2,2-dimethylpropyl 3-[4-(1H-pyrrolo[2,3-b]pyridin-3-yl)piperidin-1-yl]sulfonylazetidine-1-carboxylate; [66]
(oxolan-2-yl)methyl 3-[4-(1H-pyrrolo[2,3-b]pyridin-3-yl)piperidin-1-yl]sulfonylazetidine-1-carboxylate; [67]
3-[1-[(thiophen-2-ylmethyl)azetidin-3-yl]sulfonylpiperidin-4-yl]-1H-pyrrolo[2,3-b] pyridine; [68]
3-[1[1-(1H-pyrrol-2-ylmethyl)azetidin-3-yl]sulfonylpiperidin-4-yl]-1H-pyrrolo[2,3-b] pyridine; [69]
3-[1-[1-(furan-2-ylmethyl)azetidin-3-yl]sulfonylpiperidin-4-yl]-1H-pyrrolo[2,3-b]pyridine; [70]
3-[1-(1-pyridin-4-ylazetidin-3-yl)sulfonylpiperidin-4-yl]-1H-pyrrolo[2,3-b]pyridine; [71]
pyridin-4-yl-[3-[4-(1H-pyrrolo[2,3-b]pyridin-3-yl)piperidin-1-yl]sulfonylazetidin-1-yl]methanone; [72]
2,2-dimethyl-1-[3-[4-(1H-pyrrolo[2,3-b]pyridin-3-yl)piperidin-1-yl]sulfonylazetidin-1-yl]propan-1-one; [73]
(4-tert-butylphenyl)-[3-[4-(1H-pyrrolo[2,3-b]pyridin-3-yl)piperidin-1-yl]sulfonylazetidin-1-yl]methanone; [74]
cyclohexyl 3-[4-(1H-pyrrolo[2,3-b]pyridin-3-yl)piperidin-1-yl]sulfonylazetidine-1-carboxylate; [75]
benzyl 3-[4-(1H-pyrrolo[2,3-b]pyridin-3-yl)piperidin-1-yl]sulfonylazetidine-1-carboxylate; [76]
(4-fluorophenyl) 3-[4-(1H-pyrrolo[2,3-b]pyridin-3-yl)piperidin-1-yl]sulfonylazetidine-1-carboxylate; [77]
N-(1,3-oxazol-4-ylmethyl)-3-[4-(1H-pyrrolo[2,3-b]pyridin-3-yl)piperidin-1-yl]sulfonylazetidine-1-carboxamide; [78]
imidazol-1-yl-[3-[4-(1H-pyrrolo[2,3-b]pyridin-3-yl)piperidin-1-yl]sulfonylazetidin-1-yl]methanone; [79]
3-[4-(1H-pyrrolo[2,3-b]pyridin-3-yl)piperidin-1-yl]sulfonyl-N-(1,3-thiazol-5-ylmethyl)azetidine-1-carboxamide; [80]
N-[(1-methylpyrazol-3-yl)methyl]-3-[4-(1H-pyrrolo[2,3-b]pyridin-3-yl)piperidin-1-yl]sulfonylazetidine-1-carboxamide; [81]
N,N-diethyl-3-[4-(1H-pyrrolo[2,3-b]pyridin-3-yl)piperidin-1-yl]sulfonylazetidine-1-carboxamide; [82]
furan-2-ylmethyl 3-[4-(1H-pyrrolo[2,3-b]pyridin-3-yl)piperidin-1-yl]sulfonylazetidine-1-carboxylate; [83]

3-[4-(1H-pyrrolo[2,3-b]pyridin-3-yl)piperidin-1-yl]sulfonyl-N-(2-thiophen-2-ylethyl)azetidine-1-carboxamide; [84]
3-[4-(1H-pyrrolo[2,3-b]pyridin-3-yl)piperidin-1-yl]sulfonyl-N-(thiophen-2-ylmethyl)azetidine-1-carboxamide; [85]
piperidin-1-yl-[3-[4-(1H-pyrrolo[2,3-b]pyridin-3-yl)piperidin-1-yl]sulfonylazetidin-1-yl]methanone; [86]
pyrrolidin-1-yl-[3-[4-(1H-pyrrolo[2,3-b]pyridin-3-yl)piperidin-1-yl]sulfonylazetidin-1-yl]methanone; [87]
morpholin-4-yl-[3-[4-(1H-pyrrolo[2,3-b]pyridin-3-yl)piperidin-1-yl]sulfonylazetidin-1-yl]methanone; [88]
3-[1-(1-propan-2-ylazetidin-3-yl)sulfonylpiperidin-4-yl]-1H-pyrrolo[2,3-b]pyridine; [89]
N,N-dimethyl-3-[4-(1H-pyrrolo[2,3-b]pyridin-3-yl)piperidin-1-yl]sulfonylazetidine-1-sulfonamide; [90]
3-[1-(1-methylsulfonylazetidin-3-yl)sulfonylpiperidin-4-yl]-1H-pyrrolo[2,3-b]pyridine; [91]
tert-butyl 3-[4-[1-(dimethylsulfamoyl)pyrrolo[2,3-b]pyridin-3-yl]piperidin-1-yl]sulfonylazetidine-1-carboxylate; [92]
tert-butyl 3-[4-(1-methyl sulfonylpyrrolo[2,3-b]pyridin-3-yl)piperidin-1-yl]sulfonylazetidine-1-carboxylate; [93]
tert-butyl 3-[4-(1-methylpyrrolo[2,3-b]pyridin-3-yl)piperidin-1-yl]sulfonylazetidine-1-carboxylate; [94]
3-[4-(1H-pyrrolo[2,3-b]pyridin-3-yl)piperidin-1-yl]sulfonyl-N-[(1,3,5-trimethylpyrazol-4-yl)methyl]azetidine-1-carboxamide; [95]
N-pyridin-3-yl-3-[4-(1H-pyrrolo[2,3-b]pyridin-3-yl)piperidin-1-yl]sulfonylazetidine-1-carboxamide; [96]
propan-2-yl 3-[4-(1H-pyrrolo[2,3-b]pyridin-3-yl)piperidin-1-yl]sulfonylazetidine-1-carboxylate; [97]
N-propan-2-yl-3-[4-(1H-pyrrolo[2,3-b]pyridin-3-yl)piperidin-1-yl]sulfonylazetidine-1-carboxamide; [98]
N-(furan-2-ylmethyl)-3-[4-(1H-pyrrolo[2,3-b]pyridin-3-yl)piperidin-1-yl] sulfonylazetidine-1-carboxamide; [99]
tert-butyl 3-(4-imidazo[1,2-a]pyridin-3-ylpiperidin-1-yl)sulfonylazetidine-1-carboxylate; [100]
tert-butyl 3-[4-(5,6,7,8-tetrahydroimidazo[1,2-a]pyridin-3-yl)piperidin-1-yl] sulfonylazetidine-1-carboxylate; [101]
tert-butyl 3-[4-(3-methylimidazol-4-yl)piperidin-1-yl] sulfonylazetidine-1-carboxylate; [102]ethyl 4-(4-pyridin-4-ylpiperidin-1-yl)sulfonylpiperidine-1-carboxylate; [103]
N-cyclobutyl-4-(4-pyridin-4-ylpiperidin-1-yl)sulfonylpiperidine-1-carboxamide; [104]
propan-2-yl 4-(4-pyridin-4-ylpiperidin-1-yl)sulfonylpiperidine-1-carboxylate; [105]methyl 4-(4-pyridin-4-ylpiperidin-1-yl)sulfonylpiperidine-1-carboxylate; [106]
N-tert-butyl-4-[4-(1H-pyrrolo[2,3-b]pyridin-3-yl)piperidin-1-yl]sulfonylpiperidine-1-carboxamide; [107]
N-tert-butyl-3-[4-(1H-pyrrolo[2,3-b]pyridin-3-yl)piperidin-1-yl]sulfonylazetidine-1-carboxamide; [108]
3-[1-(azetidin-3-ylsulfonyl)piperidin-4-yl]-1H-pyrrolo[2,3-b]pyridine; [109]
tert-butyl 3-[4-(1H-pyrrolo[2,3-b]pyridin-3-yl)piperidin-1-yl]sulfonylazetidine-1-carboxylate; [110]
N-tert-butyl-4-(4-pyridin-4-ylpiperidin-1-yl)sulfonylpiperidine-1-carboxamide; [111]
tert-butyl 4-[4-[4-(dimethylamino)phenyl]piperidin-1-yl]sulfonylpiperidine-1-carboxylate; [112]4-[1-(1-phenylpiperidin-4-yl)sulfonylpiperidin-4-yl]pyridine; [113]
phenyl 4-(4-pyridin-4-ylpiperidin-1-yl)sulfonylpiperidine-1-carboxylate; [114]
tert-butyl 4-[4-(5-methoxy-1H-pyrrolo[2,3-b]pyridin-3-yl)piperidin-1-yl] sulfonylpiperidine-1-carboxylate; [115]
tert-butyl 4-[4-[5-(trifluoromethyl)-1H-pyrrolo[2,3-b]pyridin-3-yl]piperidin-1-yl]sulfonylpiperidine-1-carboxylate; [116]
tert-butyl 4-[4-[5-(1-methylpyrazol-4-yl)-1H-pyrrolo[2,3-b]pyridin-3-yl]piperidin-1-yl]sulfonylpiperidine-1-carboxylate; [117]
3-[1-(1-pyridin-2-ylazetidin-3-yl)sulfonylpiperidin-4-yl]-1H-pyrrolo[2,3-b]pyridine; [118]N-methyl-N-propan-2-yl-3-[4-(1H-pyrrolo[2,3-b]pyridin-3-yl)piperidin-1-yl] sulfonylazetidine-1-carboxamide; [119]
N-(3,5-dimethyl-1,2-oxazol-4-yl)-3-[4-(1H-pyrrolo[2,3-b]pyridin-3-yl)piperidin-1-yl]sulfonylazetidine-1-carboxamide; [120]
tert-butyl 3-[4-[5-(trifluoromethyl)-1H-pyrrolo[2,3-b]pyridin-3-yl]piperidin-1-yl]sulfonylazetidine-1-carboxylate; [121]
tert-butyl 3-[4-[5-(1-methylpyrazol-4-yl)-1H-pyrrolo[2,3-b]pyridin-3-yl]piperidin-1-yl]sulfonylazetidine-1-carboxylate; [122]
tert-butyl 3-[4-(5-methoxy-1H-pyrrolo[2,3-b]pyridin-3-yl)piperidin-1-yl]sulfonylazetidine-1-carboxylate; [123]
tert-butyl 3-(4-furo[2,3-b]pyridin-5-ylpiperidin-1-yl) sulfonylazetidine-1-carboxylate; [124]
tert-butyl 3-[4-(1H-indol-3-yl)piperidin-1-yl]sulfonylazetidine-1-carboxylate; [125]
methyl 3-(4-furo[3,2-b]pyridin-3-ylpiperidin-1-yl)sulfonylazetidine-1-carboxylate; [126]
tert-butyl 3-[4-(2,3-dihydrofuro[3,2-b]pyridin-3-yl)piperidin-1-yl]sulfonylazetidine-1-carboxylate; [127]
tert-butyl 3-[4-(5H-pyrrolo[2,3-b]pyrazin-7-yl)piperidin-1-yl]sulfonylazetidine-1-carboxylate; [128]
tert-butyl 3-[4-[5-(4-methylphenyl)sulfonylpyrrolo[2,3-b]pyrazin-7-yl]piperidin-1-yl]sulfonylazetidine-1-carboxylate; [129]
tert-butyl 3-(4-pyrazolo[1,5-a]pyrazin-3-ylpiperidin-1-yl) sulfonylazetidine-1-carboxylate; [130]
tert-butyl 3-(4-furo[3,2-b]pyridin-3-ylpiperidin-1-yl) sulfonylazetidine-1-carboxylate; [131]
tert-butyl 4-(4-furo[3,2-b]pyridin-3-ylpiperidin-1-yl) sulfonylpiperidine-1-carboxylate; [132]
tert-butyl 4-[4-(1H-indol-3-yl)piperidin-1-yl]sulfonylpiperidine-1-carboxylate; [133]
3-[1-[1-[2-(3,5-dimethyl-1,2-oxazol-4-yl)ethyl]azetidin-3-yl]sulfonylpiperidin-4-yl] furo[3,2-b]pyridine; [134]
N-(3,5-dimethyl-1,2-oxazol-4-yl)-3-(4-furo[3,2-b]pyridin-3-ylpiperidin-1-yl) sulfonylazetidine-1-carboxamide; [135]
oxan-4-yl 3-(4-furo[3,2-b]pyridin-3-ylpiperidin-1-yl) sulfonylazetidine-1-carboxylate; [136]
[3-(4-furo[3,2-b]pyridin-3-ylpiperidin-1-yl)sulfonylazetidin-1-yl]-morpholin-4-ylmethanone; [137]
2-(3,5-dimethyl-1,2-oxazol-4-yl)-1-[3-(4-furo[3,2-b]pyridin-3-ylpiperidin-1-yl) sulfonylazetidin-1-yl]ethanone; [138]
3-(4-furo[3,2-b]pyridin-3-ylpiperidin-1-yl)sulfonyl-N-[1-(trifluoromethyl)cyclopropyl]azetidine-1-carboxamide; [139]
2,2-dimethylpropyl 3-(4-furo[3,2-b]pyridin-3-ylpiperidin-1-yl)sulfonylazetidine-1-carboxylate; [140]
cyclohexyl 3-(4-furo[3,2-b]pyridin-3-ylpiperidin-1-yl) sulfonylazetidine-1-carboxylate; [141]

methyl 2-[3-[4-(1H-pyrrolo[2,3-b]pyridin-3-yl)piperidin-1-yl]sulfonylazetidin-1-yl]-1,3-oxazole-5-carboxylate; [142]

3-[1-[1-(2,2-dimethylpropyl)azetidin-3-yl]sulfonylpiperidin-4-yl]-1H-pyrrolo[2,3-b] pyridine; [143]

[1-(dimethylamino)-2-methylpropan-2-yl] 3-(4-pyridin-4-ylpiperidin-1-yl) sulfonylazetidine-1-carboxylate; [144]

N,N-diethyl-2,2-dimethyl-3-[3-[4-(1H-pyrrolo[2,3-b]pyridin-3-yl)piperidin-1-yl]sulfonylazetidin-1-yl]propan-1-amine; [145]

4-[2,2-dimethyl-3-[3-[4-(1H-pyrrolo[2,3-b]pyridin-3-yl)piperidin-1-yl]sulfonylazetidin-1-yl]propyl]morpholine; [146]

[1-(dimethylamino)-2-methylpropan-2-yl] 3-[4-(1H-pyrrolo[2,3-b]pyridin-3-yl)piperidin-1-yl]sulfonylpyrrolidine-1-carboxylate; [147]

3-[1-[1-(2,4-dimethylpentan-3-yl)azetidin-3-yl]sulfonylpiperidin-4-yl]-1H-pyrrolo[2,3-b]pyridine; [148]

N-(1-hydroxy-3-methylbutan-2-yl)-3-[4-(1H-pyrrolo[2,3-b]pyridin-3-yl)piperidin-1-yl]sulfonylpyrrolidine-1-carboxamide; [149]

tert-butyl 3-[4-(1H-pyrrolo[2,3-b]pyridin-3-yl)piperidin-1-yl]sulfonylpyrrolidine-1-carboxylate; [150]

methyl 3-[4-(1H-pyrrolo[2,3-b]pyridin-3-yl)piperidin-1-yl]sulfonylazetidine-1-carboxylate; [151]

(1-methoxy-2-methylpropan-2-yl) 3-[4-(1H-pyrrolo[2,3-b]pyridin-3-yl)piperidin-1-yl]sulfonylazetidine-1-carboxylate; [152]

[(2S)-butan-2-yl] 3-[4-(1H-pyrrolo[2,3-b]pyridin-3-yl)piperidin-1-yl]sulfonylazetidine-1-carboxylate; [153]

cyclobutylmethyl 3-[1-[1-(cyclobutylmethoxycarbonyl)azetidin-3-yl]sulfonylpiperidin-4-yl]pyrrolo[2,3-b]pyridine-1-carboxylate; [154]

3-[1-(1-pyrimidin-2-ylazetidin-3-yl)sulfonylpiperidin-4-yl]-1H-pyrrolo[2,3-b]pyridine; [155]

N-tert-butyl-N-ethyl-3-[4-(1H-pyrrolo[2,3-b]pyridin-3-yl)piperidin-1-yl]sulfonylazetidine-1-carboxamide; [156]

3-[1-[1-(pyridin-3-ylmethyl)azetidin-3-yl]sulfonylpiperidin-4-yl]-1H-pyrrolo[2,3-b] pyridine; [157]

3-[1-(1-cyclopentylazetidin-3-yl)sulfonylpiperidin-4-yl]-1H-pyrrolo[2,3-b]pyridine; [158]

3-[1-[1-[(3-methyloxetan-3-yl)methyl]azetidin-3-yl]sulfonylpiperidin-4-yl]-1H-pyrrolo[2,3-b]pyridine; [159]

(3,5-dimethyl-1,2-oxazol-4-yl) 3-[4-(1H-pyrrolo[2,3-b]pyridin-3-yl)piperidin-1-yl]sulfonylazetidine-1-carboxylate; [160]

1-adamantyl 3-[4-(1H-pyrrolo[2,3-b]pyridin-3-yl)piperidin-1-yl]sulfonylazetidine-1-carboxylate; [161]

[(2R)-oxolan-2-yl]methyl 3-[4-(1H-pyrrolo[2,3-b]pyridin-3-yl)piperidin-1-yl] sulfonylazetidine-1-carboxylate; [162]

[(2S)-oxolan-2-yl]methyl 3-[4-(1H-pyrrolo[2,3-b]pyridin-3-yl)piperidin-1-yl] sulfonylazetidine-1-carboxylate; [163]

[(2R,6R)-2,6-dimethylmorpholin-4-yl]-[3-[4-(1H-pyrrolo[2,3-b]pyridin-3-yl)piperidin-1-yl]sulfonylazetidin-1-yl]methanone; [164]

[(3S,5S)-3,5-dimethylmorpholin-4-yl]-[3-[4-(1H-pyrrolo[2,3-b]pyridin-3-yl)piperidin-1-yl]sulfonylazetidin-1-yl]methanone; [165]

[(1S,2R,5S)-5-methyl-2-propan-2-ylcyclohexyl] 3-[4-(1H-pyrrolo[2,3-b]pyridin-3-yl) piperidin-1-yl]sulfonylazetidine-1-carboxylate; [166]

N,N-dimethyl-3-[4-(1H-pyrrolo[2,3-b]pyridin-3-yl)piperidin-1-yl]sulfonylazetidine-1-carboxamide; [167]

cyclohexylmethyl 3-[4-(1H-pyrrolo[2,3-b]pyridin-3-yl)piperidin-1-yl]sulfonylazetidine-1-carboxylate; [168]

[3-[4-(1H-pyrrolo[2,3-b]pyridin-3-yl)piperidin-1-yl]sulfonylazetidin-1-yl]-(3,3,5,5-tetramethylmorpholin-4-yl)methanone; [169]

[(2R,6S)-2,6-dimethylmorpholin-4-yl]-[3-[4-(1H-pyrrolo[2,3-b]pyridin-3-yl)piperidin-1-yl]sulfonylazetidin-1-yl]methanone; [170]

N-(1-adamantyl)-3-[4-(1H-pyrrolo[2,3-b]pyridin-3-yl)piperidin-1-yl]sulfonylazetidine-1-carboxamide; [171]

tert-butyl 4-[3-[4-(1H-pyrrolo[2,3-b]pyridin-3-yl)piperidin-1-yl]sulfonylazetidin-1-yl]sulfonylpiperazine-1-carboxylate; [172]

N,N-di(propan-2-yl)-3-[4-(1H-pyrrolo[2,3-b]pyridin-3-yl)piperidin-1-yl]sulfonylazetidine-1-carboxamide; [173]

N-tert-butyl-3-[4-(1H-pyrrolo[2,3-b]pyridin-3-yl)piperidin-1-yl]sulfonylazetidine-1-carbothioamide; [174]

3-[4-(1H-pyrrolo[2,3-b]pyridin-3-yl)piperidin-1-yl]sulfonyl-N-(2,4,4-trimethylpentan-2-yl) azetidine-1-carboxamide; [175]

N-tert-butyl-N-methyl-3-[4-(1H-pyrrolo[2,3-b]pyridin-3-yl)piperidin-1-yl] sulfonylazetidine-1-carboxamide; [176]

tert-butyl 3-(4-thieno[2,3-b]pyridin-3-ylpiperidin-1-yl) sulfonylazetidine-1-carboxylate; [177]

N-(furan-2-ylmethyl)-N-methyl-3-[4-(1H-pyrrolo[2,3-b]pyridin-3-yl)piperidin-1-yl]sulfonylazetidine-1-carboxamide; [178]

N-propan-2-yl-3-[4-(1H-pyrrolo[2,3-b]pyridin-3-yl)piperidin-1-yl]sulfonylazetidine-1-carbothioamide; [179]

(4-methoxycyclohexyl) 3-[4-(1H-pyrrolo[2,3-b]pyridin-3-yl)piperidin-1-yl] sulfonylazetidine-1-carboxylate; [180]

3-[1-[1-(3-cyclopropylpyridin-2-yl)azetidin-3-yl]sulfonylpiperidin-4-yl]-1H-pyrrolo[2,3-b]pyridine; [181]

[2-[3-[4-(1H-pyrrolo[2,3-b]pyridin-3-yl)piperidin-1-yl]sulfonylazetidin-1-yl]pyridin-3-yl]methanol; [182]

(2-hydroxyphenyl) 3-[4-(1H-pyrrolo[2,3-b]pyridin-3-yl)piperidin-1-yl]sulfonylazetidine-1-carboxylate; [183]

3-[1-[1-[3,6-bis(trifluoromethyl)pyridin-2-yl]azetidin-3-yl]sulfonylpiperidin-4-yl]-1H-pyrrolo[2,3-b]pyridine; [184]

3-[1-[1-[6-methoxy-3-(trifluoromethyl)pyridin-2-yl]azetidin-3-yl]sulfonylpiperidin-4-yl]-1H-pyrrolo[2,3-b] pyridine; [185]

3-[1-[1-[3-(trifluoromethyl)pyridin-2-yl]azetidin-3-yl]sulfonylpiperidin-4-yl]-1H-pyrrolo[2,3-b]pyridine; [186]

4-methyl-2-[3-[4-(1H-pyrrolo[2,3-b]pyridin-3-yl)piperidin-1-yl]sulfonylazetidin-1-yl] pyridine-3-carbonitrile; [187]

3-[1-[1-[6-methyl-3-(trifluoromethyl)pyridin-2-yl]azetidin-3-yl]sulfonylpiperidin-4-yl]-1H-pyrrolo[2,3-b] pyridine; [188]

cyclohexyl-[3-[4-(1H-pyrrolo[2,3-b]pyridin-3-yl)piperidin-1-yl]sulfonylazetidin-1-yl]methanone; [189]

cyclopentyl-[3-[4-(1H-pyrrolo[2,3-b]pyridin-3-yl)piperidin-1-yl]sulfonylazetidin-1-yl]methanone; [190]

cyclopropyl-[3-[4-(1H-pyrrolo[2,3-b]pyridin-3-yl)piperidin-1-yl]sulfonylazetidin-1-yl]methanone; [191]

pyridin-2-yl-[3-[4-(1H-pyrrolo[2,3-b]pyridin-3-yl)piperidin-1-yl]sulfonylazetidin-1-yl]methanone; [192]

[3-[4-(1H-pyrrolo[2,3-b]pyridin-3-yl)piperidin-1-yl]sulfonylazetidin-1-yl]-thiophen-2-ylmethanone; [193]

2-methyl-1-[3-[4-(1H-pyrrolo[2,3-b]pyridin-3-yl)piperidin-1-yl]sulfonylazetidin-1-yl] propan-1-one; [194]
3-methyl-1-[3-[4-(1H-pyrrolo[2,3-b]pyridin-3-yl)piperidin-1-yl]sulfonylazetidin-1-yl] butan-1-one; [195]
[(3R)-oxolan-3-yl] 3-[4-(1H-pyrrolo[2,3-b]pyridin-3-yl)piperidin-1-yl]sulfonylazetidine-1-carboxylate; [196]
[(3S)-oxolan-3-yl] 3-[4-(1H-pyrrolo[2,3-b]pyridin-3-yl)piperidin-1-yl]sulfonylazetidine-1-carboxylate; [197]
cyclobutyl 3-[4-(1H-pyrrolo[2,3-b]pyridin-3-yl)piperidin-1-yl]sulfonylazetidine-1-carboxylate; [198]
(3-methyloxetan-3-yl)methyl 3-[4-(1H-pyrrolo[2,3-b]pyridin-3-yl)piperidin-1-yl]sulfonylazetidine-1-carboxylate; [199]
[(2R)-butan-2-yl] 3-[4-(1H-pyrrolo[2,3-b]pyridin-3-yl)piperidin-1-yl]sulfonylazetidine-1-carboxylate; [200]
cyclobutylmethyl 3-[4-(1H-pyrrolo[2,3-b]pyridin-3-yl)piperidin-1-yl]sulfonylazetidine-1-carboxylate; [201]
(3,5-dimethyl-1,2-oxazol-4-yl)methyl 3-(4-pyridin-4-ylpiperidin-1-yl)sulfonylazetidine-1-carboxylate; [202]
N-[(3,5-dimethyl-1,2-oxazol-4-yl)methyl]-3-(4-pyridin-4-ylpiperidin-1-yl) sulfonylazetidine-1-carboxamide; [203]
cyclopropylmethyl 3-[4-(1H-pyrrolo[2,3-b]pyridin-3-yl)piperidin-1-yl]sulfonylazetidine-1-carboxylate; [204]
2-(3,5-dimethyl-1,2-oxazol-4-yl)-1-[3-(4-pyridin-4-ylpiperidin-1-yl)sulfonylazetidin-1-yl]ethanone; [205]
N-ethyl-N-propan-2-yl-3-[4-(1H-pyrrolo[2,3-b]pyridin-3-yl)piperidin-1-yl] sulfonylazetidine-1-carboxamide; [206]
(3-phenoxyphenyl)methyl 3-[4-(1H-pyrrolo[2,3-b]pyridin-3-yl)piperidin-1-yl] sulfonylazetidine-1-carboxylate; [207]
(3,5-dimethylphenyl) 3-[4-(1H-pyrrolo[2,3-b]pyridin-3-yl)piperidin-1-yl]sulfonylazetidine-1-carboxylate; [208]
(3-fluoro-4-methoxyphenyl)methyl 3-[4-(1H-pyrrolo[2,3-b]pyridin-3-yl)piperidin-1-yl]sulfonylazetidine-1-carboxylate; [209]
piperidin-4-yl 3-[4-(1H-pyrrolo[2,3-b]pyridin-3-yl)piperidin-1-yl]sulfonylazetidine-1-carboxylate; [210]
tert-butyl 4-[3-[4-(1H-pyrrolo[2,3-b]pyridin-3-yl)piperidin-1-yl]sulfonylazetidine-1-carbonyl]oxypiperidine-1-carboxylate; [211]
pyridin-3-yl 3-[4-(1H-pyrrolo[2,3-b]pyridin-3-yl)piperidin-1-yl]sulfonylazetidine-1-carboxylate; [212]
(3-nitrophenyl)methyl 3-[4-(1H-pyrrolo[2,3-b]pyridin-3-yl)piperidin-1-yl] sulfonylazetidine-1-carboxylate; [213]
(4-methoxyphenyl)methyl 3-[4-(1H-pyrrolo[2,3-b]pyridin-3-yl)piperidin-1-yl] sulfonylazetidine-1-carboxylate; [214]
(3-methoxyphenyl) 3-[4-(1H-pyrrolo[2,3-b]pyridin-3-yl)piperidin-1-yl]sulfonylazetidine-1-carboxylate; [215]
[2-(trifluoromethyl)phenyl]methyl 3-[4-(1H-pyrrolo[2,3-b]pyridin-3-yl)piperidin-1-yl]sulfonylazetidine-1-carboxylate; [216]
(2-methoxyphenyl) 3-[4-(1H-pyrrolo[2,3-b]pyridin-3-yl)piperidin-1-yl]sulfonylazetidine-1-carboxylate; [217]
oxan-4-yl 3-[4-(1H-pyrrolo[2,3-b]pyridin-3-yl)piperidin-1-yl]sulfonylazetidine-1-carboxylate; [218]
(4-methoxyphenyl) 3-[4-(1H-pyrrolo[2,3-b]pyridin-3-yl)piperidin-1-yl]sulfonylazetidine-1-carboxylate; [219]
1,3-dioxan-5-yl 3-[4-(1H-pyrrolo[2,3-b]pyridin-3-yl)piperidin-1-yl]sulfonylazetidine-1-carboxylate; [220]
tert-butyl 3-[4-(4-fluoro-1H-pyrrolo[2,3-b]pyridin-3-yl)piperidin-1-yl]sulfonylazetidine-1-carboxylate; [221]
oxetan-3-yl 3-[4-(1H-pyrrolo[2,3-b]pyridin-3-yl)piperidin-1-yl]sulfonylazetidine-1-carboxylate; [222]
tert-butyl 3-[4-(4-methyl-1H-pyrrolo[2,3-b]pyridin-3-yl)piperidin-1-yl]sulfonylazetidine-1-carboxylate; [223]
tert-butyl 3-[4-(2-methyl-1H-pyrrolo[2,3-b]pyridin-3-yl)piperidin-1-yl]sulfonylazetidine-1-carboxylate; [224]
tert-butyl 3-[[4-(1H-pyrrolo[2,3-b]pyridin-3-yl)-3,6-dihydro-2H-pyridin-1-yl] sulfonyl]azetidine-1-carboxylate; [228]
tert-butyl 4-[[4-(1H-pyrazolo[3,4-b]pyridin-3-yl)-3,6-dihydro-2H-pyridin-1-yl]sulfonyl]piperidine-1-carboxylate; [229]
tert-butyl 4-[(4-thieno[3,2-b]pyridin-3-yl-3,6-dihydro-2H-pyridin-1-yl)sulfonyl]piperidine-1-carboxylate; [230]
tert-butyl 3-[(4-furo[3,2-b]pyridin-3-yl-3,6-dihydro-2H-pyridin-1-yl)sulfonyl]azetidine-1-carboxylate; [231]
tert-butyl 4-[(4-furo[3,2-b]pyridin-3-yl-3,6-dihydro-2H-pyridin-1-yl)sulfonyl]piperidine-1-carboxylate; [232]
tert-butyl 4-[[4-(7H-pyrrolo[2,3-d]pyrimidin-5-yl)-3,6-dihydro-2H-pyridin-1-yl] sulfonyl]piperidine-1-carboxylate; [233]
tert-butyl 3-[(4-furo[2,3-b]pyridin-5-yl-3,6-dihydro-2H-pyridin-1-yl)sulfonyl]azetidine-1-carboxylate; [234]
tert-butyl 4-[[4-[7-(4-methylphenyl)sulfonylpyrrolo[2,3-d]pyrimidin-5-yl]-3,6-dihydro-2H-pyridin-1-yl]sulfonyl]piperidine-1-carboxylate; [235]
tert-butyl 4-[[4-(1H-pyrrolo[2,3-b]pyridin-4-yl)-3,6-dihydro-2H-pyridin-1-yl] sulfonyl]piperidine-1-carboxylate; [236]
tert-butyl 4-[[4-[1-(4-methylphenyl)sulfonylpyrrolo[2,3-b]pyridin-4-yl]-3,6-dihydro-2H-pyridin-1-yl]sulfonyl]piperidine-1-carboxylate; [237]
tert-butyl 4-[[4-(7H-pyrrolo[2,3-d]pyrimidin-4-yl)-3,6-dihydro-2H-pyridin-1-yl] sulfonyl]piperidine-1-carboxylate; [238]
tert-butyl 4-[[4-[7-(4-methylphenyl)sulfonylpyrrolo[2,3-d]pyrimidin-4-yl]-3,6-dihydro-2H-pyridin-1-yl]sulfonyl]piperidine-1-carboxylate; [239]
methyl 2-[3-[4-(1H-pyrrolo[2,3-b]pyridin-3-yl)piperidin-1-yl]sulfonylazetidin-1-yl]-1,3-thiazole-4-carboxylate; [241]
2-[3-[4-(1H-pyrrolo[2,3-b]pyridin-3-yl)piperidin-1-yl]sulfonylazetidin-1-yl]pyridine-4-carbonitrile; [242]
3-[1-[1-(6-ethoxypyridin-2-yl)azetidin-3-yl]sulfonylpiperidin-4-yl]-1H-pyrrolo[2,3-b] pyridine; [243]
3-[1-(1-pyridin-2-ylpyrrolidin-3-yl)sulfonylpiperidin-4-yl]-1H-pyrrolo[2,3-b]pyridine; [244]
methyl 2-[3-[4-(1H-pyrrolo[2,3-b]pyridin-3-yl)piperidin-1-yl]sulfonylazetidin-1-yl]-1,3-thiazole-5-carboxylate; [245]
methyl 2-[3-[4-(1H-pyrrolo[2,3-b]pyridin-3-yl)piperidin-1-yl]sulfonylazetidin-1-yl]-1,3-oxazole-4-carboxylate; [246]
N,N-dimethyl-1-[1[[3-[4-(1H-pyrrolo[2,3-b]pyridin-3-yl)piperidin-1-yl]sulfonylazetidin-1-yl]methyl]cyclopentyl]methanamine; [247]
tert-butyl 3-[4-(1H-pyrrolo[2,3-b]pyridin-3-yl)piperidin-1-yl]sulfonylpiperidine-1-carboxylate; [248]
3-[1-(pyrrolidin-3-yl)sulfonylpiperidin-4-yl]-1H-pyrrolo[2,3-b]pyridine; [249]
N-[(2S)-1-hydroxy-3-methylbutan-2-yl]-3-[4-(1H-pyrrolo[2,3-b]pyridin-3-yl)piperidin-1-yl]sulfonylazetidine-1-carboxamide; [250]
N-[(2R)-1-hydroxy-3-methylbutan-2-yl]-3-[4-(1H-pyrrolo[2,3-b]pyridin-3-yl)piperidin-1-yl]sulfonylazetidine-1-carboxamide; [251]

4-methoxy-2-[3-[4-(1H-pyrrolo[2,3-b]pyridin-3-yl)piperidin-1-yl]sulfonylazetidin-1-yl]pyridine-3-carbonitrile; [252]
3-[1-[1-(3-fluoropyridin-2-yl)azetidin-3-yl]sulfonylpiperidin-4-yl]-1H-pyrrolo[2,3-b] pyridine; [253]
3-[1-[1-(3-methylpyridin-2-yl)azetidin-3-yl]sulfonylpiperidin-4-yl]-1H-pyrrolo[2,3-b] pyridine; [254]
2-[2-[3-[4-(1H-pyrrolo[2,3-b]pyridin-3-yl)piperidin-1-yl]sulfonylazetidin-1-yl]pyridin-3-yl]propan-2-ol; [255]
(4,4-dimethyl-1,3-oxazolidin-3-yl)-[3-[4-(1H-pyrrolo[2,3-b]pyridin-3-yl)piperidin-1-yl]sulfonylazetidin-1-yl]methanone; [256]
3-[1-[1-(4-methylpyridin-2-yl)azetidin-3-yl]sulfonylpiperidin-4-yl]-1H-pyrrolo[2,3-b]pyridine; [257]
2-[3-(4-pyridin-4-ylpiperidin-1-yl)sulfonylazetidin-1-yl]pyridine-4-carbonitrile; [258]
[2-[3-(4-pyridin-4-ylpiperidin-1-yl)sulfonylazetidin-1-yl]pyridin-3-yl]methanol; [259]
ethyl 2-[3-(4-pyridin-4-ylpiperidin-1-yl)sulfonylazetidin-1-yl]-1,3-oxazole-4-carboxylate; [260]
2-[3-(4-pyridin-4-ylpiperidin-1-yl)sulfonylazetidin-1-yl]-1,3-oxazole-4-carboxamide; [261]
N-(3,5-dimethyl-1,2-oxazol-4-yl)-3-(4-pyridin-4-ylpiperidin-1-yl)sulfonylazetidine-1-carboxamide; [262]
[(2R)-butan-2-yl] 3-(4-pyridin-4-ylpiperidin-1-yl)sulfonylazetidine-1-carboxylate; [263]
cyclohexyl 3-(4-pyridin-4-ylpiperidin-1-yl)sulfonylazetidine-1-carboxylate; [264]
3-(4-pyridin-4-ylpiperidin-1-yl)sulfonyl-N-[1-(trifluoromethyl)cyclopropyl]azetidine-1-carboxamide; [265]
cyclohexylmethyl 3-(4-pyridin-4-ylpiperidin-1-yl)sulfonylazetidine-1-carboxylate; [266]
3-[1-(azetidin-3-ylsulfonyl)piperidin-4-yl]-1-(5-methylpyridin-2-yl)pyrrolo[2,3-b]pyridine; [267]
2-[3-(4-pyridin-4-ylpiperidin-1-yl)sulfonylazetidin-1-yl]pyridine; [268]
tert-butyl 3-(4-pyridin-4-ylpiperidin-1-yl)sulfonylpyrrolidine-1-carboxylate; [269]
3-[1-(1-pyridin-3-ylazetidin-3-yl)sulfonylpiperidin-4-yl]-1H-pyrrolo[2,3-b]pyridine; [270]
N-tert-butyl-N-methyl-3-(4-pyridin-4-ylpiperidin-1-yl)sulfonylpyrrolidine-1-carboxamide; [271]
N-tert-butyl-N-methyl-3-[4-(1H-pyrrolo[2,3-b]pyridin-3-yl)piperidin-1-yl]sulfonylpyrrolidine-1-carboxamide; [272]
N-(3-methoxyphenyl)-3-[4-(1H-pyrrolo[2,3-b]pyridin-3-yl)piperidin-1-yl]sulfonyl azetidine-1-carboxamide; [275]
N-(4-methylphenyl)-3-[4-(1H-pyrrolo[2,3-b]pyridin-3-yl)piperidin-1-yl]sulfonylazetidine-1-carboxamide; [276]
N-(5-fluoro-2-methylphenyl)-3-[4-(1H-pyrrolo[2,3-b]pyridin-3-yl)piperidin-1-yl]sulfonyl azetidine-1-carboxamide; [277]
N-(3-methoxyphenyl)-N-methyl-3-[4-(1H-pyrrolo[2,3-b]pyridin-3-yl)piperidin-1-yl]sulfonylazetidine-1-carboxamide; [279]
(4-fluorophenyl) 3-(4-pyridin-4-ylpiperidin-1-yl)sulfonylazetidine-1-carboxylate; [280]
N-(3-methoxyphenyl)-3-(4-pyridin-4-ylpiperidin-1-yl)sulfonylazetidine-1-carboxamide; [281]
N-(4-methylphenyl)-3-(4-pyridin-4-ylpiperidin-1-yl)sulfonylazetidine-1-carboxamide; [282]
tert-butyl 3-[4-(1,3-benzothiazol-2-yl)piperidin-1-yl]sulfonylazetidine-1-carboxylate; [283]
N-(5-fluoro-2-methylphenyl)-3-(4-pyridin-4-ylpiperidin-1-yl)sulfonylazetidine-1-carboxamide; [286]
cyclohexyl N-[2-(4-pyridin-4-ylpiperidin-1-yl)sulfonylethyl]carbamate; [291]
cyclohexyl N-[2-[4-(1H-pyrrolo[2,3-b]pyridin-3-yl)piperidin-1-yl]sulfonylethyl] carbamate; [292]
3-[4-(1,3-benzothiazol-2-yl)piperidin-1-yl]sulfonyl-N-[1-(trifluoromethyl)cyclopropyl]azetidine-1-carboxamide; [293]
3-[4-(1,3-benzothiazol-2-yl)piperidin-1-yl]sulfonyl-N-(3,5-dimethyl-1,2-oxazol-4-yl) azetidine-1-carboxamide; [294]
tert-butyl 3-[4-(1H-benzimidazol-2-yl)piperidin-1-yl]sulfonylazetidine-1-carboxylate; [299]
3-[4-(1H-benzimidazol-2-yl)piperidin-1-yl]sulfonyl-N-[1-(trifluoromethyl)cyclopropyl]azetidine-1-carboxamide; [300]
tert-butyl 3-[4-phenylpiperidin-1-yl]sulfonylazetidine-1-carboxylate; [301]
tert-butyl 3-[4-(4-chloro-2-methylphenyl)piperidin-1-yl]sulfonylazetidine-1-carboxylate; [302]
tert-butyl 3-[4-(4-cyanophenyl)piperidin-1-yl]sulfonylazetidine-1-carboxylate; [303]
tert-butyl 3-[4-(4-chlorophenyl)piperidin-1-yl]sulfonylazetidine-1-carboxylate; [304]
3-[4-(1,3-benzoxazol-2-yl)piperidin-1-yl]sulfonyl-N-[1-(trifluoromethyl)cyclopropyl] azetidine-1-carboxamide; [305]
2-[di(propan-2-yl)amino]-1-[3-(4-phenylpiperidin-1-yl)sulfonylazetidin-1-yl]ethanone; [306]
2-(dimethylamino)-1-[3-(4-phenylpiperidin-1-yl)sulfonylazetidin-1-yl]propan-1-one; [307]
4-phenyl-2-[3-[4-(1H-pyrrolo[2,3-b]pyridin-3-yl)piperidin-1-yl]sulfonylazetidin-1-yl]-1,3-thiazole; [311]
2-[3-[4-(1H-pyrrolo[2,3-b]pyridin-3-yl)piperidin-1-yl]sulfonylazetidin-1-yl]-1,3-benzothiazole; [312]
3-[1-[1-[[1-(trifluoromethyl)cyclopropyl]methyl]azetidin-3-yl]sulfonylpiperidin-4-yl]-1H-pyrrolo[2,3-b]pyridine; [313]
3,3-dimethyl-1-[3-[4-(1H-pyrrolo[2,3-b]pyridin-3-yl)piperidin-1-yl]sulfonylazetidin-1-yl]butan-2-one; [314]
[(2S)-1-methylpyrrolidin-2-yl]-[3-(4-phenylpiperidin-1-yl)sulfonylazetidin-1-yl] methanone; [315]
(3,5-dimethyl-1,2-oxazol-4-yl)-[3-(4-phenylpiperidin-1-yl)sulfonylazetidin-1-yl] methanone; [316]
1-[3-[4-(4-chloro-2-methylphenyl)piperidin-1-yl]sulfonylazetidin-1-yl]-2-[di(propan-2-yl)amino]ethanone; [317]
[3-[4-(4-chloro-2-methylphenyl)piperidin-1-yl]sulfonylazetidin-1-yl]-[(2S)-1-methyl pyrrolidin-2-yl] methanone; [318]
N-tert-butyl-3-[4-(4-chlorophenyl)piperidin-1-yl]sulfonylazetidine-1-carboxamide; [319]
oxan-4-yl 3-[4-(4-chlorophenyl)piperidin-1-yl]sulfonylazetidine-1-carboxylate; [320]
3-[4-(4-chlorophenyl)piperidin-1-yl]sulfonyl-N-[(2R)-1-hydroxy-3-methylbutan-2-yl] azetidine-1-carboxamide; [321]
3-[4-(4-chlorophenyl)piperidin-1-yl]sulfonyl-N-(3,5-dimethyl-1,2-oxazol-4-yl)azetidine-1-carboxamide; [322]
3,3,3-trifluoro-2,2-dimethyl-1-[3-[4-(1H-pyrrolo[2,3-b]pyridin-3-yl)piperidin-1-yl]sulfonyl azetidin-1-yl]propan-1-one; [323]
4-[1-[1-[2-[di(propan-2-yl)amino]acetyl]azetidin-3-yl]sulfonylpiperidin-4-yl]benzonitrile; [324]
2-(dimethylamino)-1-[3-[4-(1H-pyrrolo[2,3-b]pyridin-3-yl)piperidin-1-yl]sulfonylazetidin-1-yl]ethanone; [325]

2-[di(propan-2-yl)amino]-1-[3-[4-(1H-pyrrolo[2,3-b]pyridin-3-yl)piperidin-1-yl]sulfonyl azetidin-1-yl]ethanone; [326]
tert-butyl 3-[4-(4-fluorophenyl)piperidin-1-yl]sulfonylazetidine-1-carboxylate; [327]
3-(4-furo[3,2-b]pyridin-3-ylpiperidin-1-yl)sulfonyl-N-[(2R)-1,1,1-trifluoropropan-2-yl]azetidine-1-carboxamide; [328]
2-(dimethylamino)-1-[3-(4-furo[3,2-b]pyridin-3-ylpiperidin-1-yl)sulfonylazetidin-1-yl]ethanone; [329]
2-[di(propan-2-yl)amino]-1-[3-(4-furo[3,2-b]pyridin-3-ylpiperidin-1-yl)sulfonylazetidin-1-yl]ethanone; [330]
3-[4-(4-cyanophenyl)piperidin-1-yl]sulfonyl-N-[1-(trifluoromethyl)cyclopropyl]azetidine-1-carboxamide; [331]
3-[4-(1H-pyrrolo[2,3-b]pyridin-3-yl)piperidin-1-yl]sulfonyl-N-[(2R)-1,1,1-trifluoropropan-2-yl]azetidine-1-carboxamide; [332]
4,4,4-trifluoro-3-hydroxy-1-[3-[4-(1H-pyrrolo[2,3-b]pyridin-3-yl)piperidin-1-yl]sulfonyl azetidin-1-yl]-3-(trifluoromethyl)butan-1-one; [333]
4,4,4-trifluoro-1-[3-(4-furo[3,2-b]pyridin-3-ylpiperidin-1-yl)sulfonylazetidin-1-yl]-3-hydroxy-3-(trifluoromethyl)butan-1-one; [334]
N-(4-cyanophenyl)-3-[4-(1H-pyrrolo[2,3-b]pyridin-3-yl)piperidin-1-yl]sulfonylazetidine-1-carboxamide; [335]
2-[3-(4-pyridin-4-ylpiperidin-1-yl)sulfonylazetidin-1-yl]-1,3-benzothiazole; [337]
2-[3-[4-(1H-pyrrolo[2,3-b]pyridin-3-yl)piperidin-1-yl]sulfonylazetidin-1-yl]-1,3-benzoxazole; [338]
tert-butyl 3-[4-(1H-pyrrolo[2,3-c]pyridin-3-yl)piperidin-1-yl]sulfonylazetidine-1-carboxylate; [339]
N-cyclopropyl-3-[4-(4-fluorophenyl)piperidin-1-yl]sulfonyl-N-methylazetidine-1-carboxamide; [340]
3-[4-(4-chlorophenyl)piperidin-1-yl]sulfonyl-N-[1-(trifluoromethyl)cyclopropyl]azetidine-1-carboxamide; [341]
2-(3,5-dimethyl-1,2-oxazol-4-yl)-1-[3-[4-(4-fluorophenyl)piperidin-1-yl]sulfonylazetidin-1-yl]ethanone; [342]
2-[di(propan-2-yl)amino]-1-[3-[4-(4-fluorophenyl)piperidin-1-yl]sulfonylazetidin-1-yl]ethanone; [343]
3-[4-(4-fluorophenyl)piperidin-1-yl]sulfonyl-N-[1-hydroxy-3-methylbutan-2-yl] azetidine-1-carboxamide; [344]
tert-butyl 3-[4-(6-methyl-1H-pyrrolo[2,3-b]pyridin-3-yl)piperidin-1-yl]sulfonylazetidine-1-carboxylate; [347]
3-[4-(4-cyanophenyl)piperidin-1-yl]sulfonyl-N-[1-hydroxy-3-methylbutan-2-yl]azetidine-1-carboxamide; [348]
4-[1-[1-[2-(3,5-dimethyl-1,2-oxazol-4-yl)acetyl]azetidin-3-yl]sulfonylpiperidin-4-yl]benzonitrile; [349]
3-[4-(4-cyanophenyl)piperidin-1-yl]sulfonyl-N-cyclopropyl-N-methylazetidine-1-carboxamide; [350]
4-[1-[1-[4,4,4-trifluoro-3-hydroxy-3-(trifluoromethyl)butanoyl]azetidin-3-yl]sulfonyl piperidin-4-yl]benzonitrile; [351]
N-tert-butyl-3-[4-(4-cyanophenyl)piperidin-1-yl]sulfonylazetidine-1-carboxamide; [352]
1-[1-[[2-(difluoromethoxy)phenyl]methyl]azetidin-3-yl]sulfonyl-4-phenylpiperidine; [353]
tert-butyl 3-[4-(2,4-dimethylphenyl)piperidin-1-yl]sulfonylazetidine-1-carboxylate; [354]
3-[4-(1H-pyrrolo[2,3-c]pyridin-3-yl)piperidin-1-yl]sulfonyl-N-[1-(trifluoromethyl) cyclopropyl]azetidine-1-carboxamide; [355]
3-[1-(1-pyridin-2-ylazetidin-3-yl)sulfonylpiperidin-4-yl]-1H-pyrrolo[3,2-b]pyridine; [356]
N-(2,4-dichlorophenyl)-3-(4-furo[3,2-b]pyridin-3-ylpiperidin-1-yl)sulfonylazetidine-1-carboxamide; [359]
N-(3-fluoro-2-methylphenyl)-3-(4-furo[3,2-b]pyridin-3-ylpiperidin-1-yl)sulfonylazetidine-1-carboxamide; [360]
N-(3-fluoro-2-methylphenyl)-3-[4-(1H-pyrrolo[2,3-b]pyridin-3-yl)piperidin-1-yl]sulfonyl azetidine-1-carboxamide; [363]
N-(2-methylphenyl)-3-[4-(1H-pyrrolo[2,3-b]pyridin-3-yl)piperidin-1-yl]sulfonylazetidine-1-carboxamide; [364]
N-(5-fluoro-2-methylphenyl)-3-(4-furo[3,2-b]pyridin-3-ylpiperidin-1-yl)sulfonylazetidine-1-carboxamide; [365]
3-[4-(4-cyanophenyl)piperidin-1-yl]sulfonyl-N-(5-fluoro-2-methylphenyl)azetidine-1-carboxamide; [366]
N-(5-fluoro-2-methylphenyl)-3-[4-(4-fluorophenyl)piperidin-1-yl]sulfonylazetidine-1-carboxamide; [367]
N-(5-fluoro-2-methylphenyl)-3-[4-(6-methyl-1H-pyrrolo[2,3-b]pyridin-3-yl)piperidin-1-yl]sulfonylazetidine-1-carboxamide; [368]
3-(4-furo[3,2-b]pyridin-3-ylpiperidin-1-yl)sulfonyl-N-(2-methylphenyl)azetidine-1-carboxamide; [369]
N-tert-butyl-3-(4-furo[3,2-b]pyridin-3-ylpiperidin-1-yl)sulfonylazetidine-1-carboxamide; [370]
[(2R)-butan-2-yl] 3-(4-furo[3,2-b]pyridin-3-ylpiperidin-1-yl)sulfonylazetidine-1-carboxylate; [371]
(4,4-dimethyl-1,3-oxazolidin-3-yl)-[3-(4-furo[3,2-b]pyridin-3-ylpiperidin-1-yl)sulfonyl azetidin-1-yl]methanone; [372]
3-(4-furo[3,2-b]pyridin-3-ylpiperidin-1-yl)sulfonyl-N-[(2S)-1-hydroxy-3-methylbutan-2-yl]azetidine-1-carboxamide; [373]
[(2R,6S)-2,6-dimethylmorpholin-4-yl]-[3-(4-furo[3,2-b]pyridin-3-ylpiperidin-1-yl)sulfonyl azetidin-1-yl]methanone; [374]
1-[3-[4-(4-fluorophenyl)piperidin-1-yl]sulfonylazetidin-1-yl]-3,3-dimethylbutan-2-one; [375]
1-[3-(4-furo[3,2-b]pyridin-3-ylpiperidin-1-yl)sulfonylazetidin-1-yl]-3,3-dimethylbutan-2-one; [376]
1-[3-(4-furo[3,2-b]pyridin-3-ylpiperidin-1-yl)sulfonylazetidin-1-yl]-2-(oxan-4-yl)ethanone; [377]
4-[1-[1-(3,3-dimethyl-2-oxobutyl)azetidin-3-yl]sulfonylpiperidin-4-yl]benzonitrile; [378]
4,4,4-trifluoro-3-hydroxy-1-[3-[4-(1H-pyrrolo[3,2-b]pyridin-3-yl)piperidin-1-yl]sulfonyl azetidin-1-yl]-3-(trifluoromethyl)butan-1-one; [379]
oxan-4-yl 3-[4-(6-methyl-1H-pyrrolo[2,3-b]pyridin-3-yl)piperidin-1-yl]sulfonylazetidine-1-carboxylate; [380]
[(2R,6S)-2,6-dimethylmorpholin-4-yl]-[3-[4-(6-methyl-1H-pyrrolo[2,3-b]pyridin-3-yl) piperidin-1-yl]sulfonylazetidin-1-yl]methanone; [381]
N-(2,6-dimethylphenyl)-3-(4-furo[3,2-b]pyridin-3-ylpiperidin-1-yl)sulfonylazetidine-1-carboxamide; [382]
N-(3-fluorophenyl)-3-(4-furo[3,2-b]pyridin-3-ylpiperidin-1-yl)sulfonylazetidine-1-carboxamide; [383]
N-(2-chloro-5-fluorophenyl)-3-(4-furo[3,2-b]pyridin-3-ylpiperidin-1-yl)sulfonylazetidine-1-carboxamide; [384]
N-(2-chloro-5-fluorophenyl)-3-[4-(1H-pyrrolo[2,3-b]pyridin-3-yl)piperidin-1-yl]sulfonyl azetidine-1-carboxamide; [385]
1-[3-[4-(4-chlorophenyl)piperidin-1-yl]sulfonylazetidin-1-yl]-2-(3,5-dimethyl-1,2-oxazol-4-yl) ethanone; [386]

N-(2-fluoro-6-methylphenyl)-3-[4-(1H-pyrrolo[2,3-b]pyridin-3-yl)piperidin-1-yl]sulfonyl azetidine-1-carboxamide; [387]

(2S)-3,3,3-trifluoro-2-hydroxy-2-methyl-1-[3-[4-(1H-pyrrolo[2,3-b]pyridin-3-yl)piperidin-1-yl]sulfonylazetidin-1-yl]propan-1-one; [388]

N-(3-fluorophenyl)-3-[4-(1H-pyrrolo[2,3-b]pyridin-3-yl)piperidin-1-yl]sulfonylazetidine-1-carboxamide; [389]

N-(2,6-difluorophenyl)-3-[4-(1H-pyrrolo[2,3-b]pyridin-3-yl)piperidin-1-yl]sulfonyl azetidine-1-carboxamide; [390]

N-(2,6-dimethylphenyl)-3-[4-(1H-pyrrolo[2,3-b]pyridin-3-yl)piperidin-1-yl]sulfonyl azetidine-1-carboxamide; [391]

N-(4-fluoro-2-methylphenyl)-3-(4-furo[3,2-b]pyridin-3-ylpiperidin-1-yl)sulfonylazetidine-1-carboxamide; [392]

[3-[4-(4-chlorophenyl)piperidin-1-yl]sulfonylazetidin-1-yl]-[(2R,6S)-2,6-dimethyl morpholin-4-yl]methanone; [393]

N-(4-fluoro-2-methylphenyl)-3-[4-(1H-pyrrolo[2,3-b]pyridin-3-yl)piperidin-1-yl]sulfonylazetidine-1-carboxamide; [394]

(2S)-3,3,3-trifluoro-1-[3-(4-furo[3,2-b]pyridin-3-ylpiperidin-1-yl)sulfonylazetidin-1-yl]-2-hydroxy-2-methylpropan-1-one; [395]

1-[3-[4-(4-chlorophenyl)piperidin-1-yl]sulfonylazetidin-1-yl]-3,3-dimethylbutan-2-one; [396]

3-hydroxy-3-methyl-1-[3-[4-(1H-pyrrolo[2,3-b]pyridin-3-yl)piperidin-1-yl]sulfonyl azetidin-1-yl]butan-1-one; [397]

1-[3-(4-furo[3,2-b]pyridin-3-ylpiperidin-1-yl)sulfonylazetidin-1-yl]-3-hydroxy-3-methylbutan-1-one; [398]

N-(4-fluoro-2-methylphenyl)-3-(4-furo[3,2-b]pyridin-3-ylpiperidin-1-yl)sulfonyl-N-methylazetidine-1-carboxamide; [399]

3-[4-(4-chlorophenyl)piperidin-1-yl]sulfonyl-N-(5-fluoro-2-methylphenyl)azetidine-1-carboxamide; [400]

4,4,4-trifluoro-3-hydroxy-1-[3-(4-pyridin-4-ylpiperidin-1-yl)sulfonylazetidin-1-yl]-3-(trifluoromethyl)butan-1-one; [401]

[3-[4-(4-chlorophenyl)piperidin-1-yl]sulfonylazetidin-1-yl]-morpholin-4-ylmethanone; [402]

N-(2,6-difluorophenyl)-3-(4-furo[3,2-b]pyridin-3-ylpiperidin-1-yl)sulfonylazetidine-1-carboxamide; [403]

3,3,3-trifluoro-1-[3-(4-furo[3,2-b]pyridin-3-ylpiperidin-1-yl)sulfonylazetidin-1-yl]-2,2-dimethylpropan-1-one; [404]

4,4,4-trifluoro-3-hydroxy-3-methyl-1-[3-[4-(1H-pyrrolo[2,3-b]pyridin-3-yl) piperidin-1-yl]sulfonylazetidin-1-yl]butan-1-one; [405]

4,4,4-trifluoro-1-[3-(4-furo[3,2-b]pyridin-3-ylpiperidin-1-yl)sulfonylazetidin-1-yl]-3-hydroxy-3-methylbutan-1-one; [406]

[3-(4-furo[3,2-b]pyridin-3-ylpiperidin-1-yl)sulfonylazetidin-1-yl]-[(2S)-1-methylpyrrolidin-2-yl]methanone; [407]

1-[3-(4-furo[3,2-b]pyridin-3-ylpiperidin-1-yl)sulfonylazetidin-1-yl]-3-methylbutan-1-one; [408]

tert-butyl 3-[4-(2-methylphenyl)piperidin-1-yl]sulfonylazetidine-1-carboxylate; [409]

tert-butyl 3-(4-quinolin-4-ylpiperidin-1-yl)sulfonylazetidine-1-carboxylate; [410] and

[3-[4-(4-chlorophenyl)piperidin-1-yl]sulfonylazetidin-1-yl]-(4,4-dimethyl-1,3-oxazolidin-3-yl)methanone; [411]

or a pharmaceutically acceptable salt or a solvate thereof.

\* \* \* \* \*